United States Patent
Ishihara et al.

(10) Patent No.: US 7,462,628 B2
(45) Date of Patent: Dec. 9, 2008

(54) PREVENTIVES/REMEDIES FOR URINARY DISTURBANCE

(75) Inventors: Yuji Ishihara, Itami (JP); Yuji Ishichi, Sakai (JP); Takayuki Doi, Osaka (JP); Hiroshi Nagabukuro, Osaka (JP); Naoyuki Kanzaki, Ibaraki (JP); Motoki Ikeuchi, Nishinomiya (JP)

(73) Assignee: Takeda Pharmaceutical Company Limited, Osaka (JP)

(*) Notice: Subject to any disclaimer, the term of this patent is extended or adjusted under 35 U.S.C. 154(b) by 365 days.

(21) Appl. No.: 11/333,375

(22) Filed: Jan. 18, 2006

(65) Prior Publication Data

US 2006/0211675 A1  Sep. 21, 2006

Related U.S. Application Data

(62) Division of application No. 10/935,646, filed on Sep. 8, 2004, now Pat. No. 7,138,533, which is a division of application No. 10/500,217, filed as application No. PCT/JP02/13653 on Dec. 26, 2002, now Pat. No. 7,132,547.

(30) Foreign Application Priority Data

Dec. 28, 2001 (JP) ............................... 2001-402064
Mar. 15, 2002 (JP) ............................... 2002-072027

(51) Int. Cl.
*A61K 31/44* (2006.01)
*C07D 451/00* (2006.01)
*C07D 453/00* (2006.01)
*C07D 455/00* (2006.01)

(52) U.S. Cl. ........................................ 514/294; 546/94
(58) Field of Classification Search ................... 546/94; 514/294
See application file for complete search history.

(56) References Cited

U.S. PATENT DOCUMENTS 3,917,838 A * 11/1975 Bass et al. .................. 514/294

FOREIGN PATENT DOCUMENTS

| EP | 0 487 071 | 5/1992 |
|----|-----------|--------|
| EP | 0 560 235 | 9/1993 |
| EP | 0 562 832 | 9/1993 |
| EP | 0 567 090 | 10/1993 |
| EP | 0 607 864 | 7/1994 |
| EP | 0 655 451 | 5/1995 |
| EP | 1 088 551 A1 | 4/2001 |
| EP | 1 118 322 | 7/2001 |
| GB | 1 489 088 | 10/1977 |
| JP | 6-263733 | 9/1994 |
| JP | 7-330725 | 12/1995 |
| JP | 7-330726 | 12/1995 |
| JP | 8-92080 | 4/1996 |
| JP | 9-143182 | 6/1997 |
| JP | 10-45597 | 2/1998 |
| WO | 99/19326 | 4/1999 |
| WO | 99/42448 * | 8/1999 |
| WO | 00/51985 | 9/2000 |
| WO | 01/16105 | 3/2001 |

OTHER PUBLICATIONS

European Office Action mailed Dec. 19, 2007 for European Application No. 02790890.4-1216.
Beilstein Registry No. 7871165, Bellstein Data: Copyright 1988-2007, Beilstein Institute.
Beilstein Registry No. 7498409, Beilstein Data: Copyright 1988-2007, Beilstein Institute.
K. Yasuda et al. "The effect of unrapidil on neurogenic bladder: a placebo controlled double-blind study", *The Journal of Neurology*, Sep. 1996, vol. 156, pp. 1125-1130.
M. Perrigot et al., "Effect of intravenous alfuzosin on urethral pressure in patients with neurogenic bladder dysfunction", *Neurology and Urodynamics*, 1996, vol. 15, pp. 119-131.

* cited by examiner

*Primary Examiner*—D. Margaret Seaman
*Assistant Examiner*—Niloofar Rahmani
(74) *Attorney, Agent, or Firm*—Wenderoth, Linds & Ponack, L.L.P.

(57) ABSTRACT

Preventives/remedies for voiding disturbance containing a compound having both of an acetylcholinesterase inhibitory action and an α1 antagonistic action which exhibits an excellent effect of improving the urinary function of the bladder (i.e., effects of improving urine flow rate and voiding efficiency) without affecting the urinary pressure or the blood pressure.

9 Claims, No Drawings

PREVENTIVES/REMEDIES FOR URINARY DISTURBANCE

This is a divisional of Ser. No. 10/935,646 filed Sep. 8, 2004, now U.S. Pat. No. 7,138,533, which is a divisional of Ser. No. 10/500,217 filed Jun. 25, 2004, now U.S. Pat. No. 7,132,547, which is a U.S. National Stage of International Application No. PCT/JP02/13653 tiled Dec. 26, 2002.

TECHNICAL FIELD

The present invention relates to medicines, more particularly, preventives/remedies for voiding disturbance.

BACKGROUND ART

Lower urinary tract disease is a generic term for subjective or objective abnormality during a process from storage of urine (urinary storage) to excretion of urine (urination), and is classified into urinary storage disturbance (urinary incontinence, voiding frequency etc.), and voiding disturbance (voiding difficulty, micturition pain, urinary tract obstruction etc.). Although lower urinary tract disease is also observed in young people, with progression of an aging society, lower urinary tract disease of the elderly, particularly, voiding disturbance, inter alia, voiding difficulty accompanied with benign prostatic hyperplasia has become a great social problem recently.

Urination is controlled by a peripheral nervous system composed of parasympathetic nerve such as pelvic nerve, sympathetic nerve such as hypogastric nerve and somatic nerve such as pudic nerve under control of micturition center, and it is suggested that various neurotransmitters (e.g. acetylcholine, noradrenaline, ATP, substance P, neuropeptide Y etc.) are involved in micturition.

As a therapeutic agent for voiding disturbance, in particular, voiding difficulty, a medicine for augmenting a contractile force of bladder muscle (detrusor muscle), or a medicine for relaxing urethral smooth muscle and alleviating urethra resistance is used. As a medicine which acts on bladder muscle and augments its contractile force, a choline agonist such as bethanechol, and acetylcholinesterase inhibitor such as distigmine are used. However, for example, bethanechol constricts also bladder muscle at a urinary storage stage and damages urinary storage function of bladder and, at the same time, has side effects such as lacrimation, sweating, gastrointestinal disorder, and bellyache and, therefore, is contraindicated, to pregnant woman, digestive ulcer, organic ileus, asthma, and hyperthyroidism. Satisfactory medicines have not been found out yet.

As an acetylcholinesterase inhibitor having augmenting action of a bladder muscle contractile force, for example, distigmine and neostigmine are known. Since an acetylcholinesterase inhibitor potentiates an action of acetylcholine which is released from a pelvic nerve terminal during voiding, it augments the contraction of a bladder muscle during voiding, and is an excellent drug in view of physiological mechanism of voiding. However, for example, while distigmine contracts a bladder muscle, it contracts urethral sphincter muscle due to its strong nicotinic action and increases urethral resistance, resulting in a deteriorated voiding efficiency and insufficient clinical effect. Further, a risk of high pressure voiding is pointed out. In addition, since neostigmine has short-lasting action, it is not used in therapy (see, for example, Non-Patent Document 1).

As a medicine for relaxing urethra smooth muscle and alleviating urethral resistance, an $\alpha_1$ receptor antagonist such as tamsulosin, prazosin, alfuzosin, naftopidil and urapidil is used, and it is reported that the antagonist has the effect of improving subjective symptom such as residual urine feeling and nocturia. However, the antagonist has an antihypertensive effect such as orthostatic hypotension as side effect, and an attention must be paid to therapy.

On the other hand, Patent Document 1 discloses an acetylcholinesterase inhibitor used as a preventive or a therapeutic agent for voiding disturbance (voiding difficulty), and it is reported that a urine flow rate is considerably improved by using, a combination of, an $\alpha_1$ receptor antagonist and an acetylcholinesterase inhibitor. However, concomitant use of two agents is not satisfactory in terms of therapy and therapeutic economy considering the burden of a patient to which agents are administered and the trouble of compounding and the like. In addition, a possibility that exacerbation of side effect and death accident might occur by drug interaction due to concomitant use is pointed out, and a sufficient attention must be paid thereto.

In addition, amine compound having various pharmacological activities are reported as follows:

(1) Patent Document 2 discloses, for example, compounds of the following formulas, as an acetylcholinesterase inhibitor used as a therapeutic for Alzheimer-type dementia.

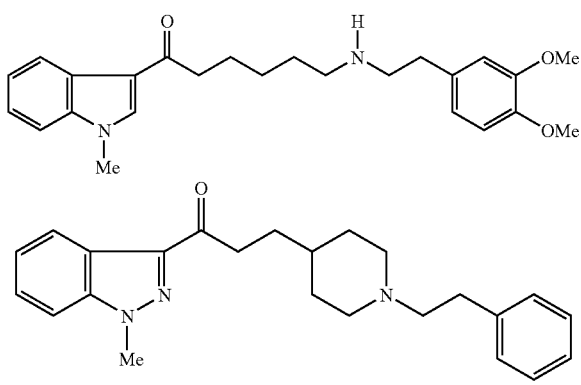

(2) Patent Document 3 discloses, for example, a compound of the following formula, as a σ ligand used as a therapeutic for central nervous disease.

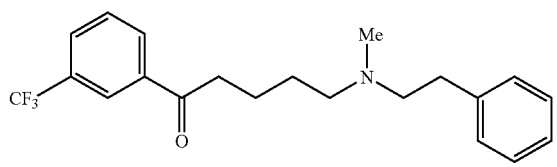

(3) Patent Document 4 discloses, for example, a compound of the following formula, as a synthetic intermediate for a sulfur-containing compound.

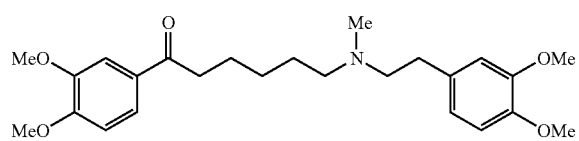

(4) Patent Document 5 discloses, for example, a compound of the following formula, as a derivative of 4-aminobutyrophenones used as a tranquilizer.

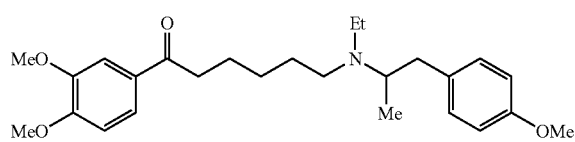

(5) Patent Document 6 discloses, for example, a compound of the following formula, as a compound used as an antibacterial agent.

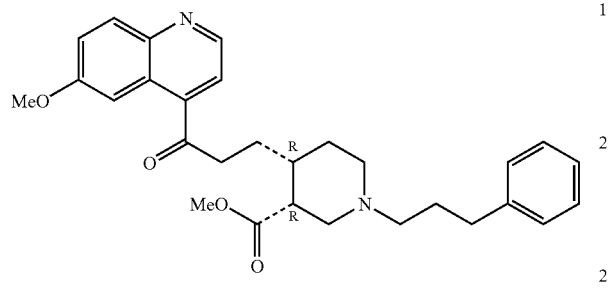

(6) Patent Document 7 discloses, for example, a compound of the following formula, as a 5-HT4 receptor ligand.

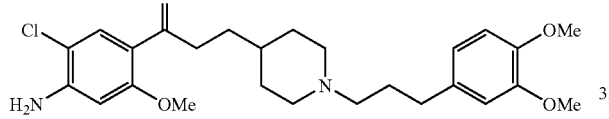

(7) Non-Patent Document 2 discloses, for example, a compound of the following formula, as a 5-HT4 receptor antagonist.

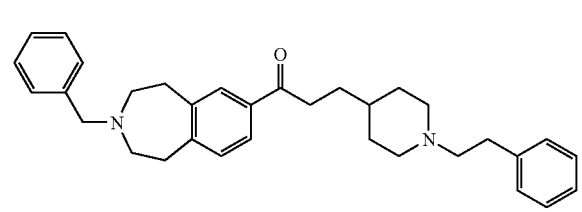

(8) Patent Document 8 discloses, for example, a compound of the following formula, as a compound having thermogenesis promoting activity and anti-obesity activity.

(9) Patent Document 9 discloses, for example, a compound of the following formula, as an acetylcholinesterase inhibitor.

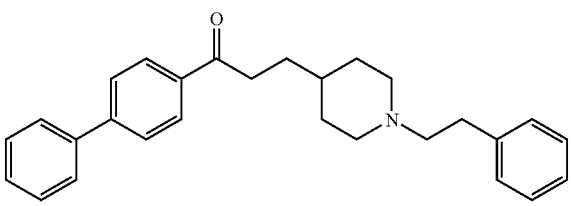

(10) Patent Document 10 discloses, for example, a compound of the following formula, as an acetylcholinesterase inhibitor used as a therapeutic for Alzheimer-type dementia.

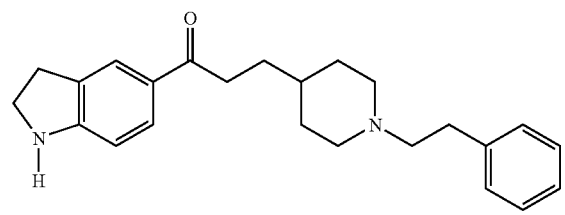

(11) Patent Document 11 discloses, for example, a compound of the following formula, as an acetylcholinesterase. inhibitor used as a therapeutic for Alzheimer-type dementia.

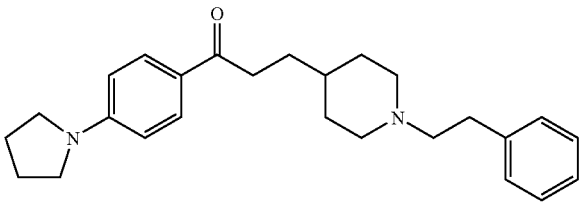

(12) Patent Document 12 discloses, for example, a compound of the following formula, as a compound used as a depressor or an antiarrhythmic.

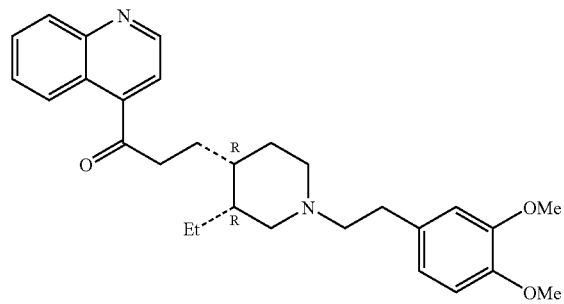

(13) Patent Document 13 discloses, for example, a compound of the following formula, as an acetylcholinesterase inhibitor used as a therapeutic for Alzheimer-type dementia.

(14) Patent Document 14 discloses, for example, a compound of the following formula, as an acetylcholinesterase inhibitor used as a therapeutic for. Alzheimer-type dementia.

(15) Patent Document 15 discloses, for example, a compound having the following formula, as an acetylcholinesterase inhibitor used as a therapeutic for Alzheimer-type dementia.

(16) Patent Document 16 discloses, for example, a compound having the following formula, as an acetylcholinesterase inhibitor used as a therapeutic for Alzheimer-type dementia.

However, a compound having both of an acetylcholinesterase inhibitory activity and an $a_1$ receptor antagonistic activity and effect thereof as a preventive or a therapeutic agent for voiding disturbance (voiding difficulty) have not been reported, suggested or disclosed at all until now.

In addition, as a method for assessing a therapeutic agent for voiding disturbance accompanied with benign prostatic hyperplasia in vivo, for example, Non-Patent Documents 3. to 5 disclose a method for measuring reduction of intraurethral pressure due to drug administration using an animal loaded with phenylephrine. However, this method is a procedure for observing the change of intraurethral pressure, and can not measure a urine flow at that time.

On the other hand, as a method for assessing an intraurethral (intravesical) pressure and an urine flow at the same time, Pressure Flow Study is known. For example, there is a description regarding application of Pressure Flow Study to a human in Non-Patent Document 6. In addition, Non-Patent Documents 7 to 9 disclose Pressure Flow Study in an experimental animal. However, these Documents do not disclose a case using an animal model loaded with phenylephrine, and assessment of a therapeutic agent for voiding disturbance accompanied with benign prostatic hyperplasia can not be properly carried out.

[Non-Patent Document 1]
"Diagnosis and Therapy of Neurogenic Bladder" $2^{nd}$ edition, Takamichi Hattori, Kosaku Yasuda, Igakushoin p. 105-106, p. 139

[Non-Patent Document 2]
Bioorganic and Medicinal Chemistry Letters, 1995, vol. 5, P. 2119-2122

[Non-Patent Document 3]
The Journal of Pharmacology and Experimental Therapeutics, 1999, vol. 291, p. 81

[Non-Patent Document 4]
The Journal of Pharmacology and Experimental Therapeutics, 2002. vol. 300, p. 487

[Non-Patent Document 5]
The Journal of Pharmacology and Experimental Therapeutics, 2002. vol. 300, p. 495

[Non-Patent Document 6]
The mechanics and hydrodynamics of the lower urinary tract, Medical physical handbooks. Bristol, 1980

[Non-Patent Document 7]
The Journal of Urology, 1995, vol.154, p. 580

[Non-Patent Document 8]
American Journal of Physiology, 1995, vol. 269, p. 98

[Non-Patent Document 9]
Neurourology and Urodynamics, 1996, vol. 15, p. 513

[Patent Document 1]
EP-A 1118322

[Patent Document 2]
EP-A 562832

[Patent Document 3]
WO 95/131

[Patent Document 4]
GB 1489080

[Patent Document 5]
U.S. Pat. No. 4,001,312

[Patent Document 6]
WO 01/25227

[Patent Document 7]
WO 94/27965

[Patent Document 8]
WO 98/46590

[Patent Document 9]
JP-A 6-263733

[Patent Document 10]
EP-A 487071

[Patent Document 11]
EP-A 378207

[Patent Document 12]
EP-A 30044

[Patent Document 13]
EP-A 560235

[Patent Document 14]
EP-A 567090

[Patent Document 15]
EP-A 607864

[Patent Document 16]
EP-A 655451

DISCLOSURE OF THE INVENTION

An object of the present invention is to develop a preventive or a therapeutic agent for voiding disturbance; in particular, voiding difficulty which has a higher therapeutic effect and convenience and less side effect, as compared with known compounds known to have voiding disturbance therapeutic activity and concomitant use thereof. A further object of the present invention is to develop a more effective method for assessing in vivo a therapeutic agent for voiding disturbance accompanied with benign prostatic hyperplasia.

In view of such the circumstances, the present inventors researched and investigated a new preventive or therapeutic agent for voiding disturbance, in particular, voiding difficulty which has a high voiding efficiency and intensively studied and, as a result, found that amine compounds of a peculiar chemical structure represented by the formula:

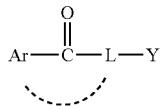

wherein meanings of respective symbols are as defined later, have unexpectedly both of an acetylcholinesterase inhibitory action and an a1 receptor antagonistic action based on its peculiar structure, exhibit an excellent effect of improving the voiding function of the bladder (i.e., effects of improving urine flow rate and voiding efficiency) and, at the same time, unexpectedly have excellent effect of preventing or treating voiding disturbance, in particular, voiding difficulty without affecting voiding pressure and blood pressure. In addition, the present inventors found that, upon in vivo assessment of these compounds, a therapeutic agent for voiding disturbance accompanied with benign prostatic hyperplasia (BPH) can be unexpectedly assessed simply and precisely by applying Pressure Flow Study to an α agonist (phenylephrine)-loaded guinea pigs. Base on these, the present invention was completed.

That is, the present invention relates to:
[1] a preventive or therapeutic agent for voiding disturbance, which comprises a compound having both of an acetylcholinesterase inhibitory action and an $\alpha_1$ antagonistic action,
[2] the agent according to the above-mentioned [1], which comprises a compound having both of an acetylcholinesterase inhibitory action and an $\alpha_1$ antagonistic action represented by the formula:

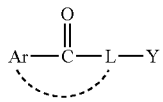

wherein Ar represents an optionally condensed 5- or 6-membered aromatic ring group and said aromatic ring group may have a substituent, L represents a spacer having a main chain of 1 to 10 of atoms which may have a substituent, or may form a ring with Ar, and Y represents an amino group which may have a substituent or a nitrogen-containing heterocyclic group which may have a substituent, or a salt thereof or a prodrug thereof,
[3] the agent according to the above-mentioned [2], wherein L is a $C_{1-10}$ alkylene group which may have a substituent,

[4] the agent according to the above-mentioned [1], which is a preventive or therapeutic agent for voiding disturbance accompanied with benign prostatic hyperplasia,
[5] the agent according to the above-mentioned [1], wherein an $IC_{50}$ value of each of an acetylcholinesterase inhibitory action and an a1 antagonistic action of the compound is a ratio of about 1:100 to about 100:1,
[6] the agent according to the above-mentioned [1], wherein an $IC_{50}$ value of each of an acetylcholinesterase inhibitory action and an a1 antagonistic action of the compound is a ratio of about 1:1 to about 30:1,
[7] the agent according to the above-mentioned [1], which does not exhibit reduction of blood pressure at a dose exhibiting an effect of improving urine flow rate,
[8] the agent according to the above-mentioned [7], wherein a reduction of blood pressure after administration is within about 10% relative to that before administration at a dose in which a urine flow rate after administration is improved by about 20% or more relative to that before administration,
[9] the agent according to the above-mentioned [1], which does not exhibit reduction of blood pressure at a dose exhibiting an effect of improving voiding efficiency,
[10] the agent according to the above-mentioned [9], wherein reduction of blood pressure after administration is within about 10% relative to that before administration at a dose that a voiding efficiency after administration is improved by about 10% or more relative to that before administration,
[11] the agent according to the above-mentioned [1], wherein orthostatic hypotension is not accompanied,
[12] a method for preventing or treating voiding disturbance, which comprises administering an effective amount of a compound having both of an acetylcholinesterase inhibitory action and an a1 antagonistic action to a mammal,
[13] use of a compound having both of an acetylcholinesterase inhibitory action and an a1 antagonistic action for preparing a preventive or therapeutic agent for voiding disturbance,
[14] a compound represented by the formula:

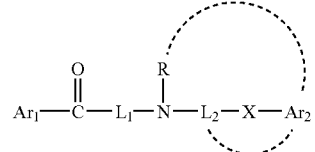

wherein $Ar_1$ represents a di- to tetra-cyclic condensed benzene ring group which may have a substituent, $L_1$ represents, a $C_{4-6}$ alkylene group which may have a substituent, $L_2$ represents a $C_{2-4}$ alkylene group which may have a substituent, R represents a hydrogen atom or a hydrocarbon group which may have a substituent, X represents a bond, an oxygen atom or $NR^{1a}$ (wherein $R^{1a}$ represents a hydrogen atom, a hydrocarbon group which may have a substituent, an acyl group or a heterocyclic group which may have a substituent), and $Ar_2$ represents an aromatic ring group which may have a substituent, or $Ar_2$ and R, or $Ar_2$ and $L_2$ may link together to form a ring, or a salt thereof,
[15] the compound according to the above-mentioned [14], wherein $Ar_1$ is a group represented by the formula: wherein A ring represents a benzene ring which may have a substituent, B ring represents a homocyclic ring or a heterocyclic ring which may have a substituent, one of C ring and D ring represents a heterocyclic ring which may have a substituent, the other represents a 5- to 9-membered ring which may have a substituent, and at least one ring of E ring, F ring and G ring represents a heterocyclic ring which may have a substituent and the other rings represent a 5- to 9-membered ring which may have a substituent,

[16] the compound according to the above-mentioned [14], wherein $Ar_1$ is a group represented by the formula:

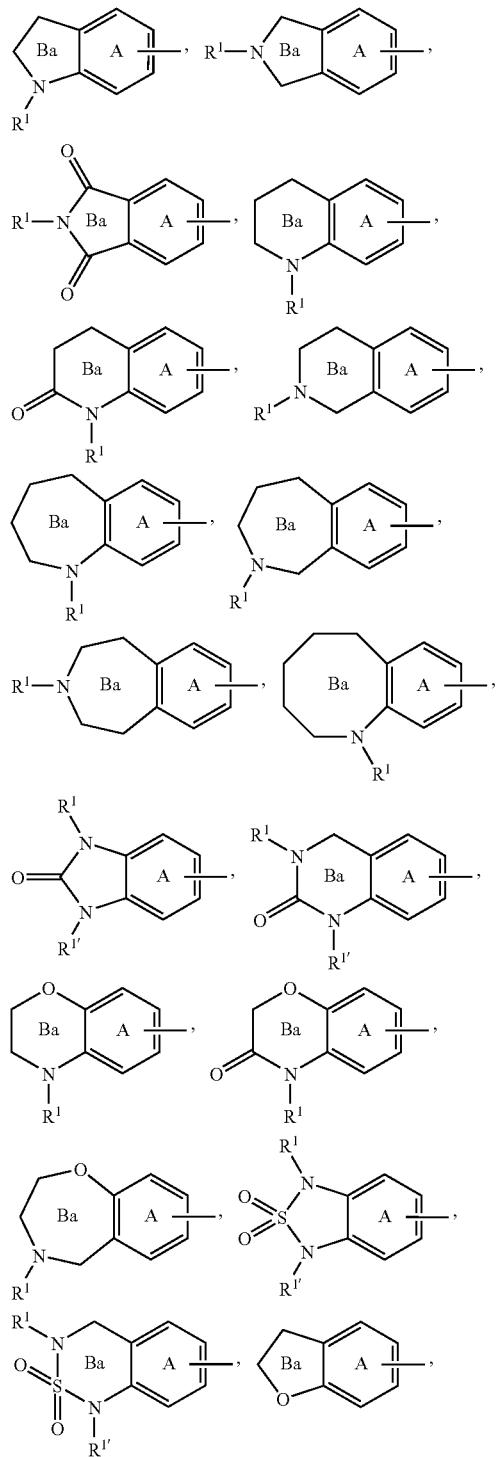

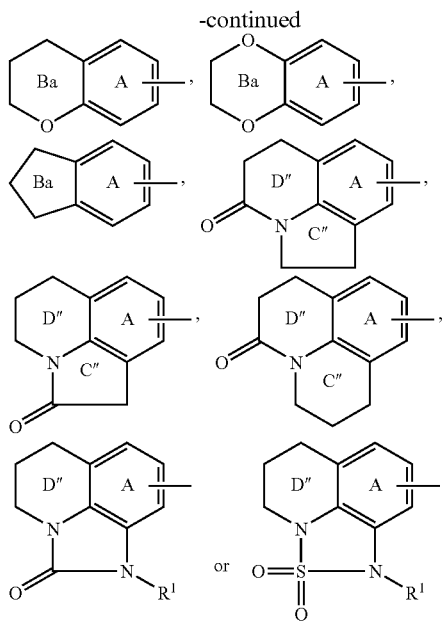

wherein A ring is as defined above, Ba ring represents a homocyclic ring or a heterocyclic ring which may have a substituent, C" ring and D" ring represent a nitrogen-containing heterocyclic ring which may have a substituent respectively, $R^1$ and $R^{1'}$ represent a hydrogen atom, a hydrocarbon group which may have a substituent, an acyl group or a heterocyclic group which may have a substituent respectively.

[17] the compound according to the above-mentioned [16], wherein A ring represents a benzene ring which may have 1 or 2 substituent(s) selected from aminosulfonyl, mono- or di-$C_{1-6}$ alkylaminosulfonyl, carbamoyl and mono- or di-$C_{1-6}$ alkyl-carbamoyl, Ba ring, C" ring and D" ring may have 1 or 2 substituent(s) selected from $C_{1-6}$ alkyl, $C_{1-6}$ alkyl-carbonylamino and $C_{1-6}$ alkylsulfonylamino, respectively, and $R^1$ and $R^{1'''}$ represent (1) a hydrogen atom, (2) a $C_{1-6}$ alkyl group or a $C_{7-16}$ aralkyl group, each of which may have 1 or 2 sustituent(s) selected from hydroxy and $C_{1-6}$ alkoxycarbonyl, or (3) formula —(C=O)—$R^{2'}$, —(C=O)—$NR^{2'}R^{3'}$ or —$SO_2R^{2'}$ [wherein $R^{2'}$ and $R^{3'}$ represent hydrogen atom, optionally halogenated $C_{1-6}$ alkyl or $C_{6-10}$ aryl, respectively],

[18] the compound according to the above-mentioned [14], wherein R is a hydrogen atom or a $C_{1-4}$ alkyl group,

[19] the compound according to the above-mentioned [14], wherein $L_1$ is a $C_{4-5}$ alkylene group, and $L_2$ is a $C_{2-3}$ alkylene group which may have phenyl, hydroxy or oxo,

[20] the compound according to the above-mentioned [14], wherein $Ar_2$ is a $C_{6-10}$ aryl group or a 5- or 6-membered aromatic heterocyclic group (optionally condensed with a benzene ring) containing 1 to 4 hetero atom(s) selected from a nitrogen atom, an oxygen atom and a sulfur atom, each of which may have 1 to 3 substituent(s) selected from halogen, nitro, hydroxy, optionally halogenated $C_{1-6}$ alkyl, optionally halogenated $C_{1-6}$ alkoxy and aminosulfonyl,

[21] the compound according to the above-mentioned [14], wherein the ring formed by linking $Ar_2$ and R together is a ring represented by the formula:

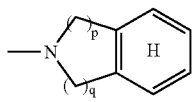

wherein, p and q represent an integer of 1 to 3, respectively, and H ring represents a benzene ring which may have 1 to 3 substituent(s) selected from halogen, hydroxy, optionally halogenated $C_{1-6}$ alkyl and optionally halogenated $C_{1-6}$ alkoxy, and the ring formed by linking $Ar_2$ and $L_2$ together is a ring represented by the formula:

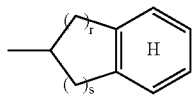

wherein, r represents an integer of 0 to 2, s represents an integer of 1 to 3 and r+s is an integer of 2 to 5, and H ring represents a benzene ring which may have 1 to 3 substituents(s) selected from halogen, hydroxy, optionally halogenated $C_{1-6}$ alkyl and optionally halogenated $C_{1-6}$ alkoxy,

[22] a compound represented by the formula:

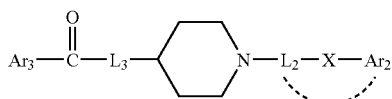
(Ib)

wherein $Ar_3$ represents a benzimidazole ring group, a quinazoline ring group, a 1,4-benzoxazine ring group or a tricyclic to tetracyclic condensed benzene ring group, each of which may have a substituent, $L_3$ represents a $C_{2-4}$ alkylene group which may have a substituent, and other symbols are as defined above, or a salt thereof,

[23] the compound according to the above-mentioned [22], wherein $Ar_3$ is a group represented by the formula:

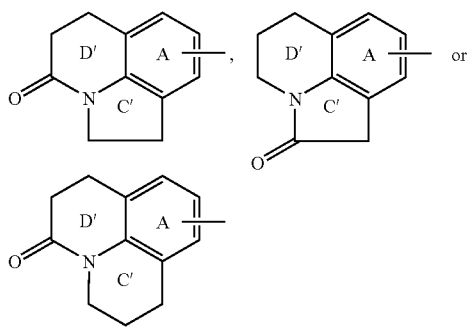

wherein A ring is as defined above, and C' ring and D' ring represent a nitrogen-containing heterocyclic ring which may have a substituent in addition to an oxo group, respectively,

[24] the compound according to the above-mentioned [22], wherein $L_3$ is an ethylene group, $L_2$ is a $C_{2-3}$ alkylene group which may have phenyl, hydroxy or oxo, and X is a bond or an oxygen atom,

[25] the compound according to the above-mentioned [22], wherein $Ar_2$ is a $C_{6-10}$ aryl group or a 5- or 6-membered aromatic heterocyclic group (optionally condensed with a benzene ring) containing 1 to 4 hetero atom(s) selected from a nitrogen atom, an oxygen atom and a sulfur atom, each of which may have 1 to 3 substituent(s) selected from halogen, nitro, hydroxy, optionally halogenated $C_{1-6}$ alkyl, optionally halogenated $C_{1-6}$ alkoxy and aminosulfonyl, and the ring formed by linking $Ar_2$ and $L_2$ together is a ring represented by the formula:

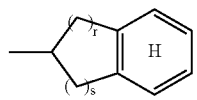

wherein respective symbols are as defined above,

[26] a compound represented by the formula:

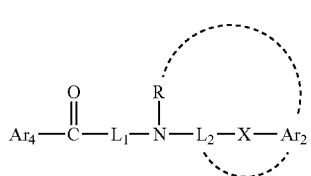
(Ic)

wherein $Ar_4$ represents a benzene ring group having 1 or 2 substituent(s) selected from aminosulfonyl, mono- or di-$C_{1-6}$ alkylaminosulfonyl, $C_{1-6}$ alkyl-carbonylamino and $C_{1-6}$ alkylsulfonylamino, and optionally further having 1 to 4 substituent(s), and the other respective symbols are as defined above, or a salt thereof,

[27] the compound according to the above-mentioned [26], wherein $Ar_4$ is a benzene ring group having 1 or 2 substituent(s) selected from aminosulfonyl, mono- or di-$C_{1-6}$ alkylaminosulfonyl, $C_{1-6}$ alkyl-carbonylamino and $C_{1-6}$ alkylsulfonylamino, and optionally further having 1 or 2 $C_{1-4}$ alkoxy(s), $L_1$ is a $C_{4-5}$ alkylene group, $L_2$ is a $C_{2-3}$ alkylene group optionally having hydroxy or oxo, R is a hydrogen atom or a $C_{1-4}$ alkyl group, X is a bond, and $Ar_2$ is a $C_{6-10}$ aryl group or a 5- or 6-membered aromatic heterocyclic group (optionally condensed with a benzene ring) containing 1 to 4 hetero atom(s) selected from a nitrogen atom, an oxygen atom and a sulfur atom, each of which may have 1 to 3 substituent(s) selected from halogen, nitro, hydroxy, optionally halogenated $C_{1-6}$ alkyl, optionally halogenated $C_{1-6}$ alkoxy and aminosulfonyl,

[28] a compound represented by the formula:

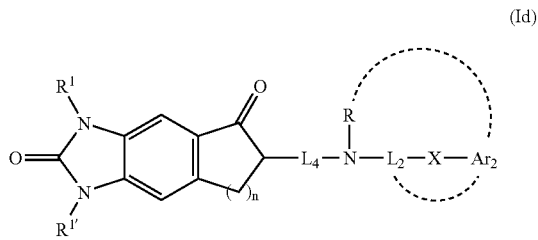
(Id)

wherein n represents an integer of 1 or 2, $L_4$ represents a $C_{3-5}$ alkylene group which may have a substituent, and the other respective symbols are as defined above, or a salt thereof,

[29] the compound according to the above-mentioned [28], wherein $R^1$ and $R^{1'}$ are a hydrogen atom or an optionally halogenated $C_{1-6}$ alkyl group, respectively, $L_4$ is a $C_{3-4}$ alkylene group, $L_2$ is a $C_{2-3}$ alkylene group which may have hydroxy or oxo, R is a hydrogen atom or a $C_{1-4}$ alkyl group, X is a bond, and $Ar_2$ is a $C_{6-10}$ aryl group or a 5- or 6-membered aromatic heterocyclic group (optionally condensed with a benzene ring) containing 1 to: 4 hetero atom(s) selected from a nitrogen atom, an oxygen atom and a sulfur atom, each of which may have 1 to 3 substituent(s) selected from halogen, nitro, hydroxy, optionally halogenated $C_{1-6}$ alkyl, optionally halogenated $C_{1-6}$ alkoxy and aminosulfonyl,

[30] 8-(5-[[2-(2-chlorophenyl)ethyl]amino]pentanoyl)-5,6-dihydro-4H-pyrrolo[3,2,1-ij]quinolin-2(1H)-one or a salt thereof, 5-[5-[[2-(2-chlorophenyl)ethyl](methyl)amino]pentanoyl]-1,3-dimethyl-1,3-dihydro-2H-benzimidazol-2-one or a salt thereof, 1,3-dimethyl-5-(5-({2-[2-(trifluoromethoxy)phenyl]ethyl}amino)pentanoyl]-1,3-dihydro-2H-benzimidazol-2-one or a salt thereof, 8-{5-[[2-(2-methoxyphenyl)ethyl](methyl)amino]pentanoyl}-5,6-dihydro-4H-imidazo[4,5,1-ij]quinolin-2(1H)-one or a salt thereof, 8-{5-[[2-(2-methoxyphenyl)ethyl](methyl)amino]pentanoyl}-1-methyl-5,6-dihydro-4H-imidazo[4,5,1-ij]quinolin-2(1H)-one or a salt thereof, 1,3-dimethyl-5-[5-({2-[2-(trifluoromethoxy)phenyl]ethyl}amino)pentanoyl]-1,3-dihydro-2H-benzimidazol-2-one or a salt thereof, 8-(5-{[2-(2-chlorophenyl)ethyl]amino}pentanoyl)-5,6-dihydro-4H-pyrrolo[3,2,1-ij]quinolin-2(1H)-one or a salt thereof, or 5-(5-{[2-(2-chlorophenyl)ethyl]amino}pentanoyl)-1,3-dimethyl-1,3-dihydro-2H-benzimidazol-2-one or a salt thereof,

[31] a prodrug of the compound according to any one of the above-mentioned [14], [22], [26] and [28] or a salt thereof,

[32] a process for preparing the compound according to the above-mentioned [14], which comprises reacting a compound represented by the formula:

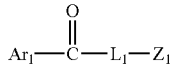

wherein $Z_1$ represents a leaving group, and the other respective symbols are as defined above, or a salt thereof with a compound represented by the formula:

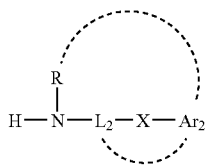

wherein respective symbols are as defined above, or a salt thereof,

[33] a process for preparing the compound represented by the formula:

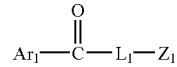

wherein $Z_1$ represents a leaving group, and the other respective symbols are as defined above, or a salt thereof, which comprises reacting a compound represented by the formula:

wherein $Ar_1$ is as defined above, or a salt thereof with a compound represented by the formula:

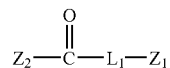

wherein $Z_2$ represents a leaving group, and $Z_1$ and $L_1$ are as defined above, or a salt thereof,

[34] the process according to the above-mentioned [33], wherein zinc chloride is used as a catalyst and nitroalkane is used as a solvent,

[35] a medicine comprising the compound according to any one of the above-mentioned [14], [22], [26] and [28], or a salt thereof or a prodrug thereof,

[36] the medicine according to the above-mentioned [35], which is a preventive or therapeutic agent for voiding disturbance,

[37] the medicine according to the above-mentioned [35], which is a preventive or therapeutic agent for voiding disturbance accompanied with benign prostatic hyperplasia,

[38] the medicine according to the above-mentioned [37], which is a preventive or therapeutic agent for voiding disturbance due to detrusor underactivity,

[39] a method for preventing or treating voiding disturbance, which comprises administering an effective amount of the compound according to any one of the above-mentioned [14], [22], [26] and [28] or a salt thereof or a prodrug thereof to a mammal,

[40] use of the compound according to any one of the above-mentioned [14], [22], [26] and [28] or a salt thereof or a prodrug thereof for preparing a preventive or therapeutic agent for voiding disturbance,

[41] a method for screening a compound having an voiding disturbance preventing or treating effect by Pressure Flow Study, which comprises using an animal model loaded with an α agonist,

[42] the screening method according to the above-mentioned [41], wherein the α agonist is phenylephrine, and

[43] a compound having an voiding disturbance preventing or treating effect obtained by the screening method according to the above-mentioned [41], or a salt thereof.

Among voiding disturbance, for example, voiding disturbance accompanied with benign prostatic hyperplasia is considered to result from compression of urethra by hypertrophied prostate, and functional constriction of prostate and urethra due to facilitation of sympathetic nervous system. In therapy thereof, administration of an acetylcholinesterase inhibitor alone, that is, enhancement of a contractile force of bladder muscle (detrusor muscle) in the state of obstruction of urethra is at risk of causing high pressure voiding. An $\alpha_1$ receptor antagonist is a drug which improves functional contraction of prostate and urethra, and there is no risk of high pressure voiding. However, since the antagonist has basically antihypertensive action, side effect such as orthostatic hypotension is accompanied. On the other hand, "a compound having both of an acetylcholinesterase inhibitory action and an $\alpha_1$ antagonistic action" (hereinafter, abbreviated as Compound A in some cases) used in the preventive or therapeutic agent for voiding disturbance of the present invention relaxes urethra smooth muscle and alleviates urethra resistance based on an a, antagonistic action and, at the same time, enhances a contractile force of bladder muscle (detrusor muscle) based on an acetylcholinesterase inhibitory action. Therefore, the preventive or therapeutic agent for voiding disturbance containing Compound A of the present invention has a smaller risk of high pressure voiding as compared with administration of an acetylcholinesterase inhibitor alone. In addition, as compared with administration of an $\alpha_1$ receptor antagonist alone, effects of improving urine flow rate and a voiding efficiency are exhibited at a lower dose and, for this reason, influence on a blood pressure is smaller.

Then, the advantages of Compound A used in the present invention for "concomitant use therapy" of an $\alpha_1$ receptor antagonist and an acetylcholinesterase inhibitor will be described. Generally, since kinetics of a drug in the body differ from drug to drug, an elaborate setting such as administration time, administration timing and the like is required in order to obtain optimal effect in "concomitant use therapy". This becomes a burden on a patient to which a drug is administered and a physician and, at the same time, increases the trouble of compounding. In addition, recently, it has been found that, when drug interaction is caused in concomitant use of drugs, there is a possibility of potentiating side effect and death accident may happen in some cases. Therefore, it is necessary to pay a sufficient attention to drug interaction in "concomitant use therapy". On the other hand, since the Compound A used in the present invention can be administered alone to provide treatment, the burden on a patient to be administered and a physician and the trouble of compounding can be alleviated and, moreover, there is no risk of drug interaction and, thus, it is more preferable in terms of treatment and therapeutic economy as compared with "concomitant use therapy".

Regarding an acetylcholinesterase inhibitory action possessed by Compound A used in the present invention, for example, in the after-mentioned in vitro enzyme inhibition test 1a), an $IC_{50}$ value, is, preferably about 1 µM or smaller, more preferably about. 0.5 µM or smaller.

In addition, an $\alpha_1$ receptor is classified into three kinds of subtypes of $\alpha_{1A}$, $\alpha_{1B}$ and $\alpha_{1D}$ (Pharmacological Reviews, 1995, 47, 267), and it is known that about 70% of an $\alpha_1$ receptor is an $\alpha_{1A}$ subtype in human prostate, and contraction of human prostate smooth muscle is controlled by an $\alpha_{1A}$ subtype (Journal of Urology, 1993, 150, 546; Molecular Pharmacology, 1994, 45, 703). Regarding an $\alpha_1$ antagonistic action possessed by Compound A, for example, in the after-mentioned in vitro test 1b), an $IC_{50}$ value of $\alpha_{1A}$ receptor binding inhibitory activity is preferably about 1 µM or smaller, more preferably about 0.5 µM or smaller.

Regarding the balance of both actions in Compound A, the ratio of $IC_{50}$ values of an acetylcholinesterase inhibitory action and an $\alpha_1$ ($\alpha_{1A}$) antagonistic action in an in vitro test is preferably, for example, about 1:1000 to about 1000:1, more preferably about 1:100 to about 100:1, further more preferably about 1:20 to about 20:1. A compound having a stronger a, antagonistic action of both actions is preferred, and examples thereof include a compound having a ratio of $IC_{50}$ values of an acetylcholinesterase inhibitory action and an a, antagonistic action of about 1:1 to about 30:1. The balance of both actions can be more precisely assessed by an in vivo test. Specifically, in a test 2 described later, it is preferable that a voiding pressure is not influenced (a voiding pressure is not increased), effects of improving a urine flow rate and a voiding efficiency are exhibited (a urine flow rate after administration is improved by about 20% or more as compared with before administration, and a voiding efficiency after administration is improved by about 10% or more as compared with before administration) and a blood pressure is not influenced at a dose exhibiting improving effects (reduction in a blood pressure after administration is within about 10% relative to before administration).

As Compound A used in the present invention, compounds having any molecular structure may be used as far as they are a compound having both of an acetylcholinesterase inhibitory action and an al antagonistic action by itself Inter alia, preferred is an amine compound in which a hydrogen atom of ammonia is substituted with a hydrocarbon group. More preferred are a primary amine compound, a secondary amine compound, and a tertiary amine compound.

Compound A used in the present invention include a compound which is converted into a compound having both of an acetylcholinesterase inhibitory action and an $a_1$ antagonistic action by converting into a salt, and a compound which is converted into a compound having both of an acetylcholinesterase inhibitory action and an $\alpha_1$ antagonistic action by a reaction with an enzyme or gastric acid under the physiological conditions in a living body, such as a salt and a prodrug of Compounds (I), (Ia), (Ib), (Ic) and (Id) described later.

Specifically, the following compound is preferred.

A compound represented by the formula:

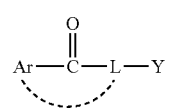

(I)

wherein Ar represents an optionally condensed 5- or 6-membered aromatic ring group and said aromatic ring group may have a substituent, L represents a spacer having a main chain of 1 to 10 atoms which may have a substituent, or may form a ring between Ar, and Y represents an amino group which may have a substituent or a nitrogen-containing heterocyclic ring which may have a substituent (hereinafter, abbreviated as Compound (I) in some cases), or a salt thereof.

In the aforementioned formula, examples of the "substituent" in "represents an optionally condensed 5- or 6-membered aromatic ring group and said aromatic ring group may have a substituent" represented by Ar include (i) an optionally halogenated lower alkyl group, (ii) a halogen atom (e.g. fluoro, chloro, bromo, iodo etc.), (iii) a lower alkylenedioxy group (e.g. $C_{1-3}$ alkylenedioxy group such as methylenedioxy, ethylenedioxy etc.), (iv) a nitro group, (v) a cyano group, (vi) a hydroxy group, (vii) an optionally halogenated lower alkoxy group, (viii) a cycloalkyl group (e.g. $C_{3-6}$ cycloalkyl group such as cyclopropyl, cyclobutyl, cyclopentyl, cyclohexyl etc.), (ix) an optionally halogenated lower alkylthio group, (x) an amino group, (xi) a mono-lower alkylamino group (e.g. mono-$C_{1-6}$ alkylamino group such as methylamino, ethylamino, propylamino etc.), (xii) a di-lower alkylamino group (e.g. di-$C_{1-6}$ alkylamino group such as dimethylamino, diethylamino etc.), (xiii) a 5- to 7-membered cyclic amino group (e.g. 5- to 7-membered cyclic amino group which may have 1 to 3 hetero atom(s) selected from a nitrogen atom, an oxygen atom and a sulfur atom in addition to one nitrogen atom (e.g. 1-pyrrolidinyl, piperidino, 1-piperazinyl, morpholino, thiomorpholino etc.) etc.), (xiv) a lower alkyl-carbonylamino group (e.g. $C_{1-6}$ alkyl-carbonylamino group such as acetylamino, propionylamino, butyrylamino etc.), (xv) a lower alkylsulfonylamino group (e.g. $C_{1-6}$ alkylsulfonylamino group such as methylsulfonylamino, ethylsulfonylamino, propylsulfonylamino etc.), (xvi) a lower alkoxy-carbonyl group (e.g. $C_{1-6}$ alkoxy-carbonyl group such as methoxycarbonyl, ethoxycarbonyl, propoxycarbonyl, isobutoxycarbonyl, etc.), (xvii) a carboxy group, (xviii) a lower alkyl-carbonyl group (e.g. $C_{1-6}$ alkyl-carbonyl group such as methylcarbonyl, ethylcarbonyl, butylcarbonyl etc.), (xix) a cycloalkyl-carbonyl group (e.g. $C_{3-6}$ cycloalkyl-carbonyl group such as cyclopropylcarbonyl, cyclobutylcarbonyl, cyclopentylcarbonyl, cyclohexylcarbonyl etc.), (xx) a carbamoyl group, a thiocarbamoyl group, (xxi) a mono-lower alkyl-carbamoyl group (e.g. mono-$C_{1-6}$ alkyl-carbamoyl group such as methylcarbamoyl, ethylcarbamoyl, propylcarbamoyl, butylcarbamoyl etc.), (xxii) a di-lower alkyl-carbamoyl group (e.g. di-$C_{1-6}$ alkyl-carbamoyl group such as diethylcarbamoyl, dibutylcarbamoyl etc.), (xxiii) a lower alkylsulfonyl group (e.g. $C_{1-6}$ alkylsulfonyl group such as methylsulfonyl, ethylsulfonyl, propylsulfonyl etc.), (xxiv) a cycloalkylsulfonyl group (e.g. $C_{3-6}$ cycloalkylsulfonyl such as cyclopentylsulfonyl, cyclohexylsulfonyl etc.), (xxv) a phenyl group, (xxvi) a naphthyl group, (xxvii) a mono-phenyl-lower alkyl group (e.g. mono-phenyl-$C_{1-6}$ alkyl group such as benzyl, phenylethyl etc.), (xxviii) a di-phenyl-lower alkyl group (e.g. di-phenyl-$C_{1-6}$ alkyl group such as diphenylmethyl, diphenylethyl etc.), (xxix) a mono-phenyl-lower alkyl-carbonyloxy group (e.g. mono-phenyl-$C_{1-6}$ alkyl-carbonyloxy group such as phenylmethylcarbonyloxy, phenylethylcarbonyloxy etc.), (xxx) a di-phenyl-lower alkyl-carbonyloxy group (e.g. di-phenyl-$C_{1-6}$ alkyl-carbonyloxy group such as diphenylmethylcarbonyloxy, diphenylethylcarbonyloxy etc.), (xxxi) a phenoxy group, (xxxii) a mono-phenyl-lower alkyl-carbonyl group (e.g. mono-phenyl-$C_{1-6}$ alkyl-carbonyl group such as phenylmethylcarbonyl, phenylethylcarbonyl etc.), (xxxiii) a di-phenyl-lower alkyl-carbonyl group (e.g. di-phenyl-$C_{1-6}$ alkyl-carbonyl group such as diphenylmethylcarbonyl, diphenylethylcarbonyl etc.), (xxxiv) a benzoyl group, (xxxv) a phenoxycarbonyl group, (xxxvi) a phenyl-lower alkyl-carbamoyl group (e.g. phenyl-$C_{1-6}$ alkyl-carbamoyl group such as phenyl-methylcarbamoyl, phenyl-ethylcarbamoyl etc.), (xxxvii) a phenylcarbamoyl group, (xxxviii) a phenyl-lower alkyl-carbonylamino group (e.g. phenyl-$C_{1-6}$ alkyl-carbonylamino group such as phenyl-methylcarbonylamino, phenyl-ethylcarbonylamino etc.), (xxxix) a phenyl-lower alkylamino group (e.g. phenyl-$C_{1-6}$ alkylamino group such as phenyl-methylamino, phenyl-ethylamino etc.), (xxxx) a phenyl-lower alkylsulfonyl group (e.g. phenyl-$C_{1-6}$ alkylsulfonyl group such as, phenyl-methylsulfonyl, phenyl-ethylsulfonyl etc.), (xxxxi) a phenylsulfonyl group, (xxxxii) a phenyl-lower alkylsulfinyl group (e.g. phenyl-$C_{1-6}$ alkylsulfinyl group such as phenyl-methylsulfinyl, phenyl-ethylsulfinyl etc.), (xxxxiii) a phenyl-lower alkylsulfonylamino group (e.g. phenyl-$C_{1-6}$ alkylsulfonylamino group such as phenyl-methylsulfonylamino, phenyl-ethylsulfonylamino etc.), (xxxxiv) a phenylsulfonylamino group, (xxxxv) a 5- to 7-membered cyclic amino-carbonyl group (e.g. 5- to 7-membered cyclic amino-carbonyl group which may have 1 to 3 hetero atom(s) selected from a nitrogen atom, an oxygen atom and a sulfur atom in addition to one nitrogen atom (e.g. (1-pyrrolidinyl)carbonyl, piperidinocarbonyl, (1-piperazinyl)carbonyl, morpholinocarbonyl, thiomorpholinocarbonyl group etc.) etc.), (xxxxvi) an aminosulfonyl group, (xxxxvii) a mono-lower alkylaminosulfonyl group (e.g. mono-$C_{1-6}$ alkylaminosulfonyl group such as methylaminosulfonyl, ethylaminosulfonyl, propylaminosulfonyl, butylaminosulfonyl etc.), (xxxxviii) a di-lower alkylaminosulfonyl group (e.g. di-$C_{1-6}$ alkylaminosulfonyl group such as diethylaminosulfonyl, dibutylaminosulfonyl etc.), (xxxxix) a 5- to 7-membered cyclic amino-sulfonyl group (e.g. 5- to 7-membered cyclic amino-sulfonyl group which may have 1 to 3 hetero atom(s) selected from a nitrogen atom, an oxygen atom and a sulfur atom in addition to one nitrogen atom (e.g. (1-pyrrolidinyl)sulfonyl, piperidinosulfonyl, (1-piperazinyl)sulfonyl, morpholinosulfonyl, thiomorpholinosulfonyl group. etc.), (xxxxx) an aminocarbonyloxy group, (xxxxxi) a mono-lower alkylaminocarbonyloxy group (e.g. mono-$C_{1-6}$ alkylaminocarbonyloxy group such as methylaminocarbonyloxy, ethylaminocarbonyloxy, propylaminocarbonyloxy etc.), (xxxxxii) a di-lower alkylaminocarbonyloxy group (e.g. di-$C_{1-6}$ alkylaminocarbonyloxy group such as dimethylaminocarbonyloxy, diethylaminocarbonyloxy etc.) and (xxxxxiii) a 5- to 7-membered cyclic amino-carbonyloxy group (e.g. 5- to 7-membered cyclic amino-carbonyloxy group which may have 1 to 3 hetero atom(s) selected from a nitrogen atom, an oxygen atom and a sulfur atom in addition to one nitrogen atom (e.g. (1-pyrrolidinyl)carbonyloxy, piperidinocarbonyloxy, (1-piperazinyl)carbonyloxy, morpholinocarbonyloxy, thiomorpholinocarbonyloxy group etc.) etc.) (the phenyl group moiety in phenyl group, naphthyl group, mono-phenyl-lower alkyl group, di-phenyl-lower alkyl group, mono-phenyl-lower alkyl-carbonyloxy group, di-phenyl-lower alkyl-carbonyloxy group, phenoxy group, mono-phenyl-lower alkyl-carbonyl group, di-phenyl-lower alkyl-carbonyl group, benzoyl group, phenoxycarbonyl group, phenyl-lower alkyl-carbamoyl group, phenylcarbamoyl group, phenyl-lower alkyl-carbonylamino group, phenyl-lower alkylamino group, phenyl-lower alkylsulfonyl group, phenylsulfonyl group, phenyl-lower alkylsulfinyl group, phenyl-lower alkylsulfonylamino group and phenylsulfonylamino group of the aforementioned (xxv) to (xxxxiv) may further have 1 to 4 substituent(s) selected from, for example, a lower alkyl group (e.g. $C_{1-6}$ alkyl such as methyl, ethyl, propyl, isopropyl, butyl, sec-butyl, tert-butyl, pentyl, hexyl etc.), a lower alkoxy group (e.g. $C_{1-6}$ alkoxy such as methoxy, ethoxy, propoxy, isopropoxy, butoxy, isobutoxy, sec-butoxy, tert-butoxy etc.), a halogen atom (e.g. chloro, bromo, iodo etc.), a hydroxy group, a benzyloxy group, an amino group, a mono-lower alkylamino group (e.g. mono-$C_{1-6}$ alkylamino such as methylamino, ethylamino, propylamino etc.), a di-lower alkylamino group (e.g. di-$C_{1-6}$ alkylamino such as dimethylamino, diethylamino etc.), a nitro group, a lower alkyl-carbonyl group (e.g. $C_{1-6}$ alkyl-carbonyl such as methylcarbonyl, ethylcarbonyl, butylcarbonyl etc.), and a benzoyl group).

The "optionally condensed 5-or 6-membered aromatic ring group" represented by Ar may have 1 to 4, preferably 1 or 2 of these substituent(s) of (i) to (xxxxxiii).

Examples of the above-mentioned "optionally halogenated lower alkyl group" include a lower alkyl group (e.g. $C_{1-6}$ alkyl group such as methyl, ethyl, propyl, isopropyl, butyl, sec-butyl, tert-butyl, pentyl, hexyl etc.) which may have 1 to 3 halogen atom(s) (e.g. chloro, bromo, iodo, etc.), specifically, methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, and 6,6,6-trifluorohexyl.

Examples of the above-mentioned "optionally halogenated lower alkoxy group" include a lower alkoxy group (e.g. $C_{1-6}$ alkoxy group such as methoxy, ethoxy, propoxy, isopropxy, butoxy, isobutoxy, sec-butoxy, tert-butoxy etc.) which may have 1 to 3 halogen atom(s) (e.g. chloro, bromo, iodo etc.), specifically, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, and hexyloxy.

Examples of the above-mentioned "optionally halogenated lower alkylthio group" include a lower alkylthio group (e.g. $C_{1-6}$ alkylthio group such as methylthio, ethylthio, propylthio, isopropylthio, butylthio, isobutylthio, sec-butylthio, tert-butylthio etc.) which may have 1 to 3 halogen atom(s) (e.g. chloro, bromo, iodo. etc.), specifically, methylthio, difluoromethylthio, trifluoromethylthio, ethylthio, propylthio, isopropylthio, butylthio, 4,4,4-trifluorobutylthio, isobutylthio, sec-butylthio, tert-butylthio, pentylthio, and hexylthio.

Preferable examples of the "substituent" in the "represents an optionally condensed 5-or 6-membered aromatic ring group and said aromatic ring group, may have a substituent" include (i) an amino group, (ii) a mono-lower alkylamino group (e.g. mono-$C_{1-6}$ alkylamino group such as methylamino, ethylamino, propylamino etc.), (iii) a di-lower alkylamino group (e.g. di-$C_{1-6}$ alkylamino group such as dimethylamino, diethylamino etc.), (iv) a 5- to 7-membered cyclic amino group which may have 1 to 3 hetero atom(s) selected from a nitrogen atom, an oxygen atom and sulfur atom in addition to one nitrogen atom (e.g. 1-pyrrolidinyl, piperidino, 1-piperazinyl, morpholino, thiomorpholino etc.), (v) a lower alkyl-carbonylamino group (e.g. $C_{1-6}$ alkyl-carbonylamino group such as acetylamino, propionylamino, butyrylamino etc.), (vi) a lower alkylsulfonylamino group (e.g. $C_{1-6}$ alkylsulfonylamino group such as methylsulfonylamino, ethylsulfonylamino, propylsulfonylamino etc.), (vii) a phenyl-lower alkylamino (e.g. phenyl-$C_{1-6}$ alkylamino such as phenyl-methylamino, phenyl-ethylamino etc.), (viii) a phenyl-lower alkylsulfonylamino group. (e.g. phenyl-$C_{1-6}$ alkyl-sulfonylamino group such as phenyl-methylsulfonylamino, phenyl-ethylsulfonylamino etc.), (ix) a phenylsulfonylamino, (x) a halogen atom (e.g. fluoro, chloro etc.), (xi) an optionally halogenated lower alkyl group, (e.g. methyl, ethyl, isopropyl, tert-butyl, trifluoromethyl etc.), (xii) an optionally halogenated lower alkoxy group (e.g. methoxy, ethoxy, isopropoxy, tert-butoxy, trifluoromethoxy etc.), (xiii) an aminosulfonyl group, (xiv) a mono-lower alkylaminosulfonyl group (e.g. mono-$C_{1-6}$ alkylaminosulfonyl group such as methylaminosulfonyl, ethylaminosulfonyl, propylaminosulfonyl, butylaminosulfonyl etc.), (xv) a di-lower alkylaminosulfonyl group (e.g. di-$C_{1-6}$ alkylaminosulfonyl group such as diethylaminosulfonyl, dibutylaminosulfonyl etc.), (xvi) a carbamoyl group, (xvii) a mono-lower alkyl-carbamoyl group (e.g. mono-$C_{1-6}$ alkyl-carbamoyl group such as methylcarbamoyl, ethylcarbamoyl, propylcarbamoyl, butylcarbamoyl etc.), and (xviii) a di-lower alkyl-carbamoyl group (e.g. di-$C_{1-6}$ alkylcarbamoyl group such as diethylcarbamoyl, dibutylcarbamoyl etc.). Particularly, a di-lower alkylamino group (e.g. di-$C_{1-6}$ alkylamino group such as dimethylamino, diethylamino etc.), a 5- to 7-membered cyclic amino group which may have 1 to 3 hetero atom(s) selected from a nitrogen atom, an oxygen atom and a sulfur atom in addition to one nitrogen atom (e.g. 1-pyrrolidinyl, piperidino, 1-piperazinyl, morpholino, thiomorpholino etc.), an optionally halogenated lower alkoxy group (e.g. methoxy, ethoxy, isopropoxy, tert-butoxy, trifluoromethoxy etc.), an aminosulfonyl group, a mono-lower alkylaminosulfonyl group (e.g. mono-$C_{1-6}$ alkylaminosulfonyl group such as methylaminosulfonyl, ethylaminosulfonyl, propylaminosulfonyl, butylaminosulfonyl etc.), a di-lower alkyl-aminosulfonyl group (e.g. di-$C_{1-6}$ alkylaminosulfonyl group such as diethylaminosulfonyl, dibutylaminosulfonyl etc.), a carbamoyl group, a mono-lower alkyl-carbamoyl group (e.g. mono-$C_{1-6}$ alkyl-carbamoyl group such as methylcarbamoyl, ethylcarbamoyl, propylcarbamoyl, butylcarbamoyl etc.), and a di-lower alkyl-carbamoyl group (e.g. di-$C_{1-6}$ alkyl-carbamoyl group such as diethylcarbamoyl, dibutylcarbamoyl etc.) are preferred.

Examples of the "5-or 6-membered aromatic ring group" in the "optionally condensed 5- or 6-membered aromatic ring group" represented by Ar include a phenyl group (benzene ring group), and a 5- or 6-membered aromatic heterocyclic group.

Examples of the "5- or 6-membered aromatic heterocyclic group" include 5- or 6-membered aromatic heterocyclic groups containing 1 or more (e.g. 1 to 3) hetero atom(s) selected from a nitrogen atom, a sulfur atom and an oxygen atom in addition to carbon atoms. Specific examples include thienyl, furyl, pyrrolyl, imidazolyl, pyrazolyl, thiazolyl, isothiazolyl, oxazolyl, isooxazolyl, pyridyl, pyrazinyl, pyrimidinyl, pyridazinyl, oxadiazolyl, thiadiazolyl, and furazanyl.

When the "5- or 6-membered aromatic ring group" in the "optionally condensed 5- or 6-membered aromatic ring group" represented by Ar is, for example, "a phenyl group which may have a substituent", examples of condensing of the "phenyl group" include:

(a) the case where the phenyl group is condensed with a monocyclic homocyclic ring or heterocyclic ring, which may have a substituent, (b) the case where the phenyl group is condensed with a dicyclic homocyclic ring or heterocyclic ring, which may have a substituent, or is condensed with two same or different monocyclic homocyclic rings or heterocyclic rings, and (c) the case where the phenyl group is condensed with a tricyclic homocyclic ring or heterocyclic ring which may have a substituent.

Examples of the case where a phenyl group in the "optionally condensed phenyl group, and said phenyl group may have a substituent" of the above-mentioned (a) is condensed with a monocyclic homocyclic ring or heterocyclic ring include a group represented by the formula:

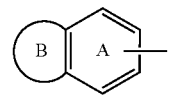

wherein A ring represents a benzene ring which may have a substituent, and B ring represents a homocyclic ring or a heterocyclic ring which may have a substituent.

Examples of a substituent of A ring include the aforementioned "substituents" of the "optionally condensed 5 or 6-membered aromatic ring group" represented by Ar, and the number of substituent(s) is 1 to 3.

Examples of the "homocyclic ring" in the "homocyclic ring which may have a substituent" represented by B ring include 5- to 9-membered carbocyclic rings (e.g. benzene, cyclopentane, cyclopentene, cyclohexane, cyclohexene, cyclohexadiene, cycloheptane, cycloheptene, cycloheptadiene etc.).

Examples of the "heterocyclic ring" in the "heterocyclic ring which may have a substituent" represented by B ring include 4- to 14-membered (preferably 5- to 9-membered) aromatic or non-aromatic heterocyclic rings containing 1 to 4 hetero atom(s) selected from a nitrogen atom, an oxygen atom and a sulfur atom. Specific examples include pyridine, pyrazine, pyrimidine, imidazole, furan, thiophen, dihydropyridine, diazepine, oxazepine, pyrrolidine, piperidine, hexamethyleneimine, heptamethyleneimine, tetrahydrofuran, tetrahydropyran, 1,4-dioxane, piperazine, homopiperazine, tetrahydrooxazepine, morpholine, thiomorpholine, pyrrole, pyrazole, 1,2,3-triazole, oxazole, oxazolidine, thiazole, thiazolidine, thiadiazolidine, thiadiazinone, isoxazole, imidazoline, imidazolidine, and hexahydropyrimidine. Among them, 5- to 9-membered non-aromatic heterocyclic rings containing one hetero atom or the same or different two hetero atoms (e.g. pyrrolidine, piperidine, hexamethyleneimine, heptamethyleneimine, tetrahydrofuran, tetrahydropyran, 1,4-dioxane, piperazine, homopiperazine, tetrahydrooxazepine, morpholine, thiomorpholine, imidazoline, thiadiazolidine, thiadiazinone, imidazolidine, hexahydropyrimidine etc.) are preferable. In particular, (1) a non-aromatic heterocyclic ring containing one hetero atom selected from a nitrogen atom, an oxygen atom and a sulfur atom, and (2) a non-aromatic heterocyclic ring containing one nitrogen atom and one hetero atom selected from a nitrogen atom, an oxygen atom and a sulfur atom are preferable.

As the "substituent" in the "homocyclic ring or heterocyclic ring which may have a substituent" represented by B ring, for example, 1 to 5 selected from (i) a halogen atom (e.g. fluoro, chloro, bromo, iodo etc.), (ii) a nitro group, (iii) a cyano group, (iv) an oxo group, (v) a hydroxy group, (vi) a lower alkyl group (e.g. $C_{1-6}$ alkyl group such as methyl, ethyl, propyl, isopropyl, butyl, isobutyl, tert-butyl, sec-butyl etc.), (vii) a lower alkoxy group (e.g. $C_{1-6}$ alkoxy group such as methoxy, ethoxy, propyloxy, isopropyloxy, butyloxy etc.), (viii) a lower alkylthio group (e.g. $C_{1-6}$ alkylthio group such as methylthio, ethylthio, propylthio etc.), (ix) an amino group, (x), a mono-lower alkylamino group (e.g. mono-$C_{1-6}$ alkylamino group such as methylamino, ethylamino, propylamino, etc.), (xi) a di-lower alkylamino group (e.g. di-$C_{1-6}$ alkylamino group such as dimethylamino, diethylamino etc.), (xii) a 5- to 7-membered cyclic, amino group which may have 1 to 3 hetero atom(s) selected from a nitrogen atom, an oxygen atom and a sulfur atom in addition to carbon atoms and one nitrogen atom (e.g. 1-pyrrolidinyl, piperidino, 1-piperazinyl, morpholino, thiomorpholino etc.), (xiii) a lower alkylcarbonylamino group (e.g. $C_{1-6}$ alkyl-carbonylamino group such as acetylamino, propionylamino, butyrylamino etc.), (xiv) a lower alkylsulfonylamino group (e.g. $C_{1-6}$ alkylsulfonylamino group such as methylsulfonylamino, ethylsulfonylamino etc.), (xv) a lower alkoxy-carbonyl group (e.g. $C_{1-6}$ alkoxy-carbonyl group such as methoxycarbonyl, ethoxycarbonyl, propoxycarbonyl etc.), (xvi) a carboxy group, (xvii) a lower alkylcarbonyl group (e.g. $C_{1-6}$ alkyl-carbonyl group such as methylcarbonyl, ethylcarbonyl, propylcarbonyl etc.), (xviii) a carbamoyl group, (xix) a mono-lower alkylcarbamoyl group (e.g. mono-$C_{1-6}$ alkyl-carbamoyl group such as methylcarbamoyl, ethylcarbamoyl etc.), (xx) a di-lower alkylcarbamoyl group (e.g. di-$C_{1-6}$ alkyl-carbamoyl group such as dimethylcarbamoyl, diethylcarbamoyl etc.), (xxi) a lower alkylsulfonyl group (e.g. $C_{1-6}$ alkylsulfonyl group such as methylsulfonyl, ethylsulfonyl, propylsulfonyl etc.), (xxii) an aminosulfonyl group, (xxiii) a mono-lower alkylaminosulfonyl group (e.g. mono-$C_{1-6}$ alkyl-aminosulfonyl group such as methylaminosulfonyl, ethylaminosulfonyl etc.), and (xxiv) a di-lower alkylaminosulfonyl group (e.g. di-$C_{1-6}$ alkyl-aminosulfonyl group such as dimethylaminosulfonyl, diethylaminosulfonyl etc.) are used. Inter alia, an oxo group, and a lower alkyl group (e.g. $C_{1-6}$ alkyl group such as methyl, ethyl, propyl, isopropyl, butyl, isobutyl, tert-butyl, sec-butyl etc.) are preferable. An oxo group, a $C_{1-6}$ alkyl group, a C1-6 alkyl-carbonylamino group and a $C_{1-6}$ alkylsulfonylamino group are particularly preferred.

When B ring has a nitrogen atom in the ring, for example, the B ring may have a group represented by the formula:

$$>N-R^1$$

wherein $R^1$ represents a hydrogen atom, a hydrocarbon group which may have a substituent, an acyl group, or a heterocyclic group which may have a substituent, in the ring. Further, the B ring may have 1 to 3 of the aforementioned substituents (i) to (xxiv).

The "hydrocarbon group" in the "hydrocarbon group which may have a substituent" represented by $R^1$ represents a group obtained by removing one hydrogen atom from a hydrocarbon compound, and examples thereof include the following alkyl group, alkenyl group, alkynyl group, cycloalkyl group, aryl group, and aralkyl group, and a combination thereof. Among them, $C_{1-16}$ hydrocarbon groups, are preferred.

(1) Alkyl group (e.g. $C_{1-6}$ alkyl group such as methyl, ethyl, propyl, isopropyl, butyl, isobutyl, tert-butyl, sec-butyl, pentyl, hexyl etc.)

(2) Alkenyl group (e.g. $C_{2-6}$ alkenyl group such as vinyl, allyl, isopropenyl, butenyl, isobutenyl, sec-butenyl etc.)

(3) Alkynyl group (e.g. $C_{2-6}$ alkynyl group such as propargyl, ethynyl, butynyl, 1-hexynyl etc.)

(4) Cycloalkyl group (e.g. $C_{3-6}$cycloalkyl group such as cyclopropyl, cyclobutyl, cyclopentyl, cyclohexyl etc.)

(5) Cross-linked cyclic lower saturated hydrocarbon group (e.g. cross-linked cyclic $C_{8-14}$ saturated hydrocarbon group such as bicyclo[3.2.1]oct-2-yl, bicyclo[3.3.1]non-2-yl, and adamantan-1-yl etc.)

(6) Aryl group (e.g. $C_{6-14}$ aryl group such as phenyl, 1-naphthyl, 2-naphthyl, biphenyl, 2-indenyl, 2-anthryl etc., preferably phenyl group)

(7) Aralkyl group (e.g. $C_{7-16}$ aralkyl group such as phenyl-$C_{1-10}$ alkyl such as benzyl, phenylethyl, phenylpropyl, phenylbutyl, phenylpentyl, phenylhexyl etc.; naphthyl-$C_{1-6}$ alkyl such as α-naphthylmethyl; diphenyl-$C_{1-3}$ alkyl such as diphenylmethyl, diphenylethyl etc.)

(8) Aryl-alkenyl group (e.g., $C_{6-14}$ aryl-$C_{2-12}$ alkenyl group such as phenyl-$C_{2-12}$ alkenyl such as styryl, cinnamyl, 4-phenyl-2-butenyl, 4-phenyl-2-butenyl etc.)

(9) Aryl-$C_{2-12}$ alkynyl group (e.g. $C_{6-14}$ aryl-$C_{2-12}$ alkynyl group such as phenyl-$C_{2-12}$ alkynyl such as phenylethynyl, 3-phenyl-2-propynyl, 3-phenyl-1-propynyl etc.)

(10) Cycloalkyl-alkyl group (e.g. $C_{3-7}$ cycloalkyl-$C_{1-6}$ alkyl group such as cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, cycloheptylethyl, cyclopropylpropyl, cyclobutylpropyl, cyclopentylpropyl, cyclohexylpropyl, cycloheptylpropyl, cyclopropylbutyl, cyclobutylbutyl, cyclopentylbutyl, cyclohexylbutyl, cycloheptylbutyl, cyclopropylpentyl, cyclobutylpentyl, cyclopentylpentyl, cyclohexylpentyl, cycloheptylpentyl, cyclopropylhexyl, cyclobutylhexyl, cyclopentylhexyl, cyclohexylhexyl etc.)

(11) Aryl-aryl-$C_{1-10}$ alkyl group (e.g. biphenylmethyl, biphenylethyl etc.)

Preferable examples of the "hydrocarbon group" in the "hydrocarbon group which may have a substituent" represented by $R^1$ include a $C_{1-6}$ alkyl group, a $C_{3-6}$ cycloalkyl group, and a $C_{7-16}$ aralkyl group. More preferred is a $C_{7-10}$ aralkyl group (e.g. phenyl-$C_{1-4}$ alkyl such as benzyl, phenylethyl, phenylpropyl. etc.).

Examples of the "substituent" in the "hydrocarbon group which may have a substituent" represented by $R^1$ include 1 to 5 (preferably 1 to 3) selected from (i) a halogen atom (e.g. fluoro, chloro, bromo, iodo etc.), (ii) a nitro group, (iii) a cyano group, (iv) an oxo group, (v) a hydroxy group, (vi) an optionally halogenated lower ($C_{1-6}$) alkyl group, (vii) an optionally halogenated lower ($C_{1-6}$) alkoxy group, (viii) an optionally halogenated lower ($C_{1-6}$) alkylthio group, (ix) an amino group, (x) a mono-lower alkylamino group (e.g. mono-$C_{1-6}$ alkylamino group such as methylamino, ethylamino, propylamino etc.), (xi) a di-lower alkylamino group (e.g. di-$C_{1-6}$ alkylamino group such as dimethylamino, diethylamino etc.), (xii) a 5- to 7-membered cyclic amino group which may have 1 to 3 hetero atom(s) selected from a nitrogen atom, an oxygen atom and a sulfur atom in addition to carbon atoms and one nitrogen atom (e.g. 1-pyrrolidinyl, piperidino, 1-piperazinyl, morpholino, thiomorpholino etc.), (xiii) a lower alkyl-carbonylamino group (e.g. $C_{1-6}$ alkyl-carbonylamino group such as acetylamino, propionylamino, butyrylamino etc.), (xiv) a lower alkylsulfonylamino group (e.g. $C_{1-6}$ alkyl-sulfonylamino group such as methylsulfonylamino, ethylsulfonylamino etc.), (xv) a lower alkoxy-carbonyl group (e.g. $C_{1-6}$ alkoxy-carbonyl group such as methoxycarbonyl, ethoxycarbonyl, propoxycarbonyl etc.), (xvi) a carboxy group, (xvii) a lower alkyl-carbonyl group (e.g. $C_{1-6}$ alkyl-carbonyl group such as methylcarbonyl, ethylcarbonyl, propylcarbonyl etc.), (xviii) a carbamoyl group, a thiocarbamoyl group, (xix) a mono-lower alkyl-carbamoyl group (e.g. mono-$C_{1-6}$ alkyl-carbamoyl group such as methylcarbamoyl, ethylcarbamoyl etc.), (xx) a di-lower alkyl-carbamoyl group (e.g. di-$C_{1-6}$ alkyl-carbamoyl group such as dimethylcarbamoyl, diethylcarbamoyl etc.), (xxi) a lower alkylsulfonyl group (e.g. $C_{1-6}$ alkylsulfonyl group such as methylsulfonyl, ethylsulfonyl, propylsulfonyl etc.), (xxii) a lower alkoxy-carbonyl-lower alkyl group (e.g. $C_{1-6}$ alkyl-carbonyl-$C_{1-6}$ alkyl group such as methoxycarbonylmethyl, ethoxycarbonylmethyl, tert-butoxycarbonylmethyl, methoxycarbonylethyl, methoxycarbonylmethyl, methoxycarbonyl(dimethyl)methyl, ethoxycarbonyl(dimethyl)methyl, tert-butoxycarbonyl(dimethyl)methyl etc.), (xxiii) a carboxy-lower alkyl group (e.g. carboxy-$C_{1-6}$ alkyl group such as carboxylmethyl, carboxylethyl, carboxyl(dimethyl)methyl etc.), (xxiv) a heterocyclic group which may have a substituent, (xxv) a $C_{6-14}$ aryl group (e.g. phenyl, naphthyl etc.), (xxvi) a $C_{7-16}$ aralkyl group (e.g. benzyl etc.), (xxvii) a ureido group which may have a substituent (e.g. $C_{1-4}$ alkyl, halogeno$C_{1-4}$ alkyl, $C_{6-10}$ aryl, halogeno$C_{6-10}$ aryl, $C_{1-4}$ alkyl-$C_{6-10}$ aryl, halogeno$C_{1-4}$ alkyl-$C_{6-10}$ aryl, $C_{1-4}$ alkoxy-$C_{6-10}$ aryl, benzyl etc.) (e.g. ureido, 3-methylureido, 3-ethylureido, 3-phenylureido, 3-(4-fluorophenyl)ureido, 3-(2-methylphenyl)ureido, 3-(4-methoxyphenyl)ureido, 3-(2,4-difluorophenyl)ureido, 3-(3,5-bis(trifluoromethyl)phenyl]ureido, 3-benzylureido, 3-(1-naphthyl)ureido, 3-(2-biphenylyl)ureido etc.), (xxviii) a thioureido group which may have a substituent (e.g. $C_{1-4}$ alkyl, halogeno$C_{1-4}$ alkyl, $C_{6-10}$ aryl, halogeno$C_{6-10}$ aryl, $C_{1-4}$ alkyl-$C_{6-10}$ aryl, halogeno$C_{1-4}$ alkyl-$C_{6-10}$ aryl, $C_{1-4}$ alkoxy-$C_{6-10}$ aryl, benzyl etc.)(e.g. thioureido, 3-methylthioureido, 3-ethylthioureido, 3-phenylthioureido, 3-(4-fluorophenyl)thioureido, 3-(4-methylphenyl)thioureido, 3-(4-methoxyphenyl)thioureido, 3-(2,4-dichlorophenyl)thioureido, 3-benzylthioureido, 3-(1-naphthyl)thioureido etc.), (xxix) an amidino group which may have a substituent (e.g. 1 to 2 selected from $C_{1-4}$ alkyl, $C_{6-10}$ aryl, nitro-$C_{6-10}$ aryl etc.) (e.g. amidino, $N^1$-methylamidino, $N^1$-ethylamidino, $N^1$-phenylamidino, $N^1$, $N^1$-dimethylamidino, $N^1,N^2$-dimethylamidino, $N^1$-methyl-$N^1$-ethylamidino, $N^1$, $N^1$-diethylamidino, $N^1$-methyl-$N^1$-phenylamidino, $N^1$, $N^1$-di(4-nitrophenyl)amidino etc.), (xxx) a guanidino group which may have a substituent (e.g. 1 to 2 selected from $C_{1-4}$ alkyl, $C_{6-10}$ aryl, nitro-$C_{6-10}$ aryl etc.) (e.g. guanidino, 3-methylguanidino, 3,3-dimethylguanidino, 3,3-diethylguanidino etc.), (xxxi) a cyclic aminocarbonyl group which may have a substituent (e.g. $C_{1-4}$ alkyl, halogeno$C_{1-4}$ alkyl, $C_{6-10}$ aryl, halogeno$C_{6-10}$ aryl, $C_{1-4}$ alkyl-$C_{6-10}$ aryl, halogeno$C_{1-4}$alkyl-$C_{6-10}$ aryl, $C_{1-4}$alkoxy-$C_{6-10}$ aryl, nitro-$C_{6-10}$ aryl, benzyl, halogenobenzyl, benzoyl, halogenobenzoyl etc.) (e.g. (1-pyrrolidinyl)carbonyl, piperidinocarbonyl, (4-methylpiperidino)carbonyl, (4-phenylpiperidino)carbonyl, (4-benzylpiperidino)carbonyl, (4-benzoylpiperidino)carbonyl, [4-(4-fluorobenzoyl)piperidinolcarbonyl, (4-methyl-1-piperazinyl)carbonyl, (4-phenyl-1-piperazinyl)carbonyl, [4-(4-nitrophenyl)-1-piperazinyl]carbonyl, (4-benzyl-1-piperazinyl)carbonyl, morpholinocarbonyl, thiomorpholinocarbonyl etc.), (xxxii) an aminothiocarbonyl group which may have a substituent (e.g. 1 to 2 selected from $C_{1-4}$ alkyl, $C_{6-10}$ aryl etc.) (e.g. aminothiocarbonyl, methylaminothiocarbonyl, dimethylaminothiocarbonyl etc.), (xxxiii) an aminosulfonyl group which may have a substituent (e.g. 1 to 2 selected from $C_{1-4}$ alkyl, $C_{6-10}$ aryl etc.) (e.g. aminosulfonyl, methylaminosulfonyl, dimethylaminosulfonyl etc.), (xxxiv) a phenylsulfonylamino group which may have a substituent (e.g. 1 to 2 selected from halogen atom, $C_{1-4}$ alkyl, halogeno$C_{1-4}$ alkyl, $C_{1-4}$ alkoxy, nitro, $C_{1-4}$ alkylcarbonylamino. etc.) (e.g. phenylsulfonylamino, (4-methylphenyl)sulfonylamino, (4-chlorophenyl)sulfonylamino, (2,5-dichlorophenyl)sulfonylamino, (4-methoxyphenyl)sulfonylamino, (4-acetylaminophenyl)sulfonylamino, (4-nitrophenyl)phenylsulfonylamino etc.), (xxxv) a sulfo group, (xxxvi) a sulfino group, (xxxvii) a sulfeno group, (xxxviii) a $C_{1-6}$ alkylsulfo group (e.g. methylsulfo, ethylsulfo, propylsulfo etc.), (xxxix) a $C_{1-6}$ alkylsulfino group (e.g. methylsulfino, ethylsulfino, propylsulfino etc.), (xxxx) a $C_{1-6}$ alkylsulfeno group (e.g. methylsulfeno, ethylsulfeno, propylsulfeno etc.), (xxxxi) a phosphono group, (xxxxii) a di-$C_{1-6}$ alkoxyphosphoryl group (e.g. dimethoxyphosphoryl, diethoxyphosphoryl, dipropoxyphosphoryl etc.), (xxxxiii) an aminocarbonyloxy group, (xxxxxi) a mono-lower alkylaminocarbonyloxy group (e.g. mono-$C_{1-6}$ alkylaminocarbonyloxy group such as methylaminocarbonyloxy, ethylaminocarbonyloxy, propylaminocarbonyloxy etc.), (xxxxxii) a di-lower alkylaminocarbonyloxy group (e.g. di-$C_{1-6}$ alkylaminocarbonyloxy group such as dimethylaminocarbonyloxy, diethylaminocarbonyloxy etc.) and (xxxxxiii) a 5- to 7-membered cyclic amino-carbonyloxy group (e.g. 5- to 7-membered cyclic amino-carbonyloxy group which may have 1 to 3 hetero atom(s) selected from a nitrogen atom, an oxygen atom and a sulfur atom in addition to one nitrogen atom (e.g. (1-pyrrolidinyl)carbonyloxy, piperidinocarbonyloxy, (1-piperazinyl)carbonyloxy, morpholinocarbonyloxy, thiomorpholinocarbonyloxy group etc.) etc.).

Among them, preferred are a halogen atom, an optionally halogenated $C_{1-6}$ alkyl group, an optionally halogenated $C_{1-6}$ alkoxy group, a hydroxy group, a nitro group, a cyano group, a carboxy group, a $C_{1-6}$ alkoxy-carbonyl group, a carbamoyl group, an aminothiocarbonyl group, a mono-$C_{1-6}$ alkyl-carbamoyl group, a di-$C_{1-6}$ alkyl-carbamoyl group, an amino group, a mono-$C_{1-6}$ alkylamino group, a di-$C_{1-6}$ alkylamino group, a 5- to 7-membered cyclic amino group, a $C_{1-6}$ alkyl-carbonylamino group, an aminosulfonyl group, a mono-$C_{1-6}$ alkylaminosulfonyl group, a di-$C_{1-6}$ alkylaminosulfonyl group, a phenylsulfonylamino group, and a $C_{1-6}$ alkylsulfonylamino group.

As the "heterocyclic group" in the aforementioned "(xxiv) heterocyclic group which may have a substituent", for example, groups obtained by removing one hydrogen atom from a 5- to 14-membered (monocyclic or di- to tetra-cyclic) heterocyclic ring containing 1 to 6 (preferably 1 to 4) hetero atom(s) selected from a nitrogen atom, an oxygen atom and a sulfur atom are used.

Examples of the monocyclic heterocyclic group include groups obtained by removing one hydrogen atom from monocyclic heterocyclic rings such as pyridine, pyrazine, pyrimidine, imidazole, furan, thiophen, dihydropyridine, diazepine, oxazepine, pyrrolidine, piperidine, hexamethyleneimine, heptamethylemeimine, tetrahydrofuran, piperazine, homopiperazine, tetrahydrooxazepine, morpholine, thiomorpholine, pyrrole, pyrazole, 1,2,3-triazole, oxazole, oxazolidine, thiazole, thiazolidine, isoxazole, imidazoline, triazole, thiadiazole, oxadiazole, oxathiadiazole, triazine, and tetrazole.

As the dicyclic heterocyclic ring, for example, groups obtained by removing one hydrogen atom from dicyclic heterocyclic rings such as indole, dihydroindole, isoindole, dihydroisoindole, benzofuran, dihydrobenzofuran, benzimidazole, benzoxazole, benzisoxazole, benzothiazole, indazole, quinoline, tetrahydroquinoline, isoquinoline, tetrahydroisoquinoline, tetrahydro-1H-1-benzazepine, tetrahydro-1H-2-benzazepine, tetrahydro-1H-3-benzazepine, tetrahydrobenzoxazepine, quinazoline, tetrahydroquinazoline, quinoxaline, tetrahydroquinoxaline, benzodioxane, benzodioxol, benzothiazine, and imidazopyridine are used.

Examples of the tri- or tetra-cyclic heterocyclic group include groups obtained by removing one hydrogen atom from tri- or tetra-cyclic heterocyclic rings such as acridine, tetrahydroacridine, pyrroloquinoline, pyrroloindole, cyclopentindole, and isoindolobenzazepine.

As the "heterocyclic group", groups obtained by removing one hydrogen atom from monocyclic or dicyclic heterocyclic rings are preferred.

Examples of the "substituent" in the "heterocyclic group which may have a substituent" include "substituents" for the "homocyclic ring or heterocyclic ring which may have a substituent" represented by the above-mentioned B ring, and the number of substituent(s) is 1 to 5.

Preferable examples of the "hydrocarbon group which may have a substituent" represented by $R^1$ include a $C_{7-16}$ aralkyl group (preferably benzyl etc.) which may have 1 to 5 substituent(s) selected from halogen atom, $C_{1-6}$ alkyl, $C_{1-6}$ alkoxy, nitro, cyano, carbamoyl, mono-$C_{1-6}$ alkyl-carbamoyl, di-$C_{1-6}$ alkyl-carbamoyl, aminosulfonyl, mono-$C_{1-6}$ alkylaminosulfonyl, di-$C_{1-6}$ alkylaminosulfonyl and hydroxy.

Examples of the "acyl group" represented by the above-mentioned $R^1$ include acyl groups represented by the formulas:

—(C=O)—R², —(C=O)—OR², —(C=O)—NR²R³, —SO₂—R², —SO—R², SO₂—NR²R³, —(C=S)—OR² or —(C=S)NR²R³ wherein $R^2$ and $R^3$ represent (i) a hydrogen atom, (ii) a hydrocarbon group which may have a substituent or (iii) a heterocyclic group which may have a substituent, respectively, or $R^2$ and $R^3$ may be linked together with an adjacent nitrogen atom to form a nitrogen-containing cyclic group which may have a substituent.

Among them, preferred are acyl groups represented by the formulas: —(C=O)—R², —(C=O)—NR²R³, —SO₂—R² or —SO₂—NR²R³ [wherein respective symbols are as defined above].

Examples of the "hydrocarbon group which may have a substituent" and the "heterocyclic group which may have a substituent" represented by $R^2$ or $R^3$ include the same "hydrocarbon group which may have a substituent" and "heterocyclic group which may have a substituent" as those represented by the above-mentioned $R^1$.

Examples of the "nitrogen-containing cyclic group which may have a substituent" formed by $R^2$ and $R^3$ include 5- to 9-membered (preferably 5- to 7-membered) nitrogen-containing saturated heterocyclic groups which may have 1 to 3 hetero atom(s) selected from a nitrogen atom, an oxygen atom and a sulfur atom in addition to carbon atoms and one nitrogen atom. More specific examples include groups represented by the formulas:

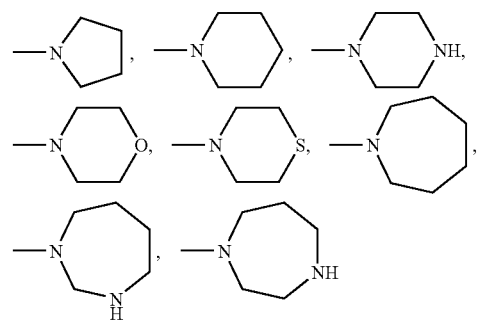

Examples of the "substituent" in the "nitrogen-containing cyclic group which may have a substituent" include the same "substituents" in the "homocyclic ring or heterocyclic ring which may have a substituent" represented by the above-mentioned B ring, and the number of substituent(s) is 1 to 5.

Preferable examples of $R^2$ and $R^3$ include (i) a hydrogen atom, (ii) optionally halogenated $C_{1-6}$ alkyl, (iii) $C_{6-10}$ aryl which may have 1 to 3 substituent(s) selected from $C_{1-6}$ alkyl and $C_{1-6}$ alkoxy, (iii) $C_{7-16}$ aralkyl (e.g. benzyl etc.), and (iv) a 5- or 6-membered heterocyclic group (e.g. pyridyl, thienyl, furyl etc.).

Preferable examples of the "acyl group" represented by the above-mentioned $R^1$ include formyl, optionally halogenated $C_{1-6}$ alkyl-carbonyl (e.g. acetyl, trifluoroacetyl, propionyl etc.), 5- or 6-membered heterocyclic carbonyl (e.g. pyridylcarbonyl, thienylcarbonyl, furylcarbonyl etc.), $C_{6-14}$ aryl-carbonyl (e.g. benzoyl, 1-naphthoyl, 2-naphthoyl etc.), $C_{7-16}$ aralkyl-carbonyl (e.g. phenylacetyl, 3-phenylpropionyl etc.), optionally halogenated $C_{1-6}$ alkylsulfonyl (e.g. methanesulfonyl, trifluoromethanesulfonyl, propylsulfonyl etc.), $C_{6-14}$ arylsulfonyl (e.g. benzenesulfonyl, naphthylsulfonyl etc.), carbamoyl, mono-$C_{1-6}$ alkyl-carbamoyl (e.g. methylcarbamoyl, ethylcarbamoyl etc.), $C_{1-6}$ alkyl-carbamoyl (e.g. dimethylcarbamoyl, diethylcarbamoyl etc.), aminosulfonyl, mono-$C_{1-6}$ alkylaminosulfonyl. (e.g. methylaminosulfonyl, ethylaminosulfonyl. etc.), and di-$C_{1-6}$ alkylaminosulfonyl (e.g. dimethylaminosulfonyl, diethylaminosulfonyl etc.).

Preferable examples of $R^1$ include hydrogen atom, $C_{1-6}$ alkyl, $C_{1-6}$ alkyl-carbonyl, carbamoyl, mono-$C_{1-6}$ alkyl-carbamoyl, di-$C_{1-6}$ alkyl-carbamoyl, aminosulfonyl, mono-$C_{1-6}$ alkylaminosulfonyl, and di-$C_{1-6}$ alkylaminosulfonyl.

Specific examples of the group represented by the above-mentioned formula:

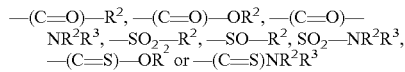

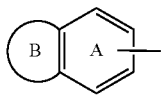

include groups obtained by removing one hydrogen atom from dicyclic condensed benzene rings such as naphthalene tetrahydronaphthalene; indane; indene; benzo[a]cycloheptene; benzofuran such as 2,3-dihydro-1-benzofuran, 1,3-dihydro-2-benzofuran etc.; chroman; 3,4-dihydro-1H-isochromen; benzoxepine such as 2,3,4,5-tetrahydro-1-benzoxepine, 1,3,4,5-tetrahydro-2-benzoxepine, 1,2,4,5-tetrahydro-3-benzoxepine etc.; benzothiophen such as 2,3-dihydro-1-benzothiophen, 1,3-dihydro-2-benzothiophen etc.; thiochroman; 3,4-dihydro-1H-isothiochromen; benzothiepine such as 2,3,4,5-tetrahydro-1-benzothiepine, 1,3,4,5-tetrahydro-2-benzothiepine, 1,2,4,5-tetrahydro-3-benzothiepine; 3,4-dihydro-2H-1-benzothiopyran;. 2,3-dihydro-1H-indole; and 1,2,3,4-tetrahydroquinoline; 2,3-dihydro-1H-isoindole;. 1,2,3,4-tetrahydroisoquinoline; benzazepine such as 2,3,4,5-tetrahydro-1H-1-benzazepine, 2,3,4,5-tetrahydro-1H-2-benzazepine, 2,3,4,5-tetrahydro-1H-3-benzazepine; benzazocine such as 1,2,3,4,5,6-hexahydro-1-benzazocine, 1,2,3,4,5,6-hexahydro-2-benzazocine, 1,2,3,4,5,6-hexahydro-3-benzazocine; benzazonine such as 2,3,4,5,6,7-hexahydro-1H-1-benzazonine, 2,3,4,5,6,7-hexahydro-1H-2-benzazonine, 2,3,4,5,6,7-hexahydro-1H-3-benzazonine, and 2,3,4,5,6,7-hexahydro-1H-4-benzazonine; benzoxazole such as 2,3-dihydrobenzoxazole; benzothiazole such as 2,3-dihydrobenzothiazole; benzisothiazole such as 2,3-dihydro-1,2-benzisothiazole, and 1,3-dihydro-2,1-benzisothiazole; benzimidazole such as 2,3-dihydro-1H-benzimidazole; 1,3-dihydro-2,1,3-benzothiadiazole; benzoxazine such as 3,4-dihydro-1H-2,1-benzoxazine, 3,4-dihydro-1H-2,3-benzoxazine, 3,4-dihydro-2H-1,2-benzoxazine, 3,4-dihydro-2H-1,4-benzoxazine, 3,4-dihydro-2H-1,3-benzoxazine, and 3,4-dihydro-2H-3,1-benzoxazine; benzothiazine such as 3,4-dihydro-1H-2,1-benzothiazine, 3,4-dihydro-1H-2,3-benzothiazine, 3,4-dihydro-2H-1,2-benzothiazine, 3,4-dihydro-2H-1,4-benzothiazine, 3,4-dihydro-2H-1,3-benzothiazine, and 3,4-dihydro-2H-3,1-benzothiazine; benzoisothiazine such as 3,4-dihydro-2H-1,2-benzoisothiazine, and 3,4-dihydro-1H-2,1-benzoisothiazine; 3,4-dihydro-1H-2,13-benzothiadiazine; benzodiazine such as 1,2,3,4-tetrahydrocinnoline, 1,2,3,4-tetrahydrophthalazine, 1,2,3,4-tetrahydroquinazoline and 1,2,3,4-tetrahydroquinoxaline; benzoxathiine such as 3,4-dihydro-1,2-benzoxathiine, 3,4-dihydro-2,1-benzoxathiine, 2,3-dihydro-1,4-benzoxathiine, 1,4-dihydro-2,3-benzoxathiine, 4H-1,3-benzoxathiine, and 4H-3,1-benzoxathiine; 1,3-benzodioxol; 1,3-benzodithiol; benzodioxine such as 3,4-dihydro-1,2-benzodioxine, 2,3-dihydro-1,4-benzodioxine, 1,4-dihydro-2,3-benzodioxine, and 4H-1,3-benzodioxine; benzdithiin such as 3,4-dihydro-1,2-benzdithiine, 2,3-dihydro-1,4-benzdithiine, 1,4-dihydro-2,3-benzdithiine, and 4H-1,3-benzdithiine; benzoxazepine such as 2,3,4,5-tetrahydro-1,2-benzoxazepine, 2,3,4,5-tetrahydro-1,3-benzoxazepine, 2,3,4,5-tetrahydro-1,4-benzoxazepine, 2,3,4,5-tetrahydro-1,5-benzoxazepine, 1,3,4,5-tetrahydro-2,1-benzoxazepine, 1,3,4,5-tetrahydro-2,3-benzoxazepine, 1,3,4,5-tetrahydro-2,4-benzoxazepine, 1,2,4,5-tetrahydro-3,1-benzoxazepine, 1,2,4,5-tetrahydro-3,2-benzoxazepine, and 1,2,3,5-tetrahydro-4,1-benzoxazepine; benzothiazepine such as 2,3,4,5-tetrahydro-1,2-benzothiazepine, 2,3,4,5-tetrahydro-1,4-benzothiazepine, 2,3,4,5-tetrahydro-1,5-benzothiazepine, 1,3,4,5-tetrahydro-2,1-benzothiazepine, 1,3,4,5-tetrahydro-2,4-benzothiazepine, 1,2,4,5-tetrahydro-3,1-benzothiazepine, 1,2,4,5-tetrahydro-3,2-benzothiazepine, and 1,2,3,5-tetrahydro-4,1-benzothiazepine; benzodiazepine such as 2,3,4,5-tetrahydro-1H-1,2-benzodiazepine, 2,3,4,5-tetrahydro-1H-1,3-benzodiazepine, 2,3,4,5-tetrahydro-1H-1,4-benzodiazepine, 2,3,4,5-tetrahydro-1H-1,5-benzodiazepine, 2,3,4,5-tetrahydro-1H-2,3-benzodiazepine, and 2,3,4,5-tetrahydro-1H-2,4-benzodiazepine; benzodioxepine such as 4,5-dihydro-1,3-benzodioxepine, 4,5-dihydro-3H-1,2-benzodioxepine, 2,3-dihydro-5H-1,4-benzodioxepine, 3,4-dihydro-2H-1,5-benzodioxepine, 4,5-dihydro-1H-2,3-benzodioxepine, and 1,5-dihydro-2,4-benzodioxepine; benzodithiepine such as 4,5-dihydro-1H-2,3-benzothiepine, 1,5-dihydro-2,4-benzodithiepine, 3,4-dihydro-2H-1,5-benzodithiepine, and 2,3-dihydro-5H-1,4-benzodithiepine; benzoxazocine such as 3,4,5,6-tetrahydro-2H-1,5-benzoxazocine, and 3,4,5,6-tetrahydro-2H-1,6-benzoxazocine; benzothiazocine such as 3,4,5,6-tetrahydro-2H-1,5-benzothiazocine, and 3,4,5,6-tetrahydro-2H-1,6-benzothiazocine; benzodiazocine such as 1,2,3,4,5,6-hexahydro-1,6-benzodiazocine; benzoxathiocine such as 2,3,4,5-tetrahydro-1,6-benzoxathiocine; benzodioxocine such as 2,3,4,5-tetrahydro-1,6-benzodioxocine; benzotrioxepine such as 1,3,5-benzotrioxepine, and 5H-1,3,4-benzotrioxepine; benzoxathiazepine such as 3,4-dihydro-1H-5,2,1-benzoxathiazepine, 3,4-dihydro-2H-5,1,2-benzoxathiazepine, 4,5-dihydro-3,1,4-benzoxathiazepine, and 4,5-dihydro-3H-1,2,5-benzoxathiazepine; benzoxadiazepine such as 2,3,4,5-tetrahydro-1,3,4-benzoxadiazepine; benzthiadiazepine such as 2,3,4,5-tetrahydro-1,3,5-benzthiadiazepine; benzotriazepine such as 2,3,4,5-tetrahydro-1H-1,2,5-benzotriazepine; 4,5-dihydro-1,3,2-benzoxathiepine, 4,5-dihydro-1H-2,3-benzoxathiepine, 3,4-dihydro-2H-1,5-benzoxathiepine, 4,5-dihydro-3H-1,2-benzoxathiepine, 4,5-dihydro-3H-2,1-benzoxathiepine, 2,3-dihydro-5H-1,4-benzoxathiepine, and 2,3-dihydro-5H-4,1-benzoxathiepine, inter alia, naphthalene, tetrahydronaphthalene, indane, indene, 2,3,4,5-tetrahydro-1H-3-benzazepine, 2,3,4,5-tetrahydro-1H-2-benzazepine, 2,3-dihydro-1H-indole, 2,3,4,5-tetrahydro-1,4-benzoxazepine, 2,3-dihydro-1-benzofuran, chroman, 1,3-dihydro-2H-benzimidazole-2-one, and 1,3-dihydro-2,1,3-benzothiadiazole.

Preferable Examples of the case where B ring is a heterocyclic ring include the groups represented by the formula:

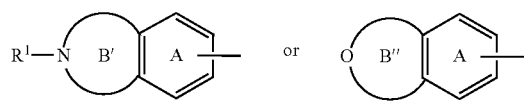

wherein B' ring represents a 5- to 9-membered nitrogen-containing heterocyclic ring which may have a substituent, B" ring represents a 5- to 9-membered oxygen-containing heterocyclic ring which may have a substituent, and the other respective symbols are as defined above.

Examples of the "5- to 9-membered nitrogen-containing heterocyclic ring" in the "5- to 9-membered nitrogen-containing heterocyclic ring which may have a substituent" include 5- to 9-membered nitrogen-containing heterocyclic rings which may have 1 to 3 hetero atom(s) selected from a nitrogen atom, an oxygen atom and a sulfur atom in addition to carbon atoms and one nitrogen atom, and 5- to 9-membered non-aromatic nitrogen-containing heterocyclic rings (e.g. pyrrolidine, piperidine, hexamethyleneimine, heptamethyleneimine, piperazine, homopiperazine, tetrahydrooxazepine, morpholine, thiomorpholine, hexahydropyrimidine, imidazolidine, thiadiazolidine etc.) are preferably used. Examples of the "substituent" include 1 to 3 substituent(s) selected from the same substituents as "substituents" in the "homocyclic ring or heterocyclic ring which may have a substituent" represented by above-mentioned B ring.

Examples of the "5- to 9-membered oxygen-containing heterocyclic ring" in the "5- to 9-membered oxygen-containing heterocyclic ring which may have a substituent" include 5- to 9-membered oxygen-containing heterocyclic rings which may contain 1 to 3 hetero atom(s) selected from an oxygen atom and a sulfur atom in addition to carbon atoms and one oxygen atom, and 5- to 9-membered non-aromatic oxygen-containing heterocyclic rings (e.g. tetrahydrofuran, tetrahydropyran, oxepane etc.) are preferably used. Examples of the "substituent" include 1 to 3 substituent(s) selected from the same substituents as those in the "homocyclic ring or heterocyclic ring which may have a substituent" represented by above-mentioned B ring, and preferred are oxo, $C_{1-6}$ alkyl, $C_{1-6}$ alkyl-carbonylamino, and $C_{1-6}$ alkylsulfonylamino.

Among the groups represented by the formula:

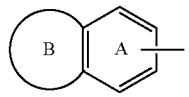

, more preferable examples include the groups represented by the formulas:

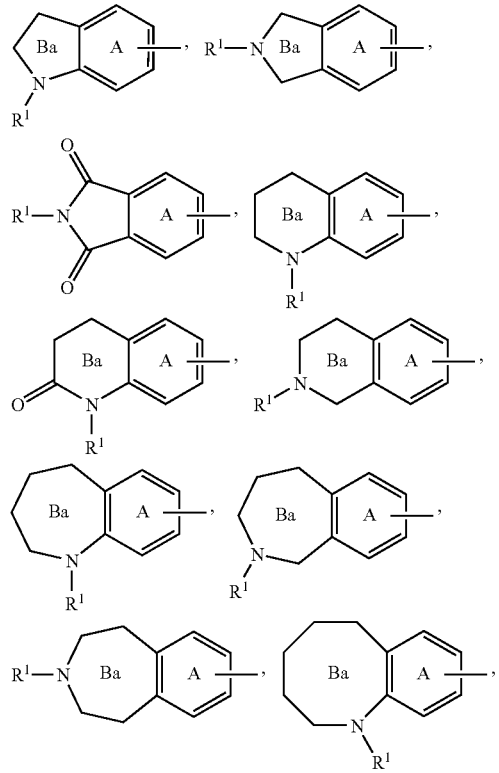

-continued

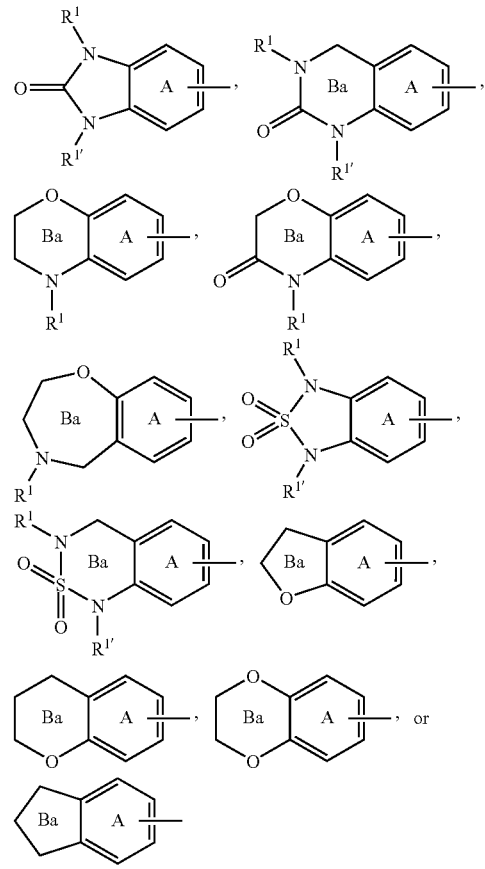

wherein Ba ring represents a homocyclic ring or a heterocyclic ring which may have a substituent, $R^{1'}$ is as defined above for $R^1$, and the other symbols are as defined above.

Examples of the "substituent" in the "homocyclic ring or heterocyclic ring which may have a substituent" represented by Ba ring include 1 or 2 substituent(s) selected from substituents other than an oxo group among "substituents" in the "homocyclic ring or heterocyclic ring which may have a substituent" represented by above-mentioned B ring.

It is preferable that A ring is a benzene ring which may have 1 or 2 substituent(s) selected from aminosulfonyl, mono- or di-$C_{1-6}$ alkylaminosulfonyl, carbamoyl and mono- or di-$C_{1-6}$ alkyl-carbamoyl, Ba ring may have 1 or 2 substituent(s) selected from $C_{1-6}$ alkyl, $C_{1-6}$ alkyl-carbonylamino and $C_{1-6}$ alkylsulfonylamino, and $R^1$ and $R^{1'}$ represent (1) a $C_{1-6}$ alkyl group or a $C_{7-16}$ aralkyl group, each of which may have 1 or 2 substituent(s) selected from hydroxy and $C_{1-6}$ alkoxy-carbonyl, or (2) formulas: —(C=O)—$R^{2'}$, —(C=O)—$NR^{2'}R^{3'}$ or —$SO_2R^{2'}$ [wherein $R^{2'}$ and $R^{3'}$ represent hydrogen atom, optionally halogenated $C_{1-6}$ alkyl or $C_{6-10}$ aryl], respectively.

Specific examples of the case where the phenyl group in the "optionally condensed phenyl group, and said phenyl group may have a substituent" of the above-mentioned (b) is condensed with a dicyclic homocyclic ring or heterocyclic ring which may have a substituent, or is condensed with two same or different monocyclic homocyclic rings or heterocyclic rings include groups represented by the formula:

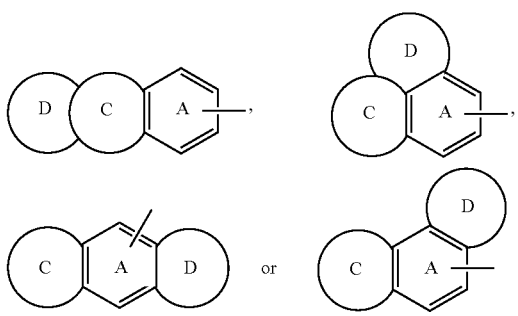

wherein A ring is as defined above, and C ring and D ring represent a homocyclic ring or a heterocyclic ring which may have a substituent.

Examples of the "homocyclic ring" in the "homocyclic ring which may have a substituent" represented by C ring or D ring include the same homocyclic rings as "homocyclic rings" in the "homocyclic ring which may have a substituent" represented by B ring.

Examples of the "heterocyclic ring" in the "heterocyclic ring which may have a substituent" represented by C ring or D ring include 5- to 9-membered heterocyclic rings which may have 1 to 3 hetero atom(s) selected from a nitrogen atom, an oxygen atom and a sulfur atom (e.g. pyridine, pyrazine, pyrimidine, imidazole, furan, thiophen, dihydropyridine, diazepine, oxazepine, pyrrolidine, piperidine, hexamethyleneimine, heptamethyleneimine, tetrahydrofuran, piperazine, homopiperazine, tetrahydrooxazepine, morpholine, thiomorpholine, hexahydropyrimidine, imidazolidine, thiadiazolidine etc.).

Examples of the "substituent" in the "homocyclic ring or heterocyclic ring optionally having a substituent" represented by C ring or D ring include the same substituents as "substituents" in the "homocyclic ring or heterocyclic ring which may have a substituent" represented by above-mentioned B ring.

Specific examples of the groups represented by the aforementioned formula:

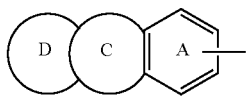

wherein respective symbols are as defined above, include groups obtained by removing one hydrogen atom from tricyclic condensed benzene rings such as anthracene, carbazole, 1,2,3,4,4a,9a-hexahydrocarbazole, 9,10-dihydroacridine, 1,2,3,4-tetrahydroacridine, 10,11-dihydro-5H-dibenz(b,f] azepine, 5,6,7,12-tetrahydrodibenz[b,g]azocine, 6,11-dihydro-5H-dibenz[b,e]azepine, 6,7-dihydro-5H-dibenz[c,e] azepine, 5,6,11,12-tetrahydrodibenz[b,f]azocine, dibenzofuran, 9H-xanthene, 10,11-dihydrodibenz[b,f]oxepine, 6,11-dihydrodibenz[b,e]oxepine, 6,7-dihydro-5H-dibenz[b,g]oxocine, dibenzothiophen, 9H-thioxanthene, 10,11-dihydrodibenzo[b,f]thiepine 6,11-dihydrodibenzo[b, e]thiepine, 6,7-dihydro-5H-dibenzo[b,g]thiocine, 10H-phenothiazine, 10H-phenoxazine, 5,10-dihydrophenazine, 10,11-dibenzo[b,f][1,4]thiazepine, 10,11-dihydrodibenz[b, f][1,4]oxazepine, 2,3,5,6,11,11a-hexahydro-1H-pyrrolo[2,1-b][3]benzazepine, 10,11-dihydro-5H-dibenzo[b,e][1,4]diazepine, 5,11-dihydrodibenz[b,e][1,4]oxazepine, 5,11-dihydrodibenzo[b,f][1,4]thiazepine, 10,11-dihydro-5H-dibenzo[b,e][1,4]diazepine, and 1,2,3,3a, 8,8a-hexahydropyrrolo[2,3-b]indole.

Examples of the groups represented by the above-mentioned formula:

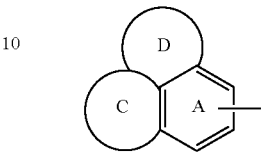

wherein respective symbols are as defined above, include groups obtained by removing one hydrogen atom from tricyclic condensed benzene rings such as phenalene, acenaphthylene, 1H,3H-naphtho[1,8-cd][1,2]oxazine, naphtho[1,8-de]-1,3-oxazine, naphtho[1,8-de]-1,2-oxazine, 1,2,2a,3,4,5-hexahydrobenz[cd]indole, 2,3,3a,4,5,6-hexahydro-1H-benzo[de]quinoline, 4H-pyrrolo[3,2,1-ij]quinoline, 1,2,5,6-tetrahydro-4H-pyrrolo[3,2,1-ij]quinoline, 5,6-dihydro-4H-pyrrolo[3,2,1-ij]quinoline, 1H-pyrrolo[3,2,1-ij]quanazoline, 4H-imidazo[4,5,1-ij]quinoline, 2,3,7,8-tetrahydro[1,2,6] thiadiazino[4,3,2-hi]indole, 1,2,6,7-tetrahydro-3H,5H-pyrido(3,2,1-ij]quinazoline, 2,3,8,9-tetrahydro-7H-[1,2,6]thiadiazino[4,3,2-ij]quinoline, 5,6-dihydro-1H,4H-[1,2,5] thiadiazolo[4,3,2-ij]quinoline, 1H,5H-benzo[ij]quinolizine, azepino[3,2,1-hi]indole, 1,2,4,5,6,7-hexahydroazepino[3,2, 1-hi]indole, 1H-pyrido[3,2,1-jk][1]benzazepine, 5,6,7,8-tetrahydro-1H-pyrido[3,2,1-jk][1]benzazepine, 1,2,5,6,7,8-hexahydro-1H-pyrido[3,2,1-jk][1]benzazepine, 2,3-dihydro-1H-benz[de]isoqiunoline, 1,2,3,4,4a,5,6,7-octahydronaphtho[1,8-bc]azepine, and 2,3,5,6,7,8-hexahydro-1H-pyrido[3,2,1-jk][1]benzazepine.

Specific examples of the group represented by the above-mentioned formula:

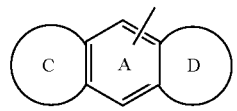

wherein respective symbols are as defined above, include groups obtained by removing one hydrogen atom from tricyclic condensed benzene rings such as anthracene, 1,2,3,5,6, 7-hexahydrobenzo[1,2-b:4,5-b']dipyrrole, and 1,2,3,5,6,7-hexahydrocyclopenta[f]indole.

Specific examples of the group represented by the above-mentioned formula:

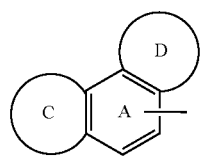

wherein respective symbols are as defined above, include groups obtained by removing one hydrogen atom from tricyclic condensed benzene rings such as phenanthrolene, 1,2,3, 6,7,8-hexahydrocyclopenta[e]indole, and 2,3,4,7,8,9-hexahydro-1H-cyclopenta[f]quinoline.

Among them, groups represented by the formulas:

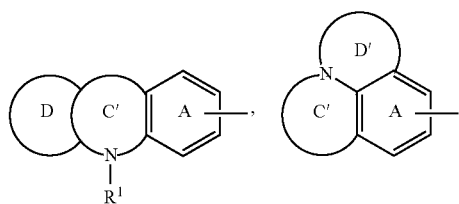

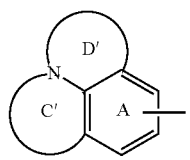

wherein C' ring and D' ring represent a 5- to 9-membered nitrogen-containing heterocyclic ring which may have a substituent, respectively, and other respective symbols are as defined above, are preferable. Among them, groups represented by the formula:

wherein respective symbols are as defined above, are further preferred.

Examples of the "5- to 9-membered nitrogen-containing heterocyclic ring which may have a substituent" represented by C' ring or D' ring include the same "5- to 9-membered nitrogen-containing heterocyclic ring which may have a substituent" as those represented by B' ring. As the substituent, an oxo group is preferable.

Inter alia, more preferable examples include groups represented by the formulas:

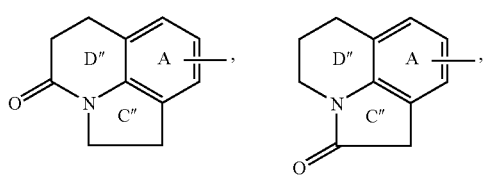

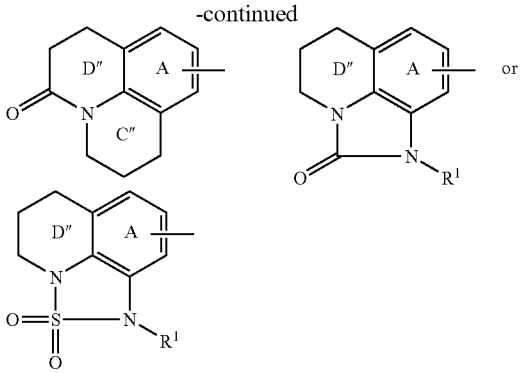

wherein C" ring and D" ring represent a nitrogen-containing heterocyclic ring which may have a substituent, and the other symbols are as defined above.

Examples of the "substituent" in the "nitrogen-containing heterocyclic ring which may have a substituent" represented by C" ring and D" ring include 1 to 2 substituent(s) selected from "substituents" other than an oxo group in the "homocyclic ring or heterocyclic ring which may have a substituent" represented by B ring.

Herein, it is preferable that A ring is a benzene ring which may have 1 or 2 substituent(s) selected from aminosulfonyl, mono- or di-$C_{1-6}$ alkylaminosulfonyl, carbamoyl and mono- or di-$C_{1-6}$ alkyl-carbamoyl, C" ring and D" ring may have 1 or 2 substituent(s) selected from $C_{1-6}$ alkyl, $C_{1-6}$ alkyl-carbonylamino and $C_{1-6}$ alkylsulfonylamino, and $R^1$ is (1) a $C_{1-6}$ alkyl group or a $C_{7-16}$ aralkyl group, each of which may have 1 or 2 substituent(s) selected from hydroxy and $C_{1-6}$ alkoxy-carbonyl, or (2) the formulas: —(C=O)—$R^{2'}$, —(C=O)—$NR^{2'}R^{3'}$ or —$SO_2R^{2'}$ [wherein $R^{2'}$ and $R^{3'}$ represent hydrogen atom, optionally halogenated $C_{1-6}$ alkyl or $C_{6-10}$ aryl].

Specific examples of the case where the phenyl group in the "optionally condensed phenyl group, and said phenyl group may have a substituent" of the above-mentioned (c) is condensed with a tricyclic homocyclic ring or heterocyclic ring which may have a substituent include groups represented by the formulas:

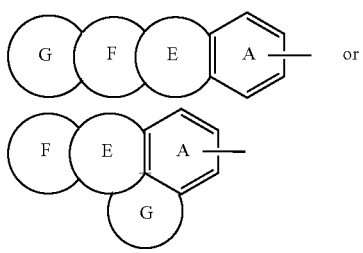

wherein A ring is as defined above, and E ring, F ring and G ring represent a homocyclic ring or a heterocyclic ring which may have a substituent].

Examples of the "homocyclic ring or heterocyclic ring which may have a substituent" represented by E ring, F ring or G ring include the same "homocyclic ring or heterocyclic ring which may have a substituent" as those represented by C ring or D ring.

Among them, preferable examples include:
(i) a group represented by the formula:

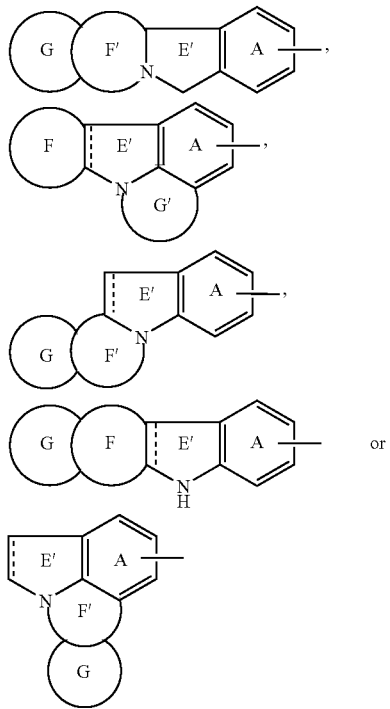

wherein E' ring, F' ring and G' ring represent a 5- to 9-membered nitrogen-containing heterocyclic ring which may have a substituent, ----- represents a single bond or a double bond, and the other symbols are as defined above, (ii) a group obtained by removing one hydrogen atom from rings such as fluoranthene, acephenanthrylene, aceanthrylene, triphenylene, pyrene, chrysene, naphthacene, preyadene, benzo[a]anthracene, indeno[1,2-a]indene, cyclopenta[a]phenanthrene, pyrido[1',2':1,2]imidazo[4,5-b]quinoxaline, 1H-2-oxapyrene, and spiro[piperidine-4.9'-xanthene], and dihydro, tetrahydro, hexahydro, octahydro, decahydro compounds thereof.

Examples of the "5- to 9-membered nitrogen-containing heterocyclic ring which may have a substituent" represented by E' ring, F' ring and G' ring include the same "5- to 9-membered nitrogen-containing heterocyclic rings which may have a substituent" as those represented by B'-ring. As the substituent, an oxo group is preferred.

Specific examples of the group represented by the above-mentioned formula:

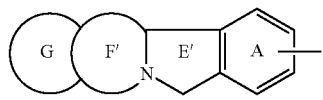

wherein respective symbols are as defined above, include groups obtained by removing one hydrogen atom from tetracyclic condensed benzene rings such as 2H-isoindolo[2,1-e]purine, 1H-pyrazolo[4',3':3,4]pyrido[2,1-a]isoindole, 1H-pyrido[2',3':4,5]imidazo[2,1-a]isoindole, 2H,6H-pyrido[1',2':3,4]imidazo[5,1-a]isoindole, 1H-isoindolo[2,1-a]benzimidazole, 1H-pyrido[3',4':4,5]pyrrolo[2,1-a]isoindole, 2H-pyrido[4',3':4,5]pyrrolo[2,1-a]isoindole, 1H-isoindolo[2,1-a]indole, 2H-isoindolo[1,2-a]isoindole, 1H-cyclopenta[4,5]pyrimido[2,1-a]isoindole, 2H,4H-pyrano[4',3:4,5][1,3]oxazino[2,3-a]isoindole, 2H-isoindolo[2,1-a][3,1]benzoxazine, 7H-isoindolo[1,2-b][1,3]benzoxazine, 2H-pyrido[2',1':3,4]pyrazino[2,1-a]isoindole, pyrido[2',3':4,5]pyrimido[2,1-a]isoindole, pyrido[3',2':5,6]pyrimido[2,1-a]isoindole, 1H-pyrido[1',2':3,4]pyrimido[2,1-a]isoindole, isoindolo[2,1-a]quinazoline, isoindolo[2,1-a]quinoxaline, isoindolo[1,2-a]isoquinoline, isoindolo[2,1-b]isoquinoline, isoindolo[2,1-a]quinoline, 6H-oxazino[3',4':3,4][1,4]diazepino[2,1-a]isoindole, azepino[2',1':3,4]pyrazino[2,1-a]isoindole, 2H,6H-pyrido[2',1':3,4][1,4]diazepino[2,1-a]isoindole, 1H-isoindolo[1,2-b][1,3,4]benzotriazepine, 2H-isoindolo[2,1-a][1,3,4]benzotriazepine, isoindolo[2,1-d][1,4]benzoxazepine, 1H-isoindolo[2,1-b][2,4]benzodiazepine, 1H-isoindolo[2,1-c][2,3]benzodiazepine, 2H-isoindolo[1,2-a][2,4]benzodiazepine, 2H-isoindolo[2,1-d][1,4]benzodiazepine, 5H-indolo[2,1-b][3]benzazepine, 2H-isoindolo[1,2-a][2]benzazepine, 2H-isoindolo[1,2-b][3]benzazepine, 2H-isoindolo[2,1-b][2]benzazepine, 2H-isoindolo[1,2-b][1,3,4]benzoxadiazocine, isoindolo[2,1-b][1,2,6]benzotriazocine, and 5H-4,8-methano-1H-[1,5]diazacycloundecino[1,11-a]indole.

Specific examples of the group represented by the above-mentioned formula:

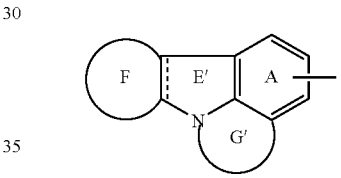

wherein respective symbols are as defined above, include groups obtained by removing one hydrogen atom from tetracyclic condensed benzene rings such as 1H,4H-pyrrolo[3',2':4,5]pyrrolo[3,2,1-ij]quinoline, pyrrolo[3,2,1-jk]carbazole, 1H-furo[2',3':4,5]pyrrolo[3,2,1-ij]quinoline, 1H,4H-cyclopenta[4,5]pyrrolo[1,2,3-de]quinoxaline, 1H,4H-cyclopenta[4,5]pyrrolo[3,2,1-ij]quinoline, pyrido[3',4':4,5]pyrrolo[1,2,3-de]benzoxazine, [1,4]oxazino[2,3,4-jk]carbazole, 1H,3H-[1,3]oxazino[5,4,3-jk]carbozole, pyrido[3',4':4,5]pyrrolo[1,2,3-de][1,4]benzothiazine, 4H-pyrrolo[3,2,1-de]phenanthridine, 4H,5H-pyrido[3,2,1-de]phenanthridine, 1H,4H-3a,6a-diazafluoroanthene, 1-oxa-4,6a-diazafluoroanthene, 4-oxa-2,10b-diazafluoroanthene, 1-thia-4,6a-diazafluoroanthene, 1H-pyrazino[3,2,1-jk]carbazole, 1H-indolo[3,2,1-de][1,5]naphthyridine, benzo[b]pyrano[2,3,4-hi]indolizine, 1H,3H-benzo[b]pyrano[3,4,5-hi]indolizine, 1H,4H-pyrano[2',3':4,5]pyrrolo[3,2,1-ij]quinoline, 1H,3H-benzo[b]thiopyrano[3,4,5-hi]indolizine, 1H-pyrido[3,2,1-jk]carbazole, 4H-3-oxa-11b-azacyclohepta[jk]fluorene, 2H-azepino[1',2':1,2]pyrimidino[4,5-b]indole, 1H,4H-cyclohepta[4,5]pyrrolo[1,2,3-de]quinoxaline, 5H-pyrido[3',4':4,5]pyrrolo[1,2,3-ef][1,5]benzoxazepine, 4H-pyrido[3',4':4,5]pyrrolo[3,2,1-jk][4,1]benzothiazepine, 5H-pyrido[3',4':4,5]pyrrolo[1,2,3-ef][1,5]benzothiazepine, 5H-pyrido[4',3':4,5]pyrrolo[1,2,3-ef][1,5]benzothiazepine, [1,2,4]triazepino[6,5,4-jk]carbazole, [1,2,4]triazepino[6,7,1-jk]carbazole, [1,2,5]triazepino[3,4,5-jk]carbazole, 5H-[1,4]oxazepino[2,3,4-jk]carbazole, 5H-[1,4]thiazepino[2,3,4-jk]carbazole, [1,4]diazepino[3,2,1-jk]carbazole, [1,4]diazepino[6,7,1-jk]

carbazole, azepino[3,2,1-jk]carbazole, 1H-cycloocta[4,5]pyrrolo[1,2,3-de]quinoxaline, and 1H-cycloocta[4,5]pyrrolo[3,2,1-ij]quinoline.

Specific examples of the group represented by the above-mentioned formula:

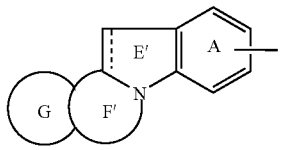

wherein respective symbols are as defined above, include groups obtained by removing one hydrogen atom from tetracyclic condensed benzene rings such as 1H-indolo[1,2-a]benzimidazole, 1H-indolo[1,2-b]indazole, pyrrolo[2',1':3,4]pyrazino[1,2-a]indole, 1H,5H-pyrrolo[1',2':4,5]pyrazino[1,2-a]indole, 2H-pyrido[2',3':3,4]pyrrolo[1,2-a]indole, 1H-pyrrolo[2',3':3,4]pyrido[1,2-a]indole, 1H-indolo[1,2-a]indole, 6H-isoindolo[2,1-a]indole, 6H-indolo[1,2-c][1,3]benzoxazine, 1H-indolo[1,2-b][1,2]benzothiazine, pyrimido[4',5':4,5]pyrimido[1,6-a]indole, pyrazino[2',3':3,4]pyrido[1,2-a]indole, 6H-pyrido[1',2':3,4]pyrimido[1,6-a]indole, indolo[1,2-b]cinnoline, indolo[1,2-a]quinazoline, indolo[1,2,-c]quinazoline, indolo[2,1-b]quinazoline, indolo[1,2-a]quinoxaline, indolo[1,2-a] [1,8]naphthyridine, indolo[1,2-b]-2,6-naphthyridine, indolo[1,2-b][2,7]naphthyridine, indolo[1,2-h]-1,7-naphthyridine, indolo[1,2-b]isoquinoline, indolo[2,1-a]isoquinoline, indolo[1,2-a]quinoline, 2H-6H-pyrido[2',1':3,4][1,4]diazepino[1,2-a]indole, 1H-indolo[2,1-c][1,4]benzodiazepine, 2H-indolo[1,2-d][1,4]benzodiazepine, 2H-indolo[2,1-a][2,3]benzodiazepine, 2H-indolo[2,1-b][1,3]benzodiazepine, 1H-indolo[1,2-b][2]benzazepine, 2H-indolo[1,2-a][1]benzazepine, 2H-indolo[2,1-a][2]benzazepine, indolo[1,2-e][1,5]benzodiazocine, and indolo[2,1-b][3]benzazocine.

Specific examples of the group represented by the above-mentioned formula:

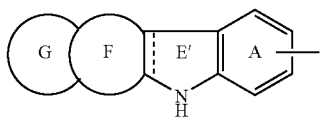

wherein respective symbols are as defined above, include groups obtained by removing one hydrogen atom from tetracyclic condensed benzene rings such as 1H-imidazo[1',2':1,2]pyrido[3,4-b]indole, 1H-imidazo[1',2':1,6]pyrido[4,3-b]indole, 1H-imidazo[1',5':1,2]pyrido[3,4-b]indole, 1H-imidazo[1',5':1,6]pyrido[4,3-b]indole, 1H-pyrido[2',1':2,3]imidazo[4,5-b]indole, imidazo[4,5-a]carbazole, imidazo[4,5-c]carbazole, pyrazolo[3,4-c]carbazole, 2H-pyrazino[1',2':1,5]pyrrolo[2,3-b)indole, 1H-pyrrolo[1',2':1,2]pyrimido[4,5-b]indole, 1H-indolizino[6,7-b]indole, 1H-indolizino[8,7-b]indole, indolo[2,3-b]indole, indolo[3,2-b]indole, pyrrolo[2,3-a]carbazole, pyrrolo[2,3-b]carbazole, pyrrolo[2,3-c]carbazole, pyrrolo[3,2-a]carbazole, pyrrolo[3,2-b]carbazole, pyrrolo[3,2-c]carbazole, pyrrolo[3,4-a]carbazole, pyrrolo[3,4-b]carbazole, pyrrolo[3,4-c]carbazole, 1H-pyrido[3',4':4,5]furo[3,2-b]indole, 1H-furo[3,4-a]carbazole, 1H-furo[3,4-b]carbazole, 1H-furo[3,4-c]carbazole, 2H-furo[2,3-a]carbazole, 2H-furo[2,3-c]carbazole, 2H-furo[3,2-a]carbazole, 2H-furo[3,2-c]carbazole, 1H-pyrido[3',4':4,5]thieno[2,3-b]indole, thieno[3',2':5,6]thiopyrano[4,3-b]indole, thieno[3',4':5,6]thiopyrano[4,3-b]indole, 1H-[1]benzothieno[2,3-b]indole, 1H-[1]benzothieno[3,2-b]indole, 1H-thieno[3,4-a]carbazole, 2H-thieno[2,3-b]carbazole, 2H-thieno[3,2-a]carbazole, 2H-thieno[3,2-b]carbazole, cyclopenta[4,5]pyrrolo[2,3-f]quinoxaline, cyclopenta[5,6]pyrido[2,3-b]indole, pyrido[2',3':3,4]cyclopenta[1,2-b]indole, pyrido[2',3':4,5]cyclopenta[1,2-b]indole, pyrido[3',4':3,4]cyclopenta[1,2-b]indole, pyrido[3',4':4,5]cyclopenta[1,2-b]indole, pyrido[4',3':4,5]cyclopenta[1,2-b]indole, 1H-cyclopenta[5,6]pyrano[2,3-b]indole, 1H-cyclopenta[5,6]thiopyrano[4,3-b]indole, cyclopenta[a]carbazole, cyclopenta[c]carbazole, indeno[1,2-b]indole, indeno[2,1-b]indole, [1,2,4]triazino[4',3':1,2]pyrido[3,4-b]indole, 1,3,5-triazino[1',2':1,1]pyrido[3,4-b]indole, 1H-[1,4]oxazino[4',3':1,2]pyrido[3,4-b]indole, 1H-[1,4]oxazino[4',3':1,6]pyrido[3,4-b]indole, 4H-[1,3]oxazino[3',4':1,2]pyrido[3,4-b]indole, indolo[3,2-b][1,4]benzoxazine, 1,3-oxazino[6,5-b]carbazole, 2H-pyrimido[2',1':2,3][1,3]thiazino[5,6-b]indole, 2H-[1,3]thiazino[3',2':1,2]pyrido[3,4-b]indole, 4H-[1,3]thiazino[3',4':1,2]pyrido[3,4-b]indole, indolo[2,3-b][1,4]benzothiazine, indolo[3,2-b][1,4]benzothiazine, indolo[3,2-c][2,1]benzothiazine, 1,4-thiazino[2,3-a]carbazole, [1,4]thiazino[2,3-b]carbazole, (1,4]thiazino[2,3-c]carbazole, 1,4-thiazino[3,2-b]carbazole, 1,4-thiazino[3,2-c]carbazole, 1H-indolo[2,3-g]pteridine, 1H-indolo[3,2-g]pteridine, pyrazino[1',2':1,2]pyrido[3,4-b]indole, pyrazino[1',2':1,2]pyrido[4,3-b]indole, 1H-pyrido[2',3':5,6]pyrazino[2,3-b]indole, 1H-pyrido[3',2':5,6]pyrazino[2,3-b]indole, 1H-pyrido[3',4':5,6]pyrazino[2,3-b]indole, pyrido[1',2':1,2]pyrimido[4,5-b]indole, pyrido[1',2':1,2]pyrimido[5,4-b]indole, pyrido[2',1':2,3]pyrimido[4,5-b]indole, pyrimido[1',2':1,2]pyrido[3,4-b]indole, pyrimido[1',2':1,6]pyrido[3,4-b]indole, pyrimido[5',4':5,6]pyrano[2,3-b]indole, pyridazino[4',5':5,6]thiopyrano[4,5-b]indole, 1H-indolo[3,2-c]cinnoline, 1H-indolo[2,3-b]quinoxaline, 1H-pyrazino[2,3-a]carbazole, 1H-pyrazino[2,3-b]carbazole, 1H-pyrazino[2,3-c]carbazole, 1H-pyridazino[3,4-c]carbazole, 1H-pyridazino[4,5-b]carbazole, 1H-pyrimido[4,5-a]carbazole, 1H-pyrimido[4,5-c]carbazole, 1H-pyrimido[5,4-a]carbazole, 1H-pyrimido[5,4-b]carbazole, 1H-pyrimido[5,4-c]carbazole, 7H-1,4-dioxino[2',3':5,6][1,2]dioxino[3,4-b]indole, 6H-[1,4]benzodioxino[2,3-b]indole, 6H-[1,4]benzodithiino[2,3-b]indole, 1H-indolo[2,3-b]-1,5-naphthyridine, 1H-indolo[2,3-b][1,6]naphthyridine, 1H-indolo[2,3-b][1,8]naphthyridine, 1H-indolo[2,3-c]-1,5-naphthyridine, 1H-indolo[2,3-c][1,6]naphthyridine, 1H-indolo[2,3-c][1,7]naphthyridine, 1H-indolo[2,3-c][1,8]naphthyridine, 1H-indolo[3,2-b]-1,5-naphthyridine, 1H-indolo[3,2-b][1,7]naphthyridine, 1H-indolo[3,2-b][1,8]naphthyridine, 1H-indolo[3,2-c][1,8]naphthyridine, indolo[2,3-a]quinolizine, indolo[2,3-b]quinolizine, indolo[3,2-a]quinolizine, indolo[3,2-b]quinolizine, pyrano[4',3':5,6]pyrido[3,4-b]indole, pyrido[4',3':4,5]pyrano[3,2-b]indole, pyrido[4',3':5,6]pyrano[2,3-b]indole, pyrido[4',3':5,6]pyrano[3,4-b]indole, 1H-indolo[2,3-c]isoquinoline, 1H-indolo[3,2-c]isoquinoline, 1H-indolo[2,3-c]quinoline, 1H-indolo[3,2-c]quinoline, 1H-pyrido[2,3-a]carbazole, 1H-pyrido[2,3-b]carbazole, 1H-pyrido[2,3-c]carbazole, 1H-pyrido[3,2-a]carbazole, 1H-pyrido[3,2-b]carbazole, 1H-pyrido[3,2-c]carbazole, 1H-pyrido[3,4-a]carbazole, 1H-pyrido[3,4-b]carbazole, 1H-pyrido[3,4-c]carbazole, 1H-pyrido[4,3-a]carbazole, 1H-pyrido[4,3-b]carbazole, 1H-pyrido[4,3-c]carbazole, 1H-quindoline, 1H-quininedoline, 1H-pyrano[3',4':5,6]pyrano[4,3-b]indole, [1]benzopyrano[2,3-b]indole, [1]benzopyrano[3,2-b]indole, [1]benzopyrano[3,4-b]indole, [1]benzopyrano[4,3-b]indole, [2]benzopyrano[4,3-b]indole, pyrano[2,3-a]carbazole, pyrano[2,3-b]carbazole, pyrano[2,3-c]carbazole, pyrano[3,2-a]carbazole, pyrano[3,2-c]carbazole, pyrano[3,4-a]carbazole, 1H-phosphinolino[4,3-b]indole, [1]benzothiopyrano[2,3-b]indole, [1]benzothiopyrano[3,2-b]indole, [1]benzothiopyrano[3,4-b]indole, [1]benzothiopyrano[4,3-b]indole, [2]benzothiopyrano[4,3-b]indole, 1H-benzo[a]carbazole, 1H-benzo[b]carbazole, 1H-benzo[c]carbazole, [1,6,2]oxathiazepino[2',3':1:2]pyrido[3,4-b]indole, 1H-azepino[1',2':1,2]pyrido[3,4-b]indole, 1H-pyrido[1',2':1,2]azepino[4,5-b]indole, 2H-pyrido[1',2':1,2]azepino,[3,4-b]indole, 1H-pyrido[3',2':5,6]oxepino[3,2-b]indole, 1H-pyrido[4',3':5,6]oxepino[3,2-b]indole, 2H-pyrido[2',3':5,6]oxepino[2,3-b]indole, 2H-pyrido[2',3':5,6]oxepino[3,2-b]indole, 2H-pyrido[3',4':5,6]oxepino[3,2-b]indole, pyrido[2',3':4,5]cyclohepta[1,2-b]indole, pyrido[3',2':3,4]cyclohepta[1,2-b]indole, pyrido[3',4':4,5]cyclohepta[1,2-b]indole, pyrido[3',4':5,6]cyclohepta[1,2-b]indole, 2H-pyrano[3',2':2,3]azepino[4,5-b]indole, 1H-indolo[3,2-b][1,5]benzoxazepine, 1H-indolo[3,2-d][1,2]benzoxazepine, 1H-indolo[2,3-c][1,5]benzothiazepine, [1,4]diazepino[2,3-a]carbazole, indolo[2,3-b][1,5]benzodiazepine, indolo[2,3-d][1,3]benzodiazepine, indolo[3,2-b][1,4]benzodiazepine, indolo[3,2-b][1,5]benzodiazepine, indolo[3,2-d][1,3]benzodiazepine, indolo[3,2-d][2,3]benzodiazepine, indolo[2,3-a][3]benzazepine, indolo[2,3-c][1]benzazepine, indolo[2,3-d][1]benzazepine, indolo[2,3-d][2]benzazepine, indolo[3,2-b][1]benzazepine, indolo[3,2-c][1]benzazepine, indolo[3,2-d][1]benzazepine, 1H-indolo[2,1-b][3]benzazepine, H-[1]benzoxepino[5,4-b]indole, 1H-[2]benzoxepino[4,3-b]indole, 1H-[1]benzothiepino[4,5-b]indole, 1H-[1]benzothiepino[5,4-b]indole, benzo[3,4]cyclohepta[1,2-b]indole, benzo[4,5]cyclohepta[1,2-b]indole, benzo[5,6]cyclohepta[1,2-b]indole, benzo[6,7]cyclohepta[1,2-b]indole, cyclohepta[b]carbazole, 4H-[1,5]oxazocino[5',4':1,6]pyrido[3,4-b]indole, azocino[1',2':1,2]pyrido[3,4-b]indole, 2,6-methano-2H-azecino[4,3-b]indole, 3,7-methano-3H-azecino[5,4-b]indole, pyrido[1',2':1,8]azocino[5,4-b]indole, pyrido[4',3':6,7]oxocino[2,3-b]indole, pyrido[4',3':6,7]oxocino[4,3-b]indole, 1,5-methano-1H-azecino[3,4-b]indole, 2,6-methano-1H-azecino[5,4-b]indole, 1H-pyrido[3',4':5,6]cycloocta[1,2-b]indole, 1,4-ethanooxocino[3,4-b]indole, pyrano[3',4':5,6]cycloocta[1,2-b]indole. 1H-indolo[2,3-c][1,2,5,6]benzotetrazocine, 1H-indolo[2,3-c][1,6]benzodiazocine, 6,13b-methano-13bH-azecino[5,4-b]indole, oxocino[3,2-a]carbazole, 1H-benzo[g]cycloocta[b]indole, 6,3-(iminomethano)-2H-1,4-thiazonino[9,8-b]indole, 1H,3H-[1,4]oxazonino[4',3':1,2]pyrido[3,4-b]indole, 2H-3,6-ethanoazonino[5,4-b]indole, 2H-3,7-methanoazacycloundecino[5,4-b]indole, 1H-6,12b-ethanoazonino[5,4-b]indole, indolo[3,2-e][2]benzazonine, 5,9-methanoazacycloundecino[5,4-b]indole, 3,6-ethano-3H-azecino[5,4-b]indole, 3,7-methano-3H-azacycloundecino[5,4-b]indole, pyrano[4',3':8,9]azecino[5,4-b]indole, 1H-indolo[2,3-c][1,7]benzodiazecine, 1H-indolo[3,2-e][2]benzazecine, benzo[e]pyrrolo[3,2-b]indole, benzo[e]pyrrolo[3,2-g]indole, benzo[e]pyrrolo[3,2,1-hi]indole, benzo[e]pyrrolo[3,4-b]indole, benzo[g]pyrrolo[3,4-b]indole, 1H-benzo[f]pyrrolo[1,2-a]indole, 1H-benzo[g]pyrrolo[1,2-a]indole, 2H-benzo[e]pyrrolo[1,2-a]indole, 1H-benzo[f]pyrrolo[2,1-a]isoindole, 1H-benzo[g]pyrrolo[2,1-a]isoindole, 2H-benzo[e]pyrrolo[2,1-a]isoindole, isoindolo[6,7,1-cde]indole, spiro[cyclohexane-1,5'-[5H]pyrrolo[2,1-a]isoindole], isoindolo[7,1,2-hij]quinoline, 7,11-methanoazocino[1,2-a]indole, 7,11-methanoazocino[2,1-a]isoindole, dibenz[cd,f]indole, dibenz[cd,g]indole, dibenz[d,f]indole, 1H-dibenz[e,g]indole, 1H-dibenz[e,g]isoindole, naphtho[1,2,3-cd]indole, naphtho[1,8-ef]indole, naphtho[1,8-fg]indole, naphtho[3,2,1-cd]indole, 1H-naphtho[1,2-e]indole, 1H-naphtho[1,2-f]indole, 1H-naphtho[1,2-g]indole, 1H-naphtho[2,1-e]indole, 1H-naphtho[2,3-e]indole, 1H-naphtho[1,2-f]isoindole, 1H-naphtho[2,3-e]isoindole, spiro[1H-carbazole-1,1'-cyclohexane], spiro[2H-carbazole-2,1'-cyclohexane], spiro[3H-carbazole-3,1'-cyclohexane], cyclohepta[4,5]pyrrolo[3,2-f]quinoline, cyclohepta[4,5]pyrrolo[3,2-h]quinoline, azepino[4,5-b]benz[e]indole, 1H-azepino[1,2-a]benz[f]indole, 1H-azepino[2,1-a]benz[f]isoindole, benzo[e]cyclohepta[b]indole, and benzo[g]cyclohepta[b]indole.

Specific example of the group represented by the above-mentioned formula:

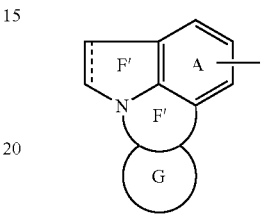

wherein respective symbols are as defined above, include groups obtained by removing one hydrogen atom from tetracyclic condensed benzene rings such as 1H-dipyrrolo[2,3-b:3',2',1'-hi]indole, spiro[cyclopentane-1,2'(1'H)-pyrrolo[3,2,1-hi]indole], spiro[imidazolidine-4,1'(2'H)-[4H]pyrrolo[3,2,1-ij]quinoline], pyrido[2,3-b]pyrrolo[3,2,1-hi]indole, pyrido[4,3-b]pyrrolo[3,2,1-hi]indole, benzo[de]pyrrolo[3,2,1-ij]quinoline, 3H-pyrrolo[3,2,1-de]acridine, 1H-pyrrolo[3,2,1-de]phenanthrydine, spiro[cyclohexane-1,6'-[6H]pyrrolo[3,2,1-ij]quinoline], 4,9-methanopyrrolo[3,2,1-1m][1]benzoazocine, spiro[cycloheptane-1,6'-[6H]pyrrolo[3,2,1-ij]quinoline], 1H-pyrano[3,4-d]pyrrolo[3,2,1-jk][1]benzazepine, 3H-benzo[b]pyrrolo[3,2,1-jk][4,1]benzoxazepine, 7H-indolo[1,7-ab][4,1]benzoxazepine, benzo[b]pyrrolo[3,2,1-jk][1,4]benzodiazepine, indolo[1,7-ab][1,4]benzodiazepine, indolo[1,7-ab][1]benzazepine, indolo[7,1-ab][3]benzazepine, 1H-cyclohepta[d][3,2,1-jk][1]benzazepine, spiro[azepino [3,2,1-hi]indole-7(4H), 1'-cycloheptane], 4H-5,11-methanopyrrolo[3,2,1-no][1]benzazacycloundecine, and spiro[azepino[3,2,1-hi]indole-7(4H),1'-cyclooctane].

Among them, further preferable is a group represented by the formula:

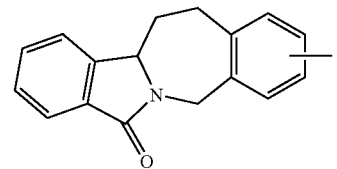

In addition, when the "aromatic ring group" in the "optionally condensed 5- or 6-membered aromatic ring group" represented by Ar is, for example, "an aromatic heterocyclic group", examples of fusion of the "aromatic heterocyclic group" include:

(d) the case where the aromatic heterocyclic group is condensed with a monocyclic aromatic ring which may have a substituent, and (e) the case where the aromatic heterocyclic group is condensed with a di- to tri-cyclic aromatic ring which may have a substituent, or condensed with two same or different monocyclic aromatic rings.

Specific examples include 1-, 2- or 3-indolyl; 1-, 2- or 3-isoindolyl; 2- or 3-benzofuranyl; 2- or 3-benzothiofuranyl; 1- or 3-benzimidazolyl; 2-benzoxazolyl; 2-benzothiazolyl; 1,2-benzisothiazol-3-yl; 1,2-benzisoxazol-3-yl, 2-, 3- or 4-quinolyl; 1-, 3- or 4-isoquinolyl; 2- or 3-quinoxalinyl; 1- or 4-phthalazinyl; naphthyridinyl such as 1,8-naphthyridin-2-yl, and 1,5-naphthyridin-3-yl; 2- or 4-quinazolinyl; 3- or 4-cinnolinyl; 9-acridinyl; 2-, 6- or 8-purinyl; 2-, 4-, 6- or 8-pteridinyl.

Preferable examples of Ar include groups represented by the formula:

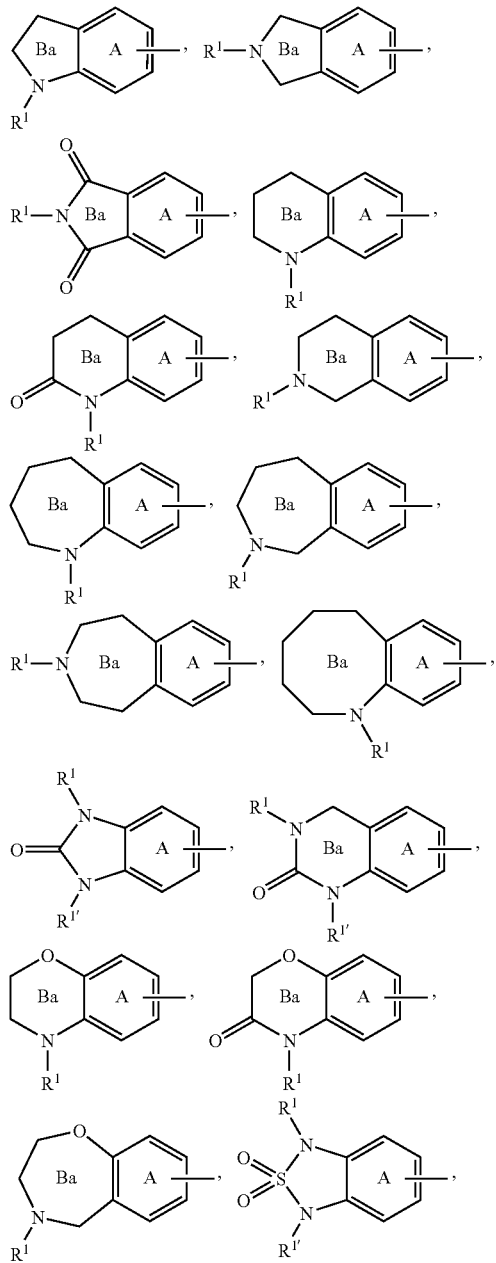

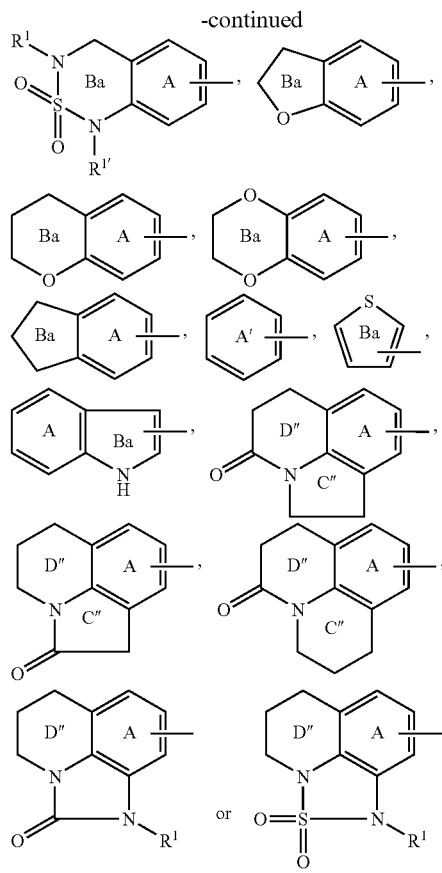

wherein A' ring is as defined for A ring, and the other symbols are as defined above.

Herein, as A ring and A' ring, a benzene ring which may have 1 to 4 substituent(s) selected from (i) halogen (fluoro ect. ), (ii) $C_{1-6}$ alkylamino (methylamino etc.), (iii) halogeno$C_{1-6}$ alkoxy (trifluoromethoxy)ect.), (iv) amino, (v) (mono or di) $C_{1-6}$ alkylamino (methylamino, ethylamino, dimethylamino, diethylamino etc.), (vi) 1-pyrrolidinyl, (vii) piperidino, (viii) 1-piperazinyl, (ix) N-methyl-1-piperazinyl, (x) N-acetyl-1-piperazinyl (xi) morpholino, (xii) hexamethyleneimino, (xiii) imidazolyl, (xiv) $C_{1-6}$ alkyl (propyl etc.) which may be substituted with carboxy optionally esterified with $C_{1-6}$alkyl (methyl etc.), (xv) lower alkyl-carbonylamino (acetylamino etc.), (xvi) lower alkylsulfonylamino (methylsulfonylamino etc.), (xvii) aminosulfonyl, (xviii) (mono or di) $C_{1-6}$ alkylaminosulfonyl, (xix) 5- to 7-membered cyclic amino-sulfonyl ((1-pyrrolidinyl)sulfonyl, piperidinosulfonyl, (1-piperazinyl) sulfonyl, morpholinosulfonyl etc.), (xx) carbamoyl, (xxi) (mono or di) $C_{1-6}$ alkylcarbamoyl, (xxi) 5- to 7-membered cyclic amino-carbonyl ((1-pyrrolidinyl)carbonyl, piperidinocarbonyl, (1-piperazinyl)carbonyl, morpholinocarbonyl etc.), and (xxii) cyano is preferred. More preferably, A ring is a benzene ring which may have 1 or 2 substituent(s) selected from aminosulfonyl, mono- or di-$C_{1-6}$ alkylaminosulfonyl, carbamoyl and mono- or di-$C_{1-6}$ alkyl-carbamoyl, and A' ring is a benzene ring which has 1 or 2 substituent(s) selected from aminosulfonyl, mono- or di-$C_{1-6}$ alkylaminosulfonyl, $C_{1-6}$ alkyl-carbonylamino and $C_{1-6}$alkylsulfonylamino, and further may have 1 to 4 substituent(s) (e.g. $C_{1-6}$alkoxy etc.).

In addition, it is, preferable that Ba ring, C" ring and D" ring may have 1 or 2 substituent(s) selected from $C_{1-6}$ alkyl, $C_{1-6}$ alkyl-carbonylamino and $C_{1-6}$ alkylsulfonylamino, and R' and $R^{1'}$ are (1) a hydrogen atom, (2) a $C_{1-6}$ alkyl group or a $C_{7-16}$ aralkyl group, each of which may have 1 or 2 substituent(s) selected from hydroxy and $C_{1-6}$alkoxy-carbonyl, or (3) a group represented by the formulas: —(C=O)—$R^{2'}$, —(C=O)—$NR^{2'}$—$R^{3'}$ or —$SO_2R^{2'}$ [wherein $R^{2'}$ and $R^{3'}$represent hydrogen atom, optionally halogenated $C_{1-6}$ alkyl or $C_{6-10}$ aryl, respectively], respectively.

The "spacer haivng a main chain of 1 to 10 of atoms" in the "spacer having a main chain of 1 to 10 of atoms which may have a substituent" represented by L means an interval in which 1 to 10 atom(s) of a main chain are linked. Herein, the "atom number of main chain" is counted so that atoms of a main chain become minimum. For example, an atom number of 1,2-cyclopentylene is counted as 2, and an atom number of 1,3-cyclopentylene is counted as 3.

Examples of the "spacer having a main chain of 1 to 10 of atoms which may have a substituent" include a combination of 1 to 5, preferably 1 to 3 divalent group(s) selected from —O—, —S—, —CO—, —SO—, —$SO_2$—, —$NR^{10}$—($R^{10}$ represents hydrogen atom, optionally halogenated $C_{1-10}$ alkyl, optionally halogenated $C_{1-6}$ alkyl-carbonyl, optionally halogenated $C_{1-6}$ alkylsulfonyl), a divalent $C_{1-10}$ non-cyclic hydrocarbon group which may have a substituent, a divalent $C_{3-9}$ cyclic hydrocarbon group which may have a substituent and a divalent heterocyclic group which may have a substituent.

Examples of the "substituent" in the "spacer having a main chain of 1 to 10 of atoms which may have a substituent", that is, the "substituent" in the "divalent $C_{1-10}$ non-cyclic hydrocarbon group which may have a substituent", the "divalent $C_{3-9}$ cyclic hydrocarbon group which may have a substituent" and the "divalent heterocyclic group which may have a substituent" include 1 to 5, preferably 1 to 3 substituent(s) selected from halogen atom (e.g fluorine, chlorine, bromine, iodine etc.), oxo, $C_{1-3}$ alkylenedioxy (e.g. methylenedioxy, ethylenedioxy etc.), nitro, cyano, optionally halogenated $C_{1-6}$alkoxy, optionally halogenated $C_{1-6}$ alkylthio, hydroxy, amino, mono- or di-$C_{1-6}$ alkylamino, formyl, carboxy, carbamoyl, thiocarbamoyl, optionally halogenated $C_{1-6}$ alkyl-carbonyl, $C_{1-6}$ alkoxy-carbonyl, mono- or di-$C_{1-6}$ alkyl-carbamoyl, optionally halogenated $C_{1-6}$ alkylsulfonyl, formylamino, optionally halogenated $C_{1-6}$ alkyl-carboxamide, $C_{1-6}$ alkoxy-carboxamide, $C_{1-6}$ alkylsulfonylamino, $C_{1-6}$ alkyl-carbonyloxy, $C_{1-6}$ alkoxy-carbonyloxy, mono-, di-$C_{1-6}$ alkyl-carbamoyloxy and phenyl. Among them, halogen atom such as fluorine, oxo, hydroxy, and phenyl are preferred.

Examples of the "divalent $C_{1-10}$ non-cyclic hydrocarbon group" in the "divalent. $C_{1-10}$ non-cyclic hydrocarbon group which may have a substituent" include $C_{1-10}$ alkylene, $C_{2-10}$ alkenylene, and $C_{2-10}$ alkynylene.

Examples of the "$C_{1-10}$ alkylene" include —$CH_2$—, —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)_3CH(CH_3)$—, —$(CH_2)_4CH(CH_3)$—, —$(CH_3)CHCH_2$—, —$(CH_3)CH(CH_2)_2$—, and —$CH(CH_3))_2$—.

Examples of the "$C_{2-10}$ alkenylene" include —CH=CH—, —$CH_2$—CH=CH—, —$C(CH_3)_2$—CH=CH—, —$CH_2$—CH=CH—$CH_2$—, —$CH_2$—$CH_2$—CH=CH—, —CH=CH—CH=CH—, and —CH=CH—$CH_2$—$CH_2$—$CH_2$—.

Examples of the "$C_{2-10}$ alkynylene" include —C≡C—, —$CH_2$—C≡C—, —$CH_2$—C≡C—$CH_2$—$CH_2$—.

Examples of the "divalent $C_{3-9}$ cyclic hydrocarbon group" in the "divalent $C_{3-9}$cyclic hydrocarbon group which may have a substituent" include $C_{3-9}$cycloalkylene, $C_{3-9}$ cycloalkenylene, and $C_{6-14}$ arylene (phenylene etc.).

Examples of the "$C_{3-9}$ cycloalkylene" include:

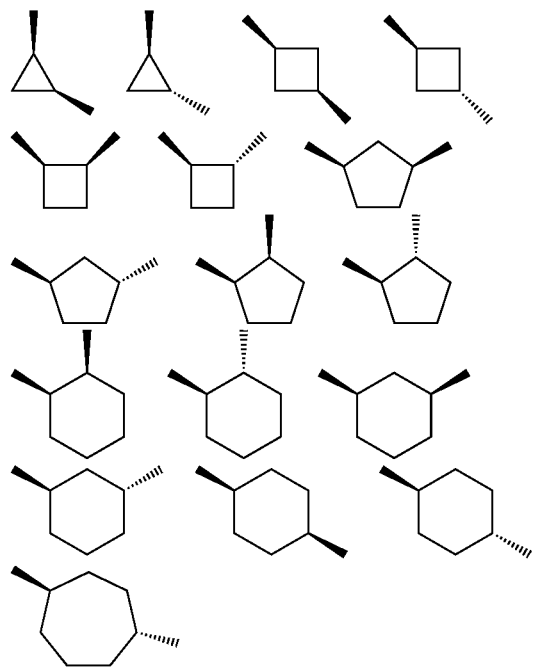

and the like.

The examples of the "$C_{3-9}$cycloalkenylene" inlude:

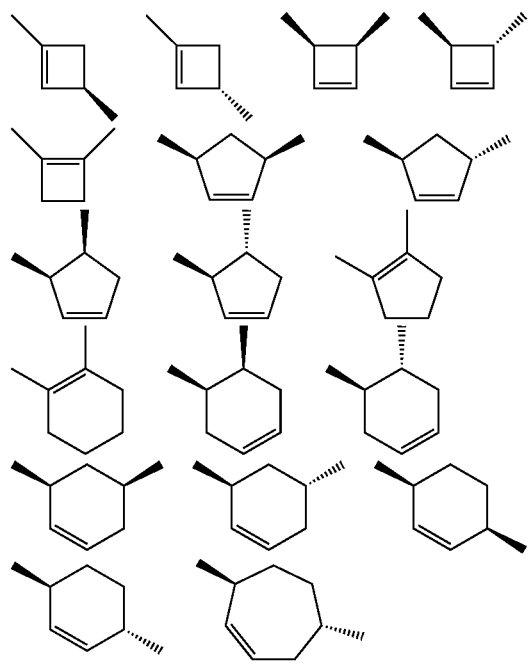

and the like.

Examples of the "divalent heterocyclic group" in the "divalent hetercyclic group which may have a substituent" include groups obtained by removing two hydrogen atoms from 4- to 14-membered (preferably 5- to 9-membered) aromatic or non-aromatic heterocyclic rings containing 1 to 4 hetero atom(s) selected from a nitrogen atom, an oxygen atom and a sulfur atom. Examples of such the aromatic or non-aromatic heterocyclic ring include the same rings as those exemplified for the "heterocyclic ring which may have a substituent" represented by the above-mentioned B ring.

As L, $C_{1-10}$ alkylene which may have a substituent is preferred, inter alia, a $C_{2-6}$ alkylene group which may have 1 to 4 substituent(s) selected from halogen atom, hydroxy, oxo and phenyl (e.g. —$(CH_2)_2$—, —$(CH_2)_3$—, —$(CH_2)_4$—, —$(CH_2)_5$—, —$(CH_2)_6$—, —$CHFCH_2$—, —$CHF(CH_2)_2$—, —$CHF(CH_2)_3$—, —$CHF(CH_2)_4$—, —$CF_2CH_2$—, —$CF_2(CH_2)_2$—, —$CF_2(CH_2)_3$—, —$CF_2(CH_2)_4$, —$(C_2)_3CH(CH_3)$——$(CH_2)_4CH(CH_3)$—, —$(CH_2)_3CH(CF_3)$—, —$(CH_2)_4CH(CF_3)$—, —$(CH_3)CHCH_2$—, —$(CH_3)CH(CH_2)_2$—, —$(CH(CH_3))_2$—, —$CH_2CH(OH)$—, —$CH_2CO$—, —(Ph)$CHCH_2$— etc.) is preferable and, further, $C_{3-7}$ cycloalkylene or a combination of $C_{3-7}$ cycloalkylene and $C_{1-4}$ alkylene (e.g.

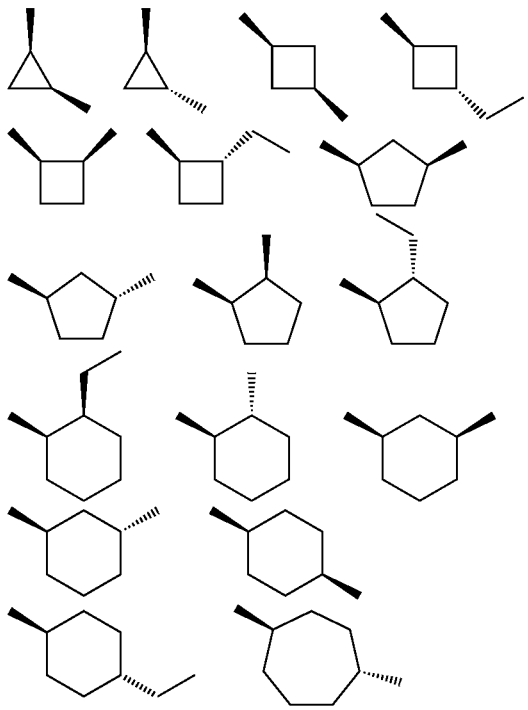

is also preferable.

Examples of the ring formed between L and Ar include 1-oxoindan-2-yl, 1-oxo-1,2,3,4-tetrahydronaphthalen-2-yl, 5-oxo-6,7,8,9-tetrahydro-5H-benzo[a]cyclohepten-6-yl, 2,5-dioxo-1,2,3,5,6,7-hexahydroindeno[5,6-d]imidazol-6-yl, 2,5-dioxo-2,3,5,6,7,8-hexahydro-1H-naphtho[2,3-d]imidazol-6-yl, 2,5-dioxo-1,2,3,5,6,7,8,9-octahydrocyclohepta[f]benzimidazol-6-yl, 2,8-dioxo-2,3,4,6,7,8-hexahydro-1H-cyclopenta[g]quinazolin-7-yl, 2,9-dioxo-1,2,3,4,6,7,8,9-octahydrobenzo[g]quinazolin-8-yl, 2,10-dioxo-2,3,4,6,7,8,9,10-octahydro-1H-cyclohepta[g]qunazolin-9-yl, 2,2-dioxido-5-oxo-3,5,6,7-tetrahydro-1H-indeno[5,6-c][1,2,5]thiadiazol-6-yl, 2,2-dioxido-5,6,7,8-hexahydronaphto[2,3-c][1,2,5]thiadiazol-6-yl, 2,2-dioxido-5-oxo-3,5,6,7,8.9-hexahydro-1H-cyclohepta[f][2,1,3]benzothiadiazol-6-yl, 2,2-dioxido-8-oxo-1,3,4,6,7,8-hexahydroindeno[5,6-c][1,2,6]thiadiazin-7-yl, 2,2-dioxide-9-oxo-3,4,6,7,8,9-hexahydro-1H-naphtho[2,3-c][1,2,6]thiadiazin-8-yl, and 2,2-dioxide-10-oxo-1,3,4,6,7,8,9,10-octahydrocyclohepta[g][2,1,3]benzothiadiazin-9-yl.

Preferable example includes a ring represented by the formula:

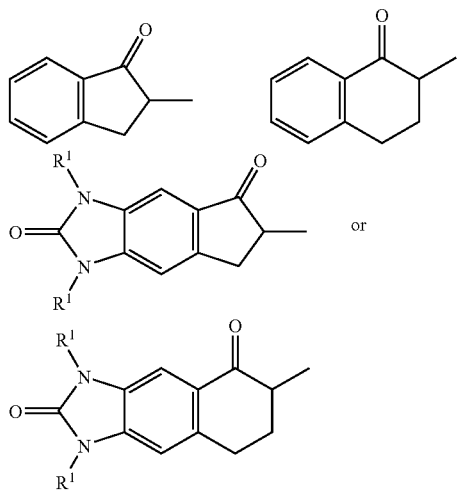

wherein symbols are as defined above.

Examples of the "amino group which may have a substituent" represented by Y include a group represented by the formula:

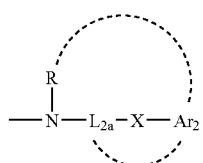

wherein R represents a hydrogen atom or a hydrocarbon group which may have a substituent, $L_{2a}$ represents a $C_{1-4}$ alkylene group which may have a substituent, X represents a bond, an oxygen atom or a nitrogen atom, and $Ar_2$ represents an aromatic ring group which may have a substituent, or $Ar_2$ and R, or $Ar_2$ and $L_{2a}$ may be linked together to form a ring.

Examples of the "hydrocarbon group which may have a substituent" represented by R include the same groups as "hydrocarbon groups which may have a substituent" represented by $R^1$.

Examples of the "substituent" in the "hydrocarbon group which may have a substituent" represented by R include the same groups as "substituents" in the "hydrocarbon group which may have a substituent" represented by $R^1$, and the number of substituents(s) is 1 to 3.

Examples of the "$C_{1-4}$ alkylene group which may have a substituent" represented by $L_{2a}$ include groups having the number of carbon chains of 1 to 4 among "$C_{1-10}$ alkylene groups" exemplified for the "spacer having a main chain of 1 to 10 atoms which may have a substituent" represented by L.

Examples of the "substituent" in the "$C_{1-4}$ alkylene group which may have a substituent" represented by $L_{2a}$ include the same groups as "substituents" in the "spacer having a main chain of 1 to 10 atoms which may have a substituent" represented by L.

Examples of the "hydrocarbon group which may have a substituent", the "acyl group" and the "heterocyclic group which may have a substituent" represented by $R^{1a}$ in the "a bond, an oxygen atom or $NR^{1a}$ ($R^{1a}$ represents a hydrogen atom, a hydrocarbon group which may have a substituent, an acyl group or a heterocyclic group which may have a substituent)" represented by X include the same groups as those in $R^1$.

Examples of the "aromatic ring group" in the "aromatic ring group which may have a substituent" represented by $Ar_2$ include the same groups as "optionally condensed 5- or 6-membered aromatic ring groups" represented by Ar. Examples of the "substituent" in the "aromatic ring group which may have a substituent" represented by $Ar_2$ include the same groups as "substituents" in the "represents an optionally condensed 5- or 6-membered aromatic ring group, and said aromatic ring group may have a substituent" represented by Ar, and the number of substituent(s) is 1 to 5.

Examples of the ring formed by binding $Ar_2$ and R together include rings represented by the formula:

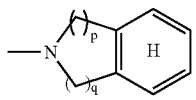

wherein p and q represent an integer of 1 to 3, respectively, and H ring represents a benzene ring which may have 1 to 3 substituent(s) selected from halogen, hydroxy, optionally halogenated $C_{1-6}$ alkyl and optionally halogenated $C_{1-6}$ alkoxy.

Examples of the ring formed by binding $Ar_2$ and $L_{2a}$ include rings represented by the formula:

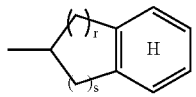

wherein r represents an integer of 0 to 2, s represents an integer of 1 to 3, and r+s is an integer of 2 to 5, and H ring is as defined above. Examples of the "nitrogen-containing saturated heterocyclic group" in the "nitrogen-containing saturated heterocyclic group which may have a substituent" represented by Y include 5- to 9-membered (preferably 5- to 7-membered) nitrogen-containing saturated heterocyclic groups which may contain 1 to 3 hetero atom(s) selected from a nitrogen atom, an oxygen atom and a sulfur atom in addition to carbon atoms and one nitrogen atom. Specific examples include groups represented by the formulas:

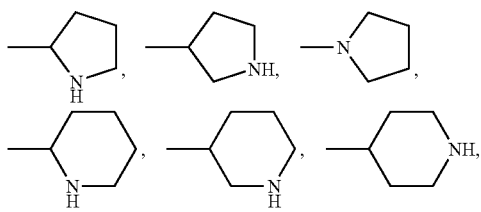

-continued

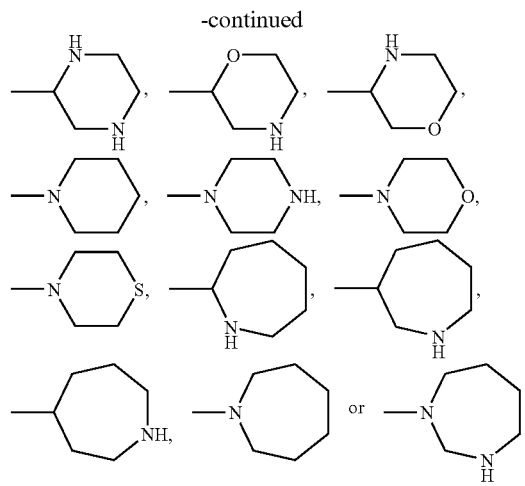

Among them, preferred is a 6-membered cyclic group.

Further preferable is a group represented by the formula:

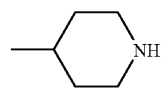

Examples of the "substituent" in the "nitrogen-saturated heterocyclic group which may have a substituent" include the same groups as "substituents" in the "heterocyclic ring which may have a substituent" represented by above-mentioned B ring, and the number of substituent(s) is 1 to 5. In addition, nitrogen in the "nitrogen-containing saturated heterocyclic group" of the "nitrogen-containing saturated heterocyclic group which may have a substituent" may have the same group as a group represented by the formula:

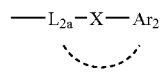

wherein respective symbols are as defined above.

Preferable examples of Y include groups represented by the formulas:

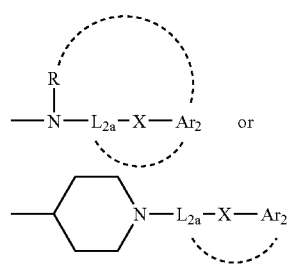

wherein respective symbols are as defined above.

As R, (i) a hydrogen atom, (ii) a $C_{1-4}$ alkyl group which may have 1 to 3 substituent(s) selected from halogen atom (preferably fluoro etc.) and hydroxy, or (iii) a C$_{7-16}$ aralkyl (benzyl etc.) is preferable, and a hydrogen atom or a C$_{1-4}$ alkyl group is more preferable.

As L$_{2a}$, a C$_{2-4}$ alkylene group which may have 1 to 4 substituent(s) selected from halogen atom, hydroxy, oxo and phenyl (e.g. —(CH$_2$)$_2$—, —(CH$_2$)$_3$—, —(CH$_2$)$_4$—, —CHFCH$_2$—, —CHF(CH$_2$)$_2$—, —CHF(CH$_2$)$_3$—, —CF$_2$CH$_2$—, —CF$_2$(CH$_2$)$_2$—, —CF$_2$(CH$_2$)$_3$—, —(CH$_3$)CHCH$_2$—, —(CH$_3$)CH(CH$_2$)$_2$—, —(CH(CH$_3$))$_2$—, —CH$_2$CH(OH)—, —CH$_2$CO—, —(Ph)CHCH$_2$— etc.) is preferable, a C$_{2-3}$ alkylene group which may have hydroxy, oxo or phenyl. (e.g. —(CH$_2$)$_2$—, —(CH$_2$)$_3$—, —(CH$_3$)CHCH$_2$—, —(Ph)CHCH$_2$—, —CH$_2$CH(OH)—, —CH$_2$CO— etc.) is more, preferable, and an ethylene group is most preferable.

As X, a bond, an oxygen atom or NH is preferable, and a bond is more preferable.

Preferable examples of Ar$_2$ include:
(1) (i) a C$_{6-10}$ aryl group (phenyl etc.). or (ii) a 5- or 6-membered aromatic heterocyclic group containing 1 to 4 hetero atom(s) selected from a nitrogen atom, an oxygen atom and a sulfur atom (optionally condensed with a benzene ring) (e.g. thienyl, furyl, pyrrolyl, imidazolyl, pyrazolyl, thiazolyl, isothiazolyl, oxazolyl, isooxazolyl, pyridyl, pyrazinyl, pyrimidinyl, pyridazinyl, oxadiazolyl, thiadiazolyl, furazanyl, indolyl, isoindolyl, benzofuranyl, quinolyl, isoquinolyl, naphthyridinyl, quinazolinyl, cinnolinyl, acridinyl etc.), each of which may have 1 to 5 (preferably 1 to 3) substituent(s) selected from halogen (fluoro, chloro etc.), C$_{1-6}$ alkyl (methyl, ethyl etc.), halogenoC$_{1-6}$alkyl (trifluoromethyl etc.), hydroxy, C$_{1-6}$alkoxy (methoxy, ethoxy etc.), halogenoC$_{1-6}$alkoxy (trifluoromethoxy, trifluoroethoxy etc.), nitro, amino, cyano, carbamoyl, each of which is optionally substituted with C$_{3-6}$ alkyl, amino which may be substituted with carbamoyl or formyl (NHCHO, NHCONH$_2$, NHCONHMe etc.), C$_{1-3}$ alkylenedioxy (methylenedioxy etc.), aminocarbonyloxy group which may be substituted with C$_{1-6}$ alkyl (aminocarbonyloxy, methylaminocarbonyloxy, ethylaminocarbonyloxy, dimethylaminocarbonyloxy, diethylaminocarbonyloxy etc.), 5- to 7-membered cyclic amino-carbonyloxy ((1-pyrrolidinyl) carbonyloxy, piperidinocarbonyloxy etc.), aminosulfonyl, mono-C$_{1-6}$ alkylaminosulfonyl and di-C$_{1-6}$ alkylaminosulfonyl,
(2) the case where Ar$_2$ and R are linked together to form a ring represented by the formula:

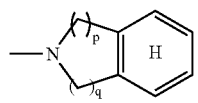

wherein symbols are defined above, or
(3) the case where Ar$_2$ and L$_2$ are linked together to form a ring represented by the formula:

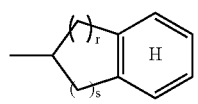

wherein symbols are as defined above.
More preferable examples of Ar$_2$ include (i) a C$_{6-10}$ aryl group (phenyl etc.) or (ii) a 5- or 6-membered aromatic heterocyclic group (optionally condensed with a benzene ring) containing 1 to 4 hetero atom(s) selected from a nitrogen atom, an oxygen atom and a sulfur atom (tienyl, indolyl etc.), each of which may have 1 to 3 substituent(s) selected from halogen, nitro, hydroxy, optionally halogenated C$_{1-6}$ alkyl, optionally halogenated C$_{1-6}$ alkoxy and aminosulfonyl.

More preferable Y is a group represented by the formula:

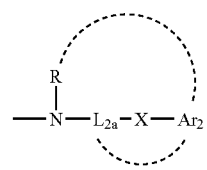

wherein respective symbols are as defined above.

Preferable Compound (I) is a compound wherein Ar is a group represented by the formulas:

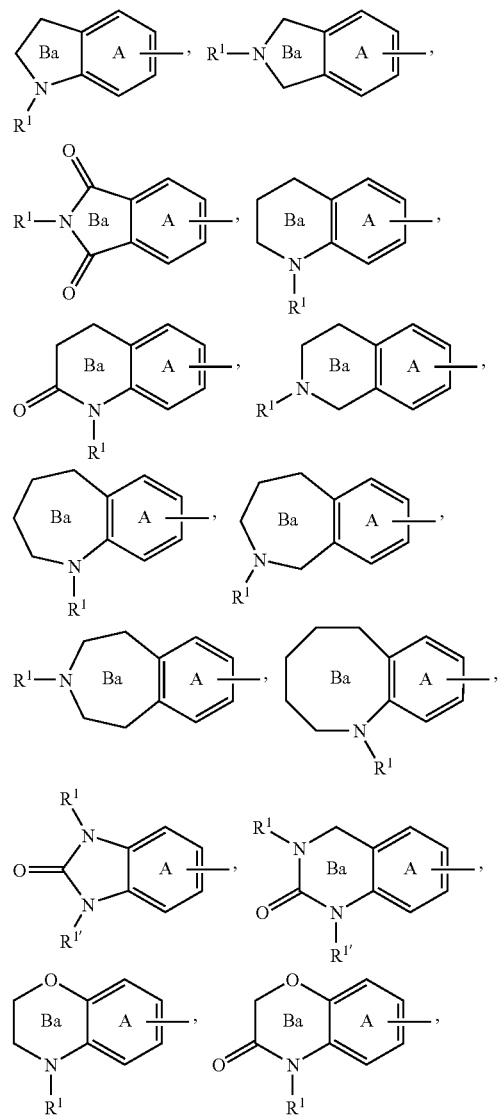

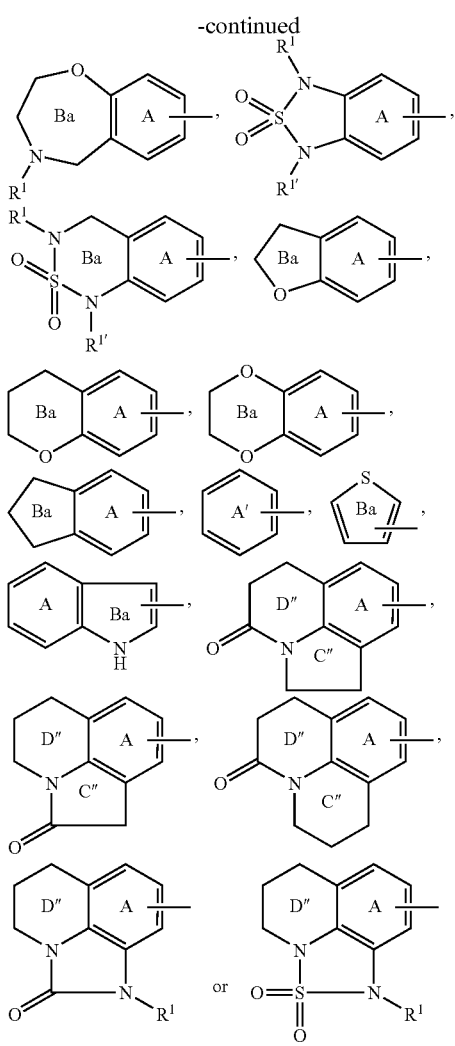

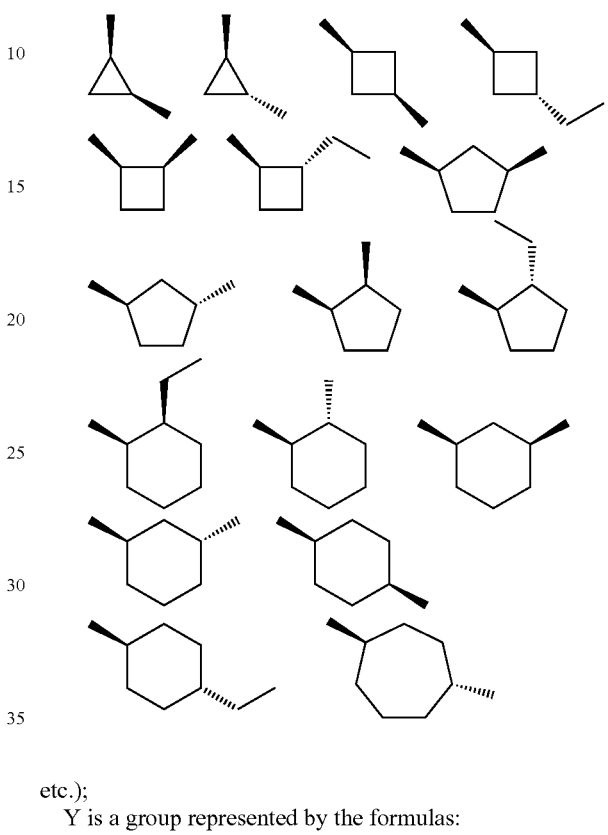

wherein symbols are as defined above, (A ring is preferably a benzene ring which may have 1 or 2 substituent(s) selected from aminosulfonyl, mono- or di-$C_{1-6}$ alkylaminosulfonyl, carbamoyl and mono- or di-$C_{1-6}$ alkyl-carbamoyl, A' ring is preferably a benzene ring which has 1 or 2 substituent(s) selected from aminosulfonyl, mono-or di-$C_{1-6}$ alkylaminosulfonyl, $C_{1-6}$ alkyl-carbonylamino and $C_{1-6}$ alkylsulfonylamino, and further may have 1 to 4 substituent(s) (e.g. $C_{1-6}$ alkoxy etc.), Ba ring, C″ ring and D″ ring may preferably have 1 or 2 substituent(s) selected from $C_{1-6}$ alkyl, $C_{1-6}$ alkylcarbonylamino and $C_{1-6}$ alkylsulfonylamino, respectively, and $R^1$ and $R^{1'}$ preferably are (1) a hydrogen atom, (2) a $C_{1-6}$ alkyl group or a $C_{7-16}$ aralkyl group (benzyl etc.), each of which may have 1 or 2 substituent(s) selected from hydroxy and $C_{1-6}$ alkoxy-carbonyl, or (3) a group represented by the formula: —(C=O)—$R^{2'}$, —(C=O)—$NR^{2'}R^{3'}$ or —$SO_2R^{2'}$ [wherein $R^{2'}$ and $R^{3'}$ represent a hydrogen atom, optionally halogenated $C_{1-6}$ alkyl or $C_{6-10}$ aryl, respectively], respectively);

L is (1) a $C_{2-6}$ alkylene group which may have 1 to 4 substituent(s) selected from halogen atom, hydroxy, oxo and phenyl (e.g., —$(CH_2)_2$—, —$(CH_2)_3$—, —$(CH_2)_4$—, —$(CH_2)_5$—, —$(CH_2)_6$—, —$CHFCH_2$—, —$CHF(CH_2)_2$—, —$CHF(CH_2)_3$—, —$CHF(CH_2)_4$—, —$CF_2CH_2$—, —$CF_2(CH_2)_2$—, —$CF_2(CH_2)_3$—, —$CF_2(CH_2)_4$—, —$(CH_2)_3CH$ ($CH_3$)—, —$(CH_2)_4CH(CH_3)$—, —$(CH_2)_3CH(CF_3)$—, —$(CH_2)_4CH(CF_3)$—, —$(CH_3)CHCH_2$—, —$(CH_3)CH (CH_2)_2$—, —$(CH(CH_3))_2$—, —$CH_2CH(OH)$—, —$CH_2CO$—, —$(Ph)CHCH_2$— etc.), or (2) $C_{3-7}$ cycloalkylene or a combination of $C_{3-7}$ cycloalkylene and $C_{1-4}$ alkylene (e.g.

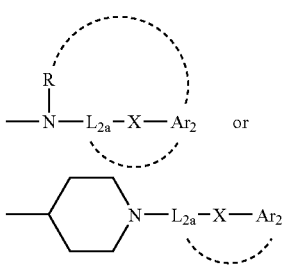

etc.);

Y is a group represented by the formulas:

wherein respective symbols are as defined above,

R is (i) a hydrogen atom, (ii) a $C_{1-4}$ alkyl group which may have 1 to 3 substituent(s) selected from a halogen atom (e.g. fluoro etc.) and hydroxy, or (iii) $C_{7-16}$ aralkyl (benzyl etc.);

$L_2a$ is a $C_{2-4}$ alkylene group which may have 1 to 4 substituent(s) selected from halogen atom, hydroxy, oxo and phenyl (e.g. —$(CH_2)_2$—, —$(CH_2)_3$—, —$(CH_2)_4$—, —$CHFCH_2$—, —$CHF(CH_2)_2$—, —$CHF(CH_2)_3$—, —$CF_2CH_2$—, —$CF_2(CH_2)_2$—, —$CF_2(CH_2)_3$—, —$(CH_3)CHCH_2$—, —$(CH_3)CH(CH_2)_2$—, —$(CH(CH_3))_2$—, —$CH_2CH(OH)$—, —$CH_2CO$—, —$(Ph)CHCH_2$— etc.);

X is a bond, an oxygen atom or NH;

$Ar_2$ is (1) (i) a $C_{6-10}$ aryl group (phenyl etc.) or (ii) a 5- or 6-membered aromatic heterocyclic group (optionally condensed with a benzene ring) containing 1 to 4 hetero atom(s) selected from a nitrogen atom, an oxygen atom and a sulfur atom (e.g. thienyl, furyl, pyrrolyl, imidazolyl, pyrazolyl, thiazolyl, isothiazolyl, oxazolyl, isooxazolyl, pyridyl, pyrazinyl, pyrimidinyl, pyridazinyl, oxadiazolyl, thiadiazolyl, furazanyl, indolyl, isoindolyl, benzofuranyl, quinolyl, isoquinolyl, naphthyridinyl, quinazolinyl, cinnolinyl, acridinyl etc.), each of which may have 1 to 5 (preferably 1 to 3) substituent(s) selected from halogen (fluoro, chloro etc,), $C_{1-6}$ alkyl (methyl, ethyl etc.), halogeno$C_{1-6}$ alkyl (trifluoromethyl etc.), hydroxy, $C_{1-6}$ alkoxy (methoxy, ethoxy etc,), halogeno$C_{1-6}$ alkoxy (trifluoromethoxy, trifluoroethoxy etc.), nitro, amino, cyano, carbamoyl, carbamoyl which may be substituted with $C_{1-6}$ alkyl or amino which may be substituted with formyl (NHCHO, NHCONH$_2$, NHCONHMe etc.), $C_{1-3}$ alkylenedioxy (methylenedioxy etc.), an aminocarbonyloxy group which may be substituted with $C_{1-6}$ alkyl (aminocarbonyloxy, methylaminocarbonyloxy, ethylaminocarbonyloxy, dimethylaminocarbonyloxy, diethylaminocarbonyloxy etc.), 5- to 7-membered cyclic amino-carbonyloxy ((1-pyrrolidinyl) carbonyloxy, piperidinocarbonyloxy etc.), aminosulfonyl, mono-$C_{1-6}$ alkylaminosulfonyl and di-$C_{1-6}$ alkylaminosulfonyl, (2) the case where $Ar_2$ and R are linked together to form a ring represented by the formula:

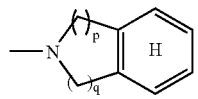

wherein symbols are as defined above, or (3) the case where $Ar_2$ and $L_2$ are linked together to form a ring represented by the formula:

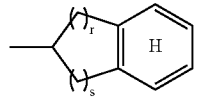

wherein symbols are as defined above.

In addition, among Compound(I), a compound represented by the formula:

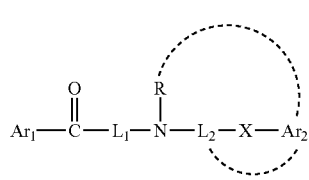

(Ia)

wherein $Ar_1$ represents a dicyclic to tetracyclic condensed benzene ring group which may have a substituent, $L_1$ represents a $C_{4-6}$ alkylene group which may have a substituent, and the other respective symbols are as defined above, (hereinafter, abbreviated as Compound (Ia) in some cases) or a salt thereof is a novel compound.

The "dicyclic to tetracyclic condensed benzene ring group" in the "dicyclic to tetracyclic condensed benzene ring which may have a substituent" represented by $Ar_1$ include the same groups as those exemplified with respect to the condensed benzene ring group exemplified as an example of condensation of the "phenyl group" in the case that the "5- or 6-membered aromatic ring group" in the "optionally condensed 5- or 6-membered aromatic ring group" represented by Ar is "phenyl group".

The "substituent" in the "dicyclic to tetracyclic condensed benzene ring group which may have a substituent" represented by $Ar_1$ include the same groups as those exemplified with respect to the "substituent" in the "represents optionally condensed 5- or 6-membered aromatic ring group, and said aromatic ring group may have a substituent" represented by Ar.

Preferable examples of $Ar_1$ include groups represented by the formulas:

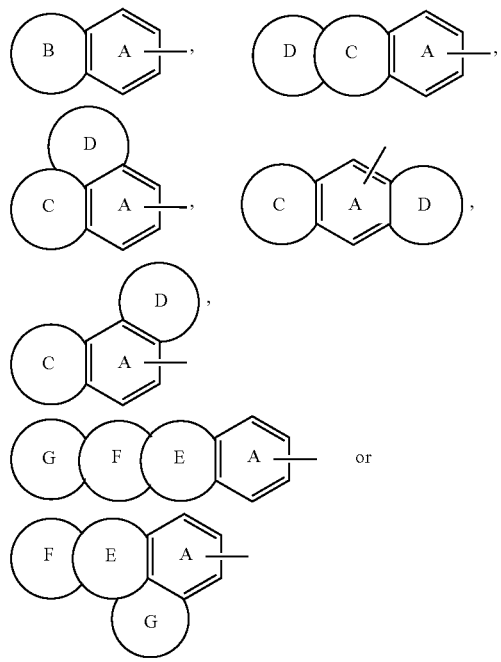

wherein respective symbols are as defined above,

More preferable examples of $Ar_1$ include groups represented by the formulas:

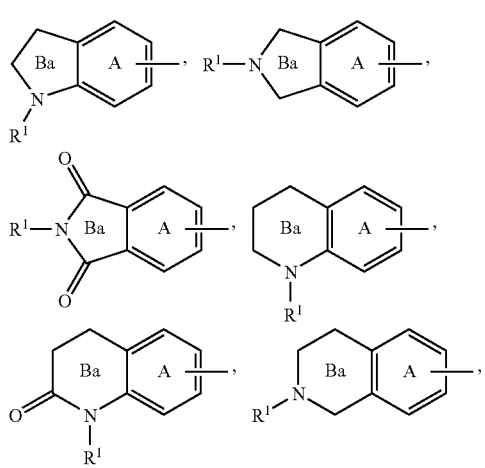

-continued

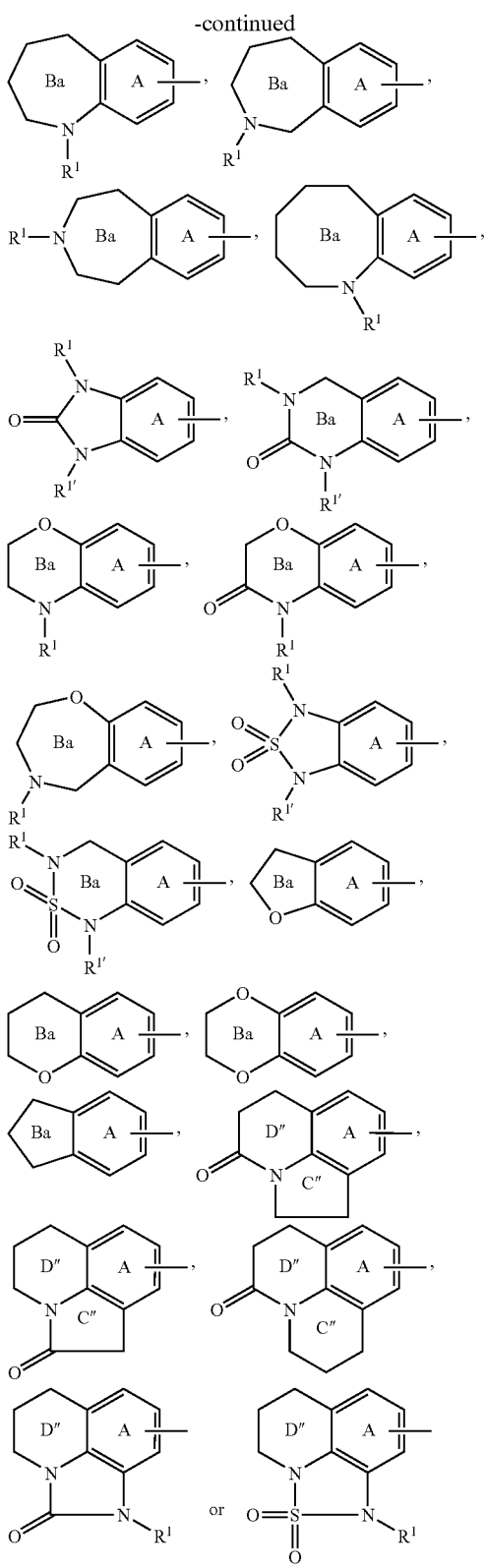

wherein symbols are as defined above.

Herein, as A ring, a benzene ring which may have 1 to 2 substituent(s) selected from (i) halogen (fluoro etc.), (ii) $C_{1-6}$ alkoxy (methoxy etc.), (iii) halogeno$C_{1-6}$ alkoxy (trifluoromethoxy etc.), (iv) amino, (v) (mono or di)$C_{1-6}$ alkylamino (methylamino, ethylamino, dimethylamino, diethylamino etc.), (vi) 1-pyrrolidinyl, (vii) piperidino, (viii) 1-piperazinyl, (ix) N-methyl-1-piperazinyl, (x) N-acetyl-1-piperadinyl, (xi) morpholino, (xii) hexamethyleneimino, (xiii) imidazolyl, (xiv) $C_{1-6}$ alkyl (propyl etc.) which may be substituted with carboxy optionally esterified with $C_{1-6}$alkyl (methyl etc.), (xv) lower alkyl-carbonylamino (acetylamino etc.), (xvi) lower alkylsulfonylamino (methylsulfonylamino etc.), (xvii) aminosulfonyl, (xviii) (mono or di) $C_{1-6}$ alkylaminosulfonyl, (xix) 5- to 7-membered cyclic amino-sulfonyl ((1-pyrrolidinyl)sulfonyl, piperidinosulfonyl, (1-piperazinyl)sulfonyl, morpholinosulfonyl etc.), (xx) carbamoyl, (xxi) (mono or di) $C_{1-6}$ alkylcarbamoyl, (xxi) 5- to 7-membered cyclic amino-carbonyl ((1-pyrrolidinyl)carbonyl, piperidinocarbonyl, (1-piperazinyl)carbonyl, morpholinocarbonyl etc.) and (xxii) cyano is preferred. More preferably, A ring is a benzene ring which may have 1 or 2 substituent(s) selected from aminosulfonyl, mono-or di-$C_{1-6}$ alkylaminosulfonyl, carbamoyl and mono-or di-$C_{1-6}$ alkyl-carbamoyl.

In addition, it is preferable that. Ba ring, C" ring and D" ring, may have 1 or 2 substituent(s) selected from $C_{1-6}$ alkyl, $C_{1-6}$ alkyl-carbonylamino and $C_{1-6}$ alkylsulfonylamino, respectively, and $R^1$ and $R^{1'}$ are (1) a hydrogen atom, (2) a $C_{1-6}$ alkyl group or a $C_{7-16}$aralkyl group, each of which may have 1 or 2 substituent(s) selected from hydroxy and $C_{1-6}$ alkoxycarbonyl, or (3) a group represented by the formula: —(C=O)—$R^{2'}$, —(C=O)—$NR^{2'}R^{3'}$ or —$SO_2R^{2'}$ [wherein $R^{2'}$ and $R^{3'}$ represent a hydrogen atom, optionally halogenated $C_{1-6}$ alkyl or $C_{6-10}$ aryl, respectively].

Examples of the "$C_{4-6}$ alkylene group which may have a substituent" represented by $L_1$ include those having carbon chain number of 4 to 6 among the "$C_{1-10}$ alkylene group" exemplified with respect to the "spacer having a main chain of 1 to 10 atoms which may have a substituent" represented by L.

The "substituent" in the "$C_{4-6}$ alkylene group which may have a substituent" represented by $L_1$ include the same groups as those exemplified with respect to the "substituent" in the "spacer having a main chain of 1 to 10 atoms which may have a substituent" represented by L. Preferable examples include 1 to 4 substituent(s) selected from halogen atom (e.g. fluorine, chlorine, bromine, iodine etc.), nitro, cyano, optionally halogenated $C_{1-6}$alkoxy, and hydroxy.

Preferable examples of $L_1$ include —$(CH_2)_4$—, —$(CH_2)_5$—, —$(CH_2)_6$—, —$CHF(CH_2)_3$—, —$CHF(CH_2)_4$—, —$CF_2(CH_2)_3$—, —$CF_2(CH_2)_4$—, $(CH_2)_3CH(CH_3)$—, —$(CH_2)_4CH(CH_3)$—, —$(CH_2)_3CH(CF_3)$—, and —$(CH_2)_4CH(CF_3)$—.

Compound (Ia) is preferably a compound wherein $Ar_1$ is a group represented by the formulas:

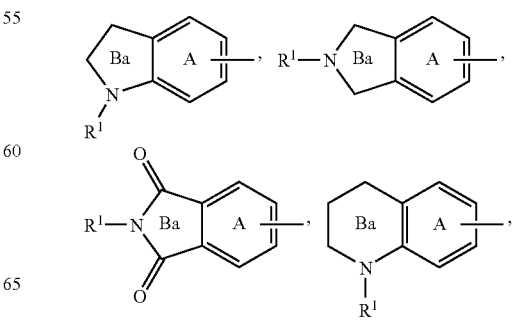

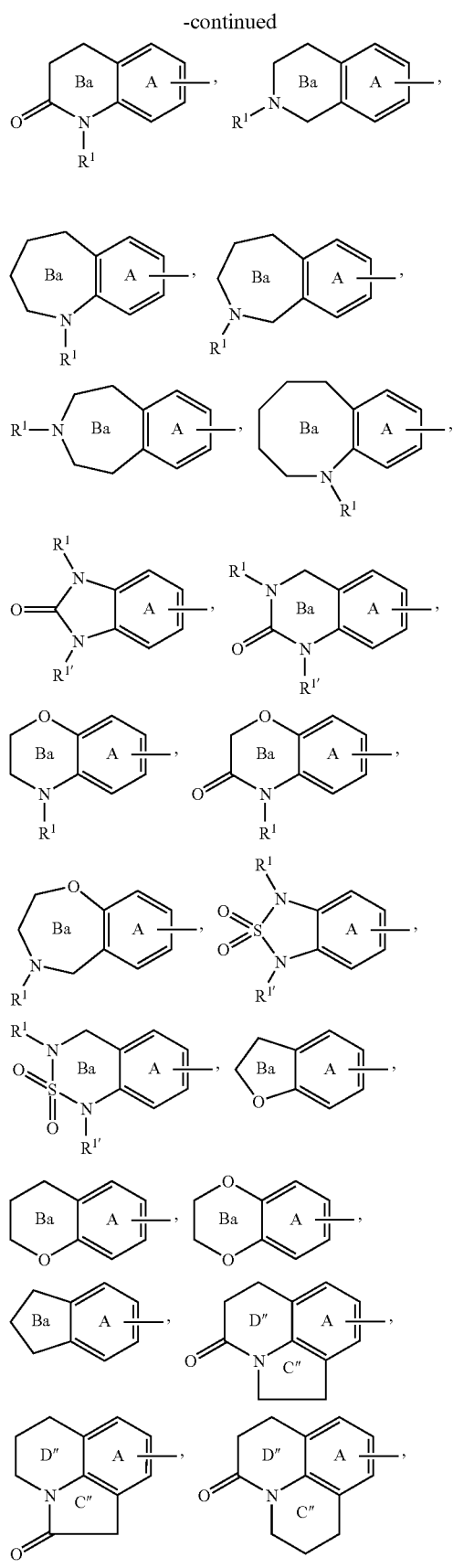
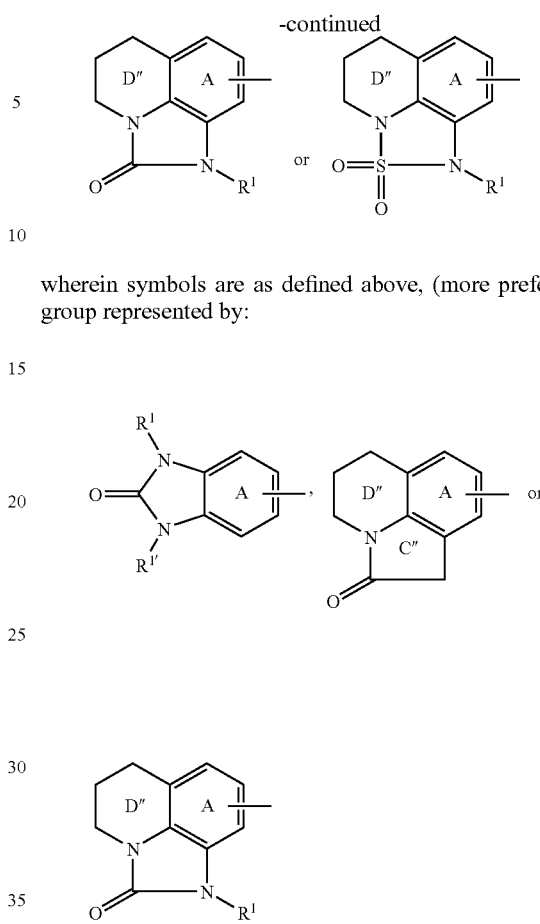

wherein symbols are as defined above, (more preferably a group represented by:

wherein symbols are as defined above) (A ring is preferably a benzene ring which may have 1 or 2 substituent(s) selected from aminosulfonyl, mono- or di-$C_{1-6}$ alkylaminosulfonyl, carbamoyl and mono- or di-$C_{1-6}$ alkyl-carbamoyl, Ba ring, C" ring and D" ring may preferably have 1 or 2 substituent(s) selected from $C_{1-6}$ alkyl, $C_{1-6}$ alkyl-carbonylamino and $C_{1-6}$ alkylsulfonylamino, respectively, and $R^{1'}$ and $R^{1'}$ are preferably (1) a hydrogen atom, (2) a $C_{1-6}$ alkyl group or a $C_{7-16}$ aralkyl group (benzyl etc.), each of which may have 1 or 2 substituent(s) selected from hydroxy and $C_{1-6}$ alkoxy-carbonyl, or (3) a group represented by the formula: —(C=O)—$R^{2'}$, —(C=O)—$NR^{2'}R^{3'}$ or —$SO_2R^{2'}$ [wherein $R^{2'}$ and $R^{3'}$ represent hydrogen atom, optionally halogenated $C_{1-6}$ alkyl or $C_{6-10}$ aryl, respectively], respectively);

$L_1$ is a $C_{4-5}$ alkylene group which may have 1 or 2 halogen atom(s) such as —$(CH_2)_4$—, —$(CH_2)_5$—, —$CHF(CH_2)_3$—, —$CHF(CH_2)_4$—, —$CF_2(CH_2)_3$—, —$CF_2(CH_2)_4$—, —$(CH_2)_3CH(CH_3)$—, and —$(CH_2)_4CH(CH_3)$— (preferably unsubstituted $C_{4-5}$ alkylene group);

R is (i) a hydrogen atom, (ii) a $C_{1-4}$ alkyl group which may have 1 to 3 substituent(s) selected from halogen atom (preferably fluoro etc.) and hydroxy, or (iii) $C_{7-16}$ aralkyl (benzyl etc.) (more preferably, hydrogen atom or $C_{1-4}$ alkyl group);

$L_2$ is a $C_{2-4}$ alkylene group which may have 1 to 4 substituent(s) selected from halogen atom, hydroxy, oxo and phenyl. (e.g. —$(CH_2)_2$—, —$(CH_2)_3$—, —$(CH_2)_4$—, —$CHFCH_2$—, $CHF(CH_2)_2$—, —$CHF(CH_2)3$—, —$CF_2CH_2$—, —$CF_2(CH_2)_2$—, —$CF_2(CH_2)_3$—, —$(CH_3)CHCH_2$—, —$(CH_3)CH(CH_2)_2$—, —$(CH(CH_3))_2$—, —$CH_2CH(OH)$—, —CH$_2$CO—, —(Ph)CHCH$_2$— etc.) (more preferably, C$_{2-3}$ alkylene group which may have hydroxy, oxo or phenyl);

X is a bond, an oxygen atom or NH (more preferably, a bond);

Ar$_2$ is (1) (i) a C$_{6-10}$ aryl group (phenyl etc.) or (ii) a 5- or 6-membered aromatic heterocyclic group (optionally condensed with a benzene ring) containing 1 to 4 hetero atom(s) selected from a nitrogen atom, an oxygen atom and a sulfur atom (e.g. thienyl, furyl, pyrrolyl, imidazolyl, pyrazolyl, thiazolyl, isothiazolyl, oxazolyl, isooxazolyl, pyridyl, pyrazinyl, pyrimidinyl, pyridazinyl, oxadiazolyl, thiadiazolyl, furazanyl, indolyl, isoindolyl, benzofuranyl, quinolyl, isoquinolyl, naphthrydinyl, quinazolinyl, cinnolinyl, acridinyl etc.), each of which may have 1 to 5 (preferably 1 to 3) substituents selected from halogen (fluoro, chloro etc.), C$_{1-6}$alkyl (methyl, ethyl etc.), halogenoC$_{1-6}$alkyl (trifluoromethyl etc.), hydroxy, C$_{1-6}$ alkoxy (methoxy, ethoxy etc.), halogenoC$_{1-6}$alkoxy (trifluoromethoxy, trifuloroethoxy etc.), nitro, amino, cyano, carbamoyl, carbamoyl which may be substituted with C$_{1-6}$ alkyl or amino which may be substituted with formyl. (NH-CHO, NHCONH$_2$, NHCONHMe etc.), C$_{1-3}$ alkylenedioxy (methylenedioxy etc.), an aminocarbonyloxy group which may be substituted with C$_{1-6}$ alkyl (aminocarbonyloxy, methylaminocarbonyloxy, ethylaminocarbonyloxy, dimethylaminocarbonyloxy, dimethylaminocarbonyloxy etc.), 5- to 7-membered cyclic amino-carbonyloxy ((1-pyrrolidinyl) carbonyloxy, piperidinocarbonyloxy etc.), aminosulfonyl, mono-C$_{1-6}$ alkylaminosulfonyl and di-C$_{1-6}$ alkylaminosulfonyl, (2) the case where Ar$_2$ and R are linked together to form a ring represented by the formula:

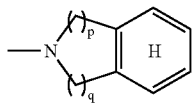

wherein symbols are as defined above, or (3) the case where Ar$_2$ and L$_2$ are linked together to form a ring represented by the formula:

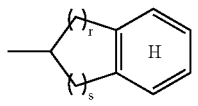

wherein symbols are as defined above (Ar$_2$ is more preferably (i) a C$_{6-10}$ aryl group (phenyl etc.) or (ii) a 5- or 6-membered aromatic heterocyclic group (optionally condensed with a benzene ring) containing 1 to 4 hetero atom(s) selected from a nitrogen atom, an oxygen atom and a sulfur atom (thienyl, indolyl etc.), each of which may have 1 to 3 substituent(s) selected from halogen, nitro; hydroxy, optionally halogenated C$_{1-6}$ alkyl, optionally halogenated C$_{1-6}$ alkoxy and aminosulfonyl).

In addition, among Compound (I), a compound represented by the formula:

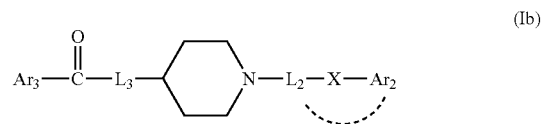

wherein Ar$_3$ represents a benzimidazole ring group, a quinazoline ring group, a 1,4-benzoxazine ring group or a tricyclic to tetracyclic condensed benzene ring group, each of which may have a substituent, L$_3$ represents a C$_{2-4}$ alkylene group which may have a substituent, and the other respective symbols are as defined above (hereinafter, abbreviated as Compound (Ib) in some cases) or a salt thereof is a novel compound.

The "tricyclic to tetracyclic condensed benzene ring group" in the "tricyclic to tetracyclic condensed benzene ring group which may have a substituent" represented by Ar$_3$ include the same groups as those exemplified with respect to the condensed benzene ring group exemplified as an example of fusing of the "phenyl group" in the case that the "5- or 6-membered aromatic ring group" in the "optionally condensed 5- or 6-membered aromatic ring group" represented by Ar is the "phenyl group".

The "substituent" in the "a benzimidazole ring group, a quinazoline ring group, a 1,4-benzoxazine ring group or a tricyclic to tetracyclic condensed benzene ring group, each of which may have a substituent" represented by Ar$_3$ include the same groups as those exemplified with respect to the "substituent" in the "represents an optionally condensed 5- or 6-membered aromatic ring group, and said aromatic ring group may have a substituent" represented by Ar.

Examples of the "C$_{2-4}$ alkylene group which may have a substituent" represented by L$_3$ include those having carbon chain number of 2 to 4 among the "C$_{1-10}$ alkylene group" exemplified with respect to the "spacer having a main chain of 1 to 10 atoms which may have a substituent" represented by L.

The "substituent" in the "C$_{2-4}$ alkylene group which may have a substituent" represented by L$_3$ include the same groups as those exemplified with respect to the "substituent" in the "spacer having a main chain of 1 to 10 atoms which may have a substituent" represented by L. Preferable examples include 1 to 4 substituent(s) selected from halogen atom (e.g. fluorine, chlorine, bromine, iodine etc.), nitro, cyano, optionally halogenated C$_{1-6}$ alkoxy, and hydroxy.

Preferable examples of L$_3$ include a C$_{2-4}$ alkylene group which may have 1 or 2 halogen atom(s), such as —(CH$_2$)$_2$—, —(CH$_2$)$_3$—, —(CH$_2$)$_4$—, —CHFCH$_2$—, —CHF(CH$_2$)$_2$—, —CF$_2$CH$_2$—, and —CF$_2$(CH$_2$)$_2$—.

Compound (Ib) is preferably a compound wherein Ar$_3$ is a group represented by the formulas:

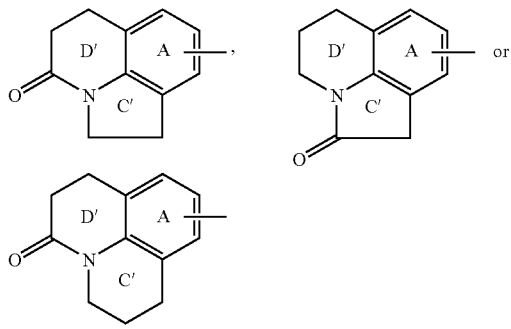

wherein respective symbols are as defined above (among the groups, it is preferable that A ring is unsubstituted, and C' ring and D' ring have no substituent other than an oxo group in the formulas);

$L_3$ is a $C_{2-3}$ alkylene group (more preferably, ethylene group) which may have 1 or 2 halogen atom(s), such as —$(CH_2)_2$—, —$(CH_2)_3$—, —$CHFCH_2$—, —$CHF(CH_2)_2$—, —$CF_2CH_2$— and —$CF_2(CH_2)_2$—;

$L_2$ is a $C_{2-4}$ alkylene group which may have 1 to 4 substituent(s) selected from halogen atom, hydroxy, oxo and phenyl, such as —$(CH_2)_2$—, —$(CH_2)_3$—, —$CF_2CH_2$—, —$CF_2(CH_2)_2$—, —$(CH_3)CHCH_2$—, —$(CH_3)CH(CH_2)_2$—, —$CH_2CH(OH)$—, —$CH_2CO$—, and —$(Ph)CHCH_2$— (more preferably, $C_{2-3}$ alkylene group which may have hydroxy, oxo or phenyl);

X is a bond, an oxygen atom or NH (more preferably, bond or oxygen atom);

$Ar_2$ is (1) (i) a $C_{6-10}$ aryl group (phenyl etc.) or (ii) a 5- or 6-membered aromatic heterocyclic group (optionally condensed with a benzene ring) containing 1 to 4 hetero atom(s) selected from a nitrogen atom, an oxygen atom and a sulfur atom (e.g. thienyl, furyl, pyrrolyl, imidazolyl, pyrazolyl, thiazolyl, isothiazolyl, oxazolyl, isooxazolyl, pyridyl, pyrazinyl, pyrimidinyl, pyridazinyl, oxadiazolyl, thiadiazolyl, furazanyl, indolyl, isoindolyl, benzofuranyl, quinolyl, isoquinolyl, naphthyridinyl, quinazolinyl, cinnolinyl, acridinyl etc.), each of which may have 1 to 5 (preferably 1 to 3) substituent(s) selected from halogen (fluoro, chloro etc.), $C_{1-6}$ alkyl (methyl, ethyl etc.), halogeno$C_{1-6}$ alkyl (trifluoromethyl etc.), hydroxy, $C_{1-6}$ alkoxy (methoxy, ethoxy etc.), halogeno$C_{1-6}$alkoxy (trifluoromethoxy, trifluoroethoxy etc.), nitro, amino, cyano, carbamoyl, carbamoyl which may be substituted with $C_{1-6}$ alkyl or amino which may be substituted with formyl ($NHCHO$, $NHCONH_2$, $NHCONHMe$ etc.), $C_{1-3}$ alkylenedioxy (methylenedioxy etc.), an aminocarbonyloxy group which may be substituted with $C_{1-6}$ alkyl (aminocarbonyloxy, methylaminocarbonyloxy, ethylaminocarbonyloxy, dimethylaminocarbonyloxy, diethylaminocarbonyloxy etc.), 5- to 7-membered cyclic amino-carbonyloxy ((1-pyrrolidinyl)carbonyloxy, piperidinocarbonyloxy etc.), aminosulfonyl, mono-$C_{1-6}$ alkylaminosulfonyl and di-$C_{1-6}$ alkylaminosulfonyl (more preferably, (i) a $C_{6-10}$ aryl group (phenyl etc.) or (ii) a 5- or 6-membered aromatic heterocyclic group (optionally condensed with a benzene ring) containing 1 to 4 hetero atom(s) selected from a nitrogen atom, an oxygen atom and a sulfur atom (thienyl, indolyl etc.), each of which may have 1 to 3 substituent(s) selected from halogen, nitro, hydroxy, optionally halogenated $C_{1-6}$ alkyl, optionally halogenated $C_{1-6}$ alkoxy and aminosulfonyl, or (2) $Ar_2$ and $L_2$ are linked together to form a ring represented by the formula:

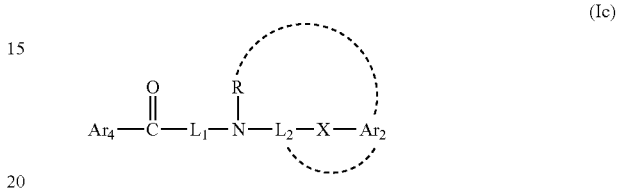

wherein symbols are as defined above.

In addition, among Compound (I), a compound represented by the formula:

(Ic)

$$Ar_4-\overset{O}{\underset{\|}{C}}-L_1-\overset{R}{\underset{|}{N}}-L_2-X-Ar_2$$

wherein $Ar_4$ represents a benzene ring group which has 1 or 2 substituent(s) selected from aminosulfonyl, mono-or di-$C_{1-6}$ alkylaminosulfonyl, $C_{1-6}$ alkyl-carbonylamino and $C_{1-6}$ alkylsulfonylamino, and further may have 1 to 4 substituent(s), and the other symbols are as defined above (hereinafter, abbreviated as Compound (Ic) in some cases) or a salt thereof is a novel compound.

The "substituent" in the "benzene ring group further may have 1 to 4 substituent(s)" represented by $Ar_4$ include the same groups as those exemplified with respect to the "substituent" in the "represents an optionally condensed 5- or 6-membered aromatic ring group, and said aromatic ring group may have a substituent" represented by Ar (provided that aminosulfonyl, mono-or di-$C_{1-6}$ alkylaminosulfonyl, $C_{1-6}$ alkyl-carbonylamino and $C_{1-6}$ alkylsulfonylamino are excluded).

Compound (Ic) is preferably a compound wherein $Ar_4$ is a benzene ring group which has 1 or 2 (more preferably 1) substituent(s) selected from aminosulfonyl, mono- or di-$C_{1-6}$ alkylaminosulfonyl, $C_{1-6}$ alkyl-carbonylamino and $C_{1-6}$ alkylsulfonylamino, and further may have 1 or 2 (more preferably 1) $C_{1-4}$ alkoxy;

$L_1$ is a $C_{4-5}$ alkylene group which may have 1 or 2 halogen atom(s) (preferably, unsubstituted $C_{4-5}$ alkylene group), such as —$(CH_2)_4$—, —$(CH_2)_5$—, —$CHF(CH_2)_3$—, —$CHF(CH_2)_4$—, —$CF_2(CH_2)_3$—, —$CF_2(CH_2)_4$—, —$(CH_2)_3CH(CH_3)$—, and —$(CH_2)_4CH(CH_3)$—;

R is (i) a hydrogen atom, (ii) a $C_{1-4}$ alkyl group which may have 1 to 3 substituent(s) selected from halogen atom (preferably fluoro etc.) and hydroxy, or (iii) a $C_{7-16}$ aralkyl (benzyl etc.) (more preferably, hydrogen atom or $C_{1-4}$ alkyl group);

$L_2$ is a $C_{2-4}$ alkylene group which may have 1 to 4 substituent(s) selected from halogen atom, hydroxy, oxo, and phenyl (e.g. —$(CH_2)_2$—, —$(CH_2)_3$—, —$(CH_2)_4$—, —$CHFCH_2$—, —$CHF(CH_2)_2$—, —$CHF(CH_2)_3$—, —$CF_2CH_2$—, —$CF_2(CH_2)_2$—, —$CF_2(CH_2)_3$—, —$(CH_3)CHCH_2$—, —$(CH_3)CH(CH_2)_2$—, —$(CH(CH_3))_2$—, —$CH_2CH(OH)$—, —$CH_2CO$—, —$(Ph)CHCH_2$— etc.) (more preferably, $C_{2-3}$ alkylene group which may have hydroxy or oxo);

X is a bond, an oxygen atom or NH (more preferably a bond);

$Ar_2$ is (1) (i) a $C_{6-10}$ aryl group (phenyl etc.) or (ii) a 5- or 6-membered aromatic heterocyclic group (optionally condensed with a benzene ring) containing 1 to 4 hetero atom(s) selected from a nitrogen atom, an oxygen atom and a sulfur atom (e.g. thienyl, furyl, pyrrolyl, imidazolyl, pyrazolyl, thiazolyl, isothiazolyl, oxazolyl, isooxazolyl, pyridyl, pyrazinyl, pyrimidinyl, pyridazinyl, oxadiazolyl, thiadiazolyl, furazanyl, indolyl, isoindolyl, benzofuranyl, quinolyl, isoqiunolyl, naphthyridinyl, quinazolinyl, cinnolinyl, acridinyl etc.), each of which may have 1 to 5 (preferably 1 to 3) substituent(s) selected from halogen (fluoro, chloro etc.), $C_{1-6}$ alkyl (methyl, ethyl etc.), halogeno$C_{1-6}$alkyl (trifluoromethyl etc.), hydroxy, $C_{1-6}$ alkoxy (methoxy, ethoxy etc.), halogeno$C_{1-6}$ alkoxy (trifluoromethoxy, trifluoroethoxy etc.), nitro, amino, cyano, carbamoyl, carbamoyl which may be substituted with $C_{1-6}$ alkyl or amino which may be substituted with formyl (NHCHO, NHCONH$_2$, NHCONHMe etc.), $C_{1-3}$ alkylenedioxy (methylenedioxy etc.), an aminocarbonyloxy group which may be substituted with $C_{1-6}$ alkyl (aminocarbonyloxy, methylaminocarbonyloxy, ethylaminocarbonyloxy, dimethylaminocarbonyloxy, diethylaminocarbonyloxy etc.), 5- to 7-membered cyclic amino-carbonyloxy ((1-pyrrolidinyl)carbonyloxy, piperidinocarbonyloxy etc.), aminosulfonyl, mono-$C_{1-6}$ alkylaminosulfonyl and di-$C_{1-6}$ alkylaminosulfonyl, (2) the case where Ar$_2$ and R are linked together to form a ring represented by the formula:

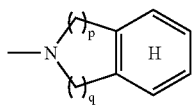

wherein symbols are as defined above, or (3) the case where Ar$_2$ and L$_2$ are linked together to form a ring represented by the formula:

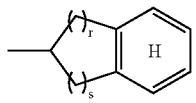

wherein symbols are as defined above (Ar$_2$ is more preferably (i) a $C_{6-10}$ aryl group (phenyl etc.) or (ii) a 5- or 6-membered aromatic heterocyclic group (optionally condensed with a benzene ring) containing 1 to 4 hetero atom(s) selected from a nitrogen atom, an oxygen atom and a sulfur atom (thienyl, indolyl etc.), each of which may have 1 to 3 substituent(s) selected from halogen, nitro, hydroxy, optionally halogenated $C_{1-6}$ alkyl, optionally halogenated $C_{1-6}$ alkoxy and aminosulfonyl).

In addition, among Compound (I), a compound represented by the formula:

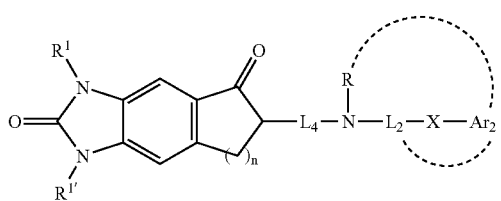

(Id)

wherein n represents an integer of 1 or 2, L$_4$ represents a $C_{3-5}$ alkylene group which may have a substituent, and the other symbols are as defined above (hereinafter, abbreviated as Compound (Id) in some cases) or a salt thereof is a novel compound.

Examples of the "$C_{3-5}$ alkylene group which may have a substituent" represented by L$_4$ include those having a carbon chain number of 3 to 5 among the "$C_{1-20}$ alkylene group" exemplified with respect to the "spacer having a main chain of 1 to 10 atoms which may have a substituent" represented by L.

The "substituent" in the "$C_{3-5}$ alkylene group which may have a substituent" represented by L$_4$ include the same groups as those exemplified with respect to the "substituent" in the "spacer having a main chain of 1 to 10 atoms which may have a subsitituent" represented by L. Preferable examples include 1 to 4 substituent(s) selected from halogen atom (e.g. fluorine, chlorine, bromine, iodine etc.), nitro, cyano, optionally halogenated $C_{1-6}$ alkoxy, and hydroxy.

Compound (Id) is preferably a compound wherein R$^1$ and R$^{1'}$ are a hydrogen atom or an optionally halogenated $C_{1-6}$ alkyl group (methyl, ethyl, trifluoromethyl etc.);

L$_4$ is a $C_{3-5}$ alkylene group (more preferably $C_{3-4}$ alkylene group) which may have 1 or 2 halogen atom(s), such as —(CH$_2$)$_3$—, —(CH$_2$)$_4$—, —(CH$_2$)$_5$—, —CHF(CH$_2$)$_2$—, —CHF(CH$_2$)$_3$—, —CF$_2$(CH$_2$)$_2$—, —CF$_2$(CH$_2$)$_3$—, —(CH$_2$)$_2$CH (CH$_3$)—, and —(CH$_2$)$_3$CH(CH$_3$)—);

R is (i) a hydrogen atom, (ii) a $C_{1-4}$ alkyl group which may have 1 to 3 substituent(s) selected from halogen atom (preferably fluoro etc.) and hydroxy, or (iii) $C_{7-16}$ aralkyl (benzyl etc.) (more preferably a hydrogen atom or a $C_{1-4}$ alkyl group);

L$_2$ is a $C_{2-4}$ alkylene group which may have 1 to 4 substituent(s) selected from halogen atom, hydroxy, oxo, and phenyl (e.g. —(CH$_2$)$_2$—, —(CH$_2$)$_3$—, —(CH$_2$)$_4$—, —CHFCH$_2$—, —CHF(CH$_2$)$_2$—, —CHF(CH$_2$)$_3$—, —CF$_2$CH$_2$—, —CF$_2$(CH$_2$)$_2$—, —CF$_2$(CH$_2$)$_3$—, —(CH$_3$)CHCH$_2$—, —(CH$_3$)CH(CH$_2$)$_2$—, —(CH(CH$_3$))$_2$—, —CH$_2$CH(OH)—, —CH$_2$CO—, —(Ph)CHCH$_2$— etc.) (more preferably $C_{2-3}$ alkylene group which may have hydroxy or oxo);

X is a bond, an oxygen atom or NH (more preferably a bond);

Ar$_2$ is (1) (i) a $C_{6-10}$ aryl group (phenyl etc.) or (ii) a 5- or 6-membered aromatic heterocyclic group (optionally condensed with a benzene ring) containing 1 to 4 hetero atom(s) selected from a nitrogen atom, an oxygen atom and a sulfur atom (e.g. thienyl, furyl, pyrrolyl, imidazolyl, pyrazolyl, thiazolyl, isothiazolyl, oxazolyl, isoxazolyl, pyridinyl, pyrazinyl, pyrimidinyl, pyridazinyl, oxadiazolyl, thiadiazolyl, furazanyl, indolyl, isoindolyl, benzofuranyl, quinolyl, isoquinolyl, naphthyridinyl, quinazolinyl, cinnolinyl, acridinyl etc.), each of which may have 1 to 5 (preferably 1 to 3) substituent(s) selected from halogen (fluoro, chloro etc.), $C_{1-6}$ alkyl (methyl, ethyl etc.), halogeno$C_{1-6}$ alkyl (trifluoromethyl etc.), hydroxy, $C_{1-6}$ alkoxy (methoxy, ethoxy etc.), halogeno$C_{1-6}$ alkoxy (trifluoromethoxy, trifluoroethoxy etc.), nitro, amino, cyano, carbamoyl, carbamoyl which may be substituted with $C_{1-6}$ alkyl or amino which may be substituted with formyl (NHCHO, NHCONH$_2$, NHCONHMe etc.), $C_{1-3}$ alkylenedioxy (methylenedioxy etc.), an aminocarbonyloxy group which may be substituted with $C_{1-6}$ alkyl (aminocarbonyloxy, methylaminocarbonyloxy, ethylaminocarbonyloxy, dimethylaminocarbonyloxy, diethylaminocarbonyloxy etc.), 5- to 7-membered cyclic amino-carbonyloxy ((1-pyrrolidinyl)carbonyloxy, piperidinocarbonyloxy etc.), aminosulfonyl, mono-$C_{1-6}$ alkylaminosulfonyl and di-$C_{1-6}$ alkylaminosulfonyl, (2) the case where Ar$_2$ and R are linked together to form a ring represented by the formula:

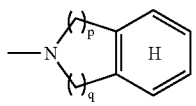

wherein symbols are as defined above, or (3) the case where $Ar_2$ and $L_2$ are linked together to form a ring represented by the formula:

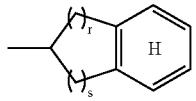

wherein symbols are as defined above ($Ar_2$ is more preferably (i) a $C_{6-10}$ aryl group (phenyl etc.) or (ii) a 5- or 6-membered aromatic heterocyclic group (optionally condensed with a benzene ring) containing 1 to 4 hetero atom(s) selected from a nitrogen atom, an oxygen atom and a sulfur atom (thienyl, indolyl etc.), each of which may have 1 to 3 substituent(s) selected from halogen, nitro, hydroxy, optionally halogenated $C_{1-6}$ alkyl, optionally halogenated $C_{1-6}$ alkoxy and aminosulfonyl).

When Compound(I), (Ia), (Ib), (Ic) or (Id) (hereinafter, referred to as Compound B) is a salt, examples of such salt include salts with an inorganic base, an ammonium salt, salts with an organic base, salts with an inorganic acid, salts with an organic acid, an salts with a basic or acidic amino acid.

Preferable examples of the salt with an inorganic base include alkali metal salts such as a sodium salt and a potassium salt; alkaline earth metal salts such as a calcium salt, a magnesium salt and a barium salt; an aluminum salt.

Preferable examples of the salt with an organic base include salts with trimethylamine, triethylamine, pyridine, picoline, ethanolamine, diethanolamine, triethanolamine, dicyclohexylamine, and N,N-dibenzylethylenediamine.

Preferable examples of the salt with an inorganic acid include salts with hydrochloric acid, hydrobromic acid, nitric acid, sulfuric acid and phosphoric acid.

Preferable examples of the salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid.

Preferable examples of the salt with a basic amino acid include salts with arginine, lysine and ornithine, and preferable examples of the salt with an acidic amino acid include aspartic acid and glutamic acid.

Among these salts, pharmaceutically acceptable salts are preferred. For example, when Compound B has an acidic functional group, it may be an inorganic salt such as an alkali metal salt (e.g. sodium salt, potassium salt etc.), and an alkaline earth metal salt (e.g. calcium salt, magnesium salt, barium salt etc.), or an ammonium salt. When Compound B has a basic functional group, it may be an inorganic salt such as hydrochloride, sulfate, phosphate and hydrobromide; or an organic salt such as acetate, maleate, fumarate, succinate, methanesulfonate, p-toluenesulfonate, citrate, and tartarate.

Compound B may be an anhydride or a hydrate. In the: case of a hydrate, Compound B may have 0.1 to 5 of water molecules.

Further, Compound B may be labeled with an isotope element (e.g. $^3H$, $^{14}C$, $^{35}S$ etc.).

When Compound B contains an optical isomer, a steric isomer, a positional isomer or a rotational isomer, these are also included in the compound of the present invention, and each of the isomers may be obtained as a single compound by a synthetic method or separation method known per se. For example, when Compound B has an optical isomer, an optical isomer resolved from the compound is included in Compound B.

The optical isomer can be prepared by a method known per se. Specifically, an optically active isomer can be obtained by using an optically active compound in the synthesis, or optically resolving the final mixture of racemic isomers with a conventional method.

As an optical resolution method, a method known per se, for example, a fractional recrystallization method, a chiral column method and a diastereomer method which will be described in detail below, is used.

1) Fractional Recrystallization Method

A method of obtaining a free optical isomer by forming a salt of a racemic compound and an optically active compound (e.g. (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc), separating this by a fractional recrystallization method and, if necessary, via a neutralizing step.

2) A Chiral Column Method

A method for separating a racemic compound or a salt thereof by applying to an optical isomer separating column (chiral column). For example, in the case of liquid chromatography, optical isomers are separated by adding a mixture of optical isomers to a chiral column such as ENANTIO-OVM (manufactured by Toso) or CHIRAL series manufactured by Daicel, and developing this with water, various buffers (e.g. phosphate buffer), or an organic solvent (e.g. ethanol, methanol, isopropanol, acetonitrile, trifluoroacetic acid, diethylamine) alone or a mixture thereof. In addition, in the case of gas chromatography, optical isomers are separated by using a chiral column such as CP-Chirasil-DeXCB (manufactured by GL Science).

3) A Diastereomer Method

A method of obtaining an optical isomer by chemically reacting a mixture of racemic compounds with an optically active reagent to give a mixture of diastereomers, separating single substance with usual separation means (e.g. fractional recrystallization, chromatography method etc.) and separating off an optically active reagent moiety by chemical treatment such as hydrolyzation reaction. For example, when Compound B has hydroxy or primary or secondary amino in a molecule, a diastereomer of ester or amido can be obtained by subjecting the compound and an optically active organic acid (e.g. MTPA [α-methoxy-α-(trifluoromethyl)phenylacetic acid], (−)-menthoxyacetic acid, etc.) to a condensation reaction. On the other hand, when Compound B has a carboxylic acid group, a diastereomer of amido or ester is obtained by subjecting the compound and an optically active amine or alcohol reagent to a condensation reaction. The separated diastereomer is converted into an optical isomer of the original compound by subjecting to acid hydrolysis or base hydrolysis reaction.

A prodrug of Compound B refers to a compound which is converted into Compound B by a reaction with an enzyme or gastric acid under a physiological condition in vivo, that is, a compound which is changed to Compound B by enzymatic oxidation, reduction or hydrolysis, and a compound which is changed into Compound B by hydrolysis with gastric acid.

Examples of a prodrug of Compound B include a compound in which an amino group of Compound B is acylated, alkylated or phosphorylated [e.g. compound in which an amino group of Compound B is eicosanoylated, alanylated, pentylaminocarbonylated, (5-methyl-2-oxo-1,3-dioxolen-4-yl) methoxycarbonylated, tetrahydrofuranylated, pyrrolidylmethylated, pivaloyloxymethylated, or tert-butylated]; a compoound in which a hydroxy group of Compound B is acylated, alkylated, phosphorylated or converted into borate (e.g. compound in which a hydroxy group of Compound B is acetylated, palmitoylated, propanoylated, pivaloylated, succinylated, fumarylated, alanylated, or dimethylaminomethylcarbonylated); a compound in which a carboxyl group of Compound B is esterified or amidated (e.g. compound in which a carboxyl group of Compound B is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, or methylamidated). These compounds can be prepared from Compound B with a method known per se.

A prodrug of Compound B may be a compound which is converted into Compound B under physiological conditions as described in "Development of Drugs", Volume 7, Molecular Design, Hirokawa Shoten, 1990; pages 163-198.

Then, a process for preparing Compound (Ia), (Ib), (Ic) and (Id) will be described. Compound (I) is prepared according to the process for preparing (Ia), (Ib), (Ic) and (Id) below.

Compounds (Ia), (Ic) and (Id) are prepared, for example, by a method of the following [Process A] or [Process B], and Compound (Ib) is prepared, for example, by the following [Process C]. In [Process A] to [Process C], when an alkylation reaction, a hydrolyzation reaction, an amination reaction, an esterification reaction, an amidation reaction, an esterification reaction, an etherification reaction, an oxidization reaction, a reduction reaction, and a reductive amination reaction are carried out, these reactions are performed according to a method known per se. Examples of these methods include the methods described in ORGANIC FUNCTIONAL GROUP PREPARATIONS, $2^{nd}$ edition, ACADEMIC PRESS INC., 1989; Comprehensive Organic Transformations, VCH Publishers Inc., 1989.

In the following processes, Compounds (II), (II'), (II"), (III), (IV), (V), (VI), (VI'), (VI"), (VII), (VIII), (IX), (X), (XI), (XII), (XIII), (XIV), (XV), (XVI), (XVII), (XVIII), (XIX), (XX), and (XXI) may form a salt, respectively. As the "salt", for example, the "salt" of the aforementioned "when Compound B is a salt" can be applied.

[Process A] Process for preparing Compound (Ia), (Ic) or (Id) by a coupling reaction of Compound (II), (II') or (II") with Compound (III).

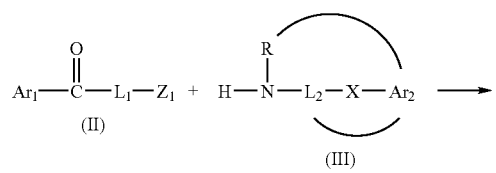

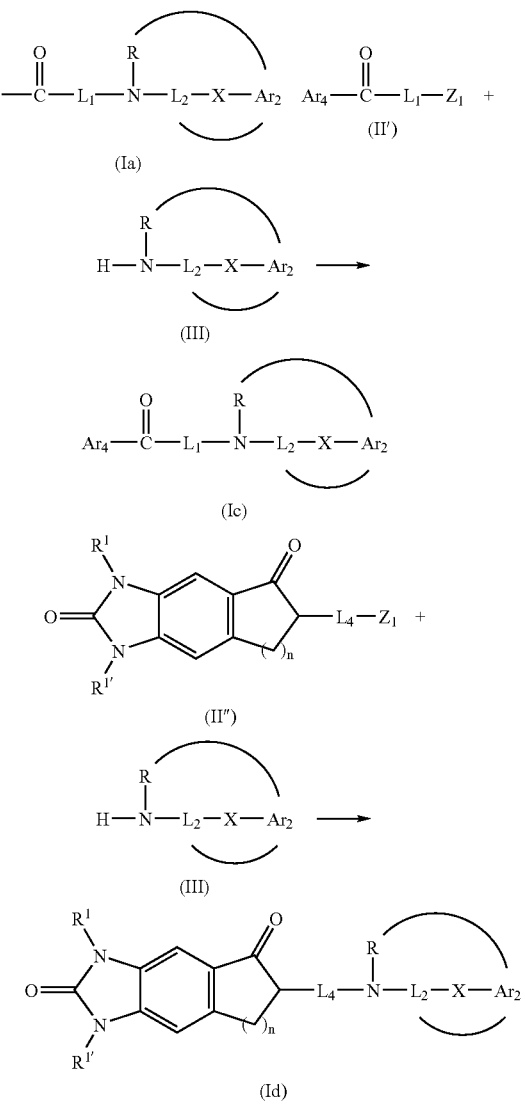

wherein $Z_1$ represents a leaving group, and other respective symbols are as defined above.

As the "leaving group" represented by $Z_1$, for example, halogen atom (e.g. chloro, bromo, iodo), $C_{1-6}$ alkylsulfonyloxy (e.g. methanesulfonyloxy, ethanesulfonyloxy, trifluoromethanesulfonyloxy), and $C_{6-10}$ arylsulfonyloxy (e.g. benzenesulfonyloxy, p-toluenesulfonyloxy) are used. In particular, halogen atom (e.g. chloro, bromo etc.), and methanesulfonyloxy are preferable.

The present coupling reaction can be carried out without a solvent, or by dissolving or suspending the compounds in a suitable solvent such as a hydrocarbon solvent, an alcohol solvent, an ether solvent, a halogenated hydrocarbon solvent, an aromatic solvent, a nitrile solvent, an amide solvent, a ketone solvent, a sulfoxide solvent, carboxylic acid solvent, or water. These solvents may be used by mixing two or more at an appropriate ratio. Preferably, no solvent, or an alcohol solvent such as ethanol, an aromatic solvent such as toluene, or an amide solvent such as dimethylformamide is used.

The present coupling reaction may be carried out by adding a suitable base. Alternatively, the base can be used as a solvent.

Examples of the "base" include:

1) strong basis such as hydride of an alkali metal or an alkaline earth metal (e.g. lithium hydride, sodium hydride, potassium hydride, calcium-hydride etc.), amides of an alkali metal or an alkaline earth metal (e.g. lithium amide, sodium amide, lithium diisopropylamide, lithium dicyclohexylamide, lithium hexamethyidisilazide, sodium hexamethyldisilazide, potassium hexamethyldisilazide etc.), and lower alkoxide of an alkali, metal or an alkaline earth metal (e.g. sodium methoxide, sodium ethoxide, potassium tert-butoxide etc.);

2) inorganic bases such as hydroxide of an alkali metal or an alkaline earth metal (e.g. sodium hydroxide, potassium hydroxide, lithium hydroxide, barium hydroxide etc.), carbonate of an alkali metal or an alkaline earth metal (e.g. sodium carbonate, potassium carbonate, cesium carbonate etc.), and bicarbonate of an alkali metal or an alkaline earth metal (e.g. sodium bicarbonate, potassium bicarbonate); and 3) organic bases such as amines such as triethylamine, diisopropylethylamine, and N-methylmorpholine; amidines such as DBU (1,8-diazabicyclo[5.4.0]undec-7-ene), and DBN (1,5-diazabicyclo[4,3,0]non-5-ene); basic heterocyclic compounds such as pyridine, dimethylaminopyridine, imidazole, and 2,6-lutidine.

As the "base", alkali metal salts such as potassium carbonate, and amines such as triethylamine and diisopropylethylamine are preferable.

Upon the present coupling reaction, a hydrogen atom of Compound (III) may be substituted with a metal atom, for example, an alkali metal such as lithium and sodium in advance.

The present coupling reaction can be carried out at −100° C. to 300° C., preferably 0° C. to 150° C. A reaction time is 1 minute to 1 day.

The present coupling reaction can be carried out at an arbitrary ratio of Compound (II), (II') or (II") and Compound (III), and either of them may be used as a solvent.

Compound (III) can be prepared by a method known per se or a similar method thereto. For example, Compound (III) can be prepared by the method described in Comprehensive Organic Transformation VIH Publishers Inc., 1989, more specifically, the method described in J. Org. Chem. 24, 1106 (1959), Bull. Chem. Soc. Jpn. 63, 1252(1990), Synth. Commun. 14, 1099(1984), Tetrahedron 49, 1807(1993), J. Heterociclic Chem. 28, 1587(1991), J. Org. Chem. 60, 7086(1995) or a similar method thereto.

Compound (II) or (II') can be prepared, for example, by a method such as Friedel-Crafts reaction shown below.

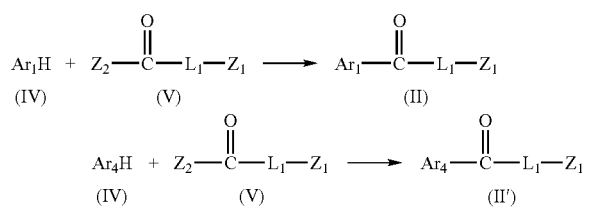

wherein $Z_2$ represents a leaving group, and the other respective symbols are as defined above.

As the "leaving group" represented by $Z_2$, the same leaving groups as those for the above-mentioned $Z_1$ can be applied. Preferred is a halogen atom (e.g. chloro, bromo etc.) or a hydroxy group.

The present reaction can be preferably carried out by adding an acid catalyst, but the reaction can be carried out without adding an acid catalyst. As the acid catalyst used in the reaction, mineral acids such as sulfuric acid, phosphoric anhydride, and polyphosphoric acid, and Lewis acids such as aluminum chloride, tin tetrachloride, titanium tetrachloride, boron trifuloride, triethylaluminum, diethylaluminum chloride, and zinc chloride can be used. Preferable examples include polyphosphoric acid, aluminum chloride, diethylaluminum chloride, and zinc chloride. An acid catalyst can be used at an arbitrary equivalent, usually, 0.1 equivalent to 10 equivalent relative to Compound (IV) or Compound (V). Occasionally, an acid catalyst can be used as a solvent.

The present reaction can be carried out without a solvent, or by dissolving or suspending reactants in a suitable solvent such as a hydrocarbon solvent, an ether solvent a halogenated hydrocarbon solvent, a nitrated hydrocarbon solvent, an aromatic solvent, a nitrile solvent, an amide solvent, a ketone solvent, a sufoxide solvent, and a carboxylic acid solvent. These may be used by mixing two or more at an appropriate ratio. Preferably, for example, no solvent, or a halogenated hydrocarbon solvent such as dichloromethane and 1,2-dichlroethane, a nitrated hydrocarbon solvent such as nitromethane, an aromatic solvent such as nitrobenzene, and carbon disulfide are used.

The present reaction can be carried out at −100° C. to 300° C. and, usually, 0° C. to 150° C. is preferable. A reaction time is, for examle, 1 minute to 3 days.

The present reaction can be carried out at an arbitrary ratio of Compound (IV) and Compound (V), and either of them can be also used as a solvent.

Compound (IV) can be prepared by a method known per se or a similar method thereto. Compound (IV) can be prepared by the method, for example, described in Synthesis 10, 862 (1984), J. Chem. Soc. 1518 (1964), Synthesis 851 (1984), and JP-A No.9-124605 or a similar method thereto.

Compound (V) can be prepared by a method known per se or a similar method thereto. Compound (V) can be prepared by the method, for example, described in Org. Syn. Coll. Vol. 1, 12 (1941), Helv. Chem. Acta 42, 1653 (1959) or a similar method thereto.

Compound (II) or (II') can be prepared by a method other than the aforementioned Friedel-Crafts reaction. Examples of the "method other than the Friedel-Crafts reaction" include a method using an organic metal reagent such as a method using an arylmagnesium reagent described in Tetrahedron Lett. 27, 929(1986), J. Am. Chem. Soc. 70, 426 (1948), Synlett 3, 225 (1996), a method using an organic zinc reagent described in Tetrahedron 46, 6061(1990). Alternatively, for example, Compound (II) or (II') can be prepared using a method for synthesis from an active methylene derivative described in JP-A 3-95143.

Compound (II") can be prepared, for example, by a method of introducing a substituent V into Compound (XII) to obtain Compound (XIII), coupling Compound (XIII) and Compound (XIV), and removing the substituent V as shown below:

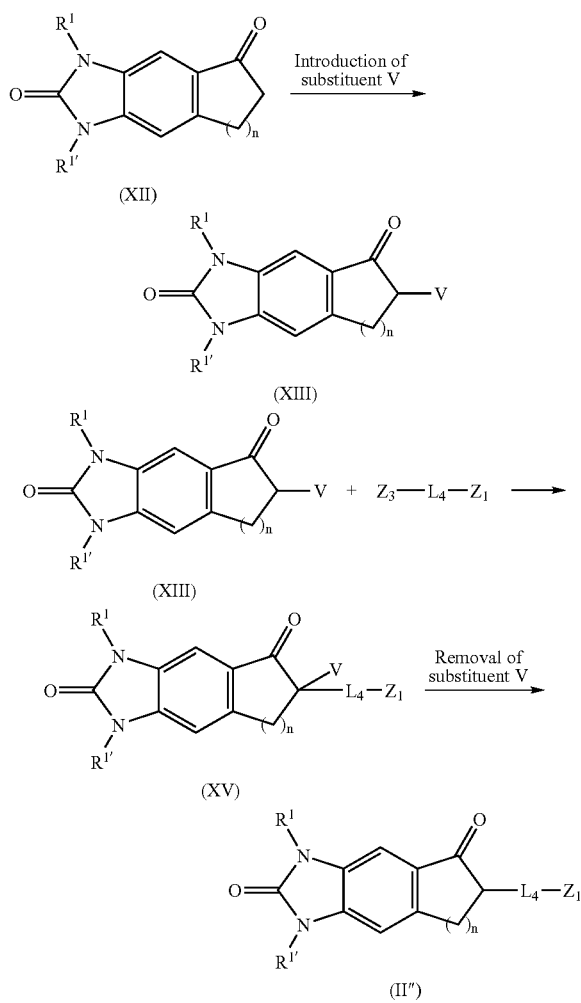

wherein substituent V represents an electron withdrawing group, $Z_3$ represents a leaving group, and the other respective symbols are as defined above.

As the "electron withdrawing group" represented by the substituent V, for example, a $C_{1-8}$ alkoxycarbonyl group (e.g. methoxycarbonyl, tert-butoxycarbonyl group etc.), a $C_{7-16}$ aralkyloxycarbonyl group (e.g. benzyloxycarbonyl group etc.), a carboxyl group, and a cyano group are used. Preferable is a $C_{1-4}$ alkoxycarbonyl group (e.g. methoxycarbonyl, tert-butoxycarbonyl group etc.).

As the "leaving group" represented by $Z_3$, the same leaving groups as those for the above-mentioned $Z_1$ can be applied. Preferred is a halogen atom (e.g. chloro, bromo etc.), a p-toluenesulfonyloxy group or a methanesulfonyloxy group.

The reaction of "introducing a substituent V" can be carried out without solvent, or in a suitable solvent. As the "solvent", the same solvents as "solvents" described for the above-mentioned Process A can be used. For example, no solvent, or an ether solvent such as tetrahydrofuran, an aromatic solvent such as toluene, and an amide solvent such as dimethylformamide are preferred.

As a precursor of the substituent V in the present reaction "of introducing a substituent V", for example, carbonic acid ester (dimethyl carbonate etc.), halocarbonic acid ester (methyl chlorocarbonate) or carbon dioxide is used.

Alternatively, the present reaction "of introducing a substituent V" may be carried out by adding an appropriate base. In addition, the base may be used as a solvent. As the "base", the same bases as "bases" described for the above-mentioned Process A can be used. For example, sodium hydride, sodium amide, and lithium diisopropylamide are preferred.

The present reaction "of introducing a substituent V" can be carried out at −100° C. to 300° C., and 0° C. to 150° C. is preferred. A reaction time is, for example, 1 minute to 1 day.

The coupling reaction of Compound (XIII) and Compound (XIV) can be carried out without solvent or in a suitable solvent. As the "solvent", the same solvents as "solvents" described for the above-mentioned Process A can be used. For example, no solvent, or an ether solvent such as tetrahydrofuran, an aromatic solvent such as toluene, and an amide solvent such as dimethylformamide are preferred.

Alternatively, the present "coupling reaction of Compound (XIII) and Compound (XIV)" may be carried out by adding an appropriate base. In addition, the base may be used as a solvent. As the "base", the same bases as "bases" described for the above-mentioned Process A can be used. For example, sodium hydride, sodium amide, and lithium diisopropyl amide are preferable.

The present "coupling reaction of Compound (XIII) and Compound (XIV)" can be carried out at −100° C. to 300° C., and 0° C. to 150° C. is preferred. A reaction time is, for example, 1 minute to 1 day.

A reaction "of removing a substituent V" can be carried out without solvent or in a suitable solvent. As the "solvent", the same solvents as "solvents" described for the above-mentioned Process A can be used. For example, no solvent, or an ether solvent such as diglyme, an aromatic solvent such as xylene, a sulfoxide solvent such as dimethyl sulfoxide, and water are preferred.

Alternatively, the present reaction "of removing a substituent V" may be carried out by adding an appropriate acid or salt. In addition, the acid may be used also as a solvent. As the "acid", a mineral acid such as hydrochloric acid and sulfuric acid, and p-toluenesulfonic acid are preferred. As the "salt", for example, sodium chloride is used.

The present reaction "of removing a substituent" is preferably carried out by heating. Preferably, the reaction is carried out at room temperature to 250° C. A reaction time is, for example, 1 minute to 1 day.

Compound (XII) can be prepared according to the method, for example, described in J. Org. Chem. 36, 2480 (1971). That is, for example, as shown below, Compound (XII) can be prepared by a method of preparing Compound (XVIII) by Friedel-Crafts reaction of Compound (XVI) and Compound (XVII), converting Compound (XVIII) into Compound (XIX) by reduction reaction, followed by halogenation to obtain. Compound (XX), and carrying out intermolecular Friedel-Crafts reaction. Alternatively, Compound (XII) may be also prepared by intramolecular Friedel-Crafts reaction of Compound (XIX).

Alternatively, Compound (XII) can be prepared, for example, according to the method of Org. Syn. Coll. Vol. 4, 898(1963). That is, for example, Compound (XII) can be prepared by tandem-type intramolecular Friedel-Crafts reaction of Compound (XVI) and Compound (XXI) as shown below:

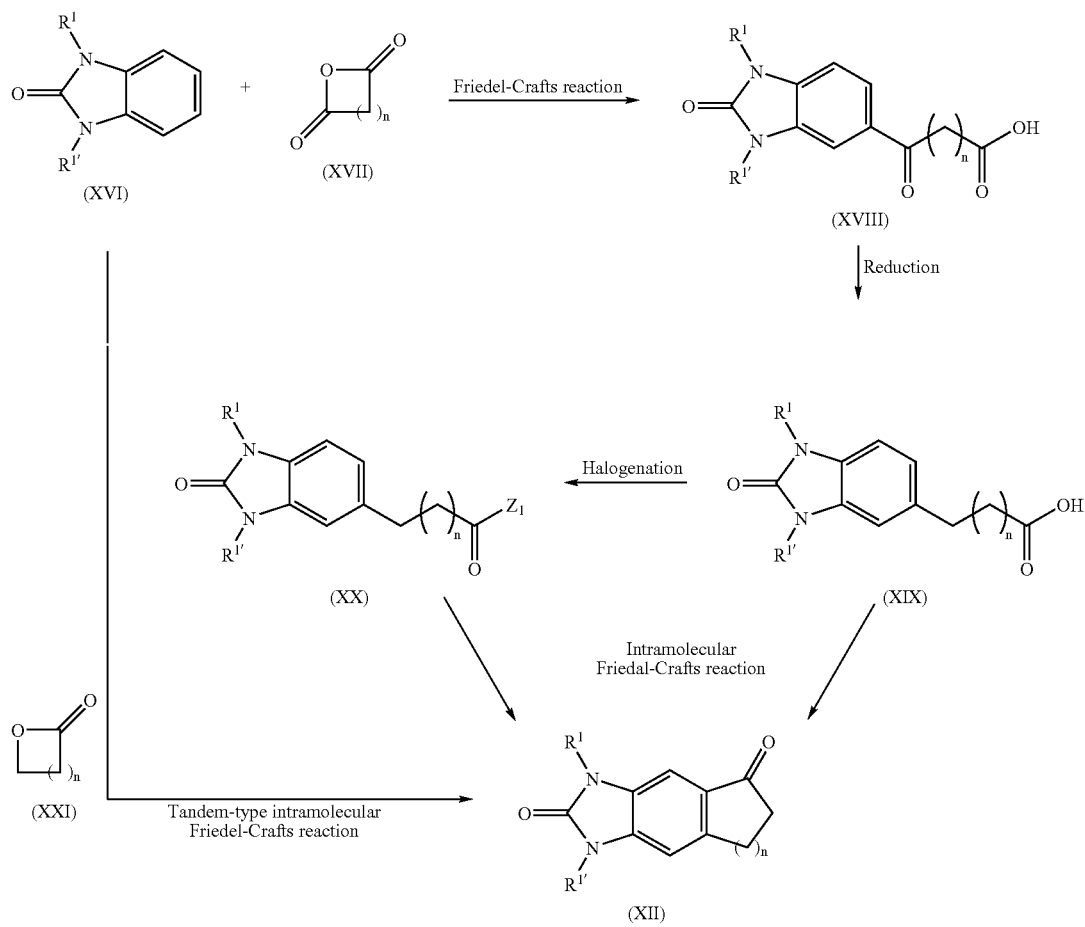

wherein respective symbols as defined above.

The "Friedel-Crafts reaction of Compound (XVI) and Compound (XVII)" can be carried out by a method according to the aforementioned "Friedel-Crafts reaction of Compound (IV) and Compound (X)". In the "reduction" reaction of Compound (XVII) to compound (XIX), catalytic reduction using, for example, a palladium catalyst, Clemmensen reduction, for example, described in Org. React. 22, 401 (1975), and Wolff-Kishner reduction, for example, described in, Org. React. 4,378 (1948) can be used.

The "halogenation" reaction of Compound (XIX) to Compound (XX) is carried out by using a reagent used for halogenation such as thionyl chloride, oxalyl chloride, and chlorine. Alternatively, a halogenation reagent may be used as a solvent.

The "intramolecular Friedel-Crafts reaction" from Compound (XIX) to Compound (XII) can be carried out by a method according to the aforementioned "Friedel-Crafts reaction of Compound (IV) and Compound (X)". As Lewis acid, polyphosphoric acid is preferable.

The "intramolecular Friedel-Crafts reaction" from Compound (XX) to Compound (XII) can be carried out by a mouthed according to the aforementioned "Friedel-Crafts reaction of Compound (IV) and Compound (X)".

The preparation of Compound (XII) by the "tandem-type intramolecular Friedel-Crafts reaction" of Compound (XVI) and Compound (XXI) can be carried out by a method according to the aforementioned "Friedel-Crafts reaction of Compound (IV) and Compound (X)".

[Process B] Process for preparing Compound (Ia), (Ic) or (Id) by a coupling reaction of Compound (VI) or (VI') and Compound (VII).

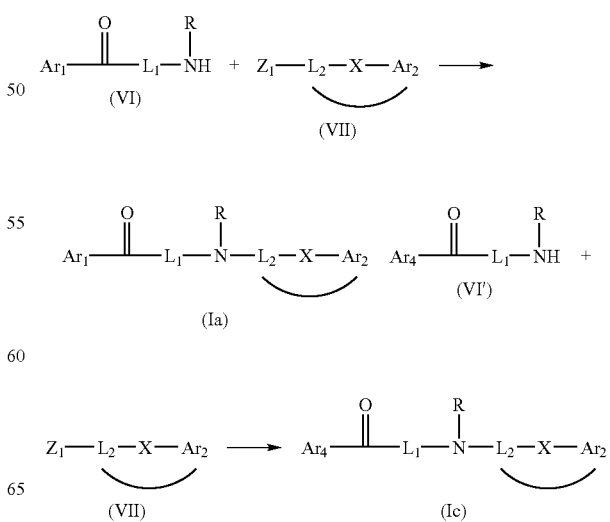

-continued

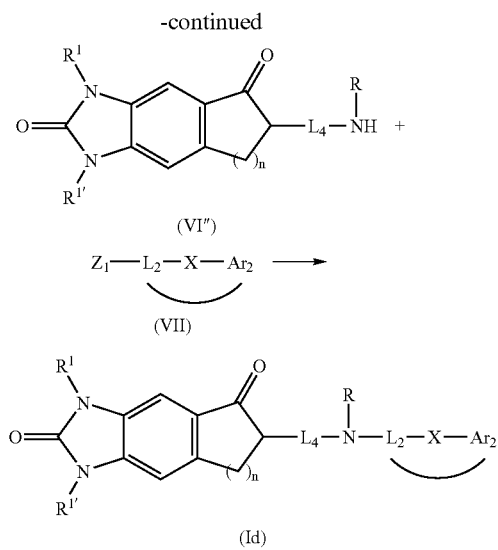

wherein respective symbols are as defined above.

The present coupling reaction can be carried out without a solvent, or in an appropriate solvent. As the "solvent", the same solvents as "solvents" described for the above-mentioned Process A can be used. For example, no solvent, or an alcohol solvent such as ethanol, an aromatic solvent such as toluene, and an amide solvent such as dimethylformamide are preferable.

Alternatively, the present coupling reaction may be carried out by adding an appropriate base. In addition, the base may be also used as a solvent. As the "base" the same bases as "bases" described for the above-mentioned Process A can be used.

Upon the present coupling reaction, a hydrogen atom of Compound (VI) or (VI') may be substituted with a metal atom, for example, an alkali metal such as lithium and sodium in advance.

The present coupling reaction may be carried out at −100° C. to 300° C., and 0° C. to 150° C. is preferred. A reaction time is, for example, 1 minute to 1 day.

The present coupling reaction can be carried out at an arbitrary ratio of Compound (VI) or (VI') and Compound (VII), and either of them may be used also as a solvent.

Compound (VII) can be prepared by a method known per se or a similar method thereto.

Compound (VI), (VI') or (VI'') can be prepared, for example, by a coupling reaction of the aforementioned Compound (II) or (II') and Compound (VIII) as shown below.

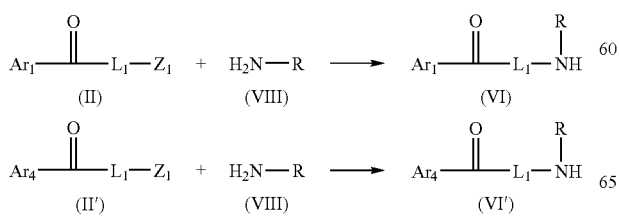

-continued

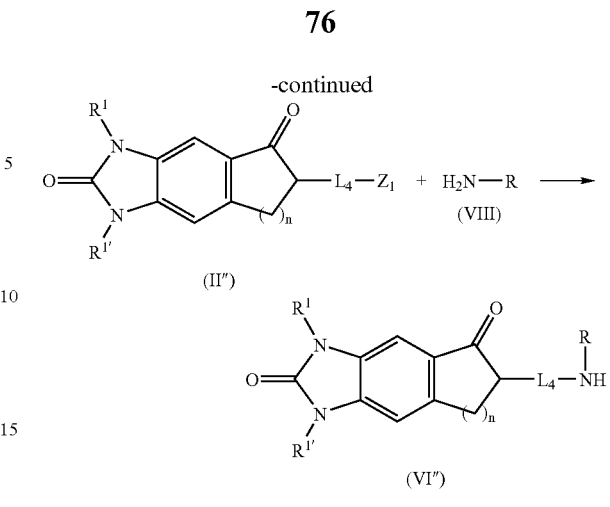

wherein respective symbols are as defined above.

The present coupling reaction can be carried out without solvent or in an appropriate solvent. As the "solvent", the same solvents as "solvents" described for the above-mentioned Process A can be used. For example, no solvent, or an alcohol solvent such as ethanol, an aromatic solvent such as toluene, and an amide solvent such as dimethylformamide are preferable.

Alternatively, the present coupling reaction may be carried out by adding an appropriate base. In addition, the base may be used also as a solvent. As the "base", the same bases as "bases" described for the above-mentioned Process A can be used.

Upon the present coupling reaction, a hydrogen atom of Compound (VIII) may be substituted with a metal atom, for example, an alkali metal such as lithium and sodium in advance.

The present coupling reaction can be carried out at −100° C. to 300° C., and 0° C. to 150° C. is preferred. A reaction time is, for example, 1 minute to 1 day.

The present coupling reaction can be carried out at an arbitrary ratio of Compound (II) or (II') and Compound (VIII), and either of them may be also used as a solvent.

Compound (VIII) can be prepared by a method known per se or a similar method thereto. For example, Compound (VIII) can be prepared by the method described in Comprehensive Organic Transformation VCH Publishers Inc., 1989, specifically, a reductive amination reaction described in Organic Reactions (Org. Rxs.) 14, 52 (1965), Synthesis 30(1972), a reduction reaction of nitrites described in Org. Rxs. 6, 469(1951), Chem. Pharm. Bull. 32, 873(1984), a reduction reaction of azide described in J. Med. Chem. 12, 658(1969), J. Am. Chem. Soc. 73, 5865(1951), and a Gabriel synthesis method described in Org. Syn. Coll. Vol. 2, 83(1943), J. Am. Chem. Soc. 72, 2786(1950).

[Process C] Process for preparing Compound (Ib) by a coupling reaction of Compound (IX) and Compound (VII).

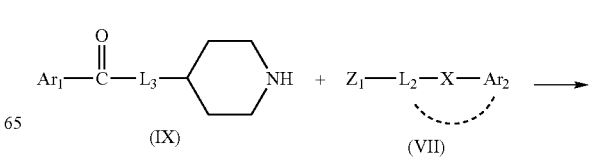

-continued

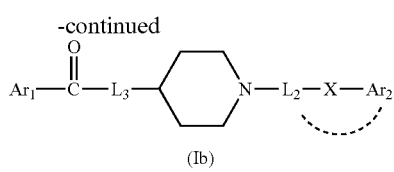

(Ib)

wherein respective symbols are as defined above.

The present coupling reaction can be carried out according to the aforementioned Process A. Specifically, the present reaction can be carried out without solvent, or in an appropriate solvent. As the "solvent", the same solvents as "solvents" described for the above-mentioned Process A can be used. For example, no solvent, or an alcohol solvent such as ethanol, an aromatic solvent such as toluene, a nitrile solvent such as acetonitrile, and an amide solvent such as dimethylformamide are preferable.

Alternatively, the present coupling reaction may be carried out by adding an appropriate base. In addition, the base may be also used as a solvent. As the "base", the same bases as "bases" described for the above-mentioned Process A can be used. Potassium carbonate, triethylamide, and diisopropylethylamine are preferred.

Upon the present coupling reaction, a hydrogen atom of Compound (IX) may be substituted with a metal atom, for example, an alkali metal such as lithium and sodium in advance.

The present coupling reaction can be carried out at −100° C. to 300° C., and 0° C. to 150° C. is preferred. A reaction time is, for example, 1 minute to 1 day.

The present coupling reaction can be carried out at an arbitrary ratio of Compound (IX) and Compound (VII), and further either of them may be also used as a solvent.

Compound (IX) can be prepared, for example, by a method such as preparing Compound (XI) by Friedel-Crafts reaction of Compound (IV) and Compound (X), followed by subjecting to a deprotection reaction as shown below.

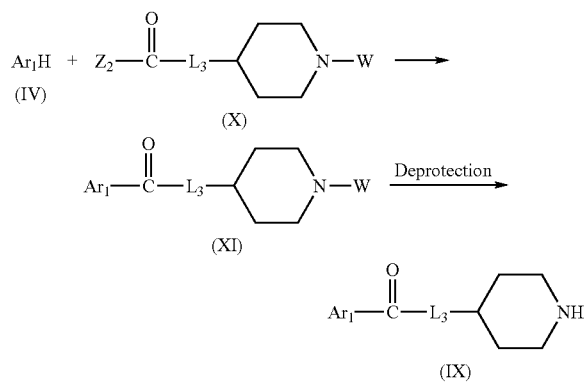

wherein W represents a protecting group for amine, and the other respective symbols are as defined above.

As the protecting group W for amine, for example, protecting groups described in Protective Groups in Organic Synthesis, Third Edition, Wiley-Interscience (1999) can be used. Specifically, examples thereof include acyl groups such as formyl, $C_{1-6}$ alkyl-carbonyl which may have a substituent (e.g. acetyl, ethylcarbonyl, trifluoroacetyl, chloroacetyl etc.), benzoyl, $C_{1-6}$ alkyl-oxycarbonyl (e.g. methoxycarbonyl, ethoxycarbonyl, t-butoxycarbonyl etc.), phenyloxycarbonyl (e.g. phenoxycarbonyl etc.), and $C_{7-15}$ aralkyloxy-carbonyl (e.g. benzyloxycarbonyl, fluorenyloxycarbonyl etc.), and hydrocarbon groups such as trityl and phthaloyl. Inter alia, acetyl, trifluoroacetyl and benzyloxycarbonyl are preferred.

$Z_2$ is preferably a halogen atom (e.g. chloro, bromo etc.) or a hydroxy group.

The Friedel Crafts reaction of Compound (IV) and Compound (X) can be preferably carried out by adding an acid catalyst, and may be carried out without adding an acid catalyst. As the acid catalyst used in the reaction, the same acid catalysts as those used in preparation of the above-mentioned Compound (II) are used. Preferable examples include polyphosphoric acid, aluminum chloride, diethylaluminum chloride, and zinc chloride. The acid catalyst can be used at an arbitrary equivalent, usually at 0.1 equivalent to 10 equivalents relative to Compound (IV) or Compound (X). Occasionally, the acid catalyst may be also used as a solvent.

As the solvent, same solvents as those used in preparation of the above-mentioned Compound (II) can be applied. Preferable examples include no solvent, or a halogenated hydrocarbon solvent such as dichloromethane, and 1,2-dichloroethane, a nitrated hydrocarbon solvent such as nitromethane, an aromatic solvent such as nitrobenzene, and carbon disulfide.

The present reaction can be carried out at −100° C. to 300° C. and, usually, 0° C. to 150° C. is preferred. A reaction time is, for example, 1 minute to 3 days.

Deprotection of Compound (XI) can be carried out according to the method described in the aforementioned Protective Groups in Organic Synthesis, Third Edition, Wiley-Interscience (1999). Specifically, deprotection is carried out by acid treatment, alkali hydrolysis, or catalytic reduction reaction.

Compound (X) can be prepared by a method known per se or a similar method thereto. For example, Compound (X) can be prepared by the method described in Chem. Pharm. Bull., 34, 3747 (1986), Chem. Pharm. Bull., 41, 529 (1993), and EP-A-0,378,207 or a similar method thereto.

When Compounds (Ia) to (Id) prepared by the aforementioned [Process A] to [Process C] are primary or secondary amine, those compounds can be isolated and purified after derived to other derivatives, if necessary. Preferable examples of "other derivatives" include compounds in which the primary or secondary amine is protected with a general amine protecting group. Examples of the "general amine protecting group" include the protecting groups described in Protective Groups in Organic Synthesis, Third Edition, Wiley-Interscience (1999). Specifically, examples include an acyl group such as formyl, $C_{1-6}$ alkyl-carbonyl which may have a substituent (e.g. acetyl, ethylcarbonyl etc.), benzoyl, $C_{1-6}$ alkyl-oxycarbonyl (e.g. methoxycarbonyl, ethoxycarbonyl, t-butoxycarbonyl etc.), phenyloxycarbonyl (e.g. phenoxycarbonyl etc.), and $C_{7-15}$ aralkyloxy-carbonyl (e.g. benzyloxycarbonyl, fluorenyloxycarbonyl etc.), and hydrocarbon groups such as trityl and phthaloyl. Preferably, an acetyl group, a benzoyl group, a t-butoxycarbonyl group, a benzyloxycarbonyl group, and a benzyl group are used. Purified "other derivatives" can be derived to the original primary or secondary amine or a salt thereof by a deprotection reaction suitable for each of them. The "deprotection reaction" can be carried out according to the method, for example, described in the aforementioned Protective Groups in Organic Synthesis, Third Edition, Wiley-Interscience (1999). Specifically, the deprotecting reaction is carried out by acid treatment, alkaline hydrolysis, or catalytic reducing reaction.

As the "salt" in the "primary or secondary amine or a salt thereof", the "salt" in the aforementioned "when Compound B is a salt" can be applied.

Compounds (Ia) to (Id) can be prepared by processes other than the aforementioned processes. For example, they may be prepared by reductive amination reaction described in J. Am. Chem. Soc. 2897 (1971), Synthesis 135 (1976), Tetrahedron Lett. 5595 (1990), an addition reaction of amine to epoxide described in Synth. Commun. 177 (1973), Tetrahedron Lett. 4661 (1990), Michael addition reaction of amine to a conjugated double bond described in Org. Rxs. 79 (1949), Organic Synthesis Coll. Vol. 1, 196 (1941), a reduction reaction of amide described in Synthesis 752 (1978), Org. Rxs. 303 (1942), or a Mannich reaction described in Org. Rxs. 469. (1941), Angew. Chem. 265 (1956).

Since Compound (A) and Compound (B) used in the present invention have low toxicity and exhibit excellent effects of improving an urine flow rate and a voiding efficiency and, at the same time, do not influence on a voiding pressure and a blood pressure, they can be used as a preventive or therapeutic agent for voiding disturbance of a mammal such as human and the like. For example, they can be used as a preventive or therapeutic agent for voiding disturbance, in particular, voiding difficulty derived from the following 1) to 7). 1) benign prostatic hyperplasia, 2) bladder cervical atresia, 3) neurogenic bladder, 4) diabetes, 5) operation, 6) detrusor underactivity, and 7) Sjögren's syndrome (dry eye, dry mouth, vagina drying etc.).

More specifically, those compounds can be used as a preventive or therapeutic agent for voiding difficulty due to detrusor underactivity due to benign prostatic hyperplasia, detrusor underactivity due to diabetes, detrusor underactivity due to diabetic neuropathy, idiopathic detrusor underactivity (including those due to aging), detrusor underactivity due to multiple sclerosis, detrusor underactivity due to Perkinson's disease, detrusor underactivity due to spinal cord injury, detrusor underactivity after operation, detrusor underactivity due to cerebral infarction, neurogenic bladder due to diabetes, neurogenic bladder due to diabetic neuropathy, neurogenic bladder due to multiple sclerosis, neurogenic bladder due to Perkinson's disease, neurogenic bladder due to spinal cord injury, and neurogenic bladder due to cerebral infarction.

Further, Compound A and Compound B can be also used as a preventive or therapeutic agent for urinary storage disturbance such as urinary urgency due to overactive bladder, urinary frequency, detrusor underactivity accompanied with overactive bladder, and urinary incontinence.

In addition, Compound A and Compound B can be also used as a preventive or therapeutic agent for glaucoma.

The present invention also provides a method for screening a compound having effects of preventing or treating voiding disturbance or a salt thereof by Pressure Flow Study, which comprises using an animal model loaded with an α agonist.

The screening method of the present invention can be performed by measuring influence of the test substance on voiding function of bladder of the animal model (maximum urine flow rate, intravesical pressure, voiding efficiency etc.) by Pressure Flow Study, in the case where a test substance is administered to an animal model loaded with an α agonist or the case where the test substance is not administered to the animal model.

Examples of the "animal model" used in the screening method of the present invention include a non-human mammal such as a rabbit, a guinia pig, a hamster, a rat, a mouse, a gerbil, a dog and a monkey. Preferable examples include a guinea pig (Hartley male guinea pig).

A week age, a body weight, the presence or absence of delivery of an animal model used in the present invention is not particularly limited as far as the model can be applied to the intended screening, and these conditions may be appropriately changed.

An animal model loaded with an α-agonist (preferably phenylephrine) can be prepared by a known method, for example, a method described in the aforementioned Non-Patent documents 3 to 5.

As a test substance, a tissue extract, and a cell culture supernatant of a warm-blooded mammal (e.g. mouse, rat, pig, cow, sheep, monkey, human etc.) are used in addition to a known synthetic compounds, peptides and proteins.

Measurement of voiding function (maximum urine flow rate, intravesical pressure, voiding efficiency etc.) in the screening method of the present invention can be performed according to a known method, for example, the method described in Non-Patent documents 6 to 9.

The screening method in the present invention can be usefully and effectively applied to the screening of a compound having effects of preventing or treating voiding disturbance, in particular, voiding disturbance accompanied with benign prostatic hyperplasia, and a compound having both of an acetylcholinesterase inhibitory action and an $\alpha_1$ antagonistic action.

A preventive or therapeutic agent for voiding disturbance can be assessed by administering about 0.001 to about 1000 mg/kg (preferably about 0.01 to about 100 mg/kg) of a test substance to an animal model loaded with an α agonist in the screening method of the present invention, and investigating therapeutic effects of the test substance using effects on a urine flow rate, an intravesical pressure, and a voiding efficiency as an index.

In addition, as an animal model used in the present invention, a normal animal (animal exhibiting no pathology) may be used. However, for example, the aforementioned voiding function of bladder may be measured using an animal exhibiting pathology such as voiding disturbance, benign prostatic hyperplasia, detrusor underactivity, overactive bladder, urinary frequency, urinary incontinence, diabetic neuropathy, hypertension, diabetes, obesity, hyperlipemia, arterial sclerosis, gastric ulcer, asthma, chronic obstructive respiratory disease, ovary cancer, cerebrovascular disease, brain injury, and spinal cord injury, (e.g. obesity rat (Wistar Fatty rat)). When the aforementioned voiding function of bladder is measured in an animal exhibiting such pathology, this can be effectively applied to screening of a medical substance for preventing or treating such the complex. However, this may be also applied to screening of a medical substance which is effective only for the aforementioned pathology (e.g. digestive tract disease such as gastric ulcer) and does not influence on voiding function, or may be applied to screening for the purpose of excluding a test substance which does not influence on voiding function from a medical substance to be selected.

Using this screening method, when a urine flow rate is improved by about 20% or more and a voiding efficiency is improved by about 10% or more in the case of administration of a test substance as compared with no administration of the test substance, the test substance can be determined to a compound having effects of improving voiding function or a salt thereof (hereinafter, referred to as Compound C).

Compound A, B or C can be formulated into a preparation according to means known per se. The compound can be formulated into medicines such as tablets (including sugar-coated tablets, film-coated tablets), powders, granules, capsules (including soft capsules), solutions, injectables, suppositories and sustained-release agents, as it is, or by appropriately mixing with an appropriate amount of a pharmacological acceptable carrier at a step of formulating into a preparation, and the compound can be safely administered orally or parenterally (e.g. topically, rectally, intravenously etc.) as a preparation.

Examples of the pharmacologically acceptable carrier used in preparation of the medicine, or the preventive or therapeutic agent for voiding disturbance of the present invention include various organic or inorganic carrier substances which are conventionally used as a pharmacy material, such as excipients, lubricants, binders and disintegrating agents in solid preparations; solvents, solubilizers, suspending agents, isotonics, buffers and soothing agents in liquid preparations. If necessary, additives such as antiseptics, antioxidants, coloring agents, sweeteners, adsorbing agents, and wetting agents may be used.

Examples of the excipient include lactose, white sugar, D-mannitol, starch, corn starch, crystalline cellulose, and light silicic acid anhydride.

Examples of the lubricant include magnesium stearate, calcium stearate, talc, and colloidal silica.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, and sodium carboxymethylcellulose.

Examples of the disintegrating agent include starch, carboxymethylcellulose, calcium carboxymethylcellulose, sodium carboxymethylstarch and L-hydroxypropylcellulose.

Examples of the solvent include water for injection, alcohol, propylene glycol, macrogol, sesame oil, and corn oil.

Examples of the solubilizer include polyethylene glycol, propylene glycol, D-mannitol, benzyl benzoate, ethanol, trisaminomethane, cholesterol, triethanolamine, sodium carbonate, and sodium citrate.

Examples of the suspending agent include surfactants such as stearyltriethanolamine, sodium laurylsulfate, laurylaminopropionic acid, lecithin, benzalkonium chloride, benzethonium chloride, and glycerin monostearic acid; hydrophilic polymers such as polyvinyl alcohol, polyvinylpyrrolidone, sodium carboxymethylcellulose, methylcellulose, hydroxymethylcellulose, hydroxyethylcellulose, and hydroxypropylcellulose.

Examples of the isotonic include glucose, D-sorbitol, sodium chloride, glycerin, and D-mannitol.

Examples of the buffer include buffers such as phosphate, acetate, carbonate, and citrate.

Examples of the soothing agent include benzyl alcohol

Examples of the antiseptic include paraoxybenzoic acid esters, chlorobutanol, benzyl alcohol, phenethyl alcohol, dehydroacetic acid, and sorbic acid.

Examples of the antioxidant include sulfite, and ascorbic acid.

A content of Compound A, B or C used in the medicine, or the preventive or therapeutic agent for voiding disturbance of the present invention is about 0.1 to about 100% by weight based on a total weight of the agent.

A dose of the medicine, or the preventive or therapeutic agent for voiding disturbance of the present invention differs depending on an administration subject, an administration route, and disease. For example, the dosage of a therapeutic agent for voiding difficulty is about 0.005 to 1000 mg, preferably about 0.05 to 500 mg, more preferably about 0.5 to 200 mg as one dose of active ingredient, as an oral preparation for an adult (body weight about 60 kg). The preparation may be administered once or by dividing a few times per day.

Compound A, B or C can be used in combination with a medicine for treating disease causing voiding disturbance (e.g. voiding difficulty etc.) or a medicine which is administered for treating other disease but itself induces voiding disturbance (e.g. voiding difficulty etc.).

Examples of the "medicine for treating disease causing voiding disturbance" include a therapeutic agent for benign prostatic hyperplasia, a therapeutic agent for prostate cancer, a therapeutic agent for chronic cystitis, a therapeutic agent for constipation, a therapeutic agent for large intestine cancer, a therapeutic agent for ovary cancer, a therapeutic agent for diabetes, a therapeutic agent for cerebrovascular disorder, a therapeutic agent for spinal cord injury, a therapeutic agent for spinal tumor, a therapeutic agent for multiple sclerosis, a therapeutic agent for dimentia including Alzheimer's disease, a therapeutic agent for Parkinson's disease, a therapeutic agent for progressive supranuclear palsy, a therapeutic agent for Guillain-Barré syndrome, a therapeutic agent for acute panautonomic abnormality, a therapeutic agent for olivotontocerebellar atrophy, and a therapeutic agent for cervical vertebrae disorder.

Examples of the therapeutic agent for benign prostatic hyperplasia include Allylestrenol, Chlormadinone acetate, Gestonorone caproate, Nomegestrol, Mepartricin, Finaststeried, PA-109, and THE-320. In addition, examples of the therapeutic agent for voiding disturbance accompanied with benign prostatic hyperplasia include α-reductase inhibitors such as YM-31758, YM-32906, KF-20405, MK-0434, finasteride, and CS-891.

Examples of the therapeutic agent for prostate cancer include Ifosfamide, Estramustine phosphate sodium, Cyproterone, Chlormadinone acetate, Flutamide, Cisplatin, Lonidamine, Peplomycin, Leuprorelin, Finasteride, Triptorelin-DDS, Buserelin, Goserelin-DDS, Fenretinide, Bicalutamide, Vinorelbine, Nilutamide, Leuprolide-DDS, Deslorelin, Cetrorelix, Ranpirnase, Leuprorelin-DDS, Satraplatin, Prinomastat, Exisulind, Buserelin-DDS, and Abarelix-DDS.

Examples of the therapeutic agent for chronic cystitis include Flavoxate hydrochloride.

Examples of the therapeutic agent for constipation include Sennoside A•B, and Phenovalin.

Examples of the therapeutic agent for large intestine cancer include Chromomycin A3, Fluorouracil, Tegafur and Krestin.

Examples of the therapeutic agent for ovary cancer include Chromomycin A3, Fluorouracil, Bleomycin hydrochloride, and Medroxyprogesterone acetate.

Examples of the therapeutic agent for diabetes include Insulin resistance improving drug, Insulin secretion accelerating drug, biguanide agent, Insulin, α-Glucosidase inhibitor, and β3 adrenaline receptor agonist.

Examples of the Insulin resistance improving drug include pioglitazone or a salt thereof (preferably hydrochloride), troglitazone, rosiglitazone or a salt thereof (preferably maleate), JTT-501, GI-262570, MCC-555, YM-440, DRF-2593, BM-13-1258, KRP-297, and CS-011.

Examples of the Insulin secretion accelerating drug include sulfonylurea preparation. Specific examples of the sulfonylurea preparation include tolbutamide, chloropropamide, tolazamide, acetohexamide, glyclopyramide and an ammonium salt thereof, glibenclamide, gliclazid, and glimepiride. Besides, examples of the Insulin secretion accelerating drug include repaglinide, nateglinide, KAD-1229, and JTT-608.

Examples of the biguanide agent include metformin and buformin.

Examples of the Insulin include animal Insulin extracted from cattle, pig pancreas; semi-synthetic human Insulin enzymatically syntesized from Insulin extracted from pig pancreas, human Insulin synthesized by genetic engineering using *Escherichia coli* or yeast. As the Insulin, Insulin zinc including 0.45 to 0.9(w/w) % of zinc; Protamineinsulin zinc prepared from zinc chloride, protamine sulfate and Insulin are used. Further, Insulin may be a fragment or derivative thereof (e.g. INS-1 etc.).

Examples of the α-Glucosidase inhibitor include acarbose, voglibose, miglitole, and emiglitate.

Examples of the β3 adrenaline receptor agonist include AJ-9677, BMS-196085, SB-226552, SR-58611-A, CP-114271, and L-755507.

Besides, examples of the therapeutic agent for diabetes include ergoset, pramlintide, leptin, and BAY-27-9955.

Examples of the therapeutic agent for cerebrovascular disorder include Nicaraven, Bencyclane fumarate, Eurnamonine, Flunarizine, Nilvadipine, Ibudilast, Argatroban, Nizofenone, Naftidrofuryl, Nicergoline, Nimodipine, Papaveroline, Alteplase, Viquidil hydrochloride, Moxisylyte, Pentoxifylline, Dihydroergotoxine mesylate, Lemildipine, Cyclandelate, Xanthinolnicotinate, Febarbamate, Cinnarizine, Memantine, Ifenprodil, Meclofenoxate hydrochloride, Ebselen, Clopidogrel, Nebracetam, Edaravone, Clinprost-DDS, Vatanidipine, Ancrod, Dipyridamole.

Examples of the therapeutic agent for spinal cord injury include Methylprednisolone, and Dural graft matrix.

Examples of the therapeutic agent for spinal tumor include Nimustine hydrochloride.

Examples of the therapeutic agent for multiple sclerosis include Interferon-β-1b.

Examples of the therapeutic agent for dementia including Alzheimer's disease include Aniracetam, Arginine pyroglutamte, Nefiractam, Nimodipine, Piracetam, Propentfylline, Vinpocetine, Indoloxazine, VitaminE, Cinepazide, Memantine, Lisuride hydrogen malate, Pramiracetam, Znclopenthixol, Protirelin, EGB-761, Acetyl-L-carnitine, Phosphatidylserine, Nebracetam, Taltireline, Cholinealphoscerate, Ipidacrine, Talsaclidine, Cerebrolysin, Rofecoxib, ST-618, T-588, Tacrine, Physostigmine-DOS, HuperzineA, Donepezil, Rivastigmine, Metrifonate and TAK-147.

Examples of the therapeutic agent for Parkinson's disease include Talipexole, Amantadine, Pergolide, Bromocriptine, Selegiline, Mazaticolhydrochloride, Memantine, Lisuride hydrogen malate, Trihexyphenidyl, Piroheptinhydrochloride, Terguride, Ropinirole, Ganglioside-GM1, Droxidopa, Riluzole, Gabergoline, Entacapone, Rasagiline, Pramipexole, L-dopa-methylester, Tolcapone, Remacemida, Dihydroergocryptine, Carbidopa, Selegiline-DDS, Apomorphine, Apomorphine-DDS, Etilevodopa, and Levodopa.

Examples of the therapeutic agent for progressive supranuclear palsy include L-dopa, carbidopa, bromocriptine, pergolide, lisuride, and amitriptyline.

Examples of the therapeutic agent for Guillain-Barré syndrome include steroid agent and TRH preparation such as protirelline.

Examples of the therapeutic agent for acute panautonomic abnormality include steroid agent, L-threo-DOPS, dihydrideergotamine, and amezinium.

Examples of the therapeutic agent for olivopontocerebellar atrophy include TRH preparation, steroid agent, midodrine, and amezinium.

Examples of the therapeutic agent for cervicel vertebrae disorder include an anti-inflammatory agent.

Examples of the "drug which is administered for treating other disease but itself induces voiding disturbance" include an analgesic (morphine, tramadol hydrochloride), a central skeleton muscle relaxant (baclofen), a butyrophenone antipsychotic agent (haloperidol etc.), a therapeutic agent for a voiding frequency-urinary incontinence (muscarine antagonist such as oxybutynin hydrochloride, propiverine hydrochloride, tolterodine, darifenacin, YM-905/YM-537, temiverine (NS-21), KRP-197, and trospium; smooth muscle relaxant such as flavoxate hydrochloride; muscle relaxant such as NC-1800; Beta2 agonist such as clenbuterol; potassium channel opener such as ZD-0947, NS-8, KW-7158, and WAY-151616; PGE2 antagonist such as ONO-8711; vanilloid receptor agonist such as resiniferatoxin and capsaicin; tachykinin antagonist such as TAK-637, SR-48968 (saredutant), and SB-223412 (talnerant); delta opioid agonist), antispasmodic (scopolamine butylbromide, butropium bromide, tiquizium bromide, timepidium bromide, propantheline bromide), a therapeutic agent for digestive tract ulcer (Kolantyl, Methaphynin, cimetidine), a therapeutic agent for Parkinson's disease (trihexyphenidyl hydrochloride, biperiden, mazaticol hydrochloride, levodopa), an anti-histamine drug (diphenhydramine, chlorophenylamine maleate, homochlorcyclizine hydrochloride), a tricyclic antidepressant (imipramine hydrochloride, amitriptyline hydrochloride, clomipramine hydrochloride, amoxapine, desipramine hydrochloride), phenothiazine antipsychotic agent (chlorpromazine, propericiazine, levomepromazine, thioridazine), a benzodiazepine tranquilizer•sleep-sedative (diazepam, chlordiazepoxide, clotiazepam, estazolam), an antiarrhythmic agent (disopyramide), a vasodilator (hydralazine hydrochloride), a cerebral peripheral circulation improving agent (pentoxifylline), a bronchodilator (theophylline, ephedrine hydrochloride, methylephedrine hydrochloride), a β-adrenaline blocker (propranolol hydrochloride), cold drug (Danrich), a peripheral skeleton muscle relaxant (dantrolene sodium), and a antitubercular agent (isoniazid).

When Compound A, B, or C is used in combination with the aforementioned concomitant use drug, a dose can be appropriately selected based on a minimum recommended clinical dose of individual drug as a standard, depending on an administration subject, an age and a weight of an administration subject, condition, an administration time, an administration method, a dosage form, and a combination of drugs. A dose of a particular patient is determined depending on an age, a body weight, general health state, a sex, a diet, an administration time, an administration method, an excretion rate, a combination of drugs, and an extent of disease of a patient to be treated at that time, and taking them and other factors into consideration.

Typically, an individual day dose regarding a combination of Compound A, B or C with at least one kind of a compound selected from remedies for various diseases or a salt thereof is in a range of about 1/50 a minimum recommended clinical dose to a maximum recommended level regarding the circumstances where they are administered alone.

BEST MODE FOR CARRYING OUT THE INVENTION

The present invention will be explained in detail below by way of Examples, Preparation Examples, and Experimental Examples, but the present invention is not limited by them, and may be modified without departing from the scope of the present invention.

"Room temperature" in the following Reference Examples and Examples denotes 0 to 30° C. "%" means weight percentage unless otherwise indicated.

Other abbreviations used in the present text indicate the following means.

s; singlet
d; doublet
t: triplet
q: quartet
m: multiplet
br: broad
J: coupling constant.
Hz: Hertz
CDCl$_3$: deuterochloroform
DMSO-d$_6$: deuterodimethyl sulfoxide
$^1$H NMR: proton nuclear magnetic resonance (usually, a free compound was measured in CDCl$_3$, and hydrochloride was measured in DMSO-d$_6$)
IR: infrared absorption spectrum
MS: Mass spectrum (usually, measured using an electron bombard ionization method)

In the present specification and drawings, when a base and an amino acid are denoted by an abbreviation, it is based on abbreviations by IUPAC-AUB Commission Biochemical Nomenclature or conventional abbreviations in the art, and examples are shown below. When an amino acid can have an optical isomer, it denotes a L-amino acid unless otherwise indicated.

DNA: deoxyribonucleic acid
cDNA: complementary deoxyribonucleic acid
A: adenine
T: thymine
G: guanine
C: cytosine
ATP: adenosine triphosphate
EDTA: ethylenediaminetetraacetic acid

EXAMPLES

Reference Example 1

8-(5-Chloropentanoyl)-1,2,5,6-tetrahydro-4H-pyrrolo[3,2,1-ij]quinolin-4-one

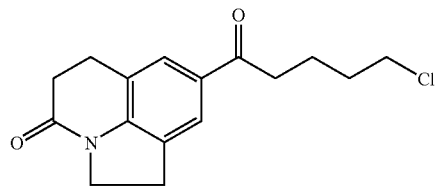

Aluminum chloride (55 g, 410 mmol) was added by portions to a solution of 1,2,5,6-tetrahydro-4H-pyrrolo[3,2,1-ij]quinolin-4-one (30.0 g) and 5-chlorovaleryl chloride (26.8 ml) in 1,2-dichloroethane (70 ml) under ice-cooling. After stirring at room temperature for 30 minutes, the reaction mixture was poured into ice (500 g), extracted with ethyl acetate, and washed with brine. The organic layer was dried over anhydrous magnesium sulfate, the solvent was evaporated under reduced pressure, and the residue was recrystallized from ethanol-diethyl ether to give a pale yellow solid (36.5 g). Further recrystallization from ethanol-diethyl ether afforded the title compound as colorless crystals (32.4 g) having a melting point of 110-111° C.

$^1$H NMR (200 MHz, CDCl$_3$) δ 1.80-2.00 (4H, m), 2.72 (2H, t, J=7.8 Hz), 2.85-3.15 (4H, m), 3.23 (2H, t, J=8.6 Hz), 3.55-3.65 (2H, m), 4.14(2H, t, J=8.6 Hz), 7.68 (1H, s), 7.72 (1H, s).

elementary analysis as C$_{16}$H$_{18}$ClNO$_2$
calculation value:C, 65.86; H, 6.22; N, 4.80.
experimental value:C, 66.29; H, 6.28; N, 4.82.

Reference Example 2

8-(6-Bromohexanoyl)-1,2,5,6-tetrahydro-4H-pyrrolo[3,2,1-ij]quinolin-4-one

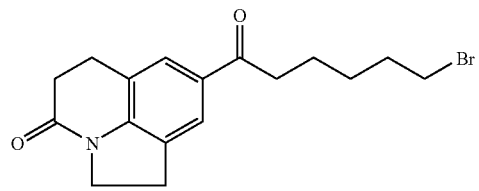

Using 1,2,5,6-tetrahydro-4H-pyrrolo[3,2,1-ij]quinolin-4-one (3.00 g) and 6-bromohexanoyl chloride (2,91 ml) according to the same method as that of Reference Example 1, the title compound (3.94 g) was obtained as white crystals having a melting point of 97 to 98° C.

$^1$H NMR (200 MHz, CDCl$_3$) δ 1.40-1.60 (2H, m), 1.65-2.00 (4H,m), 2.72 (2H, t, J=7.8 Hz), 2.94 (2H, t, J=7.0 Hz), 3.03. (2H, t, J=7.8 Hz),3.23 (2H, t, J=8.4 Hz), 3.43 (2H, t, J=7.0 Hz), 4.14 (2H, t, J=8.4 Hz), 7.68(1H, s), 7.72 (1H, s).

Reference Example 3

8-(5-Chloropentanoyl)-5,6-dihydro-4H-pyrrolo[3,2,1-ij]quinolin-2(1H)-one

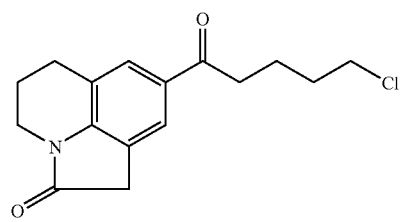

Using 5,6-dihydro-4H-pyrrolo[3,2,1-ij]quinolin-2(1H)-one (3.46 g) and 5-chlorovaleryl chloride (3.4 g) according to the same method as that of Reference Example 1, the title compound (3.78 g) was obtained as pale yellow crystals having a melting point of 89 to 90° C.

$^1$H NMR (400 MHz, CDCl$_3$) δ 1.85-1.94 (4H, m), 2.01-2.07 (2H,m), 2.83 (2H, t, J=6 Hz), 2.96 (2H, t, J=7 Hz), 3.55 (2H, s), 3.60 (2H, d, J=4 Hz), 3.74 (2H, d, J=6 Hz), 7.73 (2H, s).

IR (KBr) vcm$^{-1}$: 1718, 1667, 1605, 1501, 1345, 1289, 1152.

Reference Example 4

8-(6-bromohexanoyl)-5,6-dihydro-4H-pyrrolo[3,2,1-ij]quinolin-2(1H)-one

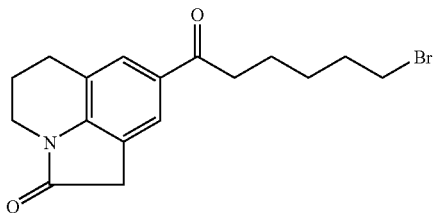

Using 5,6-dihydro-4H-pyrrolo[3,2,1-ij]quinolin-2(1H)-one and 6-bromohexanoyl chloride according to the same method as that of Reference Example 1, the title compound (5.13 g) was obtained as colorless crystals having a melting point of 86 to 87° C.

$^1$H NMR (400 MHz, CDCl$_3$) δ 1.50-1.57 (2H, m), 1.73-1.80 (2H,m), 1.88-1.96 (2H, m), 2.01-2.07 (2H, m), 2.83 (2H, t, J=6 Hz), 2.94 (2H, t, J=7 Hz), 3.43 (2H, t, J=7 Hz), 3.56 (2H, s), 3.74 (2H, d, J=6 Hz), 7.73 (2H,s).

IR (KBr) vcm$^{-1}$: 1711, 1674, 1602, 1496, 1350, 1276, 1162.

Reference Example 5

9-(5-Chloropentanoyl)-2,3,6,7-tetrahydro-1H,5H-pyrido[3,2,1-ij]quinolin-5-one

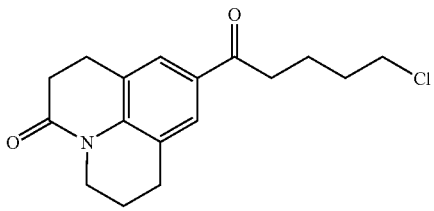

Using 2,3,6,7-tetrahydro-1H,5H-pyrido[3,2,1-ij]quinolin-5-one and 5-chlorovaleryl chloride according to the same method as that of Reference Example 1, the title compound (3.53 g) was obtained as colorless crystals, having a melting point of 83-84° C.

$^1$H NMR (400 MHz, CDCl$_3$) δ 1.35-2.00 (6H, m), 2.68. (2H, t, J=7.5 Hz), 2.85 (2H, t, J=6 Hz), 2.93-2.98 (4H, m), 3.59 (2H, t, J=6 Hz), 3.89(2H, d, J=6 Hz), 7.63 (2H, d, J=5.3 Hz).

IR (KBr) vcm$^{-1}$: 1675, 1602, 1365, 1301, 1156.

Reference Example 6

9-(6-Bromohexanoyl)-2,3,6,7-tetrahydro-1H,5H-pyrido[3,2,1-ij]quinolin-5-one

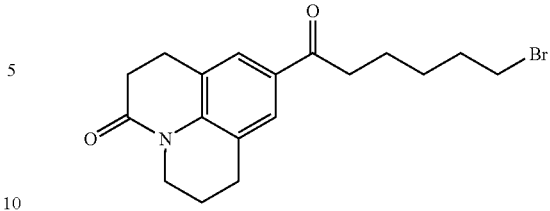

Using 2,3,6,7-tetrahydro-1H,5H-pyrido[3,2,1-ij]quinolin-5-one and 6-bromohexanoyl chloride according to the same method as that of Reference Example 1, the title compound (3.90 g) was obtained as colorless crystals having a melting point of 52-53° C.

$^1$H NMR (400 MHz, CDCl$_3$) δ 1.50-1.57 (2H, m), 1.73-1.80 (2H,m), 1.89-2.00 (4H, m), 2.68 (2H, t, J=7 Hz), 2.85 (2H, t, J=6 Hz), 2.93-2.97(4H, m), 3.43 (2H, t, J=6 Hz), 3.89 (2H, d, J=6 Hz), 7.62 (2H, d, J=5.3 Hz).IR (KBr)vcm$^{-1}$: 1667, 1600, 1358, 1337, 1158.

Reference Example 7

6-(5-Chloropentanoyl)-2H-1,4-benzoxazin-3(4H)-one

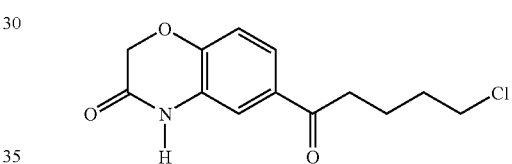

Using 2H-1,4-benzoxazin-3(4H)-one (10.0 g) and 5-chlorovaleryl chloride (12.5 g) according to the same method as that of Reference Example 1, the title compound (12.0 g) was obtained as colorless crystals.

$^1$H NMR (200 MHz, CDCl$_3$) δ 1.69-1.92 (4H, m), 2.97 (2H, t, J=6.8 Hz), 3.59 (2H, t, J=6.1 Hz), 4.71 (2H, s), 7.03. (1H, d, J=8.4 Hz), 7.52(1H, d, J=0.9 Hz), 7.61 (1H, dd, J=8.4, 2.2 Hz), 8.52 (1H, s).

elementary analysis as C$_{13}$H$_{14}$ClNO$_3$
calculation value:C, 58.32; H, 5.27; N, 5.23.
experimental value:C, 58.06; H, 5.55; N, 4.96.

Reference Example 8

6-(6-Bromohexanoyl)-2H-1,4-benzoxazin-3(4H)-one

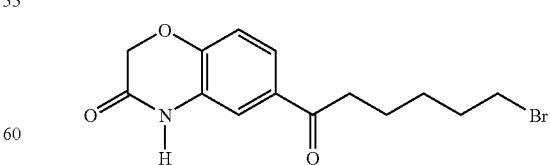

Using 2H-1,4-benzoxazin-3(4H)-one (15.0 g) and 6-bromohexanoyl chloride (2.5.8 g) according to the same method as that of Reference Example 1, the title compound (14.8 g) was obtained as colorless crystals.

$^1$H NMR (200 MHz, CDCl$_3$) δ 1.50-1.58 (2H, m), 1.73-1.83 (2H,m), 1.88-1.97 (2H, m), 2.95. (2H, t, J=4.8 Hz), 3.44 (2H, t, J=4.5 Hz), 4.71(2H, s), 7.02 (1H, d, J=5.4 Hz), 7.57 (1H, d, J=1.4 Hz), 7.61. (1H, dd, J=5.6, 1.2 Hz), 9.02 (1H, s).

elementary analysis as C$_{14}$H$_{16}$BrNO$_3$
calculation value:C, 51.55; H, 4.94; N, 4.29.
experimental value:C, 52.14; H, 4.87; N, 4.32.
MS m/z: 327 [M+H]$^+$ Reference Example 9

5-(5-Chloropentanoyl)-1,3-dihydro-2H-benzimidazol-2-one

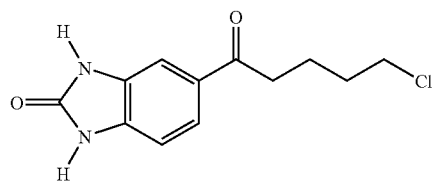

Using 1,3-dihydro-2H-benzimidazol-2-one (4.00 g) and 5-chlorovaleryl chloride (9.24 g) according to the same method as that of Reference Example 1, the title compound (4.36 g) was obtained as colorless crystals.

$^1$H NMR (300 MHz, DMSO-d$_6$) δ 1.76 (4H, m), 2.99-3.04 (2H, m),3.65-3.69 (2H, m), 7.00 (1H, d, J=8.4 Hz), 7.48 (1H, s), 7.67 (1H, dd, J=8.2, 1.4 Hz), 10.88 (1H, s), 11.04 (1H, s).
MS m/z: 253 [M+H]$^+$

Reference Example 10

5-(5-Chloropentanoyl)-1,3-dimethyl-1,3-dihydro-2H-benzimidazol-2-one

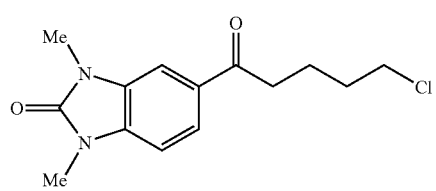

Using 1,3-dimethyl-1,3-dihydro-2H-benzimidazol-2-one (3.00 g) and 5-chlorovaleryl chloride (5.74 g) according to the same method as that of Reference Example 1, the title compound (3.67 g) was obtained as colorless crystals.

$^1$H NMR (300 MHz, DMSO-d$_6$) δ 1.74-1.80 (4H, m), 3.06-3.11 (2H,m), 3.38 (6H, d, J=3.4 Hz), 3.68-3.72 (2H, m), 7.26 (1H, d, J=8.1 Hz), 7.48(1H, d, J=1.5 Hz), 7.81 (1H, dd, J=8.3, 1.7 Hz).

Reference Example 11

1-(1-Acetyl-2,3-dihydro-1H-indol-5-yl)-5-chloropentan-1-one

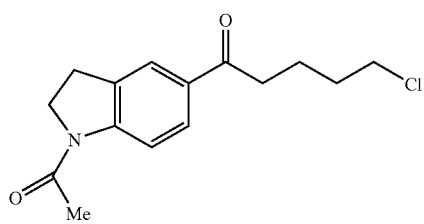

Using 1-acetylindoline (1.60 g) and 5-chlorovaleryl chloride (1.70 g) according to the same method as that of Reference Example 1, the title compound (1.26 g) was obtained as colorless crystals having a melting point of 90 to 91° C.

$^1$H NMR (400 MHz, CDCl$_3$) δ 1.84-1.88 (4H, m), 2.26 (3H, s), 2.97 (2H, t, J=7 Hz), 3.24. (2H, t, J=8 Hz), 3.58 (2H, t, J=6 Hz), 4.12 (2H,t, J=8 Hz), 7.82 (2H, br.d, J=10 Hz), 8.23 (1H, d, J=8 Hz).

IR (KBr) νcm$^{-1}$: 1666, 1603, 1488, 1442, 1398, 1336, 1235.

Reference Example 12

1-(1-Acetyl-2,3-dihydro-1H-indol-5-yl)-6-bromo-1-hexanone

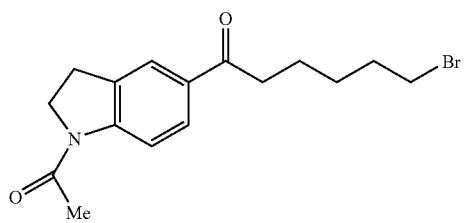

Using 1-acetylindoline and 6-bromohexanoyl chloride according to the same method as that of Reference Example 1, the title compound (1.27 g) was obtained as colorless crystals having a melting point of 110 to 111° C.

$^1$H NMR (400 MHz, CDCl$_3$) δ 1.49-1.57 (2H, m), 1.72-1.79 (2H,m), 1.88-1.95 (2H, m), 2.52 (3H, s), 2.94 (2H, t, J=7.5 Hz), 3.23 (2H, t, J=8 Hz), 3.42 (2H, t, J=6 Hz), 4.12 (2H, t, J=8 Hz), 7.82 (2H, br.d, J=10 Hz),8.23 (1H, d, J=8 Hz).

IR (KBr) νcm$^{-1}$: 1665, 1600, 1487, 1440, 1390, 1322, 1257.

Reference Example 13

N-[5-(5-Chloropentanoyl)-2-methoxyphenyl]methanesulfonamide

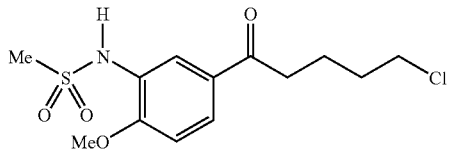

Using N-(2-methoxyphenyl)methanesulfonamide (10.0 g) and 5-chlorovaleryl chloride (7.06 ml) according to the same method as that of Reference Example 1, the title compound (9.15 g) was obtained as colorless crystals.

$^1$H NMR(300 MHz, CDCl$_3$) δ 1.80-1.95 (4H, m), 2.98 (2H, t, J=6.9 Hz), 3.00 (3H, s), 3.58 (2H, t, J=6.3 Hz), 3.97 (3H, s), 6.58 (1H, s), 6.99(1H, d, J=8.4 Hz), 7.82 (1H, dd, J=8.4, 1.8 Hz), 8.11 (1H, d, J=1.8 Hz).

Reference Example 14

N-[5-(6-Bromohexanoyl)-2-methoxyphenyl]methanesulfonamide

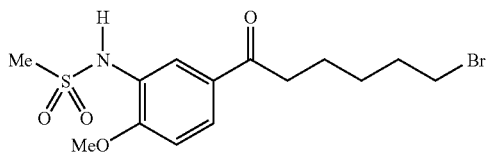

Using N-(2-methoxyphenyl)methanesulfonamide (10.0 g) and 6-bromohexanoyl chloride (8.37 ml) according to the same method as that of Reference Example 1, the title compound (9.80 g) was obtained as colorless crystals.

$^1$H NMR(300 MHz, DMSO-d$_6$) δ 1.35-1.45 (2H, m), 1.55-1.70 (2H,m), 1.75-1.90 (2H, m), 2.90-3.00 (5H, m), 3.51 (2H, t, J=6.6 Hz), 3.89 (3H,s), 7.16 (1H, d, J=8.4 Hz), 7.80-7.90 (2H, m), 9.11 (1H, s).

Reference Example 15

5-Chloro-1-(1H-indol-3-yl)-1-pentanone

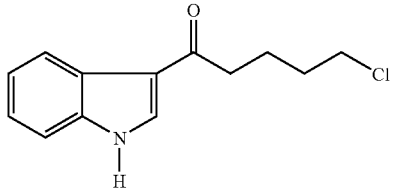

Using indole (1.00 g) and 5-chlorovaleryl chloride (1.68 ml) according to the same method as that of Reference Example 1, the title compound (1.55 g) was obtained as colorless crystals having a melting point of 165 to 167° C.

$^1$H NMR(300 MHz, DMSO-d$_6$) δ 1.60-1.90 (4H, m), 2.89 (2H, t, J=6.9 Hz), 3.69 (2H, t, J=6.1 Hz), 7.10-7.30 (2H, m), 7.40-7.50 (1H, m),8.10-8.25 (1H, m), 8.34 (1H, d, J=3.0 Hz), 11.92 (1H, s).

Reference Example 16

6-Bromo-1-(1H-indol-3-yl)-1-hexanone

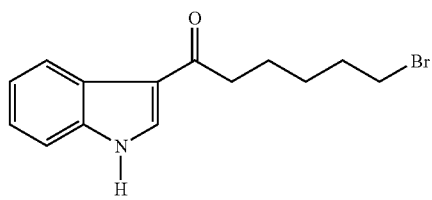

Using indole (5.00 g) and 6-bromohexanoyl chloride (9.95 ml) according to the same method as that of Reference Example 1, the title compound (9.65 g) was obtained as colorless crystals having a melting point of 150 to 151° C.

$^1$H NMR(300 MHz, DMSO-d$_6$) δ 1.40-1.95 (6H, m), 2.86 (2H, t, J=7.4 Hz), 3.54 (2H, t, J=6.8 Hz), 7.10-7.30 (2H, m), 7.40-7.50 (1H, m),8.15-8.25 (1H, m), 8.34 (1H, d, J=3.2 Hz), 11.91 (1H, s).

Reference Example 17

5-Chloro-1-(2-thienyl)-1-pentanone

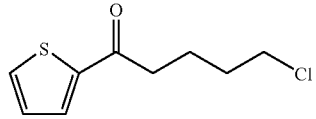

Using thiophene (1.00 ml) and 5-chlorovaleryl chloride (1.63 ml) according to the same method as that of Reference Example 1, the title compound (2.20 g) was obtained as a pale yellow solid.

$^1$H NMR(300 MHz, CDCl$_3$) δ 1.80-2.00 (4H, m), 2.96 (2H, t, J=7.2 Hz), 3.58 (2H, t, J=6.3 Hz), 7.14 (1H, dd, J=5.0, 3.6 Hz), 7.64 (1H, dd, J=5.0, 1.2 Hz), 7.77 (1H, dd, J=3.6, 1.2 Hz).

Reference Example 18

6-Bromo-1-(2-thienyl)-1-hexanone

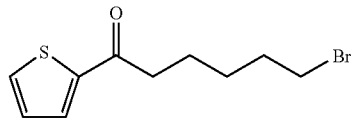

Using thiophene (5 ml) and 6-bromohexanoyl chloride (10.5 ml) according to the same method as that of Reference Example 1, the title compound (12.8 g) was obtained as a pale red solid.

¹H NMR(200 MHz, CDCl₃) δ 1.40-2.00 (6H, m), 2.93 (2H, t, J=7.2 Hz), 3.42 (2H, t, J=6.8 Hz), 7.13 (1H, dd, J=5.0, 3.6 Hz), 7.63 (1H, dd, J=5.0, 1.2 Hz), 7.71 (1H, dd, J=3.6, 1.2 Hz).

Reference Example 19 tert-Butyl 5-oxo-5-(4-oxo-1,2,5,6-tetrahydro-4H-pyrrolo[3,2,1-ij]quinolin-8-yl)pentyl(2-phenylethyl)carbamate

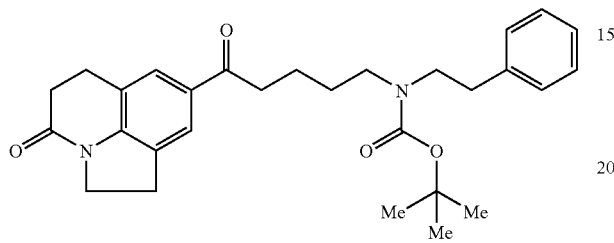

A mixture of 8-(5-chloropentanoyl)-1,2,5,6-tetrahydro-4H-pyrrolo[3,2,1-ij]quinolin-4-one (3.00 g) obtained in Reference Example 1 and 2-phenylethylamine (2.50 g) was stirred at 120° C. for 5 minutes. After cooling to room temperature, methanol (20 ml) and triethylamine (6.89 ml) were added to the reaction mixture, and a solution of di-t-butyl dicarbonate (9.00 g) in methanol (10 ml) was added dropwise, followed by stirring at room temperature for 12 hours. The solvent was evaporated under reduced pressure, water was added to the resulting residue, and extracted with ethyl acetate. The extract was washed with brine, and dried over anhydrous magnesium sulfate, and the solvent was evaporated under reduced pressure. The resulting residue was purified by silica gel chromatography (eluting solvent; hexane:ethyl acetate=1:1 ) to give the title compound as a pale yellow oil (3.00 g).

¹H NMR(200 MHz, CDCl₃) δ 1.44 (9H, s), 1.45-1.80 (4H, m),2.71 (2H, t, J=7.8 Hz), 2.75-3.00 (4H, m), 3.01 (2H, t, J=7.8 Hz), 3.05-3.30(4H, m), 3.30-3.45 (2H, m), 4.12 (2H, t, J=9.2 Hz), 7.10-7.35 (5H, m), 7.67(1H, s), 7.71 (1H, s).

Reference Example 20 tert-Butyl 2-(2-methoxyphenyl)ethyl[5-oxo-5-(4-oxo-1,2,5,6-tetrahydro-4H-pyrrolo[3,2,1-ij]quinolin-8-yl)pentyl]carbamate

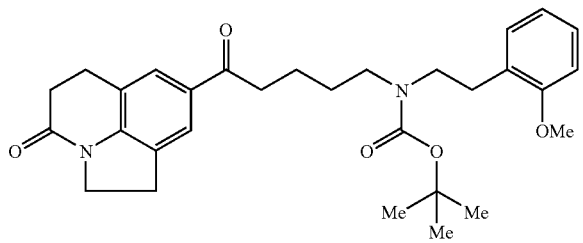

Using 8-(5-chloropentanoyl)-1,2,5,6-tetrahydro-4H-pyrrolo[3,2,1-ij]quinolin-4-one (800 mg) obtained in Reference Example 1 and 2-(2-methoxyphenyl)ethylamine (1.24 g) according to the same method as that of Reference Example 19, the title compound (1.16 g) was obtained as a pale yellow oil.

¹H NMR(300 MHz, CDCl₃) δ 1.43 (9H, s), 1.45-1.75 (4H, m), 2.71 (2H, t, J=7.8 Hz), 2.75-3.00(4H, m), 3.01 (2H, t, J=7.8 Hz), 3.05-3.30 (4H, m), 3.30-3.40 (2H, m), 3.82(3H, s), 4.12 (2H, t, J=8.4 Hz), 6.80-6.90 (2H, m), 7.05-7.25 (2H, m), 7.67(1H, s), 7.72 (1H, s).

Reference Example 21 tert-Butyl 2-(3-methoxyphenyl)ethyl[5-oxo-5-(4-oxo-1,2,5,6-tetrahydro-4H-pyrrolo[3,2,1-ij]quinolin-8-yl)pentyl]carbamate

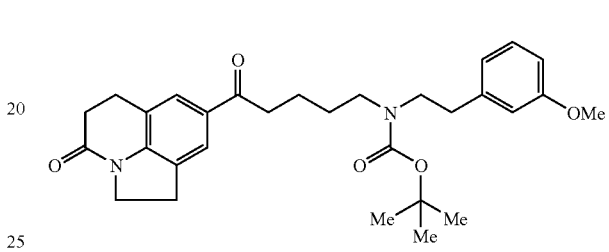

Using 8-(5-chloropentanoyl)-1,2,5,6-tetrahydro-4H-pyrrolo[3,2,1-ij]quinolin-4-one (2.00 g) obtained in Reference Example 1 and 2-(3-methoxyphenyl)ethylamine (3.11 g) according to the same method as that of Reference Example 19, the title compound (3.02 g) was obtained as a pale yellow oil.

¹H NMR(200 MHz, CDCl₃) δ 1.45 (9H, s), 1.50-1.80 (4H, m),2.71 (2H, t, J=7.8 Hz), 2.75-3.00 (4H, m), 3.02 (2H, t, J=7.8 Hz), 3.10-3.25(4H, m), 3.30-3.45 (2H, m), 3.79 (3H, s), 4.13 (2H, t, J=8.2 Hz), 6.65-6.85(3H, m), 7.20 (1H, t, J=7.8 Hz), 7.67 (1H, s), 7.72 (1H, s).

Reference Example 22 tert-Butyl 2-(3,4-dimethoxyphenyl)ethyl[5-oxo-5-(4-oxo-1,2,5,6-tetrahydro-4H-pyrrolo[3,2,1-ij]quinolin-8-yl)pentyl]carbamate

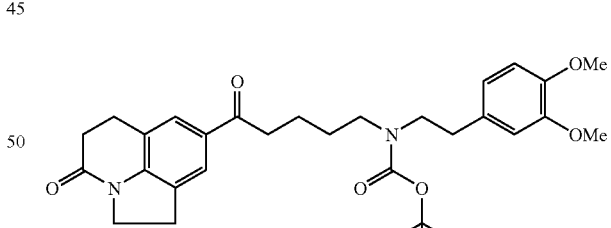

Using 8-(5-chloropentanoyl)-1,2,5,6-tetrahydro-4H-pyrrolo[3,2,1-ij]quinolin-4-one (500 mg) obtained in Reference Example 1 and 2-(3,4-dimethoxyphenyl)ethylamine (930 mg) according to the same method as that of Reference Example 19, the title compound (408 mg) was obtained as a pale yellow oil.

¹H NMR(200 MHz, CDCl₃) δ 1.45 (9H, s), 1.45-1.80 (4H, m), 2.71 (2H, t, J=7.8 Hz), 2.75-3.00(4H, m), 3.02 (2H, t, J=7.8 Hz), 3.05-3.30 (4H, m), 3.30-3.40 (2H, m), 3.86(3H, s), 3.87 (3H, s), 4.13 (2H, t, J=8.4 Hz), 6.65-6.85 (3H, m), 7.67 (1H,s), 7.71 (1H, s).

Reference Example 23 tert-Butyl 2-(2-chrolophenyl)ethyl[5-oxo-5-(4-oxo-1,2,5,6-tetrahydro-4H-pyrrolo[3,2,1-ij]quinolin-8-yl)pentyl]carbamate

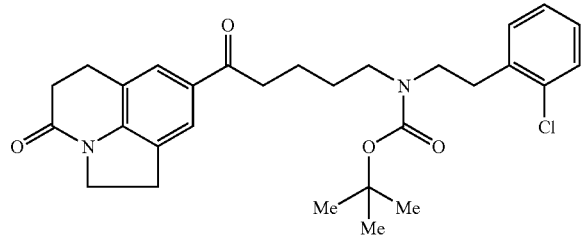

Using 8-(5-chloropentanoyl)-1,2,5,6-tetrahydro-4H-pyrrolo[3,2,1-ij]quinolin-4-one (1.00 g) obtained in Reference Example 1 and 2-(2-chlorophenyl)ethylamine (1.60 g) according to the same method as that of Reference Example 19, the title compound (1.50 g) was obtained as a pale yellow oil.

$^1$H NMR(200 MHz, CDCl$_3$) δ 1.41 (9H, s), 1.50-1.80 (4H, m), 2.71 (2H, t, J=7.8 Hz), 2.80-3.35 (10H, m), 3.41 (2H, t, J=7.8 Hz), 4.13 (2H, t, J=8.2 Hz), 7.00-7.40 (4H, m), 7.67 (1H, s), 7.72 (1H, s).

Reference Example 24 tert-Butyl 2-(3-fluorophenyl)ethyl[5-oxo-5-(4-oxo-1,2,5,6-tetrahydro-4H-pyrrolo[3,2,1-ij]quinolin-8-yl)pentyl]carbamate

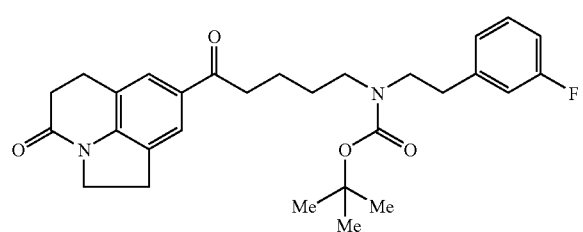

Using 8-(5-chloropentanoyl)-1,2,5,6-tetrahydro-4H-pyrrolo[3,2,1-ij]quinolin-4-one (1.00 g) obtained in Reference Example 1 and 2-(3-fluorophenyl)ethylamine (1.43 g) according to the same method as that of Reference Example 19, the title compound (1.40 g) was obtained as a pale yellow oil.

$^1$H NMR(200 MHz, CDCl$_3$) δ 1.44 (9H, s), 1.50-1.80 (4H, m), 2.71 (2H, t, J=7.8 Hz), 2.75-3.30 (10H, m), 3.39 (2H, t, J=7.8 Hz), 4.13 (2H, t, J=8.2 Hz), 6.80-7.05 (3H, m), 7.15-7.30 (1H, m), 7.68 (1H, s), 7.72 (1H, s).

Reference Example 25 tert-Butyl 2-[3-(aminosulfonyl)-4-methoxyphenyl]ethyl[5-oxo-5-(4-oxo-1,2,5,6-tetrahydro-4H-pyrrolo[3,2,1-ij]quinolin-8-yl)pentyl]carbamate

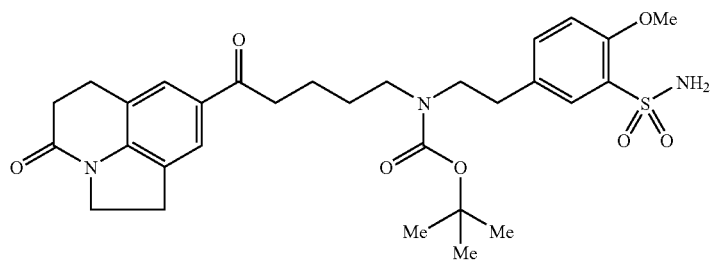

Using 8-(5-chloropentanoyl)-1,2,5,6-tetrahydro-4H-pyrrolo[3,2,1-ij]quinolin-4-one (800 mg) obtained in Reference Example 1 and 2-[3-(aminosulfonyl)-4-methoxyphenyl]ethylamine (1.89 g) according to the same method as that of Reference Example 19, the title compound (605 mg) was obtained as a pale yellow oil.

$^1$H NMR(200 MHz, CDCl$_3$) δ 1.40-1.80 (4H, m), 1.44 (9H, s), 2.70 (2H, t, J=7.6 Hz), 2.80 (2H, t, J=7.6 Hz), 2.92 (2H, t, J=7.4 Hz), 3.02 (2H, t, J=7.6 Hz), 3.10-3.25. (2H, m), 3.22 (2H, t, J=8.6 Hz), 3.35. (2H, t, J=7.6 Hz), 3.99 (3H, s), 4.10 (2H, t, J=8.8 Hz), 5.30 (2H, s), 6.98 (1H, d, J=8.4 Hz), 7.20-7.45. (1H, m), 7.60-7.75 (3H, m).

Reference Example 26 tert-Butyl 2-(2-methoxyphenyl)-1-methylethyl[5-oxo-5-(4-oxo-1,2,5,6-tetrahydro-4H-pyrrolo[3,2,1-ij]quinolin-8-yl)pentyl]carbamate

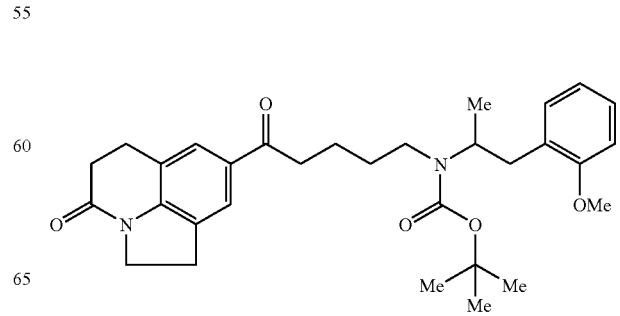

Using 8-(5-chloropentanoyl)-1,2,5,6-tetrahydro-4H-pyrrolo[3,2,1-ij]quinolin-4-one (500 mg) obtained in Reference Example, 1 and 2-(2-methoxyphenyl)-1-methylethylamine (848 mg) according to the same method as that of Reference Example 19, the title compound (641 mg) was obtained as a pale yellow oil.

¹H NMR(200 MHz, CDCl₃) δ 1.19 (3H, d, J=7.0 Hz), 1.30-2.00(9H. m), 1.37 (9H, s), 2.71 (2H, t, J=7.6 Hz), 2.80-3.10 (6H, m), 3.22 (2H, t,J=8.4 Hz), 3.82 (3H, s), 4.13 (2H, t, J=8.8 Hz), 6.75-7.20 (2H, m), 7.67 (1H,s), 7.71 (1H, s).

Reference Example 27 tert-Butyl 6-oxo-6-(4-oxo-1,2,5,6-tetrahydro-4H-pyrrolo[3,2,1-ij]quinolin-8-yl)hexyl(2-phenylethyl)carbamate

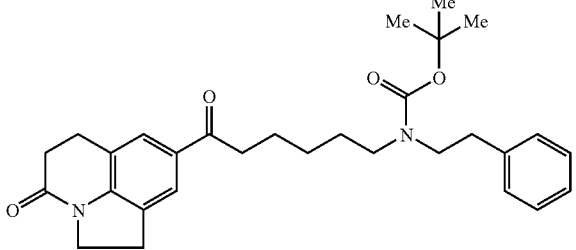

Using 8-(6-bromohexanoyl)-1,2,5,6-tetrahydro-4H-pyrrolo[3,2,1-ij]quinolin-4-one (500 mg) obtained in Reference Example 2 and 2-phenylethylamine (0.538 ml) according to the same method as that of Reference Example 19, the title compound (450 mg) was obtained as a pale yellow oil.

¹H NMR(300 MHz, CDCl₃) δ 1.25-1.60 (4H, m), 1.44 (9H, s),1.65-1.80 (2H, m), 2.71 (2H, t, J=7.5 Hz), 2.75-2.90 (2H, m), 2.90 (2H, t, J=7.5 Hz), 3.01 (2H, t, J=7.5 Hz), 3.05-3.45 (4H, m), 3.22 (2H, t, J=8.4 Hz),4.12 (2H, t, J=8.4 Hz), 7.10-7.35 (5H, m), 7.67 (1H, s), 7.71 (1H, s).

Reference Example 28 tert-Butyl 2-(2-methoxyphenyl)ethyl[6-oxo-6-(4-oxo-1,2,5,6-tetrahydro-4H-pyrrolo[3,2,1-ij]quinolin-8-yl)hexyl]carbamate

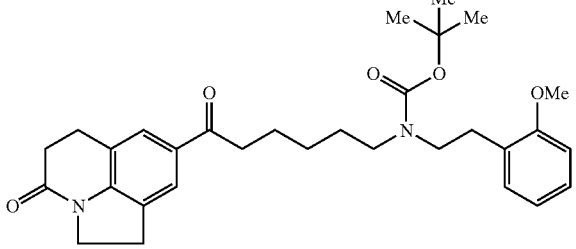

Using 8-(6-bromohexanoyl)-1,2,5,6-tetrahydro-4H-pyrrolo[3,2,1-ij]quinolin-4-one (1.50 g) obtained in Reference Example. 2 and 2-(2-methoxyphenyl)ethylamine (1.94 g) according to the same method as that of Reference Example 19, the title compound (1.51 g) was obtained as a pale yellow oil.

¹H NMR(300 MHz, CDCl₃) δ 1.25-1.60 (4H, m), 1.43 (9H, s),1.65-1.80 (2H, m), 2.71 (2H, t, J=7.5 Hz), 2.75-2.90 (2H, m), 2.90 (2H, t, J=7.5 Hz), 3.01 (2H, t, J=7.5 Hz), 3.05-3.45 (6H, m), 3.82 (3H, s), 4.12 (2H, t,J=8.4 Hz), 6.80-6.90 (2H, m), 7.00-7.20 (2H, m), 7.67 (1H, s), 7.71 (1H, s).

Reference Example 29 tert-Butyl 2-(3-methoxyphenyl)ethyl[6-oxo-6-(4-oxo-1,2,5,6-tetrahydro-4H-pyrrolo[3,2,1-ij]quinolin-8-yl)hexyl]carbamate

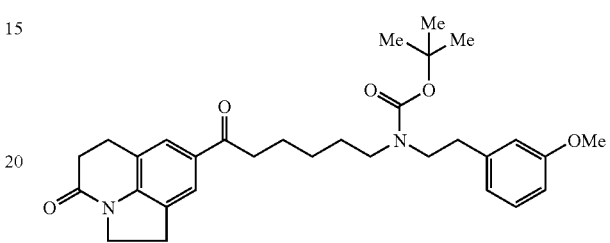

Using 8-(6-bromohexanoyl)-1,2,5,6-tetrahydro-4H-pyrrolo[3,2,1-ij]quinolin-4-one (500 mg) obtained in Reference Example 2 and 2-(3-methoxyphenyl)ethylamine (650 mg) according to the same method as that of Reference Example 19, the title compound (562 mg) was obtained as a pale yellow oil.

¹H NMR(300 MHz, CDCl₃) δ 1.25-1.60 (4H, m), 1.45 (9H, s), 1.74 (2H, tt, J=7.5, 7.5 Hz), 2.71(2H, t, J=7.8 Hz), 2.75-2.85 (2H, m), 2.90 (2H, t, J=7.5 Hz), 3.01 (2H, t, J=7.8 Hz), 3.05-3.45 (4H, m), 3.22 (2H, t, J=8.4 Hz), 3.79 (3H, s), 4.12 (2H,t, J=8.4 Hz), 6.70-6.85 (3H, m), 7.20 (1H, t, J=7.8 Hz), 7.67 (1H, s), 7.71(1H, s).

Reference Example 30 tert-Butyl 2-(4-methoxyphenyl)ethyl[6-oxo-6-(4-oxo-1,2,5,6-tetrahydro-4H-pyrrolo[3,2,1-ij]quinolin-8-yl)hexyl]carbamate

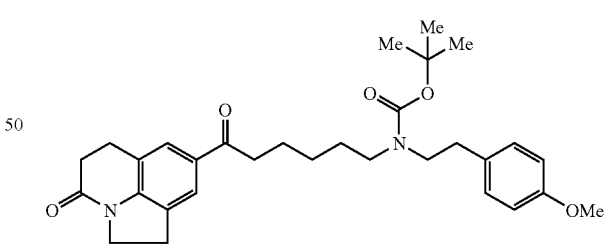

Using 8-(6-bromohexanoyl)-1,2,5,6-tetrahydro-4H-pyrrolo[3,2,1-ij]quinolin-4-one (700 mg) obtained in Reference Example 2 and 2-(4-methoxyphenyl)ethylamine (907 mg) according to the same method as that of Reference Example 19, the title compound (900 mg) was obtained as a pale yellow oil.

¹H NMR(300 MHz, CDCl₃) δ 1.25-1.55 (4H, m), 1.41 (9H, s),1.60-1.75 (2H, m), 2.60-2.75 (4H, m), 2.85 (2H, t, J=7.5 Hz), 2.97 (2H, t, J=7.8 Hz), 3.00-3.35 (4H, m), 3.17 (2H, t, J=8.4 Hz), 3.74 (3H, s), 4.08 (2H, t,J=8.4 Hz), 6.75-6.80 (2H, m), 7.00-7.10 (2H, m), 7.63 (1H, s), 7.67 (1H, s).

Reference Example 31 tert-Butyl 2-(chlorophenyl)ethyl[6-oxo-6-(4-oxo-1,2,5,6-tetrahydro-4H-pyrrolo[3,2,1-ij]quinolin-8-yl)hexyl]carbamate

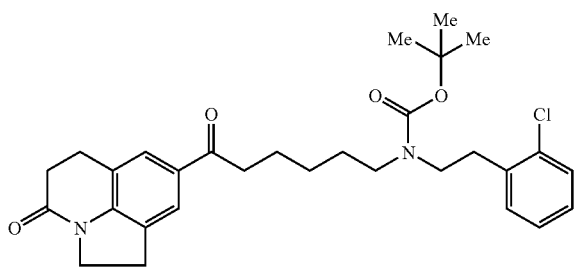

Using 8-(6-bromohexanoyl)-1,2,5,6-tetrahydro-4H-pyrrolo[3,2,1-ij]quinolin-4-one (500 mg) obtained in Reference Example 2 and 2-(chlorophenyl)ethylamine (430 mg) according to the same method as that of Reference Example 19, the title compound (540 mg) was obtained as a pale yellow oil.

$^1$H NMR(300 MHz, CDCl$_3$) δ 1.25-1.60. (4H, m), 1.41 (9H, s),1.65-1.80. (2H, m), 2.71 (2H, t, J=7.5 Hz), 2.85-3.30 (4H, m), 2.89 (2H, t, J=7.5 Hz), 3.01 (2H, t, J=7.8 Hz), 3.22 (2H, t, J=8.4 Hz), 3.39 (2H, t, J=7.5 Hz), 4.12 (2H, t, J=8.4 Hz), 7.10-7.35. (4H, m), 7.67 (1H, s), 7.71. (1H, s).

Reference Example 32 tert-Butyl 2-(3-fluorophenyl)ethyl[6-oxo-6-(4-oxo-1,2,5,6-tetrahydro-4H-pyrrolo[3,2,1-ij]quinolin-8-yl)hexyl]carbamate

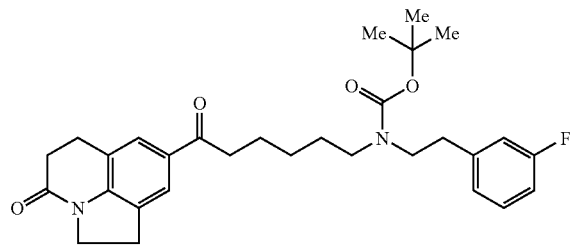

Using 8-(6-bromohexanoyl)-1,2,5,6-tetrahydro-4H-pyrrolo[3,2,1-ij]quinolin-4-one (500 mg) obtained in Reference Example 2 and 2-(3-fluorophenyl)ethylamine (600 mg) according to the same method as that of Reference Example 19, the title compound (613 mg) was obtained as a colorless oil.

$^1$H NMR(300 MHz, CDCl$_3$) δ 1.25-1.60 (4H, m), 1.44 (9H, s),1.74 (2H, tt, J=7.5, 7.5 Hz), 2.71 (2H, t, J=7.5 Hz), 2.75-2.90 (2H, m), 2.90(2H, t, J=7.5 Hz), 3.02 (2H, t, J=7.8 Hz), 3.05-3.45 (2H, m), 3.22 (2H, t, J=8.4 Hz), 3.37 (2H, t, J=7.5 Hz), 4.13 (2H, t, J=8.4 Hz), 6.80-7.00 (3H, m),7.20-7.30 (1H, m), 7.67 (1H, s), 7.71 (1H, s).

Reference Example 33 tert-Butyl 2-(2-methoxyphenyl)-1-methylethyl[6-oxo-6-(4-oxo-1,2,5,6-tetrahydro-4H-pyrrolo[3,2,1-ij]quinolin-8-yl)hexyl]carbamate

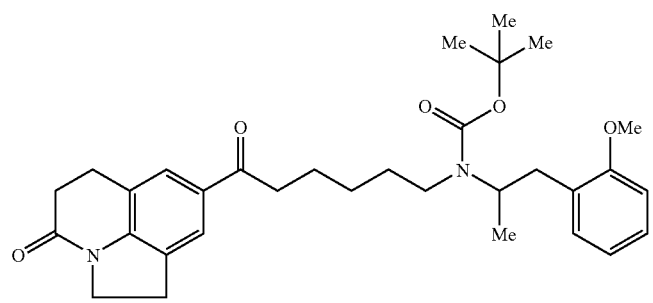

Using 8-(6-bromohexanoyl)-1,2,5,6-tetrahydro-4H-pyrrolo[3,2,1-ij]quinolin-4-one (600 mg) obtained in Reference Example 2 and 2-(2-methoxyphenyl)-1-methyl ethylamine (850 mg) according to the same method as that of Reference Example 19, the title compound (467 mg) was obtained as a pale yellow oil.

$^1$H NMR(300 MHz, CDCl$_3$) δ 1.18 (3H, d, J=6.9 Hz), 1.25-1.90(6H, m), 1.36 (9H, s), 2.71 (2H, t, J=7.5 Hz), 2.75-3.20 (5H, m), 2.88 (2H, t,J=7.5 Hz), 3.02 (2H, t, J=7.8 Hz), 3.22 (2H, t, J=8.4 Hz), 3.82 (3H, s),4.13 (2H, t, J=8.4 Hz), 6.80-7.25 (4H, m), 7.67 (1H, s), 7.72 (1H, s).

Reference Example 34 tert-Butyl 5-oxo-5-(4-oxo-1,2,5,6-tetrahydro-4H-pyrrolo[3,2,1-ij]quinolin-8-yl)pentyl(3-phenylpropyl)carmamate

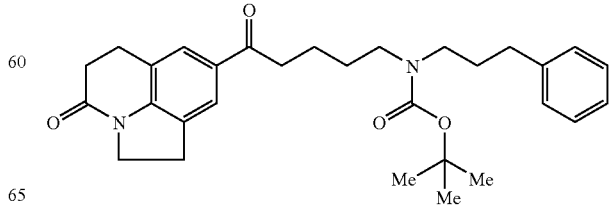

Using 8-(5-chloropentanoyl)-1,2,5,6-tetrahydro-4H-pyrrolo[3,2,1-ij]quinolin-4-one (500 mg) obtained in Reference Example 1 and 3-phenyl-1-propylamine (694 mg) according to the same method as that of Reference Example 19, the title compound (660 mg) was obtained as a pale yellow oil.

¹H NMR(200 MHz, CDCl₃) δ 1.20-2.00 (6H, m), 1.43 (9H, s), 2.60(2H, t, J=7.8 Hz), 2.71 (2H, t, J=7.5 Hz), 2.93 (2H, t, J=7.5 Hz), 3.01 (2H,t, J=7.8 Hz), 3.10-3.40 (6H, m), 4.13 (2H, t, J=8.4 Hz), 7.10-7.35 (5H, m),7.67 (1H, s), 7.71 (1H, s).

Reference Example 35 tert-Butyl 6-oxo-6-(4-oxo-1,2,5,6-tetrahydro-4H-pyrrolo[3,2,1-ij]quinolin-8-yl)hexyl(3-phenylpropyl) carbamate

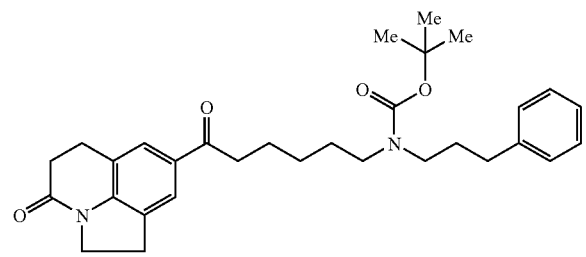

Using 8-(6-bromohexanoyl)-1,2,5,6-tetrahydro-4H-pyrrolo[3,2,1-ij]quinolin-4-one (700 mg) obtained in Reference Example 2 and 3-phenyl-1-propylamine (811 mg) according to the same method as that of Reference Example 19, the title compound (906 mg) was obtained as a colorless oil.

¹H NMR(300 MHz, CDCl₃) δ 1.20-1.60 (4H, m), 1.44 (9H, s),1.74 (2H, tt, J=7.5, 7.5 Hz), 1.84 (2H, tt, J=7.5, 7.5 Hz), 2.59 (2H, t, J=7.8 Hz), 2.71 (2H, t, J=7.5 Hz), 2.90 (2H, t, J=7.5 Hz), 3.02 (2H, t, J=7.8 Hz), 3.10-3.30 (6H, m), 4.12 (2H, t, J=8.4 Hz), 7.10-7.30 (5H, m), 7.67(1H, s), 7.72 (1H, s).

Reference Example 36 tert-Butyl 2-(2-methoxyphenyl)ethyl[5-oxo-5-(2-oxo-1,2,5,6-tetrahydro-4H-pyrrolo[3,2,1-ij]quinolin-8-yl)pentyl]carbamate

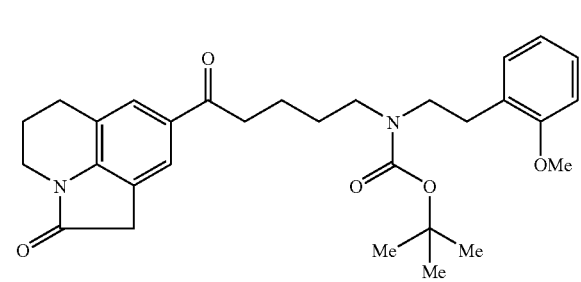

Using 8-(5-chloropentanoyl)-5,6-dihydro-4H-pyrrolo[3,2,1-ij]quinolin-2(1H)-one (293 mg) obtained in Reference Example 3 and 2-(2-methoxyphenyl)ethylamine (378 mg) according to the same method as that, of Reference Example 19, the title compound (86 mg) was obtained as a pale yellow oil.

¹H NMR(400 MHz, CDCl₃) δ 1.43. (9H, s), 1.51-1.76 (4H, m),2.00-2.07 (2H, m), 2.81 (4H, t, J=6 Hz), 2.88-2.96 (2H, m), 3.10-3.25 (2H, m),3.32-3.41 (2H, m), 3.54 (2H, s), 3.74 (2H, t, J=6 Hz), 3.82 (3H, s), 6.83-6.89(2H, m), 7.09-7.21 (2H, m), 7.73 (2H, s).

Reference Example 37 tert-Butyl 2-(2-chlorophenyl)ethyl(5-oxo-5-(2-oxo-1,2,5,6-tetrahydro-4H-pyrrolo[3,2,1-ij]quinolin-8-yl) pentyl]carbamate

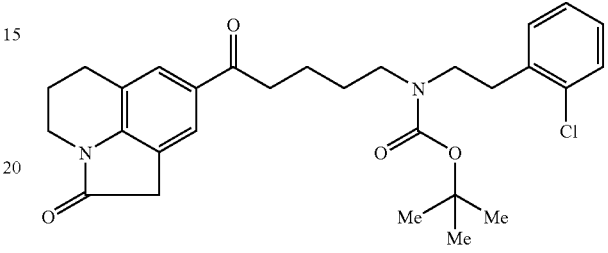

Using 8-(5-chloropentanoyl)-5,6-dihydro-4H-pyrrolo[3,2,1-ij]quinolin-2(1H)-one obtained in Reference Example 3 and 2-(2-chlorophenyl)ethylamine according to the same method as that of Reference Example 19, the title compound (147 mg) was obtained as a pale yellow oil.

¹H NMR(400 MHz, CDCl₃) δ 1.41 (9H, s), 1.51-1.76 (4H, m),2.00-2.06 (2H, m), 2.82 (2H, t, J=6 Hz), 2.87-3.00 (4H, m), 3.10-3.26 (2H, m),3.41 (2H, t, J=7 Hz), 3.54 (2H, s), 3.74 (2H, t, J=6 Hz), 7.13-7.24 (3H, m),7.33 (1H, d, J=7.2 Hz), 7.73 (2H, s).

Reference Example 38 tert-Butyl 5-oxo-5-(3-oxo-2,3,6,7-tetrahydro-1H,5H-pyrido[3,2,1-ij]quinolin-9-yl)pentyl(2-phenylethyl) carbamate

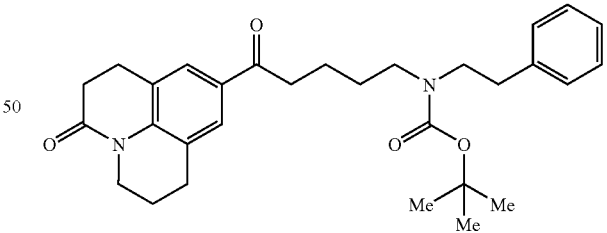

Using 9-(5-chloropentanoyl)-2,3,6,7-tetrahydro-1H,5H-pyrido[3,2,1-ij]quinolin-5-one obtained in Reference Example 5 and 2-phenylethylamine according to the same method as that of Reference Example 19, the title compound (320 mg) was obtained as a pale yellow oil.

¹H NMR(400 MHz, CDCl₃) δ 1.44 (9H, s), 1.51-1.75 (4H, m),1.93-1.99 (2H, m), 2.67 (2H, t, J=6 Hz), 2.82-2.85 (4H, m), 2.92-2.95 (4H, m),3.12-3.24 (2H, m),3.32-3.42 (2H, m), 3.89 (2H, t, J=6 Hz), 7.18-7.30 (5H, m), 7.61 (2H, d, J=5 Hz).

Reference Example 39 tert-Butyl 2-(2-methoxyphenyl)ethyl[5-oxo-5-(3-oxo-2,3,6,7-tetrahydro-1H,5H-pyrido[3,2,1-ij]quinolin-9-yl)pentyl]carbamate

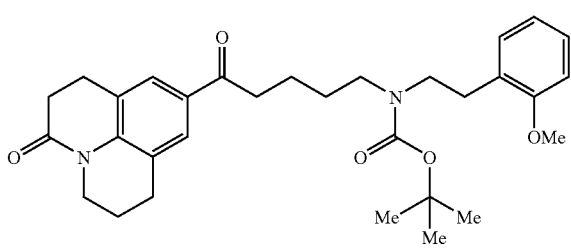

Using 9-(5-chloropentanoyl)-2,3,6,7-tetrahydro-1H,5H-pyrido[3,2,1-ij]quinolin-5-one obtained in Reference Example 5 and 2-(2-methoxyphenyl)ethylamine according to the same method as that of Reference Example 19, the title compound (414 mg) was obtained as a pale yellow oil.

$^1$H NMR(400 MHz, CDCl$_3$) δ 1.43 (9H, s), 1.51-1.76 (4H, m),1.93-1.99 (2H, m), 2.67 (2H, t, J=6 Hz), 2.82-2.85 (4H, m), 2.91-2.95 (4H, m),3.13-3.25 (2H, m), 3.31-3.42 (2H, m), 3.82 (3H, s), 3.89 (2H, t, J=6 Hz),6.83-6.89 (2H, m), 7.07-7.21 (2H, m), 7.61 (2H, d, J=5 Hz).

Reference Example 40 tert-Butyl 2-(2-chlorophenyl)ethyl[5-oxo-5-(3-oxo-2,3,6,7-tetrahydro-1H,5H-pyrido[3,2,1-ij]quinolin-9-yl)pentyl]carbamate

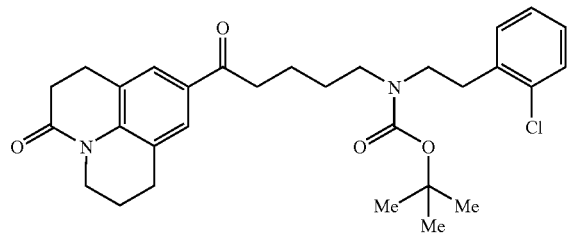

Using 9-(5-chloropentanoyl)-2,3,6,7-tetrahydro-1H,5H-pyrido[3,2,1-ij]quinolin-5-one obtained in Reference Example 5 and 2-(2-chlorophenyl)ethylamine according to the same method as that of Reference Example 19, the title compound (385 mg) was obtained as a pale yellow oil.

$^1$H NMR(400 MHz, CDCl$_3$) δ 1.41 (9H, s), 1.51-1.76 (4H, m),1.93-1.99 (2H, m), 2.67 (2H, t, J=6 Hz), 2.84 (2H, t, J=6 Hz), 2.94 (6H, t, J=6.8 Hz), 3.12-3.26 (2H, m), 3.41 (2H, t, J=7 Hz), 3.89 (2H, t, J=6 Hz),7.13-7.19 (3H, m), 7.33 (1H, d, J=7.2 Hz), 7.62 (2H, d, J=5 Hz).

Reference Example 41 tert-Butyl 5-oxo-5-(3-oxo-3,4-dihydro-2H-1,4-benzoxazin-6-yl)pentyl(2-phenylethyl)carbamate

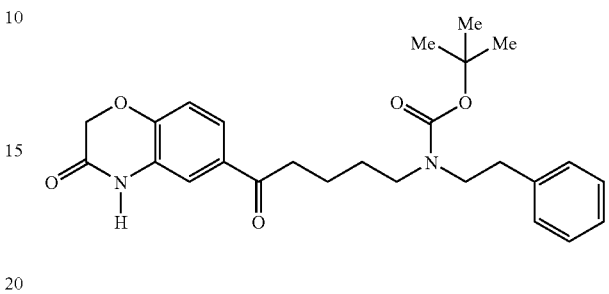

Using 6-(5-chloropentanoyl)-2H-1,4-benzoxazin-3(4H)-one obtained in Reference Example 7 and 2-phenylethylamine according to the same method as that of Reference Example 19, the title compound was obtained as a colorless oil.

$^1$H NMR(300 MHz, CDCl$_3$) δ 1.44 (9H, m), 1.58 (2H, m),1.65-1.75 (2H, m), 2.81 (2H, m), 2.90-2.94 (2H, m), 3.15-3.22 (2H, m), 3.37(2H, m), 4.69 (2H, s), 6.99 (1H, d, J=8.4 Hz), 7.16-7.30 (5H, m), 7.58-7.61(2H, m), 9.36 (1H, s).

Reference Example 42 tert-Butyl 2-(2-ethoxyphenyl)ethyl[5-oxo-5-(3-oxo-3,4-dihydro-2H-1,4-benzoxazin-6-yl)pentyl]carbamate

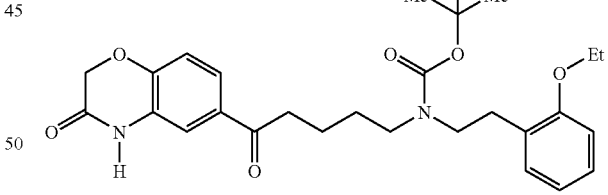

Using 6-(5-chloropentanoyl)-2H-1,4-benzoxazin-3(4H)-one obtained in Reference Example 7 and 2-(2-ethoxyphenyl)ethylamine according to the same method as that of Reference Example 19, the title compound was obtained as a colorless oil.

$^1$H NMR(300 MHz, CDCl$_3$) δ 1.42 (3H, t, J=6.4 Hz), 1.44 (9H,s), 1.60-1.73 (4H, m), 2.83-2.94 (4H, m), 3.18-3.36 (4H, m), 3.99-4.06 (2H, m),4.68 (2H, s), 6.80-6.87 (2H, m), 6.96-6.99 (1H, d, J=6.6 Hz), 7.07-7.18 (2H,m), 7.58-7.63 (2H, m), 9.67 (1H, s).

Reference Example 43 tert-Butyl 2-(2-fluorophenyl)ethyl[5-oxo-5-(3-oxo-3,4-dihydro-2H-1,4-benzoxazin-6-yl)pentyl]carbamate

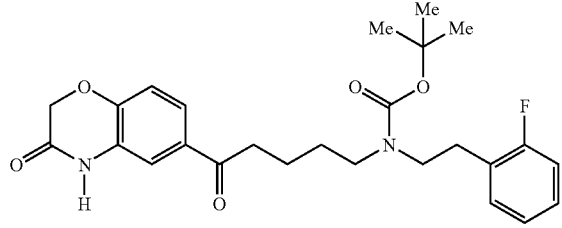

Using 6-(5-chloropentanoyl)-2H-1,4-benzoxazin-3(4H)-one obtained in Reference Example 7 and 2-(2-fluorophenyl)ethylamine according to the same method as that of Reference Example 19, the title compound was obtained as a colorless oil.

$^1$H NMR(300 MHz, CDCl$_3$) δ 1.42 (9H, m), 1.52-1.78 (4H, m), 2.82-2.96 (4H, m), 3.25 (2H, m), 3.36-3.43 (2H, m), 4.69 (2H, s), 6.96-7.08(3H, m), 7.14-7.23 (2H, m), 7.58-7.63 (2H, m), 9.16 (1H, s).

Reference Example 44 tert-Butyl 2-(2-chlorophenyl)ethyl[5-oxo-5-(3-oxo-3,4-dihydro-2H-1,4-benzoxazin-6-yl)pentyl]carbamate

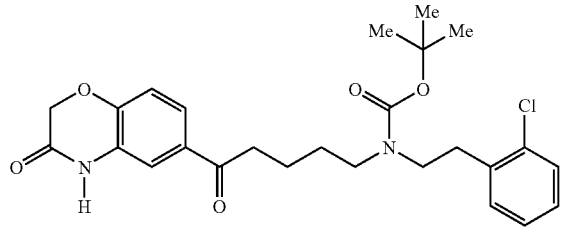

Using 6-(5-chloropentanoyl)-2H-1,4-benzoxazin-3(4H)-one obtained in Reference Example 7 and 2-(2-chlorophenyl)ethylamine according to the same method as that of Reference Example 19, the title compound was obtained as a colorless oil.

$^1$H NMR(200 MHz, CDCl$_3$) δ 1.42 (9H, m), 1.67 (4H, m), 2.92(4H, m), 3.25 (2H, m)), 3.37-3.45 (2H, m), 4.69 (2H, s), 6.99 (1H, d, J=8.8 Hz), 7.17 (3H, m), 7.30-7.34 (1H, m), 7.61-7.62 (2H, m), 9.56 (1H, s).

Reference Example 45 tert-Butyl 2-(3-methoxyphenyl)ethyl[5-oxo-5-(3-oxo-3,4-dihydro-2H-1,4-benzoxazin-6-yl)pentyl]carbamate

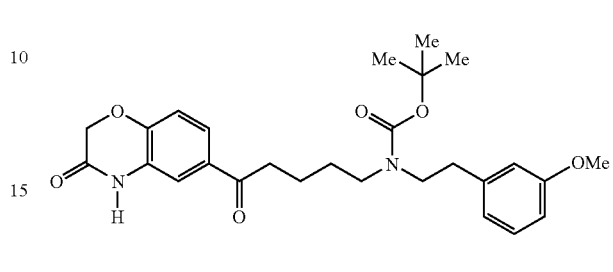

Using 6-(5-chloropentanoyl)-2H-1,4-benzoxazin-3(4H)-one obtained in Reference Example 7 and 2-(3-methoxyphenyl)ethylamine according to the same method as that of Reference Example 19, the title compound was obtained as a colorless oil.

$^1$H NMR(200 MHz, CDCl$_3$) δ 1.45 (9H, m), 1.55-1.77 (4H, m), 2.75-2.82(2H, m), 2.88-2.95 (2H, m), 3.22 (2H, m), 3.37 (2H, m), 3.79 (3H, s), 4.69 (2H,s), 6.73-6.78 (3H, m), 6.99 (1H, d, J=8.8 Hz), 7.16-7.23 (1H, m), 7.58-7.62(2H, m), 9.46 (1H, s).

Reference Example 46 tert-Butyl 2-(3-ethoxyphenyl)ethyl[5-oxo-5-(3-oxo-3,4-dihydro-2H-1,4-benzoxazin-6-yl)pentyl]carbamate

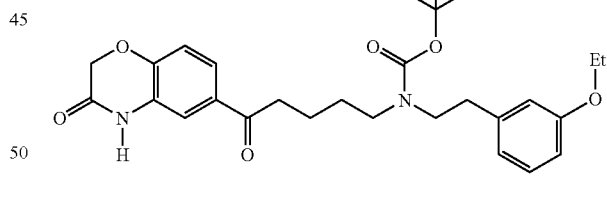

Using 6-(5-chloropentanoyl)-2H-1,4-benzoxazin-3(4H)-one obtained in Reference Example 7 and 2-(3-ethoxyphenyl)ethylamine according to the same method as that of Reference Example 19, the title compound was obtained as a colorless oil.

$^1$H NMR(200 MHz, CDCl$_3$) δ 1.40 (3H, t, J=7.0 Hz), 1.45 (9H,s), 1.55-1.77 (4H, m), 2.74-2.81 (2H, m), 2.88-2.95 (2H, m), 3.21 (2H, m), 3.36(2H, m), 4.01 (2H, q, J=7 Hz), 4.69 (2H, s), 6.72-6.76 (3H, m), 6.99 (1H, d, J=8.8 Hz), 7.14-7.22 (1H, m), 7.58-7.62 (2H, m), 9.43 (1H, s).

Reference Example 47 tert-Butyl 5-(1-acetyl-2,3-dihydro-1H-indol-5-yl)-5-oxopentyl[2-(2-methoxyphenyl)ethyl]carbamate

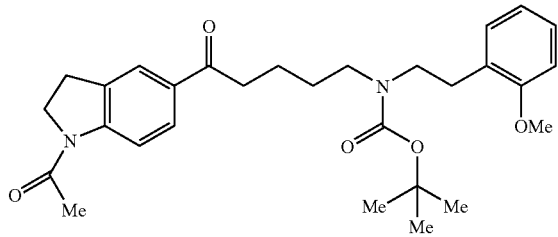

Using 1-(1-acetyl-2,3-dihydro-1H-indol-5-yl)-5-chloropentan-1-one (280 mg) obtained in Reference Example 11 and 2-(2-methoxyphenyl)ethylamine (378 mg) according to the same method as that of Reference Example 19, the title compound (170 mg) was obtained as a pale, yellow oil.

$^1$H NMR(400 MHz, CDCl$_3$) δ 1.43 (9H, s), 1.51-1.72 (4H, m), 2.22 (3H, s), 2.75-2.88 (2H, m), 2.90-2.95 (2H, m), 3.08-3.22 (4H, m), 3.32-3.41 (2H, m), 3.81 (3H, s), 4.07 (2H, t, J=7 Hz), 6.81-6.87 (2H, m), 7.08-7.19 (2H, m), 7.77-7.81 (2H, m), 8.21 (1H, d, J=8.5 Hz).

Reference Example 48 tert-Butyl 5-(1-acetyl-2,3-dihydro-1H-indol-5-yl)-5-oxopentyl(2-phenylethyl)carbamate

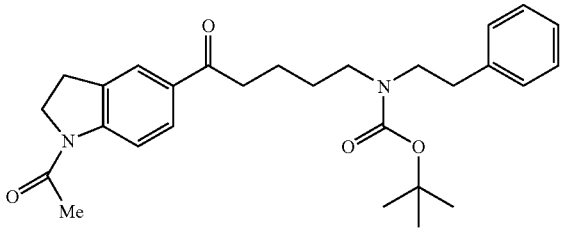

Using 1-(1-acetyl-2,3-dihydro-1H-indol-5-yl)-5-chloropentan-1-one (560 mg) obtained in Reference Example 11 and 2-phenylethylamine (606 mg) according to the same method as that of Reference Example 19, the title compound (290 mg) was obtained as a pale yellow oil.

$^1$H NMR(400 MHz, CDCl$_3$) δ 1.44(9H, s), 1.51-1.74(4H, m), 2.25(3H, s), 2.75-2.88(2H, m), 2.89-2.96(2H, m), 3.05-3.27(4H, m), 3.30-3.43(2H, m), 4.11(2H, t, J=7.3 Hz), 7.15-7.30(5H, m), 7.79-7.83(2H, m), 8.22(1H, d, J=8.5 Hz).

Reference Example 49 tert-Butyl 5-(1-acetyl-2,3-dihydro-1H-indol-5-yl)-5-oxopentyl[2-(2-chlorophenyl)ethyl]carbamate

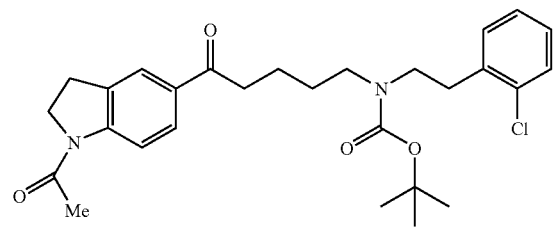

Using 1-(1-acetyl-2,3-dihydro-1H-indol-5-yl)-5-chloropentan-1-one obtained in Reference Example 11 and 2-(2-chlorophenyl)ethylamine according to the same method as that of Reference Example 19, the title compound was obtained as a pale yellow oil.

$^1$H NMR(400 MHz, CDCl$_3$) δ 1.41(9H, s), 1.51-1.76(4H, m), 2.25(3H, s), 2.94(4H, br.s), 3.12(2H, br.s), 3.22(2H, t, J=7.6 Hz), 3.41(2H, t, J=7 Hz), 4.11(2H, t, J=7.3 Hz), 7.17 (3H, br.s), 7.33(1H, d, J=7.2 Hz), 7.79-7.83(2H, m), 8.22(1H, d, J=8.5 Hz).

Reference Example 50 tert-Butyl 5-(2,3-dihydro-1H-indol-5-yl)-5-oxopentyl[2-(2-methoxyphenyl)ethyl]carbamate

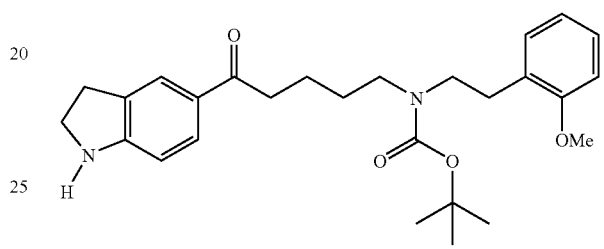

A solution of potassium hydroxide (0.22 g) in methanol (4 ml) was added at room temperature to tert-butyl 5-(1-acetyl-2,3-dihydro-1H-indol-5-yl)-5-oxopentyl[2-(2-methoxyphenyl)ethyl]carbamate (1.00 g) obtained in Reference Example 47, and heated at reflux for 2 hours with stirring. The solvent was evaporated under reduced pressure, water was added to the resulting residue, and extracted with ethyl acetate. The organic layer was washed with brine, dried over anhydrous magnesium sulfate, and the solvent was evaporated under reduced pressure. The resulting residue was purified by silica gel chromatography (eluting solvent; hexane:ethyl acetate=1:1) to give the title compound as a pale yellow oil (700 mg).

$^1$H NMR(400 MHz, CDCl$_3$) δ 1.43(9H, s), 1.51-1.72(4H, m), 2.78-2.88(4H, m), 3.06(2H, t, J=8.5 Hz), 3.08-3.24(2H, m), 3.32-3.39(2H, m), 3.65(2H, t, J=8.5 Hz), 3.81(3H, s), 4.26(1H, br.s), 6.52(1H, d, J=8 Hz), 6.82-6.88(2H, m), 7.08-7.20(2H, m), 7.69(1H, d, J=8 Hz), 7.72(1H, s).

Reference Example 51 tert-Butyl 5-(2,3-dihydro-1-methyl-1H-indol-5-yl)-5-oxopentyl[2-(2-methoxyphenyl)ethyl]carbamate

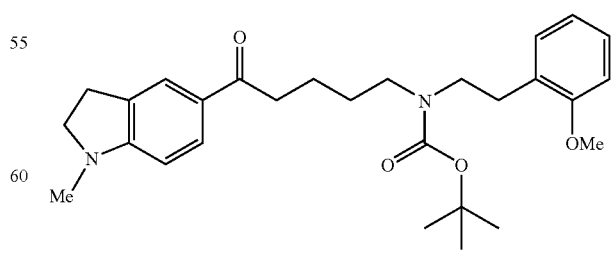

Potassium carbonate (166 mg) and methyl iodide (170 mg) were added to a solution of tert-butyl 5-(2,3-dihydro-1H-indol-5-yl)-5-oxopentyl[2-(2-methoxyphenyl)ethyl]carbamate (362 mg) obtained in Reference Example 50 in dimethylformamide (2 ml), and the mixture was stirred at 60 to 70° C. for 5 hours. The solvent was evaporated under reduced pressure, water was added to the resulting residue, and extracted with ethyl acetate. The organic layer was washed with brine, dried over anhydrous magnesium sulfate, and the solvent was evaporated under reduced pressure. The resulting residue was purified by silica gel chromatography (eluting solvent; hexane:ethyl acetate=1:1) to give the title compound as a pale yellow oil (125 mg).

$^1$H NMR(400 MHz, CDCl$_3$) δ 1.43(9H, s), 1.51-1.70(4H, m), 2.78-2.88(4H, m), 2.84(3H, s), 3.00(2H, t, J=8.5 Hz), 3.08-3.24(2H, m), 3.31-3.40(2H, m), 3.48(2H, t, J=8.5 Hz), 3.81(3H, s), 6.34(1H, d, J=8 Hz), 6.82-6.88(2H, m), 7.08-7.20(2H, m), 7.67(1H, s), 7.76(1H, d, J=8 Hz).

Reference Example 52 tert-Butyl 5-(1-ethyl-2,3-dihydro-1H-indol-5-yl)-5-oxopentyl[2-(2-methoxyphenyl)ethyl]carbamate

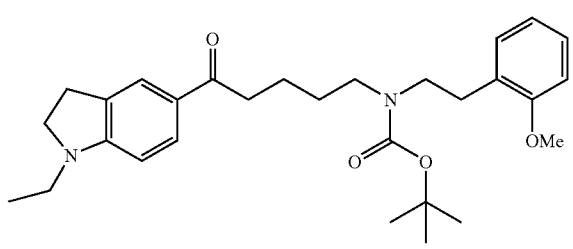

Using tert-butyl 5-(2,3-dihydro-1H-indol-5-yl)-5-oxopentyl[2-(2-methoxyphenyl)ethyl]carbamate obtained in Reference Example 50 and ethyl iodide according to the same method as that of Reference Example 50, the title compound was obtained as a pale yellow oil.

$^1$H NMR(400 MHz, CDCl$_3$) δ 1.18(3H, t, J=7.4 Hz), 1.43 (9H, s), 1.51-1.72(4H, m), 2.78-2.88(4H, m), 3.00(2H, t, J=8.5 Hz), 3.08-3.23(2H, m), 3.25(2H, q, J=7.4 Hz), 3.31-3.41(2H, m), 3.52(2H, t, J=8.5 Hz), 3.81(3H, s), 6.33(1H, d, J=8 Hz), 6.82-6.88(2H, m), 7.08-7.20(2H, m), 7.67(1H, s), 7.74(1H, d, J=8 Hz).

Reference Example 53 tert-Butyl 5-[1-(3-hydroxypropyl)-2,3-dihydro-1H-indol-5-yl]-5-oxopentyl[2-(2-methoxyphenyl)ethyl]carbamate

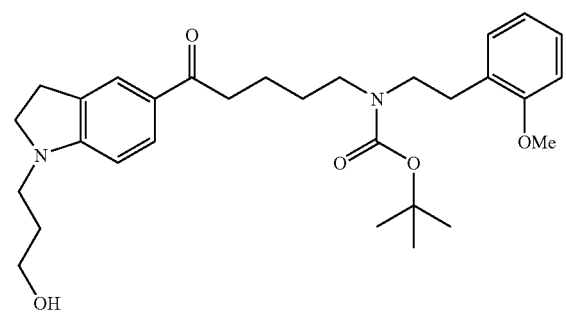

Using tert-butyl 5-(2,3-dihydro-1H-indol-5-yl)-5-oxopentyl[2-(2-methoxyphenyl)ethyl]carbamate obtained in Reference Example 50 and 3-bromo-1-propanol according to the same method as that of Reference Example 50, the title compound was obtained as a pale yellow oil.

$^1$H NMR(400 MHz, CDCl$_3$) δ 1.43(9H, s), 1.51-1.70(4H, m), 1.75(1H, br.s), 1.85(2H, t, J=6.7 Hz), 2.78-2.88(4H, m), 3.01(2H, t, J=8.5 Hz), 3.08-3.24(2H, m), 3.30-3.40(2H, m), 3.32(2H, t, J=6.7 Hz), 3.54(2H, t, J=8.5 Hz), 3.76(2H, t, J=7.6 Hz), 3.82(3H, s), 6.39(1H, d, J=8 Hz), 6.82-6.88(2H, m), 7.08-7.20(2H, m), 7.67(1H, s), 7.73(1H, d, J=8 Hz).

Reference Example 54

Ethyl [5-(5-[(tert-butoxycarbonyl)[2-(2-methoxyphenyl)ethyl]amino]pentanoyl)-2,3-dihydro-1H-indol-1-yl]acetate

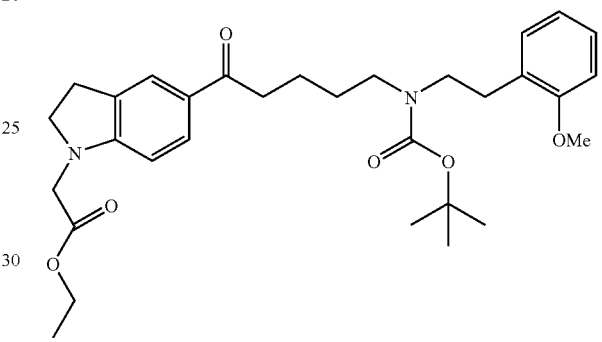

Using tert-butyl 5-(2,3-dihydro-1H-indol-5-yl)-5-oxopentyl[2-(2-methoxyphenyl)ethyl]carbamate obtained in Reference Example 50 and ethyl bromoacetate according to the same method as that of Reference Example 50, the title compound was obtained as a pale yellow oil.

$^1$H NMR(400 MHz, CDCl$_3$) δ 1.27(3H, t, J=7 Hz), 1.43 (9H, s), 1.51-1.73(4H, m), 2.75-2.88(4H, m), 3.08(2H, t, J=8.5 Hz), 3.15-3.23(2H, m), 3.30-3.40(2H, m), 3.67(2H, t, J=8.5 Hz), 3.81(3H, s), 3.96(2H, s), 4.20(2H, q, J=7 Hz), 6.29(1H, d, J=8 Hz), 6.82-6.88(2H, m), 7.08-7.20(2H, m), 7.70(1H, s), 7.73(1H, d, J=8 Hz).

Reference Example 55 tert-Butyl 5-[1-[(ethylamino)carbonyl]-2,3-dihydro-1H-indol-5-yl]-5-oxopentyl[2-(2-methoxyphenyl)ethyl]carbamate

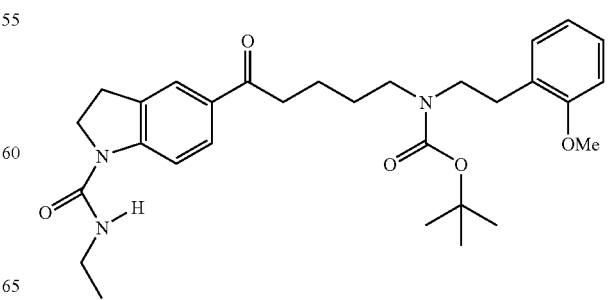

Ethyl isocyanate (85 mg) was added to a solution of tert-butyl 5-(2,3-dihydro-1H-indol-5-yl)-5-oxopentyl[2-(2-methoxyphenyl)ethyl]carbamate (362 mg) obtained in Reference Example 50 in tetrahydrofuran (2 ml), and the mixture was stirred at 60° C. for 2 hours. The solvent was evaporated under reduced pressure, water was added to the resulting residue, and extracted with ethyl acetate. The organic layer was washed with brine, dried over anhydrous magnesium sulfate, and the solvent was evaporated under reduced pressure. The resulting residue was purified by silica gel chromatography (eluting solvent; hexane:ethyl acetate=1:1) to give the title compound as a pale yellow oil (254 mg).

$^1$H NMR(400 MHz, CD$_3$OD) δ 1.22(3H, t, J=7 Hz), 1.43 (9H, s), 1.51-1.73(4H, m), 2.76-2.95(4H, m), 3.07-3.23(4H, m), 3.30-3.42(4H, m), 3.82(3H, s), 3.94(2H, t, J=8 Hz), 4.70 (1H, br.s), 6.82-6.88(2H, m), 7.08-7.20(2H, m), 7.75(1H, s), 7.80(1H, d, J=8.5 Hz), 7.96(1H, d, J=8.5 Hz).

Reference Example 56 tert-Butyl 2-(3-fluorophenyl)ethyl[5-oxo-5-(3-oxo-3,4-dihydro-2H-1,4-benzooxazin-6-yl)pentyl]carbamate

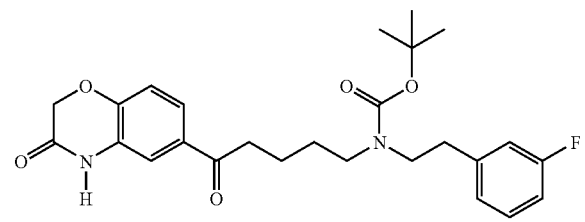

Using 6-(5-chloropentanoyl)-2H-1,4-benzooxazin-3(4H)-one obtained in Reference Example 7 and 2-(3-fluorophenyl)ethylamine according to the same method as that of Reference Example 19, the title compound was obtained as a colorless oil.

$^1$H NMR(200 MHz, CDCl$_3$) δ 1.44(9H, s), 1.52-1.76(4H, m), 2.81(2H, m), 2.91-2.95(2H, m), 3.14-3.23(2H, m), 3.38 (2H, m), 4.69(2H, s), 6.87-7.01(4H, m), 7.20-7.25(1H, m), 7.59-7.61(2H, m), 9.40(1H, s).

Reference Example 57 tert-Butyl 2-(3-chlorophenyl)ethyl[5-oxo-5-(3-oxo-3,4-dihydro-2H-1,4-benzooxazin-6-yl)pentyl]carbamate

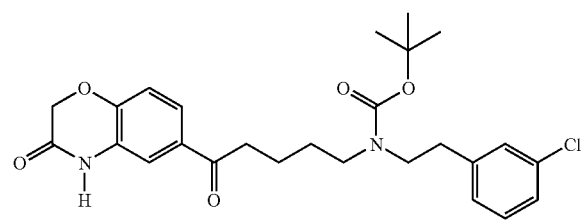

Using 6-(5-chloropentanoyl)-2H-1,4-benzooxazin-3(4H)-one obtained in Reference Example 7 and 2-(3-chlorophenyl)ethylamine according to the same method as that of Reference Example 19, the title compound was obtained as a colorless oil.

$^1$H NMR(200 MHz, CDCl$_3$) δ 1.44(9H, s), 1.58(2H, m), 1.68-1.73(2H, m), 2.79(2H, m), 2.90-2.95(2H, m), 3.14-3.23 (2H, m), 3.37(2H, m), 4.69(2H, s), 6.98-7.05(2H, m), 7.17-7.21(3H, m), 7.59-7.61(2H, m), 9.46(1H, s).

Reference Example 58 tert-Butyl 5-(1,3-dimethyl-2-oxo-2,3-dihydro-1H-benzimidazol-5-yl)-5-oxopentyl(2-phenylethyl)carbamate

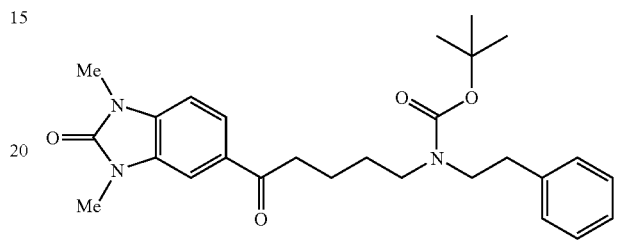

Using 5-(5-chloropentanoyl)-1,3-dimethyl-1,3-dihydro-2H-benzimidazol-2-one obtained in Reference Example 10 and 2-phenylethylamine according to the same method as that of Reference Example 19, the title compound was obtained as a colorless oil.

$^1$H NMR(300 MHz, CDCl$_3$) δ 1.44(9H, s), 1.75-1.59(4H, m), 2.79-2.81(2H, m), 3.03-2.99(2H, m), 3.22-3.18(2H, m), 3.39-3.35(2H, m), 3.46(3H, s), 3.47(3H, s), 6.99(1H, d, J=8.1 Hz), 7.31-7.16(5H, m), 7.63(1H, d, J=1.2 Hz), 7.78(1H, d, J=8.4 Hz).

Reference Example 59 tert-Butyl 5-(1,3-dimethyl-2-oxo-2,3-dihydro-1H-benzimidazol-5-yl)-5-oxopentyl[2-(2-methoxyphenyl)ethyl]carbamate

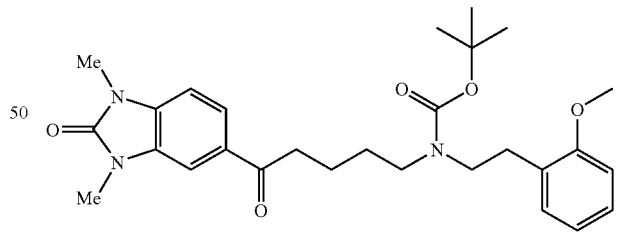

Using 5-(5-chloropentanoyl)-1,3-dimethyl-1,3-dihydro-2H-benzimidazol-2-one obtained in Reference Example 10 and 2-(2-methoxyphenyl)ethylamine according to the same method as that of Reference Example 19, the title compound was obtained as a colorless oil.

$^1$H NMR(300 MHz, CDCl$_3$) δ 1.43(9H, s), 1.73-1.64(4H, m), 2.84-2.80(2H, m), 3.03-2.99(2H, m), 3.23-3.21(2H, m), 3.37-3.33(2H, m), 3.47(6H, s), 3.82(3H, s), 6.90-6.82(2H, m), 6.98(1H, d, J=8.4 Hz), 7.21-7.17(2H, m), 7.63(1H, d, J=1.5 Hz), 7.79(1H, d, J=8.1 Hz).

Reference Example 60 tert-Butyl 2-(2-chlorophenyl)ethyl[5-(1,3-dimethyl-2-oxo-2,3-dihydro-1H-benzimidazol-5-yl)-5-oxopentyl]carbamate

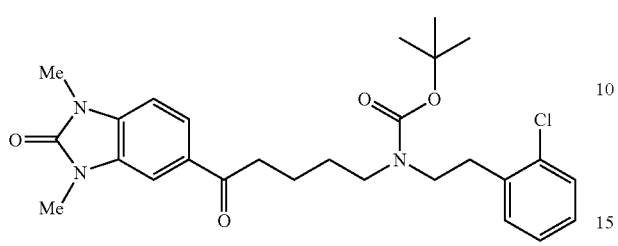

Using 5-(5-chloropentanoyl)-1,3-dimethyl-1,3-dihydro-2H-benzimidazol-2-one obtained in Reference Example 10 and 2-(2-chlorophenyl)ethylamine according to the same method as that of Reference Example 19, the title compound was obtained as a colorless oil.

¹H NMR(300 MHz, CDCl₃) δ 1.74-1.41(13H, m), 3.01-2.94(4H, m), 3.24-3.15(2H, m), 3.44-3.39(2H, m), 3.46(3H, s), 3.47(3H, s), 6.99(1H, d, J=8.1 Hz), 7.17(3H, m), 7.35-7.32 (1H, m), 7.63(1H, d, J=1.5 Hz), 7.79(1H, d, J=8.1 Hz).

Reference Example 61 tert-Butyl 5-(1-benzyl-2,3-dihydro-1H-indol-5-yl)-5-oxopentyl[2-(2-methoxyphenyl)ethyl]carbamate

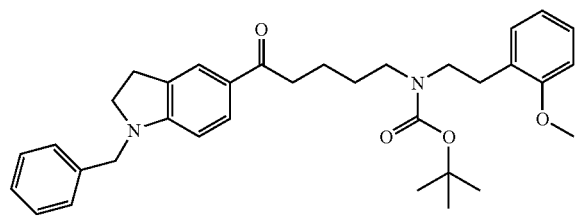

Using tert-butyl 5-(2,3-dihydro-1H-indol-5-yl)-5-oxopentyl[2-(2-methoxyphenyl)ethyl]carbamate obtained in Reference Example 50 and benzyl bromide according to the same method as that of Reference Example 51, the title compound was obtained as a colorless oil.

¹H NMR(400 MHz, CDCl₃) δ 1.43(9H, s), 1.51-1.68(4H, m), 2.85(4H, br.s), 3.03(2H, t, J=8.3 Hz), 3.07-3.20(2H, m), 3.34(2H, br.s), 3.50(2H, t, J=8.4 Hz), 3.81(3H, s), 4.37(2H, s), 6.40(1H, d, J=8.3 Hz), 6.82-6.88(2H, m), 7.08-7.20(2H, m), 7.26-7.36(5H, m), 7.70(1H, s), 7.74(1H, d, J=8.3 Hz).

Reference Example 62 tert-Butyl 5-(1-benzoyl-2,3-dihydro-1H-indol-5-yl)-5-oxopentyl[2-(2-methoxyphenyl)ethyl]carbamate

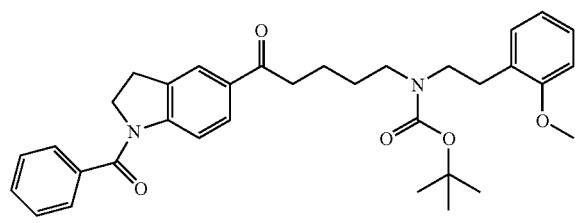

Using tert-butyl 5-(2,3-dihydro-1H-indol-5-yl)-5-oxopentyl[2-(2-methoxyphenyl)ethyl]carbamate obtained in Reference Example 50 and benzoyl chloride according to the same method as that of Reference Example 55, the title compound was obtained as a colorless oil.

¹H NMR(400 MHz, CDCl₃) δ 1.43(9H, s), 1.51-1.70(4H, m), 2.82(2H, br.s), 2.93(2H, br.s), 3.15(2H, t, J=8.5 Hz), 3.21(2H, br.s), 3.35(2H, br.s), 3.82(3H, s), 4.13(2H, t, J=8.4 Hz), 6.82-6.88(2H, m), 7.09-7.20(2H, m), 7.44-7.57(6H, m), 7.75(1H, br.s), 7.83(1H, s).

Reference Example 63 tert-Butyl 5-[1-(anilinocarbonyl)-2,3-dihydro-1H-indol-5-yl]-5-oxopentyl[2-(2-methoxyphenyl)ethyl]carbamate

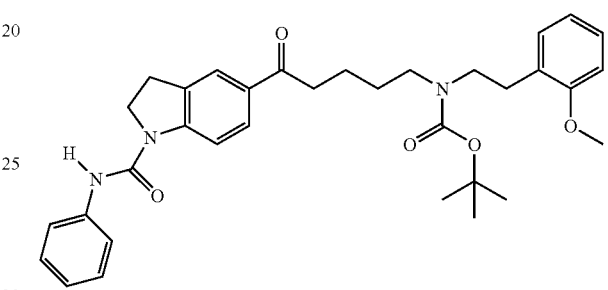

Using tert-butyl 5-(2,3-dihydro-1H-indol-5-yl)-5-oxopentyl[2-(2-methoxyphenyl)ethyl]carbamate obtained in Reference Example 50 and phenyl isocyanate according to the same method as that of Reference Example 55, the title compound was obtained as colorless crystals having a melting point of 136 to 137° C.

¹H NMR(400 MHz, CDCl₃) δ 1.43(9H, s), 1.51-1.70(4H, m), 2.82(2H, br.s), 2.91(2H, t, J=7.0 Hz), 3.13-3.26(4H, m), 3.35(2H, br.s), 3.81(3H, s), 4.11(2H, t, J=, 8.4 Hz), 6.36(1H, s), 6.82-6.88(2H, m), 7.08-7.20(3H, m), 7.33(2H, t, J=8.3 Hz), 7.45(2H, d, J=8.0 Hz), 7.78(1H, s), 7.81(1H, d, J=8.5 Hz), 7.98(1H, d, J=8.0 Hz).

Reference Example 64

5-Chloro-1-(4-methoxyphenyl)-1-pentanone

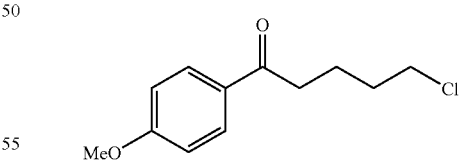

Using anisole (15.0 g) and 5-chlorovaleryl chloride (18.0 ml) according to the same method as that of Reference. Example 1, the title compound was obtained as colorless crystals (27.3 g) having a melting point of 67 to 68° C.

¹H NMR (300 MHz, CDCl₃) δ 1.80-1.95 (4H, m), 2.90-3.00 (2H, m), 3.55-3.60 (2H, m), 3.86 (3H, s), 6.90-7.00 (2H, m), 7.90-8.00 (2H, m)

elementary analysis as $C_{12}H_{15}ClO_2$
calculation value:C, 63.58; H, 6.67; N, 0.00.
experimental value:C, 63.50; H, 6.67; N, 0.00.

Reference Example 65

5-(5-Chloropentanoyl)-2-methoxybenzenesulfonyl chloride

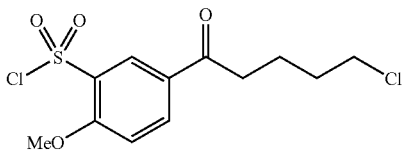

5-Chloro-1-(4-methoxyphenyl)-1-pentanone (15.0 g) obtained in Reference Example 64 was added to chlorosulfonic acid (50 ml) by portions under ice-cooling. The mixture was stirred at room temperature for 30 hours, the reaction mixture was added dropwise to a crashed ice (500 g), extracted with ethyl acetate, and washed with brine. The organic layer was dried over anhydrous magnesium sulfate, and the solvent was evaporated under reduced pressure to give the title compound as colorless crystals (7.63 g) having a melting point of 69 to 70° C.

$^1$H NMR (200 MHz, CDCl$_3$) δ 1.80-2.00 (4H, m), 2.95-3.05 (2H, m), 3.55-3.65 (2H, m), 4.15 (3H, s), 7.22 (1H, d, J=8.8 Hz), 8.33 (1H, dd, J=8.8, 2.2 Hz), 8.53 (1H, d, J=2.2 Hz).

elementary analysis as C$_{12}$H$_{14}$Cl$_2$O$_4$S
calculation value:C, 44.32; H, 4.34; N, 0.00.
experimental value:C, 43.77; H, 4.36; N, 0.00.

Reference Example 66

5-(5-Chloropentanoyl)-2-methoxybenzenesulfonamide

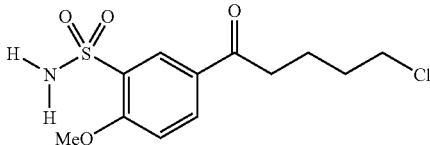

A 25% aqueous ammonium solution was added dropwise to a solution of 5-(5-chloropentanoyl)-2-methoxybenzenesulfonyl chloride (3.00 g) obtained in Reference Example 65 in tetrahydrofuran (50 ml) under ice-cooling. After stirring at room temperature for 30 minutes, the solvent was evaporated under reduced pressure, extracted with ethyl acetate, and washed with brine. The organic layer was dried over anhydrous magnesium sulfate, and the solvent was evaporated under reduced pressure to give the title compound as colorless crystals (2.54 g) having a melting point of 135 to 136° C.

$^1$H NMR (200 MHz, DMSO-d$_6$) δ 1.60-1.80 (4H, m), 3.06 (2H, t, J=6.2 Hz), 3.69 (2H, t, J=6.2 Hz), 4.00 (3H, s), 7.28 (2H, s), 7.33 (1H, d, J=8.8 Hz), 8.22 (1H, dd, J=8.8, 2.2 Hz), 8.30 (1H, d, J=2.2 Hz).

elementary analysis as C$_{12}$H$_{16}$ClNO$_4$S
calculation value:C, 47.14; H, 5.27; N, 4.58.
experimental value:C, 47.06; H, 5.25; N, 4.49.

Reference Example 67

5-(5-Chloropentanoyl)-N-isopropyl-2-methoxybenzenesulfonamide

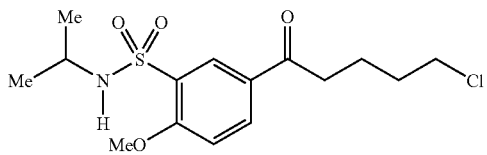

Using 5-(5-chloropentanoyl)-2-methoxybenzenesulfonyl chloride (3.50 g) obtained in Reference Example 65 and isopropylamine (1.90 ml) according to the same method as that of Reference. Example 66, the title compound was obtained as colorless crystals. (3.39 g) having a melting point of 122 to 124° C.

$^1$H NMR (200 MHz, CDCl$_3$) δ 1.08 (6H, d, J=6.6 Hz), 1.80-2.00 (4H, m), 2.95-3.05 (2H, m), 3.35-3.65 (3H, m), 4.07 (3H, s), 4.30-5.00 (1H, br), 7.12 (1H, d, J=8.8 Hz), 8.21 (1H, dd, J=8.8, 2.2 Hz), 8.50 (1H, d, J=2.2 Hz).

elementary analysis as C$_{15}$H$_{22}$ClNO$_4$S
calculation value:C, 51.79; H, 6.37; N, 4.03.
experimental value:C, 51.74; H, 6.37; N, 3.83.

Reference Example 68

5-Chloro-1-(2,3-dihydro-1-benzofuran-5-yl)-1-pentanone

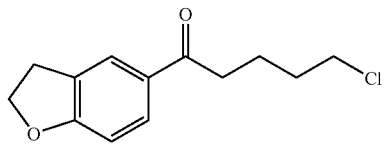

Using 2,3-dihydro-1-benzofuran (24.5 g) and 5-chlorovaleryl chloride (34.8 g) according to the same method as that of Reference Example 1, the title compound was obtained as colorless crystals (32.4 g) having a melting point of 56 to 57° C.

$^1$H NMR (300 MHz, CDCl$_3$) δ 1.80-2.00 (4H, m), 2.90-3.00 (2H, m), 3.25 (2H, t, J=8.7 Hz), 3.55-3.65 (2H, m), 4.66 (2H, t, J=8.7 Hz), 6.79 (1H, d, J=8.2 Hz), 7.79 (1H, dd, J=8.2, 2.1 Hz), 7.84 (1H, d, J=2.1 Hz).

elementary analysis as C$_{13}$H$_{15}$ClO$_2$
calculation value:C, 65.41; H, 6.33; N, 0.00.
experimental value:C, 65.18; H, 6.33; N, 0.00.

Reference Example 69

5-(5-Chloropentanoyl)-2,3-dihydro-1-benzofuran-7-sulfonyl chloride

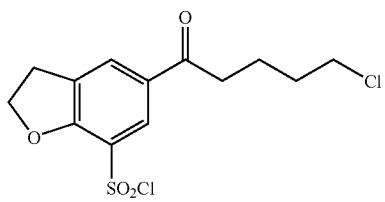

Using 5-chloro-1-(2,3-dihydro-1-benzofuran-5-yl)-1-pentanone (10.0 g) obtained in Reference Example 68 according to the same method as that of Reference Example 65, the title compound was obtained as colorless crystals (4.93 g) having a melting point of 72 to 73° C.

$^1$H NMR (200 MHz, CDCl$_3$) δ 1.80-2.00 (4H, m), 2.90-3.05 (2H, m), 3.41 (2H, t, J=8.8 Hz), 3.55-3.65 (2H, m), 5.01 (2H, t, J=8.8 Hz), 8.15-8.20 (1H, m), 8.25-8.30 (1H, m).

elementary analysis as C$_{13}$H$_{14}$Cl$_2$O$_4$S
calculation value:C, 46.30; H, 4.18; N, 0.00.
experimental value:C, 46.13; H, 4.17; N, 0.00.

Reference Example 70

5-(5-Chloropentanoyl)-2,3-dihydro-1-benzofuran-7-sulfonamide

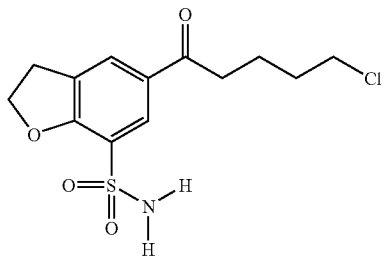

Using 5-(5-chloropentanoyl)-2,3-dihydro-1-benzofuran-7-sulfonyl chloride (4.50 g) obtained in Reference Example 69 according to the same method as that of Reference Example 66, the title compound was obtained colorless crystals (3.87 g) having a melting point of 134 to 136° C.

$^1$H NMR (200 MHz, DMSO-d$_6$) δ 1.65-1.85 (4H, m), 3.02 (2H, t, J=7.0 Hz), 3.32 (2H, t, J=8.8 Hz), 3.68 (2H, t, J=7.0 Hz), 4.82 (2H, t, J=8.8 Hz), 7.38 (2H, s), 8.05-8.10 (2H, m).

elementary analysis as C$_{13}$H$_{16}$ClNO$_4$S
calculation value:C, 49.13; H, 5.07; N, 4.41.
experimental value:C, 48.96; H, 4.99; N, 4.15.

Reference Example 71

5-(5-Chloropentanoyl)-N-isopropyl-2,3-dihydro-1-benzofuran-7-sulfonamide

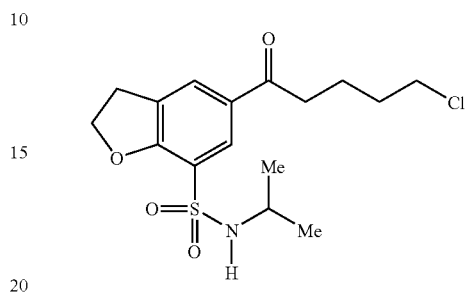

Using 5-(5-chloropentanoyl)-2,3-dihydro-1-benzofuran-7-sulfonyl chloride (4.50 g) obtained in Reference Example 69 and isopropylamine (3.80 ml) according to the same method as that of Reference Example 66, the title compound was obtained colorless crystals (6.76 g) having a melting point of 103 to 104° C.

$^1$H NMR (200 MHz, CDCl$_3$) δ 1.11 (6H, d, J=6.6 Hz), 1.80-2.00 (4H, m), 2.90-3.05 (2H, m), 3.34 (2H, t, J=8.8 Hz), 3.40-3.65 (3H, m), 4.71 (1H, d, J=7.0 Hz), 4.87 (2H, t, J=8.8 Hz), 8.00-8.10 (1H, m), 8.20-8.25 (1H, m).

elementary analysis as C$_{16}$H$_{22}$NO$_4$SCl
calculation value:C, 53.40; H, 6.16; N, 3.89.
experimental value:C, 53.32; H, 6.16; N, 3.84.

Reference Example 72

5-Chloro-1-(2,2-dimethyl-3,4-dihydro-2H-chromen-6-yl)-1-pentanone

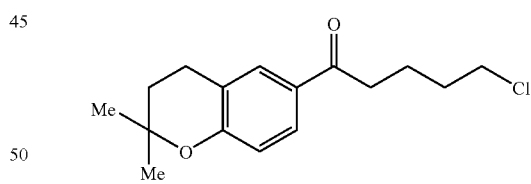

Using 2,2-dimethylchroman (19.7 g) and 5-chlorovaleryl chloride (20.7 g) according to the same method as that of Reference Example 1, the title compound was obtained as colorless crystals (22.0 g) having a melting point of 50 to 51° C.

$^1$H NMR (200 MHz, CDCl$_3$) δ 1.36 (6H, S), 1.80-1.95 (6H, m), 2.82 (2H, t, J=6.6 Hz), 2.80-3.00 (2H, m), 3.55-3.65 (2H, m), 6.80 (1H, d, J=9.0 Hz), 7.70-7.80 (2H, m).

elementary analysis as C$_{16}$H$_{21}$ClO$_2$
calculation value:C, 68.44; H, 7.68; N, 0.00.
experimental value:C, 68.31; H, 7.54; N, 0.00.

Reference Example 73

6-(5-Chloropentanoyl)-2,2-dimethyl-8-chromansulfonyl chloride

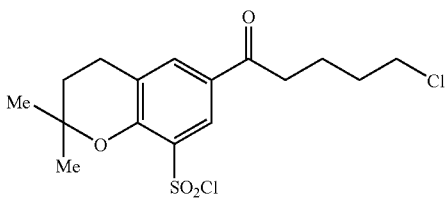

Using 5-chloro-1-(2,2-dimethyl-3,4-dihydro-2H-chromen-6-yl)-1-pentanone (5.00 g) obtained in Reference Example 72 according to the same method as that of Reference Example 65, the title compound was obtained as a colorless oil (1.30 g).

$^1$H NMR (200 MHz, CDCl$_3$) δ 1.50 (6H, s), 1.75-2.10 (6H, m), 2.85-3.05 (4H, m), 3.55-3.65 (2H, m), 8.60 (1H, s), 8.33 (1H, s).

Reference Example 74

6-(5-Chloropentanoyl)-2,2-dimethyl-8-chromansulfonamide

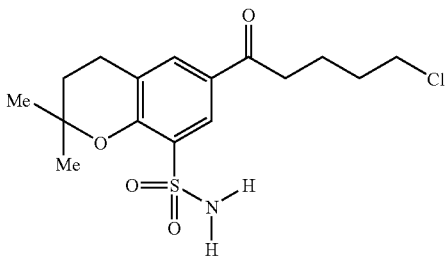

Using 6-(5-chloropentanoyl)-2,2-dimethyl-8-chromansulfonyl chloride (1.30 g) obtained in Reference Example 73 according to the same method as that of Reference Example 66, the title compound was obtained as colorless crystals (630 mg) having a melting point of 148 to 149° C.

$^1$H NMR (300 MHz, CDCl$_3$) δ 1.48 (6H, s), 1.80-1.90 (4H, m), 1.95 (2H, t, J=6.9 Hz), 2.91 (2H, t, J=6.9 Hz), 2.95-3.00 (2H, m), 3.55-3.60 (2H, m), 5.03 (2H, s), 7.95-8.00 (1H, m), 8.25-8.30 (1H, m).

Reference Example 75

5-Chloro-1-(2,3-dihydro-1,4-benzodioxin-6-yl)-1-pentanone

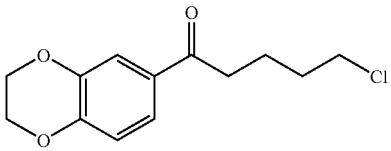

Using 2,3-dihydro-1,4-benzodioxine (10.0 g) and 5-chlorovaleryl chloride (10.4 ml) according to the same method as that of Reference Example 1, the title compound was obtained as colorless crystals (15.1 g) having a melting point of 52 to 53° C.

$^1$H NMR (300 MHz, CDCl$_3$) δ 1.80-1.95 (4H, m), 2.90-3.00 (2H, m), 3.55-3.60 (2H, m), 4.25-4.35 (4H, s), 6.85-6.95 (1H, m), 7.45-7.50 (2H, m).

elementary analysis as C$_{13}$H$_{15}$ClO$_3$
calculation value:C, 61.30; H, 5.94; N, 0.00.
experimental value:C, 61.26; H, 5.83; N, 0.00.

Reference Example 76

7-(5-Chloropentanoyl)-2,3-dihydro-1,4-benzodioxine-5-sulfonamide

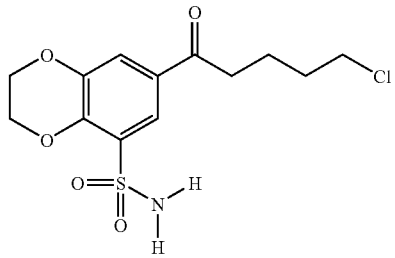

By using 5-chloro-1-(2,3-dihydro-1,4-benzodioxin-6-yl)-1-pentanone (9.00 g) obtained in Reference Example 75 and carrying out the same process as those of Reference Examples 65 and 66 successively, the title compound was obtained as colorless crystals (3.88 g) having a melting point of 141 to 142° C.

$^1$H NMR (300 MHz, CDCl$_3$) δ 1.80-1.95 (4H, m), 2.94 (2H, t, J=6.6 Hz), 3.58 (2H, t, J=6.0 Hz), 4.30-4.45 (2H, m), 4.50-4.60 (2H, m), 5.20, (2H, s), 7.67 (1H, d, J=1.8 Hz), 7.99 (1H, d, J=1.8 Hz).

elementary analysis as C$_{13}$H$_{16}$ClNO$_5$S
calculation value:C, 46.78; H, 4.83; N, 4.20.
experimental value:C, 46.63; H, 4.83; N, 4.10.

Reference Example 77 trans-N-({4-[(4-Oxo-1,2,5,6-tetrahydro-4H-pyrrolo[3,2,1-ij]quinolin-8-yl)carbonyl]cyclohexyl}methyl)acetamide

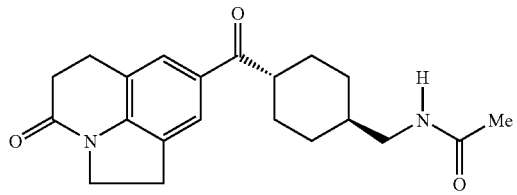

trans-4-[(Acetylamino)methyl]cyclohexanecarboxylic acid (12.1 g) was added by portions to thionyl chloride (25 ml) under ice-cooling. After stirred at room temperature for 30 minutes, thionyl chloride was evaporated under reduced pressure to give crude crystals of trans-4-[(acetylamino)methyl]cyclohexanecarbonyl chloride. Then, aluminum chloride (24.0 g) was added by portions to a solution of the crude crystals and 1,2,5,6-tetrahydro-4H-pyrrolo[3,2,1-ij]quinolin-4-one (12.1 g) in dichloromethane (30 ml) under ice-cooling. After stirring at room temperature for 12 hours, the reaction mixture was poured into ice (300 g), extracted with ethyl acetate, and washed 20 with brine. The organic layer was dried over anhydrous magnesium sulfate, and the solvent was evaporated under reduced pressure to give the title compound as colorless crystals (12.9 g) having a melting point of 178 to 180° C.

$^1$H NMR (300 MHz, CDCl$_3$) δ 1.05-1.20 (2H, m), 1.45-1.60 (3H, m), 1.70-2.05 (4H, m), 2.01 (3H, s), 2.72 (2H, t, J=7.8 Hz), 3.03 (2H, t, J=7.8 Hz), 3.10-3.30 (5H, m), 4.13 (2H, t, J=8.4 Hz), 5.55-5.70 (1H, m), 7.64 (1H, s), 7.69 (1H, s).

Reference Example 78 trans-8-{[4-(Aminomethyl)cyclohexyl]carbonyl}-1,2,5,6-tetrahydro-4H-pyrrolo[3,2,1-ij]quinolin-4-one hydrochloride

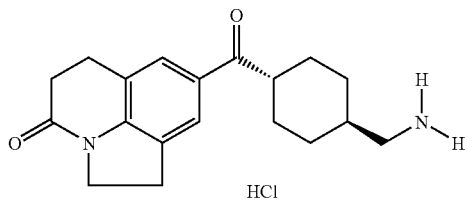

Concentrated hydrochloric acid (100 ml) was added to trans-N-({4-[(4-oxo-1,2,5,6-tetrahydro-4H-pyrrolo[3,2,1-ij]quinolin-8-yl)carbonyl]cyclohexyl}methyl)acetamide (12.0 g) obtained in Reference Example 77, and the mixture was stirred at 140° C. for 12 hours. Hydrochloric acid was evaporated under reduced pressure to give white powders. Further recrystallization from water-isopropyl ether afforded the title compound as colorless crystals (9.40 g) having a melting point of 255 to 257° C.

$^1$H NMR (200 MHz, DMSO-d$_6$) δ 1.00-1.95 (10H, m), 2.50-2.75 (3H, m), 2.98 (2H, t, J=7.8 Hz), 3.18 (2H, t, J=8.8 Hz), 3.20-3.40 (1H, m), 3.99 (2H, t, J=8.8 Hz), 7.72 (1H, s), 7.73 (1H, s), 7.90-8.20 (3H, br).

Reference Example 79 tert-Butyl 2-(4-methoxyphenyl)ethyl[5-oxo-5-(4-oxo-1,2,5,6-tetrahydro-4H-pyrrolo[3,2,1-ij]quinolin-8-yl)pentyl]carbamate

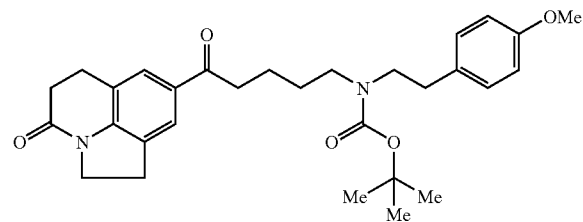

Using 8-(5-chloropentanoyl)-1,2,5,6-tetrahydro-4H-pyrrolo[3,2,1-ij]quinolin-4-one (1.00 g) obtained in Reference Example 1 and 2-(4-methoxyphenyl)ethylamine (1.06 g) according to the same method as that of Reference Example 19, the title compound (1.23 g) was obtained as a colorless oil.

$^1$H NMR (300 MHz, CDCl$_3$) δ 1.45 (9H, s), 1.50-1.95 (4H, m), 2.65-2.80 (2H, m), 2.71 (2H, t, J=7.8 Hz), 2.85-3.00 (2H, m), 3.01 (2H, t, J=7.8 Hz), 3.05-3.40 (4H, m), 3.21 (2H, t, J=8.4 Hz), 3.78 (3H, s), 4.12 (2H, t, J=8.4 Hz), 6.82 (2H, d, J=8.4 Hz), 7.00-7.15 (2H, m), 7.66 (1H, s), 7.70 (1H, s).

Reference Example 80 tert-Butyl 2-(4-chlorophenyl)ethyl[5-oxo-5-(4-oxo-1,2,5,6-tetrahydro-4H-pyrrolo[3,2,1-ij]quinolin-8-yl)pentyl]carbamate Using 8-(5-chloropentanoyl)-1,2,5,6-tetrahydro-4H-pyrrolo[3,2,1-ij]quinolin-4-one (1.00 g) obtained in Reference Example 1 and 2-(4-chlorophenyl)ethylamine (1.06 g) according to the same method as that of Reference Example 19, the title compound (941 mg) was obtained as a colorless oil.

$^1$H NMR (300 MHz, CDCl$_3$) δ 1.43 (9H, s), 1.50-1.95 (4H, m), 2.65-2.85 (2H, m), 2.71 (2H, t, J=7.8 Hz), 2.85-3.00 (2H, m), 3.01 (2H, t, J=7.8 Hz), 3.05-3.45 (4H, m), 3.22 (2H, t, J=8.4 Hz), 4.13 (2H, t, J=8.4 Hz), 7.00-7.30 (4H, m), 7.66 (1H, s), 7.70 (1H, s).

Reference Example 81 tert-Butyl 2-(3-chlorophenyl)ethyl[5-oxo-5-(4-oxo-1,2,5,6-tetrahydro-4H-pyrrolo[3,2,1-ij]quinolin-8-yl)pentyl]carbamate Using 8-(5-chloropentanoyl)-1,2,5,6-tetrahydro-4H-pyrrolo[3,2,1-ij]quinolin-4-one (1.00 g) obtained in Reference Example 1 and 2-(3-chlorophenyl)ethylamine (1.06 g) according to the same method as that of Reference Example 19, the title compound (1.19 g) was obtained as a colorless oil.

$^1$H NMR (300 MHz, CDCl$_3$) δ 1.43 (9H, s), 1.50-1.90 (4H, m), 2.65-2.85 (2H, m), 2.70 (2H, t, J=7.8 Hz), 2.85-3.00 (2H, m), 3.01 (2H, t, J=7.8 Hz), 3.05-3.25 (2H, m), 3.21 (2H, t, J=8.4 Hz), 3.36 (2H, t, J=7.5 Hz), 4.12 (2H, t, J=8.4 Hz), 7.00-7.20 (4H, m), 7.65 (1H, s), 7.70 (1H, s).

Reference Example 82 tert-Butyl 2-(2-hydroxyphenyl)ethyl[5-oxo-5-(4-oxo-1,2,5,6-tetrahydro-4H-pyrrolo[3,2,1-ij]quinolin-8-yl)pentyl]carbamate

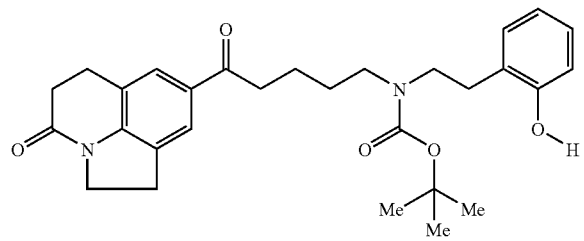

A mixture of 8-(5-chloropentanoyl)-1,2,5,6-tetrahydro-4H-pyrrolo[3,2,1-ij]quinolin-4-one (1.00 g) obtained in Reference Example 1, 2-(2-hydroxyphenyl)ethylamine•hydrobromide (1.49 g) and diisopropylethylamine (1.16 ml) in dimethylformaide (1 ml) was stirred at 120° C. for 1 hour. After cooled to room temperature, methanol (10 ml) and triethylamine (1.43 ml) were added to the reaction mixture, a solution of di-t-butyl dicarbonate (2.24 g) in methanol (5 ml) was added dropwise, and the mixture was stirred at room temperature for 12 hours. The solvent was evaporated under reduced pressure, the resulting residue was purified by silica gel chromatography (eluting solvent; hexane: ethyl acetate=2:1), and the solvent was evaporated to give the title compound as colorless crystals (687 mg) having a melting point of 154 to 155° C.

$^1$H NMR (300 MHz, CDCl$_3$) δ 1.48 (9H, s), 1.55-1.85 (4H, m), 2.71 (2H, t, J=7.8 Hz), 2.83 (2H, t, J=7.5 Hz), 2.94 (2H, t, J=7.5 Hz), 3.00 (2H, t, J=7.8 Hz), 3.15-3.35 (6H, m), 4.12 (2H, t, J=8.4 Hz), 6.70-7.15 (4H, m), 7.66 (1H, s), 7.70 (1H, s), 7.40-7.65 (1H, br).

elementary analysis as C$_{29}$H$_{36}$N$_2$O$_5$.0.2H$_2$O
calculation value:C, 70.19; H, 7.39; N, 5.65.
experimental value:C, 70.34; H, 7.35; N, 5.66.

Reference Example 83 tert-Butyl 2-(2,6-dichlorophenyl)ethyl[5-oxo-5-(4-oxo-1,2,5,6-tetrahydro-4H-pyrrolo[3,2,1-ij]quinolin-8-yl)pentyl]carbamate

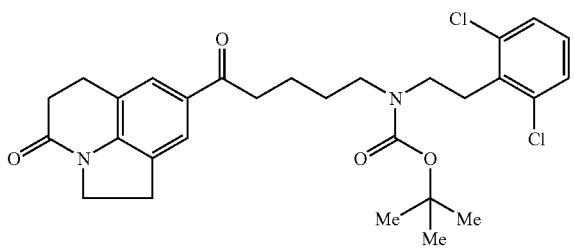

Using 8-(5-chloropentanoyl)-1,2,5,6-tetrahydro-4H-pyrrolo[3,2,1-ij]quinolin-4-one (1.00 g) obtained in Reference Example 1 and 2-(2,6-dichlorophenyl)ethylamine (650 mg) according to the same method as that of Reference Example 19, the title compound (1.08 g) was obtained as a colorless oil.

$^1$H NMR (300 MHz, CDCl$_3$) δ 1.42 (9H, s), 1.50-1.80 (4H, m), 1.80-1.95 (2H, m), 2.71 (2H, t, J=7.8 Hz), 2.85-3.65 (10H, m), 4.13 (2H, t, J=8.4 Hz), 7.10 (1H, t, J=7.8 Hz), 7.25-7.30 (2H, m), 7.68 (1H, s), 7.72 (1H, s).

Reference Example 84 tert-Butyl 2-(2,3-dimethoxyphenyl)ethyl[5-oxo-5-(4-oxo-1,2,5,6-tetrahydro-4H-pyrrolo[3,2,1-ij]quinolin-8-yl)pentyl]carbamate

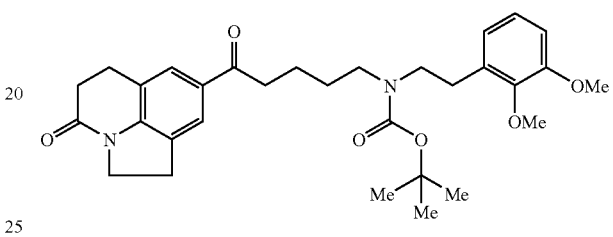

Using 8-(5-chloropentanoyl)-1,2,5,6-tetrahydro-4H-pyrrolo[3,2,1-ij]quinolin-4-one (1.00 g) obtained in Reference Example 1 and 2-(2,3-dimethoxyphenyl)ethylamine (620 mg) according to the same method as that of Reference Example 19, the title compound (1.13 g) was obtained as a colorless oil.

$^1$H NMR (300 MHz, CDCl$_3$) δ 1.46 (9H, s), 1.50-1.90 (6H, m), 2.71 (2H, t, J=7.8 Hz), 2.75-3.45 (10H, m), 3.84 (3H, s), 3.86 (3H, s), 4.12 (2H, t, J=8.4 Hz), 6.70-6.85 (2H, m), 6.98 (1H, t, J=7.8 Hz), 7.67 (1H, s), 7.72 (1H, s).

Reference Example 85 tert-Butyl 5-oxo-5-(4-oxo-1,2,5,6-tetrahydro-4H-pyrrolo[3,2,1-ij]quinolin-8-yl)pentyl[2-(2-thienyl)ethyl]carbamate

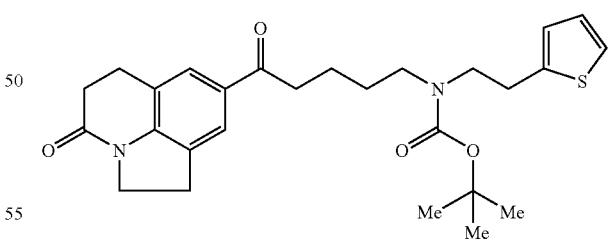

Using 8-(5-chloropentanoyl)-1,2,5,6-tetrahydro-4H-pyrrolo[3,2,1-ij]quinolin-4-one (1.00 g) obtained in Reference Example 1 and 2-(2-thienyl)ethylamine (435 mg) according to the same method as that of Reference. Example 19, the title compound (1.44 g) was obtained as a colorless oil.

$^1$H NMR (300 MHz, CDCl$_3$) δ 1.38 (9H, s), 1.40-1.85 (6H, m), 2.63 (2H, t, J=7.8 Hz), 2.80-3.55 (10H, m), 4.05 (2H, t, J=7.2 Hz), 6.70-6.80 (1H, m), 6.80-6.90 (1H, m), 7.00-7.10 (1H, m), 7.61 (1H, s), 7.65 (1H, s).

Reference Example 86 tert-Butyl 5-(2,3-dihydro-1,4-benzodioxin-6-yl)-5-oxopentyl[2-(2-methoxyphenyl)ethyl]carbamate

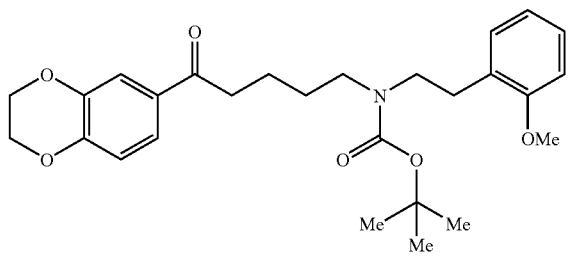

Using 5-chloro-1-(2,3-dihydro-1,4-benzodioxin-6-yl)-1-pentanone (1.00 g) obtained in Reference Example 75 and 2-(2-methoxyphenyl)ethylamine (594 mg) according to the same method as that of Reference Example 19, the title compound (1.84 g) was obtained as a colorless oil.
$^1$H NMR (300 MHz, CDCl$_3$) δ 1.43 (9H, s), 1.50-2.00 (4H, m), 2.75-3.60 (12H, m), 3.82 (3H, s), 6.80-7.25 (5H, m), 7.60-7.65 (1H, m), 7.79 (1H, dd, J=8.2, 1.5 Hz).

Reference Example 87 tert-Butyl 5-[3-(aminosulfonyl)-4-methoxyphenyl]-5-oxopentyl(2-phenylethyl)carbamate

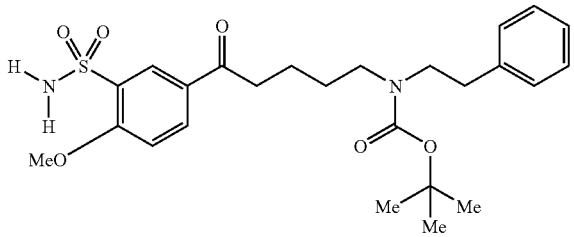

Using 5-(5-chloropentanoyl)-2-methoxybenzenesulfonamide (900 mg) obtained in Reference Example 66 and 2-phenylethylamine (713 mg) according to the same method as that of Reference Example 19, the title compound was obtained as colorless crystals (1.07 g) having a melting point of 121 to 122° C.
$^1$H NMR (300 MHz, CDCl$_3$) δ 1.30-1.75 (13H, m), 2.75-2.85 (2H, m), 2.90-3.00 (2H, m), 3.05-3.25 (2H, m), 3.36 (2H, t, J=7.8 Hz), 4.08 (3H, s), 5.37 (2H, s), 7.10 (1H, d, J=8.8 Hz), 7.10-7.30 (5H, m), 8.16 (1H, dd, J=8.8, 2.1 Hz), 8.44 (1H, d, J=2.1 Hz).

elementary analysis as C$_{25}$H$_{34}$N$_2$O$_6$S
calculation value:C, 61.20; H, 6.99; N, 5.71.
experimental value:C, 61.20; H, 7.02; N, 5.66.

Reference Example 88 tert-Butyl 5-[3-(aminosulfonyl)-4-methoxyphenyl]-5-oxopentyl[2-(2-methoxyphenyl)ethyl]carbamate

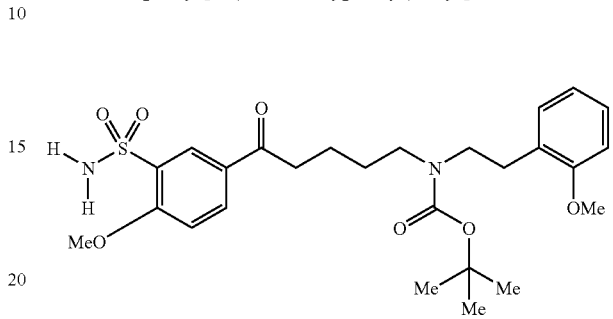

Using 5-(5-chloropentanoyl)-2-methoxybenzenesulfonamide (800 mg) obtained in Reference Example 66 and 2-(2-methoxyphenyl)ethylamine (792 mg) according to the same method as that of Reference Example 19, the title compound (740 mg) was obtained as a colorless oil.
$^1$H NMR (200 MHz, CDCl$_3$) δ 1.30-1.80 (13H, m), 2.80 (2H, t, J=7.6 Hz), 2.90-3.00 (2H, m), 3.05-3.25 (2H, m), 3.33 (2H, t, J=7.6 Hz), 3.81 (3H, s), 4.07 (3H, s), 5.66 (2H, s), 6.80-6.95 (2H, m), 7.00-7.25 (3H, m), 8.10-8.20 (1H, m), 8.40-8.45 (1H, m).

Reference Example 89 tert-Butyl 5-[3-(aminosulfonyl)-4-methoxyphenyl]-5-oxopentyl[2-(2-chlorophenyl)ethyl]carbamate

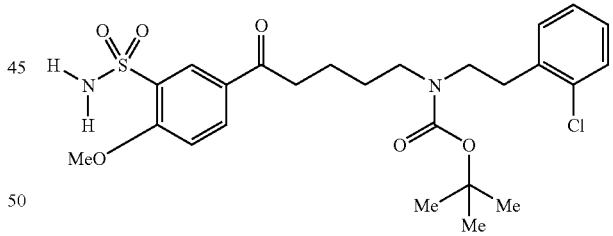

Using 5-(5-chloropentanoyl)-2-methoxybenzenesulfonamide (900 mg) obtained in Reference Example 66 and 2-(2-chlorophenyl)ethylamine (915 mg) according to the same method as that of Reference Example 19, the title compound was obtained as colorless crystals (1.07 g) having a melting point of 113 to 114° C.
$^1$H NMR (300 MHz, CDCl$_3$) δ 1.30-1.80 (13H, m), 2.90-3.00 (4H, m), 3.05-3.25 (2H, m), 3.38 (2H, t, J=7.6 Hz), 4.09 (3H, s), 5.43 (2H, s), 7.05-7.40 (5H, m), 8.16 (1H, dd, J=8.7, 2.1 Hz), 8.43 (1H, d, J=2.1 Hz).

elementary analysis as C$_{25}$H$_{33}$ClN$_2$O$_6$S
calculation value:C, 57.19; H, 6.33; N, 5.34.
experimental value:C, 57.07; H, 6.34; N, 5.22.

Reference Example 90 tert-Butyl 5-{3-[(isopropylamino)sulfonyl]-4-methoxyphenyl}-5-oxopentyl[2-(2-methoxyphenyl)ethyl]carbamate

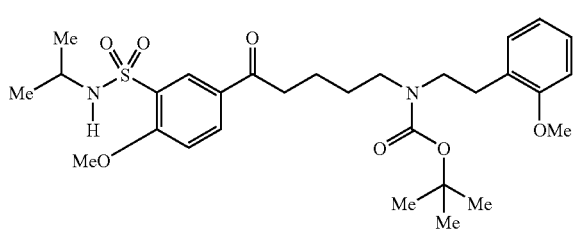

Using 5-(5-chloropentanoyl)-N-isopropyl-2-methoxybenzenesulfonamide (800 mg) obtained in Reference Example 67 and 2-(2-methoxyphenyl)ethylamine (696 mg) according to the same methods that of Reference Example 19, the title compound (1.36 g) was obtained as a colorless oil.

$^1$H NMR (200 MHz, CDCl$_3$) δ 1.07 (6H, d, J=6.6 Hz), 1.40-1.80 (13H, m), 2.80-3.50 (9H, m), 3.83 (3H, s), 4.07 (3H, s), 5.21 (1H, d, J=7.2 Hz), 6.80-6.95 (2H, m), 7.05-7.25 (3H, m), 8.20 (1H, dd, J=8.8, 2.2 Hz), 8.51 (1H, d, J=2.2 Hz).

Reference Example 91 tert-Butyl 2-(2-chlorophenyl)ethyl(5-{3-[(isopropylamino)sulfonyl]-4-methoxyphenyl}-5-oxopentyl)carbamate

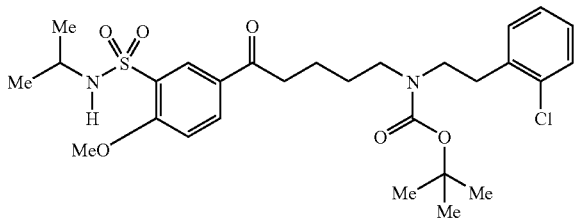

Using 5-(5-chloropentanoyl)-N-isopropyl-2-methoxybenzenesulfonamide (800 mg) obtained in Reference Example, 67 and 2-(2-chlorophenyl)ethylamine (716 mg) according to the same method as that of Reference Example 19, the title compound (1.28 g) was obtained as a colorless oil.

$^1$H NMR (200 MHz, CDCl$_3$) δ 1.07 (6H, d, J=6.6 Hz), 1.35-1.80 (13H, m), 2.85-3.50 (9H, m), 4.07 (3H, s), 4.87 (1H, d, J=6.8 Hz), 7.05-7.40 (5H, m), 8.20 (1H, dd, J=8.8, 2.2 Hz), 8.50 (1H, d, J=2.2 Hz).

Reference Example 92 tert-Butyl 5-[7-(aminosulfonyl)-2,3-dihydro-1-benzofuran-5-yl]-5-oxopentyl[2-(2-methoxyphenyl)ethyl]carbamate

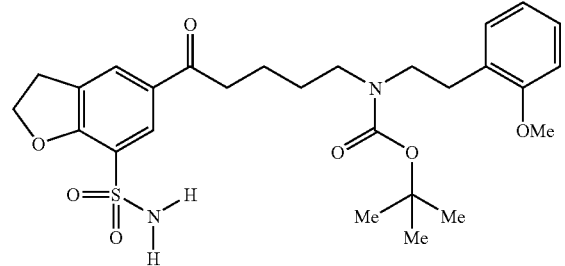

Using 5-(5-chloropentanoyl)-2,3-dihydro-1-benzofuran-7-sulfonamide (800 mg) obtained in Reference Example 70 and 2-(2-methoxyphenyl)ethylamine (762 mg) according to the same method as that of Reference Example 19, the title compound (990 mg) was obtained as a colorless oil.

$^1$H NMR (200 MHz, CDCl$_3$) δ 1.20-1.80 (13H, m), 2.75-3.00 (5H, m), 3.05-3.40 (5H, m), 3.82 (3H, s), 4.87 (2H, t, J=8.6 Hz), 5.50 (2H, s), 6.80-6.90 (2H, m), 7.00-7.25 (2H, m), 7.99 (1H, s), 8.17 (1H, s).

Reference Example 93 tert-Butyl 5-[7-(aminosulfonyl)-2,3-dihydro-1-benzofuran-5-yl]-5-oxopentyl[2-(2-chlorophenyl)ethyl]carbamate

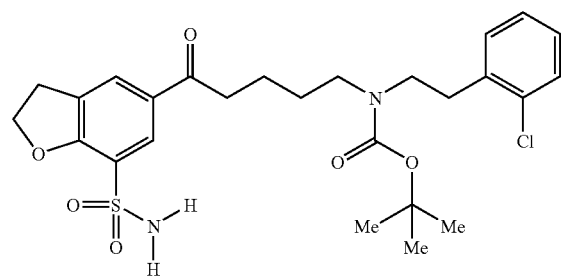

Using 5-(5-chloropentanoyl)-2,3-dihydro-1-benzofuran-7-sulfonamide (800 mg) obtained in Reference Example 70 and 2-(2-chlorophenyl)ethylamine (784 mg) according to the same method as that of Reference Example 19, the title compound was obtained as colorless crystals (1.04 g) having a melting point of 114 to 115° C.

$^1$H NMR (200 MHz, CDCl$_3$) δ 1.25-1.80 (13H, m), 2.80-3.45 (10H, m), 4.90 (2H, t, J=8.8 Hz), 5.29 (2H, s), 7.10-7.40 (4H, m), 8.02 (1H, s), 8.20 (1H, s).

elementary analysis as C$_{26}$H$_{33}$ClN$_2$O$_6$S
calculation value: C, 58.14; H, 6.19; N, 5.22.
experimental value: C, 57.93; H, 6.22; N, 5.12.

Reference Example 94 tert-Butyl 5-{7-[(isopropylamino)sulfonyl]-2,3-dihydro-1-benzofuran-5-yl}-5-oxopentyl[2-(2-methoxyphenyl)ethyl]carbamate

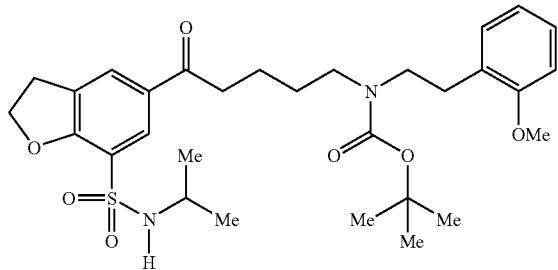

Using 5-(5-chloropentanoyl)-N-isopropyl-2,3-dihydro-1-benzofuran-7-sulfonamide (1.00 g) obtained in Reference Example 71 and 2-(2-methoxyphenyl)ethylamine (841 mg) according to the same method as that of Reference Example 19, the title compound (1.00 g) was obtained as a colorless oil.

$^1$H NMR (300 MHz, CDCl$_3$) δ 1.09 (6H, d, J=6.3 Hz), 1.35-1.75 (13H, m), 2.75-3.50 (11H, m), 3.82 (3H, s), 4.75-4.90 (3H, m), 6.80-6.90 (2H, m), 7.05-7.20 (2H, m), 8.03 (1H, s), 8.23 (1H, s).

Reference Example 95 tert-Butyl 2-(2-chlorophenyl)ethyl(5-{7-[(isopropylamino)sulfonyl]-2,3-dihydro-1-benzofuran-5-yl}-5-oxopentyl)carbamate

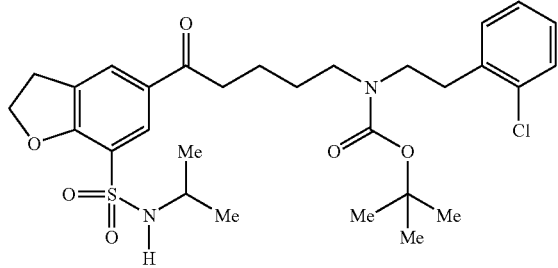

Using 5-(5-chloropentanoyl)-N-isopropyl-2,3-dihydro-1-benzofuran-7-sulfonamide (2.00 g) obtained in Reference Example 71 and 2-(2-chlorophenyl)ethylamine (1.73 g) according to the same method as that of Reference Example 19, the title compound (2.10 g) was obtained as a colorless oil.

$^1$H NMR (300 MHz, CDCl$_3$) δ 1.10 (6H, d, J=6.6 Hz), 1.30-2.00 (13H, m), 2.80-3.50 (11H, m), 4.75-4.90 (3H, m), 7.10-7.40 (4H, m), 8.04 (1H, s), 8.23 (1H, s).

Reference Example 96 tert-Butyl 5-[8-(aminosulfonyl)-2,2-dimethyl-3,4-dihydro-2H-chromen-6-yl]-5-oxopentyl[2-(2-chlorophenyl)ethyl]carbamate

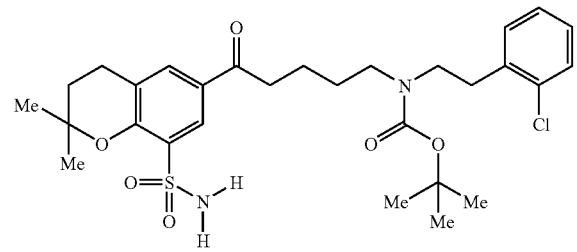

Using 6-(5-chloropentanoyl)-2,2-dimethyl-8-chromansulfonamide (600 mg) obtained in Reference Example 74 and 2-(2-chlorophenyl)ethylamine (548 mg) according to the same method as that of Reference Example 19, the title compound (715 mg) was obtained as a colorless oil.

$^1$H NMR (200 MHz, CDCl$_3$) δ 1.30-1.90 (13H, m), 1.47 (6H, s), 1.93 (2H, t, J=6.6 Hz), 2.80-3.30 (8H, m), 3.39, (2H, t, J=6.6 Hz), 5.26 (2H, s), 7.10-7.40 (4H, m), 7.92 (1H, s), 8.26 (1H, s).

Reference Example 97 tert-Butyl 5-[8-(aminosulfonyl)-2,3-dihydro-1,4-benzodioxin-6-yl]-5-oxopentyl(2-phenylethyl)carbamate

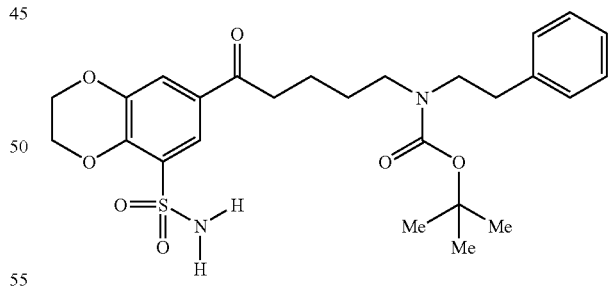

Using 7-(5-chloropentanoyl)-2,3-dihydro-1,4-benzodioxine-5-sulfonamide (800 mg) obtained in Reference Example 76 and phenethylamine (582 mg) according to the same method as that of Example 19, the title compound (1.05 g) was obtained as a colorless oil.

$^1$H NMR (300 MHz, CDCl$_3$) δ 1.35-1.80 (13H, m), 2.75-2.95 (4H, m), 3.05-3.25 (2H, m), 3.35 (2H, t, J=7.5 Hz), 4.30-4.40 (2H, m), 4.45-4.55 (2H, m), 5.40-5.50 (2H, m), 7.10-7.35 (5H, m), 7.64 (1H, s), 7.98 (1H, s).

Reference Example 98 tert-Butyl 5-[8-(aminosulfonyl)-2,3-dihydro-1,4-benzodioxin-6-yl]-5-oxopentyl[2-(2-methoxyphenyl)ethyl]carbamate

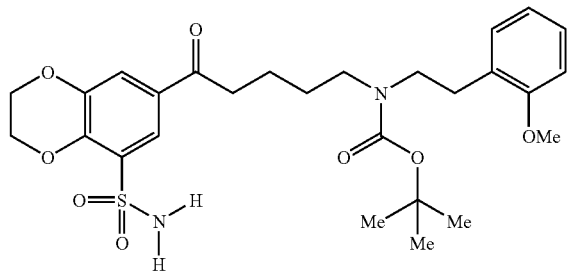

Using 7-(5-chloropentanoyl)-2,3-dihydro-1,4-benzodioxine-5-sulfonamide (800 mg) obtained in Reference Example 76 and 2-(2-methoxyphenyl)ethylamine (726 mg) according to the same method as that of Example 19, the title compound (820 mg) was obtained as a colorless oil.

$^1$H NMR (300 MHz, CDCl$_3$) δ 1.35-1.75 (13H, m), 2.80 (2H, t, J=7.2 Hz), 2.85-3.00 (2H, m), 3.05-3.25 (2H, m), 3.32 (2H, t, J=7.2 Hz), 3.82 (3H, s), 4.30-4.40 (2H, m), 4.45-4.55 (2H, m), 5.31 (2H, s), 6.80-7.20 (4H, m), 7.67 (1H, s), 8.01 (1H, s).

Reference Example 99 tert-Butyl 5-[8-(aminosulfonyl)-2,3-dihydro-1,4-benzodioxin-6-yl]-5-oxopentyl[2-(2-chlorophenyl)ethyl]carbamate

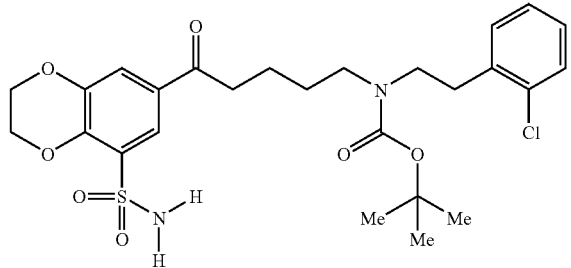

Using 7-(5-chloropentanoyl)-2,3-dihydro-1,4-benzodioxine-5-sulfonamide (800 mg) obtained in Reference Example 76 and 2-(2-chlorophenyl)ethylamine (746 mg) according to the same method as that of Example 19, the title compound (1.08 g) was obtained as a colorless oil.

$^1$H NMR (300 MHz, CDCl$_3$) δ 1.30-1.80 (13H, m), 2.80-3.00 (4H, m), 3.05-3.25 (2H, m), 3.39 (2H, t, J=7.2 Hz), 4.30-4.40 (2H, m), 4.45-4.55 (2H, m), 5.25-5.50 (2H, m), 7.05-7.40 (4H, m), 7.66 (1H, s), 7.99 (1H, s).

Reference Example 100 tert-Butyl 5-{4-methoxy-3-[(methylsulfonyl)amino]phenyl}-5-oxopentyl(2-phenylethyl)carbamate

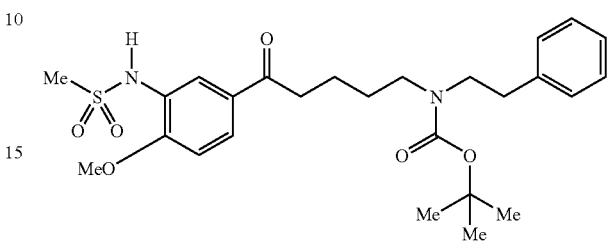

Using N-[5-(5-chloropentanoyl)-2-methoxyphenyl]methanesulfonamide (1.00 g) obtained in Reference Example 13 and phenethylamine (786 mg) according to the same method as that of Reference Example 19, the title compound (1.32 g) was obtained as a colorless oil.

$^1$H NMR (200 MHz, CDCl$_3$) δ 1.44(9H, s), 1.50-1.90(4H, m), 2.75-3.45(8H, m), 2.99(3H, s), 3.96(3H, s), 6.80-7.00 (2H, m), 7.10-7.35 (5H, m), 7.75-7.85(1H, m), 8.05-8.15(1H, m).

Reference Example 101 tert-Butyl 5-{4-methoxy-3-[(methylsulfonyl)amino]phenyl}-5-oxopentyl[2-(2-methoxyphenyl)ethyl]carbamate

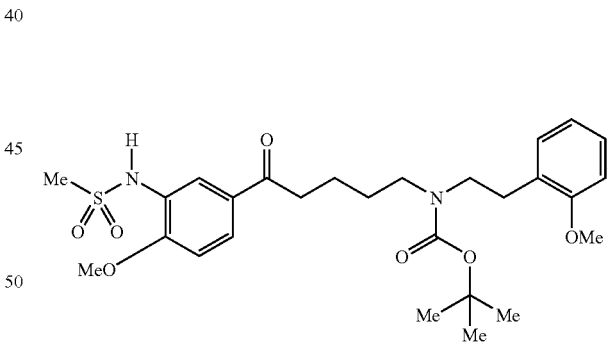

Using N-[5-(5-chloropentanoyl)-2-methoxyphenyl]methanesulfonamide (1.00 g) obtained in Reference Example 13 and 2-(2-methoxyphenyl)ethylamine (1.42 g) according to the same method as that of Reference Example 19, the title compound (550 mg) was obtained as a colorless oil.

$^1$H NMR (300 MHz, CDCl$_3$) δ 1.43 (9H, s), 1.50-1.80 (4H, m), 2.75-3.40 (4H, m), 2.99 (3H, s), 3.83 (3H, s), 3.05-3.45 (4H, m), 3.96 (3H, s), 6.80-6.90 (3H, m), 6.96 (1H, d, J=8.4 Hz), 7.05-7.25 (2H, m), 7.80 (1H, dd, J=8.4, 1.8 Hz), 8.10 (1H, d, J=1.8 Hz).

Reference Example 102 tert-Butyl 2-(2-chlorophenyl)ethyl(5-{4-methoxy-3-[(methylsulfonyl)amino]phenyl}-5-oxopentyl)carbamate

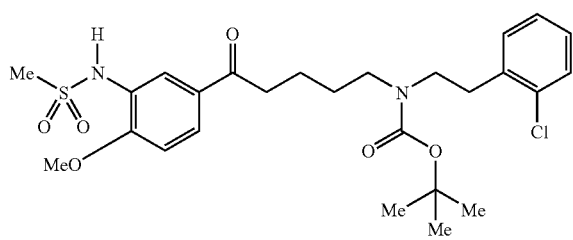

Using N-[5-(5-chloropentanoyl)-2-methoxyphenyl]methanesulfonamide (1.00 g) obtained in Reference Example 13 and 2-(2-chlorophenyl)ethylamine (1.46 g) according to the same method as that of Reference Example 19, the title compound (1.52 g) was obtained as a colorless oil.

$^1$H NMR (200 MHz, CDCl$_3$) δ 1.41(9H, s), 1.45-1.80 (4H, m), 2.75-3.50 (6H, m), 3.00 (3H, s), 3.41 (2H, t, J=7.4 Hz), 3.96 (3H, s), 6.90-7.00 (2H, m), 7.10-7.40 (4H, m), 7.75-7.85 (1H, m), 8.05-8.10 (1H, m).

Reference Example 103 tert-Butyl 6-{4-methoxy-3-[(methylsulfonyl)amino]phenyl}-6-oxohexyl(2-phenylethyl)carbamate

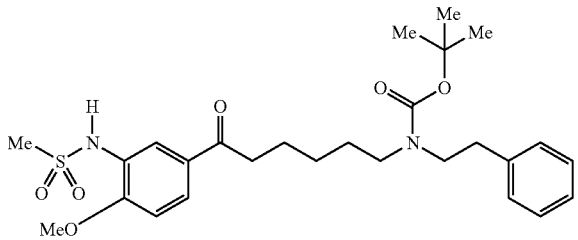

Using N-[5-(6-bromopentanoyl)-2-methoxyphenyl]methanesulfonamide (1.00 g) obtained in Reference Example 14 and phenethylamine (641 mg) according to the same method as that of Reference Example 19, the title compound (918 mg) was obtained as a colorless oil.

$^1$H NMR (300 MHz, CDCl$_3$) δ 1.30-1.90(6H, m), 1.44(9H, s), 2.75-2.85 (2H, m), 2.91(2H, t, J=7.5 Hz), 2.99(3H, s), 3.00-3.20(2H, m), 3.30-3.45(2H, m), 3.96(3H, s), 6.90(1H, s), 6.97(1H, d, J=8.4 Hz), 7.15-7.30(5H, m), 7.81(1H, dd, J=8.4, 1.8 Hz), 8.12(1H, d, J=1.8 Hz).

Reference Example 104 tert-Butyl 6-{4-methoxy-3-[(methylsulfonyl)amino]phenyl}-6-oxohexyl[2-(2-methoxyphenyl)ethyl]carbamate

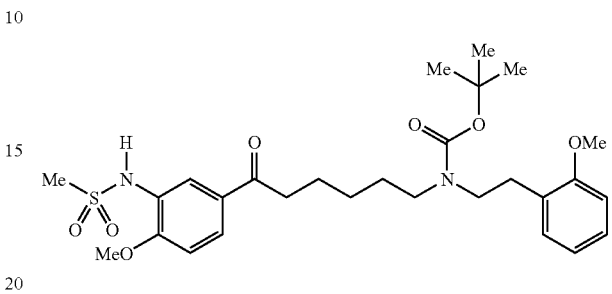

Using N-[5-(6-bromopentanoyl)-2-methoxyphenyl]methanesulfonamide (1.00 g) obtained in Reference Example 14 and 2-(2-methoxyphenyl)ethylamine (800 mg) according to the same method as that of Reference Example 19, the title compound (1.00 g) was obtained as a colorless oil.

$^1$H NMR (300 MHz, CDCl$_3$) δ 1.25-1.60(4H, m), 1.43(9H, s), 1.73(2H, quintet, J=7.5 Hz), 2.75-2.90(2H, m), 2.91(2H, t, J=7.5 Hz), 2.99(3H, s), 3.00-3.20(2H, m), 3.30-3.45(2H, m), 3.82(3H, s), 3.96(3H, s), 6.80-7.20(6H, m), 7.80(1H, dd, J=8.4, 1.8 Hz), 8.10(1H, d, J=1.8 Hz).

Reference Example 105 tert-Butyl 2-(2-chlorophenyl)ethyl(6-{4-methoxy-3-[(methylsulfonyl)amino]phenyl}-6-oxohexyl)carbamate

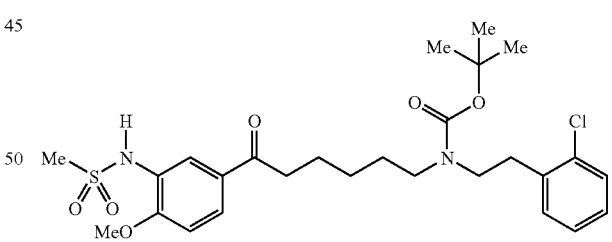

Using N-[5-(6-bromopentanoyl)-2-methoxyphenyl]methanesulfonamide (1.00 g) obtained in Reference Example 14 and 2-(2-chlorophenyl)ethylamine (823 mg) according to the same method as that of Reference Example 19, the title compound (1.03 g) was obtained as a colorless oil.

$^1$H NMR (300 MHz, CDCl$_3$) δ 1.25-1.90(6H, m), 1.41(9H, s), 2.90-3.25(6H, m), 2.99(3H, s), 3.40(2H, t, J=7.5 Hz), 3.97(3H, s), 6.89(1H, s), 6.97(1H, d, J=8.4 Hz), 7.10-7.40 (4H, m), 7.80(1H, dd, J=8.4, 1.8 Hz), 8.10(1H, d, J=1.8 Hz).

Reference Example 106 tert-Butyl 5-(1H-indol-3-yl)-5-oxopentyl(2-phenyl-ethyl)carbamate

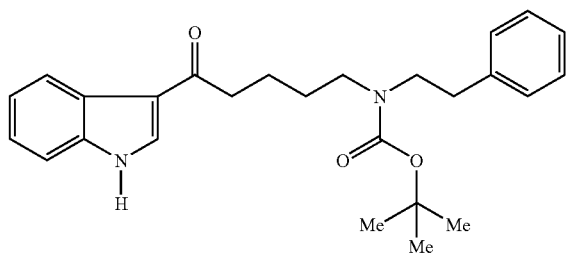

Using 5-chloro-1-(1H-indol-3-yl)-1-pentanone (1.00 g) obtained in Reference Example 15 and 2-phenylethylamine (1.03 g) according to the same method as that of Reference Example 19, the title compound was obtained as colorless crystals (1.10 g) having a melting point of 100 to 108° C.

$^1$H NMR (300 MHz, CDCl$_3$) δ 1.44(9H, s), 1.50-2.10(4H, m), 2.70-2.90(4H, m), 3.05-3.25(2H, m), 3.30-4.45(2H, m), 7.10-7.45(8H, m), 7.70-7.90(1H, m), 8.35-8.45(1H, m), 9.05-9.35(1H, br).

Reference Example 107 tert-Butyl 5-(1H-indol-3-yl)-5-oxopentyl[2-(2-methoxyphenyl)ethyl]carbamate

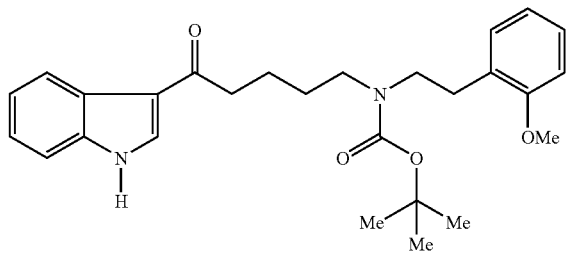

Using 5-chloro-1-(1H-indol-3-yl)-1-pentanone (1.00 g) obtained in Reference Example 15 and 2-(2-methoxyphenyl)ethylamine (1.28 g) according to the same method as that of Reference Example 19, the title compound (901 mg) was obtained as a colorless oil.

$^1$H NMR (300 MHz, CDCl$_3$) δ 1.44(9H, s), 1.50-1.80(4H, m), 2.70-2.90(4H, m), 3.10-3.45(4H, m), 3.65-3.85(3H, m), 6.75-6.90(2H, m), 7.00-7.45(5H, m), 7.60-7.90(1H, m), 8.35-8.40(1H, m), 9.70-10.00(1H, br).

Reference Example 108 tert-Butyl 2-(2-chlorophenyl)ethyl[5-(1H-indol-3-yl)-5-oxopentyl]carbamate

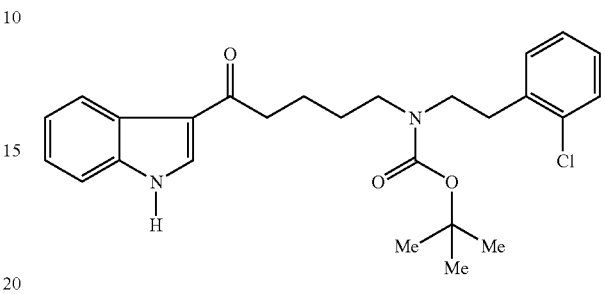

Using 5-chloro-1-(1H-indol-3-yl)-1-pentanone (1.00 g) obtained in Reference Example 15 and 2-(2-chlorophenyl)ethylamine (1.32 g) according to the same method as that of Reference Example 19, the title compound was obtained as colorless crystals (1.10 g) having a melting point of 97 to 99° C.

$^1$H NMR (300 MHz, CDCl$_3$) δ 1.42(9H, s), 1.50-1.80(4H, m), 2.70-3.50(6H, m), 3.41(2H, t, J=7.5 Hz), 7.05-7.45(7H, m), 7.65-7.90(1H, m), 8.35-8.45(1H, m), 9.20-9.40(1H, br).

Reference Example 109 tert-Butyl 6-(1H-indol-3-yl)-6-oxohexyl(2-phenyl-ethyl)carbamate

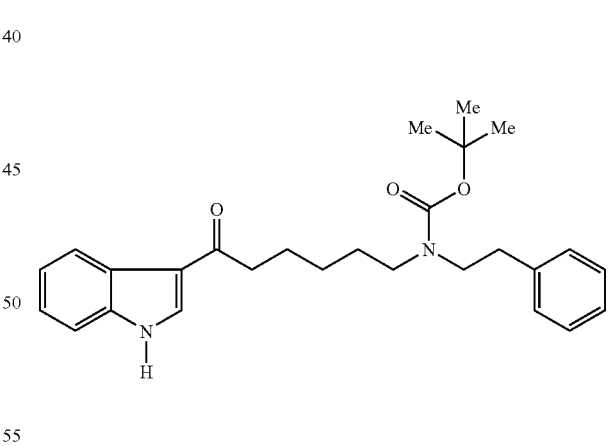

Using 6-bromo-1-(1H-indol-3-yl)-1-hexanone (1.00 g) obtained in Reference Example 16 and 2-phenylethylamine (824 mg) according to the same method as that of Reference Example 19, the title compound was obtained as colorless crystals (938 mg) having a melting point of 83 to 85° C.

$^1$H NMR (200 MHz, CDCl$_3$) δ 1.20-1.85(6H, m), 1.44(9H, s), 2.70-2.90(4H, m), 3.05-3.25(2H, m), 3.37(2H, t, J=7.5 Hz), 7.10-7.45(8H, m), 7.75-7.85(1H, m), 8.35-8.45(1H, m), 8.90-9.30(1H, br).

Reference Example 110 tert-Butyl 6-(1H-indol-3-yl)-6-oxohexyl[2-(2-methoxyphenyl)ethyl]carbamate


Using 6-bromo-1-(1H-indol-3-yl)-1-hexanone (1.00 g) obtained in Reference, Example 16 and 2-(2-methoxyphenyl)ethylamine (1.03 g) according to the same method as that of Reference Example 19, the title compound was obtained as colorless crystals (788 mg) having a melting point of 133 to 135° C.

$^1$H NMR (200 MHz, CDCl$_3$) δ 1.20-1.85(6H, m), 1.43(9H, s), 2.70-2.90(4H, m), 3.05-3.25(2H, m), 3.34(2H, t, J=7.2 Hz), 3.79(3H, s), 6.75-6.90(2H, m), 7.00-7.45(5H, m), 7.75-7.85(1H, m), 8.35-8.45(1H, m), 9.15-9.40(1H, br).

Reference Example 111 tert-Butyl 2-(2-chlorophenyl)ethyl[6-(1H-indol-3-yl)-6-oxohexyl]carbamate

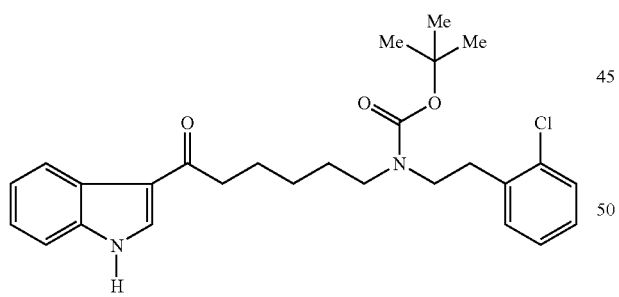

Using 6-bromo-1-(1H-indol-3-yl)-1-hexanone (1.00 g) obtained in Reference Example 16 and 2-(2-chlorophenyl)ethylamine (1.03 g) according to the same method as that of Reference Example 19, the title compound was obtained as colorless crystals (788 mg) having a melting point of 104 to 105° C.

$^1$H NMR (200 MHz, CDCl$_3$) δ 1.20-1.85(6H, m), 1.42(9H, s), 2.70-3.25(6H, m), 3.40(2H, t, J=7.2 Hz), 7.05-7.45(7H, m), 7.70-7.90(1H, m), 8.35-8.45(1H, m), 9.25-9.80(1H, br).

Reference Example 112 tert-Butyl 5-oxo-5-(2-thienyl)pentyl(2-phenylethyl)carbamate

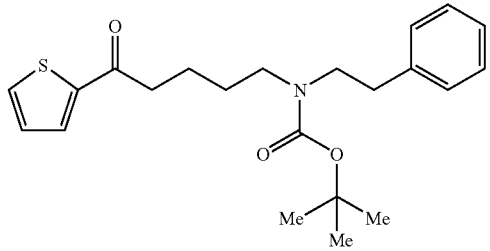

Using 5-chloro-1-(2-thienyl)-1-pentanone (1.00 g) obtained in Reference Example 17 and 2-phenylethylamine (1.19 g) according to the same method as that of Reference. Example 19, the title compound was obtained as colorless crystals (1.08 g) having a melting point of 49 to 50° C.

$^1$H NMR (300 MHz, CDCl$_3$) δ 1.44(9H, s), 1.45-1.80(4H, m), 2.75-2.95(4H, m), 3.05-3.45(4H, m), 7.10-7.35(6H, m), 7.12(1H, dd, J=5.0, 0.9 Hz), 7.71(1H, s).

Reference, Example 113 tert-Butyl 2-(2-methoxyphenyl)ethyl[5-oxo-5-(2-thienyl)pentyl]carbamate

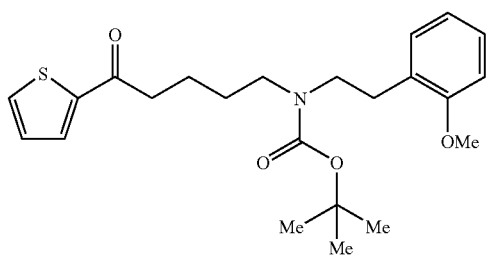

Using 5-chloro-1-(2-thienyl)-1-pentanone (1.00 g) obtained in Reference Example 17 and 2-(2-methoxyphenyl)ethylamine (1.49 g) according to the same method as that of Reference Example 19, the title compound (1.45 g) was obtained as a colorless oil.

$^1$H NMR (300 MHz, CDCl$_3$) δ 1.43(9H, s), 1.43-1.85(4H, m), 2.75-2.95(4H, m), 3.05-3.45(4H, m), 3.82(3H, s), 6.80-6.90(2H, m), 7.05-7.25(3H, m), 7.60-7.75(2H, m).

Reference Example 114 tert-Butyl 2-(2-chlorophenyl)ethyl[5-oxo-5-(2-thienyl)pentyl]carbamate

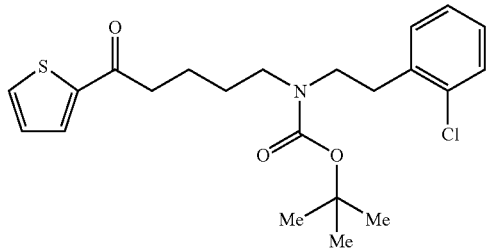

Using 5-chloro-1-(2-thienyl)-1-pentanone (1.00 g) obtained in Reference Example 17 and 2-(2-chlorophenyl)ethylamine (1.53 g) according to the same method as that of Reference Example 19, the title compound (1.47 g) was obtained as a pale yellow oil.

¹H NMR (300 MHz, CDCl₃) δ 1.41(9H, s), 1.45-1.80(4H, m), 2.85-3.30(4H, m), 3.05-3.30 (2H, m), 3.41(2H, t, J=7.2 Hz), 7.05-7.40(5H, m), 7.62(1H, dd, J 5.0, 0.9 Hz), 7.71(1H, s).

Reference Example 115 tert-Butyl 6-oxo-6-(2-thienyl)hexyl(2-phenylethyl)carbamate

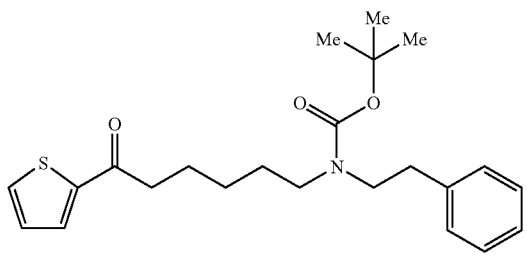

Using 6-bromo-1-(2-thienyl)-1-hexanone (1.00 g) obtained in Reference Example 18 and 2-phenylethylamine (1.53 g) according to the same method as that of Reference Example 19, the title compound (1.47 g) was obtained as a pale yellow oil.

¹H NMR (300 MHz, CDCl₃) δ 1.25-1.60(4H, m), 1.44(9H, s), 1.75(2H, quintet, J=7.5 Hz), 2.75-2.90(2H, m), 2.89(2H, t, J=7.5 Hz), 3.05-3.25(2H, m), 3.50-3.65(2H, m), 7.12(1H, dd, J=5.0, 3.6 Hz), 7.15-7.35(5H, m), 7.61(1H, dd, J=5.0, 0.9 Hz), 7.70(1H, dd, J=3.6, 0.9 Hz).

Reference Example 116 tert-Butyl 2-(2-methoxyphenyl)ethyl[6-oxo-6-(2-thienyl)hexyl]carbamate

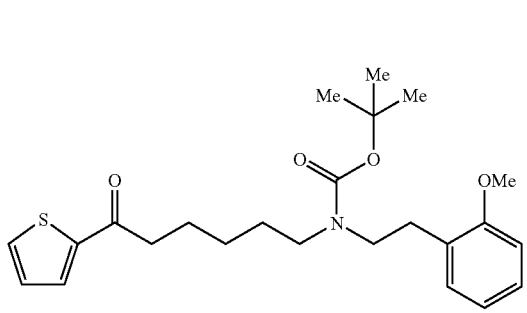

Using 6-bromo-1-(2-thienyl)-1-hexanone (1.00 g) obtained in Reference Example 18 and 2-(2-methoxyphenyl)ethylamine (1.16 g) according to the same method as that of Reference Example 19, the title compound (884 mg) was obtained as a colorless oil.

¹H NMR (300 MHz, CDCl₃) δ 1.20-1.65(4H, m), 1.43(9H, s), 1.70-1.85(2H, m), 2.75-2.90(2H, m), 2.89(2H, t, J=7.2 Hz), 3.05-3.25(2H, m), 3.25-3.40(2H, m), 3.82(3H, s), 6.83 (1H, d, J=7.5 Hz), 6.88(1H, dd, J=7.2, 0.9 Hz), 7.05-7.25(2H, m), 7.12(1H, dd, J=4.8, 3.9 Hz), 7.62(1H, dd, J=4.8, 1.2 Hz), 7.70(1H, dd, J=3.9, 1.2 Hz).

Reference Example 117 tert-Butyl 2-(2-chlorophenyl)ethyl[6-oxo-6-(2-thienyl)hexyl]carbamate

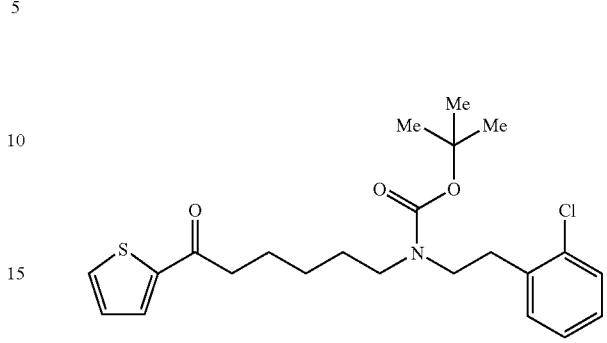

Using 6-bromo-1-(2-thienyl)-1-hexanone (1.00 g) obtained in Reference Example 18 and 2-(2-methoxyphenyl)ethylamine (1.19 g) according to the same method as that of Reference Example 19, the title compound (1.07 g) was obtained as a colorless oil.

¹H NMR (300 MHz, CDCl₃) δ 1.25-1.65(4H, m), 1.43(9H, s), 1.65-1.85(2H, m), 2.80-3.25(4H, m), 2.89(2H, t, J=7.5 Hz), 3.40(2H, t, J=7.5 Hz), 7.05-7.40(5H, m), 7.60-7.75(2H, m).

Reference Example 118 tert-Butyl (±)-5-oxo-5-(4-oxo-1,2,5,6-tetrahydro-4H-pyrrolo[3,2,1-ij]quinolin-8-yl)pentyl(1,2,3,4-tetrahydro-1-naphthalenyl)carbamate

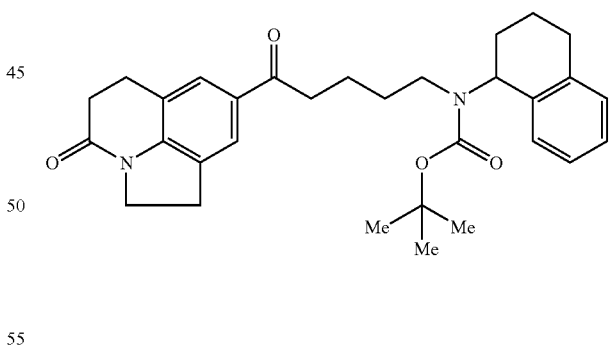

Using 8-(5-chloropentanoyl)-1,2,5,6-tetrahydro-4H-pyrrolo[3,2,1-ij]quinolin-4-one (500 mg) obtained in Reference Example 1 and (±)-1,2,3,4-tetrahydro-1-naphthalenylamine (755 mg) according to the same method as that of Reference Example 19, the title compound (528 mg) was obtained as a pale yellow oil.

¹H NMR (200 MHz, CDCl₃) δ 1.10-2.10 (19H, m), 2.60-3.05(9H, m), 3.21(2H, t, J=8.4 Hz), 4.13(2H, t, J 8.8 Hz), 7.00-7.20(4H, m), 7.60-7.70(2H, m).

Reference. Example 119 tert-Butyl (±)-1,2-diphenylethyl[5-oxo-5-(4-oxo-1,2,5,6-tetrahydro-4H-pyrrolo[3,2,1-ij]quinolin-8-yl)pentyl]carbamate

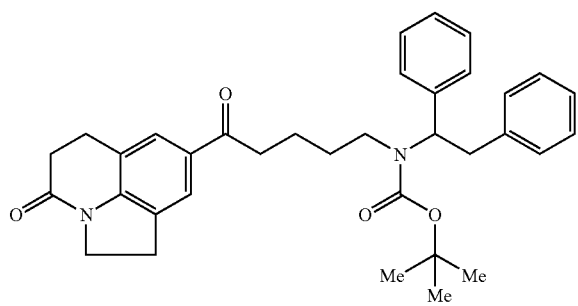

Using 8-(5-chloropentanoyl)-1,2,5,6-tetrahydro-4H-pyrrolo[3,2,1-ij]quinolin-4-one (1.00 g) obtained in Reference Example 1 and (±)-1,2-diphenylethylamine (2.02 g) according to the same method as that of Reference Example 19, the title compound (837 mg) was obtained as a pale yellow oil.

$^1$H NMR (200 MHz, CDCl$_3$) δ 1.10-1.60(6H, m), 1.31(9H, s), 1.70-2.00(2H, m), 2.71(2H, t, J=7.6 Hz), 2.80-3.10(3H, m), 3.15-3.35(3H, m), 3.55-3.65(1H, m), 4.13(2H, t, J=8.8 Hz), 7.10-7.40(10H, m), 7.60-7.75(2H, m).

Reference Example 120

5-Chloro-1-[3-(trifluoroacetyl)-2,3,4,5-tetrahydro-1H-3-benzazepin-7-yl]-1-pentanone

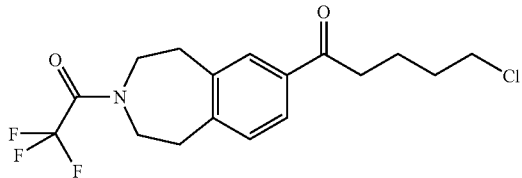

Aluminum chloride (17 g, 130 mmol) was added by portions to a solution of 3-(trifluoroacetyl)-2,3,4,5-tetrahydro-1H-3-benzazepine (15.0 g) and 5-chlorovaleryl chloride (8.8 ml) in 1,2-dichloroethane (40 ml) under ice-cooling. After stirring at room temperature for 30 minutes, the reaction mixture was poured into ice (500 g), extracted with ethyl acetate, and washed with brine. The organic layer was dried over anhydrous magnesium sulfate, the solvent was evaporated under reduced pressure, and the residue was crystallized from ethanol-diethyl ether to give a pale yellow solid (15.2 g). Further recrystallization from ethanol-diethylether afforded colorless crystals (13.2 g) as the title compound.

$^1$H NMR (200 MHz, CDCl$_3$) δ 1.87-1.91 (4H, m), 2.97-3.08 (6H, m), 3.59 (2H, t, J=6.2 Hz), 3.70-3.81 (4H, m), 7.26 (1H, s), 7.75 (2H, m).

Reference Example 121

5-Chloro-1-(2,3,4,5-tetrahydro-1H-3-benzazepin-7-yl)-1-pentanone

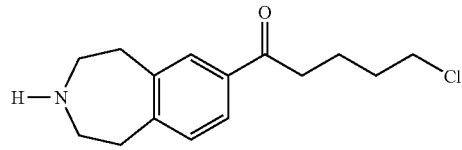

Potassium carbonate (9.2 g, 66.3 mmol) was added to a solution of 5-chrolo-1-[3-(trifluoroacetyl)-2,3,4,5-tetrahydro-1H-3-benzazepin-7-yl]-1-pentanone (8.0 g) obtained in Reference Example 120 in methanol (40 ml)-water. (40 ml). After stirring at room temperature for 60 minutes, the solvent was evaporated under reduced pressure, water (100 g) was added, extracted with ethyl acetate, and washed with brine. The organic layer was dried over anhydrous sodium sulfate, and the solvent was evaporated under reduced pressure to give an oil (6.9 g).

$^1$H NMR (200 MHz, CDCl$_3$) δ 1.88 (4H, m), 2.35 (1H, br), 2.97 (10H, m), 3.58 (2H, m), 7.16-7.20 (1H, m), 7.69 (2H, m).

Reference Example 122

1-(3-Acetyl-2,3,4,5-tetrahydro-1H-3-benzazepin-7-yl)-5-chloro-1-pentanone

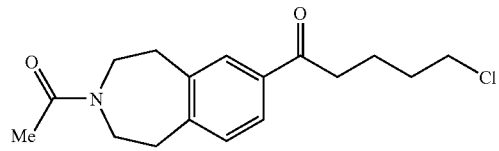

Acetyl chloride (679 µl) was added to a solution of 5-chloro-1-(2,3,4,5-tetrahydro-1H-3-benzazepin-7-yl)-1-pentanone (2.2 g) obtained in Reference Example 121 and triethylamine (1.67 ml) in tetrahydrofuran (30 ml). After stirring at room temperature for 60 minutes, water (50 g) was added, extracted with ethyl acetate, and washed with brine. The organic layer was dried over anhydrous sodium sulfate, the solvent was evaporated under reduced pressure, and the residue was purified by silica gel column chromatography to give an oil (2.54 g).

$^1$H NMR (200 MHz, CDCl$_3$) δ 1.89 (4H, m), 2.19 (3H, s), 2.99 (6H, m), 3.59 (4H, m), 3.74 (2H, m), 7.21-7.27 (1H, m), 7.74 (2H, m).

Reference Example 123

5-Chloro-1-[3-(methylsulfonyl)-2,3,4,5-tetrahydro-1H-3-benzazepin-7-yl]-1-pentanone

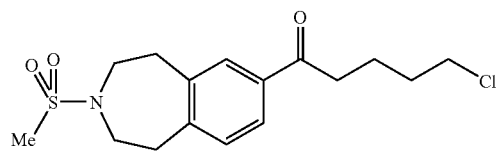

Methylsulfonyl chloride (804 μl) was added to a solution of 5-chloro-1-(2,3,4,5-tetrahydro-1H-3-benzazepin-7-yl)-1-pentanone (2.4 g) obtained in Reference Example 121 and triethylamine (1.67 ml) in tetrahydrofuran (30 ml). After stirring at room temperature for 60 minutes, water (50 g) was added, extracted with ethyl acetate, and washed with brine. The organic layer was dried over anhydrous sodium sulfate, the solvent was evaporated under reduced pressure to give a pale yellow solid (2.2 g). Further recrystallization from ethanol-diethyl ether afforded the title compound as colorless crystals (1.92 g).

$^1$H NMR (200 MHz, CDCl$_3$) δ 1.89 (4H, m), 2.80 (3H, s), 2.99 (2H, m), 3.08 (4H, m), 3.46 (4H, m), 3.59 (2H, m), 7.23-7.25 (1H, m), 7.74 (2H, m).

Reference Example 124

7-(5-Chloropentanoyl)-N-ethyl-1,2,4,5-tetrahydro-3H-3-benzazepine-3-carboxamide

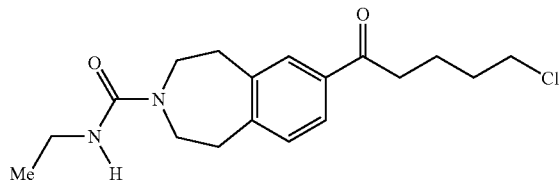

Ethyl isocyanate (781 μl) was added to a solution of 5-chloro-1-(2,3,4,5-tetrahydro-1H-3-benzazepin-7-yl)-1-pentanone (2.3 g) obtained in Reference Example 121 in tetrahydrofuran (30 ml). After stirring at room temperature for 60 minutes, water (50 g) was added, extracted with ethyl acetate, and washed with brine. The organic layer was dried over anhydrous sodium sulfate, and the solvent was evaporated under reduced pressure to give a colorless solid (2.2 g).

$^1$H NMR (200 MHz, CDCl$_3$) δ 1.17 (3H, t, J=7.0 Hz), 1.89 (4H, m), 2.99 (6H, m), 3.32 (2H, q, J=7.0 Hz), 3.56 (6H, m), 4.47 (1H, m), 7.19-7.23 (1H, m), 7.71 (2H, m).

Reference Example 125

1-(2-Acetyl-1,2,3,4-tetrahydro-7-isoquinolinyl)-5-chloro-1-pentanone

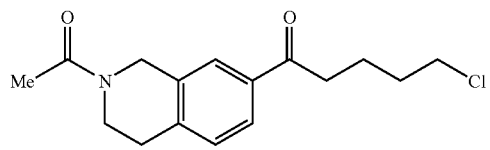

Aluminum chloride (24 g, 181 mmol) was added by portions to a solution of 2-acetyl-1,2,3,4-tetrahydroisoquinoline (15.0 g) obtained in Reference Example 121 and 5-chlorovaleryl chloride (12.0 ml) in 1,2-dichloroethane (50 ml) under ice-cooling. After stirring at room temperature for 30 minutes, the reaction mixture was poured into ice (500 g), extracted with ethyl acetate, and washed with brine. The organic layer was dried over anhydrous magnesium sulfate, and the solvent was evaporated under reduced pressure to give a pale yellow solid (14.2 g). Further recrystallization from ethanol-diethyl ether afforded the title compound as colorless crystals (12.5 g).

$^1$H NMR (200 MHz, DMSO-d$_6$) δ 1.76 (4H, m), 2.09 (3H, s), 2.86 (2H, t, J=5.8 Hz), 3.04 (2H, t, J=6.0 Hz), 3.67 (4H, m), 4.66 (2H, s), 7.30 (1H, s), 7.74 (2H, m).

Reference Example 126

1,3-Dihydro-2,1,3-benzothiadiazole 2,2-dioxide

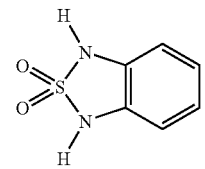

A solution of orthophenylenediamine (20 g) and sulfamide (20.4 g) in diglyme (200 ml) was stirred at 160° C. for 2 hours, the reaction mixture was cooled to room temperature, water (200 g) was poured thereto, hydrochloric acid was added until pH 1, extracted with ethyl acetate, and washed with 1N hydrochloric acid. The organic layer was dried over anhydrous magnesium sulfate, and the solvent was evaporated under reduced pressure to give a reddish brown solid (14.2 g). Further recrystallization from ethanol-diethyl ether afforded the title compound as colorless crystals (13.2 g).

$^1$H NMR (300 MHz, DMSO-d$_6$) δ 6.77-6.91 (4H, m), 10.95 (2H, s).

Reference Example 127

1,3-Dimethyl-1,3-dihydro-2,1,3-benzothiadiazole 2,2-dioxide

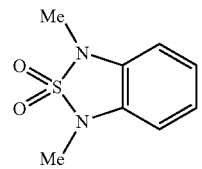

Sodium hydride (5 g) was added to a solution of 1,3-dihydro-2,1,3-benzothiadiazole 2,2-dioxide (10 g) obtained in Reference Example 126 in dimethylformamide (100 ml), the mixture was stirred at room temperature for 1 hour, methyl iodide was added, and the mixture was stirred at room temperature for 18 hours. Water (200 g) was poured into the reaction mixture, extracted with ethyl acetate, and washed with brine. The organic layer was dried over anhydrous magnesium sulfate, and the solvent was evaporated under reduced pressure to give a reddish brown solid (9.9 g). Further recrystallization from water-ethyl acetate afforded the title compound as colorless crystals (9.0 g).

$^1$H NMR (200 MHz, CDCl$_3$) δ 3.28 (6H, s), 6.74 (2H, q, J=3.2 Hz), 7.00 (2H, q, J=3.4 Hz).

Reference Example 128

5-Chloro-1-(2,2-dioxide-1,3-dihydro-2,1,3-benzothiadiazol-5-yl)-1-pentanone

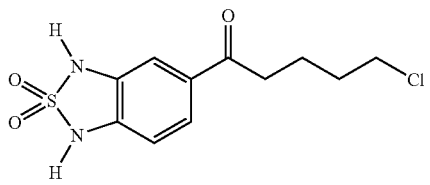

Using 1,3-dihydro-2,1,3-benzothiadiazole 2,2-dioxide obtained in Reference Example 126 and 5-chlorovaleryl chloride according to the same method as that of Reference Example 1, the title compound was obtained as colorless crystals.
$^1$H NMR (200 MHz, CDCl$_3$) δ 1.75 (4H, m), 3.03 (2H, t, J=6.6 Hz), 3.68 (2H, t, J=6.2 Hz), 6.89 (1H, d, J=8.4 Hz), 7.33 (1H, s), 7.62 (1H, d, J=8.4 Hz), 11.54 (2H, br).

Reference Example 129

5-Chloro-1-(1,3-dimethyl-2,2-dioxide-1,3-dihydro-2,1,3-benzothiadiazol-5-yl)-1-pentanone,

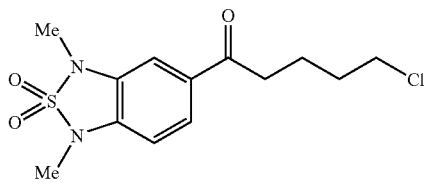

Using 1,3-dimethyl-1,3-dihydro-2,1,3-benzothiadiazole 2,2-dioxide obtained in Reference Example 127 and 5-chlorovaleryl chloride according to the same method as that of Reference Example 1, the title compound was obtained as colorless crystals.
$^1$H NMR (200 MHz, CDCl$_3$) δ 1.89 (4H, m), 2.99 (2H, t, J=7.0 Hz), 3.35 (6H, s), 3.60 (2H, t, J=6.2 Hz), 6.75 (1H, d, J=8.4 Hz), 7.39 (1H, s), 7.69 (1H, d, J=8.4 Hz).

Reference Example 130

1,2,3,4-Tetrahydro-8-quinolineamine

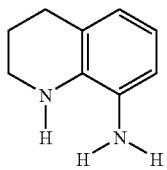

A mixed solution of 8-nitroquinoline (25.0 g), platinum oxide (600 mg) and glacial acetic acid (300 ml) was stirred at room temperature for 4 hours under the atmosphere of hydrogen at 5 atm. The reaction mixture was filtered through Celite, and the solvent was evaporated under reduced pressure. Then, the solution was extracted with ethyl acetate, and washed with brine. The organic layer was dried over anhydrous magnesium sulfate, the solvent was evaporated under reduced pressure, and purified by silica gel column chromatography to give the title compound as a reddish brown oil (15.2 g).
$^1$H NMR (200 MHz, CDCl$_3$) δ 1.96 (2H, quint, J=2.6 Hz), 2.76 (2H, t, J=6.2 Hz), 3.56 (3H, br), 3.32 (2H, t, J=5.6 Hz), 6.53 (3H, m).

Reference Example 131

5,6-Dihydro-4H-imidazo[4,5,1-ij]quinolin-2(1H)-one

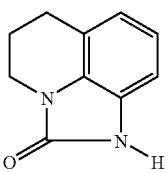

A suspension of 1,1'-carbonyldiimidazole in tetrahydrofuran was added to a solution of 1,2,3,4-tetrahydro-8-quinolineamine (10 g) obtained in Reference Example 130 in tetrahydrofuran (100 ml), and the mixture was stirred at room temperature at 4 hours. The reaction mixture was concentrated to give a brown solid (11 g). Further recrystallization from water-ethyl estate afforded the title compound as colorless crystals (10 g).
$^1$H NMR (200 MHz, CDCl$_3$) δ 2.00 (2H, t, J=5.4 Hz), 2.76 (2H, t, J=5.8 Hz), 3.69 (2H, t, J=5.6 Hz), 6.80 (3H, m), 10.61 (1H, s).

Reference Example 132

1-Methyl-5,6-dihydro-4H-imidazo[4,5,1-ij]quinolin-2(1H)-one

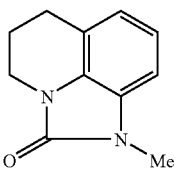

Sodium hydride (2.36 g) was added to a solution of 5,6-dihydro-4H-imidazo[4,5,1-ij]quinolin-2(1H)-one (10 g) obtained in Reference Example 131 in dimethylformamide (100 ml), the mixture was stirred at room temperature for 1 hour, methyl iodide (3.68 ml) was added, and the mixture was stirred at room temperature for 18 hours Water (200 g) was poured into the reaction mixture, extracted with ethyl acetate, and washed with brine. The organic layer was dried over anhydrous magnesium sulfate, and the solvent was evaporated under reduced pressure to give a pale yellow solid (9.7 g). Further recrystallization from water-ethyl acetate afforded the title compound as colorless crystals (9.0 g).
$^1$H NMR (200 MHz, CDCl$_3$) δ 2.12 (2H, quint, J=6.4 Hz), 2.86 (2H, t, J=6.2 Hz), 3.41 (3H, s), 3.87 (2H, t, J=5.8 Hz), 6.79-7.04 (3H, m).

Reference Example 133

8-(5-Chloropentanoyl)-5,6-dihydro-4H-imidazo[4,5,1-ij]quinolin-2(1H)-one

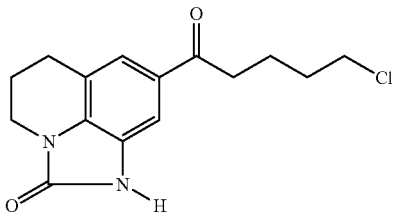

Using 5,6-dihydro-4H-imidazo[4,5,1-ij]quinolin-2(1H)-one obtained in Reference Example 131 and 5-chlorovaleryl chloride according to the same method as that of Reference Example 1, the title compound was obtained as colorless crystals.

$^1$H NMR (200 MHz, DMSO-d$_6$) δ 1.75 (4H, m), 2.00 (2H, m), 2.81 (2H, m), 3.06 (2H, m), 3.72 (4H, m), 6.91 (1H, m), 7.65 (1H, m), 10.92 (1H, s).

Reference Example 134

8-(5-Chloropentanoyl)-1-methyl-5,6-dihydro-4H-imidazo[4,5,1-ij]quinolin-2(1H)-one

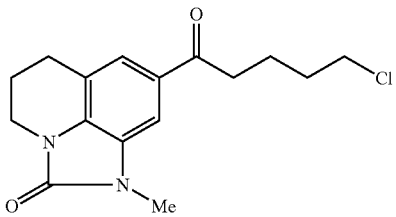

Using 1-methyl-5,6-dihydro-4H-imidazo[4,5,1-ij]quinolin-2(1H)-one obtained in Reference Example 132 and 5-chlorovaleryl chloride according to the same method as that of Reference. Example 1, the title compound was obtained as colorless crystals.

$^1$H NMR (200 MHz, CDCl$_3$) δ 1.85-1.93 (4H, m), 2.09 (2H, m), 2.88 (1H, m), 3.00 (2H, m), 3.23 (1H, m), 3.45 (3H, s), 3.59 (2H, m), 3.86 (2H, m), 6.87 (1H, t, J=8.4 Hz), 7.62 (1H, t, J=8.4 Hz).

Reference Example 135

4-(1,3-Dimethyl-2-oxo-2,3-dihydro-1H-benzimidazol-5-yl)-4-oxobutanoic acid

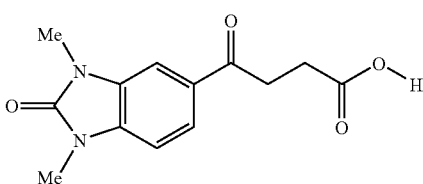

Aluminum chloride (62 g, 462 mmol) was added by portions to a mixture of 1,3-dimethyl-1,3-dihydro-2H-benzimidazol-2-one (25 g, 154 mmol) obtained in Reference Example 10 and succinic acid anhydride (15.4 g, 154 mmol) in dichloroethane. After stirring at room temperature for 30 minutes, the reaction mixture was poured into ice (500 g), extracted with ethyl acetate, and washed with brine. The organic layer was dried over anhydrous magnesium sulfate, the solvent was evaporated under reduced pressure, and the residue was crystallized from ethanol-diethyl ether to give the title compound as colorless crystals (25.0 g).

$^1$H NMR (200 MHz, DMSO-d$_6$) δ 2.59 (2H, t, J=6.4 Hz), 3.28 (2H, t, J=6.2 Hz), 3.36 (3H, s), 3.38 (3H, s), 7.24 (1H, d, J=8.4 Hz), 7.73 (1H, s), 7.78 (1H, d, J=8.4 Hz), 12.01 (1H, br).

Reference Example 136

4-(1,3-Dimethyl-2-oxo-2,3-dihydro-1H-benzimidazol-5-yl)butanoic acid

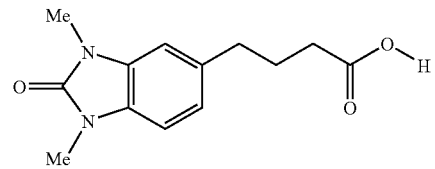

A solution of 4-(1,3-dimethyl-2-oxo-2,3-dihydro-1H-benzimidazol-5-yl)-4-oxobutanoic acid (25 g, 101 mmol) obtained in Reference Example 135, 10% palladium carbon (2 g) and concentrated hydrodhloric acid (3 ml) in acetic acid was stirred at room temperature for 5 hours under the atmosphere of hydrogen at 5 atm, and the reaction mixture was filtered through Celite to remove palladium carbon. The solvent was evaporated under reduced pressure, and the residue was crystallized from-ethanol-diethyl ether to give the title compound as colorless crystals (20.0 g).

$^1$H NMR (200 MHz, DMSO-d$_6$) 1.81 (2H, quint, J=7.0 Hz), 2.22 (2H, t, J=7.4 Hz), 2.63 (2H, t, J=7.4 Hz), 3.30 (3H, s), 3.31 (3H, s), 6.86-7.05 (3H, m), 12.01 (1H, br).

Reference Example 137

1,3-Dimethyl-3,6,7,8-tetrahydro-1H-naphtho[2,3-d]imidazole-2,5-dione

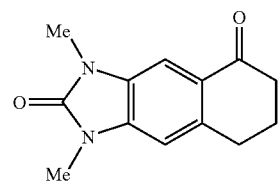

Oxalyl chloride (7.0 ml, 81 mmol). was added by portions to a solution of 4-(1,3-dimethyl-2-oxo-2,3-dihydro-1H-benzimidazol-5-yl)butanoic acid (20 g, 81 mmol) obtained in Reference Example 136 and dimethylformamide (1 ml) in tetrahydrofuran under ice-cooling. After stirring at room temperature for 30 minutes, the reaction mixture was concentrated, the reaction residue was dissolved in nitroethane, and aluminum chloride (21.6 g, 162 mmol) was added by portions under ice-cooling. After stirring at room temperature for 30 minutes, the reaction mixture was poured into ice (500 g), extracted with ethyl acetate, and washed with brine. The organic layer was dried over anhydrous magnesium sulfate, the solvent was evaporated under reduced pressure, and the residue was crystallized from ethanol-diethyl ether to give the title compound as colorless crystals (18.0 g).

$^1$H NMR (200 MHz, DMSO-d$_6$) δ 2.15 (2H, quint, J=6.6 Hz), 2.67 (2H, t, J=7.4 Hz), 3.02 (2H, t, J=7.4 Hz), 3.43 (3H, s), 3.44 (3H, s), 6.79 (1H, s), 7.67 (1H, s).

Reference Example 138

Ethyl (±)-1,3-dimethyl-2,5-dioxo-2,3,5,6,7,8-hexahydro-1H-naphtho[2,3-d]imidazole-6-carboxylate

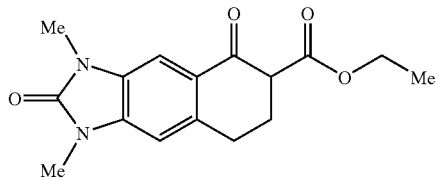

60% Oily sodium hydride (6 g) was washed with n-hexane (2×30 ml), and the solvent was removed by decantation. Tetrahydrofuran (200 ml) and subsequently diethyl carbonate (9.8 g) were added thereto, and the mixture was refluxed gently. To the suspension was added dropwise a solution of 1,3-dimethyl-3,6,7,8-tetrahydro-1H-naphtho[2,3-d]imidazole-2,5-dione (10 g, 43.4 mmol) obtained in Reference Example 137 in hot tetrahydrofuran while maintaining refluxing. The mixture was refluxed for 18 hours, and allowed to cool, and then acetic acid (18 ml) was carefully added dropwise to decompose excessive sodium hydride. Further, water was added, extracted with ethyl acetate, and washed with brine. The organic layer was dried over anhydrous magnesium sulfate, the solvent was evaporated under reduced pressure, and the residue was crystallized from ethanol-diethyl ether to give the title compound as colorless crystals (7.0 g).

$^1$H NMR (200 MHz, DMSO-d$_6$) δ 1.21 (3H, t, J=6.8 Hz), 2.27 (2H, quint, J=6.6 Hz), 3.02 (2H, m), 3.31 (3H, s), 3.33 (3H, s), 3.72 (1H, dd, J=9.6, 5.8 Hz), 4.15 (2H, q, J=7.0 Hz), 7.09 (1H, s), 7.55 (1H, s).

Reference Example 139

Ethyl (±)-6-(3-chloropropyl)-1,3-dimethyl-2,5-dioxo-2,3,5,6,7,8-hexahydro-1H-naphtho[2,3-d]imidazole-6-carboxylate

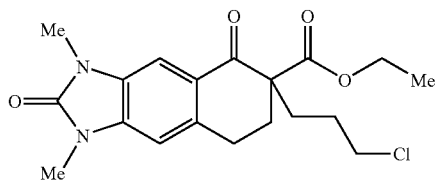

60% Oily sodium hydride (832 mg) was added to a solution of ethyl (±)-1,3-dimethyl-2,5-dioxo-2,3,5,6,7,8-hexahydro-1H-naphtho[2,3-d]imidazole-6-carboxylate (5.0 g) obtained in Reference Example 138 in dimethylformamide,and the mixture was stirred at 60° C. for 1 hour. 1-Bromo-3-chloropropane was added thereto, and the mixture was stirred at 60° C. for 4 hours. The reaction mixture was allowed to cool, and water was added to decompose excessive sodium hydride. Then, the mixture was extracted with ethyl acetate, and washed with brine. The organic layer was dried over anhydrous magnesium sulfate, the solvent was evaporated under reduced pressure, and the residue was purified by silica gel column chromatography to give the title compound as a pale yellow oil.

MS m/z: 379 [M+H]$^+$

Reference Example 140

Ethyl (±)-6-(4-chlorobutyl)-1,3-dimethyl-2,5-dioxo-2,3,5,6,7,8-hexahydro-1H-naphtho[2,3-d]imidazole-6-carboxylate

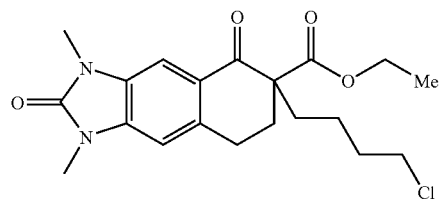

Using ethyl (±)-1,3-dimethyl-2,5-dioxo-2,3,5,6,7,8-hexahydro-1H-naphtho[2,3-d]imidazole-6-carboxylate obtained in Reference Example 138 and 1-bromo-4-chlorobutane according to the same method as that of Reference Example 139, the title compound was obtained as a pale yellow oil.

MS m/z: 393 [M+H]$^+$

Reference Example 141

(±)-6-(3-Chloropropyl)-1,3-dimethyl-3,6,7,8-tetrahydro-1H-naphtho[2,3-d]imidazole-2,5-dione

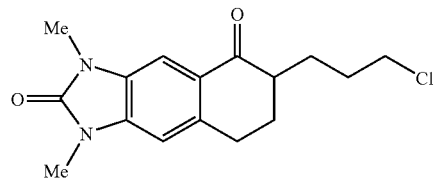

A solution of ethyl (±)-6-(3-chloropropyl)-1,3-dimethyl-2,5-dioxo-2,3,5,6,7,8-hexahydro-1H-naphtho[2,3-d]imidazole-6-carboxylate obtained in Reference Example 139 in concentrated hydrochloric acid (130 ml) was refluxed at 130° C. for 3 hours. The reaction mixture was allowed to cool, neutralized with potassium carbonate, extracted with ethyl acetate, and washed with brine. The organic layer was dried over anhydrous magnesium sulfate, and the solvent was evaporated under reduced pressure to give the title compound as a pale yellow oil.

MS m/z: 307 [M+H]$^+$

Reference Example 142

(±)-6-(4-Chlorobutyl)-1,3-dimethyl-3,6,7,8-tetrahydro-1H-naphtho[2,3-d]imidazole-2,5-dione

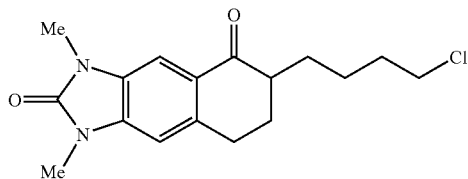

Using ethyl (±)-6-(4-chlorobutyl)-1,3-dimethyl-2,5-dioxo-2,3,5,6,7,8-hexahydro-1H-naphtho[2,3-d]imidazole-6-carboxylate obtained in Reference Example 140 according to the same method as that of Reference Example 141, the title compound was obtained as a pale yellow oil.
MS m/z: 321 [M+H]$^+$

Reference Example 143

Ethyl (±)-5,6-dimethoxy-1-oxo-2-indanecarboxylate

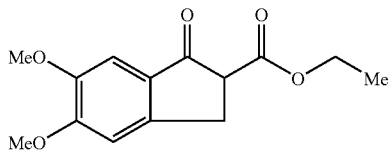

Using 5,6-dimethoxy-1-indanone according to the same method as that of Reference Example 138, the title compound was obtained as pale yellow crystals having a melting point of 140 to 141° C.
$^1$H NMR (200 MHz, CDCl$_3$) δ 1.32 (3H, t, J=6.8 Hz), 3.27 (1H, dd, J=17.2, 8.0 Hz), 3.45 (1H, dd, J=17.2, 3.6 Hz), 3.70 (1H, q, J=3.6 Hz), 3.91 (3H, s), 3.99 (3H, s), 4.27 (2H, q, J=6.8 Hz), 6.92 (1H, s), 7.18 (1H, s).

Reference Example 144

Ethyl (±)-2-(3-chloropropyl)-5,6-dimethoxy-1-oxo-2-indanecarboxylate

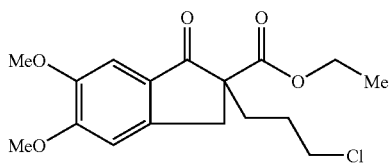

Using ethyl (±)-5,6-dimethoxy-1-oxo-2-indanecarboxylate obtained in Reference Example 143 according to the same method as that of Reference Example 139, the title compound was obtained as a pale yellow oil.
$^1$H NMR (200 MHz, CDCl$_3$) δ 1.22 (3H, t, J=6.8 Hz), 1.73 (2H, m), 2.00 (1H, m), 2.24 (1H, m), 2.98 (1H, d, J=17.2 Hz), 3.38 (1H, t, J=6.6 Hz), 3.54 (1H, t, J=6.6 Hz), 3.61 (1H, d, J=17.2 Hz), 3.91 (3H, s), 3.99 (3H, s), 4.17 (2H, q, J=6.8 Hz), 6.90 (1H, s), 7.16 (1H, s).

Reference Example 145

Ethyl (±)-2-(3-chlorobutyl)-5,6-dimethoxy-1-oxo-2-indanecarboxylate

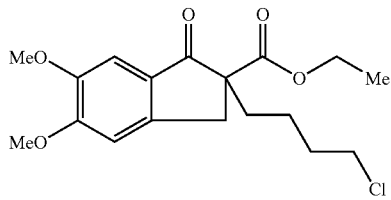

Using ethyl (±)-5,6-dimethoxy-1-oxo-2-indanecarboxylate obtained in Reference Example 143 and 1-bromo-4-chlorobutane according to the same method as that of Reference Example 139, the title compound was obtained as a pale yellow oil.
$^1$H NMR (200 MHz, CDCl$_3$) δ 1.23 (3H, t, J=7.6 Hz), 1.30-1.46 (2H, m), 1.75-1.94 (3H, m), 2.14 (1H, m), 3.00 (1H, d, J=17.2 Hz), 3.39 (1H, t, J=6.6 Hz), 3.51 (1H, t, J=6.6 Hz), 3.62 (1H, d, J=17.2 Hz), 3.91 (3H, s), 3.99 (3H, s), 4.18 (2H, q, J=7.6 Hz), 6.91 (1H, s), 7.17 (1H, s).

Reference Example 146

(±)-2-(3-Chloropropyl)-5,6-dimethoxy-1-indanone

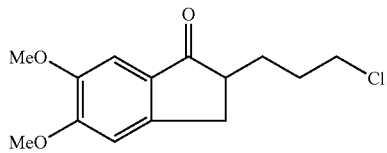

Using ethyl (±)-2-(3-chloropropyl)-5,6-dimethoxy-1-oxo-2-indanecarboxylate obtained in Reference Example 144 according to the same method as that of Reference Example 141, the title compound was obtained as colorless crystals.
$^1$H NMR (200 MHz, CDCl$_3$) δ 1.65 (2H, m), 1.95 (2H, m), 2.65-2.77 (2H, m), 3.29 (1H, dd, J=17.1, 7.8 Hz), 3.59 (2H, m), 3.91 (3H, s), 3.97 (3H, s), 6.87 (1H, s), 7.16 (1H, s).

Reference Example 147

(±)-2-(4-Chlorobutyl)-5,6-dimethoxy-1-indanone

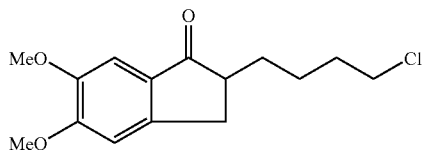

Using ethyl (±)-2-(3-chlorobutyl)-5,6-dimethoxy-1-oxo-2-indanecarboxylate obtained in Reference Example 145 according to the same method as that of Reference Example 141, the title compound was obtained as colorless crystals.
$^1$H NMR (200 MHz, CDCl$_3$) δ 1.42-1.98 (6H, m), 2.62-2.79 (2H, m), 3.28 (1H, dd, J=17.2, 7.4 Hz), 3.56 (2H, t, J=6.6 Hz), 3.91 (3H, s), 3.97 (3H, s), 6.88 (1H, s), 7.18 (1H, s).

Reference Example 148 tert-Butyl 2-(2-chlorophenyl)ethyl[5-(2,2-dioxide-1,3-dihydro-2,1,3-benzothiazol-5-yl)-5-oxopentyl]carbamate

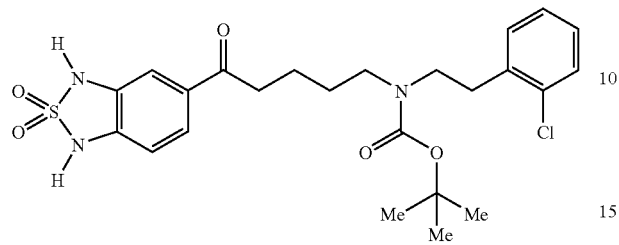

Using 5-chloro-1-(2,2-dioxide-1,3-dihydro-2,1,3-benzothiadiazol-5-yl)-1-pentanone obtained in Reference Example 128 and 2-(2-chlorophenyl)ethylamine according to the same method as that of Reference Example 19, the title compound was obtained as a pale yellow oil.

MS m/z: 508 [M+H]$^+$

Reference Example 149 tert-Butyl 2-(2-chlorophenyl)ethyl[5-(1,3-dimethyl-2,2-dioxide-1,3-dihydro-2,1,3-benzothiadiazol-5-yl)-5-oxopentyl]carbamate

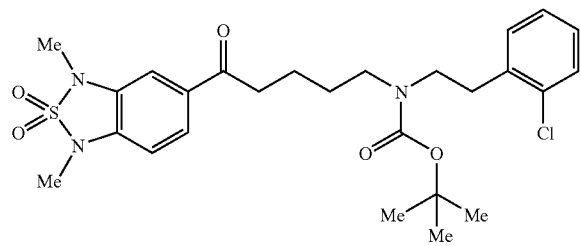

Using 5-chloro-1-(1,3-dimethyl-2,2-dioxide-1,3-dihydro-2,1,3-benzothiadiazol-5-yl)-1-pentanone obtained in Reference Example 129 and 2-(2-chlorophenyl)ethylamine according to the same method as that of Reference Example 19, the title compound was obtained as a pale yellow oil.

$^1$H NMR (200 MHz, CDCl$_3$) δ 1.41 (9H, s), 1.42-1.64 (4H, m), 2.97 (4H, m), 3.25 (2H, m), 3.34 (3H, s), 3.35 (3H, s), 3.45 (2H, m), 6.74 (1H, d, J=8.4 Hz), 7.18-7.39 (5H, m), 7.67 (1H, d, J=8.4 Hz).

Reference Example 150 tert-Butyl (±)-2-(2-chlorophenyl)ethyl[3-(1,3-dimethyl-2,5-dioxo-2,3,5,6,7,8-hexahydro-1H-naphtho[2,3-d]imidazol-6-yl)propyl]carbamate

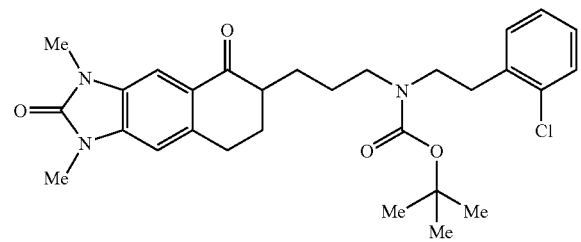

Using (±)-6-(3-chloropropyl)-1,3-dimethyl-3,6,7,8-tetrahydro-1H-naphtho[2,3-d]imidazole-2,5-dione obtained in Reference Example 141 and 2-(2-chlorophenyl)ethylamine according to the same method as that of Reference Example 19, the title compound was obtained as a pale yellow oil.

$^1$H NMR (200 MHz, CDCl$_3$) δ 1.38 (9H, m), 1.42-1.61 (4H, m), 1.87 (2H, m), 2.23 (1H, m), 2.93-3.12 (4H, m), 3.19 (2H, m), 3.32 (2H, m), 3.34 (3H, s), 3.36 (3H, s), 6.72 (1H, s), 7.11-7.30 (4H, m), 7.60 (1H, s).

Reference Example 151 tert-Butyl 2-(1H-indol-3-yl)ethyl[5-oxo-5-(4-oxo-1,2,5,6-tetrahydro-4H-pyrrolo[3,2,1-ij]quinolin-8-yl)pentyl]carbamate

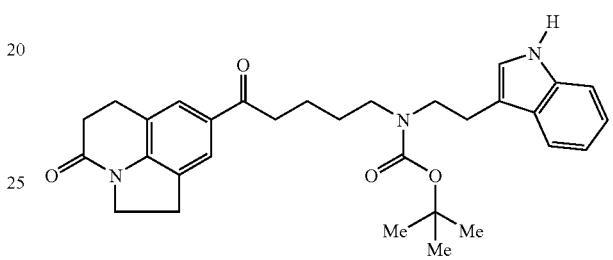

Using 8-(5-chloropentanoyl)-1,2,5,6-tetrahydro-4H-pyrrolo[3,2,1-ij]quinolin-4-one (1.00 g) obtained in Reference Example 1 and tryptamine (548 mg) according to the same method as that of Reference Example 19, the title compound (822 mg) was obtained as, pale yellow amorphous powders.

$^1$H NMR (300 MHz, CDCl$_3$) δ 1.30-1.80 (13H, m), 2.70 (2H, t, J=7.8 Hz), 2.80-3.05 (6H, m), 3.10-3.35 (4H, m), 3.40-3.55 (2H, m), 4.12 (2H, t, J=8.4 Hz), 6.95-7.25 (3H, m), 7.36 (1H, d, J=7.8 Hz), 7.60-7.75 (3H, m), 8.10-8.30 (1H, br).

Reference Example 152 tert-Butyl (±)-2-hydroxy-2-phenylethyl[5-oxo-5-(4-oxo-1,2,5,6-tetrahydro-4H-pyrrolo[3,2,1-ij]quinolin-8-yl)pentyl]carbamate

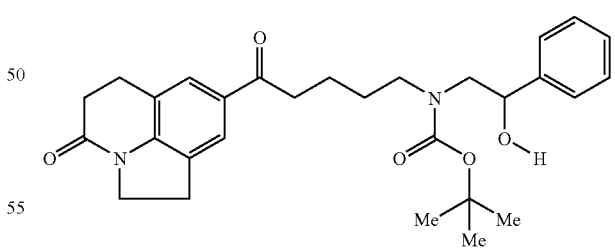

Using 8-(5-chloropentanoyl)-1,2,5,6-tetrahydro-4H-pyrrolo[3,2,1-ij]quinolin-4-one (1.00 g) obtained in Reference Example 1 and (±)-2-amino-1-phenylethanol (470 mg) according to the same method as that of Reference Example 19, the title compound (1.29 g) was obtained as a pale, yellow oil.

$^1$H NMR (200 MHz, CDCl$_3$) δ 1.47 (9H, s), 1.50-1.90 (4H, m), 2.60-3.50 (13H, m), 4.00-4.20 (2H, m), 4.70-5.00 (1H, m), 7.10-7.45 (5H, m), 7.66 (1H, s), 7.70 (1H, s).

Reference Example 153 tert-Butyl (±)-2-hydroxy-2-(3-hydroxyphenyl)ethyl [5-oxo-5-(4-oxo-1,2,5,6-tetrahydro-4H-pyrrolo[3,2,1-ij]quinolin-8-yl)pentyl]carbamate

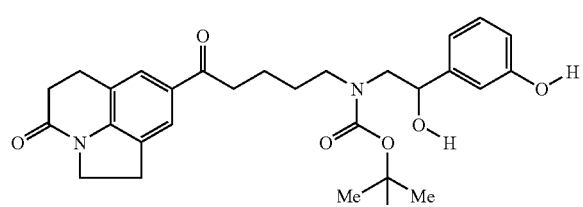

Using 8-(5-chloropentanoyl)-1,2,5,6-tetrahydro-4H-pyrrolo[3,2,1-ij]quinolin-4-one (1.00 g) obtained in Reference Example 1 and (±)-norphenylephrine hydrochloride (650 mg) according to the same method as that of Reference Example 82, the title compound (201 mg) was obtained as pale yellow amorphous powders.

$^1$H NMR (300 MHz, CDCl$_3$) δ 1.40-1.80 (4H, m), 1.47 (9H, s), 2.71 (2H, t, J=7.8 Hz), 2.91 (2H, t, J=7.2 Hz), 3.01 (2H, t, J=7.8 Hz), 3.05-3.60 (7H, m), 4.13 (2H, t, J=8.4 Hz), 4.60-4.90 (1H, m), 6.35-6.60 (1H, br), 6.75 (1H, d, J=8.5 Hz), 6.80-6.90 (2H, m), 7.18 (1H, t, J=7.8 Hz), 7.66 (1H, s), 7.70 (1H, s).

Reference Example 154

6-(5-Chloropentanoyl)-1-methyl-3,4-dihydro-2(1H)-quinolinone

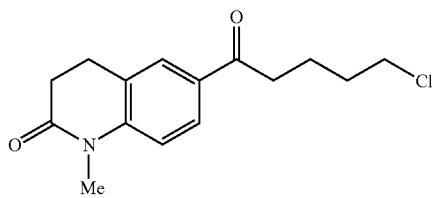

Using 1-methyl-3,4-dihydro-2(1H)-quinolinone (1.3 g) and 3-chlorovaleryl chloride (1.49 g) according to the same method as that of Reference Example 1, the title compound was obtained as colorless crystals (930 mg) having a melting point of 62 to 63° C.

$^1$H NMR (400 MHz, CDCl$_3$) δ 1.84-1.94 (4H, m), 2.69 (2H, t, J=8 Hz), 2.96-3.00 (4H, m), 3.39 (3H, s), 3.59 (2H, t, J=6 Hz), 7.04 (1H, d, J=8.3 Hz), 7.79 (1H, d, J=1.5 Hz), 7.88 (1H, dd, J=8.3, 1.5 Hz).

IR (KBr) νcm$^{-1}$: 1669, 1601, 1504, 1426, 1351, 1304, 1205, 1123.

Reference Example 155 tert-Butyl 2-(2-chloro-4-fluorophenyl)ethyl[5-oxo-5-(2-oxo-1,2,5,6-tetrahydro-4H-pyrrolo[3,2,1-ij]quinolin-8-yl)pentyl]carbamate

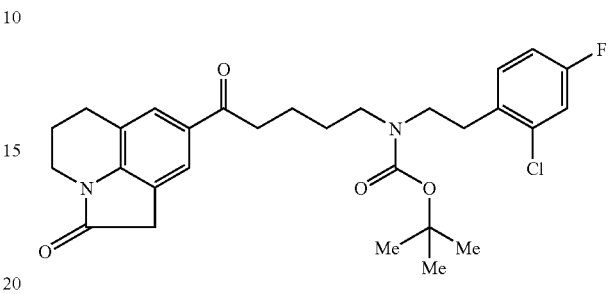

Using 8-(5-chloropentanoyl)-5,6-dihydro-4H-pyrrolo[3,2,1-ij]quinolin-2(1H)-one (438 mg) obtained in Reference Example 3 and (2-(2-chloro-4-fluorophenyl)ethylamine (573 mg) according to the same method as that of Reference Example 19, the title compound (452 mg) was obtained as a pale yellow oil.

$^1$H NMR (400 MHz, CDCl$_3$) δ 1.42 (9H, s), 1.51-1.75 (4H, m), 2.01-2.08 (2H, m), 2.82 (2H, t, J=6 Hz), 2.85-2.98 (4H, m), 3.13-3.21 (2H, m), 3.38 (2H, t, J=7 Hz), 3.54 (2H, s), 3.74 (2H, t, J=6 Hz), 6.91 (1H, dt, J=2.7, 8.0 Hz), 7.08-7.25 (2H, m), 7.72 (2H, s).

Reference Example 156 tert-Butyl 5-(1-acetyl-2,3-dihydro-1H-indol-5-yl)-5-oxopentyl[2-(2-chloro-4-fluorophenyl)ethyl]carbamate

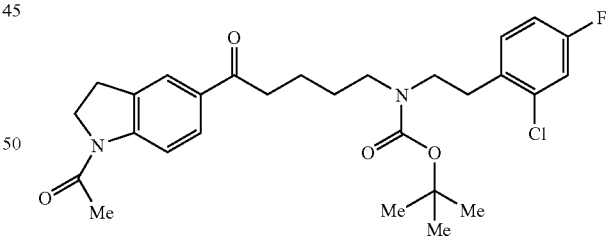

Using 1-(1-acetyl-2,3-dihydro-1H-indol-5-yl)-5-chloropentan-1-one (420 mg) obtained in Reference Example 11 and 2-(2-chloro-4-fluorophenyl)ethylamine (573 mg) according to the same method as that of Reference Example 19, the title compound (554 mg) was obtained as a pale, yellow oil.

$^1$H NMR (400 MHz, CDCl$_3$) δ 1.41 (9H, s), 1.51-1.73 (4H, m), 2.25 (3H, s), 2.94 (4H, br.s,), 3.13-3.25 (4H, m)), 3.38 (2H, t, J=7 Hz), 4.11 (2H, t, J=7 Hz), 6.91 (1H, dt, J=2.5, 7.8 Hz), 7.08-7.24 (2H, m), 7.80 (1H, s), 7.81 (1H, d, J=8.0 Hz), 8.23 (1H, d, J=8.0 Hz).

Reference Example 157 tert-Butyl 2-(2-chloro-4-fluorophenyl)ethyl[5-(1-methyl-2-oxo-1,2,3,4-tetrahydroquinolin-6-yl)-5-oxopentyl]carbamate

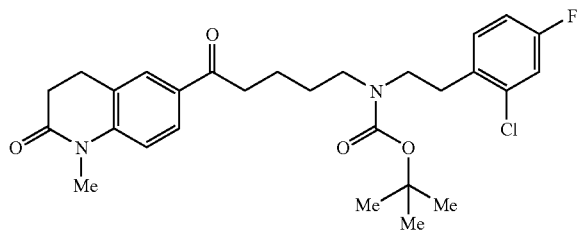

Using 6-(5-chloropentanoyl)-1-methyl-3,4-dihydroquinolin-2(1H)-one (420 mg) obtained in Reference Example 154 and 2-(2-chloro-4-fluorophenyl)ethylamine (573 mg) according to the same method as that of Reference Example 19, the title compound (472 mg) was obtained as a pale yellow oil.

$^1$H NMR (400 MHz, CDCl$_3$) δ 1.42 (9H, s), 1.51-1.73 (4H, m), 2.68 (2H, t, J=7.0 Hz), 2.95-2.99 (6H, m), 3.13-3.21 (2H, m), 3.36-3.40 (2H, m), 3.39 (3H, s), 6.91 (1H, dt, J=2.5, 8.3 Hz), 7.02 (1H, d, J=8.3 Hz), 7.09-7.22 (2H, m), 7.78 (1H, s), 7.87, (1H, d, J=8.3 Hz).

Reference Example 158 tert-Butyl 5-oxo-5-(2-oxo-1,2,5,6-tetrahydro-4H-pyrrolo[3,2,1-ij]quinolin-8-yl)pentyl{2-[2-(trifluoromethoxy)phenyl]ethyl}carbamate

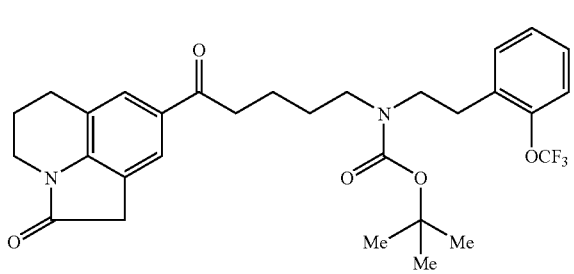

Using 8-(5-chloropentanoyl)-5,6-dihydro-4H-pyrrolo[3,2,1-ij]quinolin-2(1H)-one (292 mg) obtained in Reference Example 3 and 2-[2-(trifluoromethoxy)phenyl]ethylamine (451 mg) according to the same method as that of Reference Example 19, the title compound (205 mg) was obtained as a pale yellow oil.

$^1$H NMR (400 MHz, CDCl$_3$) δ 1.42 (9H, s), 1.51-1.72 (4H, m), 2.02-2.34 (2H, m), 2.80-2.90 (6H, m), 3.13-3.20 (2H, m), 3.38 (2H, br.s), 3.54 (2H, s), 3.72-3.75 (2H, m), 7.22 (4H, br.s), 7.72 (2H, s).

Reference Example 159 tert-Butyl 5-(1-acetyl-2,3-dihydro-1H-indol-5-yl)-5-oxopentyl{2-[2-(trifluoromethoxy)phenyl]ethyl}carbamate

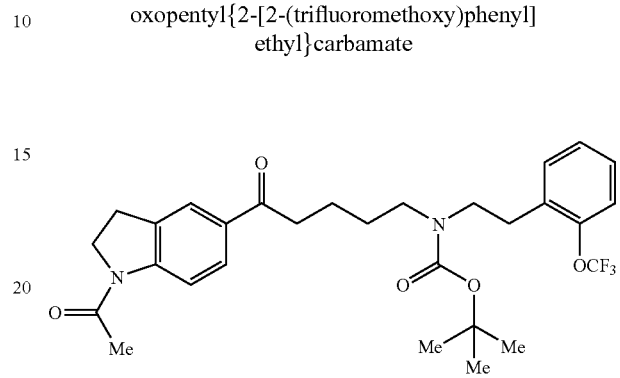

Using 1-(1-acetyl-2,3-dihydro-1H-indol-5-yl)-5-chloropentan-1-one (280 mg) obtained in Reference Example 11 and 2-[2-(trifluoromethoxy)phenyl]ethylamine (451 mg) according to the same method as that of Reference Example 19, the title compound (457 mg) was obtained as a pale yellow oil.

$^1$H NMR (400 MHz, CDCl$_3$) δ 1.42 (9H, s), 1.51-1.69 (4H, m), 2.25 (3H, s), 2.92-2.99 (4H, m), 3.12-3.25 (4H, m), 3.38 (2H, br.s), 4.09-4.15 (2H, m), 7.19-7.32 (4H, m), 7.80 (1H, s), 7.82 (1H, d, J=8.3 Hz), 8.23 (1H, d, J=8.3 Hz).

Reference Example 160 tert-Butyl 5-(1-methyl-2-oxo-1,2,3,4-tetrahydroquinolin-6-yl)-5-oxopentyl{2-[2-(trifluoromethoxy)phenyl]ethyl}carbamate

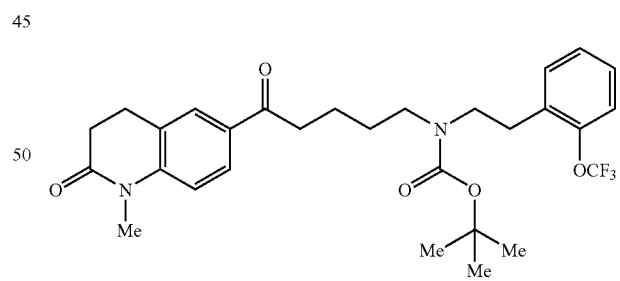

Using 6-(5-chloropentanoyl)-1-methyl-3,4-dihydroquinolin-2(1H)-one (280 mg) obtained in Reference Example 154 and 2-[2-(trifluoromethoxy)phenyl]ethylamine (451 mg) according to the same method as that of Reference Example 19, the title compound (442 mg) was obtained as a pale yellow oil.

$^1$H NMR (400 MHz, CDCl$_3$) δ 1.42 (9H, s), 1.51-1.73 (4H, m), 2.68 (2H, t, J=7.7 Hz), 2.88-3.00 (6H, m), 3.14-3.21 (2H, m), 3.35-3.42 (2H, m), 3.39 (3H, s), 7.02 (1H, d, J=8.3 Hz), 7.09-7.22 (2H, m), 7.78 (1H, s), 7.87 (1H, d, J=8.3 Hz).

Reference Example 161 tert-Butyl 5-(1,3-dimethyl-2-oxo-2,3-dihydro-1H-benzimidazol-5-yl)-5-oxopentyl{2-[2-(trifluoromethoxy)phenyl]ethyl}carbamate

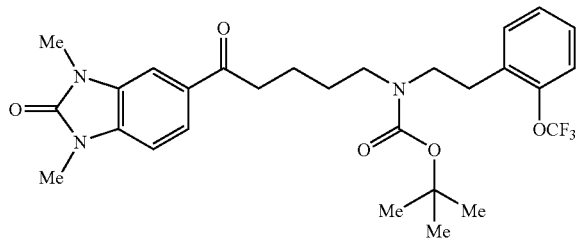

Using 5-(5-chloropentanoyl)-1,3-dimethyl-1,3-dihydro-2H-benzimidazol-2-one (281 mg) obtained in Reference Example 10 and 2-[2-(trifluoromethoxy)phenyl]ethylamine (451 mg) according to the same method as that of Reference Example 19, the title compound (244 mg) was obtained as a pale yellow oil.

$^1$H NMR (400 MHz, CDCl$_3$) δ 1.42 (9H, s), 1.51-1.78 (4H, m), 2.89 (2H, br.s), 3.01 (2H, br.s), 3.15-3.23 (2H, m), 3.38 (2H, br.s), 3.46 (6H, s), 6.98 (1H, d, J=8.0 Hz), 7.23-7.30 (4H, m), 7.63 (1H, s), 7.78 (1H, d, J=8.0 Hz).

Reference Example 162 tert-Butyl 3-(2-methoxyphenyl)propyl[5-oxo-5-(2-oxo-1,2,5,6-tetrahydro-4H-pyrrolo[3,2,1-ij]quinolin-8-yl)pentyl]carbamate

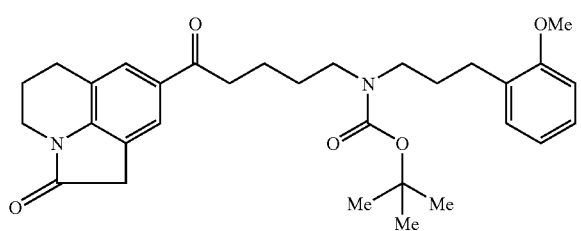

Using 8-(5-chloropentanoyl)-5-6-dihydro-4H-pyrrolo[3,2,1-ij]quinolin-2(1H)-one (292 mg) obtained in Reference Example 3 and 3-(2-methoxyphenyl)propylamine (364 mg) according to the same method as that of Reference Example 19, the title compound (165 mg) was obtained as a pale yellow oil.

$^1$H NMR (400 MHz, CDCl$_3$) δ 1.43 (9H, s), 1.60 (2H, br.s), 1.67-1.74 (2H, m), 1.76-1.84 (2H, m), 2.00-2.06 (2H, m), 2.58 (2H, t, J=7.5 Hz), 2.82 (2H, t, J=6.0 Hz), 2.94 (2H, t, J=7.0 Hz), 3.22 (4H, br.s), 3.54 (2H, s), 3.74 (2H, t, J=6.0 Hz), 3.81 (3H, s), 6.84 (1H, d, J=8.3 Hz), 6.87 (1H, t, J=7.5 Hz), 7.12 (1H, d, J=7.5 Hz), 7.17 (1H, t, J=7.5 Hz), 7.73 (2H, s).

Reference Example 163 tert-Butyl 5-(1-acetyl-2,3-dihydro-1H-indol-5-yl)-5-oxopentyl[3-(2-methoxyphenyl)propyl]carbamate

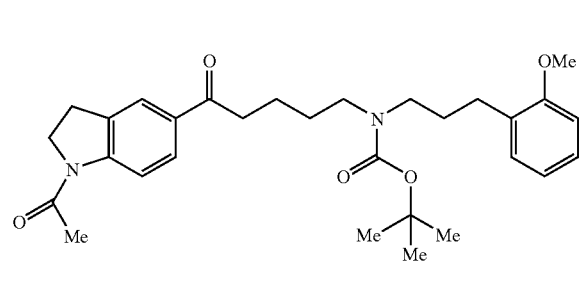

Using 1-(1-acetyl-2,3-dihydro-1H-indol-5-yl)-5-chloropentan-1-one (280 mg) obtained in Reference Example 11 and 3-(2-methoxyphenyl)propylamine (364 mg) according to the same method as that of Reference Example 19, the title compound (417 mg) was obtained as a pale yellow oil.

$^1$H NMR (400 MHz, CDCl$_3$) δ 1.44 (9H, s), 1.60 (2H, br.s), 1.67-1.72 (2H, m), 1.76-1.84 (2H, m), 2.25 (3H, s), 2.58 (2H, t, J=7.3 Hz), 2.93-2.96 (2H, m), 3.23 (6H, br.s), 3.81 (3H, s), 4.09-4.15 (2H, m), 6.83 (1H, d, J=8.3 Hz), 6.87 (1H, t, J=7.3 Hz), 7.12 (1H, d, J=7.3 Hz), 7.17 (1H, t, J=7.3 Hz), 7.81 (1H, s), 7.82 (1H, d, J=8.1 Hz), 8.23 (1H, d, J=8.1 Hz).

Reference Example 164 tert-Butyl 3-(2-methoxyphenyl)propyl[5-(1-methyl-2-oxo-1,2,3,4-tetrahydroquinolin-6-yl)-5-oxopentyl]carbamate

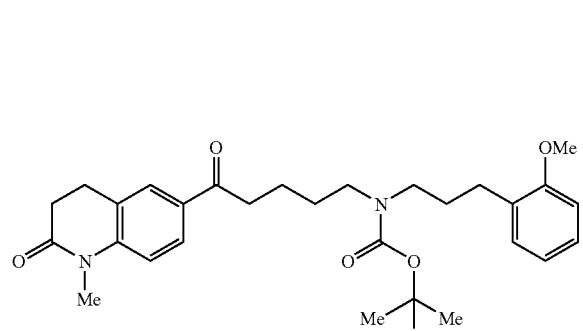

Using 6-(5-chloropentanoyl)-1-methyl-3,4-dihydroquinolin-2(1H)-one (280 mg) obtained in Reference Example 154 and 3-(2-methoxyphenyl)propylamine (364 mg) according to the same method as that of Reference Example 19, the title compound (415 mg) was obtained as a pale yellow oil.

$^1$H NMR (400 MHz, CDCl$_3$) δ 1.44 (9H, s), 1.61 (2H, br.s), 1.68-1.75 (2H, m), 1.77-1.84 (2H, m), 2.58 (2H, t, J=7.8 Hz), 2.68 (2H, t, J=7.8 Hz), 2.95-2.98 (4H, m), 3.21 (4H, br.s), 3.39 (3H, s), 3.81 (3H, s), 6.84 (1H, d, J=8.0 Hz), 6.88 (1H, t, J=7.3 Hz), 7.01 (1H, d, J=8.3 Hz), 7.12 (1H, d, J=7.3 Hz), 7.17 (1H, t, J=7.3 Hz), 7.79 (1H, s), 7.87 (1H, d, J=8.3 Hz).

Reference Example 165 tert-Butyl 5-(1,3-dimethyl-2-oxo-2,3-dihydro-1H-benzimidazol-5-yl)-5-oxopentyl[3-(2-methoxyphenyl)propyl]carbamate

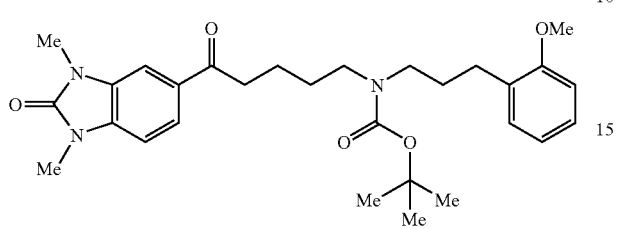

Using 5-(5-chloropentanoyl)-1,3-dimethyl-1,3-dihydro-2H-benzimidazol-2-one (281 mg) obtained in Reference. Example 10 and 3-(2-methoxyphenyl)propylamine (364 mg), according to the same method as that of Reference Example 19, that title compound (387 mg) was obtained as a pale yellow oil.
$^1$H NMR (400 MHz, CDCl$_3$) δ 1.44 (9H, s), 1.63 (2H, br.s), 1.70-1.85 (4H, m), 2.58 (2H, t, J=7.8 Hz), 3.01 (2H, t, J=7.0 Hz), 3.25 (4H, br.s), 3.46 (6H, s), 3.81 (3H, s), 6.84 (1H, d, J=8.0 Hz), 6.87 (1H, t, J=7.3 Hz), 6.98 (1H, d, J=8.0 Hz), 7.12 (1H, d, J=7.3 Hz), 7.17 (1H, t, J=7.3 Hz), 7.63 (1H, s), 7.78 (1H, d, J=8.0 Hz).

Reference Example 166 tert-Butyl 2-(2-ethoxyphenoxy)ethyl[5-oxo-5-(2-oxo-1,2,5,6-tetrahydro-4H-pyrrolo[3,2,1-ij]quinolin-8-yl)pentyl]carbamate

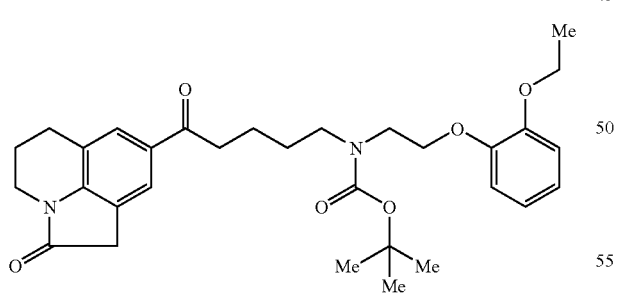

Using 8-(5-chloropentanoyl)-5,6-dihydro-4H-pyrrolo[3,2,1-ij]quinolin-2(1H)-one (292 mg) obtained in Reference Example 3 and 2-(2-ethoxyphenoxy)ethylamine (399 mg) according to the same method as that of Reference Example 19, the title compound (211 mg) was obtained as a pale yellow oil.
$^1$H NMR (400 MHz, CDCl$_3$) δ 1.42 (3H, t, J=7 Hz), 1.45 (9H, s), 1.61-1.75 (4H, m), 2.00-2.06 (2H, m), 2.81 (2H, t, J=6 Hz), 2.94 (2H, br.d, J=6.6 Hz), 3.42 (2H, t, J=7.3 Hz), 3.54 (2H, s), 3.59-3.63 (2H, m), 3.74 (2H, t, J=6 Hz), 4.03-4.08 (2H, m), 4.12 (2H, q, J=7 Hz), 6.89 (4H, br.s), 7.73 (2H, s).

Reference Example 167 tert-Butyl 5-(1-acetyl-2,3-dihydro-1H-indol-5-yl)-5-oxopentyl[2-(2-ethoxyphenoxy)ethyl]carbamate

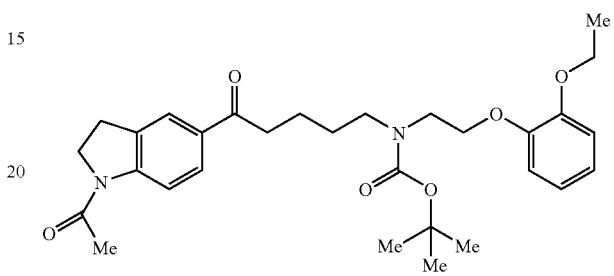

Using 1-(1-acetyl-2,3-dihydro-1H-indol-5-yl)-5-chloropentan-1-one (280 mg) obtained in Reference Example 11 and 2-(2-ethoxyphenoxy)ethylamine (399 mg) according to the same method as that of Reference Example 19, the title compound (398 mg) was obtained as a pale yellow oil.
$^1$H NMR (400 MHz, CDCl$_3$) δ 1.41 (3H, t, J=7 Hz), 1.45 (9H, s), 1.61-1.72 (4H, m), 2.25 (3H, s), 2.95-2.97 (2H, m), 3.22 (2H, t, J=8 Hz), 3.42 (2H, t, J=7 Hz), 3.58-3.68 (2H, m), 4.03-4.06 (2H, m), 4.11 (4H, q, J=7 Hz), 6.89 (4H, br.s), 7.79 (1H, s), 7.82 (1H, d, J=8.3 Hz), 8.22 (1H, d, J=8.3 Hz).

Reference Example 168 tert-Butyl 2-(2-ethoxyphenoxy)ethyl[5-(1-methyl-2-oxo-1,2,3,4-tetrahydroquinolin-6-yl)-5-oxopentyl]carbamate

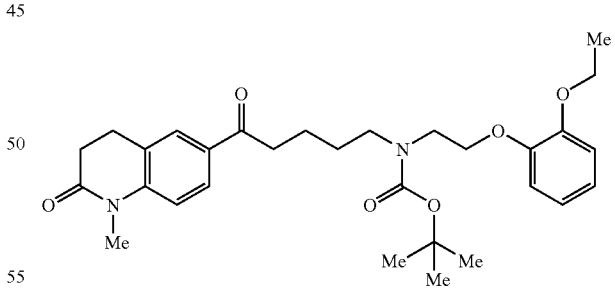

Using 6-(5-chloropentanoyl)-1-methyl-3,4-dihydroquinolin-2(1H)-one (280 mg) obtained in Reference Example 154 and 2-(2-ethoxyphenoxy)ethylamine (399 mg) according to the same method as that of Reference Example 19, the title compound (425 mg) was obtained as a pale yellow oil.
$^1$H NMR (400 MHz, CDCl$_3$) δ 1.43 (3H, t, J=7 Hz), 1.45 (9H, s), 1.70-1.76 (4H, m), 2.68 (2H, t, J=8.3 Hz), 2.94-2.98 (4H, m), 3.39 (3H, s), 3.43 (2H, t, J=7.3 Hz), 3.59-3.64 (2H, m), 4.03-4.08 (2H, m), 4.12 (2H, q, J=7 Hz), 6.89 (4H, br.s), 7.01 (1H, d, J=8.3 Hz), 7.78 (1H, s), 7.88 (1H, d, J=8.3 Hz).

Reference Example 169 tert-Butyl 5-(1,3-dimethyl-2-oxo-2,3-dihydro-1H-benzimidazol-5-yl)-5-oxopentyl[2-(2-ethoxyphenoxy)ethyl]carbamate

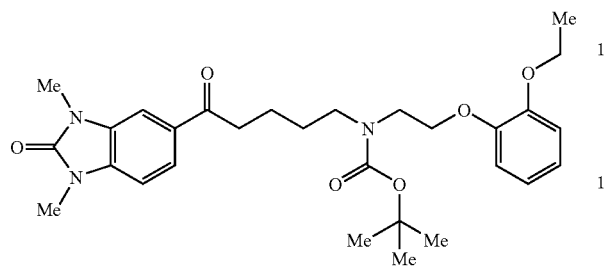

Using 5-(5-chloropentanoyl)-1,3-dimethyl-1,3-dihydro-2H-benzimidazol-2-one (281 mg) obtained in Reference Example 10 and 2-(2-ethoxyphenoxy)ethylamine (399 mg) according to the same method as that of Reference Example 19, the title compound (368 mg) was obtained as a pale yellow oil.

$^1$H NMR (400 MHz, CDCl$_3$) δ 1.42 (3H, t, J=6.7 Hz), 1.45 (9H, s), 1.70-1.78 (4H, m), 3.01-3.06 (2H, m), 3.42-3.46 (2H, m), 3.46 (6H, s), 3.59-3.64 (2H, m), 4.05 (2H, q, J=6.7 Hz), 4.10-4.15 (2H, m), 6.89 (4H, br.s), 6.97 (1H, d, J=8 Hz), 7.63 (1H, s), 7.78 (1H, d, J=8 Hz).

Reference Example 170 tert-Butyl 2-[(2-ethoxyphenyl)amino]ethyl[5-oxo-5-(2-oxo-1,2,5,6-tetrahydro-4H-pyrrolo[3,2,1-ij]quinolin-8-yl)pentyl]carbamate

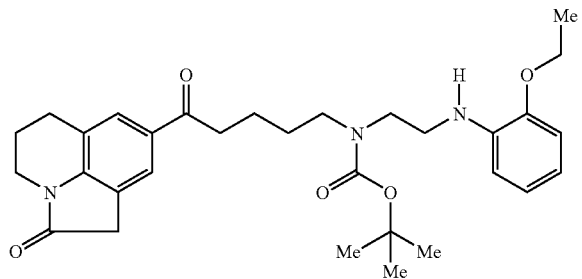

Using 8-(5-chloropentanoyl)-5,6-dihydro-4H-pyrrolo[3,2,1-ij]quinolin-2(1H)-one (584 mg) obtained in Reference Example 3 and N-(2-ethoxyphenyl)ethane-1,2-diamine (793 mg) according to the same method as that of Reference Example 19, the title compound (611 mg) was obtained as a pale yellow oil.

$^1$H NMR (400 MHz, CDCl$_3$) δ 1.42 (3H, t, J=7.0 Hz), 1.47 (9H, s), 1.63 (1H, br.s), 1.66-1.75 (4H, m), 2.00-2.06 (2H, m), 2.82 (2H, t, J=6.1 Hz), 2.92-2.98 (2H, m), 3.23-3.33 (4H, m), 3.44 (2H, br.s), 3.54 (2H, s), 3.74 (2H, t, J=6.1 Hz), 4.05 (2H, br.s), 6.63 (2H, br.s), 6.74 (1H, d, J=7.6 Hz), 6.84 (1H, t, J=7.6 Hz), 7.72 (1H, s), 7.73 (1H, s).

Reference Example 171 tert-Butyl 5-(1-acetyl-2,3-dihydro-1H-indol-5-yl)-5-oxopentyl{2-[(2-ethoxyphenyl)amino]ethyl}carbamate

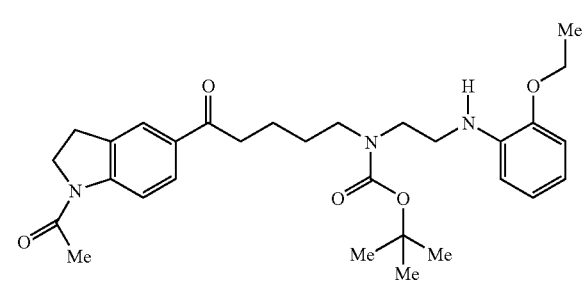

Using 1-(1-acetyl-2,3-dihydro-1H-indol-5-yl)-5-chloropentan-1-one (560 mg) obtained in Reference Example 11 and N-(2-ethoxyphenyl)ethane-1,2-diamine (793 mg) according to the same method as that of Reference Example 19, the title compound (695 mg) was obtained as a pale yellow oil.

$^1$H NMR (400 MHz, CDCl$_3$) δ 1.42 (3H, t, J=6.8 Hz), 1.47 (9H, s), 1.62 (1H, br.s), 1.67-1.74 (4H, m), 2.26 (3H, s), 2.93-2.97 (2H, m), 3.21-3.25 (4H, m), 3.31 (2H, t, J=6.8 Hz), 3.43 (2H, br.s), 4.04 (2H, br.s), 4.12 (2H, q, J=6.8 Hz), 6.63 (2H, br.s), 6.74 (1H, d, J=7.6 Hz), 6.84 (1H, t, J=7.6 Hz), 7.80 (1H, s), 7.82 (1H, d, J=8.3 Hz), 8.23 (1H, d, J=8.3 Hz).

Reference Example 172 tert-Butyl 5-(1,3-dimethyl-2-oxo-2,3-dihydro-1H-benzimidazol-5-yl)-5-oxopentyl{2-[(2-ethoxyphenyl)amino]ethyl}carbamate

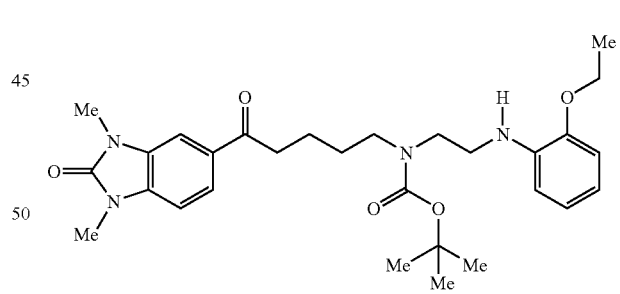

Using 5-(5-chloropentanoyl)-1,3-dimethyl-1,3-dihydro-2H-benzimidazol-2-one (562 mg) obtained in Reference Example 10 and N-(2-ethoxyphenyl)ethane-1,2-diamine (793 mg) according to the same method as that of Reference Example 19, the title compound (670 mg) was obtained as a pale yellow oil.

$^1$H NMR (400 MHz, CDCl$_3$) δ 1.42 (3H, t, J=6.8 Hz), 1.47 (9H, s), 1.63 (1H, br.s), 1.71-1.80 (4H, m), 3.00-3.05 (2H, m), 3.27-3.33 (4H, m), 3.42-3.49 (2H, m), 3.46 (6H, s), 4.04 (2H, br.s), 6.63 (2H, br.s), 6.74 (1H, d, J=7.3 Hz), 6.84 (1H, t, J=7.3 Hz), 6.98 (1H, d, J=8.0 Hz), 7.62 (1H, s), 7.78 (1H, d, J=8.0 Hz).

Reference Example 173

8-[3-(1-Acetyl-4-piperidinyl)propanoyl]-5,6-dihydro-4H-pyrrolo[3,2,1-ij]quinolin-2(1H)-one

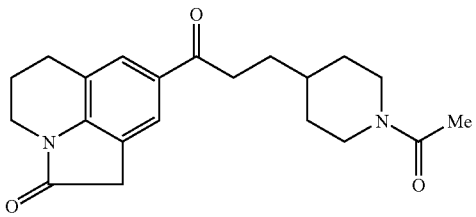

Thionyl chloride (5.6 ml) was added dropwise to a suspension of 3-(1-acetyl-4-piperidinyl)propanoic acid (13.8 g) in dichloromethane (50 ml) under ice-cooling. After stirred at the same temperature for 30 minutes, the mixture was concentrated under reduced pressure, 30 ml of hexane was added to the residue, and precipitated crystals were filtered and dried. Aluminum chloride (28 g) was added by portions to a suspension of the resulting corresponding acid chloride and 5,6-dihydro-4H-pyrrolo[3,2,1-ij]quinolin-2(1H)-one (10 g) in 1,2-dichloroethane (50 ml) under ice-cooling. After stirred at room temperature for 30 minutes, the reaction mixture was poured into ice (200 g), extracted with ethyl acetate, and washed with brine. The organic layer was dried over anhydrous magnesium sulfate, the solvent was evaporated under reduced pressure, and the residue was crystallized from ethanol-diethyl ether to give the title compound as pale yellow crystals (8.0 g) having a melting point of 119 to 120° C.

$^1$H NMR (400 MHz, CDCl$_3$) δ 1.08-1.24 (2H, m), 1.55-1.81 (5H, m), 2.00-2.10 (2H, m), 2.09 (3H, s), 2.53 (1H, d, t, J=2.5, 13 Hz), 2.83 (2H, t, J=6.7 Hz), 2.95 (2H, t, J=7.5 Hz), 3.03 (1H, d, t, J=2.5, 13 Hz), 3.56 (2H, s), 3.75 (2H, t, J=6.7 Hz), 3.80 (1H, d, J=7.5 Hz), 4.61 (1H, d, J=7.5 Hz), 7.73, (2H, s).

IR (KBr) vcm$^{-1}$: 1713, 1634, 1341, 1152.

Reference Example 174

8-[3-(4-Piperidinyl)propanoyl]-5,4-dihydro-4H-pyrrolo[3,2,1-ij]quinolin-2(1H)-one

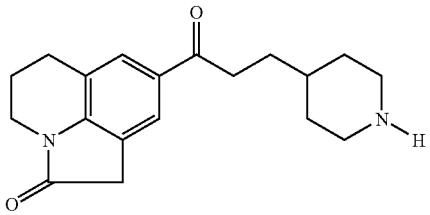

Concentrated hydrochloric acid (150 ml) was added to 8-[3-(1-acetyl-4-piperidinyl)propanoyl]-5,6-dihydro-4H-pyrrolo[3,2,1-ij]quinolin-2(1H)-one (7.5 g) obtained in Reference Example 173, and the mixture was stirred at 120° C. for 5 hours. Hydrochloric acid was evaporated under reduced pressure, pH was adjusted to 12 with 1N aqueous sodium hydroxide solution, and extracted with ethyl acetate (100 ml) three times. The organic layer was dried over anhydrous magnesium sulfate, and the solvent was evaporated to give the title compound as pale yellow crystals (3.48 g) having a melting point of 128 to 129° C.

$^1$H NMR (400 MHz, CDCl$_3$) δ 1.14 (1H, d, t, J=4, 12 Hz), 1.17 (1H, d, t, J=4, 12 Hz), 1.42-1.46 (1H, m), 1.65-1.81 (5H, m), 2.04 (2H, t, J=7 Hz), 2.58 (2H, d, t, J=2, 12 Hz), 2.83 (2H, t, J=6 Hz), 2.94 (2H, t, J=7 Hz), 3.07 (2H, br, d, J=12 Hz), 3.55 (2H, s), 3.74 (2H, t, J=6 Hz), 7.73 (2H, s).

IR (KBr) vcm$^{-1}$:1708, 1660, 1603, 1339, 1156.

Reference Example 175

9-[3-(1-Acetyl-4-piperidinyl)propanoyl]-2,3,6,7-tetrahydro-1H,5H-pyrido[3,2,1-ij]quinolin-5-one

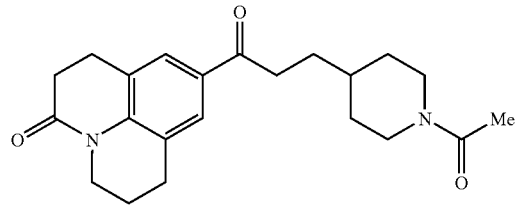

Using 3-(1-acetyl-4-piperidinyl)propanoic acid (13.8 g) and 2,3,6,7-tetrahydro-1H,5H-pyrido[3,2,1-ij]quinolin-5-one (10.8 g) according to the same method as that of Reference Example 172, the title compound was obtained as colorless crystals (15.5 g) having a melting point of 130 to 131° C.

$^1$H NMR (400 MHz, CDCl$_3$) δ 1.09-1.28 (2H, m), 1.55-1.82 (5H, m), 1.93-2.00 (2H, m), 2.09 (3H, s), 2.53 (1H, d, t, J=2.5, 12.7 Hz), 2.68 (2H, t, J=7 Hz), 2.85 (2H, t, J=6 Hz), 2.93-2.98 (4H, m), 3.03 (1H, d, t, J=2.5, 12.7 Hz), 3.82 (1H, d, J=12.7 Hz ), 3.90 (2H, t, J=6 Hz), 4.61 (1H, d, J=13 Hz), 7.62 (2H, d, J=6 Hz).

IR (KBr) vcm$^{-1}$: 1671, 1634, 1360, 1160, 972.

Reference Example 176

9-[3-(4-Piperidinyl)propanoyl]-2,3,6,7-tetrahydro-1H,5H-pyrido[3,2,1-ij]quinolin-5-one

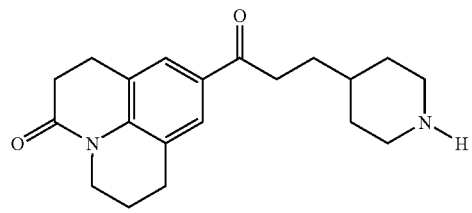

Using 9-[3-(1-acetyl-4-piperidinyl)propanoyl]-2,3,6,7-tetrahydro-1H,5H-pyrido[3,2,1-ij]quinolin-5-one (15 g) obtained in Reference Example 175 according to the same method as that of Reference Example 173, the title compound was obtained as pale yellow crystals (8.9 g) having a melting point of 81 to 82° C.

$^1$H NMR (400 MHz, CDCl$_3$) δ 1.14 (1H, d, t, J=4, 12 Hz), 1.17 (1H, d, t, J=4, 12 Hz), 1.41-1.48 (1H, m), 1.65-1.70 (4H, m), 1.73 (1H, br.s), 1.94-2.00 (2H, m), 2.58 (2H, d, t, J=2, 12 Hz), 2.68 (2H, t, J=6.7 Hz), 2.84 (2H, t, J=6 Hz), 2.92-2.96 (4H,m), 3.07 (2H, br, d, J=12 Hz), 3.89 (2H, t, J=6 Hz),7.62 (2H, d, J=5 Hz).

IR (KBr) vcm$^{-1}$: 3442, 2905, 1673, 1588, 1361, 1164.

Reference Example 177

6-(5-Chloropentanoyl)-3,4-dihydro-2(1H)-quinazoline

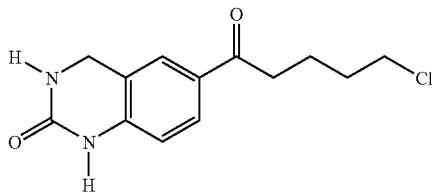

Using 3,4-dihydro-2(1H)-quinazoline (4.0 g) and 5-chlorovaleryl chloride (8.37 g) according to the same method as that of Reference Example 1, the title compound was obtained as colorless crystals (3.9 g)

$^1$H NMR (200 MHz, DMSO-d$_6$) δ 1.73 (4H, m), 2.96 (2H, t, J=7.0 Hz), 3.67 (2H, t, J=6.4 Hz), 4.38 (2H, s), 6.83 (1H, d, J=8.8 Hz), 7.01 (1H, s), 7.75-7.80 (2H, m), 9.44 (1H, s).

elementary analysis as C$_{13}$H$_{15}$ClN$_2$O$_2$
calculation value:C, 58.54; H, 5.67; N, 10.50.
experimental value:C, 58.47; H, 5.51; N, 10.39.
MS m/z: 267 [M+H]$^+$

Reference Example 178

6-(5-Chloropentanoyl)-1,3-dimethyl-3,4-dihydro-2(1H)-quinazoline

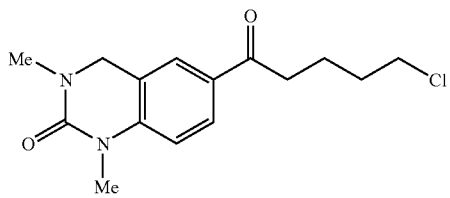

Using 1,3-dimethyl-3,4-dihydro-2(1H)-quinazoline (4.0 g) and 5-chlorovaleryl chloride (6.46 g) according to the same method as that of Reference Example 1, the title compound was obtained as colorless crystals (3.5 g).

$^1$H NMR (300 MHz, CDCl$_3$) δ 1.91-1.87 (4H, m), 2.99-2.94 (2H,m), 3.06 (3H, s) 3.35 (3H, s), 3.61-3.57 (2H, m), 4.43 (2H, s), 6.87 (1H, d, J=8.4 Hz), 7.07 (1H, d, J=2.1 Hz), 7.88 (1H, d, J=8.4, 2.1 Hz).

Reference Example 179

8-(4-Chlorobutanoyl)-1,2,5,6-tetrahydro-4H-pyrrolo[3,2,1-ij]quinolin-4-one

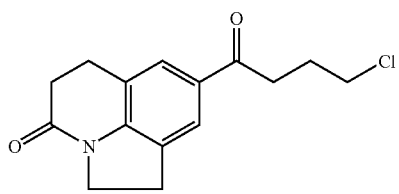

Using 1,2,5,6-tetrahydro-4H-pyrrolo[3,2,1-ij]quinolin-4-one (20.0 g) and 5-chlorovaleryl chloride (17.8 ml) according to the same method as that of Reference Example 1, the title compound (23.0 g) was obtained as colorless crystals having a melting point of 123 to 124° C.

$^1$H NMR (200 MHz, CDCl$_3$) δ 2.23 (2H, quintet, J=6.4 Hz), 2.72 (2H, t, J=7.6 Hz), 3.04 (2H, t, J=7.6 Hz), 3.13 (2H, t, J=6.4 Hz), 3.24 (2H, t, J=8.6 Hz), 3.68 (2H, t, J=6.4 Hz), 4.14 (2H, t, J=8.6 Hz), 7.70 (1H, s), 7.75 (1H, s).

elementary analysis as C$_{15}$H$_{16}$ClNO$_2$
calculation value:C, 64.87; H, 5.81; N, 5.04.
experimental value:C, 64.88; H, 5.72; N, 4.91.

Reference Example 180 tert-Butyl benzyl[4-oxo-4-(4-oxo-1,2,5,6-tetrahydro-4H-pyrrolo[3,2,1-ij]quinolin-8-yl)butyl]carbamate

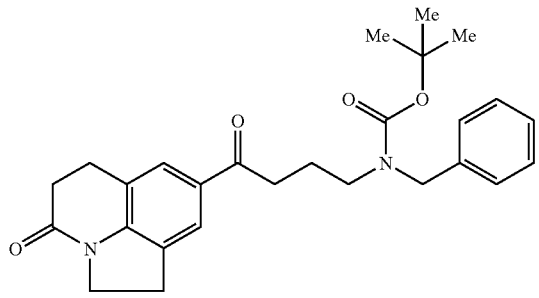

Using 8-(4-chlorobutanoyl)-1,2,5,6-tetrahydro-4H-pyrrolo[3,2,1-ij]quinolin-4-one (1.00 g) obtained in Reference Example 179 and benzylamine (1.16 g) according to the same method as that of Reference Example 19, the title compound (526 mg) was obtained as a pale yellow oil.

$^1$H NMR (200 MHz, CDCl$_3$) δ 1.44 (9H, s), 1.80-2.05 (2H, m), 2.71 (2H, t, J=7.6 Hz), 2.80-2.95 (2H, m), 3.11 (2H, t, J=7.6 Hz), 3.15-3.40 (4H, m), 4.13 (2H, t, J=8.8 Hz), 4.45 (2H, s), 7.20-7.40 (5H, m), 7.64 (1H, s), 7.68 (1H, s).

Reference Example 181 tert-Butyl 2-(2-methoxyphenyl)ethyl[4-oxo-4-(4-oxo-1,2,5,6-tetrahydro-4H-pyrrolo[3,2,1-ij]quinolin-8-yl)butyl]carbamate

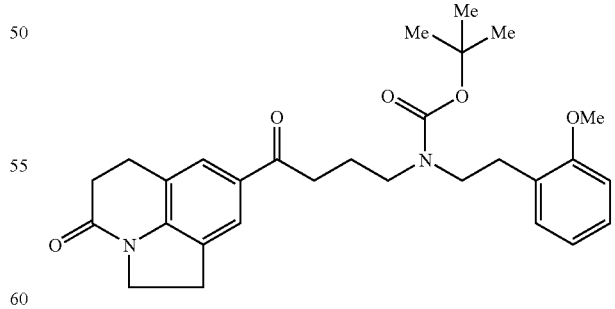

Using 8-(4-chlorobutanoyl)-1,2,5,6-tetrahydro-4H-pyrrolo[3,2,1-ij]quinolin-4-one (1.00 g) obtained in Reference Example 179 and 2-(2-methoxyphenyl)ethylamine (1.63 g) according to the same method as that of Reference Example 19, the title compound (797 mg) was obtained as a pale yellow oil.

$^1$H NMR (200 MHz, CDCl$_3$) δ 1.41 (9H, s), 1.85-2.00 (2H, m), 2.71 (2H, t, J=5.2 Hz), 2.75-2.95 (4H, m), 3.01 (2H, t, J=5.2 Hz), 3.15-3.45 (6H, m), 3.83 (3H, s), 4.13 (2H, t, J=5.8 Hz), 6.80-6.90 (2H, m), 7.05-7.20 (2H, m), 7.66 (1H, s), 7.71 (1H, s).

Reference Example 182 tert-Butyl benzyl[5-oxo-5-(4-oxo-1,2,5,6-tetrahydro-4H-pyrrolo[3,2,1-ij]quinolin-8-yl)pentyl]carbamate

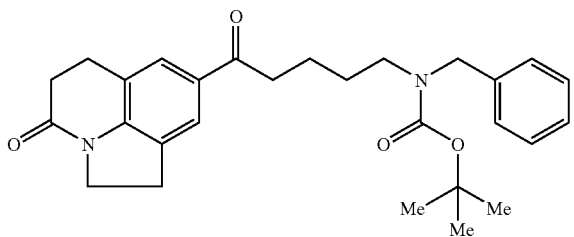

Using 8-(5-chloropentanoyl)-1,2,5,6-tetrahydro-4H-pyrrolo[3,2,1-ij]quinolin-4-one (500 mg) obtained in Reference Example 1 and benzylamine (550, mg) according to the same method as that of Reference Example 19, the title compound (498 mg) was obtained as a pale yellow oil.

$^1$H NMR (200 MHz, CDCl$_3$) δ 1.40-1.90 (4H, m), 1.45 (9H, s), 2.71 (2H, t, J=7.4 Hz), 2.80-3.35, (8H, m), 4.00-4.50 (4H, m), 7.15-7.40 (5H, m), 7.66 (1H, s), 7.70 (1H, s).

Reference Example 183 tert-Butyl 2-methoxybenzyl[5-oxo-5-(4-oxo-1,2,5,6-tetrahydro-4H-pyrrolo[3,2,1-ij]quinolin-8-yl)pentyl]carbamate

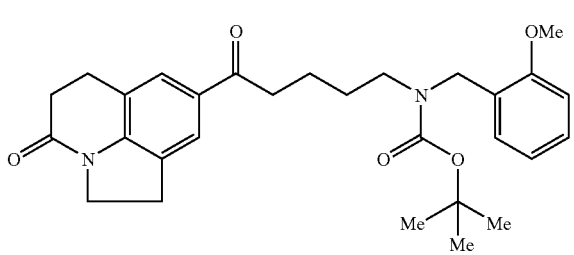

Using 8-(5-chloropentanoyl)-1,2,5,6-tetrahydro-4H-pyrrolo[3,2,1-ij]quinolin-4-one (500 mg) obtained in Reference Example 1 and 2-methoxybenzylamine (704 mg) according to the same method as that of Reference Example 19, the title compound (524 mg) was obtained as a pale yellow oil.

$^1$H NMR (200 MHz, CDCl$_3$) δ 1.40-1.80 (4H, m), 1.41 (9H, s), 2.71 (2H, t, J=7.6 Hz.), 2.80-3.40 (8H, m), 3.82 (3H, s), 4.00-4.50 (4H, m), 6.80-7.00 (2H, m), 7.05-7.30 (2H, m), 7.67 (1H, s), 7.71 (1H, s).

Reference Example 184 tert-Butyl benzyl[6-oxo-6-(4-oxo-1,2,5,6-tetrahydro-4H-pyrrolo[3,2,1-ij]quinolin-8-yl)hexyl]carbamate

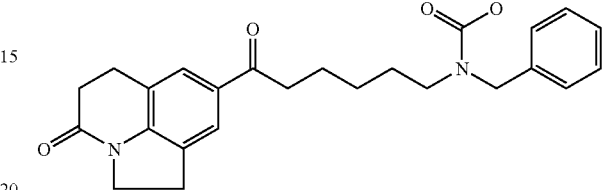

Using 8-(6-bromohexanoyl)-1,2,5,6-tetrahydro-4H-pyrrolo[3,2,1-ij]quinolin-4-one (700 mg) obtained in Reference Example 2 and benzylamine (643 mg) according to the same method as that of Reference Example 19, the title compound (554 mg) was obtained as a pale yellow oil.

$^1$H NMR (200 MHz, CDCl$_3$) δ 1.10-1.80 (6H, m), 1.45 (9H, s), 2.71 (2H, t, J=7.6 Hz), 2.68 (2H, t, J=7.6 Hz), 3.02 (2H, t, J=7.6 Hz), 3.10-3.30 (4H, m), 4.13 (2H, t, J=8.8 Hz), 4.42 (2H, s), 7.15-7.40 (5H, m), 7.67 (1H, s), 7.71 (1H, s).

Reference Example 185 tert-Butyl 2-methoxybenzyl[6-oxo-6-(4-oxo-1,2,5,6-tetrahydro-4H-pyrrolo[3,2,1-ij]quinolin-8-yl)hexyl]carbamate

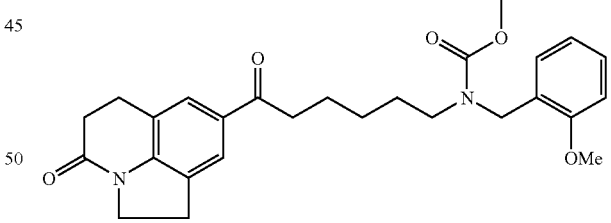

Using 8-(6-bromohexanoyl)-1,2,5,6-tetrahydro-4H-pyrrolo[3,2,1-ij]quinolin-4-one (600 mg) obtained in Reference Example 2 and 2-methoxybenzylamine (704 mg) according to the same method as that of Reference Example 19, the title compound (486 mg) was obtained as a pale yellow oil.

$^1$H NMR (300 MHz, CDCl$_3$) δ 1.15-1.60 (4H, m), 1.42 (9H, s), 2.72 (2H, quintet, J=7.5 Hz), 2.71 (2H, t, J=7.5 Hz), 2.88 (2H, t, J=7.5 Hz), 3.02 (2H, t, J=7.5 Hz), 3.10-3.30 (4H, m), 3.82 (3H, s), 4.13 (2H, t, J=8.4 Hz), 4.40-4.50 (2H, m), 6.80-6.95 (2H, m), 7.10-7.30 (2H, m), 7.67 (1H, s), 7.71 (1H, s).

Reference Example 186 tert-Butyl 6-oxo-6-(3-oxo-3,4-dihydro-2H-1,4-benzoxazin-6-yl)hexyl(2-phenylethyl)carbamate

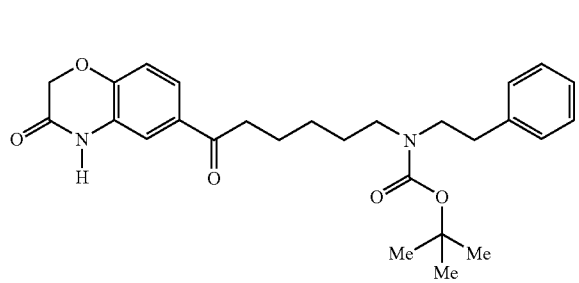

Using 6-(6-bromohexanoyl)-2H-1,4-benzoxazin-3(4H)-one (1.00 g) obtained in Reference Example 8 and 2-phenylethylamine (800 mg) according to the same method as that of Reference Example 19, the title compound (842 mg) was obtained as a pale yellow oil.

$^1$H NMR (300 MHz, CDCl$_3$) δ 1.20-1.85 (6H, m), 1.47 (9H, s), 2.75-2.95 (4H, m), 3.00-3.25 (2H, m), 3.30-3.45 (2H, m), 4.68 (2H, s), 7.00 (1H, d, J=8.7 Hz), 7.10-7.35 (5H, m), 7.50-7.65 (2H, m), 8.90-9.25 (1H, br).

Reference Example 187 tert-Butyl 2-(2-methoxyphenyl)ethyl[6-oxo-6-(3-oxo-3,4-dihydro-2H-1,4-benzoxazin-6-yl)hexyl]carbamate

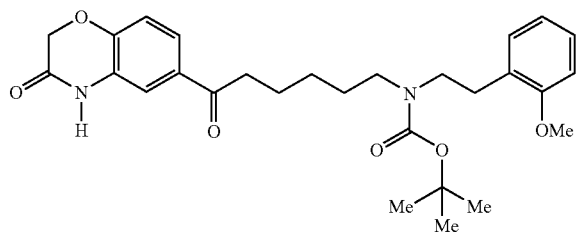

Using 6-(6-bromohexanoyl)-2H-1,4-benzoxazin-3(4H)-one (1.00 g) obtained in Reference Example 8 and 2-(2-methoxyphenylethylamine (925 mg) according to the same method as that of Reference Example 19, the title compound (974 mg) was obtained as a pale yellow oil.

$^1$H NMR (200 MHz, CDCl$_3$) δ 1.20-1.85 (6H, m), 1.46 (9H, s), 2.75-2.95 (4H, m), 3.00-3.25 (2H, m), 3.30-3.45 (2H, m), 3.82 (3H, s), 4.68 (2H, s), 6.80-7.25 (5H, m), 7.50-7.65 (2H, m), 8.90-9.30 (1H, br).

Reference Example 188 tert-Butyl 2-(2-chlorophenyl)ethyl[6-oxo-6-(3-oxo-3,4-dihydro-2H-1,4-benzoxazin-6-yl)hexyl]carbamate

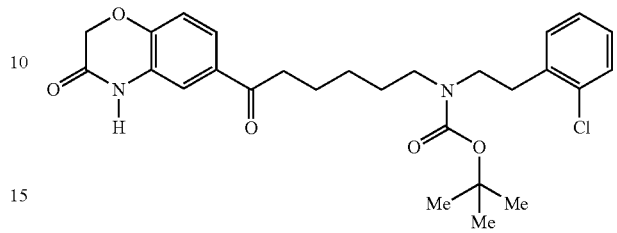

Using 6-(6-bromohexanoyl)-2H-1,4-benzoxazin-3(4H)-one (1.00 g) obtained in Reference Example 8 and 2-(2-chlorophenyl)ethylamine (952 mg) according to the same method as that of Reference Example 19, the title compound (974 mg) was obtained as a pale yellow oil.

$^1$H NMR (200 MHz, CDCl$_3$) δ 1.20-1.85 (6H, m), 1.44 (9H, s), 2.80-3.25 (6H, m), 3.35-4.45 (2H, m), 4.69 (2H, s), 6.95-7.40 (5H, m), 7.50-7.65 (2H, m), 9.00-9.40 (1H, br).

Reference Example 189

N-{5-[3-(1-acetyl-4-piperidinyl)propanoyl]-2-methoxyphenyl}-2,2,2-trifluoroacetamide

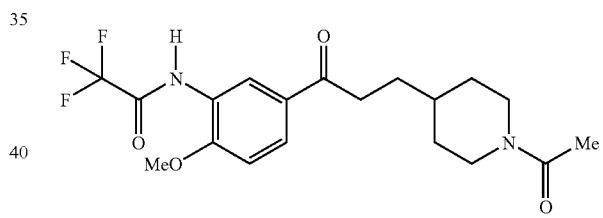

3-(1-Acetyl-4-piperidinyl)propionic acid (10.0 g) was added by portions to thionyl chloride (30 ml) at room temperature. After stirring at room temperature for 30 minutes, thionyl chloride was evaporated under reduced pressure to give the crude product of 3-(1-acetyl-4-piperidinyl)propionyl chloride. Aluminum chloride (20 g) was added by portions to a suspension of the crude product and 2,2,2-trifluoro-N-(2-methoxyphenyl)acetamide (10.0 g) at room temperature. After stirring at room temperature for 1 hour, the reaction mixture was poured into ice (200 g), extracted with ethyl acetate, and washed with brine. The organic layer was, dried over anhydrous magnesium sulfate, the solvent was evaporated under reduced pressure, the resulting residue was purified by silica gel chromatography (eluting solvent; ethyl acetate), and the solvent was evaporated to give the title compound as colorless crystals (8.83 g) having a melting point of 77 to 79° C.

$^1$H NMR (200 MHz, CDCl$_3$) δ 1.00-1.30 (3H, m), 1.50-1.90 (4H, m), 2.09 (3H, s), 2.53 (1H, tt, J=12.8, 2.8 Hz), 2.90-3.05 (3H, m), 3.70-3.90 (1H, m), 4.02 (3H, s), 4.50-4.70 (1H, m), 7.02 (1H, d, J=8.8 Hz), 7.89 (1H, dd, J=8.8, 2.2 Hz), 8.50-8.65 (1H, br), 8.95 (1H, d, J=2.2 Hz).

Reference Example 190

3-(1-Acetyl-4-piperidinyl)-1-(3-amino-4-methoxyphenyl)-1-propanone

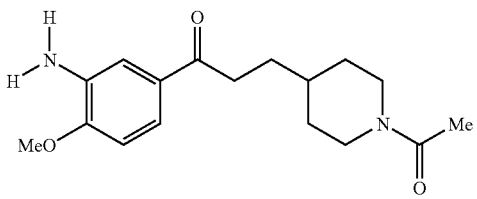

A suspension of N-{5-[3-(1-acetyl-4-piperidinyl)propanoyl]-2-methoxyphenyl}-2,2,2-triofluoroacetamide (3.00 g) obtained in Reference Example 189 in saturated potassium carbonate aqueous solution (20 ml), water (10 ml) and methanol (30 ml) was stirred at room temperature for 5 hours. Methanol was evaporated under reduced pressure, the residue was extracted with ethyl acetate, and washed with brine. The organic layer was dried over anhydrous magnesium sulfate and the solvent was evaporated under reduced pressure to give the title compound as colorless crystals (1.57 g) having a melting point of 101 to 103° C.

$^1$H NMR (200 MHz, CDCl$_3$) δ 1.00-1.25 (3H, m), 1.45-1.85 (4H, m), 2.08 (3H, s), 2.52 (1H, tt, J=12.8, 3.0 Hz), 2.85-3.10 (3H, m), 3.70-3.90 (1H, m), 3.91 (3H, s), 3.90-4.00 (2H, br), 4.50-4.70 (1H, m), 6.80 (1H, d, J=8.4 Hz), 7.30-7.45 (2H, m).

elementary analysis as C$_{17}$H$_{24}$N$_2$O$_3$
calculation value:C, 67.08; H, 7.95; N, 9.20.
experimental value:C, 66.83; H, 7.73; N, 9.18.

Reference Example 191

1-(3-Amino-4-methoxyphenyl)-3-(4-piperidinyl)-1-propanone dihydrochloride

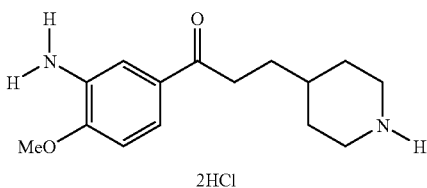

A solution of 3-(1-acetyl-4-piperidinyl)-1-(3-amino-4-methoxyphenyl)-1-propanone (500 mg) obtained in Reference Example 190 in concentrated hydrochloric acid (10 ml) was stirred at 130° C. for 6 hours. The solvent was evaporated, the residue was filtered, and washed successively with ethanol and diethyl ether. The resulting crystals were air-dried to give the title compound as colorless crystals (544 mg) having a melting point of 210° C. (dec).

$^1$H NMR (300 MHz, DMSO-d$_6$) δ 1.25-1.45 (2H, m), 1.50-1.65 (3H, m), 1.75-1.90 (2H, m), 2.70-2.90 (2H, m), 2.97 (2H, t, J=6.9 Hz), 3.15-3.25 (2H, m), 3.94 (3H, s), 7.00-9.50 2H, br), 7.20 (1H, d, J=8.4 Hz), 7.80-7.90 (2H, m), 8.75-9.25 (3H, br).

Reference Example 192

8-(3-Chloropropanoyl)-1,2,5,6-tetrahydro-4H-pyrrolo[3,2,1-ij]quinolin-4-one

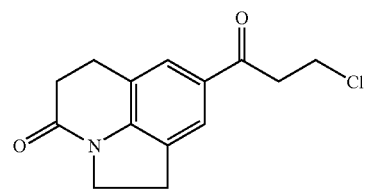

Using 1,2,5,6-tetrahydro-4H-pyrrolo[3,2,1-ij]quinolin-4-one (10.0 g) and 3-chloropropanoyl chloride (6.06 ml) according to the same method as that of Reference Example 1, the title compound (12.0 g) was obtained as colorless crystals having a melting point of 154 to 155° C.

$^1$H NMR (300 MHz, CDCl$_3$) δ 2.72 (2H, t, J=7.8 Hz), 3.03 (2H, t, J=7.8 Hz), 3.23 (2H, t, J=8.7 Hz), 3.39 (2H, t, J=6.9 Hz), 3.91 (2H, t, J=6.9 Hz), 4.13 (2H, t, J=8.7 Hz), 7.67 (1H, s), 7.71 (1H, s).

Reference Example 193 tert-Butyl (±)-2,3-dihydro-1H-inden-1-yl-[5-oxo-5-(4-oxo-1,2,5,6-tetrahydro-4H-pyrrolo[3,2,1-ij]quinolin-8-yl)pentyl]carbamate

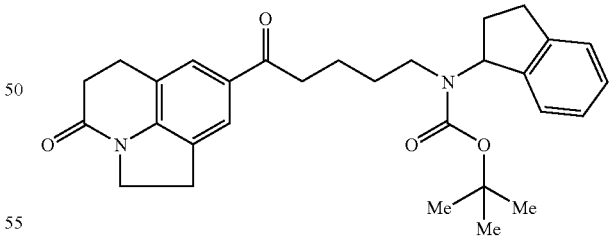

Using 8-(5-chloropentanoyl)-1,2,5,6-tetrahydro-4H-pyrrolo[3,2,1-ij]quinolin-4-one (500 mg) obtained in Reference Example 1 and (±)-2,3-dihydro-1H-inden-1-ylamine (683 mg) according to the same method as that of Reference Example 19, the title compound (332 mg) was obtained as a pale yellow oil.

$^1$H NMR (200 MHz, CDCl$_3$) δ 1.20-2.10 (13H, m), 2.60-3.10 (12H, m), 3.10-3.30 (2H, m), 3.50-3.65 (1H, m), 4.00-4.20 (2H, m), 7.10-7.30 (3H, m), 7.60-7.80 (3H, m).

Reference Example 194 tert-Butyl 2,3-dihydro-1H-inden-2-yl-[5-oxo-5-(4-oxo-1,2,5,6-tetrahydro-4H-pyrrolo[3,2,1-ij]quinolin-8-yl)pentyl]carbamate

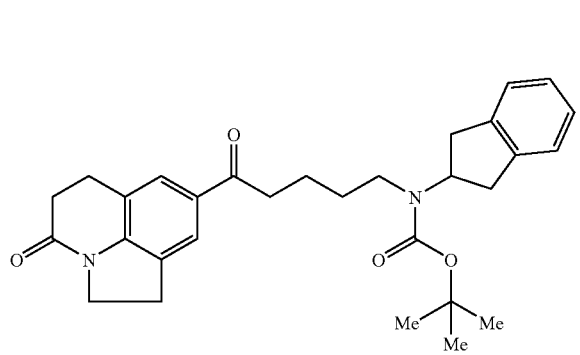

Using 8-(5-chloropentanoyl)-1,2,5,6-tetrahydro-4H-pyrrolo[3,2,1-ij]quinolin-4-one (500 mg) obtained in Reference Example 1 and 2,3-dihydro-1H-inden-2-ylamine (683 mg) according to the same method as that of Reference Example 19, the title compound (461 mg) was obtained as a pale yellow oil.

$^1$H NMR (200 MHz, CDCl$_3$) δ 1.42 (9H, s), 1.50-1.75 (2H, m), 1.80-2.00 (2H, m), 2.72 (2H, t, J=7.6 Hz), 2.80-3.30 (11H, m), 3.50-3.65 (1H, m), 4.00-4.20 (3H, m), 7.05-7.20 (4H, m), 7.60-7.75 (2H, m).

Reference Example 195

6-(5-Chloropentanoyl)-3,4-dihydroquinolin-2(1H)-one

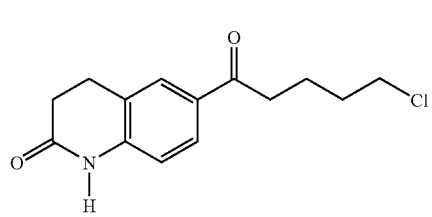

Using 3,4-dihydroquinolin-2(1H)-one (2.94 g) and 5-chloropentanoyl chloride (3.7 g) according to the same method as that of Reference Example 1, the title compound was obtained as colorless crystals (1.59 g) having a melting point of 145 to 146° C.

$^1$H NMR (400 MHz, CDCl$_3$) δ 1.84-1.94 (4H, m), 2.67 (2H, t, J=6.4 Hz), 2.96 (2H, t, J=6.8 Hz), 3.05 (2H, t, J=7.5 Hz), 3.59 (2H, t, J=6.4 Hz), 6.90 (1H, d, J=8.7 Hz), 7.81 (1H, d, J=8.7 Hz), 7.82 (1H, s), 9.28 (1H, s).

IR (KBr) vcm$^{-1}$: 3273, 1680, 1604, 1361, 1314, 1227, 1145.

Reference Example 196 tert-Butyl 5-oxo-5-(2-oxo-1,2,3,4-tetrahydroquinolin-6-yl)pentyl(2-phenylethyl)carbamate

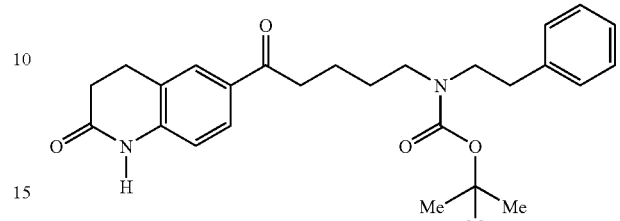

Using 6-(5-chloropentanoyl)-3,4-dihydroquinolin-2(1H)-one (399 mg) obtained in Reference Example 195 and 2-phenylethylamine (454 mg) according to the same method as that of Reference Example 19, the tile compound (530 mg) was obtained as a pale yellow oil.

$^1$H NMR (400 MHz, CDCl$_3$) δ 1.44 (9H, s), 1.51-1.73 (4H, m), 2.68 (2H, t, J=7 Hz), 2.75-2.86 (2H, m), 2.88-2.98 (2H, m), 3.03 (2H, t, J=7 Hz), 3.08-3.24 (2H, m), 3.32-3.42 (2H, m), 6.87 (1H, d, J=8.4 Hz), 7.18-7.30 (5H, mi), 7.79 (1H, d, J=6 Hz), 7.80 (1H, s), 9.09 (1H, br).

Reference Example 197 tert-Butyl 2-(2-methoxyphenyl)ethyl[5-oxo-5-(2-oxo-1,2,3,4-tetrahydroquinolin-6-yl)pentyl]carbamate

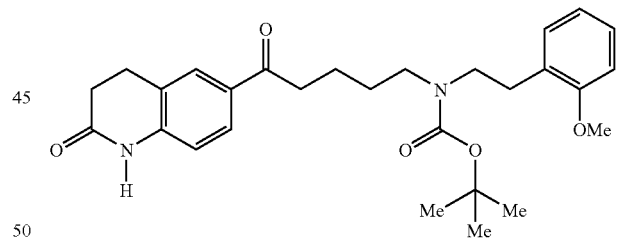

Using 6-(5-chloropentanoyl)-3,4-dihydroquinolin-2(1H)-one (399 mg) obtained in Reference Example 195 and 2-(2-methoxyphenyl)ethylamine (567 mg) according to the same method as that of Reference Example 19, the title compound (638 mg) was obtained as a pale yellow oil.

$^1$H NMR (400 MHz, CDCl$_3$) δ 1.43 (9H, s), 1.51-1.72 (4H, m), 2.68 (2H, t, J=8 Hz), 2.78-2.88 (2H, m), 2.89-2.97 (2H, m), 3.03 (2H, t, J=7.3 Hz), 3.08-3.28 (2H, m), 3.30-3.42 (2H, m), 3.82 (3H, s) 6.83 (1H, d, J=8.4 Hz), 6.87-6.90 (2H, m), 7.09-7.21 (2H, m), 7.79 (1H, d, J=6 Hz), 7.80 (1H, s) 9.31 (1H, br).

Reference Example 198 tert-Butyl 2-(2-chlorophenyl)ethyl[5-oxo-5-(2-oxo-1,2,3,4-tetrahydroquinolin-6-yl)pentyl]carbamate

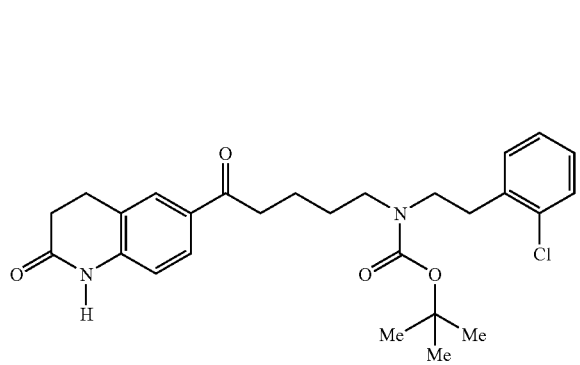

Using 6-(5-chloropentanoyl)-3,4-dihydroquinolin-2(1H)-one (399 mg) obtained in Reference Example 195 and 2-(2-chlorophenyl)ethylamine (584 mg) according to the same method as that of Reference Example 19, the title compound (682 mg) was obtained as a pale yellow oil.

$^1$H NMR (400 MHz, CDCl$_3$) δ 1.41 (9H, s), 1.51-1.73 (4H, m), 2.68 (2H, t, J=7.3 Hz), 2.91-3.01 (4H, m), 3.03 (2H, t, J=7.3 Hz), 3.12-3.25 (2H, m), 3.41 (2H, t, J=7.3 Hz), 6.87 (1H, d, J=8.4 Hz), 7.17-7.20 (3H, m), 7.33 (1H, d, J=7 Hz), 7.80 (1H, d, J=6 Hz), 7.81 (1H, s) 9.01 (1H, br).

Reference Example 199

6-(6-Bromohexanoyl)-3,4-dihydroquinolin-2(1H)-one

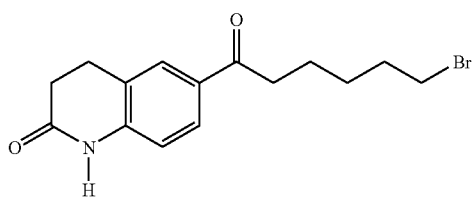

Using 3,4-dihydroquinolin-2(1H)-one (2.94 g) and 6-bromohexanoyl chloride (5.1 g) according to the same method as that of Reference Example 1, the title compound was obtained as colorless crystals (1.62 g) having a melting point of 116 to 117° C.

$^1$H NMR (400 MHz, CDCl$_3$) δ 1.50-1.57 (2H, m), 1.73-1.79 (2H, m), 1.88-1.96 (2H, m), 2.69 (2H, t, J=6.4 Hz), 2.95 (2H, t, J=7.5 Hz), 3.05 (2H, t, J=7.5 Hz), 3.43 (2H, t, J=6.4 Hz), 6.92 (1H, d, J=8.7 Hz), 7.80 (1H, d, J=8.7 Hz), 7.85 (1H, s), 9.51 (1H, s).

IR (KBr) vcm$^{-1}$: 3192, 3055, 1679, 1593, 1367, 1321, 1254.

Reference Example 200 tert-Butyl 2-(2-methoxyphenyl)ethyl[5-(1-methyl-2-oxo-1,2,3,4-tertahydroquinolin-6-yl)-5-oxopentyl]carbamate

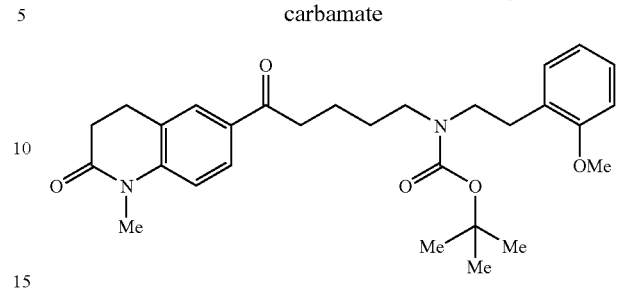

Using 6-(5-chloropentanoyl)-1-methyl-3,4-dihydroquinolin-2(1H)-one (224 mg) obtained in Reference Example 154 and 2-(2-methoxyphenyl)ethylamine (266 mg) according to the same method as that of Reference Example 19, the title compound (230 mg) was obtained as a pale yellow oil.

$^1$H NMR (400 MHz, CDCl$_3$) δ 1.43 (9H, s), 1.51-1.76 (4H, m), 2.68 (2H, t, J=7 Hz), 2.77-2.88 (2H, m), 2.96 (4H, t, J=7 Hz), 3.12-3.24 (2H, m), 3.32-3.37 (2H, m), 3.38 (3H, s), 3.82 (3H, s), 6.83-6.89 (2H, m), 7.01 (1H, d, J=8.5 Hz), 7.06-7.21 (2H, m), 7.78 (1H, s) 7.87 (1H, d, J=8 Hz).

Reference Example 201 tert-Butyl 2-(2-chlorophenyl)ethyl[5-(1-methyl-2-oxo-1,2,3,4-tertahydro-6-quinolinyl)-5-oxopentyl]carbamate

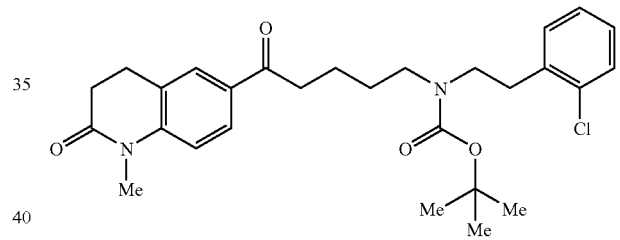

Using 6-(5-chloropentanoyl)-1-methyl-3,4-dihydroquinolin-2(1H)-one (224 mg) obtained in Reference Example 154 and 2-(2-chlorophenyl)ethylamine (274 mg) according to the same method as that of Reference Example 19, the title compound (244 mg) was obtained as a pale yellow oil.

$^1$H NMR (400 MHz, CDCl$_3$) δ 1.41 (9H, s), 1.51-1.76 (4H, m), 2.68 (2H, t, J=7 Hz), 2.92-2.98 (6H, m), 3.12-3.24 (2H, m), 3.39 (3H, s), 3.41 (2H, t, J=7 Hz), 7.02 (1H, d, J=8.5 Hz), 7.14-7.28 (3H, m), 7.33 (1H, d, J=7 Hz), 7.78 (1H, s,), 7.87 (1H, d, J=8 Hz).

Reference Example 202

(±)-5-[[2-(2-Chlorophenyl)ethyl](methyl)amino]hexanoic acid

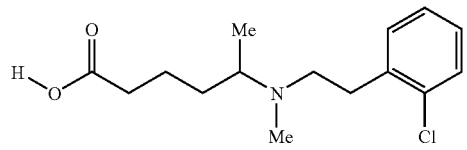

4.75 g (30 mmol) of Ethyl 5-oxohexanoate was placed into a 300 ml four-neck flask, and 100 ml of THF was added thereto to dissolve them At room temperature, 5.1 g (30 mmol) of N-methyl-2-(2-chlorophenyl)ethylamine was added, and further 8.3 g (39 mmol) of NaBH(OAc)$_3$ was added. After stirring overnight at room temperature, the reaction mixture was, concentrated, and each 50 ml of 6% sodium bicarbonate was added to the residue to neutralize. The liberated oil was extracted with ethyl acetate (50ml×2), dried over MgSO$_4$, and concentrated to give 5-ethyl (±)-[[2-(2-chlorophenyl)ethyl](methyl)amino]hexanoate as a pale yellow oil (6.38 g).

$^1$H NMR (400 MHz, CDCl$_3$) δ 0.94 (3H, d, J=6.6 Hz), 1.19-1.28 (1H, m), 1.25 (3H, t, J=7.0 Hz), 1.44-1.52 (1H, m), 1.56-1.64 (2H, m), 2.25 (2H, t, J=7.3 Hz), 2.29 (3H, s), 2.51-2.69 (3H, m), 2.84-2.89 (2H, m), 4.12 (2H, q, J=7.0 Hz), 7.12-7.25 (3H, m), 7.32 (1H, dd, J=7.6, 1.5 Hz).

IR (neat) vcm$^{-1}$: 1735, 1652, 1476, 1249, 1177, 1053, 752.

6.2 g (20 mmol) of 5-ethyl (±)-[[2-(2-chlorophenyl)ethyl](methyl)amino]hexanoate was placed into a 100 ml eggplant-type flask, and EtOH (10 ml) was added to dissolve them. At room temperature, 1.35 g (24 mmol) of KOH dissolved in 10 ml of water was added. After stirring at room temperature for 16 hours, EtOH was evaporated, 4 ml (24 mmol) of 6N hydrochloric, acid was added to the residue to neutralize, concentrated to dryness, and 20 ml of EtOH was added to the residue to dissolve it. The insolubles were filtered off, and the filtrated was concentrated to dryness to give the title compound as a pale yellow oil (6.16 g).

$^1$H NMR (400 MHz, CDCl$_3$) δ 1.21 (3H, d, J=6.6 Hz), 1.41-1.51 (1H, m), 1.65-1.74 (2H,m), 1.99-2.01 (1H, m), 2.24-2.41 (2H, m), 2.61 (3H, s), 2.92-3.04 (3H, m), 3.20 (2H, t, J=8.3 Hz), 7.16-7.23 (2H, m), 7.32-7.36 (2H, m), 9.35 (1H, br).

IR (neat) vcm$^{-1}$: 3418, 1718, 1630, 1476, 1398, 1053, 757.

Reference Example 203

5-(5-Chloropentanoyl)-N-methyl-2,3-dihydro-1-benzofuran-7-sulfonamide

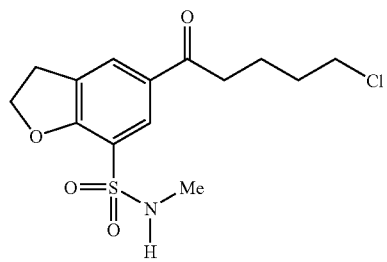

Using 5-(5-chloropentanoyl)-2,3-dihydro-1-benzofuran-7-sulfonyl chloride (5.06 g) obtained in Reference Example 69 and a 40% mehtylamine-methanol solution (2.6 g) according to the same method as that of Reference Example 66, the title compound was obtained as colorless crystals (4.82 g) having a melting point of 120 to 121° C.

$^1$H NMR (400 MHz, CDCl$_3$) δ 1.85-1.92 (4H, m), 2.66 (3H, d, J=5.4 Hz), 2.98-3.01 (2H, m), 3.35 (2H, t, J=8.8 Hz), 3.57-3.60 (2H, m), 4.78 (1H, q, J=5.4 Hz), 4.88 (2H, t, J=8.8 Hz), 8.06 (1H, s), 8.22 (1H, s).

IR (KBr) vcm$^{-1}$:3326, 1664, 1603, 1586, 1480, 1383, 1357, 1328, 1266, 1161, 1115, 868, 579.

Reference Example 204

5-(5-Chloropentanoyl)-N,N-dimethyl-2,3-dihydro-1-benzofuran-7-sulfonamide

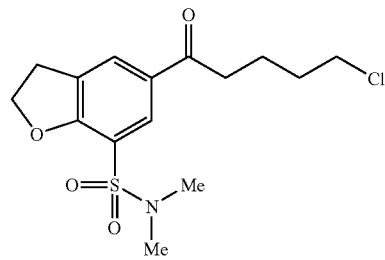

Using 5-(5-chloropentanoyl)-2,3-duhydro-1-benzofuran-7-sulfonyl chloride (5.06 g) obtained in Reference Example 69 and dimethylamine (3 ml) according to the same method as that of Reference Example 66, the title compound was obtained as colorless crystals (4.93 g) having a melting point of 113 to 114° C.

$^1$H NMR (400 MHz, CDCl$_3$) δ 1.84-1.93 (4H, m), 2.84 (6H, s), 2.96-3.00 (2H, m), 3.33 (2H, t, J=8.8 Hz), 3.57-3.60 (2H, m), 4.83 (2H, q, J=5.4 Hz), 8.03 (1H, s), 8.18 (1H, s).

IR (KBr) vcm$^{-1}$:1681, 1603, 1479, 1462, 1422, 1340, 1264, 1154, 1119, 956, 710, 583.

Reference Example 205

5-Chloro-1-(2,3-dihydro-2,2-dimethyl-1-benzofuran-5-yl)pentane-1-one

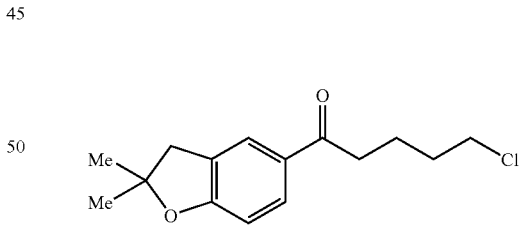

Using 2,2-dimethyl-2,3-dihydro-1-benzofuran (3.0 g) and 5-chlorovaleryl chloride (3.4 g) according to the same method as that of Reference Example 1, the title compound was obtained as a fine yellow oil (3.6 g).

$^1$H NMR (400 MHz, CDCl$_3$) δ 1.50 (6H, s), 1.83-1.92 (4H, m), 2.91-2.95 (2H, m), 3.04 (2H, s), 3.56-3.59 (2H, m), 6.74 (1H, d, J=8.8 Hz), 7.79 (1H, d, J=8.8 Hz), 7.81 (1H, s).

IR (neat) vcm$^{-1}$: 1674, 1607, 1490, 1441, 1372, 1245, 1225, 1094, 868

Reference Example 206

5-Chloro-1-(3,4-dihydro-2H-chromen-6-yl)pentane-1-one

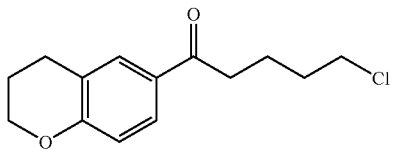

Using chroman (5.40 g) and 5-chlorovaleryl chloride (6.82 g) according to the same method as that of Reference Example 1, the title compound was obtained as a fine yellow oil (7.9 g).

$^1$H NMR (400 MHz, CDCl$_3$) δ 1.83-1.91 (4H, m), 2.00-2.06 (2 H, m), 2.83 (2H, t, J=6.6 Hz), 2.91-2.96 (2H, m,) 3.58 (2H, t, J=6.6 Hz), 4.24 (2H, t, J=5.2 Hz), 6.81 (1H, d, J=8.8 Hz), 7.70 (1H, s), 7.71 (1H, d, J=8.8 Hz).

IR (neat) vcm$^{-1}$: 1675, 1606, 1577, 1499, 1317, 1247, 1162, 1133, 1118, 1060, 1005, 821.

Reference Example 207

6-(5-Chloropentanoyl)chroman-8-sulfonyl chloride

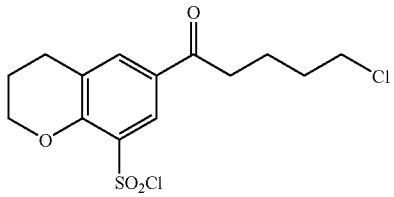

Using 5-chloro-1-(3,4-dihydro-2H-chromen-6-yl)pentan-1-one (5.1 g) obtained in Reference Example 206 according to the same method as that of Reference Example 65, the title compound was obtained as a colorless oil (3.57 g).

$^1$H NMR (400 MHz, CDCl$_3$) δ 1.85-1.94 (4H, m), 2.14-2.19 (2H, m), 2.93-3.00 (4H, m), 3.59 (2H, t, J=5.9 Hz), 4.54 (2H, t, J=5.6 Hz), 8.03 (1H, s), 8.33 (1H, s).

IR (neat) vcm$^{-1}$: 1686, 1600, 1567, 1485, 1371, 1278, 1258, 1172, 1132, 1002, 579, 557.

Reference Example 208

6-(5-Chloropentanoyl)-8-chromansulfonamide

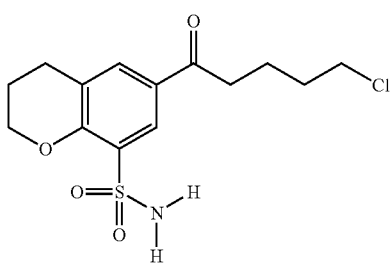

Using 6-(5-chloropentanoyl)-8-chromansulfonyl chloride (3.5 g) obtained in Reference Example 207 according to the same method as that of Reference Example 66, the title compound was obtained as colorless crystals (2.9 g) having a melting point of 168 to 169° C.

$^1$H NMR (400 MHz, CDCl$_3$) δ 1.67-1.80 (4H, m), 1.97 (2H, t, J=5.3 Hz), 2.86 (2H, t, J=6.1 Hz), 3.00 (2H, t, J=6.6 Hz), 3.67 (2H, t, J=6.1 Hz), 4.36 (2H, t, J=5.3 Hz), 7.15 (2H, s), 7.94 (1H, d, J=1.8 Hz), 8.10 (1H, d, J=1.8 Hz).

IR (KBr) vcm$^{-1}$: 3376, 3272, 1695, 1599, 1482, 1459, 1419, 1309, 1244, 1137, 906, 744.

Reference Example 209 tert-Butyl 5-(2,3-dihydro-2,2-dimethyl-1-benzofuran-5-yl)-5-oxopentyl[2-(2-chlorophenyl)ethyl]carbamate


Using 5-chloro-1-(2,3-dyhydro-2,2-dimethyl-1-benzofuran-5-yl)pentan-1-one (543 mg) obtained in Reference Example 205 and 2-(2-chlorophenyl)ethylamine (778 mg) according to the same method as that of Reference Example 19, the title compound was obtained as a fine yellow oil (612 mg).

$^1$H NMR (400 MHz, CDCl$_3$) δ 1.41 (9H, s), 1.49 (6H, s), 1.51-1.72 (4H, m), 2.85-3.00 (4H, m), 3.03 (2H, s), 3.07-3.25 (2H, m), 3.41 (2H, t, J=7.3 Hz), 6.73 (1H, d, J=9.1 Hz), 7.12-7.34 (4H, m), 7.80 (2H, br.s).

Reference Example 210 tert-Butyl 5-(3,4-dihydro-2H-chromen-6-yl)-5-oxopentyl[2-(2-chlorophenyl)ethyl]carbamate

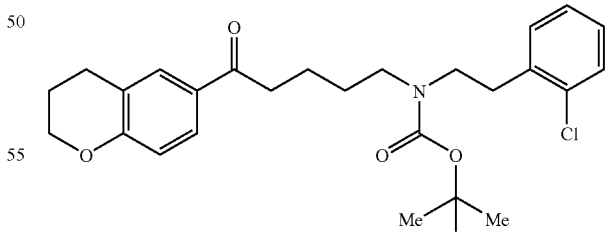

Using 5-chloro-1-(3,4-dihydro-2H-chromen-6-yl)pentan-1-one (505 mg) obtained in Reference Example 206 and 2-(2-chlorophenyl)ehtylamine (778 mg) according to the same method as that of Reference Example 19, the title compound was obtained as a fine yellow oil (793 mg).

$^1$H NMR (400 MHz, CDCl$_3$) δ 1.41 (9H, s), 1.51-1.73 (4H, m), 2.01 (2H, t, J=6 Hz), 2.82 (2H, t, J=6 Hz), 2.85-3.01 (4H, m), 3.07-3.23 (2H, m), 3.41 (2H, t, J=7 Hz), 4.23 (2H, q, J=5.3 Hz), 6.80 (1H, d, J=9.1 Hz), 7.12-7.34 (4H, m), 7.70 (2H, br.s).

Reference Example 211 tert-Butyl 5-{7-[(methylamino)sulfonyl]-2,3-dihydro-1-benzofuran-5-yl}-5-oxopentyl[2-(2-methoxyphenyl)ethyl]carbamate

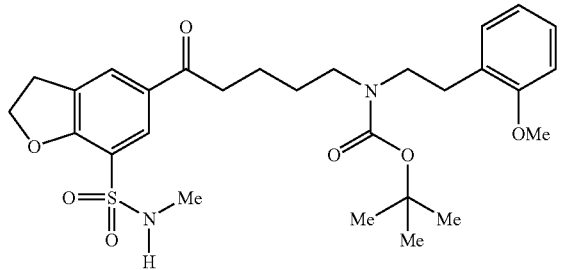

Using 5-(5-chloropentanoyl)-N-methyl-2,3-dihydro-1-benzofuran-7-sulfonamide (664 mg) obtained in Reference Example 203 and 2-(2-methoxyphenyl)ethylamine (762 mg) according to the same method as that of Reference Example 19, the title compound was obtained as a colorless oil (864 mg).

$^1$H NMR (400 MHz, CDCl$_3$) δ 1.43 (9H, s), 1.50-1.73 (4H, m), 2.65 (3H, d, J=5.4 Hz), 2.82 (2H, br.s), 2.95 (2H, br.s), 3.08-3.23 (2H, m), 3.31-3.37 (4H, m), 3.83 (3H, s), 4.81 (1H, q, J=5.4 Hz), 4.86 (2H, t, J=8.8 Hz), 6.83-6.89 (2H, m), 7.09-7.21 (2H, m), 8.04 (1H, d, J=1.5 Hz), 8.22, (1H, d, J=1.5 Hz).

Reference Example 212 tert-Butyl 5-{7-[(methylamino)sulfonyl]-2,3-dihydro-1benzofuran-5-yl}-5-oxopentyl[2-(2-chloroyphenyl)ethyl]carbamate

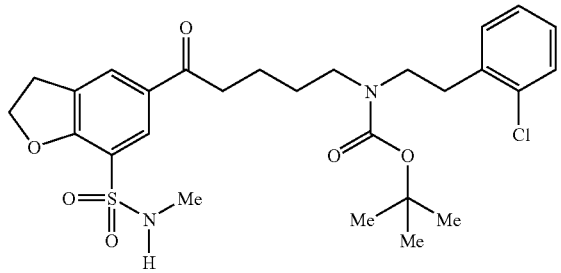

Using 5-(5-chloropentanoyl)-N-methyl-2,3-dihydro-1-benzofuran-7-sulfonamide (664 mg) obtained in Reference Example 203 and 2-(2-chlorophenyl)ethylamine (778 mg) according to the same method as that of Reference Example 19, the title compound was obtained as colorless crystals (890 mg) having a melting point of 87 to 88° C.

$^1$H NMR (400 MHz, CDCl$_3$) δ 1.41 (9H, s), 1.50-1.73 (4H, m), 2.66 (3H, d, J=5.4 Hz), 2.95 (4H, br.s), 3.08-3.27 (2H, m), 3.34 (2H, t, J=8.8 Hz), 3.41 (2H, t, J=7.5 Hz), 4.78 (1H, q, J=5.4 Hz), 4.87 (2H, t, J=8.8 Hz), 7.13-7.29 (3H, m), 7.33 (1H, d, J=6.6 Hz), 8.04 (1H, d, J=1.2 Hz), 8.22 (1H, d, J=1.2 Hz).

Reference Example 213 tert-Butyl 5-{7-[(dimethylamino)sulfonyl]-2,3-dihydro-1-benzofuran-5-yl}-5-oxopentyl[2-(2-methoxyphenyl)ethyl]carbamate

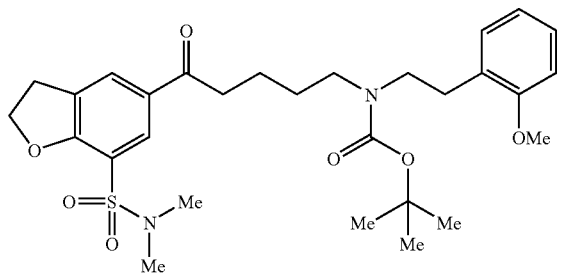

Using 5-(5-chloropentanoyl)-N,N-dimethyl-2,3-dihydro-1-benzofuran-7-sulfonamide (692 mg) obtained in Reference Example 204 and 2-(2-methoxyphenyl)ethylamine (762 mg) according to the same method as that of Reference Example 19, the title compound was obtained as a colorless oil (875 mg).

$^1$H NMR (400 MHz, CDCl$_3$) δ 1.43 (9H, s), 1.50-1.73 (4H, m), 2.79-2.87 (2H, m), 2.83 (6H, s), 2.94 (2H, br.s), 3.08-3.23 (2H, m), 3.29-3.51 (4H, m), 3.83 (3H, s), 4.82 (2H, t, J=8.8 Hz), 6.83-6.88 (2H, m), 7.09-7.21 (2H, m), 8.01 (1H, d, J=1.5 Hz), 8.17 (1H, d, J=1.5 Hz).

Reference Example 214 tert-Butyl 2-(2-chlorophenyl)ethyl(5-{7-[(dimethylamino)sulfonyl]-2,3-dihydro-1-benzofuran-5-yl}-5-oxopentyl)carbamate

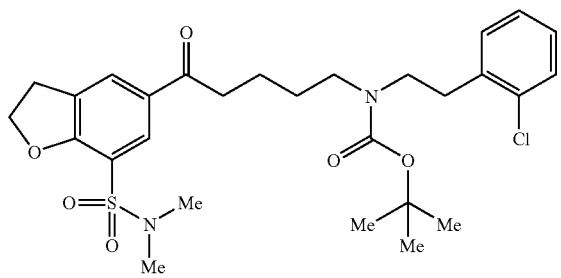

Using 5-(5-chloropentanoyl)-N,N-dimethyl-2,3-dihydro-1-benzofuran-7-sulfonamide (692 mg) obtained in Reference Example 204 and 2-(2-chlorophenyl)ethylamine (778 mg) according to the same method as that of Reference Example 19, the title compound was obtained as colorless crystals (960 mg) having a melting point of 86 to 87° C.

$^1$H NMR (400 MHz, CDCl$_3$) δ 1.41 (9H, s), 1.50-1.73 (4H, m), 2.84 (6H, s), 2.95 (4H, br.s), 3.08-3.25 (2H, m), 3.32 (2H, t, J=8.8 Hz), 3.41 (2H, t, J=7.5 Hz), 4.82 (2H, t, J=8.8 Hz), 7.13-7.29 (3H, m), 7.33 (1H, d, J=6.6 Hz), 8.01 (1H, d, J=1.4 Hz), 8.17 (1H, d, J=1.4 Hz).

Reference Example 215 tert-Butyl 5-[8-(aminosulfonyl)-3,4-dihydro-2H-chromen-6-yl]-5-oxopentyl[2-(2-methoxyphenyl)ethyl]carbamate

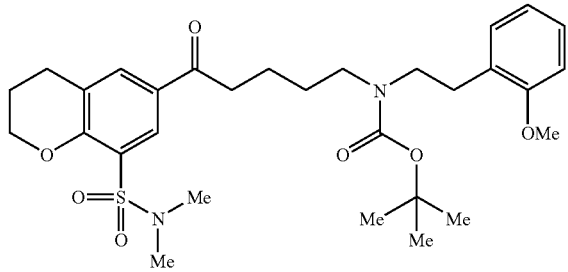

Using 6-(5-chloropentanoyl)-8-chromansulfonamide (664 mg) obtained in Reference Example 208 and 2-(2-methoxyphenyl)ethylamine (762 mg) according to the same method as that of Reference Example 19, the title compound was obtained as a colorless oil (650 mg).

$^1$H NMR (400 MHz, CDCl3) δ 1.40 (9H, s), 1.51-1.70 (4H, m), 2.11 (2H, br.s), 2.79-2.89 (6H, m), 3.07-3.23, (2H, m), 3.33 (2H, t, J=7.1 Hz), 3.82 (3H, s), 4.47 (2H, t, J=5.1 Hz), 5.29 (2H, s), 6.83-6.88 (2H, m), 7.06-7.20 (2H, m), 7.89 (1H, s), 8.27 (1H, s).

Reference Example 216 tert-Butyl 5-[8-(aminosulfonyl)-3,4-dihydro-2H-chromen-6-yl]-5-oxopentyl[2-(2-chlorophenyl)ethyl]carbamate

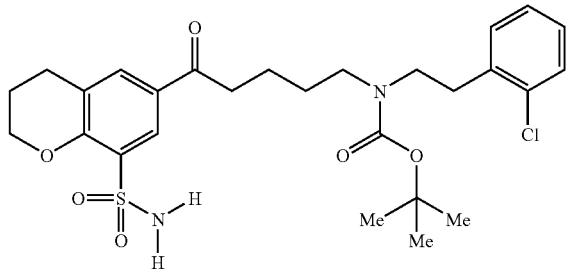

Using 6-(5-chloropentanoyl)-8-chromansulfonamide (664 mg) obtained in Reference Example 208 and 2-(2-chlorophenyl)ethylamine (778 mg) according to the same method as that of Reference Example 19, the title compound was obtained as a colorless oil (677 mg).

$^1$H NMR (400 MHz, CDCl$_3$) δ 1.38 (9H, s), 1.51-1.71 (4H, m), 2.12 (2H, br.s), 2.89-2.93 (6H, m), 3.11-3.21 (2H, m), 3.39 (2H, br.s), 4.47 (2H, t, J=5.1 Hz), 5.23 (2H, s), 7.13-7.34 (4H, m), 7.90 (1H, s), 8.27 (1H, s).

Reference Example 217

5-(5-Chloropentanoyl)-1-methyl-1,3-dihydro-2H-benzimidazol-2-one and 6-(5-chloropentanoyl)-1-methyl-1,3-dihydro-2H-benzimidazol-2-one

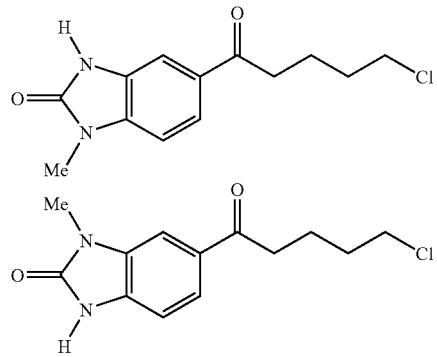

Using 1-methyl-1,3-dihydro-2H-benzimidazol-2-one (4.45 g) and 5-chlorovaleryl chloride (5.58 g) according to the same method as that of Reference Example 1, a mixture of the title compound (1.5:1) was obtained as colorless crystals (5.5 g).

$^1$H NMR (400 MHz, DMSO-d$_6$) δ 1.67-1.81 (4H, m), 2.99-3.05 (2H, m), 3.30 (3H×⅗, s), 3.32 (3H×⅖, s), 3.61-3.69 (2H, m,), 7.03 (1H×⅖, d, J=8.3 Hz), 7.14 (1H×⅗, d, J=8.3 Hz), 7.49 (1H×⅗, d, J=1.5 Hz), 7.64 (1H×⅖, d, J=1.5 Hz), 7.69 (1H×⅖, dd, J=8.3, 1.5 Hz), 7.73 (1H×⅗, dd, J=8.8, 1.5 Hz), 11.09 (1H×⅗, s), 11.23 (1H×⅖, s).

Reference Example 218 tert-Butyl 2-(2-chlorophenyl)ethyl[5-(1-methyl-2-oxo-2,3-dihydro-1H-benzimidazol-5-yl)-5-oxopentyl]carbamate (A) and tert-butyl 2-(2-chlorophenyl)ethyl[5-(3-methyl-2-oxo-2,3-dihydro-1H-benzimidazol-5-yl)-5-oxopentyl]carbamate (B)

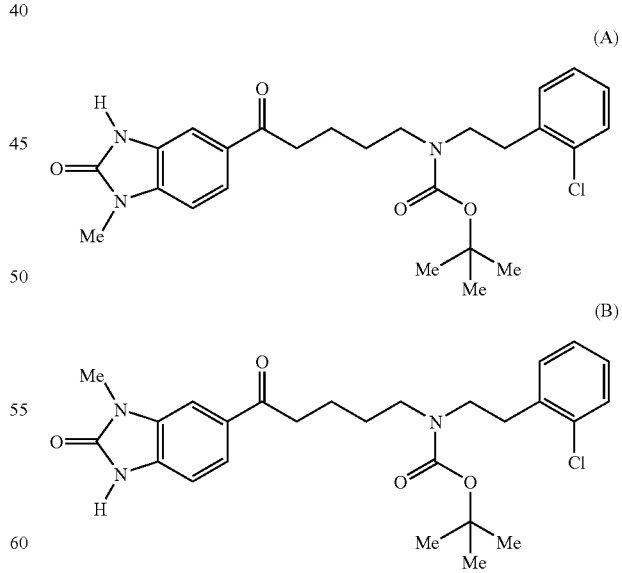

Using a mixture of 5-(5-chloropentanoyl)-1-methyl-1,3-dihydro-2H-benzimidazol-2-one and 6-(5-chloropentanoyl)-1-methyl-1,3-dihydro-2H-benzimidazol-2-one (1.60 g) obtained in Reference Example 217 and 2-(2-chlorophenyl) ehtylamine (2.33 g) according to the same method as that of Reference Example 19, the title compound was obtained as colorless crystals (1-methyl compound (A):1.0 g) having a melting point of 121 to 122° C. and a fine yellow oil (3-methyl compound (B):645 mg).

¹H NMR (1-methyl compound (A);400 MHz, CDCl₃) δ 1.41 (9H, s), 1.52-1.76 (4H, m), 2.97 (4H, br.s), 3.14-3.25 (2H, m), 3.42 (2H, t, J=7.0 Hz), 3.45 (3H, s), 6.98 (1H, d, J=7.8 Hz), 7.16-7.33 (4H, m), 7.75 (1H, s), 7.77 (1H, d, J=7.8 Hz), 10.76-10.84 (1H, m).

¹H NMR (3-methyl compound (B);400 MHz, CDCl₃) δ 1.41 (9H, s), 1.52-1.76 (4H, m), 2.95-3.01 (4H, m), 3.15-3.25 (2H, m), 3.42 (2H, t, J=7.3 Hz), 3.48 (3H, s), 7.15 (1H, d, J=8.0 Hz), 7.16-7.34 (4H, m), 7.65 (1H, s), 7.76 (1H, d, J=8.0 Hz), 10.65 (1H, br.s).

Reference Example 219 tert-Butyl 2-(2-chloro-4-hydroxyphenyl)ethyl[5-(1-methyl-2-oxo-2,3-dihydro-1H-benzimidazol-5-yl)-5-oxopentyl]carbamate (A) and tert-butyl 2-(2-chloro-4-hydroxyphenyl)ethyl[5-(3-methyl-2-oxo-2,3-dihydro-1H-benzimidazol-5-yl)-5-oxopentyl]carbamate (B)

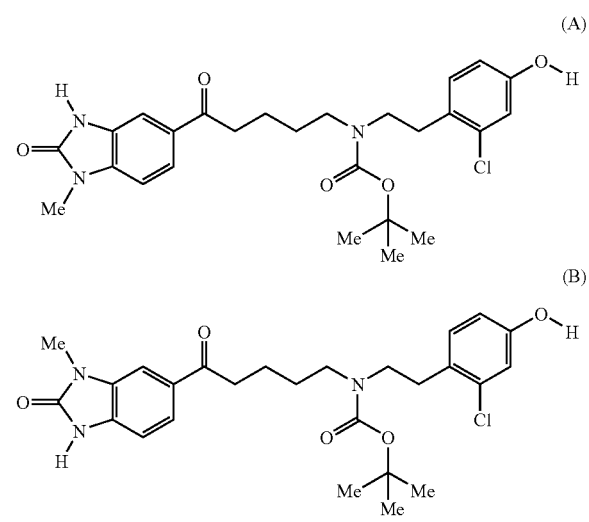

Using a mixture of 5-(5-chloropentanoyl)-1-methyl-1,3-dihydro-2H-benzimidazol-2-one and 6-(5-chloropentanoyl)-1-methyl-1,3-dihydro-2H-benzimidazol-2-one (1.60 g) obtained in Reference Example 217 and 4-(2-aminoethyl)-3-chlorophenol hydrobromide (3.3 g) according to the same method as that of Reference Example 82, the title compound was obtained as a fine yellow oil (1-methyl compound (A): 428 mg) and colorless crystals (3-methyl compound (B):290 mg) having a melting point of 157 to 158° C.

¹H NMR (1-methyl compound (A); 400 MHz, CDCl₃) δ 1.41 (9H, s), 1.51 (2H, br.s), 1.62-1.72 (2H, m), 2.84-2.91 (4H, m), 3.03-3.12 (2H, m), 3.36 (2H, t, J=7.1 Hz), 3.45 (3H, s), 6.72 (1H, d, J=8.3 Hz), 6.92 (1H,br.s), 6.97 (1H, d, J=7.6 Hz), 7.01 (1H, d, J=8.3 Hz), 7.67 (1H, br.s), 7.72 (1H, br.s), 7.77 (1H, d, J=7.6 Hz), 10.08-10.23 (1H, m).

¹H NMR (3-methyl compound (B); 400 MHz, CDCl₃) δ 1.29 (9H, s), 1.45-1.58 (4H, m), 2.74 (2H, t, J=7.3 Hz), 3.00 (2H, t, J=6.6 Hz), 3.05-3.17 (2H, m), 3.27 (2H, br.s), 3.32 (3H, s), 6.65 (1H, dd, J=8.3, 2.4 Hz), 6.77 (1H, d, J=2.4 Hz), 7.04 (2H, br.d, J=8.0 Hz), 7.64 (1H, br.s), 7.69 (1H, d, J=8.0 Hz), 9.66 (1H, s), 11.22 (1H, s)

Reference Example 220 tert-Butyl 2-(2-chloro-4-hydroxyphenyl)ethyl[5-(1,3-dimethyl-2-oxo-2,3-dihydro-1H-benzimidazol-5-yl)-5-oxopentyl]carbamate

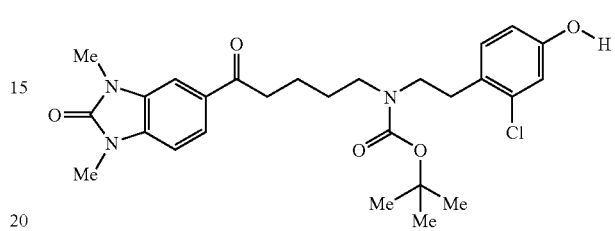

Using 5-(5-chloropentanoyl)-1,3-dimethyl-1,3-dihydro-2H-benzimidazol-2-one (562 mg) obtained in Reference Example 10 and 4-(2-aminoethyl)-3-chlorophenol hydrobromide (1.1 g) according to the same method as that of Reference Example 82, the title compound was obtained as a fine yellow oil (272 mg).

¹H NMR (400 MHz, CDCl₃) δ 1.40 (9H, s), 1.60 (2H, br.s), 1.68-1.74 (2H, m), 2.85 (2H, m), 3.00 (2H, t, J=7.3 Hz), 3.18 (2H, t, J=7.3 Hz), 3.36 (2H, br.s), 3.46 (6H, s), 6.70 (1H, d, J=8.0 Hz), 6.90 (1H,br.s), 6.95-7.24 (3H, m), 7.62 (1H, d, J=1.7 Hz), 7.78 (1H, dd, J=8.0, 1.7 Hz).

Reference Example 221

1-Methyl-5,6-dihydro-1H,4H-[1,2,5]thiadiazolo[4,3,2-ij]quinoline 2,2-dioxide

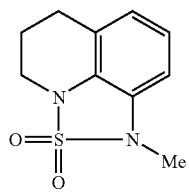

Using 5,6-dihydro-1H,4H-[1,2,5]thiadiazolo[4,3,2-ij]quinoline 2,2-oxide according to the same method as that of Reference Example 132, the title compound was obtained as brown crystals having a melting point of 103 to 104° C.

¹H NMR (200 MHz, CDCl₃) δ 2.17 (2H, quintet, J=6.2 Hz), 2.77 (2H, t, J=6.4 Hz), 3.25 (3H, s), 3.69 (2H, t, J=5.6 Hz), 6.56 (1H, d, J=7.8 Hz), 6.74 (1H, d, J=6.8 Hz), 6.88 (1H, t, J=7.6 Hz).

Reference Example 222

5-Chloro-1-(1-methyl-2,2-dioxide-5,6-dihydro-1H,4H-[1,2,5]thiadiazolo[4,3,2-ij]quinolin-8-yl)-1-pentanone

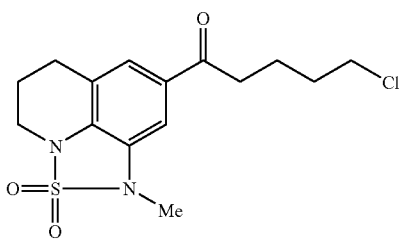

Using 1-methyl-5,6-dihydro-1H,4H-[1,2,5]thiadiazolo[4,3,2-ij]quinoline 2,2-dioxide and 5-chlorovaleryl chloride according to the same method as that of Reference Example 1, the title compound was obtained as pale red crystals having a melting point of 99 to 100° C., $^1$H NMR (200 MHz, CDCl$_3$) δ 1.89 (4H, t, J=2.8 Hz), 2.21 (2H, quintet, J=5.6 Hz), 2.83, (2H, t, J=6.2 Hz), 2.96 (2H, t, J=6.8 Hz), 3.21 (3H, s), 3.58 (2H, t, J=6.8 Hz), 3.77 (2H, t, J=5.6 Hz), 7.24 (1H, s), 7.44 (1H, s).

Reference Example 223 tert-Butyl 2-(2-chlorophenyl)ethyl[5-(1-methyl-2,2-dioxide-5,6-dihydro-1H,4H-[1,2,5]thiadiazolo[4,3,2-ij]quinoline-8-yl)-5-oxopentyl]carbamate

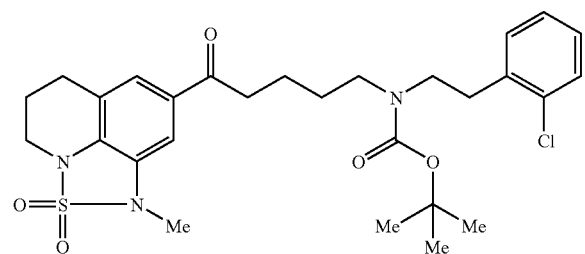

Using 5-chloro-1-(1-methyl-2,2-dioxide-5,6-dihydro-1H,4H-[1,2,5]thiadiazolo[4,3,2-ij]quinolin-8-yl)-1-pentanone obtained in Reference Example 222 and 2-(2-chlorophenyl)ethylamine according to the same method as that of Reference Example 19, the title compound was is obtained as a pale yellow oil.

$^1$H NMR (200 MHz, CDCl$_3$) δ 1.42 (9H, br), 1.53-1.71 (4H, m), 2.19 (2H, quintet, J=5.6 Hz), 2.81 (2H, t, J=6.2 Hz), 2.94 (4H, m), 3.22 (2H, m), 3.31 (3H, s), 3.41 (2H, t, J=6.8 Hz), 3.75 (2H, t, J=5.6 Hz), 7.15-7.35 (5H, m), 7.44 (1H, s).

Reference Example 224

5-Chloro-1-(2,2-dioxide-5,6-dihydro-1H,4H-[1,2,5]thiadiazolo[4,3,2-ij]quinolin-8-yl)-1-pentanone

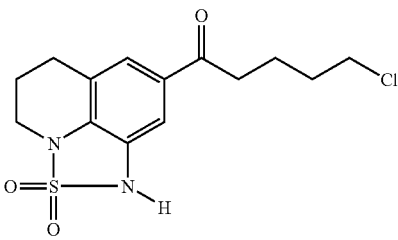

Using 5,6-dihydro-1H,4H-[1,2,5]thiadiazolo[4,3,2-ij]quinoline 2,2-dioxide and 5-chlorovaleryl chloride according to the same method as that of Reference Example 1, the title compound was obtained as pale red crystals having a melting point of 118 to 119° C.

$^1$H NMR (200 MHz, DMSO-d$_6$) δ 1.74 (4H, m), 2.06 (2H, t, J=6.0 Hz), 2.77 (2H, t, J=5.8 Hz), 2.99 (2H, t, J=7.0 Hz), 3.65 (4H, m), 7.24 (1H, s), 7.53 (1H, s), 11.58 (1H, s).

Reference Example 225

3,4-Dihydro-1H-2,1,3-benzothiadiazine 2,2-dioxide

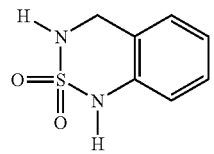

Using 2-aminobenzylamine according to the same method as that of Reference Example 126, the title compound was obtained as pale yellow crystals having a melting point of 178 to 180° C.

$^1$H NMR (200 MHz, DMSO-d$_6$) δ 4.40 (2H, d, J=7.8 Hz), 6.71 (1H, d, J=7.0 Hz), 6.92 (1H, t, J=7.2 Hz), 7.11-7.32 (3H, m), 10.16 (1H, s).

Reference Example 226

5-Chloro-1-(2,2-dioxide-3,4-dihydro-1H-2,1,3-benzothiadiazin-6-yl)-1-pentanone

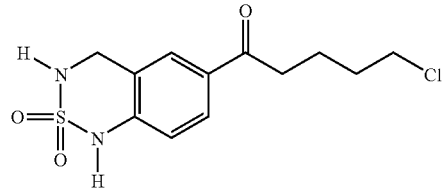

Using 3,4-dihydro-1H-2,1,3-benzothiadiazine 2,2-dioxide obtained in Reference Example 225 and 5-chlorovaleryl chloride according to the same method as that of Reference Example 1, the title compound was obtained as colorless crystals having a melting point of 116 to 117° C.

$^1$H NMR (200 MHz, DMSO-d$_6$) δ 1.74 (4H, m), 2.98 (2H, t, J=6.6 Hz), 3.68 (2H, t, J=6.2 Hz), 4.48 (2H, d, J=7.6 Hz), 6.78 (1H, d, J=8.8 Hz), 7.17 (1H, m), 7.51 (1H, t, J=8.0 Hz), 7.83 (1H, s), 10.81 (1H, s).

Reference. Example 227

1,3-Dimethyl-3,4-dihydro-1H-2,1,3-benzothiadiazine 2,2-dioxide

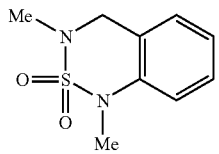

Using 3,4-dihydro-1H-2,1,3-benzothiadiazine 2,2-dioxide obtained in Reference Example 225 according to the same method as that of Reference Example 127, the title compound was obtained as colorless crystals having a melting point of 59 to 60° C.

$^1$H NMR (200 MHz, CDCl$_3$) δ 2.77 (3H, s), 3.34 (3H, s), 4.62 (2H, s), 6.90 (1H, d, J=7.6 Hz), 7.04 (2H, m), 7.30 (1H, d, J=9.4 Hz).

Reference Example 228

5-Chloro-1-(1,3-dimethyl-2,2-dioxide-3,4-dihydro-1H-2,1,3-benzothiadiazin-6-yl)-1-pentanone

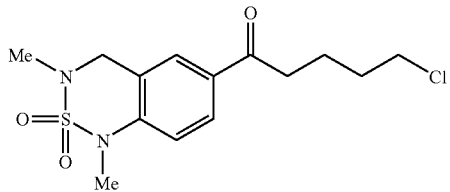

Using 1,3-dimethyl-3,4-dihydro-1H-2,1,3-benzothiadiazine 2,2-dioxide obtained in Reference Example 227 and 5-chlorovaleryl chloride according to the same method as that of Reference Example 1, the title compound was obtained as colorless crystals having a melting point of 78 to 79° C.

$^1$H NMR, (200 MHz, DMSO-d$_6$) δ 1.75 (4H, m), 2.67 (3H, s), 3.03 (2H, t, J=5.4 Hz), 3.32 (3H, s), 3.69 (2H, t, J=5.4 Hz), 4.74 (2H, S), 7.15, (1H, d, J=8.8 Hz), 7.84 (1H, s), 7.95 (1H, d, =8.8 Hz).

Reference Example 229

2-Methyl-1,3-dioxo-5-isoindolinecarboxylic acid

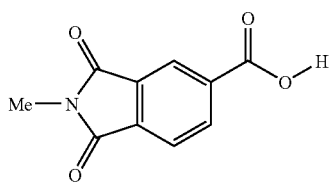

An aqueous methyl amine solution (50 ml) was added to a solution of trimellitic anhydride (30 g) in. tetrahydrofuran (100 ml). After stirred at room temperature for 15 hours, the solvent was evaporated by heating under a normal pressure. 1N hydrochloric acid was added to the residue to adjust to pH 1, the precipitates were filtered, and washed successively with water, ethanol and diethyl ether. Further air-drying afforded the title compound as colorless crystals (11.6 g) having a melting point of 226 to 232° C.

$^1$H NMR (200 MHz, DMSO-d$_6$) δ 3.06 (3H, s), 7.97 (1H, d, J=7.6 Hz), 8.19. (H, s), 8.33 (1H, dd, J=7.7, 1.6 Hz), 8.00-10.00. (1H, br).

Reference Example 230

2-Methyl-1,3-dioxo-5-isoindolinecarbonyl chloride

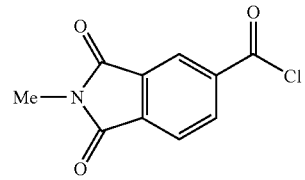

Oxalyl chloride (5.86 ml) was added by portions to a solution of 2-methyl-1,3-dioxo-5-isoindolinecarboxylic acid (9.2 g) obtained in Reference Example 229. and dimethylformamide (catalytic amount) in tetrahydrofuran (100 ml) at room temperature. After stirred at room temperature for 1 hour, the solvent was evaporated under reduced pressure. The resulting residue was filtered, washed with diethyl ether and dried under reduced pressure to give the title compound as a white solid.

$^1$H NMR (200 MHz, DMSO-d$_6$) δ 3.06 (3H, s), 7.97 (1H, d, J=7.6 Hz), 8.19 (1H, s), 8.33 (1H, dd, J=7.9, 1.0 Hz).

Reference Example 231

5-(5-Chloropentanoyl)-2-methyl-1H-isoindole-1,3 (2H)-dione

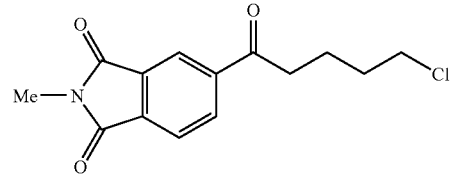

Synthesis of the present compound was carried out according to the method of Y. Tamaru et al. (Tetrahedron Lett. 1985, 26(45), 5529). That is, a solution of Zn—Cu couple (4.6 g) and 1-chloro-4-iodobutane (10.0 g) in toluene (60 ml) and dimethylfomamide (6 ml) was stirred at 60° C. for 3 hours under nitrogen atmosphere. Then, a suspension of 2-methyl-1,3-dioxo-5-isoindolinecarbonyl chloride (6.82 g) obtained in Reference Example 230 and tetrakistriphenylphosphine-palladium (1.4 g) in toluene (30 ml) was added to the aforementioned solution at room temperature. After stirring at room temperature for 1 hour, the reaction was quenched with water, and the solvent was evaporated under reduced pressure. Water was added to the residue, extracted with ethyl acetate, and washed successively with 1N hydrochloric acid, water, aqueous potassium carbonate, water and saturated brine. The organic layer was dried over anhydrous magnesium sulfate, and the solvent was evaporated under reduced pressure to give the title compound as colorless crystals (5.15 g) having a melting point of 97 to 98° C.

$^1$H NMR (200 MHz, DMSO-d$_6$) δ 1.65-1.90 (4H, m), 3.06 (3H, s), 3.22 (2H, t, J=6.8 Hz), 3.71 (2H, t, J=6.2 Hz), 7.98 (1H, d, J=7.6 Hz), 8.25-8.40 (2H, m).

Reference Example 232

N-[5-(5-chloropentanoyl)-2,3-dihydro-1H-inden-2-yl]acetamide

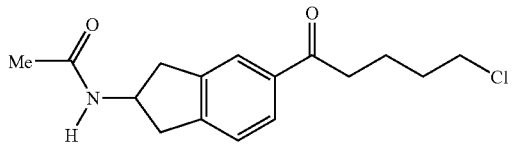

Using N-(2,3-dihydro-1H-inden-2-yl)acetamide and 5-chlorovaleryl chloride according to the same method as that of Reference Example 1, the title compound was obtained as colorless crystals having a melting point of 106 to 108° C.

$^1$H NMR (200 MHz, DMSO-d$_6$) δ 1.75 (4H, m), 1.79 (3H, s), 2.77 (2H, dd, J=10.8, 3.0. Hz), 3.04 (2H, t, J=6.6 Hz), 3.21 (2H, dd, J=11.2, 5.2 Hz), 3.69 (2H, t, J=6.3 Hz), 4.46 (1H, m), 7.35 (1H, d, J=7.6 Hz), 7.80 (2H, m), 8.16 (1H, d, J=5.4 Hz).

Reference Example 233

N-[5-(5-chloropentanoyl)-2,3-dihydro-1H-inden-2-yl]methanesulfonamide

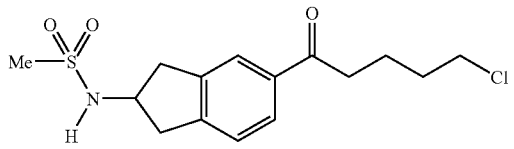

Using N-(2,3-dihydro-1H-inden-2-yl)nethanesulfonamide and 5-chlorovaleryl chloride according to the same method as that of Reference Example 1, the title compound was obtained as colorless crystals having a melting point of 71 to 72° C.

$^1$H NMR (200 MHz, DMSO-d$_6$) δ 1.86 (4H, m), 2.96 (4H, m), 3.01 (3H, s), 3.35 (2H, dd, J=10.8, 4.6 Hz), 3.58. (2H, t, J=4.2 Hz), 4.29 (1H, m), 5.21 (1H, m), 7.27 (1H, d, J=5.4 Hz), 7.79 (2H, m).

Reference Example 234

5-(5-Chloropentanoyl)-1,3-dimethyl-1,3-dihydro-2H-benzimidazol-2-one (compound of Reference Example 10)

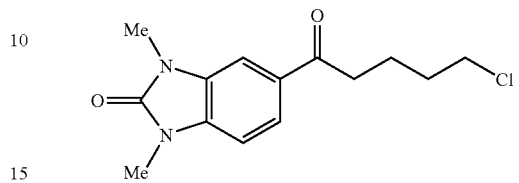

25.00 g Of 1,3-dimethyl-1,3-dihydro-2H-benzimidazol-2-one was dissolved in 250 mL of acetonitrile, and 25.9 mL (1.3 equivalent) of 5-chlorovaleryl chloride and 4.20 g (0.2 equivalent) of zinc chloride were added. After stirring at 80° C. for 6 hours, the reaction mixture was concentrated under reduced pressure. 250 mL of Ethyl acetate and 250 mL of water were added, and the layers were separated. The organic layer was washed with 125 mL of water two times, and concentrated under reduced pressure to give 53.16 g of pale yellow brown crystals. 125 mL of ethanol was added, and warmed to 55° C. to dissolve crystals. 375 mL of diisopropyl ether was added dropwise to crystallize the material, which was cooled to 25° C., and stirred at the same temperature for 1 hour. After cooling to 5° C. or lower and stirring for 1 hour, crystals were collected by filtration. Crystals were washed with 125 mL of cold ethanol-diisopropyl ether (1:3), and dried under reduced pressure to give 27.16 g of the title compound as fine yellow brown crystals.

Reference Example 235 tert-Butyl 2-(2-chlorophenyl)ethyl[5-(1,3-dimethyl-2-oxo-2,3-dihydro-1H-benzimidazol-5-yl)-5-hydroxypentyl]carbamate

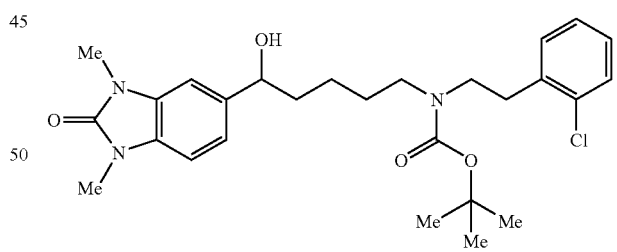

95 mg of Sodium tetrahydroborate was added to a solution of tert-butyl 2-(2-chlorophenyl)ethyl[5-(1,3-dimethyl-2-oxo-2,3-dihydro-1H-benzimidazol-5-yl)-5-oxopentyl]carbamate obtained in Reference Example 60 in methanol (10 ml) at room temperature. After stirring at room temperature for 2 hours, 20 ml of an aqueous saturated ammonium chloride solution was added. The liberated oil was extracted with chloroform (30 ml×2), dried over anhydrous magnesium sulfate, and the solvent was evaporated under reduced pressure to give the title compound as a pale yellow oil (1.25 g).

$^1$H NMR (400 MHz, CDCl$_3$) δ 1.21-1.52 (4H, m), 1.40 (9H, s), 1.63-1.90 (2H, m), 2.92 (2H, br.s), 3.08-3.23 (2H, m), 3.31-3.41 (2H, m), 3.36 (6H, s), 4.68 (1H, br.s), 5.10-5.18 (1H, m), 6.85 (1H, d, J=8.1 Hz) 6.96 (1H, m), 7.02 (1H, d, J=8.1 Hz), 7.16-7.34 (4H, m).

Reference Example 236 tert-Butyl 2-(2-chloro-4-hydroxyphenyl)ethyl[5-oxo-5-(4-oxo-1,2,5,6-tetrahydro-4H-pyrrolo[3,2,1-ij]quinolin-8-yl)pentyl]carbamate

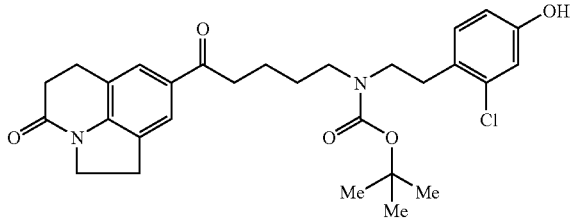

Using 8-(5-chloropentanoyl)-1,2,5,6-tetrahydro-4H-pyrrolo[3,2,1-ij]quinolin-4-one (584 mg) obtained in Reference Example 1 and 4-(2-aminoethyl)-3-chlorophenol hydrobromide (1.1 g) according to the same method as that of Reference Example 82, the title compound was obtained as a pale yellow oil (250 mg).

$^1$H NMR (400 MHz, CDCl$_3$) δ 1.41 (9H, s), 1.51-1.73 (4H, m), 2.72 (2H, t, J=7.5 Hz), 2.85 (2H, br.s), 2.92 (2H, t, J=6.8 Hz), 3.01 (2H, t, J=7.5 Hz), 3.15-3.24 (4H, m), 3.36 (2H, br.s), 4.13 (2H, t, J=8.3 Hz), 6.69 (1H, d, J=7.0 Hz), 6.89-7.07 (3H, m), 7.66 (1H, s), 7.71 (1H, s).

Reference Example 237 tert-Butyl 5-(1-acetyl-2,3-dihydro-1H-indol-5-yl)-oxopentyl[2-(2-chloro-4-hydroxyphenyl)ethyl]carbamate

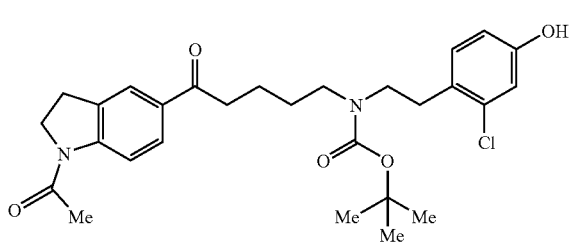

Using 1-(1-acetyl-2,3-dihydro-1H-indol-5-yl)-5-chloropentan-1-one (560 mg) obtained in Reference Example 11 and 4-(2-aminoethyl)-3-chlorophenol-hydrobromide (1.1 g) according to the same method as that of Reference Example 82, the title compound was obtained as a pale yellow oil (320 mg).

$^1$H NMR (400 MHz, CDCl$_3$) δ 1.41 (9H, s), 1.51-1.72 (4H, m), 2.26 (3H, s), 2.85 (2H, br.s), 2.95 (2H, t, J=7.3 Hz), 3.15 (2H, br.s), 3.23 (2H, t, J=8.0 Hz), 3.36 (2H, t, J=7.0 Hz), 4.11 (2H, t, J=7.0 Hz), 6.69 (1H, d, J=6.3 Hz), 6.90-7.07 (3H, m), 7.80 (1H, s), 7.81 (1H, d, J=8.0 Hz), 8.22 (1H, d, J=8.0 Hz).

Reference Example 238 tert-Butyl 2-(2-chloro-4-hydroxyphenyl)ethyl[5-(1-methyl-2-oxo-1,2,5,6-tetrahydro-4H-imidazo[4,5,1-ij]quinolin-8-yl)-5-oxopentyl]carbamate

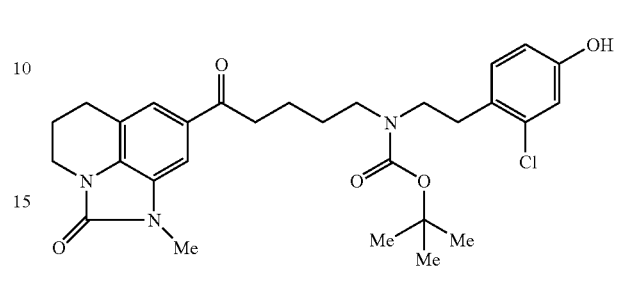

Using 8-(5-chloropentanoyl)-1-methyl-5,6-dihydro-4H-imidazo[4,5,1-ij]quinolin-2(1H)-one (460 mg) obtained in Reference Example 134 and 4-(2-aminoethyl)-3-chlorophenol hydrobromide (796 mg) according to the same method as that of Reference Example 82, the title compound was obtained as a pale yellow oil (114 mg).

$^1$H NMR (400 MHz, CDCl$_3$) δ 1.40 (9H, s), 1.60 (2H, br.s), 1.66-1.75 (2H, m), 2.10-2.16 (2H, m), 2.84-3.00 (6H, m), 3.16-3.22 (2H, m), 3.31-3.38 (2H, m), 3.45 (3H, s), 3.82-3.89 (2H,m), 6.70 (1H, d, J=7.8 Hz), 6.83-7.02 (2H, m), 7.23 (1H, br.), 7.49 (1H, s), 7.56 (1H, s).

Reference Example 239 tert-Butyl 2-(2-chloro-4-hydroxyphenyl)ethyl[5-oxo-5-(2-oxo-1,2,5,6-tetrahydro-4H-imidazo[4,5,1-ij]quinolin-8-yl)pentyl]carbamate

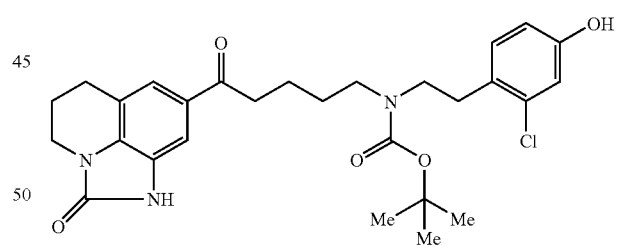

Using 8-(5-chloropentanoyl)-5,6-dihydro-4H-imidazo[4,5,1-ij]quinolin-2(1H)-one (439 mg) obtained in Reference Example 133 and 4-(2-aminoethyl)-3-chlorophenol hydrobromide (796 mg) according to the same method as that of Reference Example 82, the title compound was obtained as a pale yellow oil (55 mg).

$^1$H NMR (400 MHz, CDCl$_3$) δ 1.43 (9H, s), 1.49-1.72 (4H, m), 2.13 (2H, br.s), 2.83-2.89 (6H, m), 3.08 (2H, br.s), 3.35 (2H, t, J=6.8 Hz), 3.88 (2H, br.s), 6.88-7.02 (3H, m), 7.51 (1H, s), 7.56 (1H, br.s), 8.09 (1H, br), 9.95 (1H, s).

Reference Example 240 tert-Butyl 2-(2-chloro-4-hydroxyphenyl)ethyl[5-oxo-5-(2-oxo-1,2,5,6-tetrahydro-4H-imidazo[4,5,1-ij]quinolin-9-yl)pentyl]carbamate

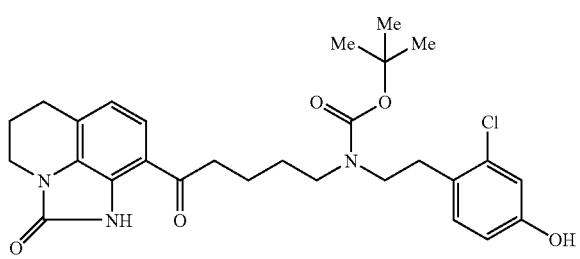

Using 5,6-dihydro-4H-imidazo[4,5,1-ij]quinolin-2(1H)-one obtained in Reference Example 131 according to the same method as those of Reference Example 1 and Reference Example 82, the title compound was obtained as a pale yellow oil.

$^1$H NMR (400 MHz, CDCl$_3$) δ 1.43 (9H, s), 1.56 (2H, br.s), 1.68 (2H, br.s), 2.09-2.16 (2H, m), 2.84-2.90 (4H, m), 2.95 (2H, t, J=7.0 Hz), 3.13 (2H, t, J=7.3 Hz),. 3.35. (2H, t, J=7.0 Hz), 3.87 (2H, t, J=6.0 Hz), 6.88-7.04 (4H, m), 7.44 (1H, d, J=8.0 Hz), 7.89 (1H, br.), 9.34 (1H, s).

Reference Example 241

N-[5-(5-chloropentanoyl)-2,3-dihydro-1H-inden-2-yl]acetamide

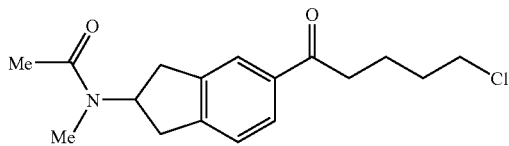

Using N-(2,3-dihydro-1H-inden-2-yl)-N-methylacetamide and 5-chlorovaleryl chloride according to the same method as that of Example 1, the title compound was obtained as colorless crystals.

$^1$H NMR (200 MHz, CDCl$_3$) δ 1.81 (4H, m), 2.20 (3H, s), 2.41 (2H, m), 2.79 (3H, s), 3.06 (2H, t, J=6.6 Hz), 3.18-3.22 (2H, m), 3.59 (2H, t, J=6.3 Hz), 5.46 (1H, m), 7.30 (1H, m), 7.81 (2H, m).

Reference Example 242

N-[5-(5-chloropentanoyl)-2,3-dihydro-1H-inden-2-yl]methanesulfonamide

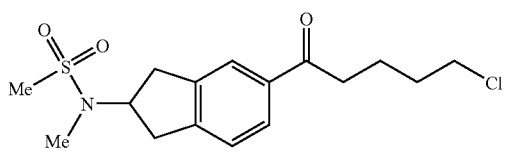

Using N-(2,3-dihydro-1H-inden-2-yl)methanesulfonamide and 5-chlorovaleryl chloride according to the same method as that of Example 1, the title compound was obtained as colorless crystals.

MS m/z: 344 [M+H]$^+$

Example 1

8-[5-[(2-Phenylethyl)amino]pentanoyl]-1,2,5,6-tetrahydro-4H-pyrrolo[3,2,1-ij]quinolin-4-one hydrochloride

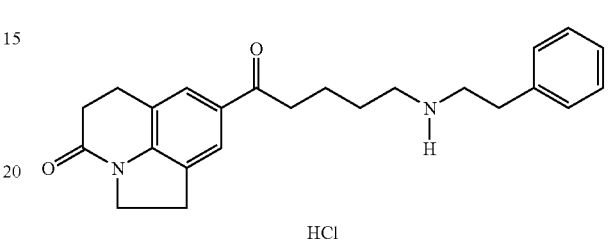

A 4N hydrogen chloride-ethyl acetate solution was added to a solution of tert-butyl 5-oxo-5-(4-oxo-1,2,5,6-tetrahydro-4H-pyrrolo[3,2,1-ij]quinolin-8-yl)pentyl(2-phenylethyl)carbamate (3.00 g) obtained in Reference Example 19 in ethanol (5 ml), and the mixture was stirred at room temperature for 1 hour. The solvent was evaporated under reduced pressure, and the resulting residue was crystallized from ethanol-ethyl acetate to give the title compound as colorless crystals (1.98 g) having a melting point of 166 to 168° C.

$^1$H NMR(300 MHz, DMSO-d$_6$) δ 1.60-1.75 (4H, m), 2.59 (2H, t, J=7.6 Hz), 2.90-3.20 (10H, m), 3.18 (2H, t, J=8.4 Hz), 3.99 (2H, t, J=8.4 Hz), 7.20-7.40 (5H, m), 7.73 (1H, s), 7.74 (1H, s), 8.95-9.10 (2H, br).

elementary analysis as C$_{24}$H$_{28}$N$_2$O$_2$.HCl
calculation value: C, 69.80; H, 7.08; N, 6.78.
experimental value: C, 69.43; H, 7.06;. N, 6.72.

Example 2

8-(5-[[2-(2-Methoxyphenyl)ethyl]amino]pentanoyl)-1,2,5,6-tetrahydro-4H-pyrrolo[3,2,1-ij]quinolin-4-one hydrochloride

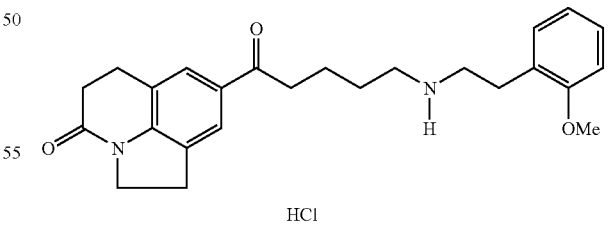

Using tert-butyl 2-(2-methoxyphenyl)ethyl[5-oxo-5-(4-oxo-1,2,5,6-tetrahydro-4H-pyrrolo[3,2,1-ij]quinolin-8-yl)pentyl]carbamate (1.16 g) obtained in Reference Example 20 according to the same method as that of Example 1, the title compound (835 mg) was obtained as colorless crystals having a melting point of 94 to 96° C.

$^1$H NMR(200 MHz, DMSO-d$_6$) δ 1.60-1.80 (4H, m), 2.59 (2H, t, J=7.6 Hz), 2.85-3.15 (10H, m), 3.18 (2H, t, J=8.4 Hz), 3.80 (3H, s), 3.99 (2H, t, J=8.4 Hz), 6.91 (1H, dt, J=7.3, 1.0 Hz), 7.00 (1H, d, J=7.6 Hz), 7.15-7.30 (2H, m), 7.74 (2H, s), 8.95-9.15 (2H, br).
elementary analysis as $C_{25}H_{30}N_2O_3 \cdot HCl \cdot H_2O$
calculation value: C, 62.69; H, 7.36; N, 5.85.
experimental value: C, 63.02; H, 7.15; N, 5.82.

Example 3

8-(5-[[2-(3-Methoxyphenyl)ethyl]amino]pentanoyl)-1,2,5,6-tetrahydro-4H-pyrrolo[3,2,1-ij]quinolin-4-one hydrochloride

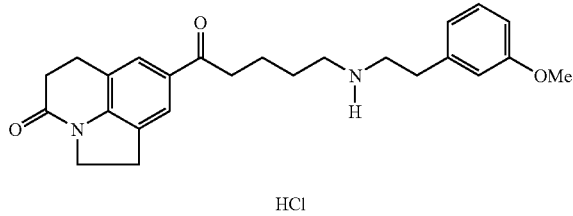

HCl

Using tert-butyl 2-(3-methoxyphenyl)ethyl[5-oxo-5-(4-oxo-1,2,5,6-tetrahydro-4H-pyrrolo[3,2,1-ij]quinolin-8-yl)pentyl]carbamate (3.02 g) obtained in Reference Example 21 according to the same method as that of Example 1, the title compound (2.32 g) was obtained as colorless crystals having a melting point of 97 to 100° C.
$^1$H NMR(200 MHz, DMSO-$d_6$) δ 1.55-1.80 (4H, m), 2.59 (2H, t, J=7.6 Hz), 2.85-3.20 (10H, m), 3.17 (2H, t, J=8.4 Hz), 3.75 (3H, s), 3.99 (2H, t, J=8.4 Hz), 6.75-6.85 (3H, m), 7.25 (1H, t, J=8.2 Hz), 7.74 (2H, s), 9.15-9.35 (2H, br).
elementary analysis as $C_{25}H_{30}N_2O_3 \cdot HCl \cdot 1.5H_2O$
calculation value: C, 63.89; H, 7.29; N, 5.96.
experimental value: C, 64.01; H, 7.01; N, 6.01.

Example 4

8-(5-[[2-(3,4-Dimethoxyphenyl)ethyl]amino]pentanoyl)-1,2,5,6-tetrahydro-4H-pyrrolo[3,2,1-ij]quinolin-4-one hydrochloride

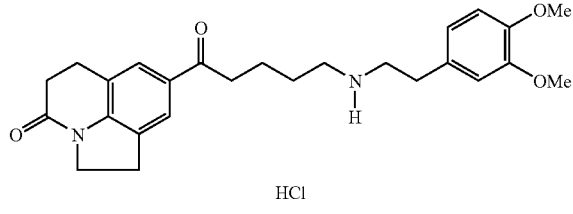

HCl

Using tert-butyl 2-(3,4-dimethoxyphenyl)ethyl[5-oxo-5-(4-oxo-1,2,5,6-tetrahydro-4H-pyrrolo[3,2,1-ij]quinolin-8-yl)pentyl]carbamate (408 mg) obtained in Reference Example 22 according to the same method as that of Example 1, the title compound (290 mg) was obtained as colorless crystals having a melting point of 175 to 176° C.
$^1$H NMR(200 MHz, DMSO-$d_6$) δ 1.55-1.80 (4H, m), 2.59 (2H, t, J=7.6 Hz), 2.80-3.20 (10H, m), 3.18 (2H, t, J=8.4 Hz), 3.72 (3H, s), 3.75 (3H, s), 3.99 (2H, t, J=8.4 Hz), 6.76 (1H, dd, J=8.2, 1.8 Hz), 6.90 (2H, d, J=8.2 Hz), 7.73 (2H, s), 8.85-9.05 (2H, br).

Example 5

8-(5-[[2-(2-Chlorophenyl)ethyl]amino]pentanoyl)-1,2,5,6-tetrahydro-4H-pyrrolo[3,2,1-ij]quinolin-4-one hydrochloride

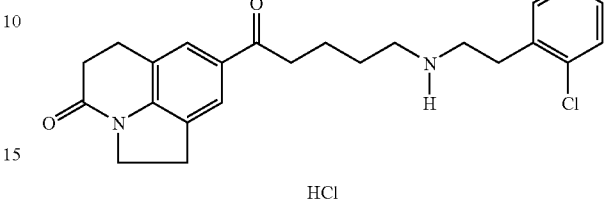

HCl

Using 2-(2-chlorophenyl)ethyl[5-oxo-5-(4-oxo-1,2,5,6-tetrahydro-4H-pyrrolo[3,2,1-ij]quinolin-8-yl)pentyl]carbamate (1.50 g) obtained in Reference Example 23 according to the same method as that of Example 1, the title compound (989 mg) was obtained as colorless crystals having a melting point of 128 to 130° C.
$^1$H NMR(200 MHz, DMSO-$d_6$) δ 1.55-1.80 (4H, m), 2.59 (2H, t, J=7.6 Hz), 2.90-3.25 (12H, m), 3.99 (2H, t, J=8.4 Hz), 7.00-7.55 (4H, m), 7.73 (2H, s), 9.10-9.30 (2H, br).
elementary analysis as $C_{24}H_{27}ClN_2O_2 \cdot HCl \cdot H_2O$
calculation value: C, 60.76; H, 6.59; N, 5.90.
experimental value: C, 61.15; H, 6.20; N, 5.77.

Example 6

8-(5-[[2-(3-Fluorophenyl)ethyl]amino]pentanoyl)-1,2,5,6-tetrahydro-4H-pyrrolo[3,2,1-ij]quinolin-4-one hydrochloride

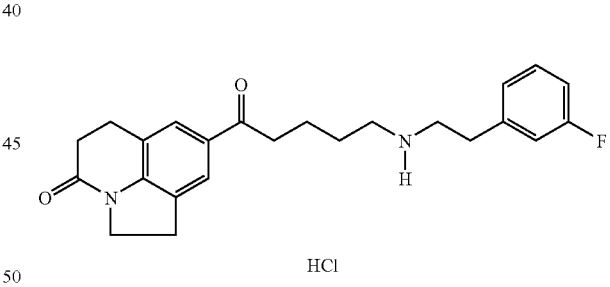

HCl

Using 2-(3-fluorophenyl) ethyl[5-oxo-5-(4-oxo-1,2,5,6-tetrahydro-4H-pyrrolo[3,2,1-ij]quinolin-8-yl)pentyl]carbamate (1.40 g) obtained in Reference Example 24 according to the same method as that of Example 1, the title compound (905 mg) was obtained as colorless crystals having a melting point of 172 to 173° C.
1H NMR(200 MHz, DMSO-$d_6$) δ 1.55-1.80 (4H, m), 2.59 (2H, t, J=7.6 Hz), 2.85-3.25 (12H, m), 3.99 (2H, t, J=8.4 Hz), 7.00-7.20 (3H, m), 7.50-7.65 (1H, m), 7.74 (2H, s), 8.90-9.10 (2H, br).
elementary analysis as $C_{24}H_{27}FN_2O_2 \cdot HCl$
calculation value: C, 66.89; H, 6.55;. N, 6.50.
experimental value: C, 66.50; H, 6.21; N, 6.20.

Example 7

2-Methoxy-5-(2-[[5-oxo-5-(4-oxo-1,2,5,6-tetrahydro-4H-pyrrolo[3,2,1-ij]quinolin-8-yl)pentyl]amino]ethyl)benzenesulfonamide hydrochloride

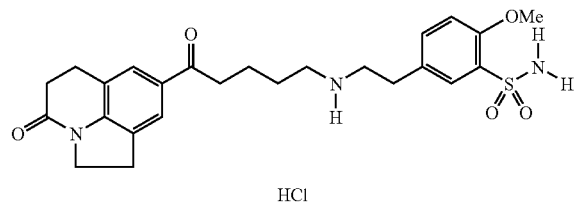

HCl

Using tert-butyl 2-[3-(aminosulfonyl)-4-methoxyphenyl]ethyl[5-oxo-5-(4-oxo-1,2,5,6-tetrahydro-4H-pyrrolo[3,2,1-ij]quinolin-8-yl)pentyl]carbamate (605 mg) obtained in Reference Example 25 according to the same method as that of Example 1, the title compound (325 mg) was obtained as colorless crystals having a melting point of 145° C. (dec).

$^1$H NMR(200 MHz, DMSO-$d_6$) δ 1.55-1.75 (4H, m), 2.60 (2H, t, J=7.6 Hz), 2.85-3.20 (10H, m), 3.18 (2H, t, J=8.4 Hz), 3.89 (3H, s), 3.99 (2H, t, J=8.4 Hz), 7.08 (2H,. s), 7.18 (1H, d, J=8.8 Hz), 7.47 (1H, dd, J=8.6, 2.2 Hz), 7.63 (1H, d, J=2.2 Hz), 7.74. (2H, s), 8.85-9.05 (2H, br).

elementary analysis as $C_{25}H_{31}N_3O_5S.HCl.H_2O$
calculation value: C, 55.60; H, 6.35; N, 7.78.
experimental value: C, 55.51; H, 6.50; N, 7.46.

Example 8

8-(5-[[2-(2-Methoxyphenyl)-1-methylethyl]amino]pentanoyl)-1,2,5,6-tetrahydro-4H-pyrrolo[3,2,1-ij]quinolin-4-one hydrochloride

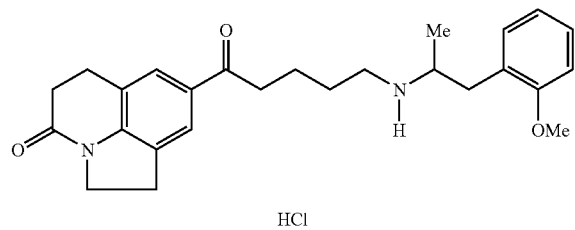

HCl

Using tert-butyl 2-(2-methoxyphenyl)-1-methylethyl[5-oxo-5-(4-oxo-1,2,5,6-tetrahydro-4H-pyrrolo[3,2,1-ij]quinolin-8-yl)pentyl]carbamate (641 mg) obtained in Reference Example 26 according to the same method as that of Example 1, the title compound (438 mg) was obtained as pale yellow amorphous powders.

$^1$H NMR(200 MHz, DMSO-$d_6$) δ 1.10 (3H, d, J=6.2 Hz), 1.60-1.90 (4H, m), 2.59 (2H, t, J=7.6 Hz), 2.80-3.20 (9H, m), 3.18 (2H, t, J=8.4 Hz), 3.80 (3H, s), 3.99 (2H, t, J=8.4 Hz), 6.80-7.60 (4H, m), 7.73 (2H, s), 8.90-9.25 (2H, br)

elementary analysis as. $C_{26}H_{32}N_2O_3.HCl.H_2O$
calculation value: C, 65.74; H, 7.43; N, 5.90.
experimental value: C, 65.44; H, 7.09; N, 5.72.

Example 9

8-[5-[Methyl(2-phenylethyl)amino]pentanoyl]-1,2,5,6-tetrahydro-4H-pyrrolo[3,2,1-ij]quinolin-4-one hydrochloride

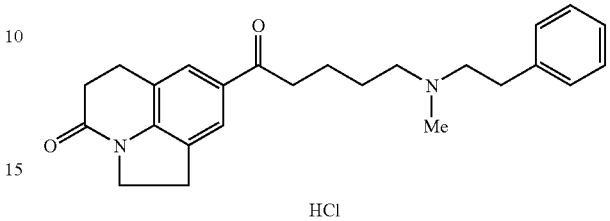

HCl

A mixed solution of 8-(5-chloropentanoyl)-1,2,5,6-tetrahydro-4H-pyrrolo[3,2,1-ij]quinolin-4-one (800 mg) obtained in Reference Example 1, N-methyl-N-(2-phenylethyl)amine (0.438 ml) and potassium carbonate (830 mg) in toluene (10 ml) was heated under reflux for 12 hours with stirring. After cooling, water (15 ml) and ethyl acetate (20 ml) were added to the reaction mixture, and the mixture was extracted with ethyl acetate. The extract was washed with brine, dried over anhydrous magnesium sulfate, and the solvent was evaporated under reduced pressure. The resulting residue was purified by silica gel chromatography (eluting solvent; ethyl acetate) to give a free base compound of the title compound as a pale yellow oil (519 mg).

$^1$H NMR(free base; 300 MHz, CDCl$_3$) δ 1.50-1.65 (2H, m), 1.74 (2H, tt, J=7.5, 7.5 Hz), 2.31 (3H, s), 2.45 (2H, t, J=7.5 Hz), 2.55-2.65 (2H, m), 2.65-2.80 (4H, m), 2.92 (2H, t, J=7.5 Hz), 3.01 (2H, t, J=8.1 Hz), 3.21 (2H, t, J=8.1 Hz), 4.12 (2H, t, J=8.4 Hz), 7.15-7.30 (5H, m), 7.67 (1H, s), 7.72 (1H, s)

A solution of the free base compound (519 mg) in ethanol was treated with 1 equivalent or more of hydrogen chloride (ethyl acetate solution) to give the title compound as pale yellow amorphous powders (539 mg).

elementary analysis as $C_{25}H_{30}N_2O_2.HCl$
calculation value: C, 70.32; H, 7.32; N, 6.56.
experimental value: C, 70.04; H, 7.56; N, 6.59.

Example 10

8-[5-[[2-(2-Methoxyphenyl)ethyl](methyl)amino]pentanoyl]-1,2,5,6-tetrahydro-4H-pyrrolo[3,2,1-ij]quinolin-4-one hydrochloride

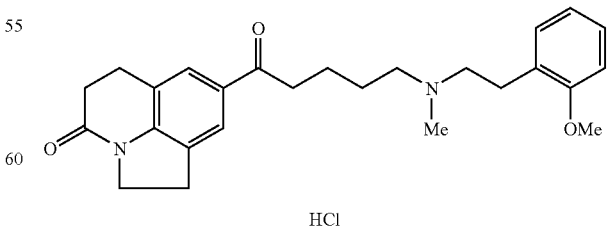

HCl

Using 8-(5-chloropentanoyl)-1,2,5,6-tetrahydro-4H-pyrrolo[3,2,1-ij]quinolin-4-one (500 mg) obtained in Reference Example 1 and N-[2-(2-methoxyphenyl)ethyl]-N-methylamine (322 mg) according to the same method as that of Example 9, the title compound (280 mg) was obtained as pale yellow amorphous powders.

¹H NMR(free base; 300 MHz, CDCl₃) δ 1.50-1.65 (2H, m), 1.75 (2H, tt, J=7.5, 7.5 Hz), 2.32 (3H, s), 2.47 (2H, t, J=7.5 Hz), 2.50-2.60 (2H, m), 2.65-2.80 (4H, m), 2.93 (2H, t, J=7.5 Hz), 3.02 (2H, t, J=8.1 Hz), 3.22 (2H, t, J=8.1 Hz), 3.81 (3H, s), 4.13 (2H, t, J=8.4 Hz), 6.84 (1H, d, J=7.5 Hz), 6.88 (1H, d, J=7.8 Hz), 7.10-7.20 (2H, m), 7.68 (1H, s), 7.72 (1H, s).
elementary analysis as $C_{26}H_{32}N_2O_3 \cdot HCl \cdot 0.5H_2O$
calculation value: C, 67.01; H, 7.35; N, 6.01.
experimental value: C, 67.03; H, 7.68; N, 5.97.

Example 11

8-[5-[[2-(3-Methoxyphenyl)ethyl](methyl)amino]pentanoyl]-1,2,5,6-tetrahydro-4H-pyrrolo[3,2,1-ij]quinolin-4-one hydrochloride

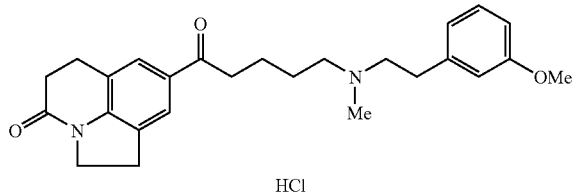

HCl

Using 8-(5-chloropentanoyl)-1,2,5,6-tetrahydro-4H-pyrrolo[3,2,1-ij]quinolin-4-one (500 mg) obtained in Reference Example 1 and N-[2-(3-methoxyphenyl)ethyl]-N-methylamine (322 mg) according to the same method as that of Example 9, the title compound (160 mg) was obtained as pale yellow amorphous powders.

¹H NMR(free base; 300 MHz, CDCl₃) δ 1.50-1.65 (2H, m), 1.75 (2H, tt, J=7.5, 7.5 Hz), 2.30 (3H, s), 2.45 (2H, t, J=7.5 Hz), 2.55-2.65 (2H, m), 2.65-2.80 (4H, m), 2.92 (2H, t, J=7.2 Hz), 3.01 (2H, t, J=7.8 Hz), 3.21 (2H, t, J=8.1 Hz), 3.78 (3H, s), 4.12 (2H, t, J=8.4 Hz), 6.70-6.80 (3H, m), 7.16 (1H, t, J=7.8 Hz), 7.67 (1H, s), 7.72 (1H, s).

Example 12

8-(5-[[2-(2-Chlorophenyl)ethyl](methyl)amino]pentanoyl]-1,2,5,6-tetrahydro-4H-pyrrolo[3,2,1-ij]quinolin-4-one hydrochloride

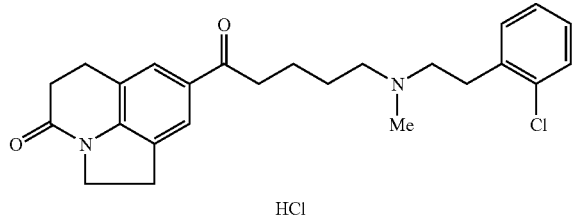

HCl

Using 8-(5-chloropentanoyl)-1,2,5,6-tetrahydro-4H-pyrrolo[3,2,1-ij]quinolin-4-one (500 mg) obtained in Reference Example 1 and N-[2-(2-chlorophenyl)ethyl]-N-methylamine (330 mg) according to the same method as that of Example 9, the title compound (310 mg) was obtained as pale yellow amorphous powders.

¹H NMR(free base; 300 MHz, CDCl₃) δ 1.50-1.65 (2H, m), 1.74 (2H, tt, J=7.5, 7.5 Hz), 2.34 (3H, s), 2.47 (2H, t, J=7.5 Hz), 2.55-2.65 (2H, m), 2.71 (2H, t, J=7.5 Hz), 2.85-2.95 (4H, m), 3.02 (2H, t, J=7.8 Hz), 3.22 (2H, t, J=8.1 Hz), 4.13 (2H, t, J=8.4 Hz), 7.05-7.35 (4H, m), 7.68 (1H, s), 7.72 (1H, s).

Example 13

8-[5-[[2-(3-Chlorophenyl)ethyl](methyl)amino]pentanoyl]-1,2,5,6-tetrahydro-4H-pyrrolo[3,2,1-ij]quinolin-4-one hydrochloride

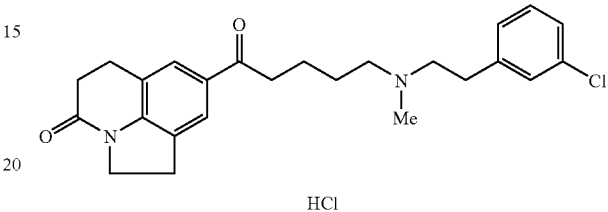

HCl

Using 8-(5-chloropentanoyl)-1,2,5,6-tetrahydro-4H-pyrrolo[3,2,1-ij]quinolin-4-one (500 mg) obtained in Reference Example 1 and N-[2-(3-chlorophenyl)ethyl]-N-methylamine (345 mg) according to the same method as that of Example 9, the title compound (298 mg) was obtained as pale yellow amorphous powders.

¹H NMR(free base; 200 MHz, CDCl₃) δ 1.50-1.65 (2H, m), 1.73 (2H, tt, J=7.4, 7.4 Hz), 2.29 (3H, s), 2.44 (2H, t, J=7.4 Hz), 2.50-2.80 (6H, m), 2.92 (2H, t, J=7.2 Hz), 3.02 (2H, t, J=7.8 Hz), 3.22 (2H, t, J=8.4 Hz), 4.13 (2H, t, J=8.4 Hz), 7.00-7.20 (4H, m), 7.67 (1H, s), 7.71 (1H, s).
elementary analysis as $C_{25}H_{29}ClN_2O_2 \cdot HCl \cdot H_2O$
calculation value: C, 62.63; H, 6.73; N, 5.84.
experimental value: C, 62.51; H, 6.53; N, 5.70.

Example 14

8-[5-[[2-(3-Fluorophenyl)ethyl](methyl)amino]pentanoyl]-1,2,5,6-tetrahydro-4H-pyrrolo[3,2,1-ij]quinolin-4-one hydrochloride

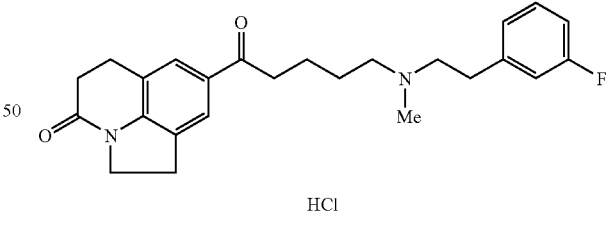

HCl

Using 8-(5-chloropentanoyl)-1,2,5,6-tetrahydro-4H-pyrrolo[3,2,1-ij]quinolin-4-one (500 mg) obtained in Reference Example 1 and N-[2-(3-fluorophenyl)ethyl]-N-methylamine (276 mg) according to the same method as that of Example 9, the title compound (340 mg) was obtained as pale yellow amorphous powders.

¹H NMR(free base; 300 MHz, CDCl₃) δ 1.50-1.65 (2H, m), 1.74 (2H, tt, J=7.5, 7.5 Hz), 2.29 (3H, s), 2.44 (2H, t, J=7.5 Hz), 2.55-2.65 (2H, m), 2.65-2.80 (4H, m), 2.92 (2H, t, J=7.5 Hz), 3.01 (2H, t, J=7.8 Hz), 3.22 (2H, t, J=8.1 Hz), 4.12 (2H, t, J=8.4 Hz), 6.80-7.00 (3H, m), 7.15-7.25 (1H, m), 7.67 (1H, s), 7.72 (1H, s).

elementary analysis as $C_{25}H_{29}FN_2O_2 \cdot HCl \cdot 0.5H_2O$
calculation value: C, 66.14; H, 6.88; N, 6.17.
experimental value: C, 66.23; H, 6.38; N, 5.74.

Example 15

8-[5-[Ethyl(2-phenylethyl)amino]pentanoyl]-1,2,5,6-tetrahydro-4H-pyrrolo[3,2,1-ij]quinolin-4-one hydrochloride

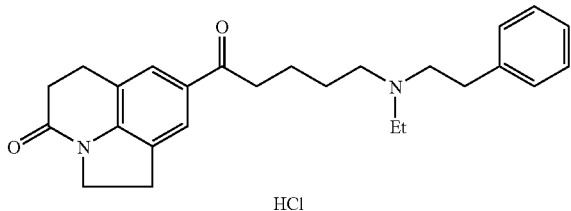

HCl

Using 8-(5-chloropentanoyl)-1,2,5,6-tetrahydro-4H-pyrrolo[3,2,1-ij]quinolin-4-one (500 mg) obtained in Reference Example 1 and N-ethyl-N-(2-phenylethyl)amine (281 mg) according to the same method as that of Example 9, the title compound (230 mg) was obtained as pale yellow amorphous powders.

$^1$H NMR(free base; 300 MHz, CDCl$_3$) δ 1.06 (3H, t, J=7.2 Hz), 1.56 (2H, tt, J=7.5, 7.5 Hz), 1.73 (2H, tt, J=7.5, 7.5 Hz), 2.50-2.80 (10H, m), 2.92 (2H, t, J=7.2 Hz), 3.01 (2H, t, J=7.8 Hz), 3.22 (2H, t, J=8.4 Hz), 4.12 (2H, t, J=8.4 Hz), 7.10-7.30 (5H, m), 7.67 (1H, s), 7.72 (1H, s).

elementary analysis as $C_{26}H_{32}N_2O_2 \cdot HCl \cdot 0.5H_2O$
calculation value: C, 69.39; H, 7.62; N, 6.23.
experimental value: C, 69.50; H, 7.69; N, 6.17.

Example 16

8-(5-[Ethyl[2-(2-methoxyphenyl)ethyl]amino]pentanoyl)-1,2,5,6-tetrahydro-4H-pyrrolo[3,2,1-ij]quinolin-4-one hydrochloride

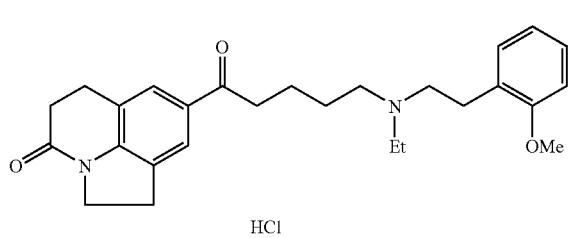

HCl

Using 8-(5-chloropentanoyl)-1,2,5,6-tetrahydro-4H-pyrrolo[3,2,1-ij]quinolin-4-one (500 mg) obtained in Reference Example 1 and N-ethyl-N-[2-(2-methoxyphenyl)ethyl]amine (337 mg) according to the same method as that of Example 9, the title compound (300 mg) was obtained as pale yellow amorphous powders.

$^1$H NMR(free base; 300 MHz, CDCl$_3$) δ 1.07 (3H, t, J=7.2 Hz), 1.35-1.45 (2H, m), 1.75 (2H, tt, J=7.5, 7.5 Hz), 2.50-2.80 (10H, m), 2.93 (2H, t, J=7.2 Hz), 3.02 (2H, t, J=7.8 Hz), 3.22 (2H, t, J=8.4 Hz), 3.81 (3H, s), 4.13 (2H, t, J=8.4 Hz), 6.84 (1H, d, J=8.1 Hz), 6.88 (1H, d, J=7.2 Hz), 7.10-7.20 (2H, m), 7.68 (1H, s), 7.73 (1H, s).

elementary analysis as $C_{27}H_{34}N_2O_3 \cdot HCl \cdot H_2O$
calculation value: C, 66.31; H, 7.63; N, 5.73.
experimental value: C, 66.58; H, 7.36; N, 5.49.

Example 17

8-(5-[Isopropyl[2-(2-methoxyphenyl)ethyl]amino]pentanoyl)-1,2,5,6-tetrahydro-4H-pyrrolo[3,2,1-ij]quinolin-4-one hydrochloride

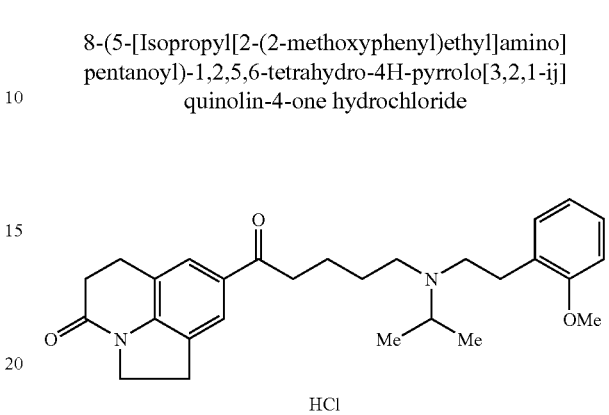

HCl

Using 8-(5-chloropentanoyl)-1,2,5,6-tetrahydro-4H-pyrrolo[3,2,1-ij]quinolin-4-one (700 mg) obtained in Reference Example 1 and N-isopropyl-N-[2-(2-methoxyphenyl)ethyl]amine (510 mg) according to the same method as that of Example 9, the title compound (310 mg) was obtained as pale yellow amorphous powders.

$^1$H NMR(free base; 300 MHz, CDCl$_3$) δ 1.00 (6H, d, J=6.6 Hz), 1.50-1.60 (2H, m), 1.74 (2H, tt, J=7.4, 7.4 Hz), 2.51 (2H, t, J=7.5 Hz), 2.55-3.05 (11H, m), 3.22 (2H, t, J=8.4 Hz), 3.81 (3H, s), 4.12 (2H, t, J=8.4 Hz), 6.80-6.95 (2H, m), 7.10-7.20 (2H, m), 7.69 (1H, s), 7.73 (1H, s).

Example 18

8-[5-[[2-(2-Chlorophenyl)ethyl](isopropyl)amino]pentanoyl]-1,2,5,6-tetrahydro-4H-pyrrolo[3,2,1-ij]quinolin-4-one hydrochloride

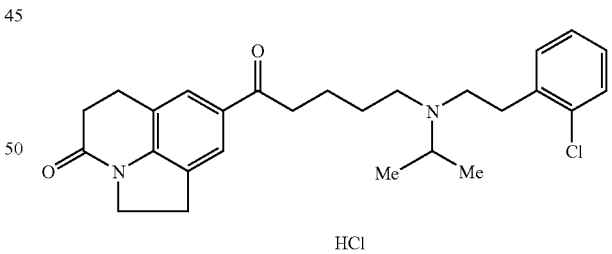

HCl

Using 8-(5-chloropentanoyl)-1,2,5,6-tetrahydro-4H-pyrrolo[3,2,1-ij]quinolin-4-one (700 mg) obtained in Reference Example 1 and N-[2-(2-chlorophenyl)ethyl]-N-isopropylamine (522 mg) according to the same method as that of Example 9, the title compound (70 mg) was obtained as pale yellow amorphous powders.

$^1$H NMR(free base; 300 MHz, CDCl$_3$) δ 1.00 (6H, d, J=6.6 Hz), 1.50-1.60 (2H, m), 1.73 (2H, tt, J=7.4, 7.4 Hz), 2.51 (2H, t, J=7.5 Hz), 2.55-2.65 (2H, m), 2.71 (2H, t, J=7.5 Hz), 2.80-3.05 (5H, m), 3.22 (2H, t, J=8.4 Hz), 4.13 (2H, t, J=8.4 Hz), 7.05-7.40 (4H, m), 7.68 (1H, s), 7.72 (1H, s).

Example 19

8-[6-[(2-Phenylethyl)amino]hexanoyl]-1,2,5,6-tetrahydro-4H-pyrrolo[3,2,1-ij]quinolin-4-one hydrochloride

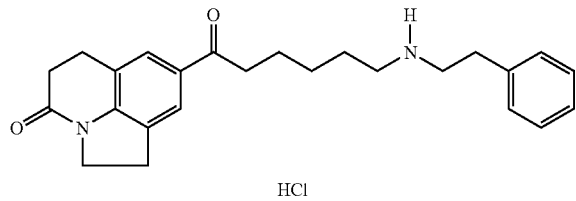

HCl

Using tert-butyl 6-oxo-6-(4-oxo-1,2,5,6-tetrahydro-4H-pyrrolo[3,2,1-ij]quinolin-8-yl)hexyl(2-phenylethyl)carbamate (450 mg) obtained in Reference Example 27 according to the same method as that of Example 1, the title compound (283 mg) was obtained as colorless crystals having a melting point of 144 to 146° C.

$^1$H NMR(200 MHz, DMSO-$d_6$) δ 1.25-1.45 (2H, m), 1.55-1.80 (4H, m), 2.59 (2H, t, J=7.6 Hz), 2.80-3.25 (12H, m), 3.99 (2H, t, J=8.4 Hz), 7.20-7.40 (5H, m), 7.73 (2H, s), 8.90-9.10 (2H, br).

Example 20

8-(6-[[2-(2-Methoxyphenyl)ethyl]amino]hexanoyl]-1,2,5,6-tetrahydro-4H-pyrrolo[3,2,1-ij]quinolin-4-one hydrochloride

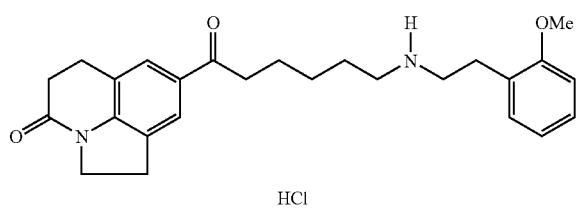

HCl

Using tert-butyl 2-(2-methoxyphenyl)ethyl[6-oxo-6-(4-oxo-1,2,5,6-tetrahydro-4H-pyrrolo[3,2,1-ij]quinolin-8-yl)hexyl]carbamate (1.51 g) obtained in Reference Example 28 according to the same method as that of Example 1, the title compound (1.04 g) was obtained as colorless crystals having a melting point of 105 to 107° C.

$^1$H NMR(300 MHz, DMSO-$d_6$) δ 1.30-1.45 (2H, m), 1.55-1.75 (4H, m), 2.59 (2H, t, J=7.6 Hz), 2.85-3.10 (10H, m), 3.17 (2H, t, J=8.4 Hz), 3.80 (3H, s), 3.99 (2H, t, J=8.4 Hz), 6.91 (1H, t, J=7.5 Hz), 7.00 (1H, d, J=8.4 Hz), 7.15-7.30 (2H, m), 7.73 (2H, s), 8.75-9.00 (2H, br).

elementary analysis as $C_{26}H_{32}N_2O_3 \cdot HCl \cdot H_2O$
calculation value: C, 65.74; H, 7.43; N, 5.90.
experimental value: C, 66.09; H, 7.01; N, 5.80.

Example 21

8-(6-[[2-(3-Methoxyphenyl)ethyl]amino]hexanoyl]-1,2,5,6-tetrahydro-4H-pyrrolo[3,2,1-ij]quinolin-4-one hydrochloride

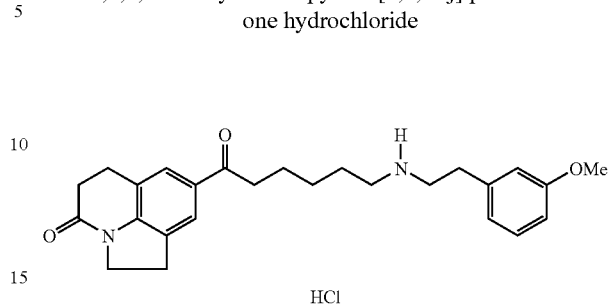

HCl

Using tert-butyl 2-(3-methoxyphenyl)ethyl[6-oxo-6-(4-oxo-1,2,5,6-tetrahydro-4H-pyrrolo[3,2,1-ij]quinolin-8-yl)hexyl]carbamate (562 mg) obtained in Reference. Example 29 according to the same method as that of Example 1, the title compound (435 mg) was obtained as colorless crystals having a melting point of 136 to 138° C.

$^1$H NMR(200 MHz, DMSO-$d_6$) δ 1.25-1.45 (2H, m), 1.55-1.80 (4H, m), 2.59 (2H, t, J=7.6 Hz), 2.85-3.25 (12H, m), 3.75 (3H, s), 3.99 (2H, t, J=8.4 Hz), 6.80-6.85 (3H, m), 7.25 (1H, t, J=7.8 Hz), 7.73 (2H, s), 9.00-9.20 (2H, br).

elementary analysis as $C_{26}H_{32}N_2O_3 \cdot HCl \cdot H_2O$
calculation value: C, 65.74; H, 7.43; N, 5.90.
experimental value: C, 65.54; H, 7.28; N, 5.80.

Example 22

8-(6-[[2-(4-Methoxyphenyl)ethyl]amino]hexanoyl]-1,2,5,6-tetrahydro-4H-pyrrolo[3,2,1-ij]quinolin-4-one hydrochloride

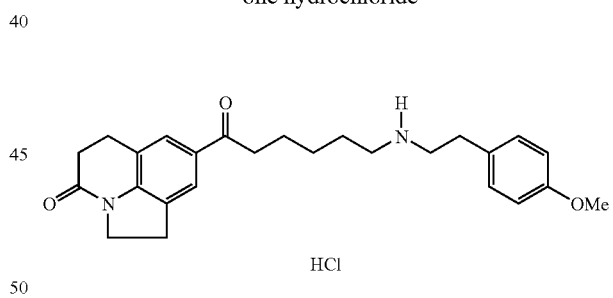

HCl

Using tert-butyl 2-(4-methoxyphenyl)ethyl[6-oxo-6-(4-oxo-1,2,5,6-tetrahydro-4H-pyrrolo[3,2,1-ij]quinolin-8-yl)hexyl]carbamate (900 mg) obtained in Reference Example 30 according to the same method as that of. Example 1, the title compound (707 mg) was obtained as colorless crystals having a melting point of 179 to 180° C.

$^1$H NMR(300 MHz, DMSO-$d_6$) δ 1.25-1.45 (2H, m), 1.55-1.75 (4H, m), 2.59 (2H, t, J=7.5 Hz), 2.80-3.10 (10H, m), 3.17 (2H, t, J=8.4 Hz), 3.73 (3H, s), 3.98 (2H, t, J=8.4 Hz), 6.89 (2H, d, J=7.5 Hz), 7.18 (2H, d, J=7.5 Hz), 7.73 (2H, s), 8.90-9.10 (2H, br).

elementary analysis as $C_{26}H_{32}N_2O_3 \cdot HCl \cdot 0.5H_2O$
calculation value: C, 67.01; H, 7.35; N, 6.01.
experimental value: C, 67.53; H, 7.40; N, 6.03.

Example 23

8-(6-[[2-(2-Chlorophenyl)ethyl]amino]hexanoyl]-1,2,5,6-tetrahydro-4H-pyrrolo[3,2,1-ij]quinolin-4-one hydrochloride

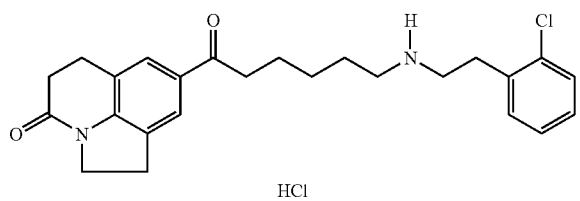

Using tert-butyl 2-(2-chlorophenyl)ethyl[6-oxo-6-(4-oxo-1,2,5,6-tetrahydro-4H-pyrrolo[3,2,1-ij]quinolin-8-yl)hexyl]carbamate (540 mg) obtained in Reference Example 31 according to the same method as that of Example 1, the title compound (368 mg) was obtained as colorless crystals having a melting point of 172 to 174° C.

1H NMR(200 MHz, DMSO-$d_6$) δ 1.25-1.45 (2H, m), 1.55-1.80 (4H, m), 2.59 (2H, t, J=7.6 Hz), 2.85-3.25 (12H, m), 3.99 (2H, t, J=8.4 Hz), 7.25-7.50 (4H, m), 7.73, (2H, s), 9.05-9.30 (2H, br).

elementary analysis as $C_{25}H_{29}ClN_2O_2 \cdot HCl \cdot 0.5H_2O$
calculation value: C, 63.83; H, 6.64; N, 5.95.
experimental value: C, 63.68; H, 6.57; N, 5.80.

Example 24

8-(6-[[2-(3-Fluorophenyl)ethyl]amino]hexanoyl]-1,2,5,6-tetrahydro-4H-pyrrolo[3,2,1-ij]quinolin-4-one hydrochloride

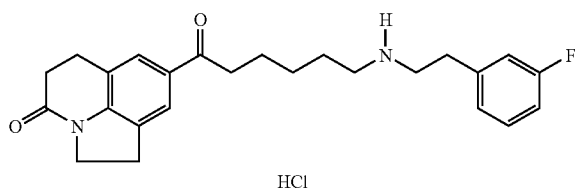

Using tert-butyl 2-(3-fluorophenyl)ethyl[6-oxo-6-(4-oxo-1,2,5,6-tetrahydro-4H-pyrrolo[3,2,1-ij]quinolin-8-yl)hexyl]carbamate (613 mg) obtained in Reference Example 32 according to the same method as that of Example 1, the title compound (493 mg) was obtained as colorless crystals having a melting point of 182 to 184° C.

1H NMR(200 MHz, DMSO-$d_6$) δ 1.25-1.45 (2H, m), 1.55-1.80 (4H, m), 2.59 (2H, t, J=7.6 Hz), 2.85-3.25 (12H, m), 3.99 (2H, t, J=8.4 Hz), 7.00-7.20 (3H, m), 7.30-7.45 (1H, m), 7.73 (2H, s), 9.00-9.20 (2H, br).

Example 25

8-(6-[[2-(2-Methoxyphenyl)-1-methylethyl]amino]hexanoyl]-1,2,5,6-tetrahydro-4H-pyrrolo[3,2,1-ij]quinolin-4-one hydrochloride

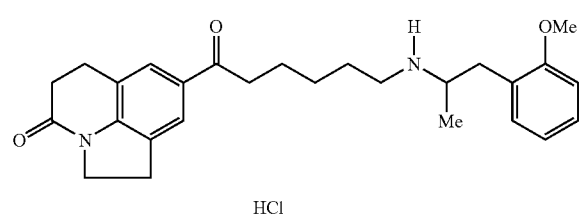

Using tert-butyl 2-(2-methoxyphenyl)-1-methylethyl[6-oxo-6-(4-oxo-1,2,5,6-tetrahydro-4H-pyrrolo[3,2,1-ij]quinolin-8-yl)hexyl]carbamate (467 mg) obtained in Reference Example 33 according to the same method as that of Example 1, the title compound (348 mg) was obtained as pale yellow amorphous powders.

1H NMR(300 MHz, DMSO-$d_6$) δ 1.10 (3H, d, J=6.3 Hz), 1.25-1.50 (2H, m), 1.55-1.80 (4H, m), 2.59 (2H, t, J=7.5 Hz), 2.60-2.80 (1H, m), 2.80-3.40 (10H, m), 3.80 (3H, s), 3.99 (2H, t, J=8.4 Hz), 6.91 (1H, t, J=7.2 Hz), 7.00 (1H, d, J=8.4 Hz), 7.18 (1H, d, J=7.2 Hz), 7.26 (1H, t, J=8.4 Hz), 7.74 (2H, s), 9.00-9.20 (2H, br).

elementary analysis as $C_{27}H_{34}N_2O_3 \cdot HCl \cdot 0.5H_2O$
calculation value: C, 67.55; H, 7.56; N, 5.84.
experimental value: C, 67.40; H, 7.55; N, 5.63.

Example 26

8-[6-[Methyl(2-phenylethyl)amino]hexanoyl]-1,2,5,6-tetrahydro-4H-pyrrolo[3,2,1-ij]quinolin-4-one hydrochloride

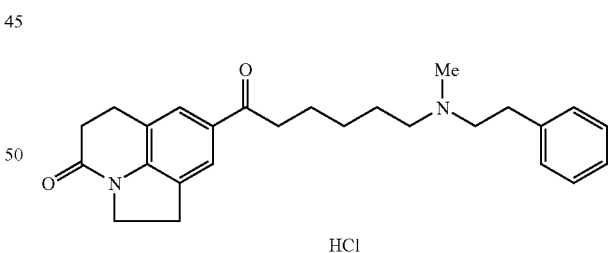

Using 8-(6-bromohexanoyl)-1,2,5,6-tetrahydro-4H-pyrrolo[3,2,1-ij]quinolin-4-one (650 mg) obtained in Reference Example 2 and N-methyl-N-(2-phenylethyl)amine (0.297 ml) according to the same method as that of Example 9, the title compound (326 mg) was obtained as colorless crystals having a melting point of 83 to 85° C.

1H NMR(free base; 300 MHz, CDCl$_3$) δ 1.35-1.50 (2H, m), 1.56 (2H, tt, J=7.5, 7.5 Hz), 1.75 (2H, tt, J=7.5, 7.5 Hz), 2.32 (3H, s), 2.44 (2H, t, J=7.5 Hz), 2.55-2.65 (2H, m), 2.71 (2H, t, J=7.5 Hz), 2.75-2.85 (2H, m), 2.91 (2H, t, J=7.2 Hz), 3.02 (2H, t, J=7.8 Hz), 3.22 (2H, t, J=8.4 Hz), 4.12 (2H, t, J=8.4 Hz), 7.15-7.35 (5H, m), 7.67 (1H, s), 7.71 (1H, s).

elementary analysis as $C_{26}H_{32}N_2O_2 \cdot HCl \cdot 0.5H_2O$
calculation value: C, 69.39; H, 7.62; N, 6.23.
experimental value: C, 69.08; H, 7.41; N, 6.09.

Example 27

8-[6-[[2-(2-Methoxyphenyl)ethyl](methyl)amino]hexanoyl]-1,2,5,6-tetrahydro-4H-pyrrolo[3,2,1-ij]quinolin-4-one hydrochloride

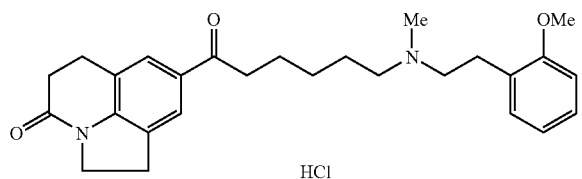

Using 8-(6-bromohexanoyl)-1,2,5,6-tetrahydro-4H-pyrrolo[3,2,1-ij]quinolin-4-one (500 mg) obtained in Reference Example 2 and N-[2-(2-methoxyphenyl)ethyl]-N-methylamine (282 mg) according to the same method as that of Example 9, the title compound (100 mg) was obtained as pale yellow amorphous powders.

$^1$H NMR(free base; 300 MHz, CDCl$_3$) δ 1.35-1.45 (2H, m), 1.50-1.60 (2H, m), 1.75 (2H, tt, J=7.5, 7.5 Hz), 2.32 (3H, s), 2.43 (2H, t, J=7.5 Hz), 2.50-2.60 (2H, m), 2.71 (2H, t, J=7.5 Hz), 2.75-2.85 (2H, m), 2.91 (2H, t, J=7.2 Hz), 3.02 (2H, t, J=7.8 Hz), 3.22 (2H, t, J=8.4 Hz), 3.82 (3H, s), 4.13 (2H, t, J=8.4 Hz), 6.80-6.85 (2H, m), 7.10-7.20 (2H, m), 7.67 (1H, s), 7.72 (1H, s).

Example 28

8-[6-[[2-(3-Methoxyphenyl)ethyl](methyl)amino]hexanoyl]-1,2,5,6-tetrahydro-4H-pyrrolo[3,2,1-ij]quinolin-4-one hydrochloride

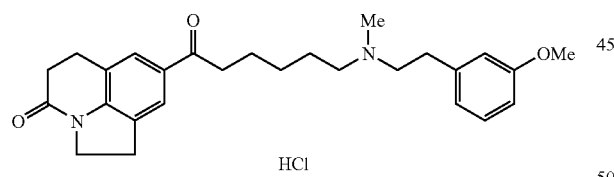

Using 8-(6-bromohexanoyl)-1,2,5,6-tetrahydro-4H-pyrrolo[3,2,1-ij]quinolin-4-one (500 mg) obtained in Reference Example 2 and N-[2-(3-methoxyphenyl)ethyl]-N-methylamine (282 mg) according to the same method as that of Example 9, the title compound (528 mg) was obtained as colorless crystals having a melting point of 116 to 118° C.

$^1$H NMR(free base; 300 MHz, CDCl$_3$) δ 1.30-1.45 (2H, m), 1.50-1.60 (2H, m), 1.74 (2H, tt, J=7.5, 7.5 Hz), 2.30 (3H, s), 2.42 (2H, t, J=7.5 Hz), 2.55-2.80 (6H, m), 2.91 (2H, t, J=7.2 Hz), 3.01 (2H, t, J=7.8 Hz), 3.21 (2H, t, J=8.4 Hz), 3.78 (3H, s), 4.11 (2H, t, J=8.4 Hz), 6.70-6.85 (3H, m), 7.18 (1H, dt, J=7.5, 0.9 Hz), 7.67 (1H, s), 7.71 (1H, s).
elementary analysis as $C_{27}H_{34}N_2O_3 \cdot HCl \cdot H_2O$
calculation value: C, 66.31; H, 7.63; N, 5.73.
experimental value: C, 66.27; H, 7.49; N, 5.55.

Example 29

8-[6-[[2-(2-Chlorophenyl)ethyl](methyl)amino]hexanoyl]-1,2,5,6-tetrahydro-4H-pyrrolo[3,2,1-ij]quinolin-4-one hydrochloride

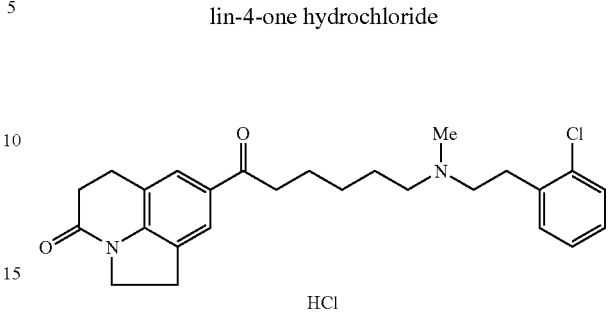

Using 8-(6-bromohexanoyl)-1,2,5,6-tetrahydro-4H-pyrrolo[3,2,1-ij]quinolin-4-one (500 mg) obtained in Reference Example 2 and N-[2-(2-chlorophenyl)ethyl]-N-methylamine (288 mg) according to the same method as that of Example 9, the title compound (330 mg) was obtained as pale yellow amorphous powders.

$^1$H NMR(free base; 200 MHz, CDCl$_3$) δ 1.35-1.65 (4H, m), 1.75 (2H, quintet, J=7.4 Hz), 2.33 (3H, s), 2.44 (2H, t, J=7.5 Hz), 2.55-2.65 (2H, m), 2.71 (2H, t, J=7.5 Hz), 2.85-2.95 (4H, m), 3.02 (2H, t, J=7.8 Hz), 3.22 (2H, t, J=8.4 Hz), 4.13 (2H, t, J=8.4 Hz), 7.05-7.40 (4H, m), 7.67 (1H, s), 7.72 (1H, s).

elementary analysis as $C_{26}H_{31}ClN_2O_2 \cdot HCl \cdot 0.5H_2O$
calculation value: C, 64.46; H, 6.87; N, 5.78.
experimental value: C, 64.75; H, 6.70; N, 5.65.

Example 30

8-[6-[[2-(3-Chlorophenyl)ethyl](methyl)amino]hexanoyl]-1,2,5,6-tetrahydro-4H-pyrrolo[3,2,1-ij]quinolin-4-one hydrochloride

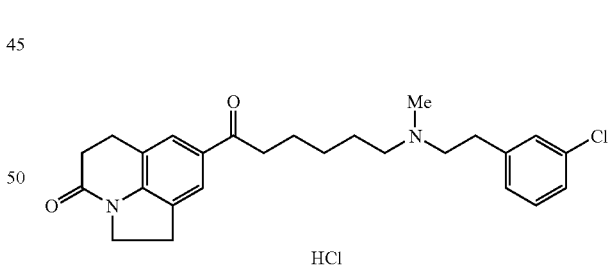

Using 8-(6-bromohexanoyl)-1,2,5,6-tetrahydro-4H-pyrrolo[3,2,1-ij]quinolin-4-one (500 mg) obtained in Reference Example 2 and N-[2-(3-chlorophenyl)ethyl]-N-methylamine (288 mg) according to the same method as that of Example 9, the title compound (235 mg) was obtained as pale yellow amorphous powders.

$^1$H NMR(free base; 200 MHz, CDCl$_3$) δ 1.35-1.60 (4H, m), 1.74 (2H, tt, J=7.4, 7.4 Hz), 2.29 (3H, s), 2.40 (2H, t, J=7.5 Hz), 2.50-2.80 (6H, m), 2.91 (2H, t, J=7.5 Hz), 3.02 (2H, t, J=7.8 Hz), 3.22 (2H, t, J=8.4 Hz), 4.13 (2H, t, J=8.4 Hz), 7.00-7.40 (4H, m), 7.67 (1H, s), 7.71 (1H, s).

Example 31

8-[6-[[2-(3-Fluorophenyl)ethyl](methyl)amino]hexanoyl]-1,2,5,6-tetrahydro-4H-pyrrolo[3,2,1-ij]quinolin-4-one hydrochloride

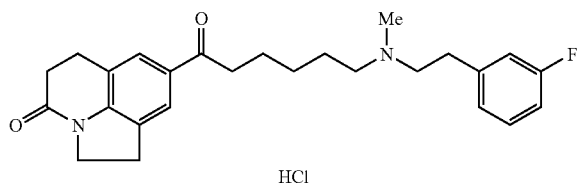

Using 8-(6-bromohexanoyl)-1,2,5,6-tetrahydro-4H-pyrrolo[3,2,1-ij]quinolin-4-one (500 mg) obtained in Reference Example 2 and N-[2-(3-fluorophenyl)ethyl]-N-methylamine (241 mg) according to the same method as that of Example 9, the title compound (120 mg) was obtained as pale yellow amorphous powders.

$^1$H NMR(free base; 300 MHz, CDCl$_3$) δ 1.35-1.65 (4H, m), 1.74 (2H, quintet, J=7.4 Hz), 2.29 (3H, s), 2.41 (2H, t, J=7.5 Hz), 2.55-2.65 (2H, m), 2.65-2.80 (4H, m), 2.91 (2H, t, J=7.5 Hz), 3.02 (2H, t, J=7.8 Hz), 3.22 (2H, t, J=8.4 Hz), 4.12 (2H, t, J=8.4 Hz), 6.80-7.00 (3H, m), 7.20-7.30 (1H, m), 7.67 (1H, s), 7.72 (1H, s).

Example 32

8-[6-[Ethyl-(2-phenylethyl)amino]hexanoyl]-1,2,5,6-tetrahydro-4H-pyrrolo[3,2,1-ij]quinolin-4-one hydrochloride

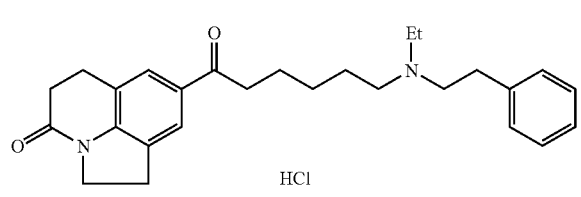

Using 8-(6-bromohexanoyl)-1,2,5,6-tetrahydro-4H-pyrrolo[3,2,1-ij]quinolin-4-one (500 mg) obtained in Reference Example 2 and N-ethyl-N-(2-phenylethyl)amine (234 mg) according to the same method as that of Example 9, the title compound (140 mg) was obtained as pale yellow amorphous powders.

$^1$H NMR(free base; 300 MHz, CDCl$_3$) δ 1.05 (3H, t, J=7.2 Hz), 1.30-1.65 (4H, m), 1.75 (2H, tt, J=7.5, 7.5 Hz), 2.51 (2H, t, J=7.5 Hz), 2.61 (2H, q, J=7.2 Hz), 2.65-2.80 (6H, m), 2.91 (2H, t, J=7.2 Hz), 3.02 (2H, t, J=7.8 Hz), 3.23 (2H, t, J=8.4 Hz), 4.12 (2H, t, J=8.4 Hz), 7.15-7.30 (5H, m), 7.67 (1H, s), 7.72 (1H, s).

Example 33

8-(6-[Ethyl-[2-(2-methoxyphenyl)ethyl]amino]hexanoyl)-1,2,5,6-tetrahydro-4H-pyrrolo[3,2,1-ij]quinolin-4-one hydrochloride

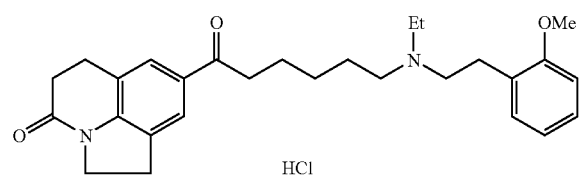

Using 8-(6-bromohexanoyl)-1,2,5,6-tetrahydro-4H-pyrrolo[3,2,1-ij]quinolin-4-one (500 mg) obtained in Reference Example 2 and N-ethyl-N-[2-(2-methoxyphenyl)ethyl]amine (281 mg) according to the same method as that of Example 9, the title compound (190 mg) was obtained as pale yellow amorphous powders.

$^1$H NMR(free base; 200 MHz, CDCl$_3$) δ 1.07 (3H, t, J=7.2 Hz), 1.30-1.65 (4H, m), 1.76 (2H, tt, J=7.4, 7.4 Hz), 2.40-2.80 (10H, m), 2.91 (2H, t, J=7.4 Hz), 3.02 (2H, t, J=7.8 Hz), 3.22 (2H, t, J=8.4 Hz), 3.81 (3H, s), 4.13 (2H, t, J=8.4 Hz), 6.80-6.95 (2H, m), 7.10-7.20 (2H, m), 7.67 (1H, s), 7.72 (1H, s).

Example 34

8-(6-[Isopropyl-[2-(2-methoxyphenyl)ethyl]amino]hexanoyl)-1,2,5,6-tetrahydro-4H-pyrrolo[3,2,1-ij]quinolin-4-one hydrochloride

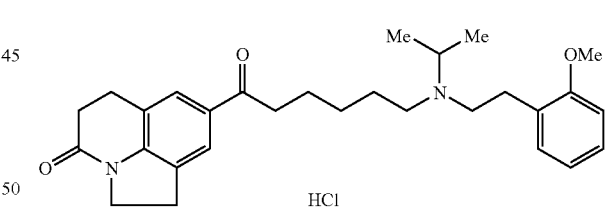

Using 8-(6-bromohexanoyl)-1,2,5,6-tetrahydro-4H-pyrrolo[3,2,1-ij]quinolin-4-one (700 mg) obtained in Reference Example 2 and N-isopropyl-N-[2-(2-methoxyphenyl)ethyl]amine (425 mg) according to the same method as that of Example 9, the title compound (400 mg) was obtained as pale yellow amorphous powders.

$^1$H NMR(free base; 300 MHz, CDCl$_3$) δ 1.00 (6H, d, J=6.6 Hz), 1.30-1.60 (4H, m), 1.75 (2H, tt, J=7.4, 7.4 Hz), 2.47 (2H, t, J=7.5 Hz), 2.55-2.75 (6H, m), 2.85-3.05 (5H, m), 3.21 (2H, t, J=8.4 Hz), 3.81 (3H, s), 4.12 (2H, t, J=8.4 Hz), 6.80-6.90 (2H, m), 7.10-7.20 (2H, m), 7.67 (1H, s), 7.72 (1H, s).

Example 35

8-[6-[[2-(2-Chlorophenyl)ethyl](isopropyl)amino]hexanoyl]-1,2,5,6-tetrahydro-4H-pyrrolo[3,2,1-ij]quinolin-4-one hydrochloride

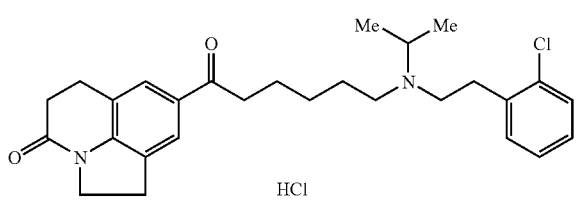

Using 8-(6-bromohexanoyl)-1,2,5,6-tetrahydro-4H-pyrrolo[3,2,1-ij]quinolin-4-one (700 mg) obtained in Reference Example 2 and N-[2-(2-chlorophenyl)ethyl]-N-isopropylamine (435 mg) according to the same method as that of Example 9, the title compound (350 mg) was obtained as pale yellow amorphous powders.

$^1$H NMR(free base; 300 MHz, CDCl$_3$) δ 1.00 (6H, d, J=6.6 Hz), 1.30-1.55 (4H, m), 1.73 (2H, tt, J=7.4, 7.4 Hz), 2.46 (2H, t, J=7.5 Hz), 2.55-2.65 (2H, m), 2.71, (2H, t, J=7.8 Hz), 2.75-3.05 (7H, m), 3.21 (2H, t, J=8.4 Hz), 4.12 (2H, t, J=8.4 Hz), 7.05-7.35 (4H, m), 7.67 (1H, s), 7.72 (1H, s).

Example 36

8-[5-[(3-Phenylpropyl)amino]pentanoyl]-1,2,5,6-tetrahydro-4H-pyrrolo[3,2,1-ij]quinolin-4-one hydrochloride

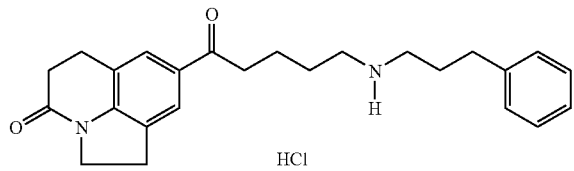

Using tert-butyl 5-oxo-5-(4-oxo-1,2,5,6-tetrahydro-4H-pyrrolo[3,2,1-ij]quinolin-8-yl)pentyl(3-phenylpropyl)carbamate (660 mg) obtained in Reference Example 34 according to the same method as that of Example 1, the title compound (443 mg) was obtained as colorless crystals having a melting point of 116 to 118° C.

$^1$H NMR(200 MHz, DMSO-d$_6$) δ 1.50-1.80 (4H, m), 1.94 (2H, tt, J=7.5, 7.5 Hz), 2.50-2.70 (4H, m), 2.75-3.05 (8H, m), 3.17 (2H, t, J=8.4 Hz), 3.99 (2H, t, J=8.4 Hz), 7.15-7.35 (5H, m), 7.73 (2H, s), 8.80-9.10 (2H, br).

elementary analysis as C$_{25}$H$_{30}$N$_2$O$_2$.HCl.H$_2$O
calculation value: C, 67.48; H, 7.47; N, 6.30.
experimental value: C, 67.45; H, 7.71; N, 6.26.

Example 37

8-[6-[(3-Phenylpropyl)amino]hexanoyl]-1,2,5,6-tetrahydro-4H-pyrrolo[3,2,1-ij]quinolin-4-one hydrochloride

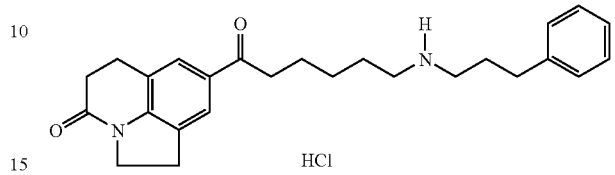

Using tert-butyl 6-oxo-6-(4-oxo-1,2,5,6-tetrahydro-4H-pyrrolo[3,2,1-ij]quinolin-8-yl)hexyl(3-phenylpropyl)carbamate (906 mg) obtained in Reference Example 35 according to the same method as that of Example 1, the title compound (350 mg) was obtained as colorless crystals having a melting point of 132 to 134° C.

$^1$H NMR(300 MHz, DMSO-d$_6$) δ 1.30-1.45 (2H, m), 1.50-1.75 (4H, m), 1.94 (2H, tt, J=7.5, 7.5 Hz), 2.59 (2H, t, J=7.8 Hz), 2.65 (2H, t, J=7.8 Hz), 2.75-3.00 (8H, m), 3.17 (2H, t, J=8.4 Hz), 3.98 (2H, t, J=8.4 Hz), 7.15-7.35 (5H, m), 7.72 (2H, s), 8.80-9.10 (2H, br).

Example 38

8-(5-[[2-(2-Methoxyphenyl)ethyl]amino]pentanoyl)-5,6-dihydro-4H-pyrrolo[3,2,1-ij]quinolin-4-one hydrochloride

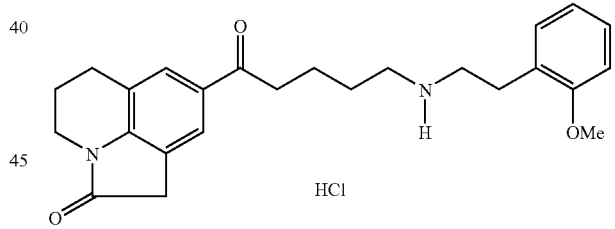

Using tert-butyl 2-(2-methoxyphenyl)ethyl[-oxo-5-(2-oxo-1,2,5,6-tetrahydro-4H-pyrrolo[3,2,1-ij]quinolin-8-yl)pentyl]carbamate obtained in Reference Example 36 according to the same method as that of Example 1, the title compound (535 mg) was obtained as pale yellow crystals having a melting point of 169 to 170° C.

$^1$H NMR(400 MHz, DMSO-d$_6$) δ 1.61-1.73 (4H, m), 1.88-1.97 (2H, m), 2.76 (2H, t, J=6 Hz), 2.93-3.00 (8H, m), 3.57 (2H, s), 3.60 (2H, t, J=6 Hz), 3.79 (3H, s), 6.89 (1H, t, J=7.5 Hz) 6.98 (1H, d, J=7.5 Hz), 7.17 (1H, d, J=7.4 Hz), 7.24 (1H, t, J=7.4 Hz), 7.71 (1H, s), 7.75 (1H, s), 9.12 (2H, br s).

IR (KBr) νcm$^{-1}$: 3418, 2951, 2771, 1708, 1670, 1604, 1498, 1343, 1251, 1150.

elementary analysis as C$_{25}$H$_{30}$N$_2$O$_3$.HCl
calculation value: C, 67.78; H, 7.05; N, 6.32.
experimental value: C, 67.45; H, 7.01; N, 6.27.

Example 39

8-(5-[[2-(2-Chlorophenyl)ethyl]amino]pentanoyl)-5,6-dihydro-4H-pyrrolo[3,2,1-ij]quinolin-2(1H)-one hydrochloride

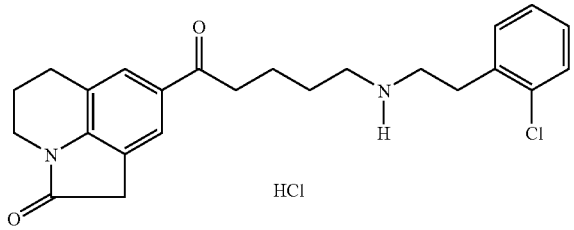

Using tert-butyl 2-(2-chlorophenyl)ethyl[5-oxo-5-(2-oxo-1,2,5,6-tetrahydro-4H-pyrrolo[3,2,1-ij]quinolin-8-yl)pentyl]carbamate obtained in Reference Example 37 according to the same method as that of Example 1, the title compound (585 mg) was obtained as pale yellow crystals having a melting point of 179 to 180° C.

$^1$H NMR(400 MHz, DMSO-d$_6$) δ 1.66-1.72 (4H, m), 1.88-1.94 (2H, m), 2.76 (2H, t, J=6 Hz), 2.96-3.01 (4H, m), 3.11-3.15 (4H, m), 3.57 (2H, s), 3.60 (2H, t, J=6 Hz), 7.27-7.34 (2H, m), 7.38-7.41 (1H, m), 7.44-7.46 (1H, m), 7.71 (1H, s), 7.75 (1H, s), 9.25 (2H, br s).

IR (KBr) vcm$^{-1}$: 3424, 2952, 2772, 1709, 1666, 1602, 1499, 1341, 1149.

elementary analysis as C$_{24}$H$_{27}$ClN$_2$O$_2$.HCl calculation value: C, 64.43; H, 6.31; N, 6.26.

experimental value: C, 64.08; H, 6.36; N, 5.96.

Example 40

8-[5-[Methyl(2-phenylethyl)amino]pentanoyl]-5,6-dihydro-4H-pyrrolo[3,2,1-ij]quinolin-2(1H)-one hydrochloride

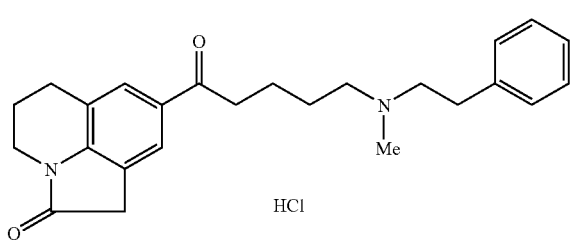

Using 8-(5-chloropentanoyl)-5,6-dihydro-4H-pyrrolo[3,2,1-ij]quinolin-2(1H)-one obtained in Reference Example 3 and N-methyl-N-(2-phenylethyl)amine according to the same method as that of Example 9, the title compound (297 mg) was obtained as colorless amorphous powders.

$^1$H NMR(free base; 400 MHz, CDCl$_3$) δ 1.53-1.61 (2H, m), 1.71-1.78 (2H, m), 2.00-2.06 (2H, m), 2.30 (3H, s), 2.45 (2H, t, J=7.4 Hz), 2.58-2.62 (2H, m), 2.75-2.83 (4H, m), 2.93 (2H, t, J=7.4 Hz), 3.54 (2H, s), 3.74 (2H, t, J=6 Hz), 7.16-7.29 (5H, m), 7.73 (2H, s).

IR (free base; KBr) vcm$^{-1}$: 1718, 1673, 1604, 1496, 1343, 1151.

Example 41

8-(5-[[2-(2-Methoxyphenyl)ethyl]amino]pentanoyl]-5,6-dihydro-4H-pyrrolo[3,2,1-ij]quinolin-2(1H)-one hydrochloride

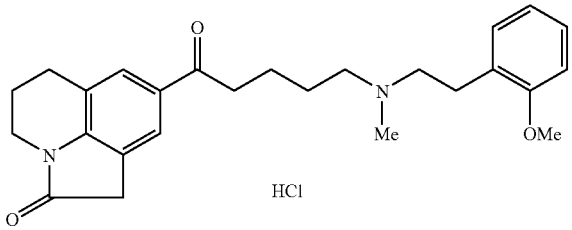

Using 8-(5-chloropentanoyl)-5,6-dihydro-4H-pyrrolo[3,2,1-ij]quinolin-2(1H)-one (292 mg) obtained in Reference Example 3 and N-[2-(2-methoxyphenyl)ethyl]-N-methylamine (363 mg) according to the same method as that of Example 9, the title compound (130 mg) was obtained as W yellow amorphous powders.

$^1$H NMR(free base; 400 MHz, CDCl$_3$) δ 1.55-1.63 (2H, m), 1.72-1.79 (2H, m), 2.00-2.06 (2H, m), 2.32 (3H, s), 2.47 (2H, t, J=7.5 Hz), 2.56-2.60 (2H, m), 2.77-2.83 (4H, m), 2.94 (2H, t, J=7.5 Hz), 3.54 (2H, s), 3.74 (2H, t, J=6 Hz), 3.81 (3H, s), 6.83-6.89 (2H, m), 7.12-7.19 (2H, m), 7.74 (2H, s).

IR (free base; KBr) vcm$^{-1}$: 1716, 1672, 1603, 1495, 1343, 1243, 1152.

Example 42

8-[(5-[[2-(2-Chlorophenyl)ethyl](methyl)amino]pentanoyl]-5,6-dihydro-4H-pyrrolo[3,2,1-ij]quinolin-2(1H)-one hydrochloride

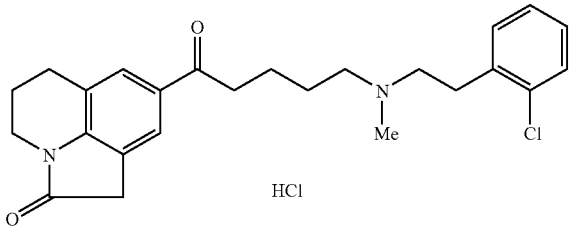

Using 8-(5-chloropentanoyl)-5,6-dihydro-4H-pyrrolo[3,2,1-ij]quinolin-2(1H)-one obtained in Reference Example. 3 and N-[2-(2-chlorophenyl)ethyl]-N-methylamine according to the same method as that of Example 9, the title compound (85 mg) was obtained as pale yellow amorphous powders.

$^1$H NMR(free base; 400 MHz, CDCl$_3$) δ 1.56-1.64 (2H, m), 1.71-1.79 (2H, m), 2.00-2.07 (2H, m), 2.36 (3H, s), 2.50 (2H, t, J=7.5 Hz), 2.61-2.67 (2H, m), 2.82 (2H, t, J=6 Hz), 2.90-2.95 (4H, m), 3.55 (2H, s), 3.74 (2H, t, J=6 Hz), 7.11-7.25 (3H, m), 7.32 (1H, dd, J=5.5, 2 Hz) 7.74 (2H, s).

IR (free base; KBr) vcm$^{-1}$: 1716, 1672, 1604, 1496, 1343, 1151.

Example 43

8-[(5-[[2-(3-Fluorophenyl)ethyl](methyl)amino]pentanoyl]-5,6-dihydro-4H-pyrrolo[3,2,1-ij]quinolin-2(1H)-one hydrochloride

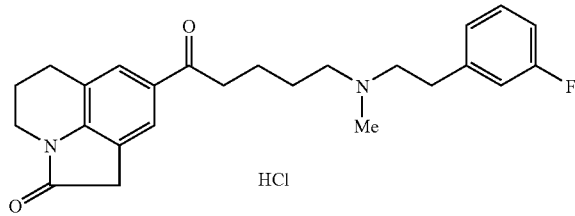

Using 8-(5-chloropentanoyl)-5,6-dihydro-4H-pyrrolo[3,2,1-ij]quinolin-2(1H)-one obtained in Reference Example 3 and N-[2-(3-fluorophenyl)ethyl]-N-methylamine according to the same method as that of Example 9, the title compound (68 mg) was obtained as pale yellow amorphous powders.

$^1$H NMR(free base; 400 MHz, CDCl$_3$) δ 1.52-1.60 (2H, m), 1.72-1.78 (2H, m), 2.00-2.08 (2H, m), 2.29 (3H, s), 2.44 (2H, t, J=7.5 Hz), 2.58-2.62 (2H, m), 2.74-2.78 (2H, m), 2.82 (2H, t, J=6 Hz), 2.93 (2H, t, J=7 Hz), 3.55 (2H, s), 3.74 (2H, t, J=6 Hz), 6.85-6.93 (2H, m), 6.96 (1H, d, J=7.5 Hz), 7.20-7.25 (1H, m), 7.73 (2H, s).

IR (free base; KBr) vcm$^{-1}$: 1717, 1673, 1604, 1496, 1343, 1151.

Example 44

8-[5-[Ethyl(2-phenylethyl)amino]pentanoyl]-5,6-dihydro-4H-pyrrolo[3,2,1-ij]quinolin-2(1H)-one hydrochloride

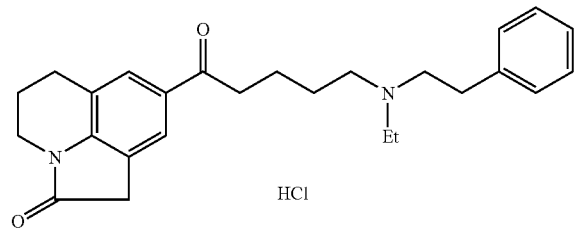

Using 8-(5-chloropentanoyl)-5,6-dihydro-4H-pyrrolo[3,2,1-ij]quinolin-2(1H)-one obtained in Reference Example 3 and N-ethyl-N-(2-phenylethyl)amine according to the same method as that of Example 9, the title compound (45 mg) was obtained as pale yellow amorphous powders.

$^1$H NMR(free base; 400 MHz, CDCl$_3$) δ 1.05 (3H, t, J=7 Hz), 1.54-1.59 (2H, m), 1.70-1.78 (2H, m), 2.00-2.06 (2H, m), 2.54 (2H, t, J=7 Hz), 2.61 (2H, q, J=7 Hz), 2.68-2.75 (4H, m), 2.82 (2H, t, J=6 Hz), 2.92 (2H, t, J=. 6 Hz), 3.54 (2H, s), 3.74 (2H, t, J=6 Hz), 7.16-7.19 (3H, m) 7.25-7.30 (2H, m), 7.73 (2H, s).

IR (free base; KBr) vcm$^{-1}$: 1718, 1671, 1603, 1496, 1342, 1150.

Example 45

8-(5-[Ethyl[2-(2-methoxyphenyl)ethyl]amino]pentanoyl)-5,6-dihydro-4H-pyrrolo[3,2,1-ij]quinolin-2(1H)-one hydrochloride

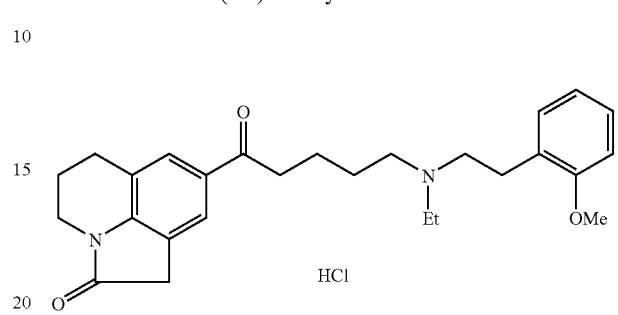

Using 8-(5-chloropentanoyl)-5,6-dihydro-4H-pyrrolo[3,2,1-ij]quinolin-2(1H)-one obtained in Reference Example 3 and N-ethyl-N-[2-(2-methoxyphenyl)ethyl]amine according to the same method as that of Example 9, the title compound (44 mg) was obtained as pale yellow amorphous powders.

$^1$H NMR(free base; 400 MHz, CDCl$_3$) δ 1.07 (3H, t, J=7 Hz), 1.57-1.62 (2H, m), 1.71-1.79 (2H, m), 1.99-2.06 (2H, m), 2.57 (2H, t, J=7 Hz), 2.62 (2H, q, J=7 Hz), 2.66-2.70 (2H, m), 2.73-2.78 (2H, m), 2.82 (2H, t, J=6 Hz), 2.93 (2H, t, J=6 Hz), 3.54 (2H, s), 3.74 (2H, t, J=6 Hz), 3.81 (3H, s), 6.83-6.89 (3H, m), 7.11-7.19 (2H, m), 7.74 (2H, s).

IR (free base; KBr) vcm$^{-1}$: 1717, 1672, 1602, 1494, 1342, 1243, 1150.

Example 46

8-[6-[(2-Phenylethyl)amino]hexanoyl]-5,6-dihydro-4H-pyrrolo[3,2,1-ij]quinolin-2(1H)-one hydrochloride

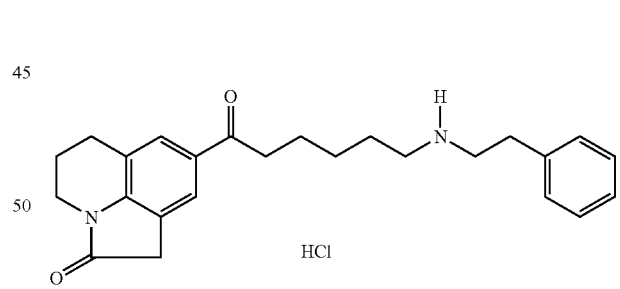

Using 8-(6-bromohexanoyl)-5,6-dihydro-4H-pyrrolo[3,2,1-ij]quinolin-2(1H)-one (350 mg) obtained in Reference Example 4 and 2-phenylethylamine (364 mg) according to the same method as that of Example 9, the title compound (73 mg) was obtained as pale yellow amorphous powders.

$^1$H NMR(free base; 400 MHz, CDCl$_3$) δ 1.35-1.42 (2H, m), 1.49-1.56 (2H, m), 1.60 (1H, br s), 1.69-1.77 (2H, m), 2.00-2.06 (2H, m), 2.63 (2H, t, J=7.4 Hz), 2.75-2.97 (8H, m), 3.54 (2H, s), 3.74 (2H, t, J=6 Hz), 7.18-7.31 (5H, m), 7.72 (2H, s).

IR (free base; KBr) vcm$^{-1}$: 1716, 1672, 1604, 1496, 1343, 1150.

Example 47

8-(6-[[2-(2-Methoxyphenyl)ethyl]amino]hexanoyl)-5,6-dihydro-4H-pyrrolo[3,2,1-ij]quinolin-2(1H)-one hydrochloride

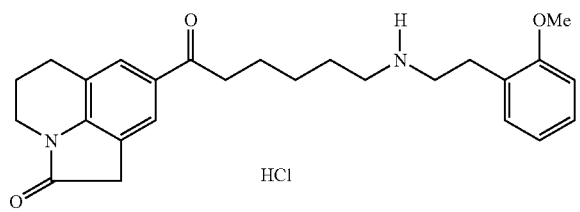

Using 8-(6-bromohexanoyl)-5,6-dihydro-4H-pyrrolo[3,2,1-ij]quinolin-2(1H)-one obtained in Reference Example 4 and 2-(2-methoxyphenyl)ethylamine according to the same method as that of Example 9, the title compound (190 mg) was obtained as pale yellow amorphous powders.

$^1$H NMR(free base; 400 MHz, CDCl$_3$) δ 1.36-1.43 (2H, m), 1.49-1.57 (3H, m), 1.70-1.77 (2H, m), 2.00-2.06 (2H, m), 2.64 (2H, t, J=7.4 Hz), 2.80-2.83 (6H, m), 2.90 (2H, t, J=7.4 Hz), 3.54 (2H, s), 3.73 (2H, t, J=6 Hz), 3.81 (3H, s), 6.86 (1H, t, J=8.3 Hz), 6.89 (1H, d, J=7.3 Hz), 7.13-7.21 (2H, m), 7.72 (2H, s)

IR (free base; KBr) νcm$^{-1}$: 1715, 1672, 1603, 1495, 1343, 1242, 1150.

Example 48

8-(6-[[2-(2-Chlorophenyl)ethyl]amino]hexanoyl)-5,6-dihydro-4H-pyrrolo[3,2,1-ij]quinolin-2(1H)-one hydrochloride

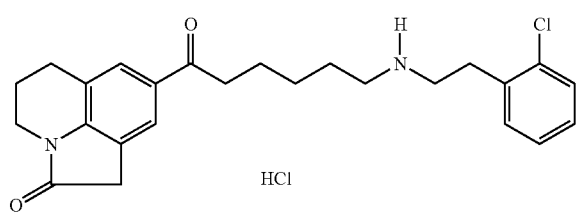

Using 8-(6-bromohexanoyl)-5,6-dihydro-4H-pyrrolo[3,2,1-ij]quinolin-2(1H)-one obtained in Reference Example 4 and 2-(2-chlorophenyl)ethylamine according to the same method as that of Example 9, the title compound (30 mg) was obtained as pale yellow amorphous powders.

$^1$H NMR(free base; 400 MHz, CDCl$_3$) δ 1.37-1.45 (2H, m), 1.51-1.58 (2H, m), 1.56 (1H, br s), 1.71-1.78 (2H, m), 2.00-2.07 (2H, m), 2.66 (2H, t, J=7.5 Hz), 2.82 (2H, t, J=6 Hz), 2.85-2.98 (6H, m), 3.55 (2H, s), 3.74 (2H, t, J=6 Hz), 7.13-7.25 (3H, m), 7.34 (1H, dd, J=7, 2 Hz), 7.73 (2H, s).

IR (free base; KBr) νcm$^{-1}$: 1715, 1671, 1604, 1496, 1343, 1150.

Example 49

8-[6-[(2-Phenylethyl]amino]hexanoyl)-5,6-dihydro-4H-pyrrolo[3,2,1-ij]quinolin-2(1H)-one hydrochloride

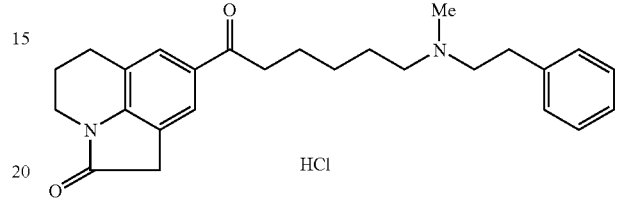

Using 8-(6-bromohexanoyl)-5,6-dihydro-4H-pyrrolo[3,2,1-ij]quinolin-2(1H)-one obtained in Reference Example 4 and N-methyl-N-(2-phenylethyl)amine according to the same method as that of Example 9, the title compound (30 mg) was obtained as pale yellow amorphous powders.

$^1$H NMR(free base; 400 MHz, CDCl$_3$) δ 1.36-1.42 (2H, m), 1.50-1.58 (2H, m), 1.71-1.78 (2H, m), 2.00-2.06 (2H, m), 2.30 (3H, s), 2.41 (2H, t, J=7 Hz), 2.58-2.62 (2H, m), 2.75-2.83 (4H, m), 2.91 (2H, t, J=7 Hz), 3.54 (2H, s), 3.73 (2H, t, J=6 Hz), 7.16-7.29 (5H, m), 7.73 (2H, s).

IR (free base; KBr) νcm$^{-1}$: 1718, 1673, 1604, 1496, 1343, 1151.

Example 50

8-(6-[[2-(2-Methoxyphenyl)ethyl]amino]hexanoyl)-5,6-dihydro-4H-pyrrolo[3,2,1-ij]quinolin-2(1H)-one hydrochloride

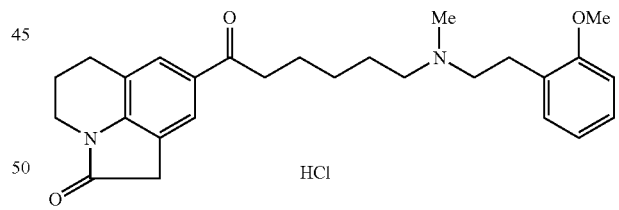

Using 8-(6-bromohexanoyl)-5,6-dihydro-4H-pyrrolo[3,2,1-ij]quinolin-2(1H)-one obtained in Reference Example 4 and N-[2-(2-methoxyphenyl)ethyl]-N-methylamine according to the same method as that of Example 9, the title compound (250 mg) was obtained as pale yellow amorphous powders.

$^1$H NMR(free base; 400 MHz, CDCl$_3$) δ 1.37-1.43 (2H, m), 1.51-1.59 (2H, m), 1.71-1.79 (2H, m), 2.00-2.06 (2H, m), 2.31 (3H, s), 2.42 (2H, t, J=7.5 Hz), 2.55-2.59 (2H, m), 2.76-2.83 (4H, m), 2.92 (2H, t, J=7.5 Hz), 3.54 (2H, s), 3.73 (2H, t, J=6 Hz), 3.81 (3H, s), 6.83-6.89 (2H, m), 7.12-7.19 (2H, m), 7.74 (2H, s).

IR (free base; KBr) νcm$^{-1}$: 1715, 1672, 1603, 1495, 1343, 1242, 1150.

Example 51

8-(6-[[2-(2-Chlorophenyl)ethyl]amino]hexanoyl)-5,6-dihydro-4H-pyrrolo[3,2,1-ij]quinolin-2(1H)-one hydrochloride

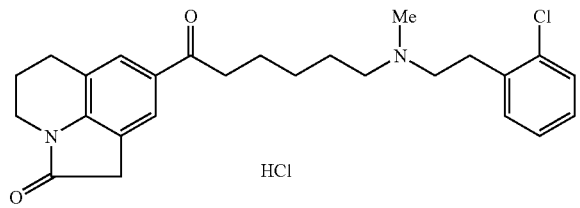

Using 8-(6-bromohexanoyl)-5,6-dihydro-4H-pyrrolo[3,2,1-ij]quinolin-2(1H)-one obtained in Reference Example 4 and N-[2-(2-chlorophenyl)ethyl]-N-methylamine according to the same method as that of Example 9, the title compound (256 mg) was obtained as pale yellow amorphous powders.

$^1$H NMR(free base; 400 MHz, CDCl$_3$) δ 1.37-1.43 (2H, m), 1.51-1.58 (2H, m), 1.71-1.79 (2H, m), 2.00-2.06 (2H, m), 2.33 (3H, s), 2.44 (2H, t, J=7.5 Hz), 2.58-2.62 (2H, m), 2.82 (2H, t, J=6 Hz), 2.88-2.94 (4H, m), 3.54 (2H, s), 3.74 (2H, t, J=6 Hz), 7.11-7.24 (3H, m), 7.32 (1H, dd, J=5.5, 2 Hz), 7.73 (2H, s).

IR (free base; KBr) vcm$^{-1}$: 1718, 1673, 1604, 1496, 1343, 1151.

Example 52

8-(6-[[2-(3-Fluorophenyl)ethyl]amino]hexanoyl)-5,6-dihydro-4H-pyrrolo[3,2,1-ij]quinolin-2(1H)-one hydrochloride

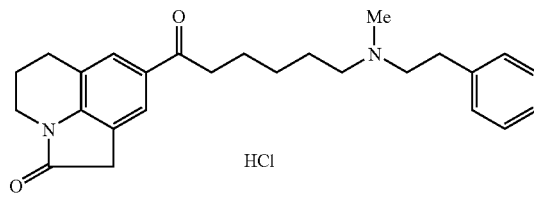

Using 8-(6-bromohexanoyl)-5,6-dihydro-4H-pyrrolo[3,2,1-ij]quinolin-2(1H)-one obtained in Reference Example 4 and N-[2-(3-fluorophenyl)ethyl]-N-methylamine according to the same method as that of Example 9, the title compound (190 mg) was obtained as pale yellow amorphous powders.

$^1$H NMR(free base; 400 MHz, CDCl$_3$) δ 1.36-1.42 (2H, m), 1.49-1.57 (2H, m), 1.71-1.78 (2H, m), 2.00-2.07 (2H, m), 2.29 (3H, s), 2.40 (2H, t, J=7.5 Hz), 2.57-2.61 (2H,m), 2.74-2.79 (2H, m), 2.84 (2H, t, J=6 Hz), 3.54 (2H, s), 3.74 (2H, t, J=6 Hz), 6.85-6.91 (2H, m), 6.97 (1H, d, J=7.5 Hz), 7.20-7.25 (1H, m), 7.74 (2H, s).

IR (free base; KBr) vcm$^{-1}$: 1717, 1672, 1604, 1496, 1343, 1150.

Example 53

8-[6-[Ethyl(2-phenylethyl)amino]hexanoyl]-5,6-dihydro-4H-pyrrolo[3,2,1-ij]quinolin-2(1H)-one hydrochloride

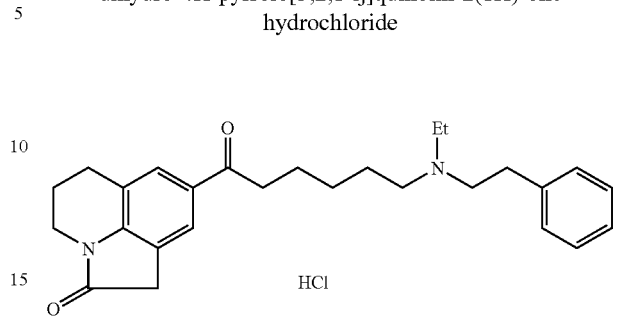

Using 8-(6-bromohexanoyl)-5,6-dihydro-4H-pyrrolo[3,2,1-ij]quinolin-2(1H)-one obtained in Reference Example 4 and N-ethyl-N-(2-phenylethyl)amine according to the same method as that of Example 9, the title compound (137 mg) was obtained as pale yellow amorphous powders.

$^1$H NMR(free base; 400 MHz, CDCl$_3$) δ 1.05 (3H, t, J=7 Hz), 1.36-1.42 (2H, m), 1.49-1.56 (2H, m), 1.71-1.79 (2H, m), 2.00-2.06 (2H, m), 2.50 (2H, t, J=7.5 Hz), 2.61 (2H, q, J=7 Hz), 2.67-2.76 (4H, m), 2.82 (2H, t, J=6 Hz), 2.91 (2H, t, J=6 Hz), 3.54 (2H, s), 3.73 (2H, t, J=6 Hz), 7.16-7.19 (3H, m), 7.25-7.29 (2H, m), 7.73 (2H, s).

IR (free base; KBr) vcm$^{-1}$: 1718, 1673, 1604, 1496, 1342, 1150.

Example 54

8-(6-[Ethyl[2-(2-methoxyphenyl)ethyl]amino]hexanoyl)-5,6-dihydro-4H-pyrrolo[3,2,1-ij]quinolin-2(1H)-one hydrochloride

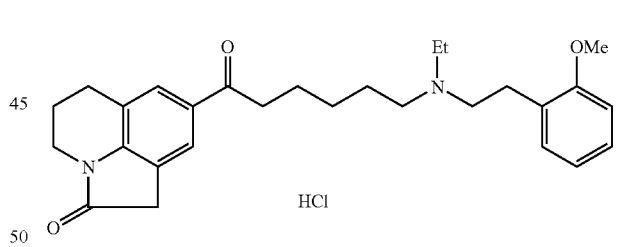

Using 8-(6-bromohexanoyl)-5,6-dihydro-4H-pyrrolo[3,2,1-ij]quinolin-2(1H)-one obtained in Reference Example 4 and N-(2-(2-methoxyphenyl)ethyl]amine according to the same method as that of Example 9, the title compound (145 mg) was obtained as pale yellow amorphous powders.

$^1$H NMR(free base; 400 MHz, CDCl$_3$) δ 1.06 (3H, t, J=7 Hz), 1.37-1.43 (2H, m), 1.51-1.59 (2H, m), 1.72-1.80 (2H, m), 2.00-2.06 (2H, m), 2.52 (2H, t, J=7.5 Hz), 2.61 (2H, q, J=7 Hz), 2.66-2.69 (2H, m), 2.72-2.77 (2H, m), 2.82 (2H, t, J=6 Hz), 2.92 (2H, t, J=6 Hz), 3.54 (2H, s), 3.73 (2H, t, J=6 Hz), 3.81(3H, s), 6.83-6.89(2H, m), 7.11-7.19 (2H, m), 7.73 (2H, s).

IR (free base; KBr) vcm$^{-1}$: 1718, 1673, 1603, 1495, 1342, 1242, 1150.

Example 55

8-(6-[Isopropyl[2-(2-methoxyphenyl)ethyl]amino]hexanoyl)-5,6-dihydro-4H-pyrrolo[3,2,1-ij]quinolin-2(1H)-one hydrochloride

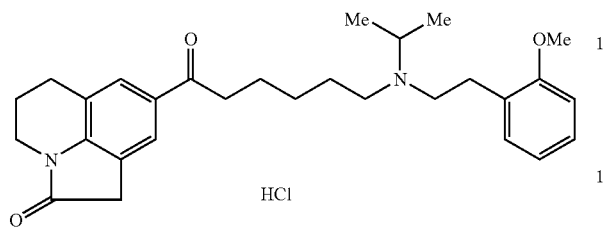

Using 8-(6-bromohexanoyl)-5,6-dihydro-4H-pyrrolo[3,2,1-ij]quinolin-2(1H)-one obtained in Reference Example 4 and N-isopropyl-N-[2-(2-methoxyphenyl)ethyl]amine (425 mg) according to the same method as that of Example 9, the title compound (45 mg) was obtained as pale yellow amorphous powders.

$^1$H NMR(free base; 400 MHz, CDCl$_3$) δ 1.00 (6H, d, J=6.3 Hz), 1.36-1.42 (2H, m), 1.48-1.55 (2H, m), 1.71-1.78 (2H, m), 1.99-2.05 (2H, m), 2.46 (2H, t, J=7.3 Hz), 2.56-2.60 (2H, m), 2.69-2.73 (2H, m), 2.81 (2H, t, J=6 Hz), 2.91 (2H, t, J=7.3 Hz), 2.99 (1H, q, J=6.3 Hz), 3.53 (2H, s), 3.72 (2H, t, J=6 Hz), 3.81 (3H, s), 6.82-6.88 (2H, m), 7.10-7.18 (2H, m), 7.73 (2H, s).

IR (free base; neat) νcm$^{-1}$: 1713, 1674, 1603, 1495, 1344, 1243, 1150.

Example 56

9-[5-[(2-Phenylethyl)amino]pentanolyl)-2,3,6,7-tetrahydro-1H,5H-pyrido[3,2,1-ij]quinolin-5-one hydrochloride

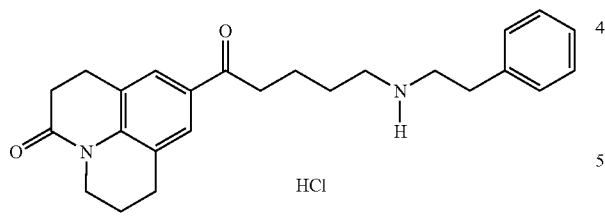

Using tert-butyl 5-oxo-5-(3-oxo-2,3,6,7-tetrahydro-1H,5H-pyrido[3,2,1-ij]quinolin-9-yl)pentyl(2-phenylethyl)carbamate (315 mg) obtained in Reference. Example 38 according to the same method as that of Example 1, the title compound (264 mg) was obtained as yellow amorphous powders.

$^1$H NMR(400 MHz, CD$_3$OD) δ 1.71-1.85 (4H, m), 1.98-2.02 (2H, m), 2.69 (2H, t, J=7 Hz), 2.90 (2H, t, J=6 Hz), 3.00 (2H, t, J=7 Hz), 3.04-3.08 (2H, m), 3.10-3.14 (4H, m), 3.28-3.32 (2H, m), 3.90 (2H, t, J=6 Hz), 4.88 (2H, s), 7.29-7.41 (5H, m), 7.74 (2H, d, J=4 Hz).

IR (neat) νcm$^{-1}$: 3427, 1670, 1604, 1484, 1366, 1298, 1165.

Example 57

9-[(5-[[2-(2-Methoxyphenyl)ethyl]amino]pentanolyl)-2,3,6,7-tetrahydro-1H,5H-pyrido[3,2,1-ij]quinolin-5-one hydrochloride

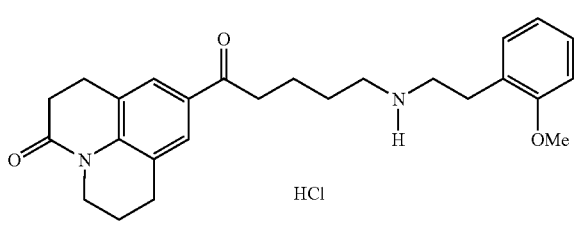

Using tert-butyl 2-(2-methoxyphenyl)ethyl[5-oxy-5-(3-oxo-2,3,6,7-tetrahydro-1H,5H-pyrido[3,2,1-ij]quinolin-9-yl)pentyl]carbamate (410 mg) obtained in Reference Example 39 according to the same method as that of Example 1, the title compound (315 mg) was obtained as yellow amorphous powders.

$^1$H NMR(400 MHz, CD$_3$OD) δ 1.71-1.78 (4H, m), 1.85-1.91 (2H, m), 2.57 (2H, t, J=7 Hz), 2.79 (2H, t, J=7 Hz), 2.88 (2H, t, J=7 Hz), 2.96-3.03 (6H, m), 3.17 (2H, t, J=7 Hz), 3.77 (2H, t, J=7.5 Hz), 3.81 (3H, s), 4.79 (2H, s), 6.87 (1H, t, J=7 Hz), 6.93 (1H, d, J=8 Hz), 7.17 (1H, d, J=7 Hz), 7.22 (1H, t, J=7 Hz), 7.64 (2H, d, J=4 Hz).

IR (neat) νcm$^{-1}$: 3431, 1671, 1603, 1496, 1439, 1366, 1247, 1165.

Example 58

9-(5-[[2-(2-Chlorophenyl)ethyl]amino]pentanolyl)-2,3,6,7-tetrahydro-1H,5H-pyrido[3,2,1-ij]quinolin-5-one hydrochloride

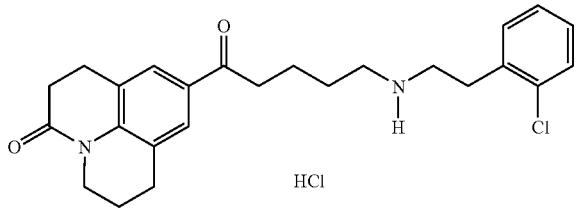

Using tert-butyl 2-(2-chlorophenyl)ethyl[5-oxy-5-(3-oxo-2,3,6,7-tetrahydro-1H,5H-pyrido[3,2,1-ij]quinolin-9-yl)pentyl]carbamate (380 mg) obtained in Reference Example 40 according to the same method as that of Example 1, the title compound (235 mg) was obtained as colorless powders having a melting point of 108 to 109° C.

$^1$H NMR(400 MHz, DMSO-d$_6$) δ 1.62-1.72 (4H, m), 1.81-1.87 (2H, m), 2.56 (2H, t, J=6 Hz), 2.79 (2H, t, J=6 Hz), 2.90 (2H, t, J=7 Hz), 2.92-3.02 (4H, m), 3.05-3.16 (4H, m), 3.75 (2H, t, J=6 Hz), 7.24-7.35 (2H, m), 7.39 (1H, dd, J=7, 2 Hz), 7.45 (1H, dd, J=7, 2 Hz), 7.66 (2H, s), 9.18 (2H, s).

IR (KBr) νcm$^{-1}$: 3429, 2948, 1671, 1603, 1363, 1338, 1165.

Example 59

9-[5-[Methyl(2-phenylethyl]amino]pentanolyl)-2,3,6,7-tetrahydro-1H,5H-pyrido[3,2,1-ij]quinolin-5-one hydrochloride

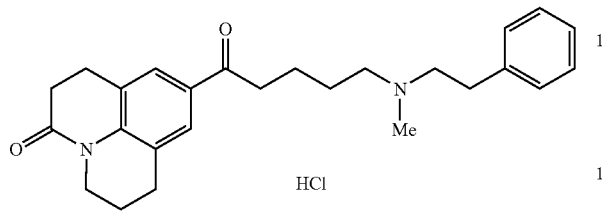

Using 9-(5-chloropentanoyl)-2,3,6,7-tetrahydro-1H,5H-pyrido[3,2,1-ij]quinolin-5-one obtained in Reference Example 5 and N-methyl-N-(2-phenylethyl)amine according to the same method as that of Example 9, the title compound (310 mg) was obtained as pale yellow amorphous powders.

$^1$H NMR(free base; 400 MHz, CDCl$_3$) δ 1.53-1.61 (2H, m), 1.71-1.78 (2H, m), 1.93-1.99 (2H, m), 2.31 (3H, s), 2.45 (2H, t, J=7.4 Hz), 2.59-2.63 (2H, m), 2.66-2.69 (2H, m), 2.75-2.79 (2H, m), 2.84 (2H, t, J=6 Hz), 2.91-2.95 (4H, m), 3.89 (2H, t, J=6 Hz), 7.17-7.29 (5H, m), 7.61 (2H, d, J=5 Hz).

IR (free base; KBr) vcm$^{-1}$: 1676, 1604, 1590, 1484, 1361, 1339, 1161.

Example 60

9-[5-[[2-(2-Methoxyphenyl)ethyl](methyl)amino]pentanolyl)-2,3,6,7-tetrahydro-1H,5H-pyrido[3,2,1-ij]quinolin-5-one hydrochloride

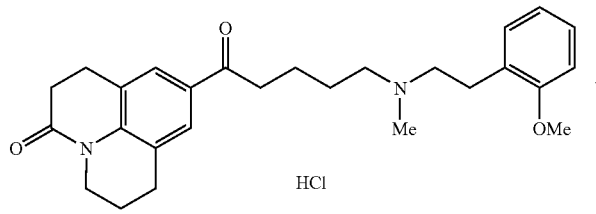

Using 9-(5-chloropentanoyl)-2,3,6,7-tetrahydro-1H,5H-pyrido[3,2,1-ij]quinolin-5-one obtained in Reference Example 5 and N-[2-(2-methoxyphenyl)ethyl]-N-methylamine according to the same method as that of Example 9, the title compound (165 mg) was obtained as pale yellow amorphous powders.

$^1$H NMR(free base; 400 MHz, CDCl$_3$) δ 1.55-1.62 (2H, m), 1.71-1.79 (2H, m), 1.93-1.99 (2H, m), 2.32 (3H, s), 2.46 (2H, t, J=7.4 Hz), 2.56-2.60 (2H, m), 2.68 (2H, t, J=. 6 Hz), 2.77-2.80 (2H, m), 2.84 (2H, t, J=6 Hz), 2.91-2.95 (4H, m), 3.81 (3H, s), 3.89 (2H, t, J=6 Hz), 6.83-6.89 (2H, m), 7.12-7.19 (2H, m), 7.62 (2H, d, J=5 Hz).

IR (free base; KBr) vcm$^{-1}$: 1674, 1603, 1494, 1361, 1339, 1243, 1160.

Example 61

9-[5-[[2-(2-Chlorophenyl)ethyl](methyl)amino pentanolyl)-2,3,6,7-tetrahydro-1H,5H-pyrido[3,2,1-ij]quinolin-5-one hydrochloride

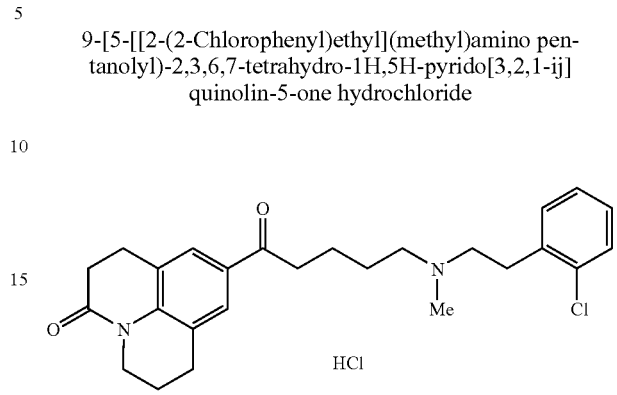

Using 9-(5-chloropentanoyl)-2,3,6,7-tetrahydro-1H,5H-pyrido[3,2,1-ij]quinolin-5-one obtained in Reference Example 5 and N-[2-(2-chlorophenyl)ethyl]-N-methylamine according to the same method as that of Example 9, the title compound (188 mg) was obtained as pale yellow amorphous powders.

$^1$H NMR(free base; 400 MHz, CDCl$_3$) δ 1.54-1.62 (2H, m), 1.71-1.78 (2H, m), 1.93-1.99 (2H, m), 2.32 (3H, s), 2.48 (2H, t, J=7 Hz), 2.59-2.63 (2H, m), 2.67 (2H, t, J=6 Hz), 2.84 (2H, t, J=6 Hz), 2.88-2.96 (6H, m), 3.89 (2H, t, J=6 Hz), 7.11-7.24 (3H, m), 7.32 (1H, d, d, J=5, 2 Hz), 7.62 (2H, d, J=5 Hz).

IR (free base; KBr) vcm$^{-1}$: 1673, 1604, 1483, 1438, 1361, 1159.

Example 62

9-[5-[Ethyl(2-phenylethyl]amino)pentanolyl)-2,3,6,7-tetrahydro-1H,5H-pyrido[3,2,1-ij]quinolin-5-one hydrochloride

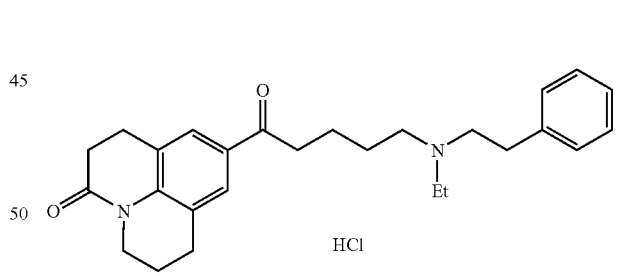

Using 9-(5-chloropentanoyl)-2,3,6,7-tetrahydro-1H,5H-pyrido[3,2,1-ij]quinolin-5-one obtained in Reference Example 5 and N-ethyl-N-(2-phenylethyl)amine according to the same method as that of Example 9, the title compound (45 mg) was obtained as pale yellow amorphous powders.

$^1$H NMR(free base; 400 MHz, CDCl$_3$) δ 1.05 (3H, t, J=7 Hz), 1.52-1.60 (2H, m), 1.70-1.77 (2H, m), 1.95-1.99 (2H, m), 2.55 (2H, t, J=7 Hz), 2.61 (2H, q, J=7 Hz), 2.65-2.77 (6H, m), 2.84 (2H, t, J=6 Hz), 2.89-2.97 (4H, m), 3.89 (2H, t, J=6 Hz), 7.16-7.19 (3H, m), 7.25-7.30 (2H, m), 7.62 (2H, d, J=5 Hz).

IR (free base; KBr) vcm$^-$: 1675, 1604, 1484, 1361, 1299, 1160.

Example 63

9-(5-[Ethyl[2-(2-methoxyphenyl)ethyl]amino]pentanolyl)-2,3,6,7-tetrahydro-1H,5H-pyrido[3,2,1-ij]quinolin-5-one hydrochloride

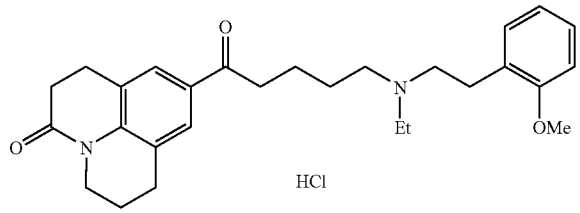

Using 9-(5-chloropentanoyl)-2,3,6,7-tetrahydro-1H,5H-pyrido[3,2,1-ij]quinolin-5-one obtained in Reference Example 5 and N-ethyl-N-[2-(2-methoxyphenyl)ethyl]amine according to the same method as that of Example 9, the title compound (70 mg) was obtained as pale yellow amorphous powders.

$^1$H NMR(free base; 400 MHz, CDCl$_3$) δ 1.07 (3H, t, J=7 Hz), 1.55-1.62 (2H, m), 1.71-1.78 (2H, m), 1.93-1.99 (2H, m), 2.56 (2H, t, J=7.5 Hz), 2.62 (2H, q, J=7 Hz), 2.66-2.69 (4H, m), 2.73-2.78 (2H, m), 2.84 (2H, t, J=6 Hz), 2.93 (4H, t, J=6 Hz), 3.81 (3H, s), 3.89 (2H, t, J=6 Hz), 6.83-6.89 (2H, m), 7.11-7.19 (2H, m), 7.62 (2H, d, J=5 Hz).

IR (free base; KBr) νcm$^{-1}$: 1674, 1603, 1494, 1361, 1339, 1243, 1160.

Example 64

9-[6-[(2-Phenylethyl)amino]hexanoyl]-2,3,6,7-tetrahydro-1H,5H-pyrido[3,2,1-ij]quinolin-5-one hydrochloride

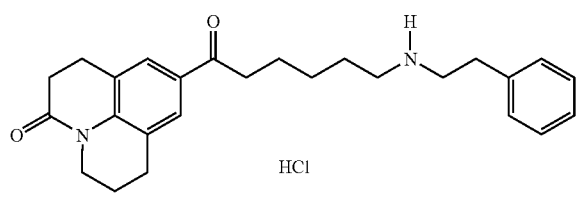

Using 9-(6-bromohexanoyl)-2,3,6,7-tetrahydro-1H,5H-pyrido[3,2,1-ij]quinolin-5-one obtained in Reference Example 6 and 2-phenylethylamine according to the same method as that of Example 9, the title compound (123 mg) was obtained as pale yellow amorphous powders.

$^1$H NMR(free base; 400 MHz, CDCl$_3$) δ 1.35-1.42 (2H, m), 1.49-1.56 (3H, m), 1.69-1.77 (2H, m), 1.93-1.99 (2H, m), 2.61-2.69 (4H, m), 2.78-2.95 (10H, m), 3.8.9 (2H, t, J=6 Hz), 7.18-7.31 (5H, m), 7.61 (2H, d, J=5 Hz) IR (free base; KBr) νcm$^{-1}$: 1675, 1604, 1484, 1437, 1362, 1339, 1161.

Example 65

9-(6-[[2-(2-Methoxyphenyl)ethyl]amino]hexanoyl]-2,3,6,7-tetrahydro-1H,5H-pyrido[3,2,1-ij.]quinolin-5-one hydrochloride

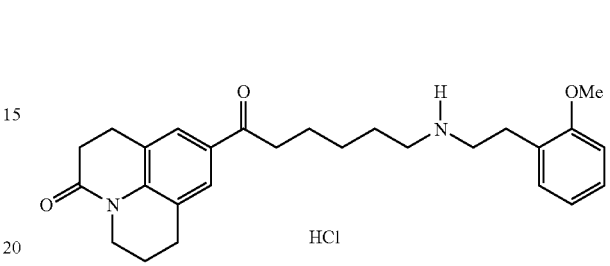

Using 9-(6-bromohexanoyl)-2,3,6,7-tetrahydro-1H,5H-pyrido[3,2,1-ij]quinolin-5-one obtained in Reference Example 6 and 2-(2-methoxyphenyl)ethylamine according to the same method as that of Example 9, the title compound (190 mg) was obtained as pale yellow amorphous powders.

$^1$H NMR(free base; 400 MHz, CDCl$_3$) δ 1.36-1.44 (2H, m), 1.50-1.57 (3H, m), 1.70-1.77 (2H, m), 1.92-1.99 (2H, m), 2.62-2.69 (4H, m), 2.82-2.85 (6H, m), 2.89-2.96 (4H, m), 3.81 (3H, s), 3.89 (2H, t, J=6 Hz), 6.85 (1H, d, J=8.3 Hz), 6.89 (1H, d, J=7.4 Hz), 7.14-7.20 (2H, m), 7.61 (2H, d, J=5 Hz).

IR (free base; KBr) νcm$^{-1}$: 1673, 1603, 1494, 1362, 1339, 1243, 1160.

Example 66

9-(6-[[2-(2-Chlorophenyl)ethyl]amino]hexanoyl)-2,3,6,7-tetrahydro-1H,5H-pyrido[3,2,1-ij]quinolin-5-one hydrochloride

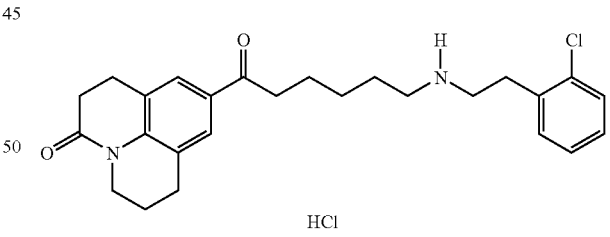

Using 9-(6-bromohexanoyl)-2,3,6,7-tetrahydro-1H,5H-pyrido[3,2,1-ij]quinolin-5-one obtained in Reference Example 6 and 2-(2-chlorophenyl)ethylamine according to the same method as that of Example 9, the title compound (148 mg) was obtained as pale yellow amorphous powders.

$^1$H NMR(free base; 400 MHz, CDCl$_3$) δ 1.37-1.43 (2H, m), 1.51-1.58 (3H, m), 1.71-1.78 (2H, m), 1.95-2.00 (2H, m), 2.65-2.70 (4H, m), 2.84 (2H, t, J=7.5 Hz), 2.86-2.96 (8H, m), 3.89 (2H, t, J=6 Hz), 7.13-7.25 (3H, m), 7.34 (1H, dd, J=7, 2 Hz), 7.61 (2H, d, J=5 Hz).

IR (free base; KBr) νcm$^{-1}$: 1673, 1603, 1483, 1361, 1159.

Example 67

9-(6-[(2-Phenylethyl)amino]hexanoyl]-2,3,6,7-tetrahydro-1H,5H-pyrido[3,2,1-ij]quinolin-5-one hydrochloride

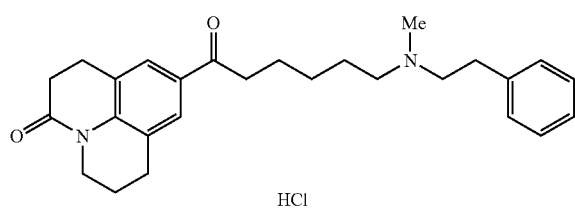

Using 9-(6-bromohexanoyl)-2,3,6,7-tetrahydro-1H,5H-pyrido[3,2,1-ij]quinolin-5-one obtained in Reference Example 6 and N-methyl-N-(2-phenylethyl)amine according to the same method as that of Example 9, the title compound (225 mg) was obtained as pale yellow amorphous powders.

$^1$H NMR(free base; 400 MHz, CDCl$_3$) δ 1.37-1.43 (2H, m), 1.51-1.58 (2H, m), 1.71-1.78 (2H, m), 19.3-1.99 (2H, m), 2.30 (3H, s), 2.41 (2H, t, J=7 Hz), 2.58-2.62 (2H, m), 2.67 (2H, t, J=6 Hz), 2.75-2.79 (2H, m), 2.84 (2H, t, J=6 Hz), 2.89-2.95 (4H, m), 3.89 (2H, t, J=6 Hz), 7.18-7.29 (5H, m), 7.61 (2H, d, J=5 Hz).

IR (free base; KBr) νcm$^{-1}$: 1676, 1604, 1590, 1484, 1361, 1338, 1161.

Example 68

9-(6-[[2-(2-Methoxyphenyl)ethyl]amino]hexanoyl]-2,3,6,7-tetrahydro-1H,5H-pyrido[3,2,1-ij]quinolin-5-one hydrochloride

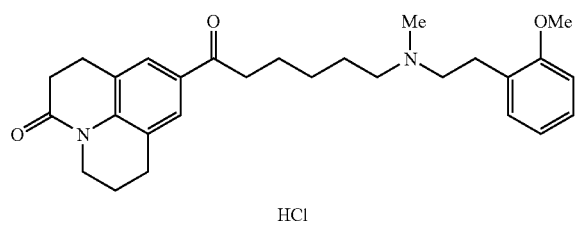

Using 9-(6-bromohexanoyl)-2,3,6,7-tetrahydro-1H,5H-pyrido[3,2,1-ij]quinolin-5-one obtained in Reference Example 6 and N-[2-(2-methoxyphenyl)ethyl]-N-methylamine according to the same method as that of Example 9, the title compound (255 mg) was obtained as pale yellow amorphous powders.

$^1$H NMR(free base;. 400 MHz, CDCl$_3$) δ 1.36-1.43 (2H, m), 1.51-1.58 (2H, m), 1.71-1.79 (2H, m), 1.93-1.99 (2H, m), 2.32 (3H, s), 2.42 (2H, t, J=7 Hz), 2.55-2.59 (2H, m), 2.67 (2H, t, J=6 Hz), 2.76-2.80 (2H, m), 2.83 (2H, t, J=6 Hz), 2.90-2.95 (4H, m), 3.81 (3H, s), 3.89 (2H, t, J=6 Hz), 6.83-6.89 (2H, m), 7.12-7.19 (2H, m), 7.61 (2H, d, J=5 Hz).

IR (free base; KBr) νcm$^{-1}$: 1676, 1603, 1589, 1494, 1361, 1243, 1161.

Example 69

9-[6-[[2-(2-Chlorophenyl)ethyl](methyl)amino]hexanoyl]-2,3,6,7-tetrahydro-1H,5H-pyrido[3,2,1-ij]quinolin-5-one hydrochloride

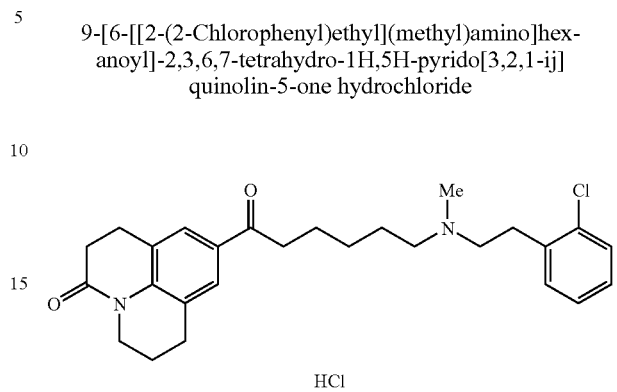

Using 9-(6-bromohexanoyl)-2,3,6,7-tetrahydro-1H,5H-pyrido[3,2,1-ij]quinolin-5-one obtained in Reference. Example 6 and N-[2-(2-chlorophenyl)ethyl]-N-methylamine according to the same method as that of Example 9, the title compound (372 mg) was obtained as pale yellow amorphous powders.

$^1$H NMR(free base; 400 MHz, CDCl$_3$) δ 1.35-1.43 (2H, m), 1.51-1.59 (2H, m), 1.71-1.78 (2H, m), 1.93-i.99 (2H, m), 2.33 (3H, s), 2.44 (2H, t, J=7.5 Hz), 2.58-2.62 (2H, m), 2.68 (2H, t, J=6 Hz), 2.84 (2H, t, J=6 Hz), 2.88-2.99 (6H, m), 3.89 (2H, t, J=6 Hz), 7.11-7.24 (3H, m), 7.32 (1H, d, d, J=5, 2 Hz), 7.62 (2H, d, J=5 Hz).

IR (free base; KBr) νcm$^{-1}$: 1674, 1604, 1438, 1360, 1299, 1159.

Example 70

9-[6-[[2-(3-Flurophenyl)ethyl](methyl)amino]hexanoyl]-2,3,6,7-tetrahydro-1H,5H-pyrido[3,2,1-ij]quinolin-5-one hydrochloride

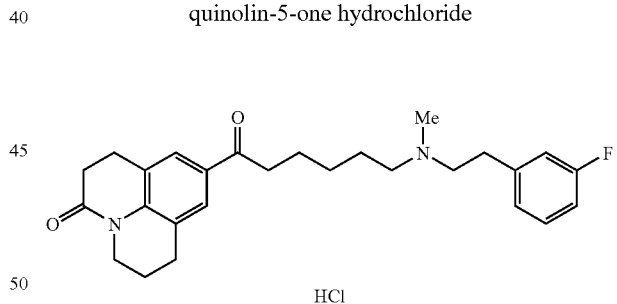

Using 9-(6-bromohexanoyl)-2,3,6,7-tetrahydro-1H,5H-pyrido[3,2,1-ij]quinolin-5-one obtained in Reference. Example 6 and N-[2-(3-fluorophenyl)ethyl]-N-methylamine according to the same method as that of Example 9, the title compound (303 mg) was obtained as pale yellow amorphous powders.

$^1$H NMR(free base; 400 MHz, CDCl$_3$) δ 1.36-1.42 (2H, m), 1.49-1.55 (2H, m), 1.70-1.78 (2H, m), 1.93-1.99 (2H, m), 2.29 (3H, s), 2.40 (2H, t, J=7.5 Hz), 2.58-2.62 (2H, m), 2.68 (2H, t, J=6 Hz), 2.74-2.78 (2H, m), 2.85 (2H, t, J=6 Hz), 2.89-2.96 (4H, m), 3.89 (2H, t, J=6 Hz), 6.86-6.92 (2H, m), 6.97 (1H, d, J=7.5 Hz), 7.20-7.25 (1H, m), 7.62 (2H, d, J=5 Hz).

IR (free base; KBr) νcm$^{-1}$: 1676, 1604, 1589, 1486, 1361, 1339, 1161.

Example 71

9-[6-[Ethyl(2-phenylethyl)amino]hexanoyl]-2,3,6,7-tetrahydro-1H,5H-pyrido[3,2,1-ij]quinolin-5-one hydrochloride

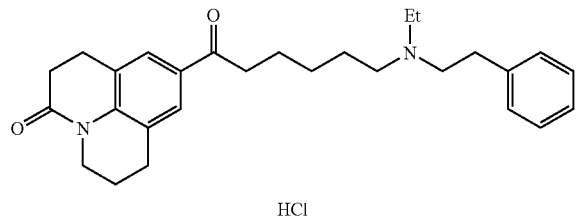

Using 9-(6-bromohexanoyl)-2,3,6,7-tetrahydro-1H,5H-pyrido[3,2,1-ij]quinolin-5-one obtained in Reference Example 6 and N-ethyl-N-(2-phenylethyl)amine according to the same method as that of Example 9, the title compound (285 mg) was obtained as pale yellow amorphous powders.

$^1$H NMR(free base; 400 MHz, CDCl$_3$) δ 1.05 (3H, t, J=7 Hz), 1.34-1.42 (2H, m), 1.49-1.56 (2H, m), 1.71-1.78 (2H, m), 1.93-1.99 (2H, m), 2.50 (2H, t, J=7.5 Hz), 2.61 (2H, q, J=7 Hz), 2.66-2.77 (6H, m), 2.84 (2H,t,J=6 Hz), 2.89-2.95 (4H, m), 3.89 (2H, t, J=6 Hz), 7.16-7.20 (3H, m), 7.25-7.29 (2H, m), 7.62 (2H, d, J=5 Hz).

IR (free base; KBr) vcm$^{-1}$: 1676, 1603, 1589, 1494, 1361, 1243, 1161.

Example 72

9-(6-[Ethyl[2-(2-methoxyphenyl)ethyl]amino]hexanoyl)-2,3,6,7-tetrahydro-1H,5H-pyrido[3,2,1-ij]quinolin-5-one hydrochloride

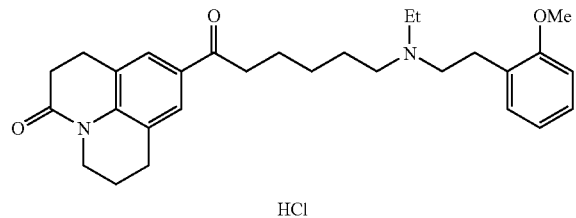

Using 9-(6-bromohexanoyl)-2,3,6,7-tetrahydro-1H,5H-pyrido[3,2,1-ij]quinolin-5-one obtained in Reference Example 6 and N-ethyl-N-[2-(2-methoxyphenyl)ethyl]amine according to the same method as that of Example 9, the title compound (395 mg) was obtained as pale yellow amorphous powders.

$^1$H NMR(free base; 400 MHz, CDCl$_3$) δ 1.07 (3H, t, J=7 Hz), 1.37-1.43 (2H, m), 1.51-1.59 (2H, m), 1.72-1.79 (2H, m), 1.93-1.99 (2H, m), 2.52 (2H, t, J=7.5 Hz), 2.62 (2H, q, J=7 Hz), 2.66-2.69 (4H, m), 2.72-2.82 (2H, m), 2.85 (2H, t, J=6 Hz), 2.92 (4H, t, J=6 Hz), 3.81 (3H, s), 3.89 (2H, t, J=6 Hz), 6.83-6.89 (2H, m), 7.11-7.19 (2H, m), 7.62 (2H, d, J=5 Hz).

IR (free base; KBr) vcm$^{-1}$: 1675, 1603, 1493, 1361, 1242, 1159.

Example 73

9-(6-[Isopropyl[2-(2-methoxyphenyl)ethyl]amino]hexanoyl)-2,3,6,7-tetrahydro-1H,5H-pyrido[3,2,1-ij]quinolin-5-one hydrochloride

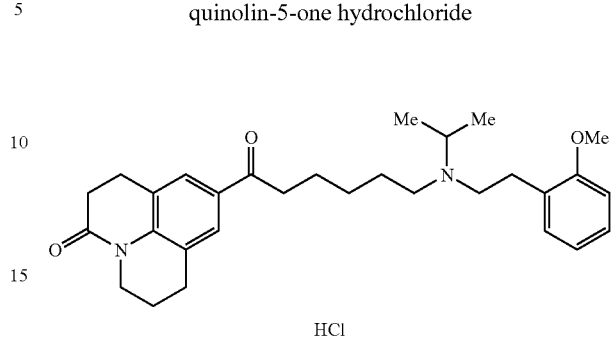

Using 9-(6-bromohexanoyl)-2,3,6,7-tetrahydro-1H,5H-pyrido[3,2,1-ij]quinolin-5-one obtained in Reference Example 6 and N-isopropyl-N-[2-(2-methoxyphenyl)ethyl]amine according to the same method as that of Example 9, the title compound (147 mg) was obtained as pale yellow amorphous powders.

$^1$H NMR(free base; 400 MHz, CDCl$_3$) δ 1.00 (6H, d, J=6.3 Hz), 1.36-1.42 (2H, m), 1.48-1.54 (2H, m), 1.71-1.78 (2H, m), 1.93-1.99 (2H, m), 2.47 (2H, t, J=7.3 Hz), 2.57-2.60 (2H, m), 2.65-2.74 (4H, m), 2.82-2.85 (2H, m), 2.89-2.95 (4H, m), 2.98 (1H, q, J=6.3 Hz), 3.81 (3H, s), 3.89 (2H, t, J=6 Hz), 6.82-6.88 (2H, m), 7.11-7.19 (2H, m), 7.62 (2H, d, J=5 Hz).

IR (free base; neat) vcm$^{-1}$: 1676, 1604, 1494, 1360, 1243, 1162.

Example 74

1-(1-Acetyl-2,3-dihydro-1H-indol-5-yl)-5-[[2-(2-methoxyophenyl)ethyl]amino]-1-pentanone hydrochloride

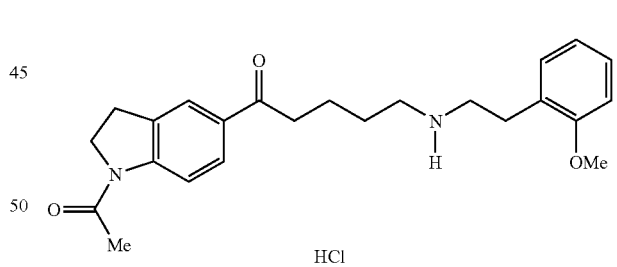

Using tert-butyl 5-(1-acetyl-2,3-dihydro-1H-indol-5-yl)-5-oxopentyl[2-(2-methoxyphenyl)ethyl]carbamate. (170 mg) obtained in Reference Example 7 according to the same method as that of Example. 1, the title compound (87 mg) was obtained as colorless crystals having a melting point of 175 to 176° C.

$^1$H NMR(400 MHz, DMSO-d$_6$) δ 1.58-1.72 (4H, m), 2.18 (3H, s), 2.90-3.05 (8H, m), 3.17 (2H, t, J=8.5 Hz), 3.79 (3H, s), 4.14 (2H, t, J=8.5 Hz), 6.90 (1H, t, J=7.5 Hz), 6.99 (1H, d, J=7.5 Hz), 7.16 (1H, d, J=7.5 Hz), 7.24 (1H, t, J=8.3 Hz), 7.82-7.85 (2H, m), 8.08 (1H, d, J=8.3 Hz), 8.91 (2H, br s).

IR (KBr) vcm$^{-1}$: 2955, 2789, 1680, 1661, 1603, 1496, 1441, 1440, 1255.

Example 75

6-(5-[[2-(2-Methoxyphenyl)ethyl]amino]pentanoyl)-2H-1,4-benzoxazin-3(4H)-one hydrochloride

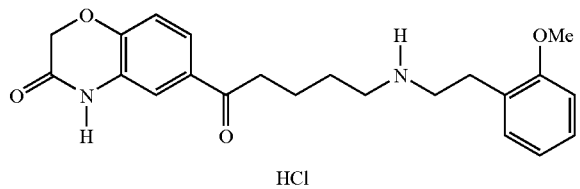

Using 6-(5-chloropentanoyl)-2H-1,4-benzoxazin-3(4H)-one obtained in Reference Example 7 and 2-(2-methoxyphenyl)ethylamine according to the same method as that of Example 1, the title compound was obtained as colorless amorphous powders.

$^1$H NMR(300 MHz, DMSO-d$_6$) δ 1.66 (4H, s), 2.93-3.02 (8H, m), 3.80 (3H, s), 4.69 (2H, s), 6.89-6.94 (1H, m), 6.99-7.07 (2H, m), 7.18 (1H, d, J=6.3 Hz), 7.23-7.28 (1H, m), 7.52 (1H, d, J=2.1 Hz), 7.63 (1H, dd, J=8.6, 2.1 Hz), 8.98 (2H, br s), 10.94 (1H, s).

MS m/z: 383 [M+H]$^+$

Example 76

8-[5-(1,3,4,5-Tetrahydro-2H-2-benzazepin-2-yl)pentanoyl]-1,2,5,6-tetrahydro-4H-pyrrolo[3,2,1-ij]quinolin-4-one

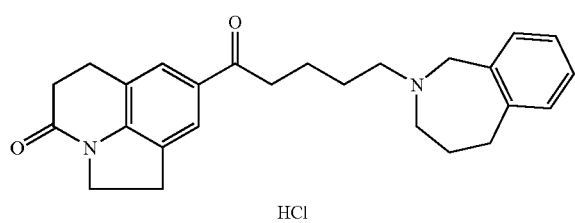

Using 8-(5-chloropentanoyl)-1,2,5,6-tetrahydro-4H-pyrrolo[3,2,1-ij]quinolin-4-one (600 mg) obtained in Reference Example 1 and 2,3,4,5-tetrahydro-1H-2-benzazepine (332 mg) according to the same method as that of Example 9, the title compound (407 mg) was obtained as colorless amorphous powders.

$^1$H NMR(free base; 200 MHz, CDCl$_3$) δ 1.45-1.80 (6H, m), 2.39 (2H, t, J=7.4 Hz), 2.71 (2H, t, J=7.6 Hz), 2.80-3.30 (10H, m), 3.88 (2H, s), 4.12 (2H, t, J=8.4 Hz), 7.00-7.20 (4H, m), 7.65 (1H, s), 7.69 (1H, s).

Example 77

8-(5-(7-Methoxy-1,3,4,5-tetrahydro-2H-2-benzazepin-2-yl)pentanoyl]-1,2,5,6-tetrahydro-4H-pyrrolo[3,2,1-ij]quinolin-4-one hydrochloride

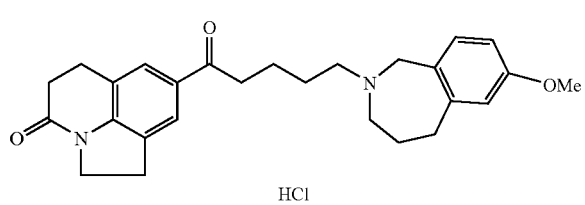

Using 8-(5-chloropentanoyl)-1,2,5,6-tetrahydro-4H-pyrrolo[3,2,1-ij]quinolin-4-one (500 mg) obtained in Reference Example 1 and 7-methoxy-2,3,4,5-tetrahydro-1H-2-benzazepine (304 mg) according to the same method as that of Example 9, the title compound (294 mg) was obtained as colorless crystals having a melting point of 167 to 168° C.

$^1$H NMR(free base; 200 MHz, CDCl$_3$) δ 1.45-1.80 (6H, m), 2.38 (2H, t, J=7.4 Hz), 2.71 (2H, t, J=7.6 Hz), 2.80-3.15 (8H, m), 3.21 (2H, t, J=8.4 Hz), 3.78 (3H, s), 3.84 (2H, s), 4.13 (2H, t, J=8.4 Hz), 6.61 (1H, dd, J=8.0, 2.6 Hz), 6.69 (1H, d, J=2.6 Hz), 7.02 (1H, d, J=8.4 Hz), 7.66 (1H, s), 7.70 (1H, s).

Example 78

8-[6-(1,3,4,5-Tetrahydro-2H-2-benzazepin-2-yl)pentanoyl]-1,2,5,6-tetrahydro-4H-pyrrolo[3,2,1-ij]quinolin-4-one hydrochloride

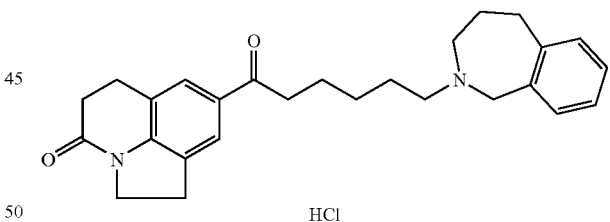

Using 8-(6-bromohexanoyl)-1,2,5,6-tetrahydro-4H-pyrrolo[3,2,1-ij]quinolin-4-one (500 mg) obtained in Reference Example 2 and 2,3,4,5-tetrahydro-1H-2-benzazepine (252 mg) according to the same method as that of Example 9, the title compound (463 mg) was obtained as colorless crystals having a melting point of 195 to 197° C.

$^1$H NMR(free base; 200 MHz, CDCl$_3$) δ 1.25-1.85 (8H, m), 2.35 (2H, t, J=7.4 Hz), 2.71 (2H, t, J=7.6 Hz), 2.80-3.00 (4H, m), 3.02 (2H, t, J=7.6 Hz), 3.11 (2H, t, J=5.4 Hz), 3.22 (2H, t, J=8.4 Hz), 3.88 (2H, s), 4.13 (2H, t, J=8.4 Hz), 7.00-7.20 (4H, m), 7.66 (1H, s), 7.70 (1H, s).

elementary analysis as C$_{27}$H$_{32}$N$_2$O$_2$·HCl
calculation value: C, 70.58; H, 7.34; N, 6.18.
experimental value: C, 70.16; H, 7.32; N, 6.08.

Example 79

8-[6-(7-Methoxy-1,3,4,5-tetrahydro-2H-2-benzazepin-2-yl)pentanoyl]-1,2,5,6-tetrahydro-4H-pyrrolo[3,2,1-ij]quinolin-4-one hydrochloride

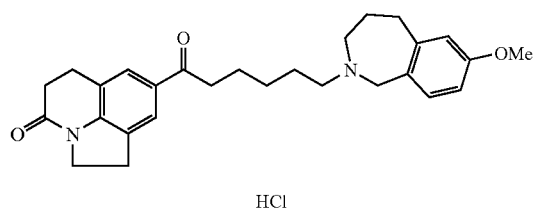

HCl

Using 8-(6-bromohexanoyl)-1,2,5,6-tetrahydro-4H-pyrrolo[3,2,1-ij]quinolin-4-one (500 mg) obtained in Reference Example 2 and 7-methoxy-2,3,4,5-tetrahydro-1H-2-benzazepine (253 mg) according to the same method as that of Example 9, the title compound (366 mg) was obtained as pale yellow amorphous powders.

$^1$H NMR(free base; 200 MHz, CDCl$_3$) δ 1.24-1.80 (8H, m), 2.34 (2H, t, J=7.4 Hz), 2.71 (2H, t, J=7.6 Hz), 2.80-3.15 (8H, m), 3.22 (2H, t, J=8.4 Hz), 3.78 (3H, s), 3.84 (2H, s), 4.13 (2H, t, J=8.4 Hz), 6.61 (1H, dd, J=8.0, 2.6 Hz), 6.69 (1H, d, J=2.6 Hz), 7.02 (1H, d, J=8.4 Hz), 7.66 (1H, s), 7.70 (1H, s).

Example 80

8-[5-(1,3-Dihydro-2H-isoindol-2-yl) pentanolyl]-1,2,5,6-tetrahydro-4H-pyrrolo[3,2,1-ij]quinolin-4-one hydrochloride

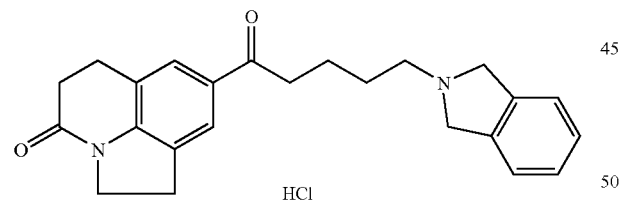

HCl

Using 8-(5-chloropentanoyl)-1,2,5,6-tetrahydro-4H-pyrrolo[3,2,1-ij]quinolin-4-one (600 mg) obtained in Reference Example 1 and isoindiline (269 mg) according to the same method as that of Example 9, the title compound (191 mg) was obtained as colorless crystals having a melting point of 219 to 221° C.

$^1$H NMR(free base; 200 MHz, CDCl$_3$) δ 1.60-1.95 (4H, m), 2.60-2.80 (4H, m), 2.90-3.05 (4H, m), 3.19 (2H, t, J 8.4 Hz), 3.92 (4H, s), 4.12 (2H, t, J=8.4 Hz), 7.10 (4H, s), 7.69 (1H, s), 7.73 (1H, s).

Example 81

8-[3-[1-(2-Phenylethyl)-4-piperidinyl]propanoyl]-1,2,5,6-tetrahydro-4H-pyrrolo[3,2,1-ij]quinolin-4-one hydrochloride

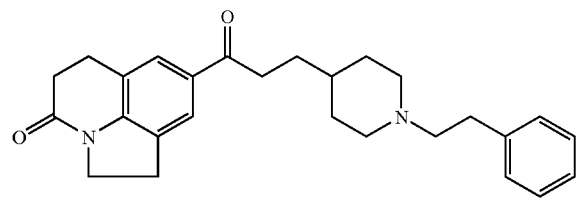

(2-Bromoethyl)benzene (0.22 ml) was added dropwise to a suspension of 8-[3-(4-piperidinyl)propanoyl]-1,2,5,6-tetrahydro-4H-pyrrolo[3,2,1-ij]quinolin-4-one (500 mg) and potassium carbonate (500 mg) in acetonitrile (10 ml) at room temperature. After stirring at room temperature for 12 hours, the reaction mixture was concentrated under reduced pressure. Water (15 ml) and ethyl acetate (20 ml) were added to the residue, and extracted with ethyl acetate. The extract was washed with brine, dried over anhydrous magnesium sulfate, and the solvent was evaporated under reduced pressure. The resulting residue was purified by silica gel chromatography (eluting solvent; ethyl acetate-methanol. (9:1)) to give a free base compound of the title compound as a pale yellow oil (617 mg).

$^1$H NMR(200 MHz, CDCl$_3$) δ 1.20-1.50(3H, m), 1.60-1.85 (4H, m), 1.90-2.10(2H, m), 2.50-3.10(12H, m), 3.21(2H, t, J=8.4 Hz), 4.12(2H, t, J=8.4 Hz), 7.10-7.35(5H, m), 7.68(1H, s), 7.72(1H, s).

A solution of the above free base compound (610 mg) in ethanol was treated with 1 equivalent or more of hydrogen chloride (ethyl acetate solution) to give the title compound as colorless crystals having a melting point of 219 to 221° C.

elementary analysis as C$_{27}$H$_{32}$N$_2$O$_2$.HCl
calculation value: C, 71.58; H, 7.34; N, 6.18.
experimental value: C, 71.27; H, 7.13; N, 6.20.

Example 82

8-(3-[1-[2-(2-Methylphenyl)ethyl]-4-piperidinyl]propanoyl)-1,2,5,6-tetrahydro-4H-pyrrolo[3,2,1-ij]quinolin-4-one hydrochloride

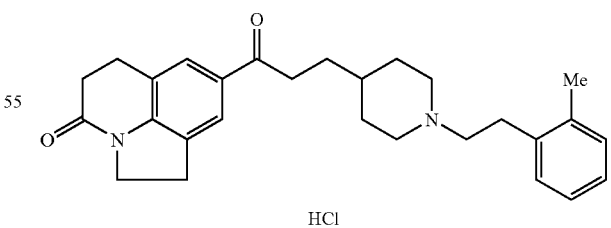

HCl

Using 8-[3-(4-piperidinyl)propanoyl]-1,2,5,6-tetrahydro-4H-pyrrolo[3,2,1-ij]quinolin-4-one (600 mg) and 1-(2-bromoethyl)-2-methylbenzene (432 mg) according to the same method as that of Example 81, the title compound (624 mg) was obtained as colorless crystals having a melting point of 215 to 216° C.

¹H NMR(free base; 200 MHz, CDCl₃) δ 1.25-1.50 (3H, m), 1.55-1.85 (4H, m), 1.90-2.20 (2H, m), 2.33 (3H, s), 2.45-2.60 (2H, m), 2.65-3.10 (10H, m), 3.23 (2H, t, J=8.4 Hz), 4.14 (2H, t, J=8.4 Hz), 7.13 (4H, s), 7.68 (1H, s), 7.72 (1H, s).
elementary analysis as $C_{28}H_{34}N_2O_2 \cdot HCl \cdot 0.5H_2O$
calculation value: C, 70.64; H, 7.62; N, 5.88.
experimental value: C, 70.24; H, 7.66; N, 5.81.

Example 83

8-(3-[1-[2-(2-Fluorophenyl)ethyl]-4-piperidinyl] propanoyl)-1,2,5,6-tetrahydro-4H-pyrrolo[3,2,1-ij] quinolin-4-one hydrochloride

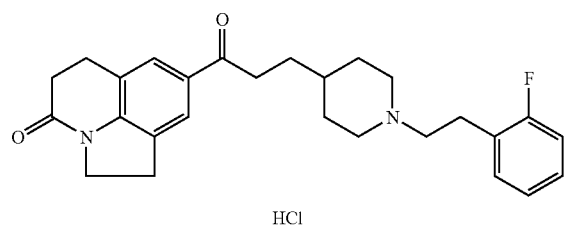

HCl

Using 8-[3-(4-piperidinyl)propanoyl]-1,2,5,6-tetrahydro-4H-pyrrolo[3,2,1-ij]quinolin-4-one (600 mg) and 1-(2-bromoethyl)-2-fluorobenzene (367 mg) according to the same method as that of Example 81, the title compound (380 mg) was obtained as colorless crystals having a melting point of 210 to 212° C.
¹H NMR(free base; 200 MHz, CDCl₃) δ 1.20-1.45 (3H, m), 1.55-2.10 (6H, m), 2.50-3.10 (12H, m), 3.23 (2H, t, J=8.4 Hz), 4.14 (2H, t, J=8.4 Hz), 6.95-7.30 (4H, m), 7.68 (1H, s), 7.72 (1H, s).
elementary analysis as $C_{27}H_{31}FN_2O_2 \cdot HCl \cdot 0.5H_2O$
calculation value: C, 67.56; H, 6.93; N, 5.84.
experimental value: C, 67.92; H, 6.68; N, 5.79.

Example 84

8-(3-[1-[2-(3-Fluorophenyl)ethyl]-4-piperidinyl] propanoyl)-1,2,5,6-tetrahydro-4H-pyrrolo[3,2,1-ij] quinolin-4-one hydrochloride

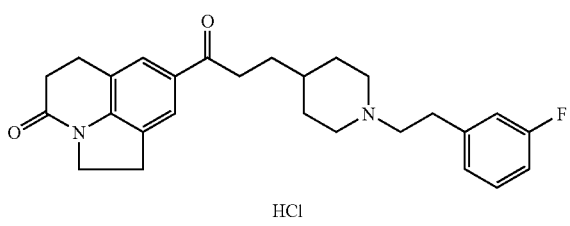

HCl

Using 8-[3-(4-piperidinyl)propanoyl]-1,2,5,6-tetrahydro-4H-pyrrolo[3,2,1-ij]quinolin-4-one (500 mg) and 1-(2-bromoethyl)-3-fluorobenzene (367 mg) according to the same method as that of Example 81, the title compound (351 mg) was obtained as colorless crystals having a melting point of 225 to 227° C.
¹H NMR(free base; 200 MHz, CDCl₃) δ 1.20-1.50 (3H, m), 1.60-1.85 (4H, m), 1.90-2.10 (2H, m), 2.50-3.10 (12H, m), 3.23 (2H, t, J=8.4 Hz), 4.14 (2H, t, J=8.4 Hz), 6.80-7.00 (3H, 20 m), 7.15-7.30 (1H, m), 7.68 (1H, s), 7.72 (1H, s).

Example 85

8-(3-[1-[2-(3-Chlorophenyl)ethyl]-4-piperidinyl] propanoyl)-1,2,5,6-tetrahydro-4H-pyrrolo[3,2,1-ij] quinolin-4-one hydrochloride

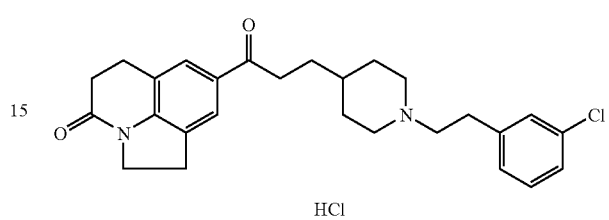

HCl

Using 8-[3-(4-piperidinyl)propanoyl]-1,2,5,6-tetrahydro-4H-pyrrolo[3,2,1-ij]quinolin-4-one (500 mg) and 1-(2-bromoethyl)-3-chlorobenzene (394 mg) according to the same method as that of Example 81, the title compound (369 mg) was obtained as colorless crystals having a melting point of 223 to 225° C.
¹H NMR(free base; 200 MHz, CDCl₃) δ 1.20-1.50 (3H, m), 1.60-1.85 (4H, m), 1.90-2.10 (2H, m), 2.45-3.10 (12H, m), 3.23 (2H, t, J=8.4 Hz), 4.14 (2H, t, J=8.4 Hz), 7.00-7.30 (4H, m), 7.68 (1H, s), 7.73 (1H, s).
elementary analysis as $C_{27}H_{31}ClN_2O_2 \cdot HCl \cdot H_2O$
calculation value: C, 64.16; H, 6.78; N, 5.54.
experimental value: C, 63.92; H, 6.75; N, 5.52.

Example 86

8-[3-[1-(2,3-Dihydro-1H-inden-2-yl)-4-piperidinyl] propanoyl]-1,2,5,6-tetrahydro-4H-pyrrolo[3,2,1-ij] quinolin-4-one hydrochloride

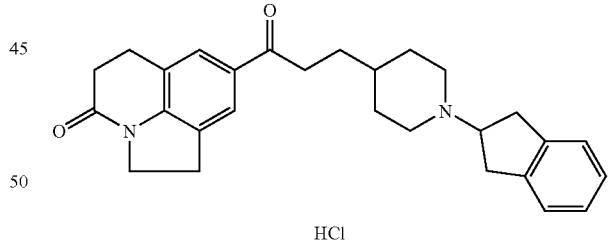

HCl

Using 8-[3-(4-piperidinyl)propanoyl]-1,2,5,6-tetrahydro-4H-pyrrolo[3,2,1-ij]quinolin-4-one (600 mg) and 2,3-dihydro-1H-inden-2-yl methanesulfonate (428 mg) according to the same method as that of Example 81, the title compound (326 mg) was obtained as colorless crystals having a melting point of 290° C. (dec.)
¹H NMR(free base; 200 MHz, CDCl₃) δ 1.10-1.40 (3H, m), 1.45-1.80 (4H, m), 1.85-2.00 (2H, m), 2.61 (2H, t, J=7.6 Hz), 2.70-3.20 (13H, m), 4.03 (2H, t, J=8.4 Hz), 7.00-7.15 (4H, m), 7.57 (1H, s), 7.62 (1H, s).
elementary analysis as $C_{28}H_{32}N_2O_2 \cdot HCl \cdot 0.5H_2O$
calculation value: C, 70.94; H, 7.23; N, 5.91.
experimental value: C, 71.19; H, 6.97; N, 5.71.

Example 87

8-[3-[1-(3-Phenylpropyl)-4-piperidinyl]propanoyl]-1,2,5,6-tetrahydro-4H-pyrrolo[3,2,1-ij]quinolin-4-one hydrochloride

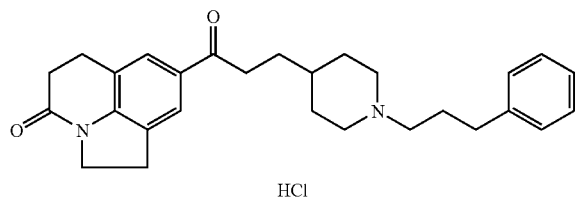

HCl

Using 8-[3-(4-piperidinyl)propanoyl]-1,2,5,6-tetrahydro-4H-pyrrolo[3,2,1-ij]quinolin-4-one (500 mg) and (3-bromopropyl)benzene (0.245 ml) according to the same method as that of Example 81, the title compound (488 mg) was obtained as colorless crystals having a melting point of 173 to 175° C.

$^1$H NMR(free base; 200 MHz, CDCl$_3$) δ 1.20-1.45 (3H, m), 1.60-2.00 (8H, m), 2.35 (2H, t, J=7.6 Hz), 2.61 (2H, t, J=8.0 Hz), 2.70 (2H, t, J=8.4 Hz), 2.80-2.95 (4H, m), 3.01 (2H, t, J=8.0 Hz), 3.21 (2H, t, J=8.4 Hz), 4.12 (2H, t, J=8.4 Hz), 7.05-7.35 (5H, m), 7.67 (1H, s), 7.71 (1H, s).

elementary analysis as C$_{28}$H$_{34}$N$_2$O$_2$.HCl
calculation value: C, 72.01; H, 7.55; N, 6.00.
experimental value: C, 71.68; H, 7.50; N, 5.73.

Example 88

8-[3-(1-(2-Phenoxyethyl)-4-piperidinyl]propanoyl]-1,2,5,6-tetrahydro-4H-pyrrolo[3,2,1-ij]quinolin-4-one hydrochloride

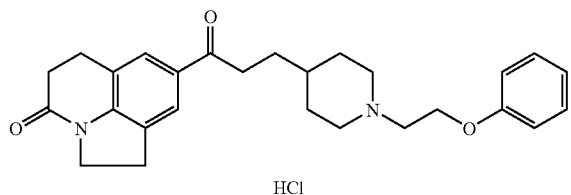

HCl

Using 8-[3-(4-piperidinyl)propanoyl]-1,2,5,6-tetrahydro-4H-pyrrolo[3,2,1-ij]quinolin-4-one (500 mg) and (2-bromoethoxy)benzene (0.222 ml) according to the same method as that of Example 81, the title compound (190 mg) was obtained as colorless amorphous powders.

$^1$H NMR(free base; 200 MHz, CDCl$_3$) δ 1.20-1.45 (3H, m), 1.60-1.85 (4H, m), 2.00-2.25 (2H, m), 2.71 (2H, t, J=7.6 Hz), 2.80 (2H, t, J=6.2 Hz), 2.85-3.10 (6H, m), 3.22 (2H, t, J=8.4 Hz), 4.00-4.20 (4H, m), 6.85-7.00 (3H, m), 7.20-7.35 (2H, m), 7.67 (1H, s), 7.71 (1H, s).

elementary analysis as C$_{27}$H$_{32}$N$_2$O$_3$.HCl.0.5H$_2$O
calculation value: C, 67.84; H, 7.17; N, 5.86.
experimental value: C, 68.10; H, 7.22; N, 5.83.

Example 89

8-(3-[1-[2-(2-Ethoxyphenoxy)ethyl]-4-piperidinyl]propanoyl)-1,2,5,6-tetrahydro-4H-pyrrolo[3,2,1-ij]quinolin-4-one hydrochloride

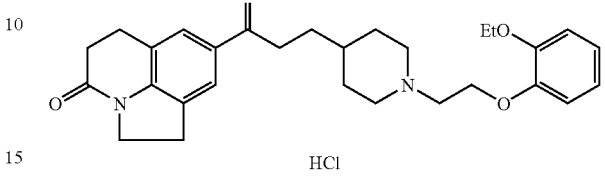

HCl

Using 8-[3-(4-piperidinyl)propanoyl]-1,2,5,6-tetrahydro-4H-pyrrolo[3,2,1-ij]quinolin-4-one (500 mg) and 1-(2-bromoethoxy)-2-ethoxybenzene (412 mg) according to the same method as that of Example 81, the title compound (583 mg) was obtained as colorless amorphous powders.

$^1$H NMR(free base; 200 MHz, CDCl$_3$) δ 1.20-1.50 (6H, m), 1.60-1.80 (4H, m), 2.00-2.25 (2H, m), 2.71 (2H, t, J=7.6 Hz), 2.80-3.15 (8H, m), 3.22 (2H, t, J=. 8.4 Hz), 4.00-4.20 (6H, m), 6.85-6.95 (4H, m), 7.67 (1H, s), 7.72 (1H, s).

elementary analysis as C$_{29}$H$_{36}$N$_2$O$_4$.HCl.0.5H$_2$O
calculation value: C, 66.72; H, 7.34; N, 5.37.
experimental value: C, 66.75; H, 7.26; N, 5.28.

Example 90

5-(5-[[2-(2-Chlorophenyl)ethyl](methyl)amino]pentanoyl)-1,3-dihydro-2H-benzimidazol-2-one hydrochloride

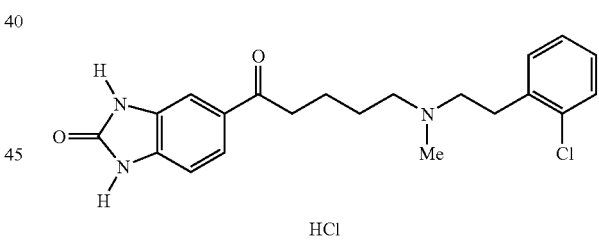

HCl

Using 5-(5-chloropentanoyl)-1,3-dihydro-2H-benzimidazol-2-one obtained in Reference Example 9 and N-[2-(2-chlorophenyl)ethyl]-N-methylamine according to the same method as that of Example 9, the title compound was obtained as colorless crystals having a melting point of 234 to 235° C.

$^1$H NMR(300 MHz, DMSO-d$_6$) δ 1.68-1.79 (4H, m), 2.83 (3H, d, J=4.8 Hz), 3.04-3.30 (8H, m), 7.03 (1H, d, J=8.4 Hz), 7.31-7.50 (5H, m), 7.69 (1H, dd, J=8.3, 1.7 Hz), 10.46 (1H, br s), 10.96 (1H, s), 11.10 (1H, s).
MS m/z: 386 [M+H]$^+$
elementary analysis as C$_{21}$H$_{24}$ClN$_3$O$_2$.HCl.0.5H$_2$O
calculation value: C, 58.47; H, 6.08; N, 9.74.
experimental value: C, 58.49; H, 6.05; N, 9.51.
MS m/z: 386 [M+H]$^+$

Example 91

5-[5-[[2-(2-Chlorophenyl)ethyl](methyl)amino]pentanoyl]-1,3-dimethyl-1,3-dihydro-2H-benzimidazol-2-one hydrochloride

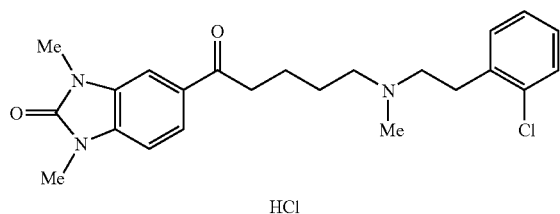

HCl

Using 5-(5-chloropentanoyl)-1,3-diemthyl-1,3-dihydro-2H-benzimidazol-2-one obtained in Reference Example 10 and N-[2-(2-chlorophenyl)ethyl]-N-methylamine according to the same method as that of Example 9, the title compound was obtained as colorless crystals having a melting point of 142 to 143° C.

$^1$H NMR(Free base; 200 MHz, CDCl$_3$) δ 1.64-1.83 (4H, m), 2.42 (3H, s), 2.54-2.74 (4H, m), 2.93-3.02 (4H, m), 3.46 (3H, s), 3.47 (3H, s), 6.99 (1H, d, J=8.4 Hz), 7.13-7.35 (4H, m), 7.63 (1H, d, J=1.2 Hz), 7.79 (1H, dd, J=8.2, 1.6 Hz).

MS m/z: 414 [M+H]$^+$

Example 92

1-(1-Acetyl-2,3-dihydro-1H-indol-5-yl)-5-[(2-phenylethyl)amino]-1-pentanone hydrochloride

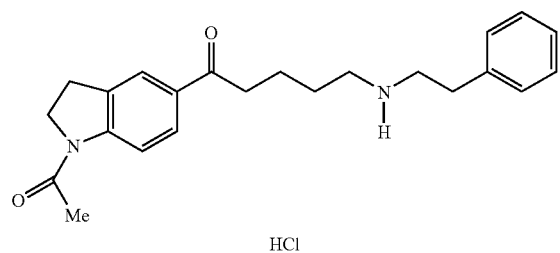

HCl

Using tert-butyl 5-(1-acetyl-2,3-dihydro-1H-indol-5-yl)-5-oxopentyl(2-phenylethyl)carbamate (280 mg) obtained in Reference Example 48 according to the same method as that of Example 1, the title compound (220 mg) was obtained as colorless crystals.

$^1$H NMR(400 MHz, DMSO-d$_6$) δ 1.60-1.73(4H, m), 2.18 (3H, s), 2.90-3.01(6H, m), 3.05-3.10(2H, m), 3.16(2H, t, J=8.4 Hz), 4.13(2H, t, J=8.4 Hz), 7.21-7.34(5H, m), 7.81(1H, s), 7.82(1H, d, J=8 Hz), 8.08(1H, t, J=8 Hz), 9.21(2H, br.s).

IR (KBr) vcm$^{-1}$: 3438, 2783, 1679, 1662, 1604, 1495, 1440, 1401, 1334, 1260.

Example 93

1-(1-Acetyl-2,3-dihydro-1H-indol-5-yl)-5-[[2-(2-chlorophenyl)ethyl]amino]-1-pentanone hydrochloride

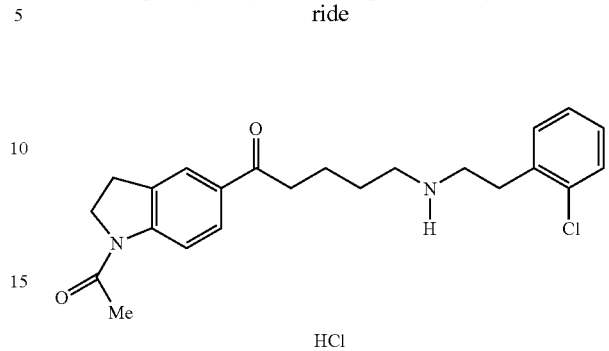

HCl

Using tert-butyl 5-(1-acetyl-2,3-dihydro-1H-indol-5-yl)-5-oxopentyl[2-(2-chlorophenyl)ethyl]carbamate (330 mg) obtained in Reference Example 49 according to the same method as that of Example 1, the title compound (175 mg) was obtained as colorless crystals having a melting point of 185 to 186° C.

$^1$H NMR(400 MHz, DMSO-d$_6$) δ 1.63-1.74(4H, m), 2.17 (3H, s), 2.92-3.01(4H, m), 3.08-3.18(6H, m), 4.13(2H, t, J=8 Hz), 7.26-7.34(2H, m), 7.39(1H, d, d, J=7, 2 Hz), 7.44(1H, d, d, J=7, 2 Hz), 7.81(1H, s), 7.82(1H, d, J=8 Hz), 8.07(1H, d, J=8 Hz), 9.35(2H, s).

IR (KBr) vcm$^{-1}$: 3434, 2947, 2782, 1683, 1660, 1441, 1403, 1335, 1259.

Example 94

1-(2,3-Dihydro-1H-indol-5-yl)-5-[[2-(2-methoxyphenyl)ethyl]amino]-1-pentanone dihydrochloride

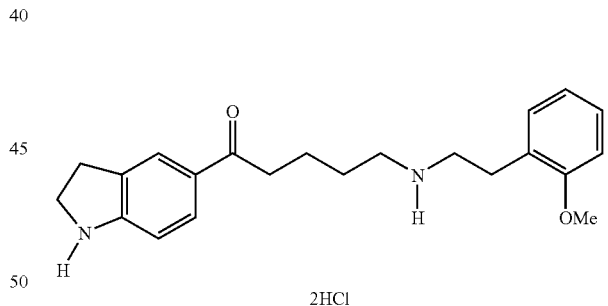

2HCl

Using tert-butyl 5-(2,3-dihydro-1H-indol-5-yl)-5-oxopentyl[2-(2-methoxyphenyl)ethyl]carbamate (452 mg) obtained in Reference Example 50 according to the same method as that of Example 1, the title compound (330 mg) was obtained as colorless crystals having a melting point of 164 to 165° C.

$^1$H NMR(400 MHz, DMSO-d$_6$) δ 1.58-1.72(4H, m), 2.93 (6H, t, J=7 Hz), 2.99-3.03(2H, m), 3.05(2H, t, J=8.2 Hz), 3.60(2H, t, J=8.2 Hz), 3.78(3H, s), 6.81(1H, d, J=8 Hz), 6.89(1H, t, J=7 Hz), 6.98(1H, d, J=7 Hz), 7.17(1H, d, J=7 Hz), 7.24(1H, t, J=7 Hz), 7.74(1H, d, J=8 Hz), 7.75(1H, s), 9.06 (4H, br.s).

IR (KBr) νcm$^{-1}$: 3429, 2950, 2781, 2460, 1694, 1497, 1247.

Example 95

1-(2,3-Dihydro-1H-indol-5-yl)-5-[[2-(2-methoxyphenyl)ethyl]amino]-1-pentanone dihydrochloride

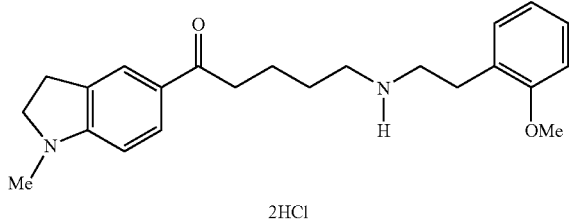

2HCl

Using tert-butyl 5-(2,3-dihydro-1H-indol-5-yl)-5-oxopentyl[2-(2-methoxyphenyl)ethyl]carbamate (120 mg) obtained in Reference Example 51 according to the same method as that of Example 1, the title compound (106 mg) was obtained as colorless crystals having a melting point of 150 to 151° C.

$^1$H NMR(400 MHz, DMSO-d$_6$) δ 1.60-1.67(4H, m), 2.80 (3H, s), 2.85-3.01(10H, m), 3.44(2H, t, J=8.4 Hz), 3.78(3H, s), 6.46(1H, d, J=8.3 Hz), 6.89(1H, t, J=7.4 Hz), 6.98(1H, d, J=8.3 Hz), 7.16(1H, d, J=7.4 Hz), 7.23(1H, t, J=8.3 Hz), 7.60(1H, s), 7.72(1H, d, J=8.3 Hz), 9.10(3H, br.s).

IR (KBr) νcm$^{-1}$: 3436, 2583, 2424, 1675, 1600, 1494, 1464, 1249, 1032, 760.

Example 96

1-(1-Ethyl-2,3-dihydro-1H-indol-5-yl)-5-[[2-(2-methoxyphenyl)ethyl]amino]-1-pentanone dihydrochloride

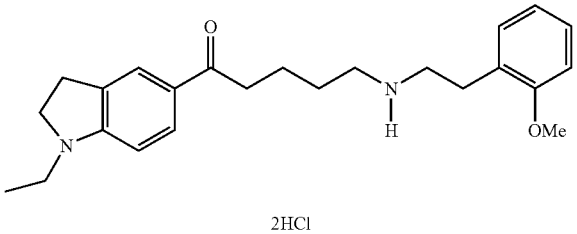

2HCl

Using tert-butyl 5-(1-ethyl-2,3-dihydro-1H-indol-5-yl)-5-oxopentyl[2-(2-methoxyphenyl)ethyl]carbamate (165 mg) obtained in Reference Example 52 according to the same method as that of Example 1, the title compound (145 mg) was obtained as colorless crystals having a melting point of 131 to 133° C.

$^1$H NMR(400 MHz, DMSO-d$_6$) δ 1.08(3H, t, J=7.2 Hz), 1.61-1.69(4H, m), 2.84-3.01(10H, m), 3.23(2H, q, J=7.2 Hz), 3.48(2H, t, J=8.4 Hz), 3.78(3H, s), 6.45(1H, d, J=8.4 Hz), 6.89(1H, t, J=7 Hz), 6.98(1H, d, J=8.4 Hz), 7.16(1H, d, J=7 Hz), 7.23(1H, t, J=8.4 Hz), 7.59(1H, s), 7.70(1H, d, J=8.4 Hz), 9.11(3H, br).

IR (KBr) νcm$^{-1}$: 3426, 2777, 2458, 1697, 1602, 1496, 1442, 1317, 1248, 1051, 763.

Example 97

1-[1-(3-Hydroxypropyl)-2,3-dihydro-1H-indol-5-yl]-5-[[2-(2-methoxyphenyl)ethyl]amino]-1-pentanone dihydrochloride

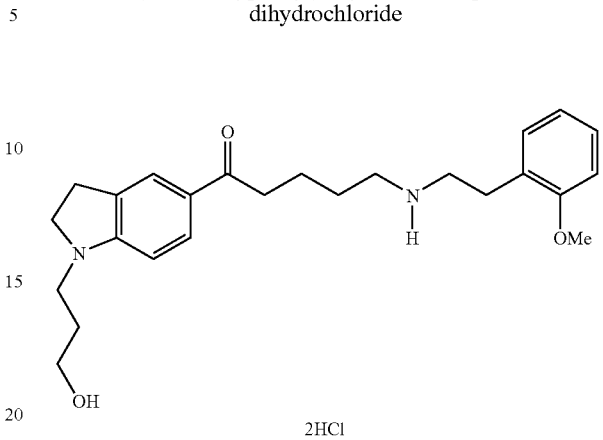

2HCl

Using tert-butyl 5-[1-(3-hydroxypropyl)-2,3-dihydro-1H-indol-5-yl]-5-oxopentyl[2-(2-methoxyphenyl)ethyl]carbamate (60 mg) obtained in Reference Example 53 according to the same method as that of Example 1, the title compound (55 mg) was obtained as pale yellow amorphous powders.

$^1$H NMR(400 MHz, CD$_3$OD) δ 1.68-1.79(4H, m), 1.84 (2H, t, J=7.4 Hz), 1.90-1.99(2H, m), 2.92-3.18(8H, m), 3.35 (2H, t, J=6 Hz), 3.57-3.70(4H, m), 3.82(3H, s), 4.82(4H, s), 6.63(1H, d, J=8 Hz), 6.88(1H, t, J=7 Hz), 6.95(1H, d, J=8 Hz), 7.16(1H, d, J=7.4 Hz), 7.23(1H, t, J=7.4 Hz), 7.69(1H, s), 7.79(1H, d, J=7 Hz).

IR (neat) νcm$^{-1}$: 3402, 2920, 1693, 1602, 1496, 1443, 1247, 760.

Example 98

Ethyl [5-(5-[[2-(2-metoxyphenyl)ethyl]amino]pentanoyl)-2,3-dihydro-1H-indol-1-yl]acetate dihydrochloride

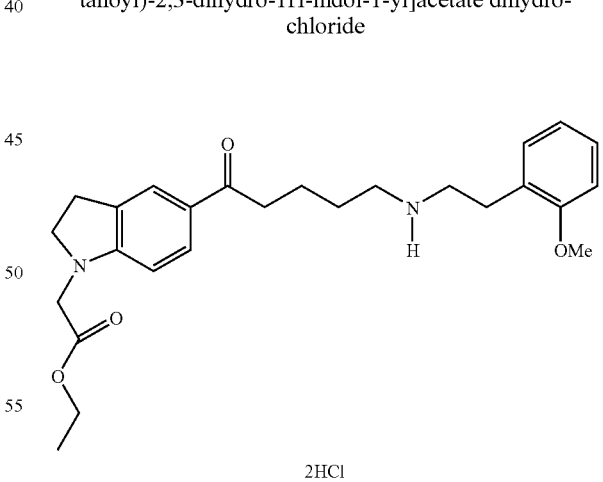

2HCl

Using ethyl (5-(5-[(tert-butoxycarbonyl)[2-(2-methoxyphenyl)ethyl]amino]pentanoyl)-2,3-dihydro-1H-indol-1-yl]acetate (270 mg) obtained in Reference Example 54 according to the same method as that of Example 1, the title compound (255 mg) was obtained as pale yellow amorphous powders.

$^1$H NMR(400 MHz, CD$_3$OD) δ 1.26(3H, t, J=7 Hz), 1.70-1.80(4H, m), 2.96-3.21(10H, m), 3.82-3.85(2H, m), 3.81(3H, s), 3.86(2H, s), 4.18(2H, q, J=7.2 Hz), 4.84(3H, s), 6.37(1H, d, J=8.34 Hz), 6.91(1H, t, J=7.4 Hz), 6.98(1H, d, J=8.3 Hz), 7.20(1H, d, J=7.4 Hz), 7.26(1H, t, J=8.3 Hz), 7.68(1H, s), 7.76(1H, d, J=8.3 Hz).

IR (KBr) vcm$^{-1}$: 3420, 2774, 1736, 1663, 1603, 1496, 1443, 1248, 1182, 1026, 759.

Example 99

N-Ethyl-5-(5-[[2-(2-metoxyphenyl)ethyl]amino]pentanoyl)-1-indolinecarboxamide hydrochloride

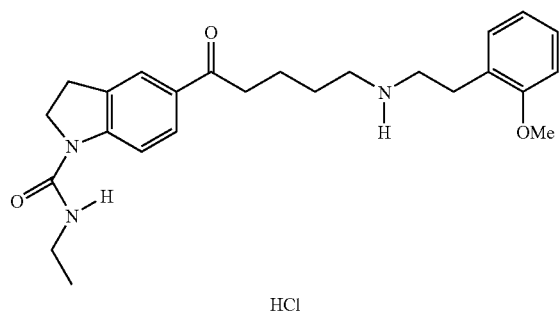

Using tert-butyl 5-[1-[(ethylamino)carbonyl]-2,3-dihydro-1H-indol-5-yl]-5-oxopentyl[2-(2-methoxyphenyl)ethyl]carbamate (250 mg) obtained in Reference Example 55 according to the same method as that of Example 1, the title compound (205 mg) was obtained as colorless crystals having a melting point of 185 to 186° C.

$^1$H NMR(400 MHz, DMSO-d$_6$) δ 1.08(3H, t, J=7.3 Hz), 1.63-1.70(4H, m), 2.92-3.03(8H, m), 3.11-3.18(4H, m), 3.79(3H, s), 3.93(2H, t, J 8.4 Hz), 6.87-6.91(2H, m), 6.98(1H, d, J=8.4 Hz), 7.16(1H, d, J=7.4 Hz), 7.24(1H, t, J=8.4 Hz), 7.73(1H, s), 7.76(1H, d, J=8.4 Hz), 7.88(1H, d, J=8.4 Hz), 9.06(2H, s).

IR (KBr) vcm$^{-1}$: 3315, 2773, 1667, 1604, 1526, 1494, 1442, 1319, 1245, 754.

Example 100

1-(1-Acetyl-2,3-dihydro-1H-indol-5-yl)-5-[[2-(2-methoxyphenyl)ethyl](methyl)amino]-1-pentanone hydrochloride

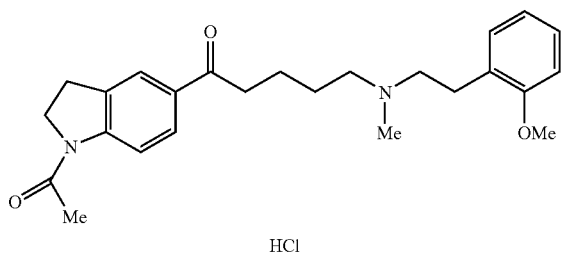

Using 1-(1-acetyl-2,3-dihydro-1H-indol-5-yl)-5-chloropentan-1-one obtained in Reference Example 11 and N-[2-(2-methoxyphenyl)ethyl]-N-methylamine according to the same method as that of Example 9, the title compound was obtained as yellow amorphous powders.

$^1$H NMR(free base; 400 MHz, CDCl$_3$) δ 1.54-1.61(2H, m), 1.70-1.78(2H, m), 2.25(3H, s), 2.31(3H, s), 2.46(2H, t, J=7.5 Hz), 2.55-2.59(2H, m), 2.76-2.80(2H, m), 2.94(2H, t, J=7.3 Hz), 3.23(2H, t, J=8.3 Hz), 3.81(3H, s), 4.11(2H, t, J=8.3 Hz), 6.82-6.87(2H, m), 7.12-7.19(2H, m), 7.81-7.84(2H, m), 8.23(1H, d, J=8.3 Hz).

IR (free base; neat) vcm$^{-1}$: 1673, 1603, 1493, 1440, 1394, 1329, 1244.

Example 101

1-(1-Acetyl-2,3-dihydro-1H-indol-5-yl)-5-[[2-(2-chlorophenyl)ethyl](methyl)amino]-1-pentanone hydrochloride

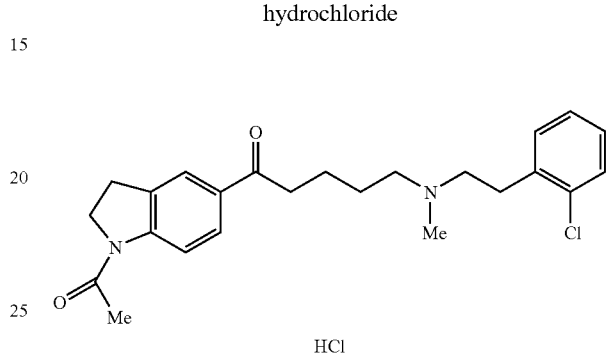

Using 1-(1-acetyl-2,3-dihydro-1H-indol-5-yl)-5-chloropentan-1-one obtained in Reference Example 11 and N-[2-(2-chlorophenyl)ethyl]-N-methylamine according to the same method as that of Example 9, the title compound was obtained as yellow amorphous powders.

$^1$H NMR(free base; 400 MHz, CDCl$_3$) δ 1.54-1.61(2H, m), 1.70-1.77(2H, m), 2.24(3H, s), 2.33(3H, s), 2.47(2H, t, J=6.3 Hz), 2.61(2H, t, J=7 Hz), 2.88-2.95(4H, m), 3.22(2H, t, J=7.5 Hz), 4.10(2H, t, J=7.5 Hz), 7.11-7.33(4H, m), 7.79-7.83(2H, m), 8.22(1H, d, J=8.5 Hz).

IR (free base; neat) vcm$^{-1}$: 1673, 1604, 1489, 1440, 1391, 1330, 1256.

Example 102

1-(1-Acetyl-2,3-dihydro-1H-indol-5-yl)-6-[[2-(2-methoxyphenyl)ethyl]amino]-1-hexanone hydrochloride

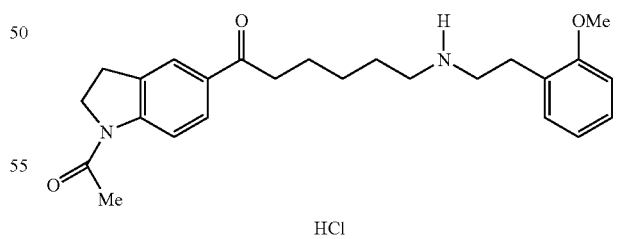

Using 1-(1-acetyl-2,3-dihydro-1H-indol-5-yl)-6-bromo-1-hexanone (388 mg) obtained in Reference Example 12 and 2-(2-methoxyphenyl)ethylamine. (378 mg) according to the same method as that of Example 9, the title compound (140 mg) was obtained as colorless crystals having a melting point of 186 to 187° C.

$^1$H NMR(free base; 400 MHz, CDCl$_3$) δ 1.35-1.43(2H, m), 1.49-1.56(2H, m), 1.64(1H, br.s), 1.69-1.76(2H, m), 2.24(3H, s), 2.68(2H, t, J=7 Hz), 2.83(4H, br.s), 2.91(2H, t, J=7 Hz), 3.22(2H, t, J=8.3 Hz), 3.81(3H, s), 4.11(2H, t, J 8.3 Hz), 6.83-6.88(2H, m), 7.13-7.20(2H, m), 7.79-7.82(2H, m), 8.23(1H, d, J=8.3 Hz).

IR (free base; neat) vcm$^{-1}$: 1673, 1602, 1493, 1440, 1394, 1329, 1243.

Example 103

1-(1-Acetyl-2,3-dihydro-1H-indol-5-yl)-6-([2-(2-chlorophenyl)ethyl]amino]-1-hexanone hydrochloride

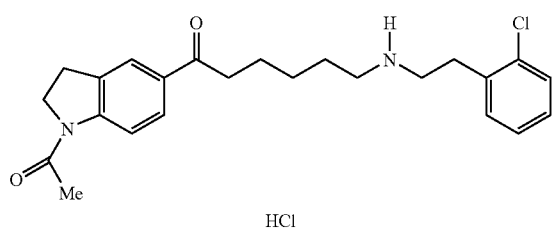

Using 1-(1-acetyl-2,3-dihydro-1H-indol-5-yl)-6-bromo-1-hexanone (270 mg) obtained in Reference Example 12 and 2-(2-chlorophenyl)ethylamine (311 mg) according to the same method as that of Example 9, the title compound (128 mg) was obtained as colorless crystals having a melting point of 182 to 183° C.

$^1$H NMR(free base; 400 MHz, CDCl$_3$) δ 1.38-1.44(2H, m), 1.47(1H, br.s), 1.50-1.57(2H, m), 1.70-1.77(2H, m), 2.24(3H, s), 2.66(2H, t, J=7.5 Hz), 2.85-2.94(6H, m), 3.22 (2H, t, J=8 Hz), 4.10(2H, t, J=8 Hz), 7.14-7.35(4H, m), 7.79-7.82(2H, m), 8.22(1H, d, J=8.5 Hz).

IR (free base; neat) vcm$^{-1}$: 1673, 1604, 1489, 1441, 1395, 1330, 1262.

Example 104

1-(1-Acetyl-2,3-dihydro-1H-indol-5-yl)-6-[[2-(2-methoxyphenyl)ethyl](methyl)amino]-1-hexanone hydrochloride

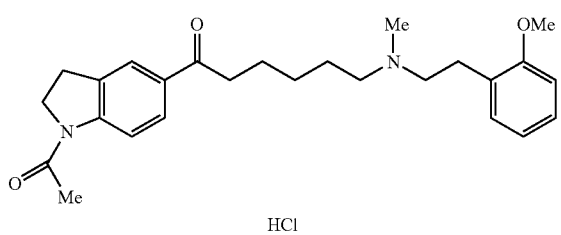

Using 1-(1-acetyl-2,3-dihydro-1H-indol-5-yl)-6-bromo-1-hexanone obtained in Reference Example 12 and N-[2-(2-methoxyphenyl)ethyl]-N-methylamine according to the same method as that of Example 9, the title compound was obtained as yellow amorphous powders.

$^1$H NMR(free base; 400 MHz, CDCl$_3$) δ 1.36-1.42(2H, m), 1.51-1.58(2H, m), 1.70-1.78(2H, m), 2.24(3H, s), 2.31(3H, s), 2.42(2H, t, J=7.5 Hz), 2.55-2.59(2H, m), 2.76-2.80(2H, m), 2.92(2H, t, J=7.5 Hz), 3.21(2H, t, J=8.3 Hz), 3.81(3H, s), 4.09(2H, t, J=8.3 Hz), 6.82-6.89(2H, m), 7.12-7.19(2H, m), 7.79-7.83(2H, m), 8.23(1H, d, J=8.3 Hz).

IR (free base; neat) vcm$^{-1}$: 1674, 1603, 1493, 1440, 1394, 1329, 1244.

Example 105

1-(1-Acetyl-2,3-dihydro-1H-indol-5-yl)-6-[[2-(2-chlorophenyl)ethyl](methyl)amino]-1-hexanone hydrochloride

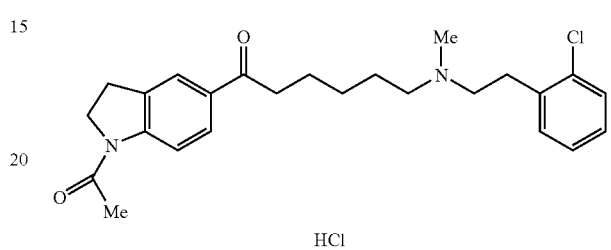

Using 1-(1-acetyl-2,3-dihydro-1H-indol-5-yl)-6-bromo-1-hexanone obtained in Reference Example 12 and N-[2-(2-chlorophenyl)ethyl]-N-methylamine according to the same method as that of Example 9, the title compound was obtained as colorless crystals having a melting point of 177 to 178° C.

$^1$H NMR(free base; 400 MHz, CDCl$_3$) δ 1.35-1.42(2H, m), 1.50-1.58(2H, m), 1.70-1.78(2H, m), 2.25(3H, s), 2.33(3H, s), 2.43(2H, t, J=7 Hz), 2.58-2.62(2H, m), 2.88-2.95(4H, m), 3.23(2H, t, J=8 Hz), 4.10(2H, t, J=8 Hz), 7.11-7.33(4H, m), 7.80-7.83(2H, m), 8.22(1H, d, J=8.5 Hz).

IR (free base; neat) vcm$^{-1}$: 1674, 1604, 1489, 1441, 1394, 1329, 1246.

Example 106

6-[5-[(2-Phenylethyl)amino]pentanoyl]-2H-1,4-benzoxazin-3(4H)-one hydrochloride

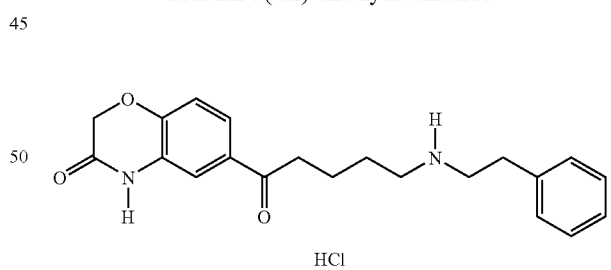

Using tert-butyl 5-oxo-5-(3-oxo-3,4-dihydro-2H-1,4-benzoxazin-6-yl)pentyl(2-phenylethyl)carbamate obtained in Reference Example 41 according to the same method as that of Example 1, the title compound was obtained as colorless amorphous powders.

$^1$H NMR(300 MHz, DMSO-d$_6$) δ 1.68 (4H, br.), 2.96-3.01 (6H, m), 3.10(2H, br.s), 4.69(2H, s), 7.05(1H, d, J=8.4 Hz), 7.26-7.37(5H, m), 7.53(1H, d, J=1.8 Hz), 7.63(1H, dd, J=8.4, 1.5 Hz), 9.13(2H, br), 10.95(1H, s).

[M+H]$^+$ (ESI+)=353, HPLC purity 94%(220 nm)

Example 107

N-(5-{5-[[2-(2-chlorophenyl)ethyl](methyl)amino]pentanoyl}-2,3-dihydro-1H-inden-2-yl)methanesulfonamide hydrochloride

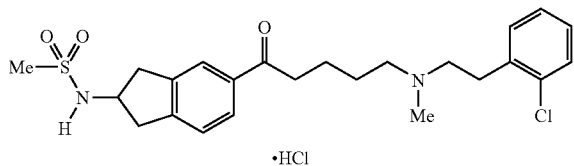

Using N-[5-(5-chloropentanoyl)-2,3-dihydro-1H-inden-2-yl]methanesulfonamide obtained in Reference Example 233 and N-[2-(2-chlorophenyl)ethyl]-N-methylamine according to the same method as that of Example 9, the title compound was obtained as colorless amorphous powders.

$^1$H NMR (free base; 200 MHz, CDCl$_3$) δ 1.52-1.81 (4H, m), 2.33 (3H, s), 2.47 (2H, t, J=7.4 Hz), 2.60 (2H, m), 2.64-2.98 (6H, m), 3.01 (3H, s), 3.35 (2H, dd, J=16.4, 7.2 Hz), 4.30 (1H, m), 5.08 (1H, br), 7.07-7.34 (5H, m), 7.78 (2H, m).

Example 108

6-(5-[[2-(2-Ethoxyphenyl)ethyl]amino]pentanoyl)-2H-1,4-benzoxazin-3(4H)-one hydrochloride

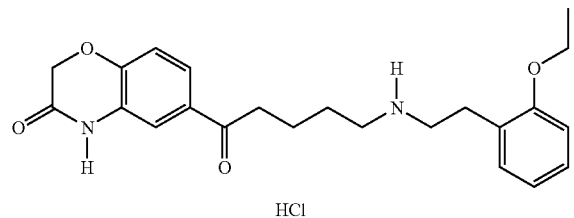

Using tert-butyl 2-(2-ethoxyphenyl)ethyl[5-oxo-5-(3-oxo-3,4-dihydro-2H-1,4-benzoxazin-6-yl)pentyl]carbamate obtained in Reference Example 42 according to the same method as that of Example 1, the title compound was obtained as colorless amorphous powders.

$^1$H NMR(300 MHz, DMSO-d$_6$) δ 1.67(4H, br.), 2.95-3.02 (8H, m), 3.52(2H, br.s), 3.80(3H, s), 4.69(2H, s), 6.89-6.99 (1H, m), 6.99-7.04(2H, m), 7.20-7.28(2H, m), 7.54(1H, d, J=1.8 Hz), 7.63(1H, dd, J=8.4, 1.5 Hz), 9.11(2H, br.), 10.96 (1H,s).

MS m/z: 397 [M+H]$^+$

Example 109

6-(5-[[2-(2-Flurophenyl)ethyl]amino]pentanoyl)-2H-1,4-benzoxazin-3(4H)-one hydrochloride

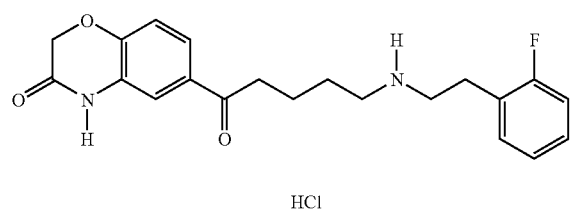

Using tert-butyl 2-(2-flurohenyl)ethyl[5-oxo-5-(3-oxo-3,4-dihydro-2H-1,4-benzoxazin-6-yl)pentyl]carbamate obtained in Reference Example 43 according to the same method as that of Example 1, the title compound was obtained as colorless amorphous powders.

$^1$H NMR(300 MHz, DMSO-d$_6$) δ 1.67(4H, m), 3.00-3.04 (6H, m), 3.09(2H, m), 4.69(2H, s), 7.06(1H, d, J=8.1 Hz), 7.17-7.24(2H, m), 7.30-7.38(2H, m), 7.51(1H, d, J=1.8 Hz), 7.63(1H, dd, J=8.4, 1.8 Hz), 9.04(2H, br.), 10.93(1H, s).

MS m/z: 371 [M+H]$^+$

Example 110

6-(5-[[2-(2-Chlorophenyl)ethyl]amino]pentanoyl)-2H-1,4-benzoxazin-3(4H)-one hydrochloride

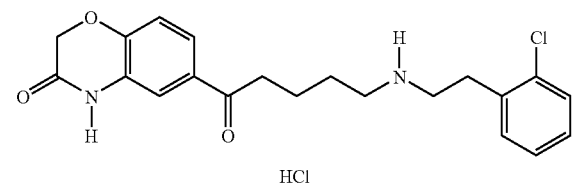

Using tert-butyl 2-(2-chlorophenyl)ethyl[5-oxo-5-(3-oxo-3,4-dihydro-2H-1,4-benzoxazin-6-yl)pentyl]carbamate obtained in Reference Example 44 according to the same method as that of Example 1, the title compound was obtained as colorless amorphous powders.

$^1$H NMR(300 MHz, DMSO-d$_6$) δ 1.68(4H,m), 2.98-3.02 (4H, m), 3.11(4H, br.), 4.69(2H, s), 7.04(1H, d, J=8.1 Hz), 7.31-7.49(4H, m), 7.52(1H, d, J=1.5 Hz), 7.63(1H, dd, J=8.3, 1.4 Hz), 9.13(2H, br.), 10.93(1H, s).

MS m/z: 387 [M+H]$^+$

Example 111

6-(5-[[2-(3-Methoxyphenyl)ethyl]amino]pentanoyl)-2H-1,4-benzoxazin-3(4H)-one hydrochloride

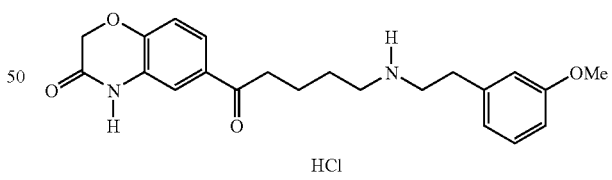

Using tert-butyl 2-(3-methoxyphenyl)ethyl[5-oxo-5-(3-oxo-3,4-dihydro-2H-1,4-benzoxazin-6-yl)pentyl]carbamate obtained in Reference Example 45 according to the same method as that of Example 1, the title compound was obtained as colorless amorphous powders.

$^1$H NMR(300 MHz, DMSO-d$_6$) δ 1.67(4H, br.), 2.92-3.02 (6H, m), 3.13(2H, br.), 3.75(3H, s), 4.69(2H, s), 6.82-6.84 (3H, m), 7.05(1H, d, J=8.4 Hz), 7.23-7.28(1H, m), 7.52(1H, d, J=2.1 Hz), 7.63(1H, dd, J=8.3, 2.0 Hz), 9.03(2H, br.), 10.93(1H, s).

MS m/z: 383 [M+H]$^+$

Example 112

6(5-[[2-(3-Ethoxyphenyl)ethyl]amino]pentanoyl)-2H-1,4-benzoxazin-3(4H)-one hydrochloride

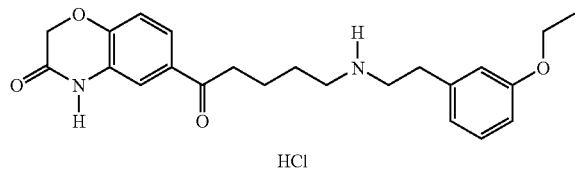

Using tert-butyl 2-(3-ethoxyphenyl)ethyl[5-oxo-5-(3-oxo-3,4-dihydro-2H-1,4-benzoxazin-6-yl)pentyl]carbamate obtained in Reference Example 46 according to the same method as that of Example 1, the title compound was obtained as colorless amorphous powders.

$^1$H NMR(300 MHz, DMSO-$d_6$) δ 1.32(3H, t, J=6.9 Hz), 1.67(4H, br.), 2.91-3.02(6H, m), 3.11(2H, br.), 4.01(2H, q, J=6.9 Hz), 4.68(2H, s), 6.80-6.82(3H, m), 7.05(1H, d, J=8.4 Hz), 7.21-7.26(1H, m), 7.52(1H, d, J=1.8 Hz), 7.63(1H, dd, J=8.3, 1.4 Hz), 9.02(2H, br.), 10.93(1H, s).

MS m/z: 397 [M+H]$^+$

Example 113

6-(5-[[2-(3-Flurophenyl)ethyl]amino]pentanoyl)-2H-1,4-benzoxazin-3(4H)-one hydrochloride

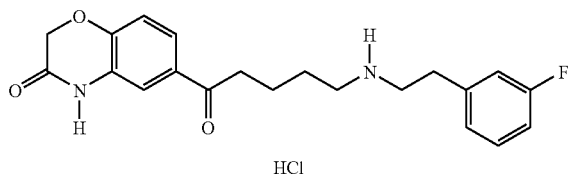

Using tert-butyl 2-(3-flurophenyl)ethyl[5-oxo-5-(3-oxo-3,4-dihydro-2H-1,4-benzoxazin-6-yl)pentyl]carbamate obtained in Reference Example 56 according to the same method as that of Example 1, the title compound was obtained as colorless amorphous powders.

$^1$H NMR(300 MHz, DMSO-$d_6$) δ 1.67(4H, br.), 2.95-3.03(6H, m), 3.14(2H, br.), 4.69(2H, s), 7.06(1H, d, J=8.4 Hz), 7.09-7.17(3H, m), 7.34-7.42(1H, m), 7.52(1H, d, J=1.8 Hz), 7.63(1H, dd, J=8.3, 1.4 Hz), 9.04(2H, br.), 10.93(1H, s).

MS m/z: 371 [M+H]$^+$

Example 114

6-(5-[(2-(3-Chlorophenyl)ethyl]amino]pentanoyl)-2H-1,4-benzoxazin-3(4H)-one hydrochloride

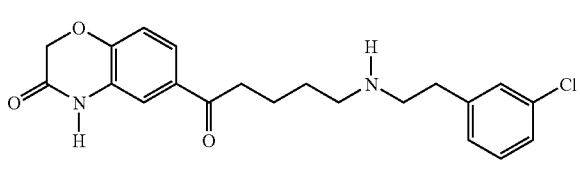

Using tert-butyl 2-(3-chlorophenyl)ethyl[5-oxo-5-(3-oxo-3,4-dihydro-2H-1,4-benzoxazin-6-yl)pentyl]carbamate obtained in Reference Example 57 according to the same method as that of Example 1, the title compound was obtained as colorless amorphous powders.

$^1$H NMR(300 MHz, DMSO-$d_6$) δ 1.67(4H, br.), 2.95-3.02(6H, m), 3.13(2H, br.), 4.69(2H, s), 7.06(1H, d, J=8.1 Hz), 7.24-7.38(4H, m), 7.52(1H, d, J=1.8 Hz), 7.63(1H, dd, J=8.3, 1.1 Hz), 9.06(2H, br.), 10.94(1H, s).

MS m/z: 387 [M+H]$^+$

Example 115

6-[5-[Methyl(2-phenylethyl)amino]pentanoyl]-2H-1,4-benzoxazin-3(4H)-one hydrochloride

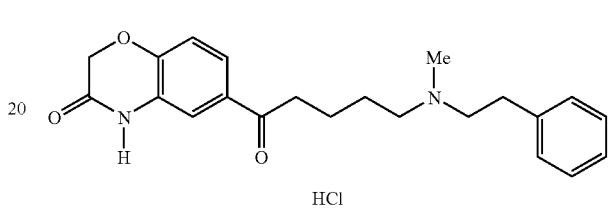

Using 6-(5-chloropentanoyl)-2H-1,4-benzoxazin-3(4H)-one obtained in Reference Example 7 and N-methyl-N-(2-phenylethyl)amine according to the same method as that of Example 9, the title compound was obtained as colorless amorphous powders.

$^1$H NMR(200 MHz, DMSO-$d_6$) δ 1.68(4H, br.), 2.81(3H, s), 2.98-3.44(8H, m), 4.67(2H, s), 7.04(1H, d, J=8.6 Hz), 7.25-7.51(5H, m), 7.49(1H, d, J=2.0 Hz), 7.62(1H, dd, J=8.6, 2.0 Hz), 9.93(1H, br.s), 10.88(1H, s).

MS m/z: 381 [M+H]$^+$

Example 116

6-[5-[[2-(2-Methoxyphenyl)ethyl](methyl)amino]pentanoyl]-2H-1,4-benzoxazin-3(4H)-one hydrochloride

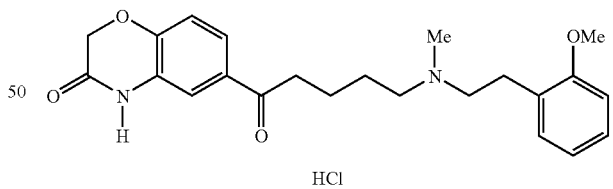

Using, 6-(5-chloropentanoyl)-2H-1,4-benzoxazin-3(4H)-one obtained in Reference Example 7 and N-[2-(2-methoxyphenyl)ethyl]-N-methylamine according to the same method as that of Example 9, the title compound was obtained as colorless amorphous powders.

$^1$H NMR(200 MHz, DMSO-$d_6$) δ 1.68(4H, br.), 2.82(3H, d, J=3.4 Hz), 2.94-3.23(8H, br.), 3.82(3H, s), 4.67(2H, s), 6.92(1H, t, J=4.9 Hz), 7.01(1H, d, J=8.4 Hz), 7.04(1H, d, J=8.2 Hz), 7.21-7.29(2H, m), 7.50(1H, d, J=1.4 Hz), 7.62(1H, dd, J=5.7, 1.3 Hz), 9.97(1H, br.s), 10.89(1H, s).

MS m/z: 397 [M+H]$^+$

Example 117

6-[5-[[2-(2-Fluorophenyl)ethyl](methyl)amino]pentanoyl]-2H-1,4-benzoxazin-3(4H)-one hydrochloride

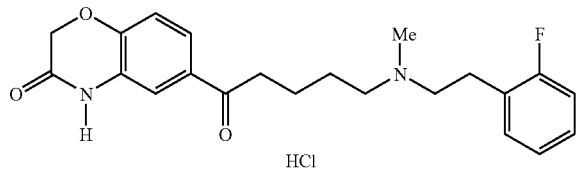

Using 6-(5-chloropentanoyl)-2H-1,4-benzoxazin-3(4H)-one obtained in Reference Example 7 and N-[2-(2-fluorophenyl)ethyl]-N-methylamine according to the same method as that of Example 9, the title compound was obtained as colorless amorphous powders.

$^1$H NMR(200 MHz, DMSO-$d_6$) δ 1.68(4H, br.), 2.82(3H, d, J=4.8 Hz), 2.98-3.34(8H, br.), 4.67(2H, s), 7.04(1H, d, J=8.0 Hz), 7.15-7.24(2H, m), 7.28-7.40(2H, m), 7.51(1H, d, J=1.8 Hz), 7.62(1H, dd, J=8.6, 2.2 Hz), 10.26(1H, br.s), 10.89 (1H, s).

MS m/z: 385 [M+H]$^+$

Example 118

6-[5-[[2-(2-Chlorophenyl)ethyl](methyl)amino]pentanoyl]-2H-1,4-benzoxazin-3(4H)-one hydrochloride

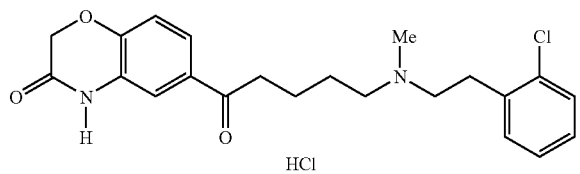

sing 6-(5-chloropentanoyl)-2H-1,4-benzoxazin-3(4H)-one obtained in Reference Example 7 and N-[2-(2-chlorophenyl)ethyl]-N-methylamine according to the same method as that of Example 9, the title compound was obtained as colorless amorphous powders.

$^1$H NMR(200 MHz, DMSO-$d_6$) δ 1.69(4H, br.), 2.83(3H, s), 2.97(2H, t, J=7 Hz), 3.18(6H, m), 4.67(2H, s), 7.04(1H, d, J=8.2 Hz), 7.30-7.38(2H, m), 7.43-7.51(2H, m), 7.59(1H, d, J=1.8 Hz), 7.62(1H, dd, J=8.4, 1.8 Hz), 10.36(1H, br.s), 10.87 (1H, s).

MS m/z: 401 [M+H]$^+$

Example 119

6-(5-[(2-(3-Methoxyphenyl)ethyl](methyl)amino]pentanoyl]-2H-1,4-benzoxazin-3(4H)-one hydrochloride

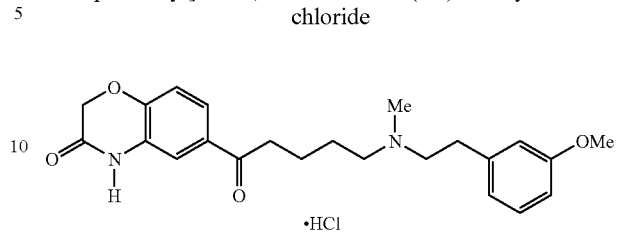

Using 6-(5-chloropentanoyl)-2H-1,4-benzoxazin-3(4H)-one obtained in Reference Example 7 and N-[2-(3-methoxyphenyl)ethyl]-N-methylamine according to the same method as that of Example 9, the title compound was obtained as colorless amorphous powders.

$^1$H NMR(200 MHz, DMSO-$d_6$) δ 1.68(4H, br.), 2.82(3H, d, J=3.2 Hz), 2.96-3.34(8H, br.), 3.76(3H, s), 4.67(2H, s), 6.81(1H, d, J=1.6 Hz), 6.86(2H, d, J=5.6 Hz), 7.04(1H, d, J=5.8 Hz), 7.25(1H, t, J=5.2 Hz), 7.50(1H, d, J=1.6 Hz), 7.61(1H, dd, J=5.6, 1.4 Hz), 9.68(1H, br.s), 10.89(1H, s).

MS m/z: 397 [M+H]$^+$

Example 120

6-[5-[[2-(3-Fluorophenyl)ethyl](methyl)amino]pentanoyl]-2H-1,4-benzoxazin-3(4H)-one hydrochloride

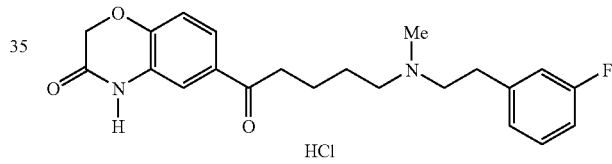

Using 6-(5-chloropentanoyl)-2H-1,4-benzoxazin-3(4H)-one obtained in Reference Example 7 and N-[2-(3-fluorophenyl)ethyl]-N-methylamine according to the same method as that of Example 9, the title compound was obtained as colorless amorphous powders.

$^1$H NMR(300 MHz, DMSO-d6) δ 1.68(4H, br.), 2.82(3H, d, J=4.5 Hz), 2.98-3.36(8H, br.), 4.67(2H, s), 7.02-7.19(4H, m), 7.34-7.42(1H, m), 7.50(1H, d, J=2.1 Hz), 7.63(1H, dd, J=8.7, 2.1 Hz), 9.69(1H, br.s), 10.88(1H, s).

MS m/z: 385 [M+H]$^+$

Example 121

6-[5-[[2-(3-Chlorophenyl)ethyl](methyl)amino]pentanoyl]-2H-1,4-benzoxazin-3(4H)-one hydrochloride

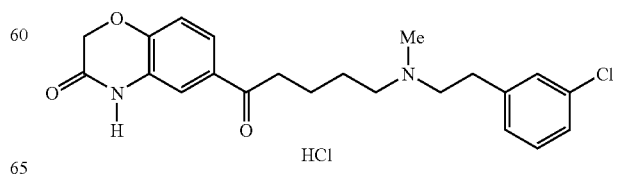

Using 6-(5-chloropentanoyl)-2H-1,4-benzoxazin-3(4H)-one obtained in Reference Example 7 and N-[2-(3-chlorophenyl)ethyl]-N-methylamine according to the same method as that of Example 9, the title compound was obtained as colorless amorphous powders.

$^1$H NMR(200 MHz, DMSO-$d_6$) δ 1.68(4H, br.), 2.81(3H, d, J=4.8 Hz), 3.03-3.63(8H, br.), 4.67(2H, s), 7.04(1H, d, J=8.4 Hz), 7.25-7.42(4H, m), 7.51(1H, d, J=1.8 Hz), 7.62(1H, dd, J=8.4, 1.8 Hz), 10.06(1H, br.s), 10.90(1H, s).

MS m/z: 401 [M+H]$^+$

Example 122

6-[6-[[2-(2-Methoxyphenyl)ethyl](methyl)amino] hexanoyl]-2H-1,4-benzoxazin-3(4H)-one hydrochloride

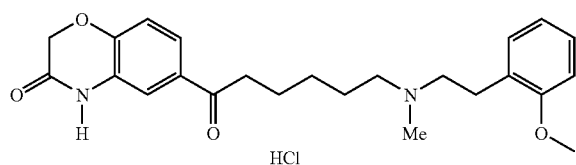

Using 6-(6-bromohexanoyl)-2H-1,4-benzoxazin-3(4H)-one obtained in Reference Example 8 and N-[2-(2-methoxyphenyl)ethyl]-N-methylamine according to the same method as that of Example 9, the title compound was obtained as colorless amorphous powders.

$^1$H NMR(200 MHz, DMSO-$d_6$) δ 1.31-1.41(2H, m), 1.61-1.79(4H, m), 2.79(3H, d, J=4.8 Hz), 2.92-3.42(8H, br.), 3.81 (3H, s), 4.67(2H, s), 6.87-7.05(3H, m), 7.20-7.30(2H, m), 7.50(1H, d, J=1.8 Hz), 7.61(1H, dd, J=8.2, 2.0 Hz), 10.13(1H, br.s), 10.85(1H, s).

MS m/z: 411 [M+H]$^+$

Example 123

6-[6-[[2-(2-Fluorophenyl)ethyl](methyl)amino]hexanoyl]-2H-1,4-benzoxazin-3(4H)-one hydrochloride

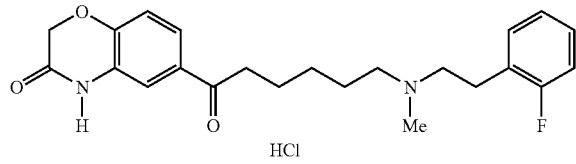

Using 6-(6-bromohexanoyl)-2H-1,4-benzoxazin-3(4H)-one obtained in Reference Example. 8 and N-[2-(2-fluorophenyl)ethyl]-N-methylamine according to the same method as that of Example 9, the title compound was obtained as colorless amorphous powders.

$^1$H NMR(200 MHz, DMSO-$d_6$) δ 1.32-1.42(2H, m), 1.61-1.78(4H, m), 2.81(3H, s), 2.92-3.30(8H, br.), 4.67(2H, s), 7.03(1H, d, J=8.4 Hz), 7.05-7.24(2H, m), 7.29-7.43(2H, m), 7.51(1H, d, J=1.8 Hz), 7.61(1H, dd, J=8.4, 1.8 Hz), 10.60(1H, br.s), 10.90(1H, s).

MS m/z: 399 [M+H]$^+$

Example 124

6-[6-[[2-(2-Chlorophenyl)ethyl](methyl)amino]hexanoyl]-2H-1,4-benzoxazin-3(4H)-one hydrochloride

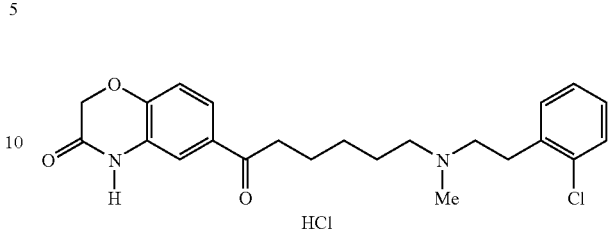

Using 6-(6-bromohexanoyl)-2H-1,4-benzoxazin-3(4H)-one obtained in Reference Example 8 and N-[2-(2-chlorophenyl)ethyl]-N-methylamine according to the same method as that of Example 9, the title, compound was obtained as colorless amorphous powders.

$^1$H NMR(200MHz, DMSO-$d_6$) δ 1.33-1.43(2H, m), 1.61-1.78(4H, m), 2.85(3H, d, J=4.8 Hz), 2.96(2H, t, J=7 Hz), 3.12-3.21(6H, m), 4.66(2H, s), 7.03(1H, d, J=8.4 Hz), 7.27-7.37(2H, m), 7.41-7.48(2H, m), 7.50(1H, d, J=2.0 Hz), 7.60 (1H, dd, J 8.2, 2.0 Hz), 10.24(1H, br.s), 10.87(1H, s).

MS m/z: 415 [M+H]$^+$

Example 125

6-[6-[[2-(3-Methoxyphenyl)ethyl](methyl)amino] hexanoyl]-2H-1,4-benzoxazin-3(4H)-one hydrochloride

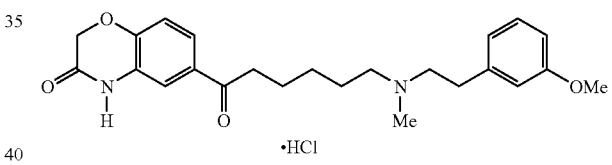

Using 6-(6-bromohexanoyl)-2H-1,4-benzoxazin-3(4H)-one obtained in Reference Example 8 and N-(2-(3-methoxyphenyl)ethyl]-N-methylamine according to the same method as that of Example 9, the title compound was obtained as colorless amorphous powders.

$^1$H NMR(200 MHz, DMSO-$d_6$) δ 1.34(2H, br.), 1.61-1.78 (4H, m), 2.79(3H, d, J=3.8 Hz), 2.96-3.26(8H, m), 3.75(3H, s), 4.67(2H, s), 6.84(3H, t, J=6.9 Hz), 7.03(1H, d, J=8.4 Hz), 7.25(1H, t, J=8.0 Hz), 7.52(1H, s), 7.61(1H, d, J=7.4 Hz), 10.5(1H, br.s), 10.91(1H, s).

MS m/z: 411 [M+H]$^+$

Example 126

6-[6-[[2-(3-Fluorophenyl)ethyl](methyl)amino]hexanoyl]-2H-1,4-benzoxazin-3(4H)-one hydrochloride

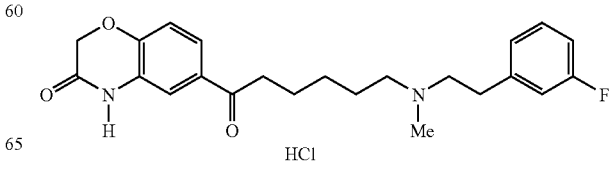

Using 6-(6-bromohexanoyl)-2H-1,4-benzoxazin-3(4H)-one obtained in Reference Example 8 and N-[2-(3-fluorophenyl)ethyl]-N-methylamine according to the same method as that of Example 9, the title compound was obtained as colorless amorphous powders.

¹H NMR(300 MHz, CD₃OD) δ 1.44-1.52(2H, br.), 1.73-1.86(4H, m), 2.94(3H, s), 3.00-3.19(4H, m), 3.23-3.49(4H, m), 4.67(2H, s), 6.98-7.15(4H, m), 7.33-7.40(1H, m), 7.54 (1H, d, J=2.1 Hz), 7.67(1H, dd, J=8.4 Hz, 2.2 Hz).

MS m/z: 399 [M+H]⁺

Example 127

6-[6-[[2-(3-Chlorophenyl)ethyl](methyl)amino]hexanoyl]-2H-1,4-benzoxazin-3(4H)-one hydrochloride

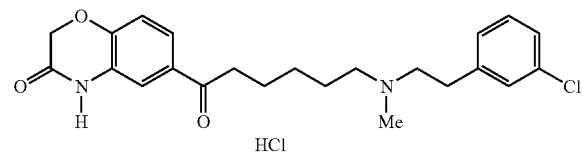

Using 6-(6-bromohexanoyl)-2H-1,4-benzoxazin-3(4H)-one obtained in Reference Example 8 and N-[2-(3-chlorophenyl)ethyl]-N-methylamine according to the same method as that of Example 9, the title compound was obtained as colorless amorphous powders.

¹H NMR(200 MHz, DMSO-d₆) δ 1.33-1.40(2H, br.), 1.62-1.76(4H, m), 2.80(3H, d, J=4.8 Hz), 2.93-3.63(8H, m), 4.67 (2H, s), 7.03(1H, d, J=8.1 Hz), 7.26-7.30(4H, m), 7.51(1H, d, J=1.8 Hz), 7.61(1H, d, J=8.4 Hz, 2.1 Hz), 10.5(1H, br.s), 10.9(1H, s).

MS m/z: 415 [M+H]⁺

Example 128

6-[5-[[2-(2-Ethoxyphenyl)ethyl](methyl)amino]pentanoyl]-2H-1,4-benzoxazin-3(4H)-one hydrochloride

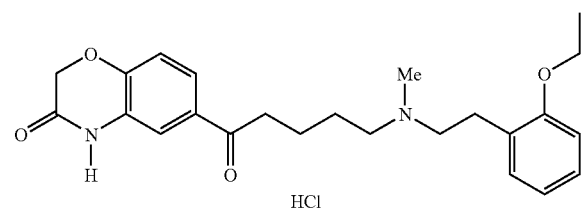

Using 6-(5-chloropentanoyl)-2H-1,4-benzoxazin-3(4H)-one obtained in Reference Example 7 and N-[2-(2-ethoxyphenyl)ethyl]-N-methylamine according to the same method as that of Example 9, the title compound was obtained as colorless amorphous powders.

¹H NMR(free base; 200 MHz, CDCl₃) δ 1.41(3H, t, J=6.9 Hz), 1.56-1.63(2H, m), 1.70-1.78(2H, m), 2.33(3H, s), 2.47 (2H, t, J=7.5), 2.57-2.62(2H, m), 2.77-2.84(2H, m), 2.93(2H, t, J=7.3 H), 3.99-4.06(2H, m), 4.68(2H, s), 5.60(1H, br.s), 6.80-6.89(2H, m), 7.00(1H, d, J=8.4 Hz), 7.10-7.26(2H, m), 7.51(1H, d, J=2.4 Hz), 7.61(1H, dd, J=8.4, 2.1 Hz).

MS m/z: 411 [M+H]⁺

Example 129

6-[5-[[2-(3-Ethoxyphenyl)ethyl](methyl)amino]pentanoyl]-2H-1,4-benzoxazin-3(4H)-one hydrochloride

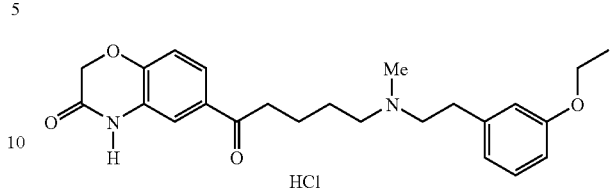

Using 6-(5-chloropentanoyl)-2H-1,4-benzoxazin-3(4H)-one obtained in Reference Example 7 and N-[2-(3-ethoxyphenyl)ethyl]-N-methylamine according to the same method as that of Example 9, the title compound was obtained as colorless amorphous powders.

¹H NMR(free base; 300 MHz, CDCl₃) δ 1.40(3H, t, J=6.9 Hz), 1.53-1.61(2H, m), 1.69-1.76(2H, s), 2.30(3H, s), 2.45 (2H, t, J=7.4 Hz), 2.57-2.63(2H, m), 2.69-2.76(2H, m), 2.91 (2H, t, J=7.2 H), 4.00(2H, t, J=6.9 Hz), 4.67(2H, s), 5.60(1H, br.s), 6.69-6.78(3H, m), 6.99(1H, d, J=8.1 Hz), 7.16(1H, t, J=8.0 Hz), 7.52(1H, d, J=1.8 Hz), 7.58(1H, dd, J=8.4, 2.1 Hz).

MS m/z: 411 [M+H]⁺

Example 130

6-[6-[[2-(2-Ethoxyphenyl)ethyl](methyl)amino]hexanoyl]-2H-1,4-benzoxazin-3(4H)-one hydrochloride

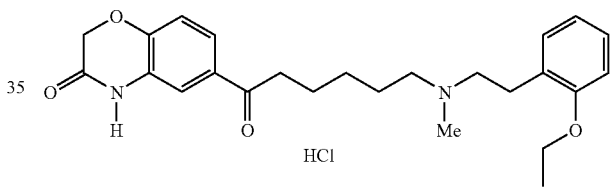

Using 6-(6-bromohexanoyl)-2H-1,4-benzoxazin-3(4H)-one obtained in Reference Example 8 and N-[2-(2-ethoxyphenyl)ethyl]-N-methylamine according to the same method as that of Example 9, the title compound was obtained as colorless amorphous powders.

¹H NMR(base free; 200 MHz, CDCl₃) δ 1.37-1.44(5H, m), 1.53-1.60(2H, m), 1.71-1.78(2H, s), 2.34(3H, s), 2.45(2H, t, J=7.4 Hz), 2.55-2.64(2H, m), 2.76-2.93(4H, m), 3.96-4.06 (2H, m), 4.67(2H, s), 5.32(1H, br.s), 6.78-6.89(2H, m), 6.99 (1H, d, J=8.0 Hz), 7.12(2H, d, J=7.2 Hz), 7.54(1H, d, J=1.8 Hz), 7.59(1H, dd, J=8.2, 2.0 Hz).

MS m/z: 425 [M+H]⁺

Example 131

6-[6-[[2-(3-Ethoxyphenyl)ethyl](methyl)amino]hexanoyl]-2H-1,4-benzoxazin-3(4H)-one hydrochloride

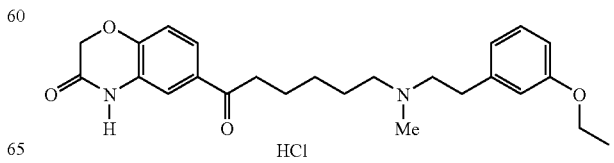

Using 6-(6-bromohexanoyl)-2H-1,4-benzoxazin-3(4H)-one obtained in Reference Example 8 and N-[2-(3-ethoxyphenyl)ethyl]-N-methylamine according to the same method as that of Example 9, the title compound was obtained as colorless amorphous powders.

¹H NMR(base free; 200 MHz, CDCl₃) δ 1.32-1.42(5H, m), 1.49-1.59(2H, m), 1.69-1.78(2H, s), 2.30(3H, s), 2.42(2H, t, J=7.6 Hz), 2.59-2.66(2H, m), 2.70-2.77(2H, m), 2.89(2H, t, J=7.2 Hz), 3.97-4.04(2H, m), 4.67(2H, s), 5.38(1H, br.s), 6.69-6.78(3H, m), 6.98(1H, d, J=8.1 Hz), 7.17(1H, t, J=7.7 Hz), 7.55(1H, d, J=1.8 Hz), 7.58(1H, dd, J=8.4, 2.1 Hz).

MS m/z: 425 [M+H]⁺

Example 132

5-[5-[Methyl(2-phenylethyl)amino]pentanoyl]-1,3-dihydro-2H-benzimidazol-2-one hydrochloride

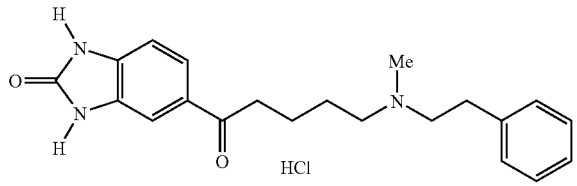

Using 5-(5-chloropentanoyl)-1,3-dihydro-2H-benzimidazol-2-one obtained in Reference Example 9 and N-methyl-N-(2-phenylethyl)amine according to the same method as that of Example 9, the title compound was obtained as colorless crystals having a melting point of 240° C.

¹H NMR(300 MHz, DMSO-d₆) δ 1.65-1.75(4H, m), 2.80 (3H, d, J=4.8 Hz), 3.00-3.08(6H, m), 3.23(2H, m), 7.03(1H, d, J=8.1 Hz), 7.26-7.36(5H, m), 7.67(1H, d, J=8.4 Hz), 10.28 (1H, s), 10.94(1H, s), 11.09(1H, s).

elementary analysis as C₂₁H₂₅N₃O₂·HCl·0.5H₂O
calculation value: C, 62.69; H, 6.91; N, 10.44.
experimental value: C, 62.87; H, 6.63; N, 10.37.

MS m/z: 352 [M+H]⁺

Example 133

5-[5-[[2-(2-Methoxyphenyl)ethyl](methyl)amino]pentanoyl]-1,3-dihydro-2H-benzimidazol-2-one hydrochloride

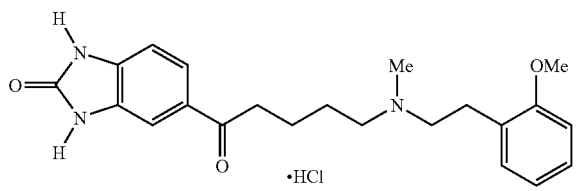

Using 5-(5-chloropentanoyl)-1,3-dihydro-2H-benzimidazol-2-one obtained in Reference Example 9 and N-[2-(2-methoxyphenyl)ethyl]-N-methylamine according to the same method as that of Example 9, the title compound was obtained as colorless crystals having a melting point of 169 to 180° C. (in a sealed tube; dec).

¹H NMR(300 MHz, DMSO-d₆) δ 1.65-1.75(4H, m), 2.80 (3H, d, J=4.8 Hz), 2.92-3.30(8H, m), 3.81(3H, s), 6.89-6.95 (1H, m), 7.00-7.04(2H, m), 7.21-7.30(2H, m), 7.50(1H, s), 7.69(1H, dd, J=8.3, 1.7 Hz), 10.09(1H, br.s), 10.95(1H, s), 11.09(1H, s).

MS m/z: 382 [M+H]⁺

Example 134

N-(5-{5-[[2-(2-methoxyphenyl)ethyl](methyl)amino]pentanoyl}-2,3-dihydro-1H-inden-2-yl)methanesulfonamide hydrochloride

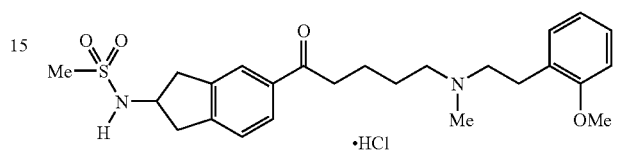

Using N-[5-(5-chloropentanoyl)-2,3-dihydro-1H-inden-2-yl]methanesulfonamide obtained in Reference Example 233 and N-[2-(2-methoxyphentyl)ethyl]-N-methylamine according to the same method as that of Example 9, the title compound was obtained as colorless amorphous powders.

¹H NMR (free base; 200 MHz, CDCl₃) δ 1.52-1.81 (4H, m), 2.33 (3H, s), 2.47 (2H, t, J=7.4 Hz), 2.60 (2H, m), 2.78 (2H, m), 2.93 (4H, m), 3.00 (3H, s), 3.35 (2H, dd, J=16.4, 7.0 Hz), 3.81 (3H, s), 4.32 (1H, m), 5.08 (1H, br), 6.81-6.90 (2H, m), 7.11-7.30 (3H, m), 7.78 (2H, m).

Example 135

1,3-Dimethyl-5-[5-[methyl(2-phenylethyl)amino]pentanoyl]-1,3-dihydro-2H-benzimidazol-2-one hydrochloride

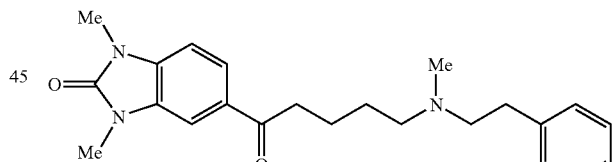

Using 5-(5-chloropentanoyl)-1,3-dimethyl-1,3-dihydro-2H-benzimidazol-2-one obtained in Reference Example 10 and N-methyl-N-(2-phenylethyl)amine according to the same method as that of Example 9, the title compound was obtained as colorless crystals having a melting point of 142 to 157° C. (in a sealed tube; dec).

¹H NMR(free base; 300 MHz, CDCl₃) δ 1.54-1.69(2H, m), 1.73-1.83(2H, m), 2.31(3H, s), 2.44-2.49(2H, m), 2.58-2.64 (2H, m), 2.75-2.80(2H, m), 2.98-3.03(2H, m), 3.46(3H, s), 3.47(3H, s), 6.99(1H, d, J=8.1 Hz), 7.15-7.30(5H, m), 7.63 (1H, d, J=1.5 Hz), 7.69(1H, dd, J=8.3, 1.7 Hz).

MS m/z: 380 [M+H]⁺

Example 136

5-[5-[(2-Methoxyphenyl)ethyl](methyl)amino]pentanoyl]-1,3-dimethyl-1,3-dihydro-2H-benzimidazol-2-one hydrochloride

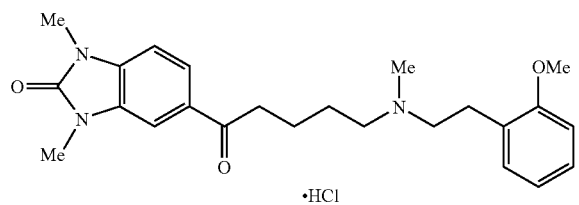

Using 5-(5-chloropentanoyl)-1,3-dimethyl-1,3-dihydro-2H-benzimidazol-2-one obtained in Reference Example 10 and N-[2-(2-methoxyphenyl)ethyl]-N-methylamine according to the same method as that of Example 9, the title compound was obtained as colorless crystals having a melting point of 125 to 140° C. (in a sealed tube; dec).

$^1$H NMR(free base; 200 MHz, CDCl$_3$) δ 1.65-1.84(4H, m), 2.39(3H, s), 2.51-2.69(4H, m), 2.77-2.87(2H, m), 2.99-3.06 (2H, m), 3.46(3H, s), 3.47(3H, s), 3.82(3H, s), 6.82-6.91(2H, m), 6.99(1H, d, J=8.0 Hz), 7.14-7.23(2H, m), 7.63(1H, d, J=1.6 Hz), 7.69(1H, dd, J=8.4, 1.4 Hz).

MS m/z: 410 [M+H]$^+$

Example 137

N-[5-(5-{[2-(2-chlorophenyl)ethyl]amino}pentanoyl)-2,3-dihydro-1H-inden-2-yl]methanesulfonamide hydrochloride

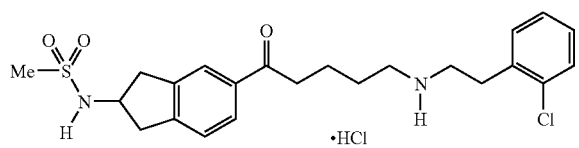

Using N-[5-(5-chloropentanoyl)-2,3-dihydro-1H-inden-2-yl]methanesulfonamide obtained in Reference Example 233 and 2-(2-chlorophenyl)ethylamine according to the same methods as those of Reference Example 19 and Example 1, the title compound was obtained as colorless crystals having a melting point of 156 to 158° C.

$^1$H NMR (free base; 200 MHz, CDCl$_3$) δ 1.52-1.81 (4H, m), 2.47 (2H, t, J=7.4 Hz), 2.60 (2H, m), 2.64-2.98 (6H, m), 3.01 (3H, s), 3.35 (2H, dd, J=16.4, 7.2 Hz), 4.30 (1H, m), 5.08, (2H, br), 7.07-7.34 (5H, m), 7.78, (2H, m).

Example 138

5-[5-[(2-Phenylethyl)amino]pentanoyl]-1,3-dihydro-2H-benzimidazol-2-one hydrochloride

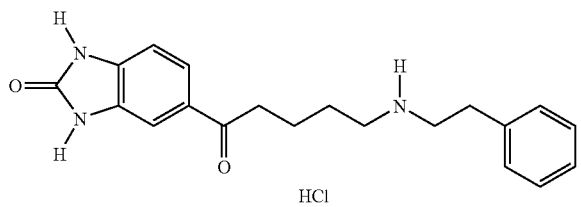

Using 5-(5-chloropentanoyl)-1,3-dihydro-2H-benzimidazol-2-one obtained in Reference 9 and 2-phenylethylamine according to the same methods as those of Reference Example 19 and Example 1, the title compound was obtained as colorless crystals having a melting point of 259° C. (in a sealed tube).

$^1$H NMR(300 MHz, DMSO-d$_6$) δ 1.68(4H, m), 2.93-3.13 (8H, m), 7.03(1H, d, J=7.8 Hz), 7.26-7.37(5H, m), 7.50(1H, s), 7.70(1H, d, J=8.1 Hz), 8.88(2H, br.s), 10.95(1H, s), 11.10 (1H, s).

elementary analysis as C$_{21}$H$_{25}$N$_3$O$_3$.HCl calculation value: C, 62.45; H, 6.49; N, 10.40.

experimental value: C, 62.20; H, 6.42; N, 10.38.

MS m/z: 368 [M+H]$^+$

Example 139

5-(5-[[2-(2-Methoxyphenyl)ethyl]amino]pentanoyl)-1,3-dihydro-2H-benzimidazol-2-one hydrochloride

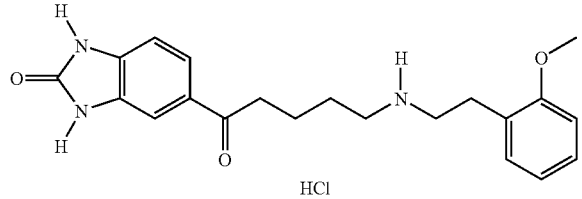

Using 5-(5-chloropentanoyl)-1,3-dihydro-2H-benzimidazol-2-one obtained in Reference 9 and 2-(2-methoxyphenyl)ethylamine according to the same methods as those of Reference Example 19 and Example 1, the title compound was obtained as colorless crystals having a melting point of 213° C. (in a sealed tube).

$^1$H NMR(300 MHz, DMSO-d$_6$) δ 1.67(4H, m), 2.94-3.04 (8H, m), 3.80(3H, s), 6.89-6.94(1H, m), 6.99-7.04(2H, m), 7.17-7.29(2H, m), 7.50(1H, s), 7.69(1H, dd, J=8.1, 1.5 Hz), 8.86(2H, br.s), 10.95(1H, s), 11.10(1H, s).

elementary analysis as C$_{20}$H$_{22}$N$_3$O$_2$Cl.HCl calculation value: C, 58.83; H, 5.68; N, 10.29.

experimental value: C, 58.51; H, 5.53; N, 10.26.

MS m/z: 372 [M+H]$^+$

Example 140

5-(5-[[2-(2-Chlorophenyl)ethyl]amino]pentanoyl)-1,3-dihydro-2H-benzimidazol-2-one hydrochloride

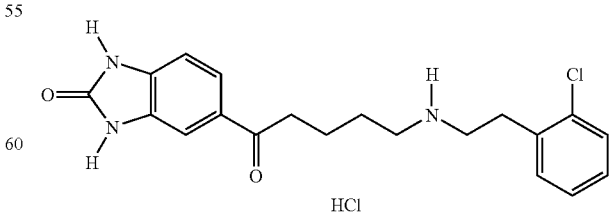

Using 5-(5-chloropentanoyl)-1,3-dihydro-2H-benzoimidazol-2-one obtained in Reference Example 9 and 2-(2-chlorophenyl)ethylamine according to the same methods as those of Reference Example 19 and Example 1, the title compound was obtained as colorless crystals having a melting point of 233° C.

$^1$H NMR(300 MHz, DMSO-d$_6$) δ 1.68(4H, m), 2.99-3.11 (8H, m), 7.03(1H, d, J=8.1 Hz), 7.31-7.48(5H, m), 7.69(1H, dd, J=8.3, 1.6 Hz), 8.99(2H, br.s), 10.95(1H, s), 11.14(1H, s).

elementary analysis as C$_{20}$H$_{22}$N$_3$O$_2$Cl.HCl
calculation value: C, 58.83; H, 5.68; N, 10.29.
experimental value: C, 58.51; H, 5.53; N, 10.26.
MS m/z: 372 [M+H]$^+$

Example 141

1,3-Dimethyl-5-[5-[(2-phenylethyl)amino]pentanoyl]-1,3-dihydro-2H-benzimidazol-2-one hydrochloride

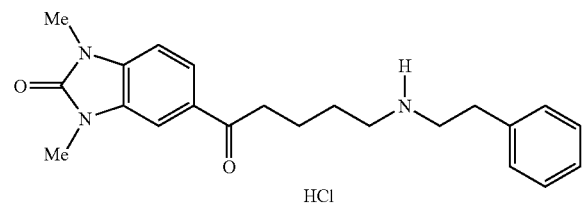

Using tert-butyl 5-(1,3-dimethyl-2-oxo-2,3-dihydro-1H-benzimidazol-5-yl)-5-oxopentyl(2-phenylethyl)carbamate obtained in Reference Example 58 according to the same method as that of Example 1, the title compound was obtained as colorless crystals having a melting point of 187 to 189° C. (in a sealed tube)

$^1$H NMR(300 MHz, DMSO-d$_6$) δ 1.71(4H, m), 2.95-3.00 (4H, m), 3.11(4H, m), 3.36(3H, s), 3.38(3H, s), 7.26-7.38(6H, m), 7.74(1H, d, J=1.2 Hz), 7.82(1H, dd, J=8.1, 1.5 Hz), 9.03 (2H, br.s).

elementary analysis as C$_{22}$H$_{27}$N$_3$O$_2$.HCl
calculation value: C, 65.74; H, 7.02; N, 10.45.
experimental value: C, 65.38; H, 7.07; N, 10.55.
MS m/z: 366 [M+H]$^+$

Example 142

5-(5-[[2-(2-Methoxyphenyl)ethyl]amino]pentanoyl)-1,3-dimethyl-1,3-dihydro-2H-benzimidazol-2-one hydrochloride

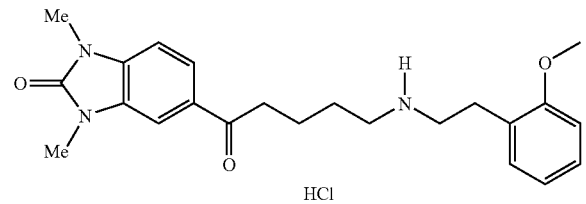

Using tert-butyl 5-(1,3-dimethyl-2-oxo-2,3-dihydro-1H-benzimidazol-5-yl)-5-oxopentyl[2-(2-methoxyphenyl)ethyl]carbamate obtained in Reference Example 59 according to the same method as that of Example 1, the title compound was obtained as colorless crystals having a melting point of 178° C. (in a sealed tube)

$^1$H NMR(300 MHz, DMSO-d$_6$) δ 1.70(4H, m), 2.91-3.13 (8H, m), 3.36(3H, s), 3.38(3H, s), 3.80(3H, s), 6.89-6.94(1H, m), 6.99-7.02(1H, s), 7.17-7.20(1H, m), 7.23-7.29(2H, m), 7.74(1H, d, J=1.2 Hz), 7.82(1H, dd, J=8.1, 1.5 Hz), 8.92(2H, br.s).

elementary analysis as C$_{23}$H$_{29}$N$_3$O$_3$.HCl
calculation value: C, 63.95; H, 7.00; N, 9.73.
experimental value: C, 63.72; H, 6.95; N, 9.75.
MS m/z: 396 [M+H]$^+$

Example 143

5-(5-[[2-(2-Chlorophenyl)ethyl]amino]pentanoyl)-1,3-dimethyl-1,3-dihydro-2H-benzimidazol-2-one hydrochloride

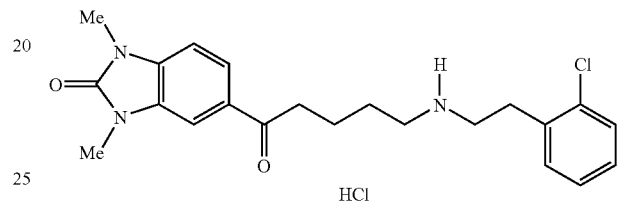

Using tert-butyl 2-(2-chlorophenyl)ethyl[5-(1,3-dimethyl-2-oxo-2,3-dihydro-1H-benzimidazol-5-yl)-5-oxopentyl]carbamate obtained in Reference Example 60 according to the same method as that of Example 1, the title compound was obtained as colorless crystals having a melting point of 168 to 169° C.

$^1$H NMR(300 MHz, DMSO-d$_6$) δ 1.71(4H, m), 3.01-3.11 (8H, m), 3.36(3H, s), 3.38(3H,s), 7.26-7.49(5H, m), 7.74(1H, d, J=1.2 Hz), 7.82(1H, dd, J=8.1, 1.5 Hz), 9.03 (2H, br.s).

elementary analysis as C$_{22}$H$_{26}$N$_3$O$_2$Cl.HCl
calculation value: C, 60.55; H, 6.24; N, 9.62.
experimental value: C, 60.33; H, 6.25; N, 9.62.
MS m/z: 400 [M+H]$^+$

Example 144

1-(1-Benzyl-2,3-dihydro-1H-indol-5-yl)-5-[[2-(2-methoxyphenyl)ethyl]amino]-1-pentanone dihydrochloride

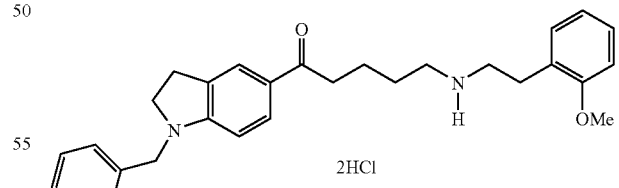

Using tert-butyl 5-(1-benzyl-2,3-dihydro-1H-indol-5-yl)-5-oxopentyl[2-(2-methoxyphenyl)ethyl]carbamate (280 mg) obtained in Reference Example 61 according to the same method as that of Example 1, the title compound (212 mg) was obtained as colorless crystals having a melting point of 88 to 89° C.

$^1$H NMR(400 MHz, DMSO-d$_6$) δ 1.61-1.65(4H, m), 2.85-3.00(10H, m), 3.47(2H, t, J=8.5 Hz), 3.78(3H, s), 4.43(2H, s), 6.57(1H, d, J=8.3 Hz), 6.89(1H, t, J=8.3 Hz), 6.98(1H, d, J=8.0 Hz), 7.17(1H, d, J=7.5 Hz), 7.22-7.35(6H, m), 7.58(1H, br), 7.61(1H, s), 7.70(1H, d, J=8.3 Hz), 9.09(2H, s).

IR (KBr) vcm$^{-1}$: 3336, 2950, 2786, 1687, 1602, 1496, 1454, 1246, 753.

Example 145

1-(1-Benzoyl-2,3-dihydro-1H-indol-5-yl)-5-[[2-(2-methoxyphenyl)ethyl]amino]-1-pentanone hydrochloride

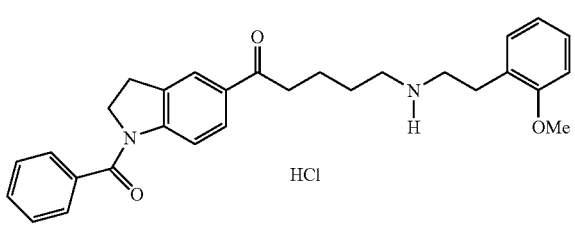

Using tert-butyl 5-(1-benzoyl-2,3-dihydro-1H-indol-5-yl)-5-oxopentyl[2-(2-methoxyphenyl)ethyl]carbamate obtained in Reference Example 62 according to the same method as that of Example 1, the title compound was obtained as colorless crystals having a melting point of 151 to 152° C.

$^1$H NMR(400 MHz, DMSO-d$_6$) δ 1.61-1.71(4H, m), 2.98-3.03(8H, m), 3.18(2H, t, J=8.0 Hz), 3.79(3H, s) 4.05(2H, t, J=8.3 Hz), 6.89(1H, t, J=7.5 Hz), 6.98(1H, d, J=7.5 Hz), 7.17(1H, d, J=7.5 Hz), 7.24(1H, t, J=7.5 Hz), 7.47-7.60(6H, m), 7.85(1H, d, J=6.6 Hz), 7.87(1H, s), 9.19(2H, s).

IR (KBr) vcm$^{-1}$: 3336, 2948, 2781, 1680, 1644, 1602, 1495, 1440, 1386, 1334, 1254, 762.

Example 146

5-(5-[[2-(2-Methoxypheny)ethyl]amino]pentanoyl)-N-phenyl-1-indolinecarboxamide hydrochloride

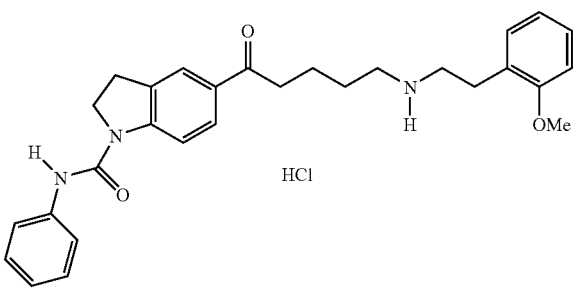

Using tert-butyl 5-[1-(anilinocarbonyl)-2,3-dihydro-1H-indol-5-yl]-5-oxopentyl[2-(2-methoxyphenyl)ethyl]carbamate obtained in Reference Example 63 according to the same method as that of Example 1, the title compound was obtained as colorless crystals having a melting point of 205 to 206° C. (dec).

$^1$H NMR(400 MHz, DMSO-d$_6$) δ 1.63-1.68(4H, m), 2.93-3.03(8H, m), 3.21(2H, t, J=8.5 Hz), 3.79(3H, s), 4.23(2H, t, J=8.3 Hz), 6.89(1H, t, J=7.5 Hz), 6.98(1H, d, J=8.3 Hz), 7.02(1H, t, J=7.5 Hz), 7.17(1H, d, J=7.5 Hz), 7.24(1H, t, J=7.5 Hz), 7.29(2H, t, J=6.6 Hz), 7.59(2H, d, J=8.5 Hz), 7.79(1H, s), 7.82(1H, d, J=8.5 Hz), 7.93(1H, d, J=8.5 Hz), 8.78(1H, s), 9.10(2H,s).

IR (KBr) vcm$^{-1}$: 3400, 2936, 2771, 1680, 1597, 1539, 1491, 1445, 1340, 1246, 752.

Example 147

8-(5-[2-(4-Methoxyphenyl)ethyl]amino}pentanoyl)-1,2,5,6-tetrahydro-4H-pyrrolo[3,2,1-ij]quinolin-4-one hydrochloride

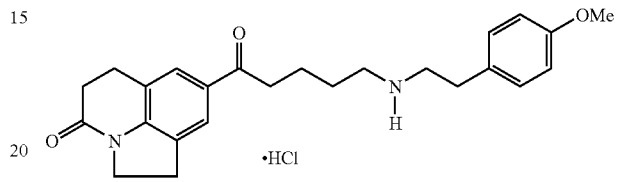

Using tert-butyl 2-(4-methoxyphenyl)ethyl[5-oxo-5-(4-oxo-1,2,5,6-tetrahydro-4H-pyrrolo[3,2,1-ij]quinolin-8-yl)pentyl]carbamate (1.23 g) obtained in Reference Example 79 according to the same method as that of Example 1, the title compound was obtained as colorless crystals (914 mg) having a melting point of 179 to 181° C.

$^1$H NMR (200 MHz, DMSO-d$_6$) δ 1.55-1.80 (4H, m), 2.59 (2H, t, J=7.8 Hz), 2.85-3.15 (10H, m), 3.17 (2H, t, J=8.4 Hz), 3.73 (3H, s), 3.99 (2H, t, J=8.4 Hz), 6.89 (2H, d, J=8.4 Hz), 7.18 (2H, d, J=8.4 Hz), 7.73 (2H, s), 9.00-9.20 (2H, br).

elementary analysis as $C_{25}H_{30}N_2O_3 \cdot HCl \cdot 0.5H_2O$
calculation value: C, 66.43; H, 7.14; N, 6.20.
experimental value: C, 66.41; H, 7.04; N, 6.06.

Example 148

8-(5-{[2-(4-Chlorophenyl)ethyl]amino}pentanoyl)-1,2,5,6-tetrahydro-4H-pyrrolo[3,2,1-ij]quinolin-4-one hydrochloride

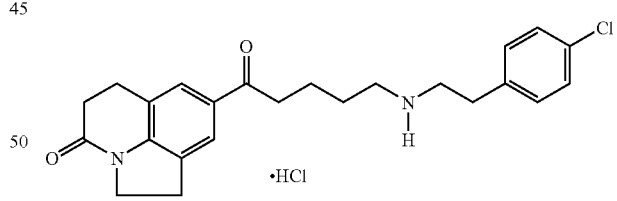

Using tert-butyl 2-(4-chlorophenyl)ethyl[5-oxo-5-(4-oxo-1,2,5,6-tetrahydro-4H-pyrrolo[3,2,1-ij]quinolin-8-yl)pentyl]carbamate (941 mg) obtained in Reference Example 80 according to the same method as that of Example 1, the title compound was obtained as colorless crystals (708 mg) having a melting point of 193 to 195° C.

$^1$H NMR (200 MHz, DMSO-d$_6$) δ 1.55-1.80 (4H, m), 2.59 (2H, t, J=7.8 Hz), 2.75-3.25 (10H, m), 3.18 (2H, t, J=8.4 Hz), 3.99 (2H, t, J=8.4 Hz), 7.31 (2H, d, J=8.4 Hz), 7.40 (2H, d, J=8.4 Hz), 7.73 (2H, s), 9.05-9.30 (2H, br).

elementary analysis as $C_{24}H_{27}ClN_2O_2 \cdot HCl$
calculation value: C, 64.43; H, 6.31; N, 6.26.
experimental value: C, 64.07; H, 6.40; N, 6.07.

Example 149

8-(5-{[2-(3-Chlorophenyl)ethyl]amino}pentanoyl)-1,2,5,6-tetrahydro-4H-pyrrolo[3,2,1-ij]quinolin-4-one hydrochloride

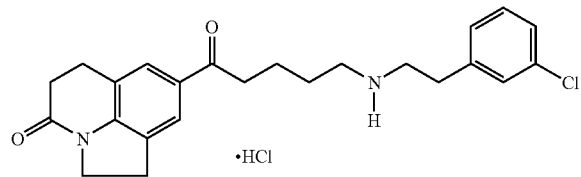

Using tert-butyl 2-(3-chlorophenyl)ethyl[5-oxo-5-(4-oxo-1,2,5,6-tetrahydro-4H-pyrrolo[3,2,1-ij]quinolin-8-yl)pentyl]carbamate (1.19 g) obtained in Reference Example 81 according to the same method as that of Example 1, the title compound was obtained as colorless crystals (972 mg) having a melting point of 157 to 159° C.

$^1$H NMR (200 MHz, DMSO-$d_6$) δ 1.55-1.80 (4H, m), 2.60 (2H, t, J=7.8 Hz), 2.85-3.20 (10H, m), 3.18 (2H, t, J=8.4 Hz), 3.99 (2H, t, J=8.4 Hz), 7.20-7.45 (4H, m), 7.73 (2H, s), 8.80-9.05 (2H, br).

Example 150

8-(5-{[2-(2-Hydroxyphenyl)ethyl]amino}pentanoyl)-1,2,5,6-tetrahydro-4H-pyrrolo[3,2,1-ij]quinolin-4-one hydrochloride

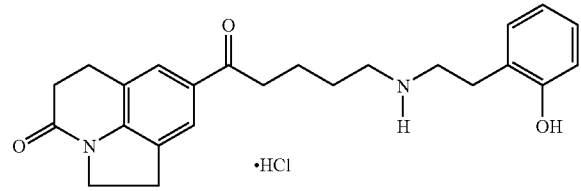

Using tert-butyl 2-(2-hydroxyphenyl)ethyl[5-oxo-5-(4-oxo-1,2,5,6-tetrahydro-4H-pyrrolo[3,2,1-ij]quinolin-8-yl)pentyl]carbamate (637 mg) obtained in Reference Example 82 according to the same method as that of Example 1, the title compound was obtained as colorless crystals (530 mg) having a melting point of 112 to 113° C.

$^1$H NMR (300 MHz, DMSO-$d_6$) δ 1.60-1.80 (4H, m), 2.59 (2H, t, J=7.8 Hz), 2.85-3.10 (10H, m), 3.17 (2H, t, J=8.4 Hz), 3.98 (2H, t, J=8.4 Hz), 4.50-5.50 (1H, br), 6.73 (1H, dt, J=7.5, 1.2 Hz), 6.88 (1H, dd, J=7.8, 1.2 Hz), 7.00-7.10 (2H, m), 7.72 (1H, s), 7.73 (1H, s), 9.00-9.20 (2H, br).

elementary analysis as $C_{24}H_{28}N_2O_3 \cdot HCl \cdot 2.0H_2O$
calculation value: C, 61.99; H, 7.15; N, 6.02.
experimental value: C, 61.97; H, 6.87; N, 5.88.

Example 151

8-(5-{[2-(2,6-Dichlorophenyl)ethyl]amino}pentanoyl)-1,2,5,6-tetrahydro-4H-pyrrolo[3,2,1-ij]quinolin-4-one hydrochloride

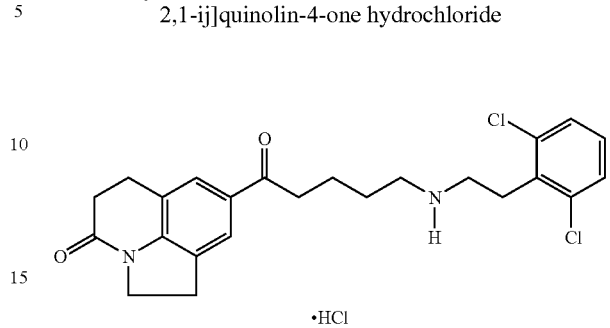

Using tert-butyl 2-(2,6-dichlorophenyl)ethyl[5-oxo-5-(4-oxo-1,2,5,6-tetrahydro-4H-pyrrolo[3,2,1-ij]quinolin-8-yl)pentyl]carbamate (1.08 g) obtained in Reference Example 83 according to the same method as that of Example 1, the title compound was obtained as colorless crystals (618 mg) having a melting point of 171 to 174° C.

$^1$H NMR (300 MHz, DMSO-$d_6$) δ 1.60-1.80 (4H, m), 2.59 (2H, t, J=7.8 Hz), 2.90-3.10 (8H, m), 3.17 (2H, t, J=8.4 Hz), 3.25-3.35 (2H, m), 3.98 (2H, t, J=8.4 Hz), 7.33 (1H, dd, J=8.7, 7.5 Hz), 7.49 (2H, d, J=7.5 Hz), 7.72 (1H, s), 7.73 (1H, s), 9.25-9.50 (2H, br).

elementary analysis as $C_{24}H_{26}Cl_2N_2O_2 \cdot HCl$
calculation value: C, 59.82; H, 5.65; N, 5.81.
experimental value: C, 59.48; H, 5.67; N, 5.53.

Example 152

8-(5-{[2-(2,3-Dimethoxyphenyl)ethyl]amino}pentanoyl)-1,2,5,6-tetrahydro-4H-pyrrolo[3,2,1-ij]quinolin-4-one hydrochloride

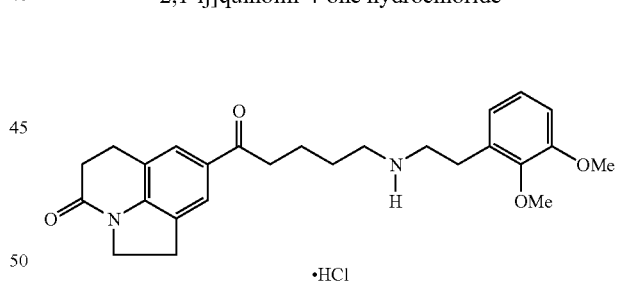

Using tert-butyl 2-(2,3-dimethoxyphenyl)ethyl[5-oxo-5-(4-oxo-1,2,5,6-tetrahydro-4H-pyrrolo[3,2,1-ij]quinolin-8-yl)pentyl]carbamate (1.13 g) obtained in Reference Example 84 according to the same method as that of Example 1, the title compound was obtained as colorless crystals (708 mg) having a melting point of 154 to 156° C.

$^1$H NMR (300 MHz, DMSO-$d_6$) δ 1.60-1.80 (4H, m), 2.58, (2H, t, J=7.8 Hz), 2.90-3.10 (10H, m), 3.16 (2H, t, J=8.4 Hz), 3.73 (3H, s), 3.78 (3H, s), 3.97 (2H, t, J=8.4 Hz), 6.79 (1H, dd, J=8.2, 1.8 Hz), 6.94 (1H, dd, J=8.0, 1.8 Hz), 6.95-7.05 (1H, m), 7.71 (1H, s), 7.72 (1H, s), 8.80-9.10 (2H, br).

elementary analysis as $C_{26}H_{32}N_2O_4 \cdot HCl \cdot 0.5H_2O$
calculation value: C, 64.79; H, 7.11; N, 5.81.
experimental value: C, 64.34; H, 7.03; N, 5.55.

Example 153

8-(5-[2-(2-Thienyl)ethyl]amino}pentanoyl)-1,2,5,6-tetrahydro-4H-pyrrolo[3,2,1-ij]quinolin-4-one hydrochloride

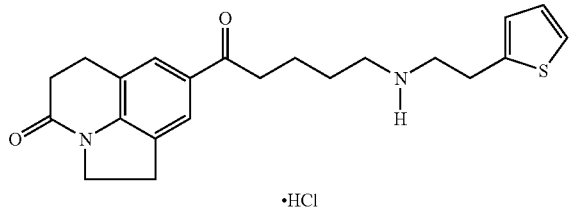

Using tert-butyl 5-oxo-5-(4-oxo-1,2,5,6-tetrahydro-4H-pyrrolo[3,2,1-ij]quinolin-8-yl)pentyl[2-(2-thienyl)ethyl]carbamate (1.44 g) obtained in Reference Example 85 according to the same method as that of Example 1, the title compound was obtained as colorless crystals (700 mg) having a melting point of 167 to 169° C.

$^1$H NMR (300 MHz, DMSO-$d_6$) δ 1.60-1.80 (4H, m), 2.59 (2H, t, J=7.8 Hz), 2.90-3.05 (6H, m), 3.10-3.30 (6H, m), 3.98 (2H, t, J=8.4 Hz), 6.95-7.00 (2H, m), 7.40(1H, dd, J=4.8, 1.5 Hz), 7.72 (1H, s), 7.73 (1H, s), 9.10-9.30 (2H, br).

Example 154

1-(2,3-Dihydro-1,4-benzodioxin-6-yl)-5-{[2-(2-methoxyphenyl)ethyl]amino}-1-pentanone hydrochloride

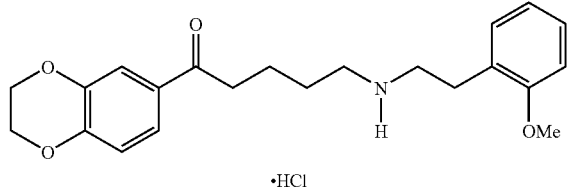

Using tert-butyl 5-(2,3-dihydro-1,4-benzodioxin-6-yl)-5-oxopentyl[2-(2-methoxypenyl)ethyl]carbamate (1.18 g) obtained in Reference Example 86 according to the same method as that of Example 1, the title compound was obtained as colorless crystals (752 mg) having a melting point of 172 to 174° C.

$^1$H NMR (300 MHz, DMSO-$d_6$) δ 1.45-1.80 (4H, m), 2.90-3.15 (6H, m), 3.30-3.45 (6H, m), 3.80 (3H, s), 6.90 (1H, t, J=7.4 Hz), 6.99 (1H, d, J=8.4 Hz), 7.18 (1H, dd, J=7.4, 1.8 Hz), 7.20-7.30 (2H, m), 7.73 (1H, d, J=1.5 Hz), 7.80 (1H, dd, J=8.1, 1.5 Hz), 8.95-9.15 (2H, br).

Example 155

2-Methoxy-5-{5-[(2-phenylethyl)amino]pentanoyl}benzenesulfonamide hydrochloride

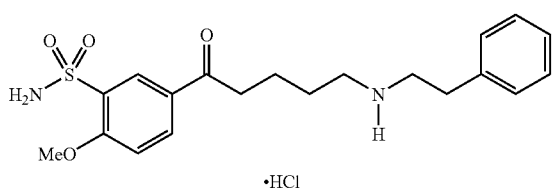

Using tert-butyl 5-[3-(aminosulfonyl)-4-methoxyphenyl]-5-oxopentyl(2-phenylethyl)carbamate (1.00 g) obtained in Reference Example 87 according to the same method as that of Example 1, the title compound was obtained as colorless crystals (833 mg) having a melting point of 160 to 168° C.

$^1$H NMR (300 MHz, DMSO-$d_6$) δ 1.60-1.80, (4H, m), 2.85-3.20 (8H, m), 3.98 (3H, s), 7.20-7.40 (8H, m), 8.20 (1H, dd, J=8.8, 2.1 Hz), 8.28 (1H, d, J=2.1 Hz), 8.80-9.10 (2H, br).

elementary analysis as $C_{20}H_{26}N_2O_4S \cdot HCl \cdot 0.5H_2O$
calculation value: C, 55.10; H, 6.47; N, 6.43.
experimental value: C, 55.08; H, 6.37; N, 6.28.

Example 156

2-Methoxy-5-(5-{[2-(2-methoxyphenyl)ethyl]amino}pentanoyl)benzenesulfonamide hydrochloride

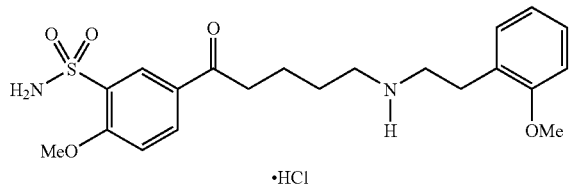

Using tert-butyl 5-[3-(aminosulfonyl)-4-methoxyphenyl]-5-oxopentyl[2-(2-methoxyphenyl)ethyl]carbamate (740 mg) obtained in Reference Example 88 according to the same method as that of Example 1, the title compound was obtained as colorless crystals (504 mg) having a melting point of 139 to 141° C.

$^1$H NMR (300 MHz, DMSO-$d_6$) δ 1.60-1.80 (4H, m), 2.85-3.10 (8H, m), 3.78 (3H, s), 3.98 (3H, s), 6.89 (1H, dt, J=7.3, 1.5 Hz), 6.98 (1H, d, J=8.1 Hz), 7.16 (1H, dd, J=7.3, 1.5 Hz), 7.20-7.25 (3H, m), 7.31 (1H, d, J=8.7 Hz), 8.20 (1H, dd, J=8.7, 2.4 Hz), 8.28 (1H, d, J=2.4 Hz), 8.80-9.05 (2H, br).

elementary analysis as $C_{21}H_{28}N_2O_5S \cdot HCl \cdot 0.5H_2O$
calculation value: C, 54.13; H, 6.49; N, 6.01.
experimental value: C, 54.71; H, 6.50; N, 5.86.

Example 157

5-(5-{[2-(2-Chlorophenyl)ethyl]amino}pentanoyl)-2-methoxybenzenesulfonamide hydrochloride

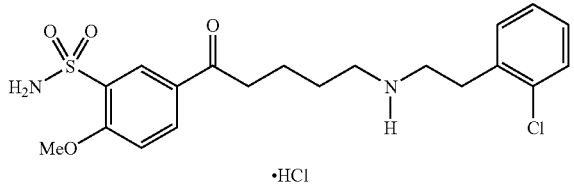

Using tert-butyl 5-[3-(aminosulfonyl)-4-methoxyphenyl]-5-oxopentyl[2-(2-chlorophenyl)ethyl]carbamate (1.00 g) obtained in Reference Example 89 according to the same method as that of Example 1, the title compound was obtained as colorless crystals (845 mg) having a melting point of 161 to 163° C.

$^1$H NMR (300 MHz, DMSO-$d_6$) δ 1.60-1.80 (4H, m), 2.90-3.20 (8H, m), 3.99 (3H, s), 7.20-7.50 (7H, m), 8.21 (1H, dd, J=8.6, 2.1 Hz), 8.30 (1H, d, J=2.1 Hz), 9.00-9.20 (2H, br).

Example 158

5-{5-[[2-(2-Chlorophenyl)ethyl](methyl)amino]pentanoyl}-2-methoxybenzenesulfonamide hydrochloride

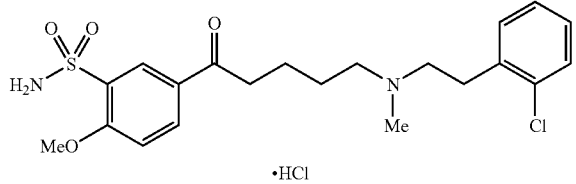

·HCl

Using 5-(5-chloropentanoyl)-2-methoxybenzenesulfonamide (800 mg) obtained in Reference Example 66 and N-[2-(2-chlorophenyl)ethyl]-N-methylamine (533 mg) according to the same method as that of Example 9, the title compound (126 mg) was obtained as pale yellow amorphous powders.

$^1$H NMR (free base; 200 MHz, CDCl$_3$) δ 1.45-1.80 (4H, m), 2.33 (3H, s), 2.40-2.65 (4H, m), 2.80-3.00 (4H, m), 4.10 (3H, s), 4.50-5.50 (2H, br), 7.00-7.40(5H, m), 8.10-8.20(1H, m), 8.20-8.30(1H, m).

Example 159

N-isopropyl-2-methoxy-5-(5-{[2-(2-methoxyphenyl)ethyl]amino}pentanoyl)benzenesulfonamide hydrochloride

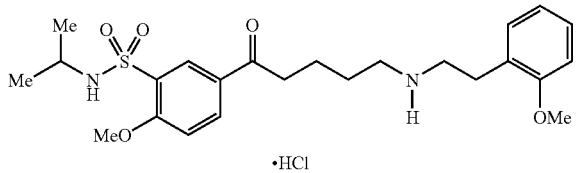

·HCl

Using tert-butyl 5-{3-[(isopropylamino)sulfonyl]-4-methoxyphenyl}-5-oxopentyl[2-(2-methoxyphenyl)ethyl]carbamate (1.36 g) obtained in Reference Example 90 according to the same method as that of Example 1, the title compound was obtained as colorless crystals (601 mg) having a melting point of 164 to 166° C.

$^1$H NMR (200 MHz, DMSO-d$_6$) δ 0.96 (6H, d, J=6.6 Hz), 1.60-1.80 (4H, m), 2.85-3.40 (9H, m), 3.80 (3H, s), 4.01 (3H, s), 6.85-7.05 (2H, m), 7.15-7.45 (4H, m), 8.25 (1H, dd, J=8.4, 2.2 Hz), 8.31 (1H, d, J=2.2 Hz), 8.90-9.10 (2H, br).

elementary analysis as C$_{24}$H$_{34}$N$_2$O$_5$S.HCl
calculation value: C, 57.76; H, 7.07; N, 5.61.
experimental value: C, 57.41; H, 7.21; N, 5.51.

elementary analysis as C$_{20}$H$_{25}$ClN$_2$O$_4$S.HCl
calculation value: C, 52.06; H, 5.68; N, 6.07.
experimental value: C, 52.04; H, 5.72; N, 5.93.

Example 160

5-(5-{[2-(2-Chlorophenyl)ethyl]amino}pentanoyl)-N-isopropyl-2-methoxybenzenesulfonamide hydrochloride

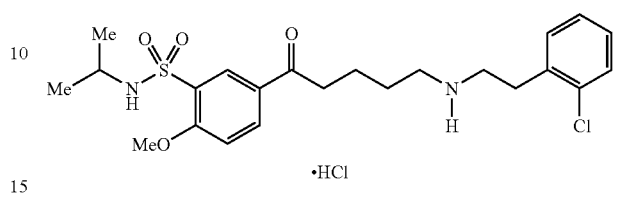

·HCl

Using tert-butyl 2-(2-chlorophenyl)ethyl(5-{3-[(isopropylamino)sulfonyl]-4-methoxyphenyl}-5-oxopentyl)carbamate (1.28 g) obtained in Reference Example 91 according to the same method as that of Example 1, the title compound was obtained as colorless crystals (1.00 g) having a melting point of 179 to 181° C.

$^1$H NMR (200 MHz, DMSO-d$_6$) δ 0.96. (6H, d, J=6.6 Hz), 1.60-1.80 (4H, m), 2.90-3.50 (9H, m), 4.01 (3H, s), 7.25-7.50 (6H, m), 8.25 (1H, dd, J=8.4, 2.2 Hz), 8.32 (1H, d, J=2.2 Hz), 9.00-9.25 (2H, br).

elementary analysis as C$_{23}$H$_{31}$ClN$_2$O$_4$S.HCl
calculation value: C, 54.87; H, 6.41; N, 5.56.
experimental value: C, 54.67; H, 6.33; N, 5.33.

Example 161

5-{5-[[2-(2-Chlorophenyl)ethyl](methyl)amino]pentanoyl}-N-isopropyl-2-methoxybenzenesulfonamide hydrochloride

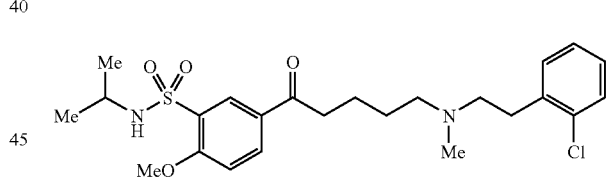

·HCl

Using 5-(5-chloropentanoyl)-N-isopropyl-2-methoxybenzenesulfonamide (800 mg) obtained in Reference Example 67 and N-[2-(2-chlorophenyl)ethyl]-N-methylamine (470 mg) according to the same method as that of Example 9, the title compound (536 mg) was obtained as pale yellow amorphous powders.

$^1$H NMR (free base; 200 MHz, CDCl$_3$) δ 1.06 (6H, d, J=6.6 Hz), 1.50-1.80 (4H, m), 2.34 (3H, s), 2.48 (2H, t, J=7.2 Hz), 2.55-2.70 (2H, m), 2.85-2.90 (2H, m), 2.98 (2H, t, J=7.2 Hz), 3.30-3.55 (1H, m), 4.07 (3H, s), 4.85-4.95 (1H, m), 7.05-7.35 (5H, m), 8.19 (1H, dd, J=8.8, 2.2 Hz), 8.50 (1H, d, J=2.2 Hz).

elementary analysis as C$_{24}$H$_{33}$ClN$_2$O$_4$S.HCl0.5H$_2$O
calculation value: C, 54.75; H, 6.70; N, 5.32.
experimental value: C, 54.45; H, 6.94; N, 5.11.

Example 162

5-(5-{[2-(2-Methoxyphenyl)ethyl]amino}pentanoyl)-2,3-dihydro-1-benzofuran-7-sulfonamide hydrochloride

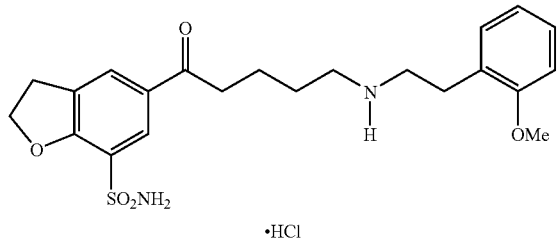

·HCl

Using tert-butyl 5-[7-(aminosulfonyl)-2,3-dihydro-1-benzofuran-5-yl]-5-oxopentyl[2-(2-methoxyphenyl)ethyl]carbamate (990 mg) obtained in Reference Example 92 according to the same method as that of Example 1, the title compound (781 mg) was obtained as pale yellow amorphous powders.

$^1$H NMR (200 MHz, DMSO-$d_6$) δ 1.50-1.90 (4H, m), 2.95-3.25 (8H, m), 3.41 (2H, t, J=8.6 Hz), 3.89 (3H, s), 4.91 (2H, t, J=8.6 Hz), 6.90-7.10 (2H, m), 7.20-7.40 (2H, m), 7.50 (2H, s), 8.71 (1H, 3), 8.20 (1H, s), 8.95-9.25 (2H, br).

elementary analysis as $C_{22}H_{28}N_2O_5S\cdot HCl\cdot 0.5H_2O$
calculation value: C, 55.28; H, 6.33; N, 5.86.
experimental value: C, 55.48; H, 6.50; N, 5.61.

Example 163

5-(5-{[2-(2-Chlorophenyl)ethyl]amino}pentanoyl)-2,3-dihydro-1-benzofuran-7-sulfonamide hydrochloride

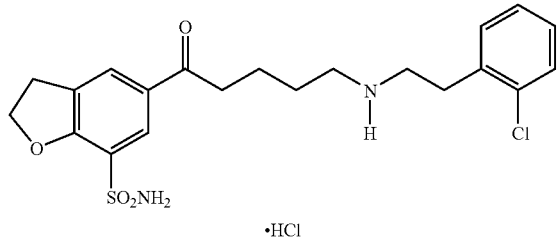

·HCl

Using tert-butyl 5-[7-(aminosulfonyl)-2,3-dihydro-1-benzofuran-5-yl]-5-oxopentyl[2-(2-chlorophenyl)ethyl]carbamate (900 mg) obtained in Reference Example 93 ccording to the same method as that of Example 1, the title compound was obtained as colorless crystals (743 mg) having a melting point of 160 to 170° C.

$^1$H NMR (200 MHz, DMSO-$d_6$) δ 1.60-1.80 (4H, m), 2.85-3.20 (8H, m), 3.32 (2H, t, J=8.6 Hz), 4.82 (2H, t, J=8.6 Hz), 7.25-7.55 (6H, m), 8.11 (1H, s), 8.12 (1H, s), 9.10-9.40 (2H, br).

elementary analysis as $C_{21}H_{25}ClN_2O_4S\cdot HCl\cdot 0.2H_2O$
calculation value: C, 52.88; H, 5.58; N, 5.87.
experimental value: C, 52.93; H, 5.42; N, 5.66.

Example 164

5-{5-[[2-(2-Methoxyphenyl)ethyl](methyl)amino]pentanoyl}-2,3-dihydro-1-benzofuran-7-sulfonamide hydrochloride

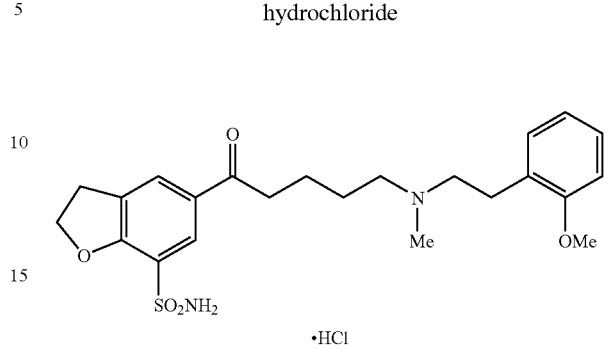

·HCl

Using 5-(5-chloropentanoyl)-2,3-dihydro-1-benzofuran-7-sulfonamide (1.00 g) obtained in Reference Example 70 and N-[2-(2-methoxyphenyl)ethyl]-N-methylamine (625 mg) according to the same method as that of Example 9, the title compound (527 mg) was obtained as pale yellow amorphous powders.

$^1$H NMR (free base; 300 MHz, CDCl$_3$) δ 1.50-1.80 (4H, m), 2.36 (3H, s), 2.52 (2H, t, J=7.2 Hz), 2.60-2.65 (2H, m), 2.75-2.80 (2H, m), 2.91 (2H, t, J=7.2 Hz), 3.00-5.00 (2H, br), 3.04 (2H, t, J=8.7 Hz), 3.81 (3H, s), 4.87 (2H, t, J=8.7 Hz), 6.80-6.90 (2H, m), 7.10-7.20 (2H, m), 7.98 (1H, s), 8.19 (1H, s).

elementary analysis as $C_{23}H_{30}N_2O_5S\cdot HCl0.5H_2O$
calculation value: C, 56.14; H, 6.56; N, 5.69.
experimental value: C, 55.83; H, 6.81; N, 5.45.

Example 165

5-{5-[[2-(2-Chlorophenyl)ethyl](methyl)amino]pentanoyl}-2,3-dihydro-1-benzofuran-7-sulfonamide hydrochloride

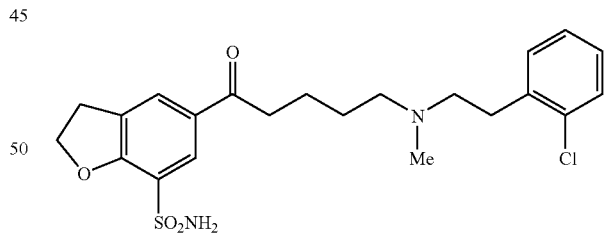

·HCl

Using 5-(5-chloropentanoyl)-2,3-dihydro-1-benzofuran-7-sulfonamide (800 mg) obtained in Reference Example 70 and N-[2-(2-chlorophenyl)ethyl]-N-methylamine (513 mg) according to the same method as that of Example 9, the title compound (519 mg) was obtained as pale yellow amorphous powders.

$^1$H NMR (free base; 300 MHz, CDCl$_3$) δ 1.45-1.80 (4H, m), 2.34 (3H, s), 2.48 (2H, t, J=7.2 Hz), 2.55-2.65 (2H, m), 2.80-2.90 (4H, m), 3.32 (2H, t, J=8.7 Hz), 3.50-5.50 (2H, br), 4.88 (2H, t, J=8.7 Hz), 7.10-7.35 (4H, m), 7.99 (1H, s), 8.18 (1H, s).

Example 166

N-isopropyl-5-(5-{[2-(2-methoxyphenyl)ethyl]amino}pentanoyl)-2,3-dihydro-1-benzofuran-7-sulfonamide hydrochloride

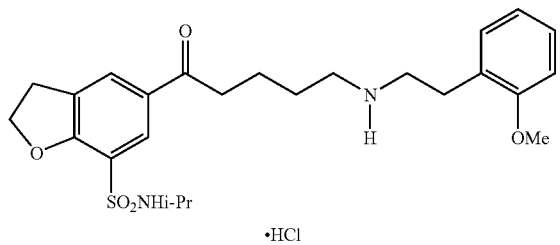

·HCl

Using tert-butyl 5-{7-[(isopropylamino)sulfonyl]-2,3-dihydro-1-benzofuran-5-yl}-5-oxopentyl[2-(2-methoxyphenyl)ethyl]carbamate (1.00 g) obtained in Reference Example 94 according to the same method as that of Example 1, the title compound was obtained as colorless crystals (707 mg) having a melting point of 157 to 159° C.

$^1$H NMR (200 MHz, DMSO-$d_6$) δ 0.99 (6H, d, J=6.6 Hz), 1.60-1.85 (4H, m), 2.80-3.15. (7H, m), 3.20-3.50 (4H, m), 3.80 (3H, s), 4.82 (2H, t, J=8.8 Hz), 6.85-7.05 (2H, m), 7.15-7.30 (2H, m), 7.60 (1H, d, J=7.6 Hz), 8.10 (2H, s), 8.90-9.15 (2H, br).

elementary analysis as $C_{25}H_{34}N_2O_5S·HCl$
calculation value: C, 58.75; H, 6.90; N, 5.48.
experimental value: C, 58.33; H, 6.92; N, 5.31.

Example 167

5-(5-{[2-(2-Chlorophenyl)ethyl]amino}pentanoyl)-N-isopropyl-2,3-dihydro-1-benzofuran-7-sulfonamide hydrochloride

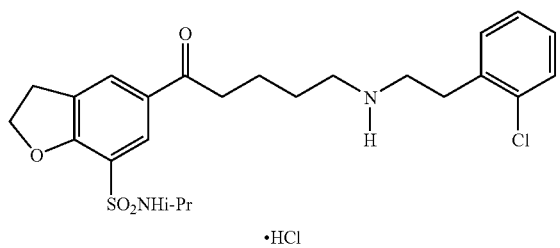

·HCl

Using tert-butyl 2-(2-chlorophenyl)ethyl(5-{7-[(isopropylamino)sulfonyl]-2,3-dihydro-1-benzofuran-5-yl}-5-oxopentyl)carbamate (2.10 g) obtained in Reference Example 95 according to the same method as that of Example 1, the title compound was obtained as colorless crystals (2.16 g) having a melting point of 149 to 151° C.

$^1$H NMR (200 MHz, DMSO-$d_6$) δ 0.99 (6H, d, J=6.6 Hz), 1.60-1.85 (4H, m), 2.90-3.20 (7H, m), 3.25-3.45 (4H, m), 4.82 (2H, t, J=8.8 Hz), 7.30-7.50 (4H, m), 7.60 (1H, d, J=7.6 Hz), 8.10 (2H, s), 8.90-9.30 (2H, br).

elementary analysis as $C_{24}H_{31}ClN_2O_4S·HCl$
calculation value: C, 55.92; H, 6.26; N, 5.43.
experimental value: C, 55.78; H, 5.99; N, 5.26.

Example 168

N-isopropyl-5-{5-[[2-(2-methoxyphenyl)ethyl](methyl)amino]pentanoyl}-2,3-dihydro-1-benzofuran-7-sulfonamide hydrochloride

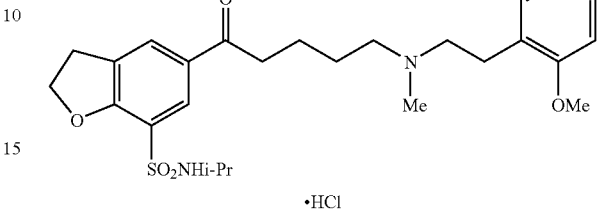

·HCl

Using 5-(5-chloropentanoyl)-N-isopropyl-2,3-dihydro-1-benzofuran-7-sulfonamide (1.00 g) obtained in Reference Example 71 and N-[2-(2-methoxyphenyl)ethyl]-N-methylamine (551 mg) according to the same method as that of Example 9, the title compound (470 mg) was obtained as pale yellow amorphous powders.

$^1$H NMR (free base; 200 MHz, CDCl$_3$) δ 1.10 (6H, d, J=6.6 Hz), 1.45-1.80 (4H, m), 2.32 (3H, s), 2.46 (2H, t, J=7.2 Hz), 2.50-2.60 (2H, m), 2.70-2.85 (2H, m), 2.96 (2H, t, J=7.2 Hz), 3.33 (2H, t, J=8.8 Hz), 3.35-3.55 (1H, m), 3.82 (3H, s), 4.65-4.80 (1H, m), 4.86 (2H, t, J=8.8 Hz), 6.80-6.90 (2H, m), 7.10-7.20 (2H, m), 8.04 (1H, d, J=2.0 Hz), 8.24 (1H, d, J=2.0 Hz).

elementary analysis as $C_{26}H_{36}N_2O_5S·HCl·0.5H_2O$
calculation value: C, 58.47; H, 7.17; N, 5.24.
experimental value: C, 58.53; H, 7.31; N, 5.15.

Example 169

5-{5-[[2-(2-Chlorophenyl)ethyl](methyl)amino]pentanoyl}-N-isopropyl-2,3-dihydro-1-benzofuran-7-sulfonamide hydrochloride

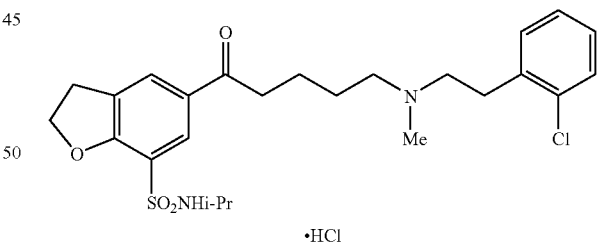

·HCl

Using 5-(5-chloropentanoyl)-N-isopropyl-2,3-dihydro-1-benzofuran-7-sulfonamide (1.00 g) obtained in Reference Example 71 and N-[2-(2-chlorophenyl)ethoxy]-N-methylamine (565 mg) according to the same method as that of Example 9, the title compound (490 mg) was obtained as pale yellow amorphous powders.

$^1$H NMR (free base; 200 MHz, CDCl3) δ 1.10 (6H, d, J=6.6 Hz), 1.45-1.80 (4H, m), 2.31 (3H, s), 2.48 (2H, t, J=7.2 Hz), 2.55-2.70 (2H, m), 2.80-3.00 (4H, m), 3.33 (2H, t, J=8.8 Hz), 3.35-3.60 (1H, m), 4.68 (1H, d, J=7.4 Hz), 4.86 (2H, t, J=8.8 Hz), 7.10-7.40 (4H, m), 8.04 (1H, d, J=2.0 Hz), 8.24. (1H, d, J=2.0 Hz).

elementary analysis as $C_{25}H_{33}ClN_2O_4S \cdot HCl \cdot 0.5H_2O$
calculation value: C, 55.76; H, 6.55; N, 5.20.
experimental value: C, 55.38; H, 6.72; N, 5.07.

Example 170

6-(6-{[2-(2-Chlorophenyl)ethyl]amino}pentanoyl)-2,2-dimethyl-8-chlomansulfonamide hydrochloride

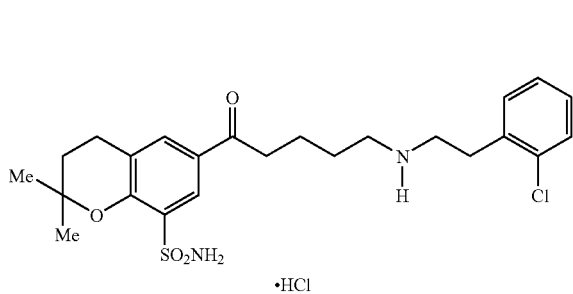

Using, tert-butyl 5-[8-(aminosulfonyl)-2,2-dimethyl-3,4-dihydro-2H-chlomen-6-yl]-5-oxopentyl[2-(2-chlophenyl)ethyl]carbamate (715 mg) obtained in Reference Example 96 according to the same method as that of Example 1, the title compound (568 mg) was obtained as colorless amorphous powders.

$^1$H NMR (300 MHz, DMSO-d$_6$) δ 1.40 (6H, s), 1.60-1.80 (4H, m), 1.87 (2H, t, J=6.6 Hz), 2.88, (2H, t, J=6.6 Hz), 2.90-3.20 (8H, m)), 7.01 (2H, s), 7.25-7.50 (4H, m), 7.39 (1H, d, J=2.1 Hz), 8.14 (1H, d, J=2.1 Hz), 9.10-9.30 (2H, br).
elementary analysis as $C_{24}H_{31}ClN_2O_4S \cdot HCl \cdot 0.5H_2O$
calculation value: C, 54.96; H, 6.34; N, 5.34.
experimental value: C, 55.00; H, 6.36; N, 5.11.

Example 171

7-{5-[(2-Phenylethyl)amino]pentanoyl}-2,3-dihydro-1,4-benzodioxin-5-sulfonamide hydrochloride

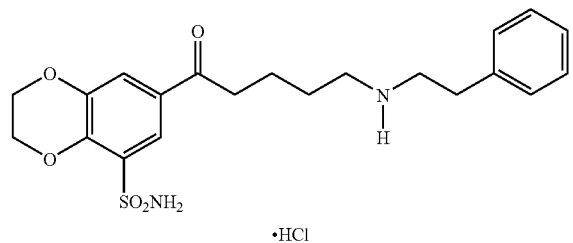

Using tert-butyl 5-[8-(aminosulfonyl)-2,3-dihydro-1,4-benzodioxin-6-yl]-5-oxopentyl(2-phenylethyl)carbamate (1.05 g) obtained in Reference Example 97 according to the same method as that of Example 1, the title compound was obtained as colorless crystals (832 mg) having a melting point of 152 to 154° C.

$^1$H NMR (300 MHz, DMSO-d$_6$) δ 1.55-1.80 (4H, m), 2.85-3.20 (8H, m), 4.30-4.40 (2H, m), 4.40-4.50. (2H, m), 7.20-7.40 (7H, m), 7.69 (1H, d, J=2.1 Hz), 7.89 (1H, d, J=2.1 Hz), 8.95-9.20 (2H, br)
elementary analysis as $C_{21}H_{26}N_2O_5S \cdot HCl$
calculation value: C, 55.32; H, 6.19; N, 6.14.
experimental value: C, 55.15; H, 6.06; N, 6.00.

Example 172

7-(5-{[2-(2-Methoxyphenyl)ethyl]amino}pentanoyl)-2,3-dihydro-1,4-benzodioxin-5-sulfonamide hydrochloride

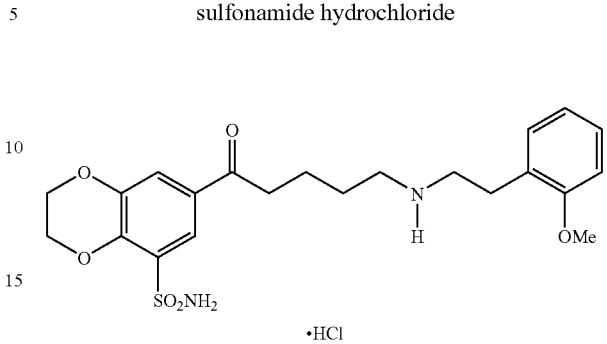

Using tert-butyl 5-[8-(aminosulfonyl)-2,3-dihydro-1,4-benzodioxin-6-yl]-5-oxopentyl[2-(2-methoxyphenyl)ethyl]carbamate (820 mg) obtained in Reference Example 98 according to the same method as that of Example 1, the title compound was obtained as colorless crystals (632 mg) having a melting point of 166 to 168° C.

$^1$H NMR (300 MHz, DMSO-d$_6$) δ 1.55-1.80 (4H, m), 2.85-3.10 (8H, m), 3.80 (3H, s), 4.30-4.40 (2H, m), 4.40-4.50 (2H, m), 6.90 (1H, t, J=7.5 Hz), 6.99 (1H, d, J=8.1 Hz), 7.17 (1H, d. J=7.5 Hz), 7.25 (1H, t, J=7.5 Hz), 7.36 (2H, s), 7.69 (1H, d, J=2.1 Hz), 7.88 (1H, d, J=2.1 Hz), 8.80-9.15 (2H, br).
elementary analysis as $C_{22}H_{28}N_2O_6S \cdot HCl$
calculation value: C, 54.48; H, 6.03; N, 5.78.
experimental value: C, 54.12; H, 6.13; N, 5.64.

Example 173

7-(5-{[2-(2-Chlorophenyl)ethyl]amino}pentanoyl)-2,3-dihydro-1,4-benzodioxin-5-sulfonamide hydrochloride

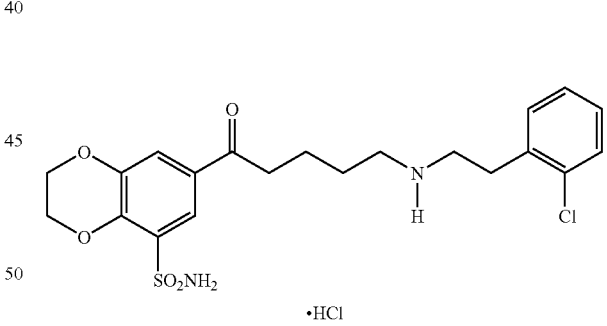

Using tert-butyl 5-[8-(aminosulfonyl)-2,3-dihydro-1,4-benzodioxin-6-yl]-5-oxopentyl[2-(2-chlorophenyl)ethyl]carbamate (1.08 g) obtained in Reference Example 99 according to the same method as that of Example 1, the title compound was obtained as colorless crystals (850 mg) having a melting point of 178 to 180° C.

$^1$H NMR (300 MHz, DMSO-d$_6$) δ 1.60-1.80 (4H, m), 2.90-3.20 (8H, m), 4.30-4.40 (2H, m), 4.40-4.50 (2H, m), 7.25-7.50 (6H, m), 7.69 (1H, d, J=2.1 Hz), 7.88 (1H, d, J=2.1 Hz), 8.95-9.25 (2H, br).
elementary analysis as $C_{21}H_{25}ClN_2O_5S \cdot HCl \cdot H_2O$
calculation value: C, 49.71; H, 5.56; N, 5.52.
experimental value: C, 49.72; H, 5.61; N, 5.35.

Example 174

7-{5-[[2-(2-Chlorophenyl)ethyl](methyl)amino]pentanoyl}-2,3-dihydro-1,4-benzodioxin-5-sulfonamide hydrochloride

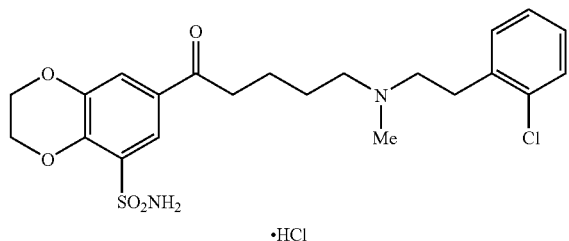

·HCl

Using 5-chloro-1-(2,3-dihydro-1,4-benzodioxin-6-yl)-1-pentanone (1.00 g) obtained in Reference Example 75 and N-[2-(2-chlorophenyl)ethyl]-N-methylamine (565 mg) according to the same method as that of Example 9, the title compound (490 mg) was obtained as pale yellow amorphous powders.

$^1$H NMR (free base; 300 MHz, CDCl$_3$) δ 1.45-1.75 (4H, m), 2.31 (3H, s), 2.45 (2H, t, J=7.2 Hz), 2.50-2.65 (2H, m), 2.80-2.95 (4H, m), 4.00-5.50 (2H, br), 4.30-4.40 (2H, m), 4.35-4.40 (2H, m), 7.05-7.35 (4H, m), 7.63 (1H, s), 7.98 (1H, s).

Example 175

N-(2-methoxy-5-{5-[(2-phenylethyl)amino]pentanoyl}phenyl)methanesulfonamide hydrochloride

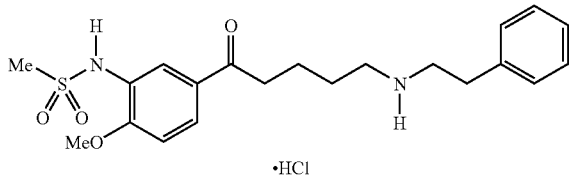

·HCl

Using tert-butyl 5-{4-methoxy-3-[(methylsulfonyl)amino]phenyl}-5-oxopentyl(2-phenylethyl)carbamate (1.32 g) obtained in Reference Example 100 according to the same method as that of Example 1, the title compound was obtained as colorless crystals (945 mg) having a melting point of 131 to 133° C.

$^1$H NMR (300 MHz, DMSO-d$_6$) δ 1.55-1.75(4H, m), 2.85-3.20(8H, m), 2.96(3H, s), 3.89(3H, s), 7.15-7.40(6H, m), 7.80-7.90(2H, m), 8.85-9.15(2H, br), 9.14(1H, s).

elementary analysis as C$_{21}$H$_{28}$N$_2$O$_4$S.HCl.0.5H$_2$O
calculation value: C, 56.05; H, 6.72; N, 6.23.
experimental value: C, 56.18; H, 6.62; N, 6.25.

Example 176

N-[2-methoxy-5-(5-{[2-(2-methoxyphenyl)ethyl]amino}pentanoyl)phenyl]methanesulfonamide hydrochloride

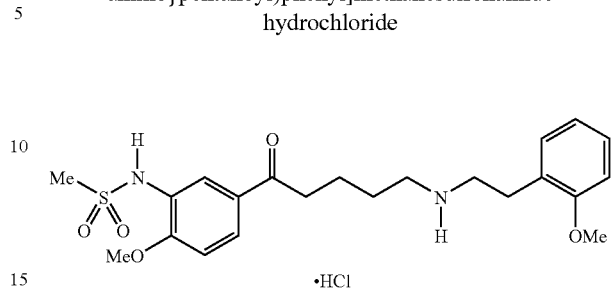

·HCl

Using tert-butyl 5-{4-methoxy-3-[(methylsulfonyl)amino]phenyl}-5-oxopentyl[2-(2-methoxyphenyl)ethyl]carbamate (550 mg) obtained in Reference Example 101 according to the same method as that of Example 1, the title compound was obtained as colorless crystals (374 mg) having a melting point of 129 to 131° C.

$^1$H NMR (300 MHz, DMSO-d$_6$) δ 1.60-1.75(4H, m), 2.90-3.10(8H, m), 2.98(3H, s), 3.80(3H, s), 3.92(3H, s), 6.91(1H, t, J=7.5 Hz), 7.00(1H, d, J=8.1 Hz), 7.15-7.30(3H, m), 7.86 (1H, d, J=1.8 Hz), 7.89(1H, dd, J=8.5, 1.8 Hz), 8.85-9.05(2H, br), 9.15(1H, s).

elementary analysis as C$_{22}$H$_{30}$N$_2$O$_5$S.HCl.0.5H$_2$O
calculation value: C, 55.05; H, 6.72; N, 5.84.
experimental value: C, 55.20; H, 6.44; N, 5.80.

Example 177

N-[5-(5-{[2-(2-chlorophenyl)ethyl]amino}pentanoyl)-2-methoxyphenyl]methanesulfonamide hydrochloride

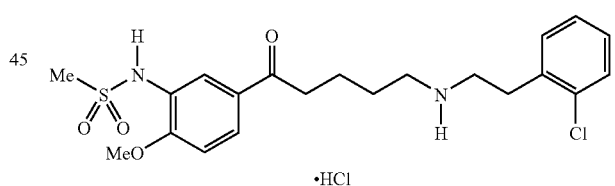

·HCl

Using tert-butyl 2-(2-chlorophenyl)ethyl(5-{4-methoxy-3-[(methylsulfonyl)amino]phenyl}-5-oxopentyl)carbamate (1.52 g) obtained in Reference Example 102 according to the same method as that of Example 1, the title compound was obtained as colorless crystals (1.03 g) having a melting point of 133 to 135° C.

$^1$H NMR (300 MHz, CDCl$_3$) δ 1.75-2.10 (4H, m), 2.95-3.15 (4H, m), 3.00 (3H, s), 3.20-3.30 (2H, m), 3.35-3.45. (2H, m), 3.96 (3H, s), 6.92 (1H, s), 6.94 (1H, d, J=8.4 Hz), 7.10-7.40 (4H, m), 7.75 (1H, dd, J=5.7, 1.4 Hz), 8.04 (1H, d, J=1.4 Hz), 9.65-9.80 (2H, br).

elementary analysis as C$_{21}$H$_{27}$ClN$_2$O$_4$S.HCl0.5H$_2$O
calculation value: C, 52.07; H, 6.03; N, 5.78.
experimental value: C, 52.43; H, 5.78; N, 5.81.

Example 178

N-(2-methoxy-5-{6-[(2-phenylethyl)amino]hexanoyl}phenyl)methanesulfonamide hydrochloride

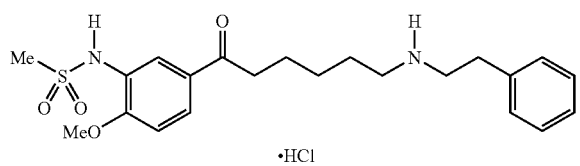

Using tert-butyl 6-{4-methoxy-3-[(methylsulfonyl)amino]phenyl}-6-oxohexyl(2-phenylethyl)carbamate (918 mg) obtained in Reference Example 103 according to the same method as that of Example 1, the title compound was obtained as colorless crystals (751 mg) having a melting point of 136 to 138° C.

$^1$H NMR (300 MHz, DMSO-$d_6$) δ 1.30-1.45(2H, m), 1.55-1.75(4H, m), 2.85-3.10(8H, m), 2.98(3H, s), 3.92(3H, s), 7.15-7.40(6H, m), 7.80-7.90(2H, m), 8.95-9.20(2H, br), 9.16(1H, s).

elementary analysis as $C_{22}H_{30}N_2O_4S·HCl·1.5H_2O$
calculation value: C, 54.82; H, 7.11; N, 5.81.
experimental value: C, 55.19; H, 7.34; N, 5.72.

Example 179

N-[2-methoxy-5-(6-{[2-(2-methoxyphenyl)ethyl]amino}hexanoyl)phenyl]methanesulfonamide hydrochloride

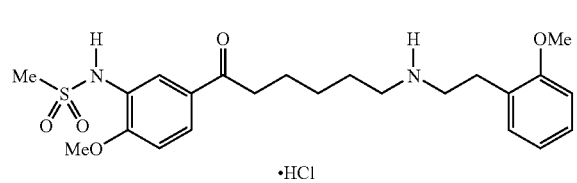

Using tert-butyl 6-{4-methoxy-3-[(methylsulfonyl)amino]phenyl}-6-oxohexyl[2-(2-methoxyphenyl)ethyl]carbamate (1.00 g) obtained in Reference Example 104 according to the same method as that of Example 1, the title compound was obtained as colorless crystals (802 mg) having a melting point of 142 to 144° C.

$^1$H NMR (300 MHz, DMSO-$d_6$) δ 1.30-1.45(2H, m), 1.55-1.75(4H, m), 2.80-3.10(8H, m), 2.98(3H, s), 3.80(3H, s), 3.92(3H, s), 6.92(1H, t, J=7.5 Hz), 7.00(1H, d, J=7.5 Hz), 7.15-7.30(3H, m), 7.80-7.90(2H, m), 8.75-9.05(2H, br), 9.16(1H, s).

elementary analysis as $C_{23}H_{32}N_2O_5S·HCl$
calculation value: C, 56.95; H, 6.86; N, 5.78.
experimental value: C, 56.61; H, 6.87; N, 5.69.

Example 180

N-[5-(6-{[2-(2-Chlorophenyl)ethyl]amino}hexanoyl)-2-methoxyphenyl]methanesulfonamide hydrochloride

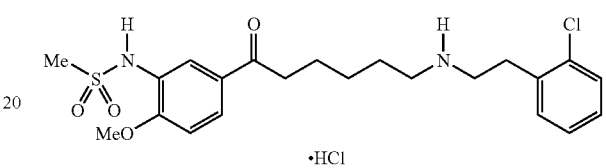

Using tert-butyl 2-(2-chlorophenyl)ethyl(6-{4-methoxy-3-[(methylsulfonyl)amino]phenyl}-6-oxohexyl)carbamate (1.26 g) obtained in Reference Example 105 according to the same method as that of Example 1, the title compound was obtained as colorless crystals (941 mg) having a melting point of 112 to 115° C.

$^1$H NMR (300 MHz, DMSO-$d_6$) δ 1.30-1.45(2H, m), 1.55-1.75(4H, m), 2.80-3.00(8H, m), 2.98(3H, s), 3.92(3H, s), 7.19(1H, d, J=8.7 Hz), 7.25-7.50(4H, m), 7.80-7.90(2H, m), 8.90-9.20(2H, br), 9.16(1H, s).

elementary analysis as $C_{22}H_{29}ClN_2O_4S·HCl·0.5H_2O$
calculation value: C, 53.01; H, 6.27; N, 5.62.
experimental value: C, 52.96; H, 6.24; N, 5.64.

Example 181

1-(1H-indol-3-yl)-5-[(2-phenylethyl)amino]-1-pentanone hydrochloride

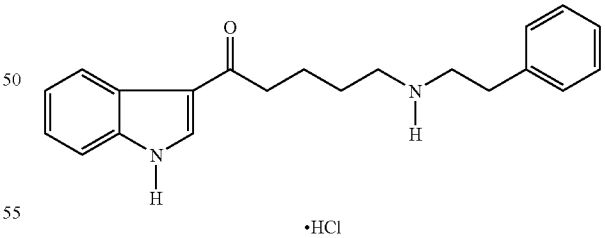

Using tert-butyl 5-(1H-indol-3-yl)-5-oxopentyl(2-phenylethyl)carbamate (1.00 g) obtained in Reference Example 106 according to the same method as that of Example 1, the title compound was obtained as colorless crystals (391 mg) having a melting point of 171 to 173° C.

$^1$H NMR (200 MHz, DMSO-$d_6$) δ 1.65-1.80(4H, m), 2.85-3.20(8H, m), 7.10-7.40(7H, m), 7.48(1H, d, J=7.2 Hz), 8.20(1H, d, J=7.5 Hz), 8.36(1H, d, J=3.2 Hz), 8.80-9.15(2H, br), 12.12(1H, s).

Example 182

1-(1H-indol-3-yl)-5-{[2-(2-methoxyphenyl)ethyl]amino]-1-pentanone hydrochloride

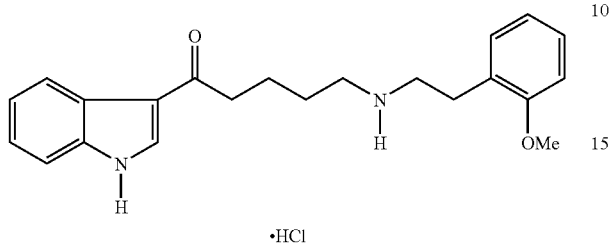

Using tert-butyl 5-(1H-indol-3-yl)-5-oxopentyl[2-(2-methoxyphenyl)ethyl]carbamate (901 mg) obtained in Reference Example 107 according to the same method as that of Example 1, the title compound was obtained as colorless crystals (672 mg) having a melting point of 143 to 145° C.

$^1$H NMR (200 MHz, DMSO-d$_6$) δ 1.65-1.80(4H, m), 2.85-3.15(8H, m), 3.80(3H, s), 6.91(1H, t, J=7.4 Hz), 6.99(1H, d, J=8.0 Hz), 7.10-7.30(4H, m), 7.45-7.55(1H, m), 8.15-8.25 (1H, m), 8.37(1H, d, J=3.2 Hz), 8.95-9.20(2H, br), 12.12(1H, s).

elementary analysis as C$_{22}$H$_{26}$N$_2$O$_2$.HCl.2.0H$_2$O
calculation value: C, 62.48; H, 7.39; N, 6.62.
experimental value: C, 62.48; H, 6.95; N, 6.30.

Example 183

5-{[2-(2-Chlorophenyl)ethyl]amino}-1-(1H-indol-3-yl)-1-pentanone hydrochloride

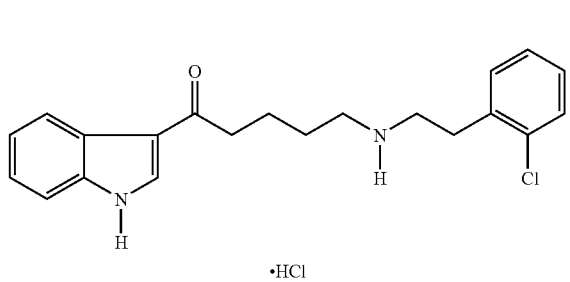

Using tert-butyl 2-(2-chlorophenyl)ethyl[5-(1H-indol-3-yl)-5-oxopentyl]carbamate (1.00 g) obtained in Reference Example 108 according to the same method as that of Example 1, the title compound was obtained as colorless crystals (925 mg) having a melting point of 149 to 151° C.

$^1$H NMR (300 MHz, DMSO-d$_6$) δ 1.65-1.85(4H, m), 2.80-3.20(8H, m), 7.05-7.50(7H, m), 8.20(1H, d, J=6.3 Hz), 8.37 (1H, d, J=3.0 Hz), 9.05-9.30(2H, br), 12.12(1H, s).

elementary analysis as C$_{21}$H$_{23}$ClN$_2$O.HCl.3H$_2$O
calculation value: C, 56.63; H, 6.79; N, 6.29.
experimental value: C, 56.41; H, 6.17; N, 6.04.

Example 184

1-(1H-indol-3-yl)-6-[(2-phenylethyl)amino]-1-hexanone hydrochloride

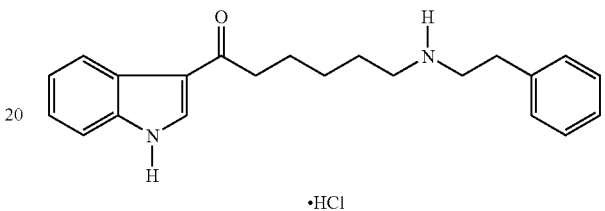

Using tert-butyl 6-(1H-indol-3-yl)-6-oxohexyl(2-phenylethyl)carbamate (838 mg) obtained in Reference Example 109 according to the same method as that of Example 1, the title compound was obtained as colorless crystals (650 mg) having a melting point of 160 to 162° C.

$^1$H NMR (300 MHz, DMSO-d$_6$) δ 1.30-1.50 (2H, m), 1.55-1.80 (4H, m), 2.80-3.20 (8H, m), 7.10-7.35 (7H, m), 7.47 (1H, d, J=7.8 Hz), 8.20 (1H, d, J=6.9 Hz), 8.35-8.40 (1H, m), 8.95-9.20 (2H, br), 12.05 (1H, s).

elementary analysis as C$_{22}$H$_{26}$N$_2$O.HCl
calculation value: C, 71.24; H, 7.34; N, 7.55.
experimental value: C, 70.87; H, 7.45; N, 7.53.

Example 185

1-(1H-indol-3-yl)-6-{[(2-(2-methoxyphenyl)ethyl)amino}-1-hexanone hydrochloride

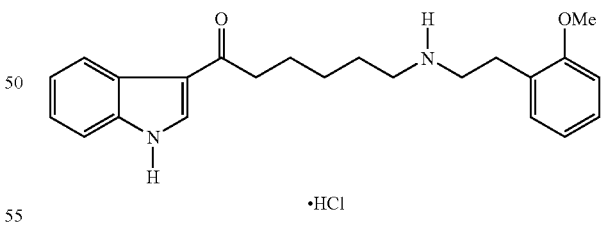

Using tert-butyl 6-(1H-indol-3-yl)-6-oxohexyl[2-(2-methoxyphenyl)ethyl]carbamate (688 mg) obtained in Reference Example 110 according to the same method as that of Example 1, the title compound was obtained as colorless crystals (552 mg) having a melting point of 171 to 173° C.

$^1$H NMR (300 MHz, DMSO-d$_6$) δ 1.30-1.45 (2H, m), 1.55-1.75 (4H, m), 2.80-3.10 (8H, m), 3.80 (3H, s), 6.91 (1H, t, J=7.5 Hz), 7.00 (1H, d, J=8.4 Hz), 7.10-7.30 (4H, m), 7.47 (1H, d, J=7.8 Hz), 8.20 (1H, d, J=6.9 Hz), 8.35 (1H, d, J=3.0 Hz), 8.85-9.05 (2H, br), 12.04 (1H, s).

Example 186

6-{[2-(2-Chlorophenyl)ethyl]amino}-1-(1H-indol-3-yl)-1-hexanone hydrochloride

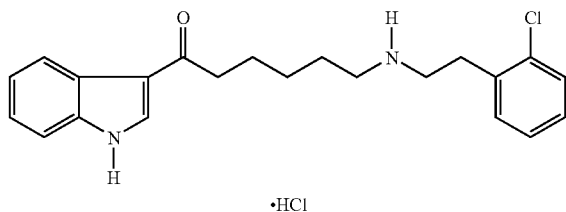

Using tert-butyl 2-(2-chlorophenyl)ethyl[6-(1H-indol-3-yl)-6-oxohexyl]carbamate (860 mg) obtained in Reference Example 111 according to the same method as that of Example 1, the title compound was obtained as colorless crystals (791 mg) having a melting point of 151 to 153° C.

$^1$H NMR (300 MHz, DMSO-$d_6$) δ 1.30-1.45(2H, m), 1.55-1.80(4H, m), 2.80-3.20(8H, m), 7.15-7.50(7H, m), 8.20(1H, d, J=6.9 Hz), 8.36(1H, d, J=3.0 Hz), 9.10-9.30(2H, br), 12.04 (1H, s).

elementary analysis as $C_{22}H_{25}ClN_2O.HCl.2.5H_2O$
calculation value: C, 58.67; H, 6.94; N, 6.22.
experimental value: C, 58.04; H, 6.56; N, 6.01.

Exampe 187

5-[(2-Phenylethyl)amino]-1-(2-thienyl)-1-pentanone hydrochloride

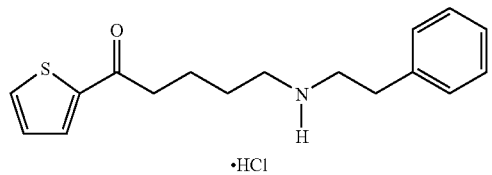

Usings tert-butyl 5-oxo-5-(2-thienyl)pentyl(2-phenylethyl)carbamate (908 mg) obtained in Reference Example 112 according to the same method as that of Example 1, the title compound was obtained as colorless crystals (908 mg) having a melting point of 161 to 163° C.

$^1$H NMR (300 MHz, DMSO-$d_6$) δ 1.60-1.80 (4H, m), 2.85-3.20 (8H, m), 7.20-7.40 (6H, m), 7.95-8.05 (2H, m), 9.10-9.35 (2H, br).

Example 188

5-{[2-(2-Methoxyphenyl)ethyl]amino}-1-(2-thienyl)-1-pentanone hydrochloride

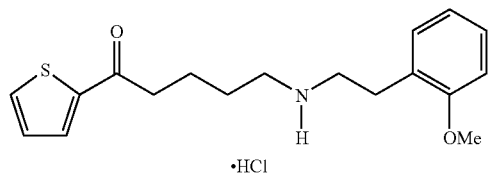

Using tert-butyl 2-(2-methoxyphenyl)ethyl[5-oxo-5-(2-thienyl)pentyl]carbamate (1.45 g) obtained in Reference Example 113 according to the same method as that of Example 1, the title compound was obtained as colorless crystals (1.04 g) having a melting point of 101 to 103° C.

$^1$H NMR (300 MHz, DMSO-$d_6$) δ 1.60-1.80(4H, m), 2.85-3.10(8H, m), 3.80(3H, s), 6.91(1H, t, J=7.2 Hz), 7.00(1H, d, J=8.1 Hz), 7.18(1H, d, J=7.2 Hz), 7.20-7.30(2H, m), 7.95-8.05(2H, m), 8.95-9.15(2H, br).

elementary analysis as $C_{18}H_{23}NO_2S.HCl$
calculation value: C, 61.09; H, 6.84; N, 3.96.
experimental value: C, 60.73; H, 6.62; N, 3.85.

Example 189

5-{[2-(2-Chlorophenyl)ethyl]amino}-1-(2-thienyl)-1-pentanone hydrochloride

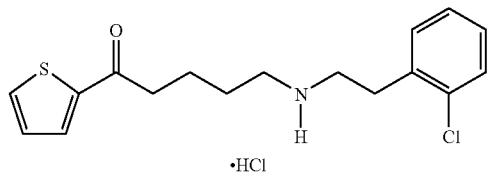

Using tert-butyl 2-(2-chrolophenyl)ethyl[5-oxo-5-(2-thienyl)pentyl]carbamate (1.47 g) obtained in Reference Example 114 according to the same method as that of Example 1, the title compound was obtained as colorless crystals (1.09. g), having a melting point of 146 to 147° C.

$^1$H NMR (300 MHz, DMSO-$d_6$) δ 1.60-1.80(4H, m), 2.85-3.20(8H, m), 7.20-7.50(5H, m), 7.95-8.05(2H, m), 9.05-9.30 (2H, br).

elementary analysis as $C_{17}H_{20}ClNOS.HCl$
calculation value: C, 56.98; H, 5.91; N, 3.91.
experimental value: C, 56.76; H, 5.82; N, 3.96.

Example 190

6-[(2-Phenylethyl)amino]-1-(2-thienyl)-1-hexanone hydrochloride

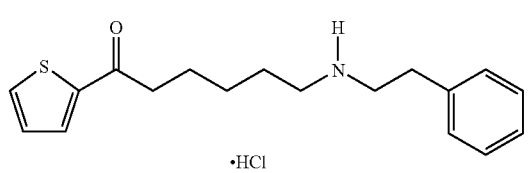

Using tert-butyl 6-oxo-6-(2-tihenyl)hexyl(2-phenylethyl)carbamate (863 mg) obtained in Reference Example 115 according to the same method as that of Example 1, the title compound was obtained as colorless crystals (685 mg) having a melting point of 152 to 154° C.

$^1$H NMR (300 MHz, DMSO-$d_6$) δ 1.30-1.45(2H, m), 1.55-1.80(4H, m), 2.80-3.20(8H, m), 7.20-7.40(6H, m), 7.95-8.05 (2H, m), 9.00-9.20(2H, br).

Example 191

6-{[2-(2-Methoxyphenyl)ethyl]amino}-1-(2-thienyl)-1-hexanone hydrochloride

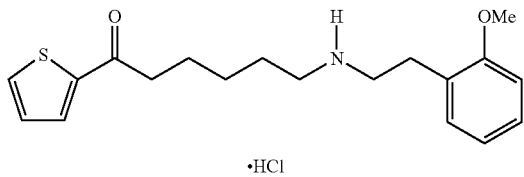

Using tert-butyl 2-(2-methoxypheny)ethyl[6-oxo-6-(2-tihenyl)hexyl]carbamate (884 mg) obtained in Reference Example 116 according to the same method as that of Example 1, the title compound was obtained as colorless, crystals (643 mg) having a melting point of 107 to 109° C.

$^1$H NMR (300 MHz, DMSO-$d_6$) δ 1.30-1.45(2H, m), 1.55-1.75(4H, m), 2.80-3.10(8H, m), 3.80(3H, s), 6.92(1H, t, J=7.5 Hz), 7.00(1H, d, J=8.4 Hz), 7.18(1H, d, J=6.9 Hz), 7.20-7.30 (2H, m), 7.95-8.05(2H, m), 8.80-9.10(2H, br).
elementary analysis as $C_{19}H_{25}NO_2S \cdot HCl$
calculation value: C, 62.02; H, 7.12; N, 3.81.
experimental value: C, 61.80; H, 7.04; N, 3.88.

Example 192

6-{[2-(2-Chlorophenyl)ethyl]amino}-1-(2-thienyl)-1-hexanone hydrochloride

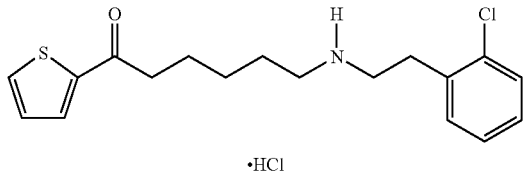

Using tert-butyl 2-(2-chloropheny)ethyl[6-oxo-6-(2-tihenyl)hexyl]carbamate (1.07 g) obtained in Reference Example 117 according to the same method as that of Example 1, the title compound was obtained as colorless crystals (849 mg) having a melting point of 149 to 151° C.

$^1$H NMR (300 MHz, DMSO-$d_6$) δ 1.30-1.45(2H, m), 1.55-1.75(4H, m), 2.80-3.20(8H, m), 7.20-7.50(5H, m), 7.95-8.05 (2H, m), 9.00-9.35(2H, br).
elementary analysis as $C_{18}H_{22}ClNOS \cdot HCl \cdot H_2O$
calculation value: C, 55.38; H, 6.46; N, 3.59.
experimental value: C, 55.20; H, 6.57; N, 3.67.

Example 193

(±)-8-[5-(1,2,3,4-Tetrahydro-1-naphthalenylamino)pentanoyl]-1,2,5,6-tetrahydro-4H-pyrrolo[3,2,1-ij]quinolin-4-one hydrochloride

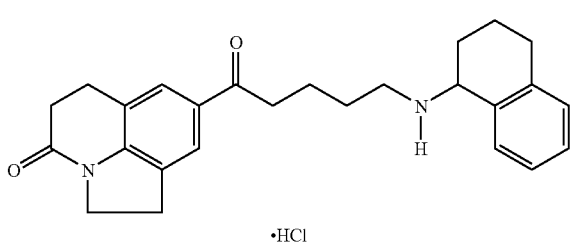

Using tert-butyl (±)-5-oxo-5-(4-oxo-1,2,5,6-tetrahydro-4H-pyrrolo[3,2,1-ij]quinolin-8-yl)pentyl(1,2,3,4-tetrahydro-1-naphthalenyl)carbamate (520 mg) obtained in Reference Example 118 according to the same method as that of Example 1, the title compound (420 mg) was obtained as pale yellow amorphous powders.

$^1$H NMR (300 MHz, DMSO-$d_6$) δ 1.60-2.25(8H, m), 2.59 (2H, t, J=7.6 Hz), 2.65-3.05(8H, m), 3.17(2H, t, J=8.4 Hz), 3.60-3.70(1H, m), 3.98(2H, t, J=8.4 Hz), 7.15-7.35(3H, m), 7.65-7.80(3H, m), 9.05-9.35(2H, br).

Example 194

(±)-8-{5-((1,2-Diphenylethyl)amino]pentanoyl}-1,2,5,6-tetrahydro-4H-pyrrolo[3,2,1-ij]quinolin-4-one hydrochloride

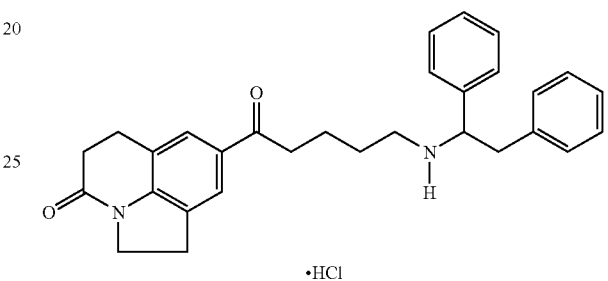

Using tert-butyl (±)-1,2-diphenylethyl[-5-oxo-5-(4-oxo-1,2,5,6-tetrahydro-4H-pyrrolo[3,2,1-ij]quinolin-8-yl)pentyl]carbamate (837 mg) obtained in Reference Example 119 according to the same method as that of Example 1, the title compound was obtained as colorless crystals (472 mg) having a melting point of 210 to 212° C.

$^1$H NMR (300 MHz, DMSO-$d_6$) δ 1.45-1.80(4H, m), 2.50-2.65(3H, m), 2.75-3.05(5H, m), 3.10-3.25(3H, m), 3.55-3.70 (1H, m), 3.99(2H, t, J=8.4 Hz), 4.40-4.55(1H, m), 6.95-7.05 (2H, m), 7.10-7.20(3H, m), 7.30-7.40(3H, m), 7.40-7.50(2H, m), 7.70-7.80(2H, m), 9.45-9.60(1H, br), 9.85-10.05(1H, br).

Example 195

8-(5-{Benzyl[2-(2-methoxyphenyl)ethyl]amino}pentanoyl)-1,2,5,6-tetrahydro-4H-pyrrolo[3,2,1-ij]quinolin-4-one hydrochloride

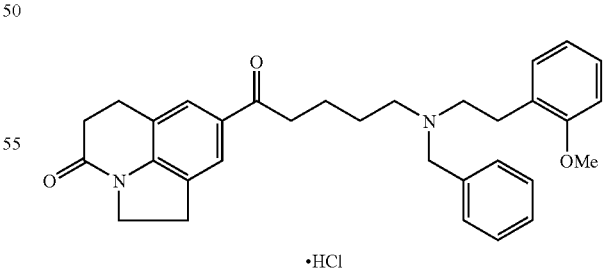

Using 8-(5-chloropentanoyl)-1,2,5,6-tetrahydro-4H-pyrrolo[3,2,1-ij]quinolin-4-one (500 mg) obtained in Reference Example 1 and N-benzyl-N-[2-(2-methoxyphenyl)ethyl]amine (455 mg) according to the same method as that of Example 9, the title compound (353 mg) was obtained as pale yellow amorphous powders.

$^1$H NMR (free base; 200 MHz, CDCl$_3$) δ 1.50-1.90(6H, m), 2.55(2H, t, J=6.8 Hz), 2.60-3.30(10H, m), 3.65(2H, s), 3.74(3H, s), 4.10(2H, t, J=8.8 Hz), 6.75-6.90(2H, m), 7.05-7.35(7H, m), 7.64(1H, s), 7.68(1H, s).

Example 196

Trans-8-[(4-{[(2-phenylethyl)amino]methyl}cyclohexyl)carbonyl]-1,2,5,6-tetrahydro-4H-pyrrolo[3,2,1-ij]quinolin-4-one hydrochloride

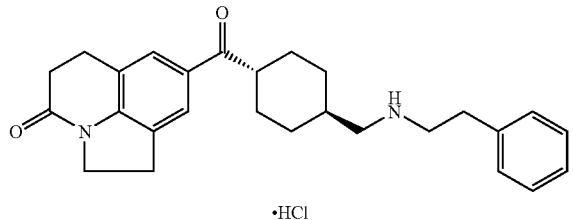

(2-Bromoethyl)benzene (471 mg) was added dropwise to a suspension of trans-8-{[4-(aminomethyl)cyclohexyl]carbonyl}-1,2,5,6-tetrahydro-4H-pyrrolo[3,2,1-ij]quinolin-4-one hydrochloride (1.00. g) obtained in Reference Example 78 and potassium carbonate (1.00 g) in dimethylformamide (3 ml) at room temperature. After stirring at 120° C. for 30 minutes, water (30 ml) and ethyl acetate (30 ml) were added to the reaction mixture, and extracted with ethyl acetate. The extract was washed with brine, dried over anhydrous magnesium sulfate, and the solvent was evaporated under reduced pressure. The resulting residue was purified by silica gel chromatography (eluting solvent; ethyl acetate methanol (9:1)) to give a free base compound of the title compound as a colorless oil (500 mg). Further treatment with a hydrogen chloride-ethyl acetate solution afforded the title compound as colorless crystals (474 mg) having a melting point of 252 to 254° C.

$^1$H NMR (free base; 300 MHz, CDCl$_3$) δ 0.95-1.20 (2H, m), 1.35-1.70 (5H, m), 1.75-2.05 (4H, m), 2.51 (2H, d, J=6.3 Hz), 2.70 (2H, t, J=7.8 Hz), 2.75-2.90 (3H, m), 3.01 (2H, t, J=7.8 Hz), 3.05-3.15 (1H, m), 3.22 (2H, t, J=8.4 Hz), 4.12 (2H, t, J=8.4 Hz), 7.10-7.35 (5H, m), 7.64 (1H, s), 7.68 (1H, s).

elementary analysis as C$_{27}$H$_{32}$ClN$_2$O$_2$.HCl
calculation value: C, 70.19; H, 7.42; N, 6.06.
experimental value: C,70.58; H,7.35; N, 5.81.

Example 197 trans-8-{[4-({[2-(2-Chlorophenyl)ethyl]amino}methyl)cyclohexyl]carbonyl}-1,2,5,6-tetrahydro-4H-pyrrolo[3,2,1-ij]quinolin-4-one hydrochloride

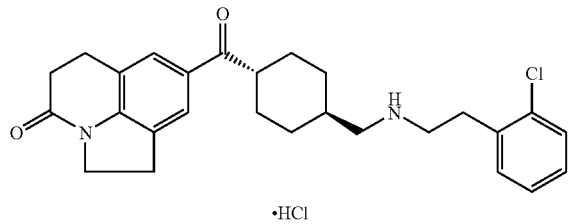

Using trans-8-{[4-(aminomethyl)cyclohexyl]carbonyl}-1,2,5,6-tetrahydro-4H-pyrrolo[3,2,1-ij]quinolin-4-one hydrochloride (758 mg) obtained in Reference Example 78 and 2-(2-chlorophenyl)ethyl methanesulfonate (510 mg) according to the same method as that of Example 196, the title compound was obtained as colorless crystals (454 mg) having a melting point of 271 to 2731° C.

$^1$H NMR (free base; 300 MHz, CDCl$_3$) δ 0.95-1.20 (2H, m), 1.35-1.70 (5H, m), 1.75-2.05 (4H, m), 2.55 (2H, d, J=6.3 Hz), 2.71 (2H, t, J=7.8 Hz), 2.80-2.95 (3H, m), 3.02 (2H, t, J=7.8 Hz), 3.05-3.20 (1H, m), 3.23 (2H, t, J=8.4 Hz), 4.13 (2H, t, J=8.4 Hz), 7.10-7.40 (4H, m), 7.65 (1H, s), 7.69 (1H, s).

elementary analysis as C$_{27}$H$_{31}$N$_2$O$_2$Cl.HCl.0.5H$_2$O
calculation value: C, 65.32; H, 6.70; N, 5.64.
experimental value: C, 65.70; H, 6.52; N, 5.54.

Example 198

1-(3-Acetyl-2,3,4,5-tetrahydro-1H-3-benzazepin-7-yl)-5-{[2-(2-chlorophenyl)ethyl]amino}-1-pentanone hydrochloride

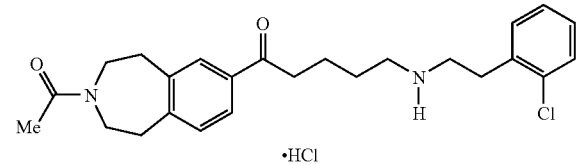

Using 1-(3-acetyl-2,3,4,5-tetrahydro-1H-3-benzazepin-7-yl)-5-chloro-1-pentanone obtained in Reference Example 122 and 2-(2-chlorophenyl)ethylamine according to the same methods as those of Example 19 and Example 1, the title compound was obtained as colorless crystals having a melting point of 117 to 119° C.

$^1$H NMR (300 MHz, DMSO-d$_6$) δ 1.68 (4H, m), 2.08 (3H, s), 2.91 (4H, m), 3.05 (8H, m), 3.56 (4H, m), 7.33-7.46 (5H, m), 7.77 (2H, m), 9.18 (2H, br).

Example 199

1-(3-Acetyl-2,3,4,5-tetrahydro-1H-3-benzazepin-7-yl)-5-{[2-(2-methoxyphenyl)ethyl]amino}-1-pentanone hydrochloride

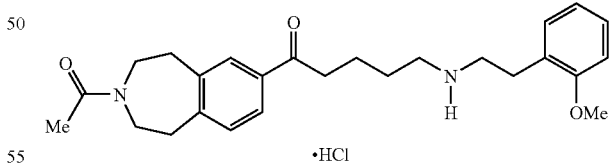

Using 1-(3-acetyl-2,3,4,5-tetrahydro-1H-3-benzazepin-7-yl)-5-chloro-1-pentanone obtained in Reference Example 122 and 2-(2-methoxyphenyl)ethylamine according to the same methods as those of Example 19 and Example 1, the title compound was obtained as colorless crystals having a melting point of 93 to 94° C.

$^1$H NMR (300 MHz, DMSO-d$_6$) δ 1.67 (4H, m), 2.08 (3H, s), 2.93 (4H, m), 3.04 (8H, m), 3.58 (4H, m), 3.80 (3H, s), 6.88-7.02 (2H, m), 7.17-7.33 (3H, m), 7.75 (2H, m), 8.83 (2H, br).

Example 200

5-{[2-(2-Chlorophenyl)ethyl]amino}-1-[3-(methyl-sulfonyl)-2,3,4,5-tetrahydro-1H-3-benzazepin-7-yl]-1-pentanone hydrochloride

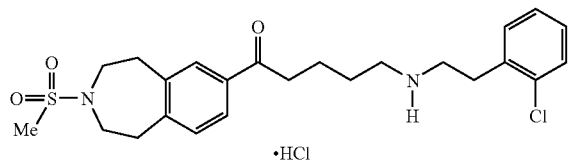

Using 5-chloro-1-[3-(methylsulfonyl)-2,3,4,5-tetrahydro-1H-3-benzazepin-7-yl]-1-pentanone obtained in Reference Example 123 and 2-(2-chlorophenyl)ethylamine according to the same methods as those of Reference Example 19 and Example 1, the title compound was obtained as colorless crystals having a melting point of 162 to 164° C.

$^1$H NMR (300 MHz, DMSO-$d_6$) δ 1.69 (4H, m), 2.88 (3H, s), 3.10 (8H, m), 3.36 (8H, m), 7.33-7.46 (5H, m), 7.78 (2H, m), 8.99 (2H, br).

Example 201

5-{[2-(2-Methoxyphenyl)ethyl]amino}-1-[3-(methylsulfonyl)-2,3,4,5-tetrahydro-1H-3-benzazepin-7-yl]-1-pentanone hydrochloride

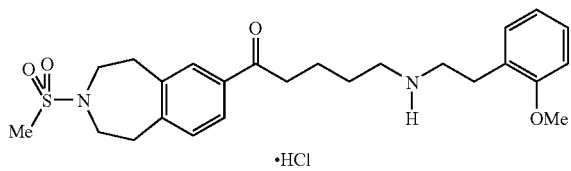

Using 5-(5-chloropentanoyl)-2-methoxybenzenesulfonamide obtained in Reference Example 66 and N-[2-(2-chlorophenyl)ethyl]-N-methylamine according to the same methods as those of Reference Example 19 and Example 1, the title compound was obtained as pale yellow amorphous powders.

$^1$H NMR (300 MHz, DMSO-$d_6$) δ 1.67 (4H, m), 2.88 (3H, s), 2.96-3.07 (10H, m), 3.36 (6H, m), 3.80 (3H, s), 6.88-7.23 (2H, m), 7.17-7.36 (3H, m), 7.78 (2H, m), 8.88 (2H, br).

Example 202

7-(5-{[2-(2-Chlorophenyl)ethyl]amino}pentanoyl)-N-ethyl-1,2,4,5-tetrahydro-3H-3-benzazepine-3-carboxamide hydrochloride

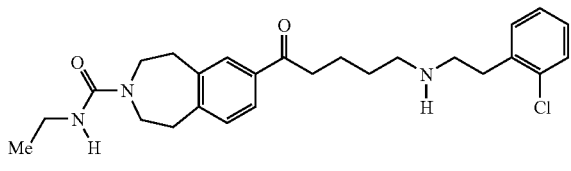

Using 7-(5-chloropentanoyl)-N-ethyl-1,2,4,5-tetrahydro-3H-3-benzazepine-3-carboxamide obtained in Reference Example 124 and 2-(2-chlorophenyl)ethylamine according to the same methods as those of Reference Example 19 and Example 1, the title compound was obtained as colorless crystals having a melting point of 149 to 150° C.

$^1$H NMR (300 MHz, DMSO-$d_6$) δ 1.02 (3H, t, J=7.0 Hz), 1.69 (4H, m), 2.91 (4H, m), 3.08 (10H, m), 3.49 (4H, m), 7.28-7.50 (5H, m), 7.75 (2H, m), 8.23 (1H, m), 9.11 (2H, br).

Example 203

N-Ethyl-7-(5-{[2-(2-methoxyphenyl)ethyl]amino}pentanoyl)-1,2,4,5-tetrahydro-3H-3-benzazepine-3-carboxamide hydrochloride

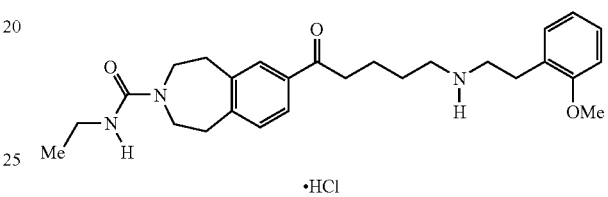

Using 7-(5-chloropentanoyl)-N-ethyl-1,2,4,5-tetrahydro-3H-3-benzazepine-3-carboxamide obtained in Reference Example 124 and 2-(2-methoxyphenyl)ethylamine according to the same methods as those of Reference Example 19 and Example 1, the title compound was obtained as colorless crystals having a melting point of 150 to 151° C.

$^1$H NMR (300 MHz, DMSO-$d_6$) δ 1.02 (3H, t, J=7.0 Hz), 1.68 (4H, m), 2.90 (4H, m), 3.07, (10H, m), 3.47 (4H, m), 3.80 (3H, s), 6.88-7.02. (2H, m), 7.17-7.31 (3H, m), 7.73 (2H, m), 8.23 (1H, m), 9.01 (2H, br).

Example 204

5-[[2-(2-Chlorophenyl)ethyl](methyl)amino]-1-[3-(trifluoroacetyl)-2,3,4,5-tetrahydro-1H-3-benzazepin-7-yl]-1-pentanone hydrochloride

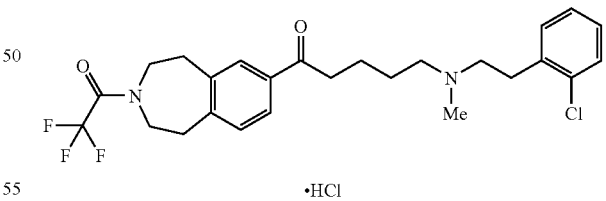

Using 5-chloro-1-[3-(trifluoroacetyl)-2,3,4,5-tetrahydro-1H-3-benzazepin-7-yl]-1-pentanone obtained in Reference Example 120 and N-[2-(2-chlorophenyl)ethyl]-N-methylamine according to the same method as that of Example 9, the title compound was obtained as pale yellow amorphous powders.

$^1$H NMR (free base; 200 MHz, CDCl$_3$) δ 1.54-1.80 (4H, m), 2.34 (3H, s), 2.48 (2H, t, J=7.4 Hz), 2.57-2.62 (2H, m), 2.86-3.07 (8H, m), 3.69-3.81 (4H, m), 7.11-7.34 (5H, m), 7.75-7.78 (2H, m).

Example 205

5-[[2-(2-Chlorophenyl)ethyl](methyl)amino]-1-(2,3,4,5-tetrahydoro-1H-3-benzazepin-7-yl)-1-pentanone dihydrochloride

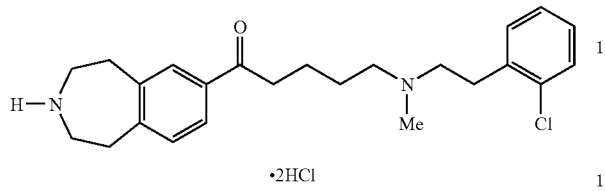

•2HCl

Potassium carbonate (3.2 g, 23.5 mmol) was added to a solution of 5-[[2-(2-chlorophenyl)ethyl](methyl)amino]-1-[3-(trifluoroacetyl)-2,3,4,5-tetrahydro-1H-3-benzazepin-7-yl]-1-pentanone (1.50 g) obtained in Reference Example 204 in methanol (40 ml)-water (40 ml). After stirring at room temperature for 60 minutes, the solvent was evaporated under reduced pressure, water (100 g) was added, extracted with ethyl acetate, and washed with brine. The organic layer was dried over anhydrous sodium sulfate, and the solvent was evaporated under reduced pressure to give a free base compound of the title compound as a pale yellow oil (1.2 g). A solution of the free base compound in ethanol was treated with hydrogen chloride (ethyl acetate solution) to give the title compound as pale yellow amorphous powders.

$^1$H NMR (free base; 200 MHz, CDCl$_3$) δ 1.54-1.79 (4H, m), 2.33 (3H, s), 2.45 (2H, t, J=7.4 Hz), 2.57-2.62 (2H, m), 2.86-2.97 (13H, m), 7.10-7.34 (5H, m), 7.68-7.71 (2H, m).

Example 206

1-(3-Acetyl-2,3,4,5-tetrahydro-1H-3-benzazepin-7-yl)-5-[[2-(2-chlorophenyl)ethyl](methyl)amino]-1-pentanone hydrochloride

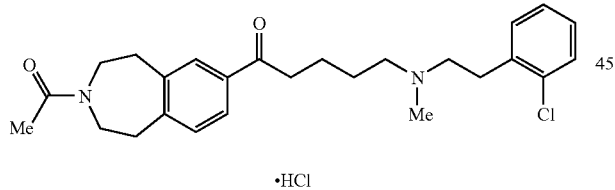

•HCl

Acetyl chloride (54 μl) was added to a solution of 5-[[2-(2-chlorophenyl)ethyl](methyl)amino]-1-(2,3,4,5-tetrahydro-1H-3-benzazepin-7-yl)-1(294 mg) obtained in Example 205 and triethylamine (139 μl) in tetrahydrofuran (2 ml). After stirring at room temperature for 60 minutes, water (10 g) was added, extracted with ethyl acetate, and washed with brine. The organic layer was dried over anhydrous sodium sulfate, the solvent was evaporated under reduced pressure, and purified by silica gel column chromatography to give a free base compound of the title compound as a pale yellow oil (280 mg). A solution of the free base compound in ethanol was treated with hydrogen chloride (ethyl acetate solution) to give the title compound as pale yellow amorphous powders (220 mg).

$^1$H NMR (free base; 200 MHz, CDCl$_3$) δ 1.54-1.80 (4H, m), 2.19 (3H, s), 2.36 (3H, s), 2.45 (2H, t, J=7.4 Hz), 2.60-2.68 (2H, m), 2.88-3.00 (8H, m), 3.58-3.86 (4H, m), 7.12-7.34 (5H, m), 7.73-7.76. (2H, m).

Example 207

5-[[2-(2-Chlorophenyl)ethyl](methyl)amino]-1-[3-(methylsulfonyl)-2,3,4,5-tetrahydro-1H-3-benzazepin-7-yl]-1-pentanone hydrochloride

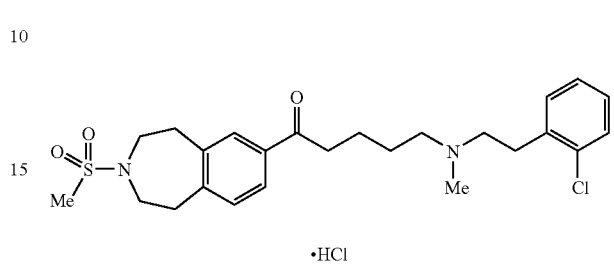

•HCl

Methylsulfonyl chloride (45 μl) was added to a solution of 5-[[2-(2-chlorophenyl)ethyl](methyl)amino]-1-(2,3,4,5-tetrahydro-1H-3-benzazepin-7-yl)-1-pentanone (223 mg) obtained in Example 205 and triethylamine (139 μl) in tetrahydrofuran (2 ml). After stirring at room temperature for 60 minute, water (10 g) was added, extracted with ethyl acetate, and washed with brine. The organic layer was dried over anhydrous sodium sulfate, the solvent was evaporated under reduced pressure, and the residue was purified by silica gel column chromatography to give a free base compound of the title compound as a pale yellow oil (230 mg). A solution of the free base compound in ethanol was treated with hydrogen chloride (ethyl acetate solution) to give the title compound as pale yellow amorphous powders (200 mg).

$^1$H NMR (free base; 200 MHz, CDCl$_3$) δ 1.54-1.79 (4H, m), 2.34 (3H, s), 2.48 (2H, t, J=7.4 Hz), 2.57-2.65 (2H, m), 2.79 (3H, s), 2.86-2.99 (4H, m), 3.08-3.11 (4H, m), 3.43-3.49 (4H, m), 7.11-7.34 (5H, m), 7.74-7.77 (2H, m).

Example 208

7-{5-[[2-(2-Chlorophenyl)ethyl](methyl)amino]pentanoyl}-N-ethyl-1,2,4,5-tetrahydro-3H-3-benzazepine-3-carboxamide hydrochloride

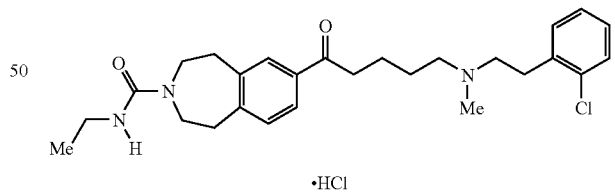

•HCl

Ethyl isocyanate (74 μl) was added to a solution of 5-[[2-(2-chlorophenyl)ethyl](methyl)amino]-1-(2,3,4,5-tetrahydro-1H-3-benzazepin-7-yl)-1-pentanone (365 mg) obtained in Example 205 in tetrahydrofuran (2 ml). After stirring at room temperature for 60 minutes, water (10 g) was added, extracted with ethyl acetate, and washed with brine. The organic layer was dried over anhydrous sodium sulfate, the solvent was evaporated under reduced pressure, and the residue was purified by silica gel column chromatography to give a free base compound of the title compound as a pale yellow oil (330 mg). A solution of the free base compound in ethanol was treated with hydrogen chloride (ethyl acetate solution) to give the title compound as pale yellow amorphous powders (290 mg).

$^1$H NMR (free base; 200 MHz, CDCl$_3$) δ 1.16 (3H, t, J=7.2 Hz), 1.58-1.77 (4H, m), 2.38 (3H, s), 2.54 (2H, t, J=7.4 Hz), 2.63-2.69 (2H, m), 2.90-3.00 (8H, m), 3.31 (2H, q, J=7.2 Hz), 3.54-3.59 (4H, m), 4.74 (1H, m), 7.11-7.32 (5H, m), 7.69-7.72 (2H, m).

Example 209

5-[[2-(2-Methoxyphenyl)ethyl](methyl)amino]-1-[3-(trifluoroacetyl)-2,3,4,5-tetrahydro-1H-3-benzazepin-7-yl]-1-pentanone

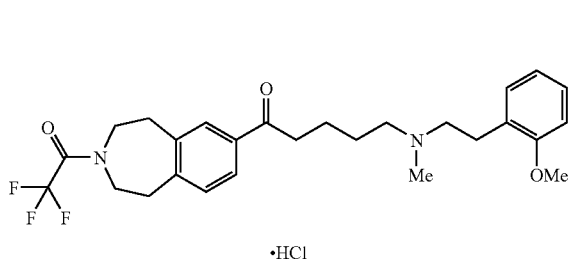

·HCl

Using 5-chloro-1-[3-(trifluoroacetyl)-2,3,4,5-tetrahydro-1H-3-benzazepin-7-yl]-1-pentanone obtained in Reference Example 120 and N-[2-(2-methoxyphenyl)ethyl]-N-methylamine according to the same method as that of Example 9, the title compound was obtained as pale yellow amorphous powders.

$^1$H NMR (free base; 200 MHz, CDCl$_3$) δ 1.54-1.80 (4H, m), 2.33 (3H, s), 2.48 (2H, t, J=7.4 Hz), 2.57-2.62 (2H, m), 2.76-2.80 (2H, m), 2.93-3.06 (6H, m), 3.68-3.81 (4H, m), 3.81 (3H, s), 6.86 (2H, t, J=9.2 Hz), 7.12-7.27 (3H, m), 7.75-7.78 (2H, m).

Example 210

5-[[2-(2-Methoxyphenyl)ethyl](methyl)amino]-1-(2,3,4,5-tetrahydro-1H-3-benzazepin-7-yl)-1-pentanone dihydrochloride

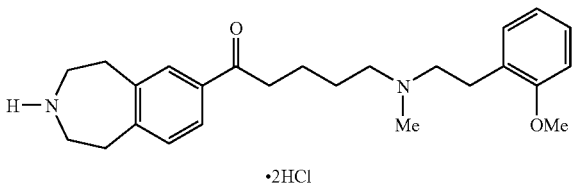

·2HCl

Using 5-[[2-(2-methoxyphenyl)ethyl](methyl)amino]-1-[3-(trifluoroacetyl)-2,3,4,5-tetrahydro-1H-3-benzazepin-7-yl]-1-pentanone obtained in Example 209 according to the same method as that of Example 205, the title compound was obtained as pale yellow amorphous powders.

$^1$H NMR (free base; 200 MHz, CDCl$_3$) δ 1.57-1.79 (4H, m), 2.31 (3H, s), 2.45 (2H, t, J=7.4 Hz), 2.53-2.60 (2H, m), 2.74-2.82 (2H, m), 2.91-2.96 (11H, m), 3.81 (3H, s), 6.81-6.90 (2H, m), 7.12-7.20 (3H, m), 7.68-7.72 (2H, m).

Example 211

1-(3-Acetyl-2,3,4-tetrahydro-1H-3-benzazepin-7-yl)-5-[[2-(2-methoxyphenyl)ethyl](methyl)amino]-1-pentanone hydrochloride

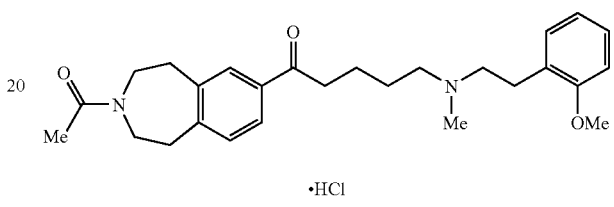

·HCl

Using 5-[[2-(2-methoxyphenyl)ethyl](methyl)amino]-1-(2,3,4,5-tetrahydro-1H-3-benzazepin-7-yl)-1-pentanone obtained in Example 210 according to the same method as that of Example 206, the title compound was obtained as pale yellow amorphous powders.

$^1$H NMR (free base; 200 MHz, CDCl$_3$) δ 1.54-1.80 (4H, m), 2.19 (3H, s), 2.35 (3H, s), 2.51 (2H, t, J=7.4 Hz), 2.58-2.65 (2H, m), 2.77-2.85 (2H, m), 2.93-3.00 (6H, m), 3.57-3.76 (4H, m), 3.81 (3H, s), 6.82-6.91 (2H, m), 7.12-7.25 (3H, m), 7.73 (2H, m).

Example 212

5-[[2-(2-Methoxyphenyl)ethyl](methyl)amino]-1-[3-(methylsulfonyl)-2,3,4,5-tetrahydro-1H-3-benzazepin-7-yl]-1-pentanone hydrochloride

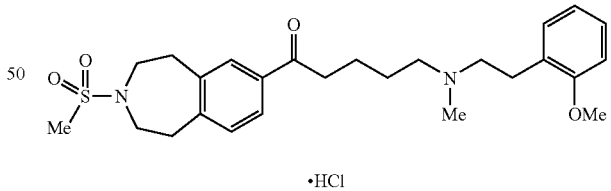

·HCl

Using 5-[[2-(2-methoxyphenyl)ethyl](methyl)amino]-1-(2,3,4,5-tetrahydro-1H-3-benzazepin-7-yl)-1-pentanone obtained in Example 210 according to the same method as that of Example 207, the title compound was obtained as pale yellow amorphous powders.

$^1$H NMR (free base; 200 MHz, CDCl$_3$) δ 1.56-1.80 (4H, m), 2.36 (3H, s), 2.52 (2H, t, J=7.4 Hz), 2.58-2.69 (2H, m), 2.78 (3H, s), 2.75-2.85 (2H, m), 3.06-3.12 (4H, m), 3.43-3.47 (4H, m), 3.81 (3H, s), 6.82-6.91 (2H, m)), 7.11-7.27 (3H, m), 7.73 (2H, m).

Example 213

N-Ethyl-7-{5-[[2-(2-methoxyphenyl)ethyl](methyl)amino]pentanoyl}-1,2,4,5-tetrahydro-3H-3-benzazepine-3-carboxamide hydrochloride

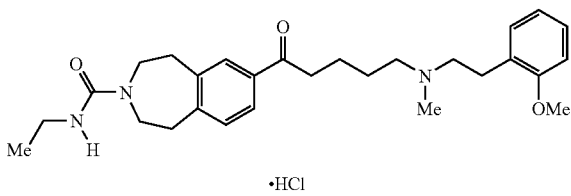

·HCl

Using 5-[[2-(2-methoxyphenyl)ethyl](methyl)amino)-1-(2,3,4,5-tetrahydro-1H-3-benzazepin-7-yl)-1-pentanone obtained in Example 210 according to the same method as that of Example 208, the title compound was obtained as pale yellow amorphous powders.

$^1$H NMR (free base; 200 MHz, CDCl$_3$) δ 1.17 (3H, t, J=7.4 Hz), 1.56-1.79 (4H, m), 2.36 (3H, s), 2.52 (2H, t, J=7.4 Hz), 2.58-2.69 (2H, m), 2.75-2.84 (2H, m), 2.93-3.00 (6H, m), 3.32 (2H, q, J=7.2 Hz), 3.53-3.58 (4H, m), 3.81 (3H, s), 4.70 (1H, m), 6.81-6.90 (2H, m), 7.12-7.21 (3H, m), 7.71 (2H, m).

Example 214

1-(2-Acetyl-1,2,3,4-tetrahydro-7-isoquinolinyl)-5-[[2-(2-chlorophenyl)ethyl](methyl)amino]-1-pentanone hydrochloride

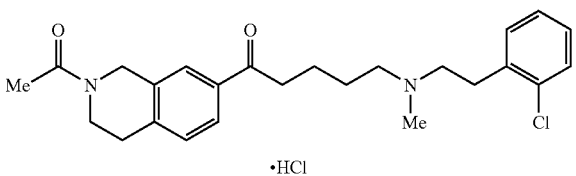

·HCl

Using 1-(2-acetyl-1,2,3,4-tetrahydro-7-isoquinolinyl)-5-chloro-1-pentanone obtained in Reference Example 125 and N-[2-(2-chlorophenyl)ethyl]-N-methylamine according to the same method as that of Example 9, the title compound was obtained as pale yellow amorphous powders.

$^1$H NMR (free base; 200 MHz, CDCl$_3$) δ 1.54-1.79 (4H, m), 2.19 (3H, s), 2.34 (3H, s), 2.48 (2H, t, J=7.0 Hz), 2.57-2.65 (2H, m), 2.87-2.98 (6H, m), 3.69 (2H, t, J=5.8 Hz), 4.67 (2H, s), 7.11-7.34 (5H, m), 8.83 (1H, s), 7.74-7.80 (2H, m).

Example 215

5-[[2-(2-Chlorophenyl)ethyl](methyl)amino]-1-(1,2,3,4-tetrahydro-7-isoquinolinyl)-1-pentanone dihydrochloride

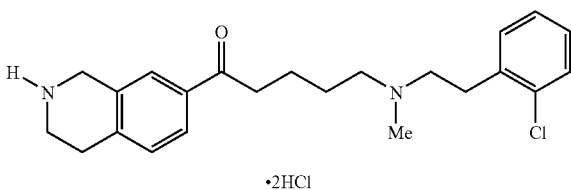

·2HCl

A solution of (1-(2-acetyl-1,2,3,4-tetrahydro-7-isoquinolinyl)-5-[[2-(2-chlorophenyl)ethyl](methyl)amino]-1-pentanone (5.0 g) obtained in Example 214 in concentrated hydrochloric acid (150 ml) was stirred at 130° C. for 2 hours, and the solvent of the reaction mixture was evaporated under reduced pressure to give the crude product of the title compound as a pale yellow solid (4.2. g). Further recrystallization from ethanol-diethyl ether afforded the title compound as colorless crystals having a melting point of 95° C. (dec).

$^1$H NMR (free base; 200 MHz, CDCl$_3$) δ 1.60-1.79 (4H, ), 2.21 (1H, br), 2-37 (3H, s), 2.52 (2H, t, J=7.4 Hz), 2.65 (2H, m), 2.88-3.26 (6H, m), 3.58 (2H, t, J=5.8 Hz), 4.10 (2H, s), 7.12-7.35 (5H, m), 7.71-7.81 (2H, m).

Example 216

5-[[2-(2-Chlorophenyl)ethyl](methyl)amino]-1-[2-(methylsulfonyl)-1,2,3,4-tetrahydro-7-isoquinolinyl]-1-pentanone hydrochloride

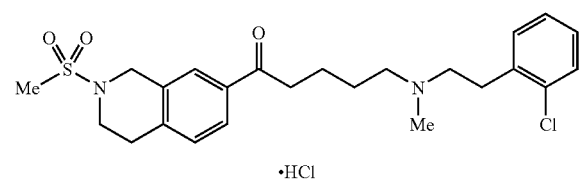

·HCl

Using 5-[[2-(2-chlorophenyl)ethyl](methyl)amino]-1-(1,2,3,4-tetrahydro-7-isoquinolinyl)-1-pentanone obtained in Example 215 according to the same method as that of Example 207, the title compound was obtained as pale yellow amorphous powders.

$^1$H NMR (free base; 200 MHz, CDCl$_3$) δ 1.60-1.79 (4H, m), 2.37 (3H, s), 2.52 (2H, t, J=7.4 Hz), 2.65 (2H, m), 2.87 (3H, s), 2.88-3.26 (6H, m), 3.58 (2H, t, J=5.8 Hz), 4.50 (2H, s), 7.12-7.35 (5H, m), 7.71-7.81 (2H, m).

Example 217

7-{5-[[2-(2-Chlorophenyl)ethyl](methyl)amino]pentanoyl}-N-ethyl-3,4-dihydro-2(1H)-isoquinolinecarboxamide hydrochloride

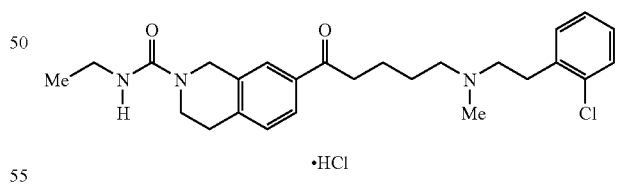

·HCl

Using 5-[[2-(2-Chlorophenyl)ethyl](methyl)amino]-1-(1,2,3,4-tetrahydro-7-isoquinolinyl)-1-pentanone obtained in Example 215 according to the same method as that of Example 208, the title compound was obtained as pale yellow amorphous powders.

$^1$H NMR (free base; 200 MHz, CDCl$_3$) δ 1.17 (3H, t, J=5.8 Hz), 1.57-1.78 (4H, m), 2.35 (3H, s), 2.48 (2H, t, J=6.6 Hz), 2.63 (2H, m), 2.89-2.99 (6H, m), 3.30-3.34 (2H, m), 3.64 (2H, t, J=5.4 Hz), 4.47 (1H, m), 4.58 (2H, s), 7.13-7.34 (5H, m), 7.73-7.79 (2H, m).

Example 218

1-(2-Acetyl-1,2,3,4-tetrahydro-7-isoqiunolinyl)-5-{ [2-(2-chlorophenyl)ethyl]amino}-1-pentanone hydrochloride

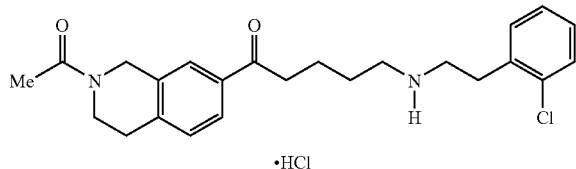

·HCl

Using 1-(2-acetyl-1,2,3,4-tetrahydro-7-isoquinolinyl)-5-chloro-1-pentanone obtained in Reference Example 125 and 2-(2-chlorophenyl)ethylamine according to the same methods as those of Reference Example 19 and Example 1, the title compound was obtained as colorless crystals having a melting point of 78° C. (dec)

$^1$H NMR (free base; 200 MHz, CDCl$_3$) δ 1.54-1.79 (4H, m), 2.19 (3H, s), 2.37 (1H, br), 2.48 (2H, t, J=7.0 Hz), 2.57-2.65 (2H, m), 2.87-2.98 (6H, m), 3.69 (2H, t, J 5.8 Hz), 4.67 (2H, s), 7.11-7.34 (5H, m), 7.74-7.80 (2H, m).

Example 219

1-(2-Acetyl-1,2,3,4-tetrahydro-7-isoquinolinyl)-5-{ [2-(2-methoxyphenyl)ethyl]amino}-1-pentanone hydrochloride

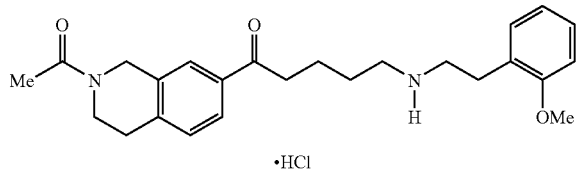

·HCl

Using 1-(2-acetyl-1,2,3,4-tetrahydro-7-isoquinolinyl)-5-chloro-1-pentanone obtained in Reference Example 125 and 2-(2-methoxyphenyl)ethylamine according to the same methods as those of Reference Example 19 and Example 1, the title compound was obtained as colorless crystals having a melting point of 78° C. (dec).

$^1$H NMR (free base; 200 MHz, CDCl$_3$) δ 1.54-1.79 (4H, m), 2.19 (3H, s), 2.37 (1H, br), 2.48 (2H, t, J=7.0 Hz), 2.57-2.65 (2H, m), 2.87-2.98 (6H, m), 3.69 (2H, t, J=5.8 Hz), 3.80 (3H, s), 4.67 (2H, s), 7.11-7.34 (5H, m), 7.74-7.80 (2H, m).

Example 220

5-{(2-(2-Chlorophenyl)ethyl]amino}-1-(2,2-dioxide-1,3-dihydro-2,1,3-benzothiadiazol-5-yl)-1-pentanone hydrochloride

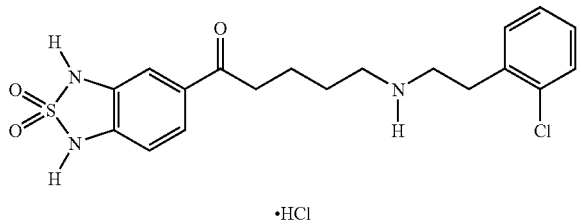

·HCl

Using tert-butyl 2-(2-chlorophenyl)ethyl[5-(2,2-dioxide-1,3-dihydro-2,1,3-benzothiadiazol-5-yl)-5-oxopentyl]carbamate obtained in Reference Example 148 according to the same method as that of Example 1, the title compound was obtained as colorless crystals.

MS m/z: 408 [M+H]$^+$

Example 221

5-{[2-(2-Chlorophenyl)ethyl]amino}-1-(1,3-dimethyl-2,2-dioxide-1,3-dihydro-2,1,3-benzothiadiazol-5-yl)-1-pentanone hydrochloride

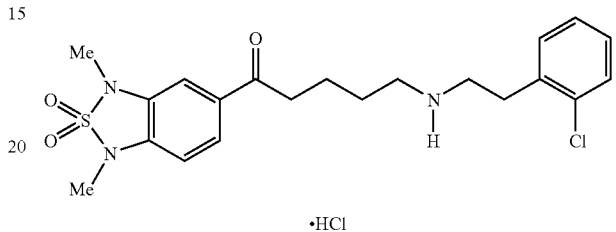

·HCl

Using tert-butyl 2-(2-chlorophenyl)ethyl[5-(1,3-dimethyl-2,2-dioxide-1,3-dihydro-2,1,3-benzothiadiazol-5-yl)-5-oxopentyl]carbamate obtained in Reference Example 149 according to the same method as that of Example 1, the title compound was obtained as colorless crystals having a melting point of 149 to 150° C.

$^1$H NMR (free base; 200 MHz, CDCl$_3$) δ 1.61-1.80 (5H, m), 2.48-2.65 (4H, m), 2.65-2.99 (4H, m), 3.34 (3H, s), 3.35 (3H, s), 6.75 (1H, d, J=8.4 Hz), 7.12-7.39 (5H, m), 7.67 (1H, d, J=8.4 Hz).

Example 222

5-[[2-(2-Chlorophenyl)ethyl](methyl)amino]-1-(1,3-dimethyl-2,2-dioxide-1,3-dihydro-2,1,3-benzothiadiazol-5-yl)-1-pentanone hydrochloride

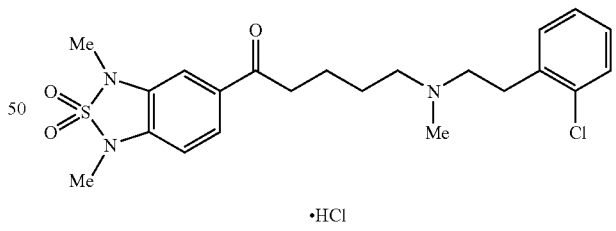

·HCl

Using 5-chloro-1-(1,3-dimethyl-2,2-dioxide-1,3-dihydro-2,1,3-benzothiadiazol-5-yl)-1-pentanone obtained in Reference Example 129 and N-[2-(2-chlorophenyl)ethyl]-N-methylamine according to the same method as that of Example 9, the title compound was obtained as pale yellow amorphous powders.

$^1$H NMR (free base; 200 MHz, CDCl$_3$) δ 1.61-1.80 (4H, m), 2.45 (3H, s), 2.48-2.65 (4H, m), 2.65-2.99 (4H, m), 3.34 (3H, s), 3.35 (3H, s), 6.75 (1H, d, J=8.4 Hz), 7.12-7.39 (5H, m), 7.67 (1H, d, J=8.4 Hz).

Example 223

1-(1,3-Dimethyl-2,2-dioxide-1,3-dihydro-2,1,3-benzothiadiazol-5-yl)-5-[[2-(2-methoxyphenyl)ethyl](methyl)amino]-1-pentanone hydrochloride

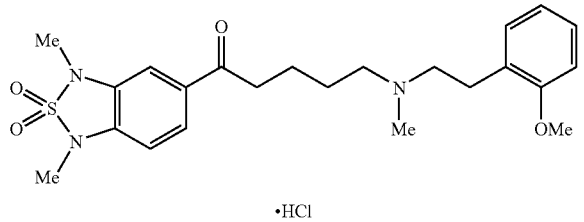

Using 5-chloro-1-(1,3-dimethyl-2,2-dioxide-1,3-dihydro-2,1,3-benzothiadiazol-5-yl)-1-pentanone obtained in Reference Example 129 and N-[2-(2-chlorophenyl)ethyl]-N-methylamine according to the same method as that of Example 9, the title compound was obtained as pale yellow amorphous powders.

$^1$H NMR (free base; 200 MHz, CDCl$_3$) δ 1.60-1.80 (4H, m), 2.34 (3H, s), 2.46-2.64 (4H, m), 2.77-2.84 (2H, m), 2.96 (2H, t, J=7.0 Hz), 3.34 (3H, s), 3.35 (3H, s), 3.81 (3H, s), 6.75 (1H, d, J=8.2 Hz), 6.82-6.91 (2H, m), 7.13-7.22 (2H, m), 7.38 (1H, s), 7.67 (1H, d, J=8.2 Hz).

Example 224

8-{5-[[2-(2-Chlorophenyl)ethyl](methyl)amino]pentanoyl}-5,6-dihydro-4H-imidazo[4,5,1-ij]quinolin-2(1H)-one hydrochloride

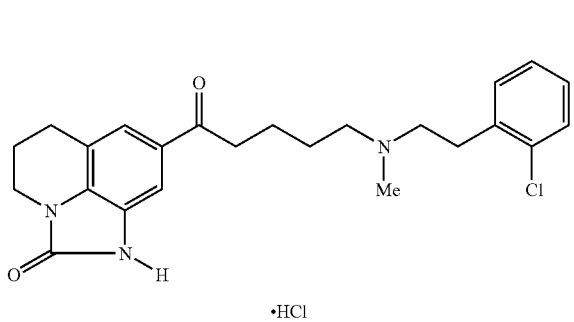

Using 8-(5-chloropentanoyl)-5,6-dihydro-4H-imidazo[4,5,1-ij]quinolin-2(1H)-one obtained in Reference Example 133 and N-[2-(2-chlorophenyl)ethyl]-N-methylamine according to the same method as that of Example 9, the title compound was obtained as pale yellow amorphous powders.

$^1$H NMR (free base; 200 MHz, CDCl$_3$) δ 1.58-1.77 (4H, m), 2.14 (2H, m), 2.35 (3H, s), 2.49 (2H, m), 2.58 (2H, m), 2.87-3.00 (6H, m), 3.89 (2H, m), 7.11-7.35 (5H, m), 7.58 (1H, m), 10.91 (1H, s).

Example 225

8-{5-[[2-(2-Methoxyphenyl)ethyl](methyl)amino]pentanoyl}-5,6-dihydro-4H-imidazo[4,5,1-ij]quinolin-2(1H)-one hydrochloride

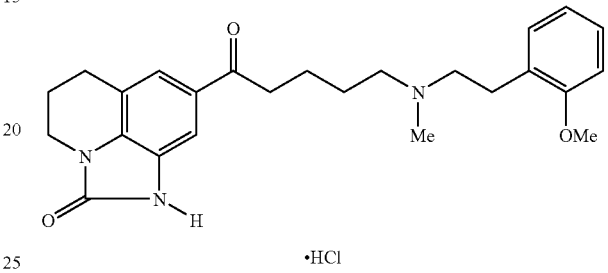

Using 8-(5-chloropentanoyl)-5,6-dihydro-4H-imidazo[4,5,1-ij]quinolin-2(1H)-one obtained in Reference Example 133 and N-[2-(2-methoxyphenyl)ethyl]-N-methylamine according to the same method as that of Example 9, the title compound was obtained as colorless crystals having a melting point of 187° C. (dec).

$^1$H NMR (free base; 200 MHz, CDCl$_3$) δ 1.58-1.77 (4H, m), 2.16 (2H, m), 2.36 (3H, s), 2.48-2.67 (4H, m), 2.78-3.00 (6H, m), 3.81 (3H, s), 3.88 (2H, m), 6.81-6.90 (3H, m), 7.12-7.16 (2H, m), 7.49 (1H, m), 7.58 (1H, m).

Example 226

8-{5-[[2-(2-Chlorophenyl)ethyl](methyl)amino]pentanoyl}-1-methyl-5,6-dihydro-4H-imidazo[4,5,1-ij]quinolin-2(1H)-one hydrochloride

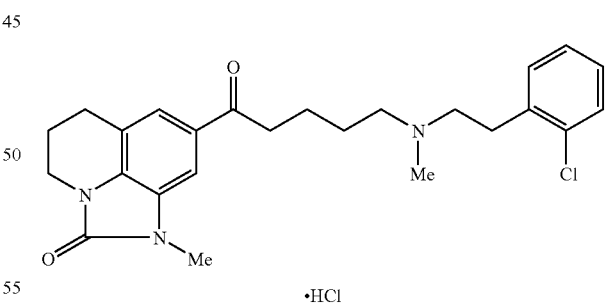

Using 8-(5-chloropentanoyl)-5,6-dihydro-4H-imidazo[4,5,1-ij]quinolin-2(1H)-one obtained in Reference Example 134 and N-[2-(2-chlorophenyl)ethyl]-N-methylamine according to the same method as that of Example 9, the title compound was obtained as pale yellow amorphous powders.

$^1$H NMR (free base; 200 MHz, CDCl$_3$) δ 1.58-1.78 (4H, m), 2.10 (2H, m), 2.34 (3H, s), 2.48 (2H, m), 2.60 (2H, m), 2.86-3.00 (5H, m), 3.22 (1H, m), 3.44 (3H, s), 3.84 (2H, m), 6.87 (1H, t, J=8.4 Hz), 7.11-7.34 (4H, m), 7.63 (1H, t, J=8.4 Hz).

Example 227

8-{5-[[2-(2-Methoxyphenyl)ethyl](methyl)amino]pentanoyl}-1-methyl-5,6-dihydro-4H-imidazo[4,5,1-ij]quinolin-2(1H)-one hydrochloride

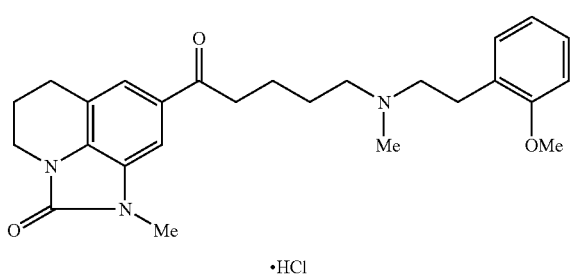

Using 8-(5-chloropentanoyl)-1-methyl-5,6-dihydro-4H-imidazo[4,5,1-ij]quinolin-2(1H)-one obtained in Reference Example 134 and N-[2-(2-methoxyphenyl)ethyl]-N-methylamine according to the same method as that of Example 9, the title compound was obtained as pale yellow amorphous powders.

$^1$H NMR (free base; 200 MHz, CDCl$_3$) δ 1.59-1.78 (4H, m), 2.10 (2H, m), 2.34 (3H, s), 2.45-2.63 (5H, m), 2.78 (2H, m), 2.93 (2H, m), 3.22 (1H, m), 3.44 (3H, s), 3.82 (3H, s), 3.88 (2H, m), 6.82-6.91 (3H, m), 7.12-7.34 (2H, m), 7.63 (1H, t, J=8.4 Hz).

Example 228

(±)-6-(3-{[2-(2-Chlorophenyl)ethyl]amino}propyl)-1,3-dimethyl-3,6,7,8-tetrahydro-1H-naphtho[2,3-d]imidazole-2,5-dione hydrochloride

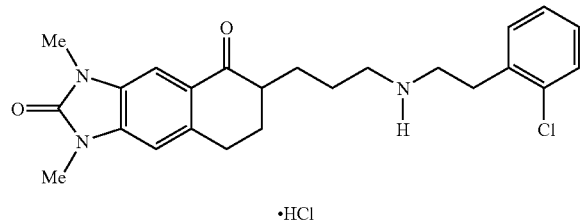

Using tert-butyl (±)-2-(2-chlorophenyl)ethyl[3-(1,3-dimethyl-2,5-dioxo-2,3,5,6,7,8-hexahydro-1H-naphtho[2,3-d]imidazol-6-yl)propyl]carbamate obtained in Reference Example 150 according to the same method as that of Example 1, the title compound was obtained as colorless crystals having a melting point of 201 to 203° C.

$^1$H NMR (free base; 200 MHz, CDCl$_3$) δ 1.58-1.68 (4H, m), 1.93 (3H, m), 2.25 (1H, m), 2.51 (2H, m), 2.65 (2H, m), 2.90 (2H, m), 3.03 (2H, m), 3.42 (3H, s), 3.43 (3H, s), 6.76 (1H, s), 7.11-7.34 (4H, m), 7.65 (1H, s).

Example 229

(±)-6-{3-[[2-(2-Chlorophenyl)ethyl](methyl)amino]propyl}-1,3-dimethyl-3,6,7,8-tetrahydro-1H-naphtho[2,3-d]imidazole-2,5-dione hydrochloride

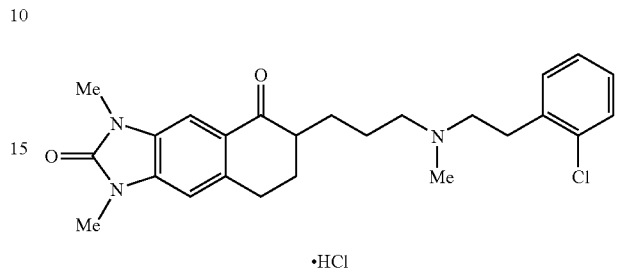

Using (±)-6-(3-chloropropyl)-1,3-dimethyl-3,6,7,8-tetrahydro-1H-naphtho[2,3-d]imidazole-2,5-dione obtained in Reference Example 141 and N-[2-(2-chlorophenyl)ethyl]-N-methylamine according to the same method as that of Example 9, the title compound was obtained as colorless crystals having a melting point of 201° C. (dec).

$^1$H NMR (free base; 200 MHz, CDCl$_3$) δ 1.58-1.68 (4H, m), 1.93 (2H, m), 2.25 (1H, m), 2.36 (3H, s), 2.51 (2H, m), 2.65 (2H, m), 2.90 (2H, m), 3.03 (2H, m), 3.42 (3H, s), 3.43 (3H, s), 6.76 (1H, s), 7.11-7.34 (4H, m), 7.65 (1H, s).

Example 230

(±)-6-{3-[[2-(2-Methoxyphenyl)ethyl](methyl)amino]propyl}-1,3-dimethyl-3,6,7,8-tetrahydro-1H-naphtho(2,3-d]imidazole-2,5-dione hydrochloride

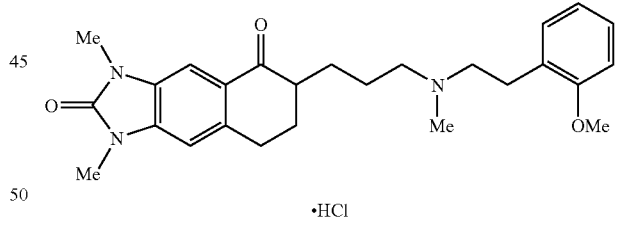

Using (±)-6-(3-chloropropyl)-1,3-dimethyl-3,6,7,8-tetrahydro-1H-naphtho[2,3-d]imidazole-2,5-dione obtained in Reference Example 141 and N-[2-(2-methoxyphenyl)ethyl]-N-methylamine according to the same method as that of Example 9, the title compound was obtained as colorless crystals having a melting point of 190 to 191° C.

$^1$H NMR (free base; 200 MHz, CDCl$_3$) δ 1.56-1.67 (4H, m), 1.94 (2H, m), 2.24 (1H, m), 2.36 (3H, s), 2.48 (2H, m), 2.61 (2H, m), 2.80 (2H, m), 3.04 (2H, m), 3.41 (3H, s), 3.42 (3H, s), 3.82 (3H, s), 6.76-6.91 (3H, m), 7.13-7.22 (2H, m), 7.65 (1H, s).

Example 231

(±)-6-(4-{[2-(2-Chlorophenyl)ethyl]amino}butyl)-1,3-dimethyl-3,6,7,8-tetrahydro-1H-naphtho[2,3-d]imidazole-2,5-dione hydrochloride

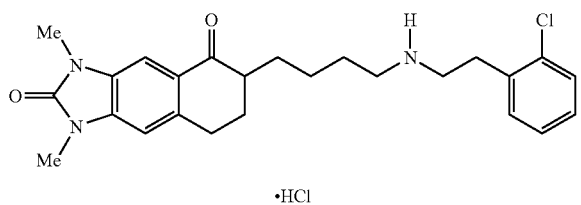

Using (±)-6-(4-chlorobutyl)-1,3-dimethyl-3,6,7,8-tetrahydro-1H-naphtho[2,3-d]imidazole-2,5-dione obtained in Reference Example 142 and 2-(2-chlorophenyl)ethylamine according to the same methods as those of Reference Example 19 and Example 1, the title compound was obtained as pale yellow amorphous powders.

$^1$H NMR (free base; 200 MHz, CDCl$_3$) δ 1.58-1.68 (6H, m), 1.98 (2H, m), 2.22 (1H, m), 2.38 (1H, br), 2.41-2.50 (2H, m), 2.57-2.65 (2H, m), 2.87-2.95 (2H, m), 2.99-3.06 (2H, m), 3.41 (3H, s), 3.42 (3H, s), 6.75 (1H, s), 7.11-7.34 (4H, m), 7.65 (1H, s).

Example 232

(±)-6-{4-[[2-(2-Chlorophenyl)ethyl](methyl)amino]butyl}-1,3-dimethyl-3,6,7,8-tetrahydro-1H-naphtho[2,3-d]imidazole-2,5-dione hydrochloride

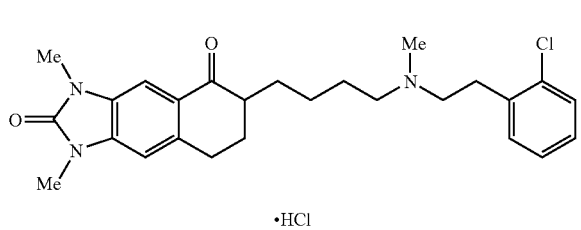

Using (±)-6-(4-chlorobutyl)-1,3-dimethyl-3,6,7,8-tetrahydro-1H-naphtho[2,3-d]imidazole-2,5-dione obtained in Reference Example 142 and N-[2-(2-chlorophenyl)ethyl]-N-methylamine according to the same method as that of Example 9, the title compound was obtained as colorless crystals having, a melting point of 202 to 204° C.

$^1$H NMR (free base; 200 MHz, CDCl$_3$) δ 1.58-1.68 (6H, m), 1.98 (2H, m), 2.22 (1H, m), 2.34 (3H, s), 2.41-2.50 (2H, m), 2.57-2.65 (2H, m), 2.87-2.95 (2H, m), 2.99-3.06 (2H, m), 3.41 (3H, s), 3.42 (3H, s), 6.75 (1H, s), 7.11-7.34 (4H, m), 7.65 (1H, s).

Example 233

(±)-6-{4-[[2-(2-Methoxyphenyl)ethyl](methyl)amino]butyl}-1,3-dimethyl-3,6,7,8-tetrahydro-1H-naphtho[2,3-d]imidazole-2,5-dione hydrochloride

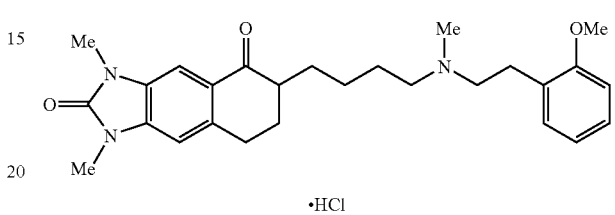

Using (±)-6-(4-chlorobutyl)-1,3-dimethyl-3,6,7,8-tetrahydro-1H-naphtho[2,3-d]imidazole-2,5-dione obtained in Reference Example 142 and N-[2-(2-chlorophenyl)ethyl]-N-methylamine according to the same method as that of Example 9, the title compound was obtained as pale yellow amorphous powders.

$^1$H NMR (free base; 200 MHz, CDCl$_3$) δ 1.58-1.68 (6H, m), 1.98 (2H, m), 2.22 (1H, m), 2.35 (3H, s), 2.44-2.52 (2H, m), 2.57-2.65 (2H, m), 2.75-2.84 (2H, m), 3.01-3.06 (2H, m), 3.41 (3H, s), 3.42 (3H, s), 3.82 (3H, s), 6.74-6.91 (3H, m), 7.13-7.21 (2H, m), 7.65 (1H, s).

Example 234

(±)-2-{3-[[2-(2-Chlorophenyl)ethyl](methyl)amino]propyl}-5,6-dimethoxy-1-indanone hydrochloride

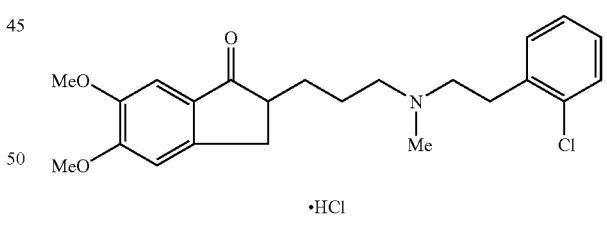

Using (±)-2-(3-chloropropyl)-5,6-dimethoxy-1-indanone obtained in Reference Example 146 and N-[2-(2-chlorophenyl)ethyl]-N-methylamine according to the same method as that of Example 9, the title compound was obtained as pale yellow amorphous powders.

$^1$H NMR (free base; 200 MHz, CDCl$_3$) δ 1.48 (1H, m), 1.59 (2H, m), 1.94 (1H, m), 2.34 (3H, s), 2.47 (2H, t, J=7.6 Hz), 2.58-2.75 (4H, m), 2.90 (2H, m), 3.24 (1H, dd, J=17.1, 7.8 Hz), 3.90 (3H, s), 3.96 (3H, s), 6.86 (1H, s), 7.08-7.32 (5H, m).

Example 235

(±)-5,6-Dimethoxy-2-{3-[[2-(2-methoxyphenyl)ethyl](methyl)amino]propyl}-1-indanone hydrochloride

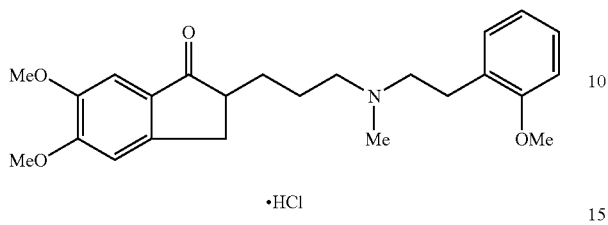

Using (±)-2-(3-chloropropyl)-5,6-dimethoxy-1-indanone obtained in Reference Example 146 and N-[2-(2-methoxyphenyl)ethyl]-N-methylamine according to the same method as that of Example 9, the title compound was obtained as pale yellow amorphous powders.

$^1$H NMR (free base; 200 MHz, CDCl$_3$) δ 1.46-1.70 (4H, m), 1.95 (2H, m), 2.33 (3H, s), 2.44-2.83 (6H, m), 3.25 (1H, dd, J=17.2, 7.4 Hz), 3.81 (3H, s), 3.91 (3H, s), 3.97 (3H, s), 6.81-6.90 (3H, m), 7.12-7.21 (3H, m).

Example 236

(±)-2-{4-[[2-(2-Chlorophenyl)ethyl](methyl)amino]butyl}-5,6-dimethoxy-1-indanone hydrochloride

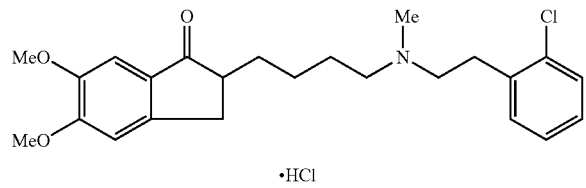

Using (±)-2-(4-chlorobutyl)-5,6-dimethoxy-1-indanone obtained in Reference Example 147 and N-[2-(2-chlorophenyl)ethyl]-N-methylamine according to the same method as that of Example 9, the title compound was obtained as pale yellow amorphous powders.

$^1$H NMR (free base; 200 MHz, CDCl$_3$) δ 1.45-1.59 (4H, m), 1.99 (2H, m), 2.33 (3H, s), 2.45 (2H, t, J=7.6 Hz), 2.54-2.62 (4H, m), 2.80 (2H, m), 3.25 (1H, dd, J=17.2, 7.4 Hz), 3.92 (3H, s), 3.96 (3H, s), 6.87 (1H, s), 7.11-7.34 (5H, m).

Example 237

(±)-5,6-Dimethoxy-2-{4-[(2-(2-methoxyphenyl)ethyl](methyl)amino]butyl}-1-indanone hydrochloride

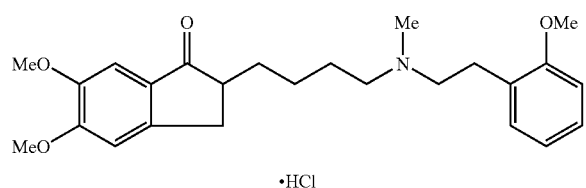

Using (±)-2-(4-chlorobutyl)-5,6-dimethoxy-1-indanone obtained in Reference Example 147 and N-[2-(2-methoxyphenyl)ethyl]-N-methylamine according to the same method as that of Example 9, the title compound was obtained as pale yellow amorphous powders.

$^1$H NMR (free base; 200 MHz, CDCl$_3$) δ 1.45-1.59 (4H, m), 1.99 (2H, m), 2.32 (3H, s), 2.45 (2H, t, J=7.6 Hz), 2.54-2.62 (4H, m), 2.80 (2H, m), 3.25 (1H, dd, J=17.2, 7.4 Hz), 3.80 (3H, s), 3.90 (3H, s), 3.96. (3H, s), 6.81-6.91 (3H, m), 7.13-7.21 (3H, m).

Example 238

8-[5-(5-Methoxy-3,4-dihydro-2(1H)-isoquinolinyl)pentanoyl]-5,6-dihydro-4H-imidazo[4,5,1-ij]quinolin-2(1H)-one hydrochloride

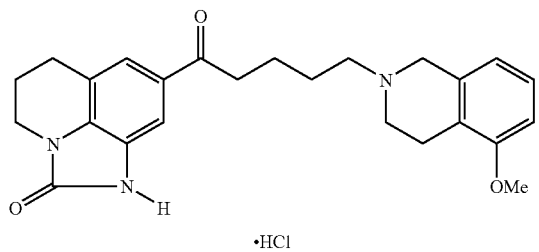

Using 8-(5-chloropentanoyl)-5,6-dihydro-4H-imidazo[4,5,1-ij]quinolin-2(1H)-one obtained in Reference Example 133 and 5-methoxy-1,2,3,4-tetrahydroisoquinoline according to the same method as that of Example 9, the title compound was obtained as pale yellow amorphous powders.

$^1$H NMR (free base; 200 MHz, CDCl$_3$) δ 1.69-1.83 (4H, m), 2.10 (2H, m), 2.57 (2H, t, J=6.0 Hz), 2.86 (2H, m), 3.01 (2H, m), 3.18 (2H, m), 3.61 (2H, s), 3.80 (3H, s), 3.72-3.90 (4H, m), 6.63-6.69 (2H, m), 6.86 (1H, t, J=8.4 Hz), 7.08 (1H, t, J=8.0 Hz), 7.56 (1H, m), 9.56 (1H, br).

Example 239

8-[5-(5-Methoxy-3,4-dihydro-2(1H)-isoquinolinyl)pentanoyl]-1-methyl-5,6-dihydro-4H-imidazo[4,5,1-ij]quinolin-2(1H)-one hydrochloride

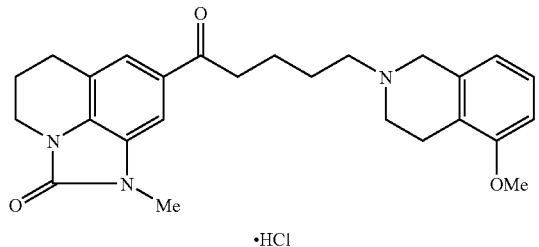

Using 8-(5-chloropentanoyl)-1-methyl-5,6-dihydro-4H-imidazo[4,5,1-ij]quinolin-2(1H)-one obtained in Reference Example 134 and 5-methoxy-1,2,3,4-tetrahydroisoquinoline according to the same method as that of Example 9, the title compound was obtained as pale yellow amorphous powders.

$^1$H NMR (free base; 200 MHz, CDCl$_3$) δ 1.69-1.83 (4H, m), 2.05 (2H, m), 2.54 (2H, t, J=6.0 Hz), 2.70-2.87 (4H, m), 3.00 (2H, m), 3.22 (2H, t, J=6.0 Hz), 3.42 (3H, s), 3.59 (2H, s), 3.80 (3H, s), 3.81-3.88 (2H, m), 6.64 (2H, t, J=8.1 Hz), 6.67 (1H, d, J=8.1 Hz), 7.80 (1H, t, J=7.8 Hz), 7.56 (1H, m).

Example 240

8-[5-(5-Chloro-3,4-dihydro-2(1H)-isoquinolinyl)pentanoyl]-5,6-dihydro-4H-pyrrolo[3,2,1-ij]quinolin-2(1H)-one hydrochloride

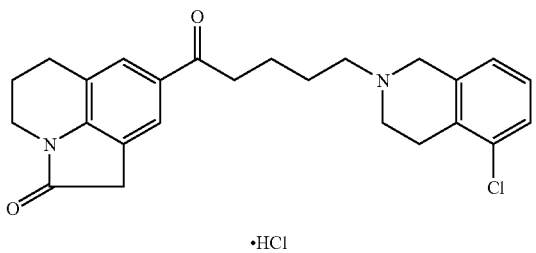

·HCl

Using 8-(5-chloropentanoyl)-5,6-dihydro-4H-pyrrolo[3,2,1-ij]quinolin-2(1H)-one obtained in Reference Example 3 and 5-chloro-1,2,3,4-tetrahydroisoquinoline according to the same method as that of Example 9, the title compound was obtained as pale yellow amorphous powders.

$^1$H NMR (free base; 200 MHz, CDCl$_3$) δ 1.68-1.86 (4H, m), 2.01 (2H, m), 2.55 (2H, t, J=7.2 Hz), 2.70-2.83 (6H, m), 2.97 (2H, t, J=7.0 Hz), 3.50 (2H, s), 3.58 (2H, s), 3.72 (2H, t, J=6.0 Hz), 6.91 (1H, d, J=7.2 Hz), 7.04 (1H, t, J=7.8 Hz), 7.17 (1H, t, J=7.6 Hz), 7.72 (2H, s).

Example 241

8-[5-(5-Methoxy-3,4-dihydro-2(1H)-isoquinolinyl)pentanoyl]-5,6-dihydro-4H-pyrrolo[3,2,1-ij]quinolin-2(1H)-one hydrochloride

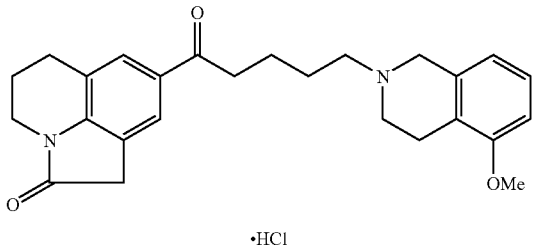

·HCl

Using 8-(5-chloropentanoyl)-5,6-dihydro-4H-pyrrolo[3,2,1-ij]quinolin-2(1H)-one obtained in Reference Example 3 and 5-methoxy-1,2,3,4-tetrahydroisoquinoline according to the same method as that of Example 9, the title compound was obtained as pale yellow amorphous powders.

$^1$H NMR (free base; 200 MHz, CDCl$_3$) δ 1.66-1.85 (4H, m), 1.98 (2H, m), 2.54 (2H, t, J=7.0 Hz), 2.71-2.81 (6H, m), 2.97 (2H, t, J=6.6 Hz), 3.48 (2H, s), 3.58 (2H, s), 3.72 (2H, t, J=6.4 Hz), 3.80 (3H, s), 6.64 (2H, t, J=7.0 Hz), 7.08 (1H, t, J=7.6 Hz), 7.73 (2H, s).

Example 242

1-(1,3-Dimethyl-2,2-dioxide-1,3-dihydro-2,1,3-benzothiadiazol-5-yl)-5-(5-methoxy-3,4-dihydro-2(1H)-isoquinolinyl)-1-pentanone hydrochloride

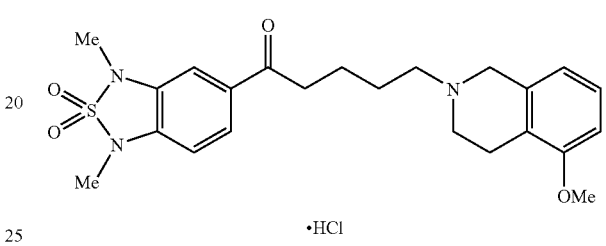

·HCl

Using 5-chloro-1-(1,3-dimethyl-2,2-dioxide-1,3-dihydro-2,1,3-benzothiadiazol-5-yl)-1-pentanone obtained in Reference Example 129 and 5-methoxy-1,2,3,4-tetrahydroisoquinoline according to the same method as that of Example 9, the title compound was obtained as pale yellow amorphous powders.

$^1$H NMR (free base; 200 MHz, CDCl$_3$) δ 1.68-1.85 (4H, m), 2.58 (2H, t, J=7.0 Hz), 2.72 (4H, m), 2.98 (2H, t, J=7.4 Hz), 3.29 (3H, s), 3.30 (3H, s), 3.58 (2H, s), 3.79 (3H, s), 6.61-6.66 (3H, m), 7.08 (1H, t, J=8.0 Hz), 7.34 (1H, m), 7.65 (1H, m).

Example 243

(±)-2-[4-(5-Chloro-3,4-dihydro-2(1H)-isoquinolinyl)butyl]-5,6-dimethoxy-1-indanone

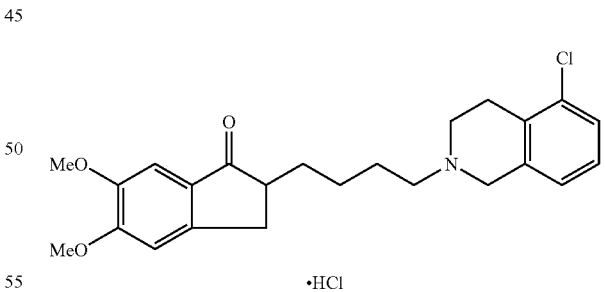

·HCl

Using (±)-2-(4-chlorobutyl)-5,6-dimethoxy-1-indanone obtained in Reference Example 147 and 5-chloro-1,2,3,4-tetrahydroisoquinoline according to the same method as that of Example 9, the title compound was obtained as pale yellow amorphous powders.

$^1$H NMR (free base; 200 MHz, CDCl$_3$) δ 1.49-1.68 (4H, m), 1.95 (2H, m), 2.52 (2H, t, J=7.6 Hz), 2.62-2.78 (4H, m), 2.87 (2H, m), 3.24 (1H, dd, J=16.8, 7.2 Hz), 3.59 (2H, s), 3.90 (3H, s), 3.96 (3H, s), 6.87-6.94 (2H, m), 7.05 (1H, t, J=7.8 Hz), 7.18 (2H, m).

Example 244

(±)-5,6-Dimethoxy-2-[4-(5-methoxy-3,4-dihydro-2 (1H)-isoquinolinyl)butyl]-indanone

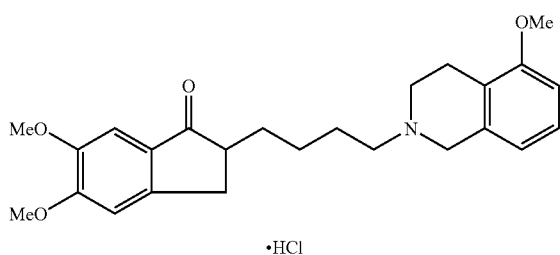

Using (±)-2-(4-chlorobutyl)-5,6-dimethoxy-1-indanone obtained in Reference Example 147 and 5-methoxy-1,2,3,4-tetrahydroisoquinoline according to the same method as that of Example 9, the title compound was obtained as pale yellow amorphous powders.

$^1$H NMR (free base; 200 MHz, CDCl$_3$) δ 1.50-1.68 (4H, m), 1.97 (2H, m), 2.51 (2H, t, J=8.2 Hz), 2.62-2.76 (6H, m), 3.23 (1H, dd, J=17.2, 7.6 Hz), 3.59 (2H, s), 3.80 (3H, s), 3.90 (3H, s), 3.96 (3H, s), 6.62-6.67 (2H, m), 6.87 (1H, s), 7.08 (1H, t, J=7.8 Hz), 7.17 (1H, s).

Example 245

8-(5-{[2-(1H-indol-3-yl)ethyl]amino}pentanoyl)-1,2, 5,6-tetrahydro-4H-pyrrolo[3,2,1-ij]quinolin-4-one hydrochloride

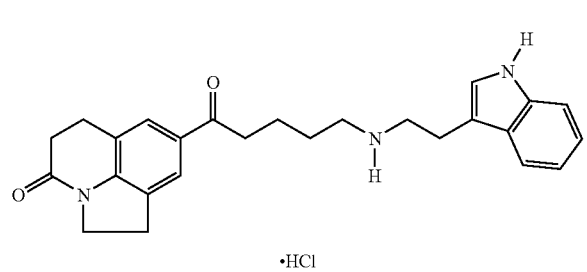

Using tert-butyl 2-(1H-indol-3-yl)ethyl[5-oxo-5-(4-oxo-1,2,5,6-tetrahydro-4H-pyrrolo[3,2,1-ij]quinolin-8-yl)pentyl]carbamate (822 mg) obtained in Reference Example 151 according to the same method as that of Example 1, the title compound was obtained as colorless crystals (630 mg) having a melting point of 179 to 180° C.

$^1$H NMR (300 MHz, DMSO-d$_6$) δ 1.55-1.80 (4H, m), 2.59 (2H, t, J=7.8 Hz), 2.80-3.25 (12H, m), 3.98 (2H, t, J=8.4 Hz), 7.00 (1H, t, J=7.8 Hz), 7.09 (1H, t, J=7.8 Hz), 7.24 (1H, d, J=2.1 Hz), 7.37 (1H, d, J=7.8 Hz), 7.61 (1H, d, J=7.8 Hz), 7.73 (1H, s), 7.74 (1H, s), 9.00-9.20 (2H, br), 11.0 (1H, s).

Example 246

(±)-8-{5-[(2-Hydroxy-2-phenyethyl)amino]pentanoyl}-1,2,5,6-tetrahydro-4H-pyrrolo[3,2,1-ij] quinolin-4-one hydrochloride

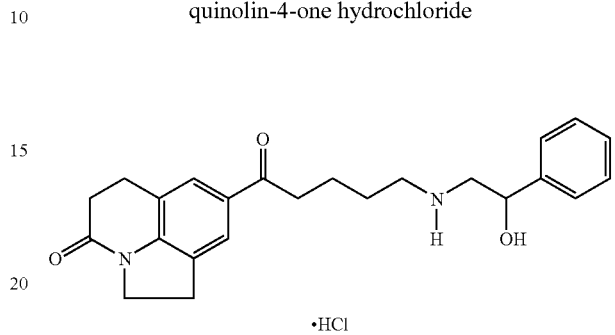

Using tert-butyl (±)-2-hydroxy-2-phenylethyl][5-oxo-5-(4-oxo-1,2,5,6-tetrahydro-4H-pyrrolo[3,2,1-ij]quinolin-8-yl)pentyl]carbamate (1.29 g) obtained in Reference Example 152 according to the same method as that of Example 1, the title compound was obtained as pale yellow crystals (680 mg).

$^1$H NMR (300 MHz, DMSO-d$_6$) δ 1.55-1.80 (4H, m), 2.59 (2H, t, J=7.8 Hz), 2.90-3.25 (10H, m), 3.99 (2H, t, J=8.4 Hz), 4.98 (1H, d, J=8.4 Hz), 6.10-6.30 (1H, br), 7.30-7.50 (5H, m), 7.73 (1H, s), 7.74 (1H, s), 8.85-9.25 (2H, br).

Example 247

(±)-8-(5-{[2-Hydroxy-2-(3-hydroxyphenyl)ethyl] amino}pentanoyl)-1,2,5,6-tetrahydro-4H-pyrrolo[3, 2,1-ij]quinolin-4-one hydrochloride

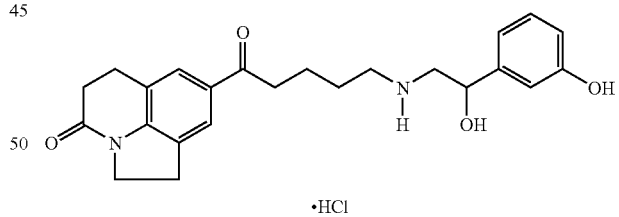

Using tert-butyl (±)-2-hydroxy-2-(3-hydroxyphenyl)ethyl [5-oxo-5-(4-oxo-1,2,5,6-tetrahydro-4H-pyrrolo[3,2,1-ij] quinolin-8-yl)pentyl]carbamate (201 mg) obtained in Reference Example 153 according to the same method as that of Example 1, the title compound was obtained as colorless crystals (169 mg) having a melting point of 178 to 179° C.

$^1$H NMR (300 MHz, DMSO-d$_6$) δ 1.55-1.80 (4H, m), 2.59 (2H, t, J=7.8 Hz), 2.80-3.60 (10H, m), 3.99 (2H, t, J=8.4 Hz), 4.90 (1H, d, J=9.9 Hz), 5.90-6.30 (1H, br), 6.65-6.90 (3H, m), 7.16 (1H, t, J=7.8 Hz), 7.73 (1H, s), 7.74 (1H, s), 8.65-8.85 (1H, br), 9.00-9.25 (1H, br), 9.40-9.65 (1H, br).

Example 248

8-(5-{[2-(2-Chloro-4-fluorophenyl)ethyl]amino}pentanoyl)-5,6-dihydro-4H-pyrrolo[3,2,1-ij]quinolin-2(1H)-one hydrochloride

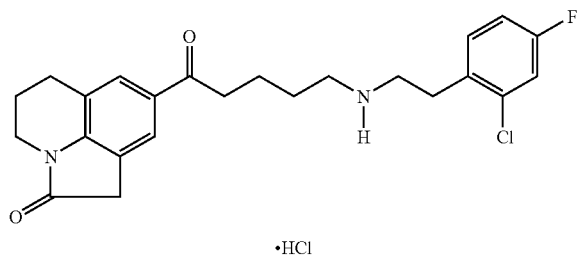

·HCl

Using tert-butyl 2-(2-chloro-4-fluorophenyl)ethyl[5-oxo-5-(2-oxo-1,2,5,6-tetrahydro-4H-pyrrolo[3,2,1-ij]quinolin-8-yl)pentyl]carbamante (440 mg) obtained in Reference Example 155 according to the same methods as that of Example 1, the title compound (282 mg) was obtained as pale yellow crystals having a melting point of 128 to 129° C. (dec).

$^1$H NMR (400 MHz, DMSO-$d_6$) δ 1.52-1.73 (4H, m), 1.90-1.94 (2H, m), 2.77 (2H, t, J=7 Hz), 2.95-3.09 (8H, m), 3.57 (2H, s), 3.60 (2H, t, J=6 Hz), 7.22 (1H, dt, J=2.7, 8.5 Hz), 7.43-7.47 (2H, m), 7.71 (1H, s), 7.75 (1H, s), 9.22 (2H, s).

IR (KBr) vcm$^{-1}$: 3491, 2945, 2774, 1712, 1671, 1604, 1495, 1346, 1153.

Example 249

1-(1-Acetyl-2,3-dihydro-1H-indol-5-yl)-5-{[2-(2-chloro-4-fluorophenyl)ethyl]amino}pentan-1-one hydrochloride

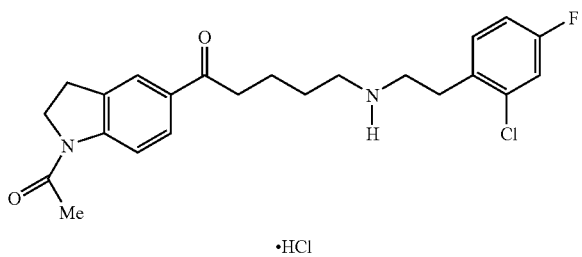

·HCl

Using tert-butyl 5-(1-acetyl-2,3-dihydro-1H-indol-5-yl)-5-oxopentyl[2-(2-chloro-4-fluorophenyl)ethyl]carbamate (540 mg) obtained in Reference Example 156 according to the same method as that of Example 1, the title compound (275 mg) was obtained as colorless crystals having a melting point of 176 to 177° C. (dec).

$^1$H NMR (400 MHz, DMSO-$d_6$) δ 1.51-1.73 (4H, m), 2.18 (3H, s), 2.95-3.08 (8H, m), 3.17 (2H, t, J =8.3Hz), 4.14 (2H, t, J=8.5Hz), 7.22 (1H, dt, J=2.7, 8.5Hz), 7.43-7.47 (2H, m), 7.82 (1H, s), 7.83 (1H, t, J=8.0 Hz), 8.08 (1H, d, J=8.5 Hz), 9.17 (2H, s).

IR (KBr) vcm$^{-1}$: 3436, 2954, 2780, 1667, 1604, 1494, 1442, 1403, 1338, 1260, 1233.

Example 250

6-(5-{[2-(2-Chloro-4-fluorophenyl)ethyl]amino}pentanoyl)-1-methyl-3,4-dihydroquinolin-2(1H)-one hydrochloride

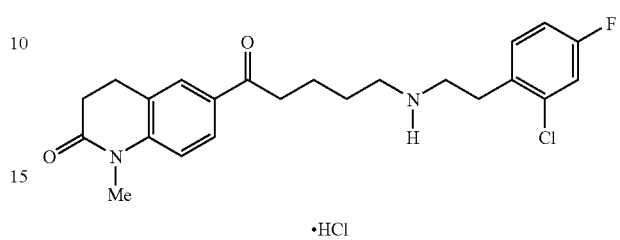

·HCl

Using tert-butyl 2-(2-chloro-4-fluorophenyl)ethyl[5-(1-methyl-2-oxo-1,2,3,4-tetrahydroquinolin-6-yl)-5-oxopentyl]carbamate (460 mg) obtained in Reference Example 157 according to the same method as that of Example 1, the title compound (356 mg) was obtained as pale yellow crystals having a melting point of 169 to 170° C. (dec).

$^1$H NMR (400 MHz, DMSO-$d_6$) δ 1.58-1.65 (4H, m), 2.49 (2H, t, J=7.0 Hz), 2.83-3.04 (10H, m), 3.19 (3H, s), 7.09 (1H, d, J=8.5 Hz), 7.13 (1H, dt, J=2.6, 8.5 Hz), 7.33-7.40 (2H, m), 7.76 (1H, s), 7.80 (1H, d, J=8.3 Hz), 9.33 (2H, s).

IR (KBr) vcm$^{-1}$: 3433, 2953, 2790, 1673, 1603, 1494, 1354, 1128.

Example 251

8-[5-({2-[2-(Trifluoromethoxy)phenyl]ethyl}amino)pentanoyl]-5,6-dihydro-4H-pyrrolo[3,2,1-ij]quinolin-2(1H)-one hydrochloride

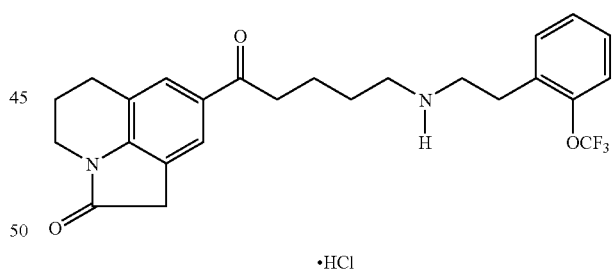

·HCl

Using tert-butyl 5-oxo-5-(2-oxo-1,2,5,6-tetrahydro-4H-pyrrolo[3,2,1-ij]quinolin-8-yl)pentyl}2-[2-(trifluoromethoxy)phenyl]ethyl)carbamate (200 mg) obtained in Reference Example 158 according to the same method as that of Example 1, the title compound (95 mg) was obtained as pale yellow crystals having a melting point of 71 to 72° C. (dec).

$^1$H NMR (400 MHz, DMSO-$d_6$) δ 1.66-1.68 (4H, m), 1.89-1.95 (2H, m), 2.77 (2H, t, J=6 Hz), 2.97-3.06 (8H, m), 3.58 (2H, s), 3.61 (2H, t, J=6 Hz), 7.35-7.47 (4H, m), 7.72 (1H, s), 7.76 (1H, s), 9.06 (2H, br.s).

IR (KBr) vcm$^{-1}$: 3422, 2943, 1711, 1605, 1496, 1344, 1256, 1154.

Example 252

1-(1-Acetyl-2,3-dihydro-1H-indol-5-yl)-5-({2-[2-(trifluoromethoxy)phenyl]ethyl}amino)pentan-1-one hydrochloride

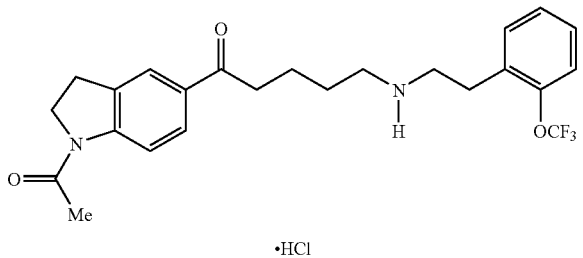

Using tert-butyl 5-(1-acetyl-2,3-dihydro-1H-indol-5-yl)-5-oxopentyl{2-[2-(trifluoromethoxy)phenyl]ethyl}carbamate (450 mg) obtained in Reference Example 159 according to the same method as that of Example 1, the title compound (274 mg) was obtained as colorless crystals having a melting point of 180 to 182° C. (dec).

$^1$H NMR (400 MHz, DMSO-$d_6$) δ 1.65-1.71 (4H, m), 2.18 (3H, s), 2.96-3.07 (8H, m), 3.17 (2H, t, J=8.3 Hz), 4.14 (2H, t, J=8.3 Hz), 7.35-7.48 (4H, m), 7.82 (1H, s), 7.83 (1H, t, J=8.3 Hz), 8.08 (1H, d, J=8.3 Hz), 9.20 (2H, br.s).

IR (KBr) vcm$^{-1}$: 3432, 2953, 2766, 1676, 1601, 1492, 1442, 1398, 1260, 1177.

Example 253

1-Methyl-6-[5-({2-[2-(trifluoromethoxy)phenyl]ethyl}amino)pentanoyl]-3,4-dihydroquinolin-2(1H)-one hydrochloride

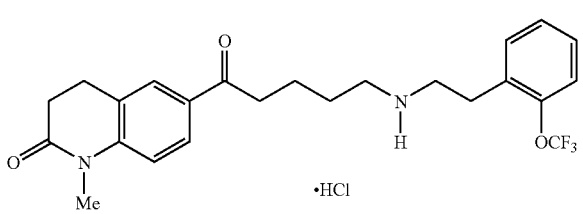

Using tert-butyl 5-(1-methyl-2-oxo-1,2,3,4-tetrahydroquinolin-6-yl)-5-oxopentyl{2-[2-(trifluoromethoxy)phenyl]ethyl}carbamate (435 mg) obtained in Reference Example 160 according to the same method as that of Example 1, the title compound (237 mg) was obtained as colorless crystals having a melting point of. 89 to 90° C. (dec).

$^1$H NMR (400 MHz, DMSO-$d_6$) δ 1.62-1.69 (4H, m), 2.58 (2H, t, J=7.0 Hz), 2.92-3.07 (10H, m), 3.28 (3H, s), 7.19. (1H, d, J=8.5 Hz), 7.35-7.48(4H, m), 7.84 (1H, s), 7.89 (1H, d, J=8.3 Hz), 9.11 (2H, br.s).

IR (KBr) vcm$^{-1}$: 3432, 2944, 1675, 1604, 1456, 1364, 1265, 1131.

Example 254

1,3-Dimethyl-5-[5-((2-[2-(trifluoromethoxy)phenyl]ethyl)amino)pentanoyl]-1,3-dihydro-2H-benzimidazol-2-one hydrochloride

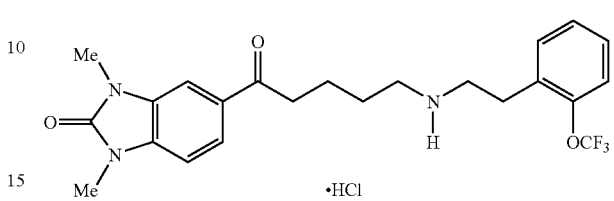

Using tert-butyl 5-(1,3-dimethyl-2-oxo-2,3-dihydro-1H-benzimidazol-5-yl)-5-oxopentyl{2-[2-(trifluoromethoxy)phenyl]ethyl}carbamate (240 mg) obtained in Reference Example 161 according to the same method as that of Example 1, the title compound (127 mg) was obtained as colorless crystals having a melting point of 133 to 134° C. (dec)

$^1$H NMR (400 MHz, DMSO-d6) δ 1.70-1.74 (4H, m), 2.98 (2H, br.s), 3.08-3.11 (6H, m), 3.36 (3H, s), 3.38 (3H, s), 7.24 (1H, d, J=8.3 Hz), 7.35-7.43 (3H, m), 7.46 (1H, dd, J=2.2, 7.0 Hz), 7.72. (1H, d, J=1.5 Hz), 7.80 (1H, dd, J=1.5, 8.3 Hz), 9.19 (2H, br.s).

IR (KBr) vcm$^{-1}$: 3496, 2954, 2782, 1720, 1675, 1513, 1456, 1255, 1213, 1178.

Example 255

8-(5-{[3-(2-Methoxyphenyl)propyl]amino}pentanoyl)-5,6-dihydro-4H-pyrrolo[3,2,1-ij]quinolin-2(1H)-one hydrochloride

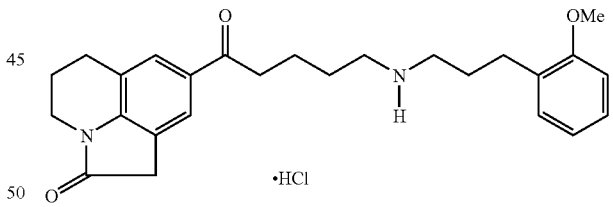

Using tert-butyl 3-(2-methoxyphenyl)propyl[5-oxo-5-(2-oxo-1,2,5,6-tetrahydro-4H-pyrrolo[3,2,1-ij]quinolin-8-yl)pentyl]carbamate (160 mg) obtained in Reference Example 162 according to the same method as that of Example 1, the title compound (113 mg) was obtained as pale yellow amorphous powders.

$^1$H NMR (400 MHz, DMSO-$d_6$) δ 1.64 (4H, br.s), 1.72-1.95 (4H, m), 2.59 (2H, t, J=6 Hz), 2.70-2.93 (6H, m), 2.98 (2H, br.s), 3.57 (2H, s), 3.60 (2H, br.s), 3.77 (3H, s), 6.87 (1H, t, J 7.3 Hz), 6.95 (1H, d, J=7.6 Hz), 7.14 (1H, d, J=7.3 Hz), 7.19 (1H, t, J=7.6 Hz), 7.71 (1H, s), 7.75 (1H, s), 8.81 (2H., br.s).

IR (KBr) vcm$^{-1}$: 3425, 2945, 1708, 1664, 1601, 1495, 1344, 1244, 1155, 759.

Example 256

1-(1-Acetyl-2,3-dihydro-1H-indol-5-yl)-5-{[3-(2-methoxyphenyl)propyl]amino}pentan-1-one hydrochloride

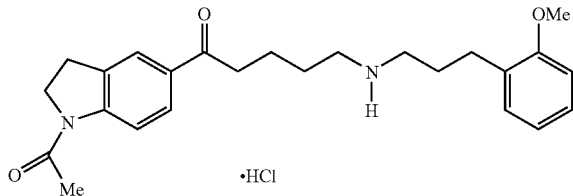

Using tert-butyl 5-(1-acetyl-2,3-dihydro-1H-indol-5-yl)-5-oxopentyl[3-(2-methoxyphenyl)propyl]carbamate (410 mg) obtained in Reference Example 163 according to the same method as that of Example 1, the title compound (290 mg) was obtained as colorless crystals having a melting point of 165 to 166° C. (dec).

$^1$H NMR (400 MHz, DMSO-$d_6$) δ 1.62-1.68 (4H, m), 1.85-1.95 (2H, m), 2.18 (3H, s), 2.59 (2H, t, J=7.3 Hz), 2.79-2.87 (4H, m), 2.98 (2H, t, J=7 Hz), 3.16 (2H, t, J=8.3 Hz), 3.77 (3H, s), 4.13 (2H, t, J=8.3 Hz), 6.89 (1H, t, J=7.6 Hz), 6.94 (1H, d, J=7.6 Hz), 7.15 (1H, d, J=7.6 Hz), 7.19 (1H, t, J=7.6 Hz), 7.81 (1H, s), 7.82. (1H, d, J=. 8.3 Hz), 8.08 (1H, d, J=8.3 Hz), 9.00. (2H, br.s).

IR (KBr) vcm$^{-1}$: 3436, 2945, 1676, 1661, 1602, 1492, 1438, 1399, 1334, 1243, 754.

Example 257

6-(5-{[3-(2-Methoxyphenyl)propyl]amino}pentanoyl)-1-methyl-3,4-dihydroquinolin-2(1H)-one hydrochloride

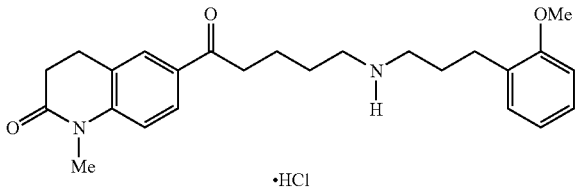

Using tert-butyl 3-(2-methoxyphenyl)propyl[5-(1-methyl-2-oxo-1,2,3,4-tetrahydroquinolin-6-yl)-5-oxopentyl]carbamate (410 mg) obtained in Reference Example 164 according to the same method as that of Example 1, the title compound (295 mg) was obtained as colorless crystals having a melting point of 88 to 89° C. (dec).

$^1$H NMR (400 MHz, DMSO-$d_6$) δ 1.57 (4H, br.s), 1.78-1.84 (2H, m), 2.47-2.53 (4H, m), 2.75-2.80 (4H, m), 2.85 (2H, t, J=7 Hz), 2.93 (2H, t, J=7 Hz), 3.19 (3H, s), 3.69 (3H, s), 6.79 (1H, t, J=7.3 Hz), 6.87 (1H, d, J=7.3 Hz), 7.07 (1H, d, J=7.3 Hz), 7.10 (1H, d, J=8.3 Hz), 7.11 (1H, t, J=7.3 Hz), 7.75 (1H, s), 7.81 (1H, d, J=8.3 Hz), 8.88 (2H, br.s).

IR (KBr) vcm$^{-1}$: 3434, 2948, 1672, 1603, 1495, 1464, 1360, 1245, 1128, 750.

Example 258

5-(5-{[3-(2-Methoxyphenyl)propyl]amino}pentanoyl)-1,3-dimethyl-1,3-dihydro-2H-benzimidazol-2-one hydrochloride

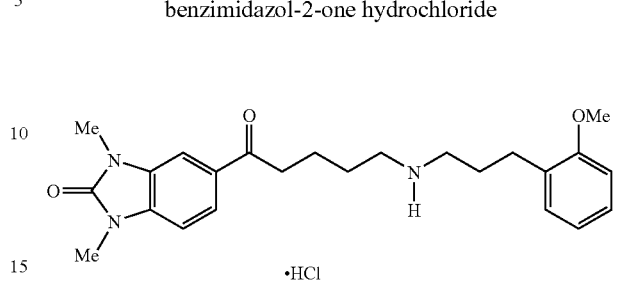

Using tert-butyl 5-(1,3-dimethyl-2-oxo-2,3-dihydro-1H-benzimidazol-5-yl)-5-oxopentyl[3-(2-methoxyphenyl)propyl]carbamate (380 mg) obtained in Reference Example 165 according to the same method as that of Example 1, the title compound (186 mg) was obtained as pale yellow amorphous powders.

$^1$H NMR (400 MHz, DMSO-d6) δ 1.53-1.63 (4H, m), 1.77-1.85 (2H, m), 2.51 (2H, t, J=7.5 Hz), 2.76-2.81 (4H, m), 2.98. (2H, t, J=6.6 Hz), 3.26 (3H, s), 3.29 (3H, s), 3.69 (3H, s), 6.78 (1H, t, J=7.3 Hz), 6.87 (1H, d, J=7.5 Hz), 7.06 (1H, d, J=7.5 Hz), 7.10 (1H, t, J=7.3 Hz), 7.15 (1H, d, J=8.3 Hz), 7.62 (1H, d, J=1.5 Hz), 7.70 (1H, dd, J=1.5, 8.3 Hz), 8.92 (2H, br.s).

IR (KBr) vcm$^{-1}$: 3443, 2943, 1715, 1673, 1621, 1512, 1495, 1462, 1244, 1200, 758.

Example 259

8-(5-{[2-(2-Ethoxyphenoxy)ethyl]amino}pentanoyl)-5,6-dihydro-4H-pyrrolo[3,2,1-ij]quinolin-2(1H)-one hydrochloride

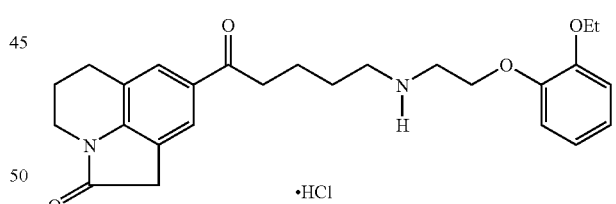

Using tert-butyl 2-(2-ethoxyphenoxy)ethyl[5-oxo-5-(2-oxo-1,2,5,6-tetrahydro-4H-pyrrolo[3,2,1-ij]quinolin-8-yl)pentyl]carbamate (205 mg) obtained in Reference Example 166 according to the same method as that of Example 1, the title compound (152 mg) was obtained as colorless crystals having a melting point of 110 to 113° C. (dec).

$^1$H NMR (400 MHz, DMSO-$d_6$) δ 1.31 (3H, t, J=6.6 Hz), 1.69 (4H, br.s), 1.91 (2H, br.s), 2.76 (2H, br.s), 3.00-3.08 (4H, m), 3.29 (2H, br.s), 3.57 (2H, s), 3.60 (2H, br.s), 4.01 (2H, q, J=6.6 Hz), 4.26 (2H, br.s), 6.88-7.04 (4H, m), 7.71 (1H, s), 7.75 (1H, s), 9.16 (2H, br.s).

IR (KBr) vcm$^{-1}$: 3418, 2940, 1708, 1671, 1603, 1507, 1348, 1254, 1213, 1155, 1127, 740.

Example 260

1-(1-Acetyl-2,3-dihydro-1H-indol-5-yl)-5-{[2-(2-ethoxyphenoxy)ethyl]amino}pentan-1-one hydrochloride

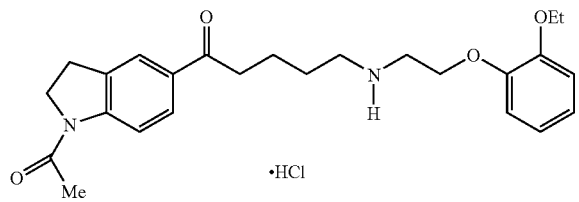

Using tert-butyl 5-(1-acetyl-2,3-dihydro-1H-indol-5-yl)-5-oxopentyl[2-(2-ethoxyphenoxy)ethyl]carbamate (390 mg) obtained in Reference. Example 167 according to the same method as that of Example 1, the title compound (275 mg) was obtained as colorless crystals having a melting point of 125. to 126° C. (dec).

$^1$H NMR (400 MHz, DMSO-$d_6$) δ 1.31 (3H, t, J=6.8 Hz), 1.65-1.71 (4H, m), 2.18 (3H, s), 2.99-3.18 (6H, m), 3.28 (2H, br.s), 4.01 (2H, q, J=6.8 Hz), 4.13 (2H, t, J=8.3 Hz), 4.28 (2H, t, J=6 Hz), 6.85-7.04 (.4H, m), 7.81 (1H, s), 7.82 (1H, d, J=8 Hz), 8.08 (1H, d, J=8 Hz), 9.30 (2H, s).

IR (KBr) vcm$^{-1}$: 3498, 2943, 1683, 16424, 1598, 1509, 1488, 1448, 1407, 1254, 1209, 1126, 746.

Example 261

6-(5-{[2-(2-Ethoxyphenoxy)ethyl]amino}pentanoyl)-1-methyl-3,4-dihydroquinolin-2(1H)-one hydrochloride

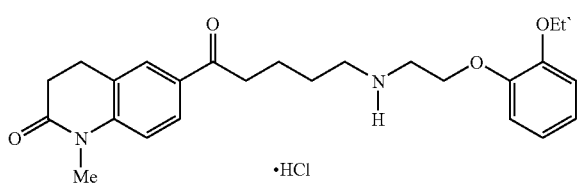

Using tert-butyl 2-(2-ethoxyphenoxy)ethyl[5-(1-methyl-2-oxo-1,2,3,4-tetrahydroquinolin-6-yl)-5-oxopentyl]carbamate (420 mg) obtained in Reference Example 168 according to the same method as that of Example 1, the title compound (292 mg) was obtained as colorless crystals having a melting point of 135 to 136° C. (dec).

$^1$H NMR (400 MHz, DMSO-$d_6$) δ 1.31 (3H, t, J=6.8 Hz), 1.65-1.76. (4H, m), 2.57 (2H, t, J=6 Hz), 2.93 (2H, t, J=7 Hz), 3.04 (2H, t, J=7 Hz), 3.09 (2H, br.s), 3.27 (3H, s), 3.29. (2H, t, J=6 Hz), 4.01 (2H, q, J=6.8 Hz), 4.28 (2H, t, J=6 Hz), 6.85-7.05 (4H, m), 7.18 (1H, d, J=8.3 Hz), 7.83 (1H, s), 7.89 (1H, d, J=8.3 Hz), 9.27 (2H, s).

IR (KBr) vcm$^{-1}$: 3436, 2954, 1671, 1605, 1508, 1455, 1358, 1256, 1220, 1130, 744.

Example 262

5-(5-{[2-(2-Ethoxyphenoxy)ethyl]amino}pentanoyl)-1,3-dimethyl-1,3-dihydro-2H-benzimidazol-2-one hydrochloride

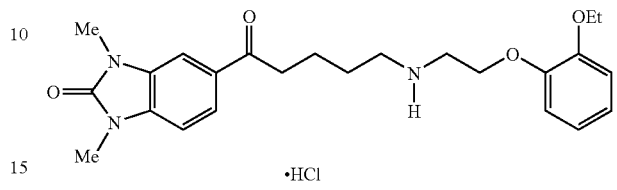

Using tert-butyl 5-(1,3-dimethyl-2-oxo-2,3-dihydro-1H-benzimidazol-5-yl)-5-oxopentyl[2-(2-ethoxyphenoxy)ethyl]carbamate (260 mg) obtained in Reference Example 169 according to the same method as that of Example 1, the title compound (156 mg) was obtained as colorless crystals having a melting point of 103 to 105° C. (dec).

$^1$H NMR (400 MHz, DMSO-$d_6$) δ 1.31 (3H, t, J=6.8 Hz), 1.67-1.77 (4H, m), 3.09 (4H, t, J=7 Hz), 3.30 (2H, t, J=7.5 Hz), 3.36 (3H, s), 3.37 (3H, s), 4.00 (2H, q, J=6.8 Hz), 4.27 (2H, t, J=5.3 Hz), 6.85-7.00 (3H, m),7.03. (1H, dd, J=1.7, 7.8 Hz), 7.24 (1H, d, J=8.3 Hz), 7.72 (1H, d, J=1.5 Hz), 7.79. (1H, dd, J=1.5, 8.3 Hz), 9.23 (2H, br.s).

IR (KBr). vcm$^{-1}$: 3527, 2942, 2742, 1719, 1667, 1620, 1506, 1456, 1249, 1202, 1128, 737.

Example 263

8-[5-({2-[(2-Ethoxyphenyl)amino]ethyl}amino)pentanoyl]-5,6-dihydro-4H-pyrrolo[3,2,1-ij]quinolin-2(1H)-one dihydrochloride

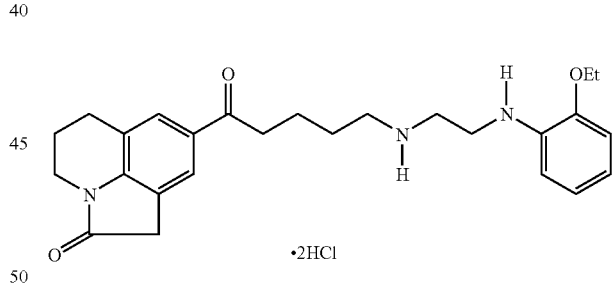

Using tert-butyl 2-[(2-ethoxyphenyl)amino]ethyl[5-oxo-5-(2-oxo-1,2,5,6-tetrahydro-4H-pyrrolo[3,2,1-ij]quinolin-8-yl)pentyl]carbamate (605 mg) obtained in Reference Example 170 according to the same method as that of Example 1, the title compound (431 mg) was obtained as colorless crystals having a melting point of 98 to 100° C. (dec).

$^1$H NMR (400 MHz, DMSO-$d_6$) δ 1.36 (3H, t, J=6.8 Hz), 1.65-1.71 (4H, m), 1.88-1.94 (2H, m), 2.76 (2H, t, J=6.0 Hz), 2.94-3.00 (4H, m), 3.11 (2H, br.s), 3.51 (2H, t, J=6.6 Hz), 3.57 (2H, s), 3.60 (2H, t, J=6.0 Hz), 4.04 (2H, q, J=6.8 Hz), 6.26 (2H, br) 6.80-6.86. (2H, m), 6.91-6.93 (2H, m), 7.71 (1H, s), 7.75 (1H, s), 9.27 (2H, s).

IR (KBr) vcm$^{-1}$: 3392, 2774, 1709, 1665, 1606, 1496, 1344, 1267, 1162, 1040, 766.

Example 264

1-(1-Acetyl-2,3-dihydro-1H-indol-5-yl)-5-({2-[(2-ethoxyphenyl)amino]ethyl}amino)pentan-1-one dihydrochloride

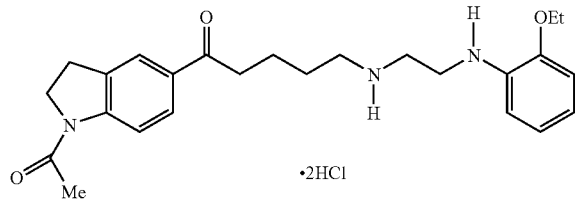

Using tert-butyl 5-(1-acetyl-2,3-dihydro-1H-indol-5-yl)-5-oxopentyl{2-[(2-ethoxyphenyl)amino]ethyl}carbamate (690 mg) obtained in Reference Example 171 according to the same method as that of Example 1, the title compound (545 mg) was obtained as colorless crystals having a melting point of 155 to 157° C. (dec).

$^1$H NMR (400 MHz, DMSO-$d_6$) δ 1.36 (3H, t, J=6.8 Hz), 1.64-1.70 (4H, m), 2.18 (3H, s), 2.95 (2H, br.s), 3.00 (2H, t, J=6.8 Hz), 3.13-3.19 (4H, m), 3.53 (2H, t, J=6.6 Hz), 4.05 (2H, q, J=6.8 Hz), 4.14 (2H, t, J=8.5 Hz), 6.85-7.02 (4H, m), 6.94 (2H, br) 7.82 (1H, s), 7.83 (1H, d, J=8.3 Hz), 8.07 (1H, d, J=8.3 Hz), 9.36 (2H, s).

IR (KBr) vcm$^{-1}$: 3546, 3467, 2748, 1678, 1600, 1504, 1439, 1393, 1322, 1265, 1122, 1042, 762.

Example 265

5-[5-({2-[(2-Ethoxyphenyl)amino]ethyl}amino)pentanoyl]-1,3-dimethyl-1,3-dihydro-2H-benzimidazol-2-one dihydrochloride

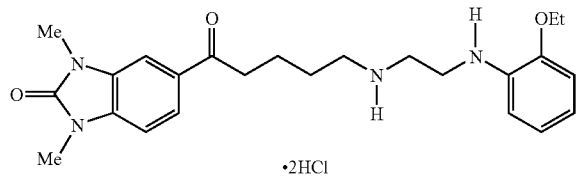

Using tert-butyl 5-(1-acetyl-2,3-dihydro-1H-indol-5-yl)-5-oxopentyl{2-[(2-ethoxyphenyl)amino]ethyl}carbamate (660 mg) obtained in Reference Example 171 according to the same method as that of Example 1, the title compound (448 mg) was obtained as colorless crystals having a melting point of 173 to 175° C. (dec).

$^1$H NMR (400 MHz, DMSO-$d_6$) δ 1.36 (3H, t, J=7.0 Hz), 1.65-1.73 (4H, m), 2.97 (2H, br.s), 3.08 (2H, t, J=6.8 Hz), 3.13 (2H, br.s), 3.35 (3H, s), 3.37 (3H, s), 3.53 (2H, t, J=6.5 Hz), 4.05 (2H, q, J=7.0 Hz), 6.85-7.02 (4H, m), 7.24 (1H, d, J=8.3 Hz), 7.46 (2H, br) 7.72 (1H, s), 7.79 (1H, d, J=8.3 Hz), 9.39 (2H, s).

IR (KBr) vcm$^{-1}$: 3423, 2749, 1718, 1673, 1619, 1506, 1394, 1263, 1200, 1041, 767.

Example 266

8-{3-[1-(2-Phenylethyl)-4-piperidinyl]propanoyl}-5,6-dihydro-4H-pyrrolo[3,2,1-ij]quinolin-2(1H)-one hydrochloride

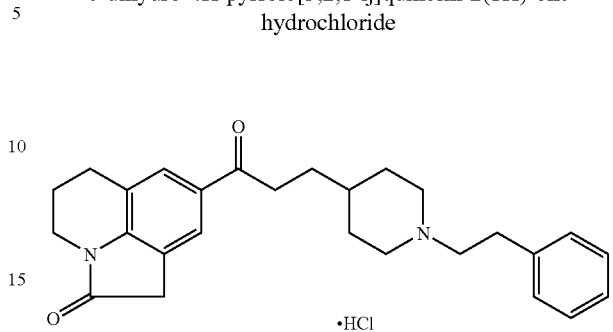

Using 8-[3-(4-piperidinyl)propanoyl]-5,6-dihydro-4H-pyrrolo[3,2,1-ij]quinolin-2(1H)-one (312 mg) obtained in Reference Example 174 and (2-bromoethyl)benzene (185 mg) according to the same method as that of Example 81, the title compound was obtained as pale yellow crystals (285 mg) having a melting point of 207 to 208° C.

$^1$H NMR (free base; 400 MHz, CDCl$_3$) δ 1.42-1.47 (3H, m), 1.69-1.80 (4H, m), 2.01-2.13 (4H, m), 2.64-2.68 (2H, m), 2.81-2.88 (4H, m), 2.95 (2H, t, J=7.6 Hz), 3.10 (2H, d, J=11.5 Hz), 3.55 (2H, s), 3.74 (2H, t, J=6 Hz), 7.18-7.30 (5H, m), 7.73 (2H, s).

IR (KBr) vcm$^{-1}$: 1715, 1672, 1604, 1343, 1152.

Example 267

8-(3-{1-[2-(2-Methoxyphenyl)ethyl]-4-piperidinyl}propanoyl)-5,6-dihydro-4H-pyrrolo[3,2,1-ij]quinolin-2(1H)-one hydrochloride

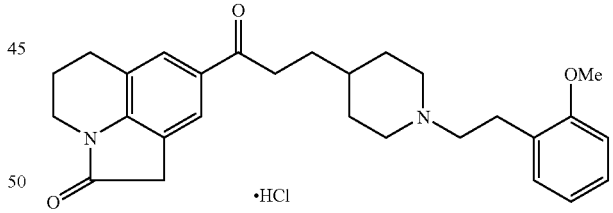

Using 8-[3-(4-piperidinyl)propanoyl]-5,6-dihydro-4H-pyrrolo[3,2,1-ij]quinolin-2(1H)-one (312 mg) obtained in Reference Example 174 and 2-(2-methoxyphenyl)ethyl methanesulfonate (230 mg) according to the same method as that of Example 81, the title compound was obtained as pale yellow amorphous powders (184 mg).

$^1$H NMR (free base; 400 MHz, CDCl$_3$) δ 1.30-1.40 (3H, m), 1.67-1.76 (4H, m), 1.97-2.07 (4H, m), 2.51-2.55 (2H, m), 2.80-2.84 (4H, m), 2.94 (2H, t, J=7.5 Hz), 3.03 (2H, d, J=11.0 Hz), 3.55 (2H, s), 3.74 (2H, t, J=6 Hz), 3.81(3H, s), 6.83-6.89 (2H, m), 7.13-7.20 (2H, m), 7.73 (2H, s).

IR (KBr) vcm$^{-1}$: 1717, 1673, 1604, 1495, 1343, 1243, 1153.

Example 268

8-(3-{1-[2-(2-Methylphenyl)ethyl]-4-piperidinyl}propanoyl)-5,6-dihydro-4H-pyrrolo[3,2,1-ij]quinolin-2(1H)-one hydrochloride

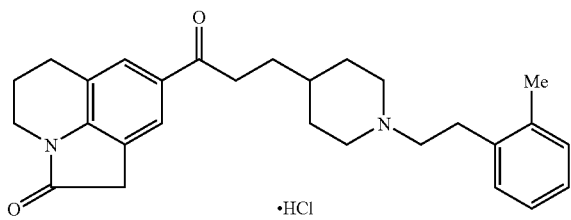

Using 8-[3-(4-piperidinyl)propanoyl]-5,6-dihydro-4H-pyrrolo[3,2,1-ij]quinolin-2(1H)-one obtained in Reference Example 174 and 2-(2-methylphenyl)ethyl methanesulfonate according to the same method as that of Example 81, the title compound was obtained as pale yellow amorphous powders.

$^1$H NMR (free base; 400 MHz, CDCl$_3$) δ 1.30-1.40 (3H, m), 1.68-1.78 (4H, m), 1.99-2.07 (4H, m), 2.32 (3H, s), 2.49-2.53 (2H, m), 2.79-2.85 (4H, m), 2.95 (2H, t, J=7.5 Hz), 3.06 (2H, d, J=10.7 Hz), 3.55 (2H, s), 3.74 (2H, t, J=6 Hz), 7.09-7.15 (4H, m), 7.73 (2H, s).

IR (KBr) vcm$^{-1}$: 1717, 1673, 1604, 1495, 1342, 1153.

Example 269

8-(3-{1-[2-(2-Chlorophenyl)ethyl]-4-piperidinyl}propanoyl)-5,6-dihydro-4H-pyrrolo[3,2,1-ij]quinolin-2(1H)-one hydrochloride

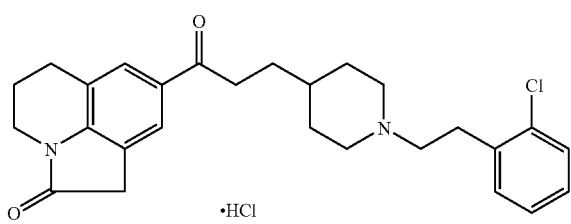

Using 8-[3-(4-piperidinyl)propanoyl]-5,6-dihydro-4H-pyrrolo[3,2,1-ij]quinolin-2(1H)-one obtained in Reference Example 174 and 2-(2-chlorophenyl)ethyl methanesulfonate according to the same method as that of Example 81, the title compound was obtained as pale yellow amorphous powders.

$^1$H NMR (free base; 400 MHz, CDCl$_3$) δ 1.30-1.40 (3H, m), 1.68-1.78 (4H, m), 2.01-2.07. (4H, m), 2.55-2.59. (2H, m), 2.82 (2H, t, J=6 Hz), 2.93-2.96 (4H, m), 3.03 (2H, d, J=11.0 Hz), 3.55 (2H, s), 3.74 (2H, t, J=6 Hz), 7.13-7.34 (4H, m), 7.73 (2H, s).

IR (KBr) vcm$^{-1}$: 1716, 1673, 1604, 1496, 1342, 1152.

Example 270

8-(3-{1-[2-(3-Methoxyphenyl)ethyl]-4-piperidinyl}propanoyl)-5,6-dihydro-4H-pyrrolo[3,2,1-ij]quinolin-2(1H)-one hydrochloride

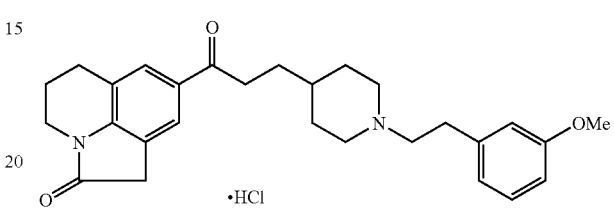

Using 8-[3-(4-piperidinyl)propanoyl]-5,6-dihydro-4H-pyrrolo[3,2,1-ij]quinolin-2(1H)-one obtained in Reference Example 174 and 2-(3-methoxyphenyl)ethyl methanesulfonate according to the same method as that of Example 81, the title compound was obtained as pale yellow amorphous powders.

$^1$H NMR (free base; 400 MHz, CDCl$_3$) δ 1.30-1.39 (3H, m), 1.68-1.77 (4H, m), 1.97-2.07 (4H, m), 2.55-2.59. (2H, m), 2.77-2.84 (4H, m), 2.93-3.02 (4H, m), 3.55. (2H, s), 3.74 (2H, t, J=6 Hz), 3.79 (3H, s), 6.73-6.80 (3H, m), 7.20. (1H, t, J=8 Hz), 7.73 (2H, s).

IR (KBr) vcm$^{-1}$: 1717, 1673, 1603, 1342, 1152.

Example 271

8-(3-{1-[2-(3-Methylphenyl)ethyl]-4-piperidinyl}propanoyl)-5,6-dihydro-4H-pyrrolo[3,2,1-ij]quinolin-2(1H)-one hydrochloride

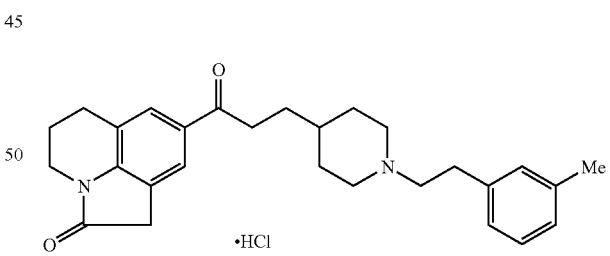

Using 8-[3-(4-piperidinyl)propanoyl]-5,6-dihydro-4H-pyrrolo[3,2,1-ij]quinolin-2(1H)-one obtained in Reference Example 174 and 2-(3-methylphenyl)ethyl methanesulfonate according to the same method as that of Example 81, the title compound was obtained as pale yellow amorphous powders.

$^1$H NMR (free base; 400 MHz, CDCl$_3$) δ 1.30-1.39 (3H, m), 1.68-1.77 (4H, m), 1.97-2.07 (4H, m), 2.32 (3H, s), 2.54-2.58 (2H, m), 2.75-2.85 (4H, m), 2.93-3.03 (4H, m), 3.55 (2H, s), 3.74 (2H, t, J=6 Hz), 6.99-7.04 (3H, m), 7.17 (1H, t, J=8 Hz), 7.73 (2H, s).

IR (KBr) vcm$^{-1}$: 1719, 1673, 1605, 1342, 1152.

Example 272

8-(3-{1-[2-(3-Chlorophenyl)ethyl]-4-piperidinyl}propanoyl)-5,6-dihydro-4H-pyrrolo[3,2,1-ij]quinolin-2(1H)-one hydrochloride

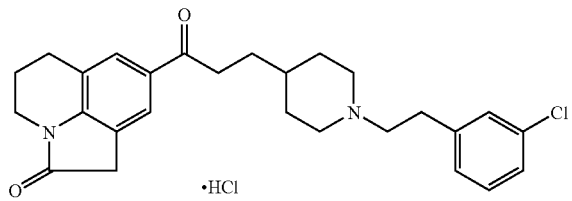

Using 8-[3-(4-piperidinyl)propanoyl]-5,6-dihydro-4H-pyrrolo[3,2,1-ij]quinolin-2(1H)-one (312 mg) obtained in Reference Example 174 and 2-(3-chlorophenyl)ethyl methanesulfonate (235 mg) according to the same method as that of Example 81, the title compound was obtained as pale yellow crystals (200 mg) having a melting point of 108 to 109° C.

$^1$H NMR (free base; 400 MHz, CDCl$_3$) δ 1.28-1.40 (3H, m), 1.67-1.77 (4H, m), 1.96-2.07 (4H, m), 2.53-2.57 (2H, m), 2.76-2.84 (4H, m), 2.90-3.00 (4H, m), 3.55 (2H, s), 3.74 (2H, t, J=6 Hz), 7.07-7.25 (4H, m), 7.73 (2H, s).

IR (KBr) vcm$^{-1}$: 1717, 1673, 1603, 1343, 1152.

Example 273

8-(3-{1-[2-(3-Fluorophenyl)ethyl]-4-piperidinyl}propanoyl)-5,6-dihydro-4H-pyrrolo[3,2,1-ij]quinolin-2(1H)-one hydrochloride

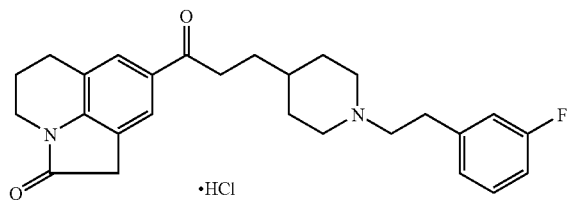

Using 8-[3-(4-piperidinyl)propanoyl]-5,6-dihydro-4H-pyrrolo[3,2,1-ij]quinolin-2(1H)-one obtained in Reference Example 174 and 2-(3-fluorophenyl)ethyl methanesulfonate according to the same method as that of Example 81, the title compound was obtained as pale yellow crystals having a melting point of 214 to 215° C.

$^1$H NMR (free base; 400 MHz, CDCl$_3$) δ 1.29-1.40 (3H, m), 1.68-1.77 (4H, m), 1.97-2.07 (4H, m), 2.54-2.58 (2H, m), 2.78-2.84 (4H, m), 2.93-3.00 (4H, m), 3.55 (2H, s), 3.74 (2H, t, J=6 Hz), 6.86-6.98 (3H, m), 7.20-7.26 (1H, m), 7.73 (2H, s).

IR (KBr) vcm$^{-1}$: 1717, 1673, 1604, 1342, 1143.

Example 274

8-{3-[1-(3-Phenylpropyl)-4-piperidinyl]propanoyl}-5,6-dihydro-4H-pyrrolo[3,2,1-ij]quinolin-2(1H)-one hydrochloride

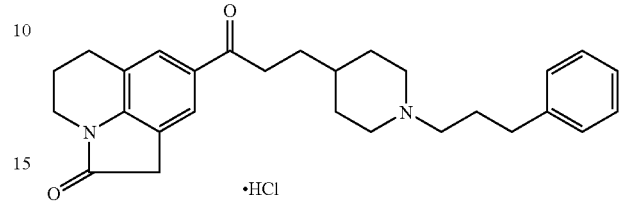

Using 8-[3-(4-piperidinyl)propanoyl]-5,6-dihydro-4H-pyrrolo[3,2,1-ij]quinolin-2(1H)-one obtained in Reference Example 174 and (3-bromopropyl)benzene according to the same method as that of Example 81, the title compound was obtained as pale yellow amorphous powders.

$^1$H NMR (free base; 400 MHz, CDCl$_3$) δ 1.25-1.40 (3H, m), 1.63-1.73 (4H, m), 1.80-1.92 (5H, m), 2.00-2.06 (2H, m), 2.35 (2H, t, J=7.6 Hz), 2.62 (2H, t, J=7.6 Hz), 2.82 (2H, t, J=6 Hz), 2.91-2.95 (3H, m), 3.55 (2H, s), 3.74 (2H, t, J=6 Hz), 7.12-7.33 (5H, m), 7.73 (2H, s).

IR (KBr) vcm$^{-1}$: 1714, 1672, 1604, 1496, 1344, 1153.

Example 275

8-(3-{1-[2-(2-Methylphenoxy)ethyl]-4-piperidinyl}propanoyl)-5,6-dihydro-4H-pyrrolo[3,2,1-ij]quinolin-2(1H)-one hydrochloride

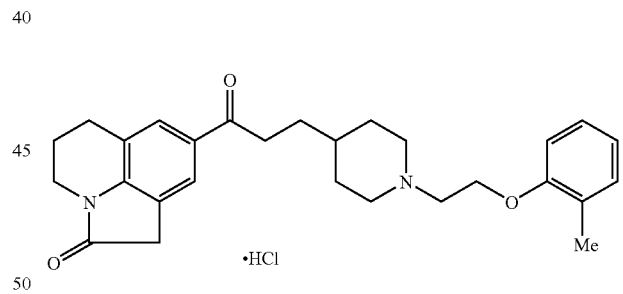

Using 8-[3-(4-piperidinyl)propanoyl]-5,6-dihydro-4H-pyrrolo[3,2,1-ij]quinolin-2(1H)-one obtained in Reference Example 174 and 1-(2-bromoethoxy)-2-methylbenzene according to the same method as that of Example 81, the title compound was obtained as pale yellow amorphous powders.

$^1$H NMR (free base; 400 MHz, CDCl$_3$) δ 1.30-1.35 (3H, m), 1.67-1.75 (4H, m), 2.00-2.06 (2H, m), 2.14 (2H, t, J=11.0 Hz), 2.21 (3H, s), 2.80-2.84 (4H, m), 2.94 (2H, t, J=7.4 Hz), 3.03 (2H, d, J=11Hz), 3.55 (2H, s), 3.74 (2H, t, J=6 Hz), 4.11 (2H, t, J=6 Hz), 6.80-6.87 (2H, m), 7.12-7.15 (2H, m), 7.73 (2H, s).

IR (KBr) vcm$^{-1}$: 1718, 1673, 1604, 1496, 1343, 1244.

Example 276

8-(3-{1-[2-(2-Ethoxyphenoxy)ethyl]-4-piperidinyl}propanoyl)-5,6-dihydro-4H-pyrrolo[3,2,1-ij]quinolin-2(1H)-one hydrochloride

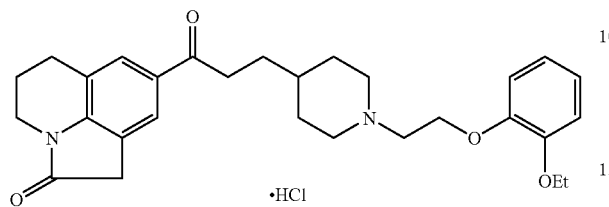

Using 8-[3-(4-piperidinyl)propanoyl]-5,6-dihydro-4H-pyrrolo[3,2,1-ij]quinolin-2(.1H)-one obtained in Reference Example 174 and 1-(2-bromoethoxy)-2-ethoxybenzene according to the same method as that of Example 81, the title compound was obtained as pale yellow amorphous powders.

$^1$H NMR (free base; 400 MHz, CDCl$_3$) δ 1.30-1.39. (3H, m), 1.43 (3H, t, J=7 Hz), 1.67-1.75 (4H, m), 2.00-2.13. (4H, m), 2.81-2.84 (4H, m), 2.94 (2H, t, J=7.5 Hz), 3.03 (2H, d, J=11 Hz), 3.55 (2H, s) 3.74 (2H, t, J=6 Hz), 4.07 (2H, q, J=7 Hz), 4.11-4.15 (2H, m), 6.87-6.91 (4H, m), 7.73 (2H, s).

IR (KBr) vcm$^{-1}$: 1717, 1672, 1604, 1499, 1342, 1253.

Example 277

9-{3-[1-(2-Phenylethyl)-4-piperidinyl]propanoyl}-2,3,6,7-tetrahydro-1H,5H-pyrido[3,2,1-ij]quinolin-5-one hydrochloride

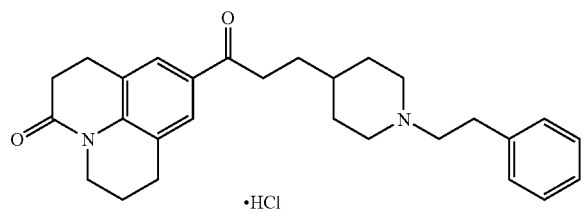

Using 9-[3-(4-piperidinyl)propanoyl]-2,3,6,7-tetrahydro-1H,5H-pyrido[3,2,1-ij]quinolin-5-one obtained in Reference Example 176 and (2-bromoethyl)benzene according to the same method as that of Example 81, the title compound was obtained as pale yellow amorphous powders.

$^1$H NMR (free base; 400 MHz, CDCl$_3$) δ 1.30-1.40 (3H, m), 1.68-1.77 (4H, m), 1.94-2.03 (4H, m), 2.56-2.69 (2H, m), 2.68 (2H, t, J=7 Hz), 2.79-2.86 (4H, m), 2.94 (4H, t, J=7 Hz), 3.02 (2H, d, J=11Hz),), 3.90 (2H, t, J=6 Hz), 7.17-7.30 (5H, m), 7.62 (2H, d, J=5.4 Hz).

IR (KBr) vcm$^{-1}$: 1674, 1604, 1360, 1158.

Example 278

9-(3-{1-[2-(2-Methoxyphenyl)ethyl]-4-piperidinyl}propanoyl)-2,3,6,7-tetrahydro-1H,5H-pyrido[3,2,1-ij]quinolin-5-one hydrochloride

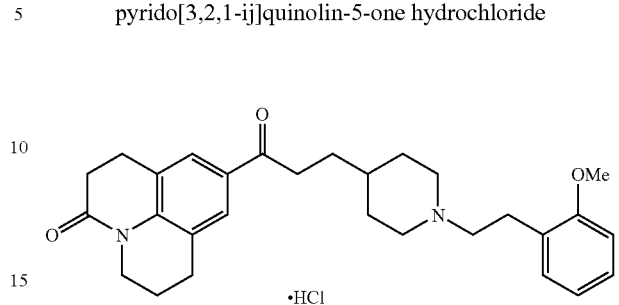

Using 9-[3-(4-piperidinyl)propanoyl]-2,3,6,7-tetrahydro-1H,5H-pyrido[3,2,1-ij]quinolin-5-one obtained in Reference Example 176 and 2-(2-methoxyphenyl)ethyl methanesulfonate according to the same method as that of Example 81, the title compound was obtained as pale yellow amorphous powders.

$^1$H NMR (free base; 400 MHz, CDCl$_3$) δ 1.30-1.40 (3H, m), 1.67-1.76 (4H, m), 1.94-2.03 (4H, m), 2.51-2.55 (2H, m), 2.68 (2H, t, J=7 Hz), 2.81-2.86 (4H, m), 2.94 (4H, t, J=7 Hz), 3.03 (2H, d, J=11 Hz), 3.81 (3H, s), 3.89 (2H, t, J=6 Hz), 6.83-6.89 (2H, m), 7.13-7.20 (2H, m), 7.62 (2H, d, J=5 Hz).

IR (KBr) vcm$^{-1}$: 1674, 1604, 1494, 1362, 1339, 1243, 1168.

Example 279

9-(3-{1-[2-(2-Chlorophenyl)ethyl]-4-piperidinyl}propanoyl)-2,3,6,7-tetrahydro-1H,5H-pyrido[3,2,1-ij]quinolin-5-one hydrochloride

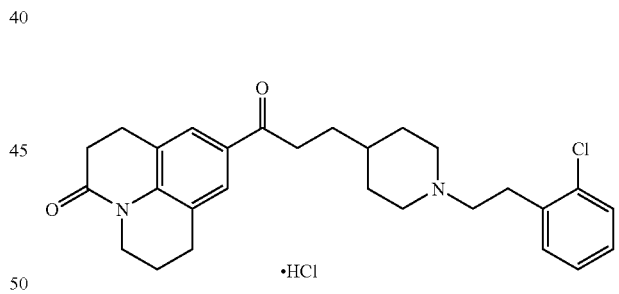

Using 9-[3-(4-piperidinyl)propanoyl]-2,3,6,7-tetrahydro-1H,5H-pyrido[3,2,1-ij]quinolin-5-one obtained in Reference Example 176 and 2-(2-methoxyphenyl)ethyl methanesulfonate according to the same method as that of Example 81, the title compound was obtained as pale yellow amorphous powders.

$^1$H NMR (free base; 400 MHz, CDCl$_3$) δ 1.30-1.40 (3H, m), 1.68-1.78 (4H, m), 1.94-2.07 (4H, m), 2.55-2.59 (2H, m), 2.68 (2H, t, J=7 Hz), 2.84 (2H, t, J=6 Hz), 2.96 (6H, t, J=7 Hz), 3.03 (2H, d, J=11Hz), 3.89(2H, d, J=6 Hz), 7.12-7.34 (4H, m), 7.62 (2H, d, J=5 Hz).

IR (KBr) vcm$^{-1}$: 1674, 1604, 1489, 1361, 1339, 1168.

Example 280

9-(3-{1-(2-(3-Methoxyphenyl)ethyl]-4-piperidinyl}propanoyl)-2,3,6,7-tetrahydro-1H,5H-pyrido[3,2,1-ij]quinolin-5-one hydrochloride

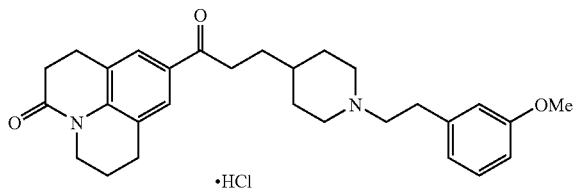

Using 9-[3-(4-piperidinyl)propanoyl]-2,3,6,7-tetrahydro-1H,5H-pyrido[3,2,1-ij]quinolin-5-one obtained in Reference Example 176 and 2-(3-methoxyphenyl)ethyl methanesulfonate according to the same method as that of Example 81, the title compound was obtained as pale yellow amorphous powders.

$^1$H NMR (free base; 400 MHz, CDCl$_3$) δ 1.30-1.40 (3H, m), 1.67-1.77 (4H, m), 1.95-2.02 (4H, m), 2.53-2.60 (2H, m), 2.68 (2H, t, J=7 Hz), 2.77-2.87 (4H, m), 2.92-3.02 (6H, m), 3.79 (3H, s), 3.89 (2H, t, J=6 Hz), 6.73-6.80 (3H, m), 7.18-7.22 (1H, m), 7.62 (2H, d, J=5 Hz).

IR (KBr) vcm$^{-1}$: 1674, 1603, 1485, 1361, 1339, 1167.

Example 281

9-(3-{1-[2-(2-Methylphenyl)ethyl]-4-piperidinyl}propanoyl)-2,3,6,7-tetrahydro-1H,5H-pyrido[3,2,1-ij]quinolin-5-one hydrochloride

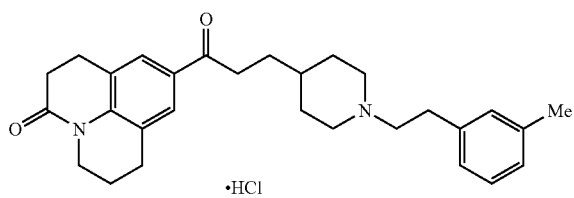

Using 9-[3-(4-piperidinyl)propanoyl]-2,3,6,7-tetrahydro-1H,5H-pyrido[3,2,1-ij]quinolin-5-one obtained in Reference Example 176 and 2-(3-methylphenyl)ethyl methanesulfonate according to the same method as that of Example 81, the title compound was obtained as pale yellow amorphous powders.

$^1$H NMR (free base; 400 MHz, CDCl$_3$) δ 1.30-1.40 (3H, m), 1.70-1.77 (4H, m), 1.94-2.02. (4H, m), 2.32. (3H, s), 2.54-2.58. (2H, m), 2.68 (2H, t, J=7 Hz), 2.75-2.80 (2H, m), 2.83-2.86 (2H, m), 2.94 (4H, t, J=7 Hz), 3.02. (2H, d, J=11 Hz), 3.89 (2H, t, J=6 Hz), 6.99-7.01 (3H, m), 7.17 (1H, t, J=7 Hz), 7.62 (2H, d, J=5 Hz).

IR (KBr) vcm$^{-1}$: 1675, 1604, 1485, 1361, 1339, 1166.

Example 282

9-(3-{1-[2-(3-Chlorophenyl)ethyl]-4-piperidinyl}propanoyl)-2,3,6,7-tetrahydro-1H,5H-pyrido[3,2,1-ij]quinolin-5-one hydrochloride

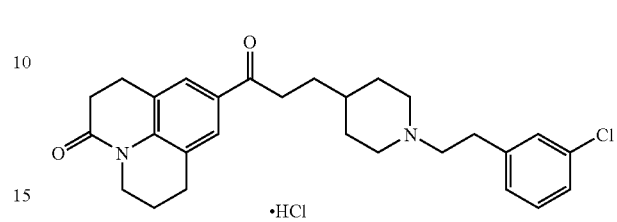

Using 9-[3-(4-piperidinyl)propanoyl]-2,3,6,7-tetrahydro-1H,5H-pyrido[3,2,1-ij]quinolin-5-one obtained in Reference Example 176 and 2-(3-chlorophenyl)ethyl methanesulfonate according to the same method as that of Example 81, the title compound was obtained as pale yellow amorphous powders.

$^1$H NMR (free base; 400 MHz, CDCl$_3$) δ 1.30-1.40 (3H, m), 1.68-1.77 (4H, m), 1.94-2.02 (4H, m), 2.54-2.58 (2H, m), 2.68 (2H, t, J=7 Hz), 2.76-2.80 (2H, m), 2.84. (2H, t, J=6 Hz), 2.90-3.00. (6H, m), 3.90 (2H, t, J=6 Hz), 7.08. (1H, d, J=7 Hz), 7.16-7.23 (3H, m), 7.62 (2H, d, J=5 Hz).

IR (KBr) vcm$^{-1}$: 1674, 1603, 1483, 1360, 1338, 1167.

Example 283

9-(3-{1-[2-(3-Fluorophenyl) ethyl]-4-piperidinyl}propanoyl)-2,3,6,7-tetrahydro-1H,5H-pyrido[3,2,1-ij]quinolin-5-one hydrochloride

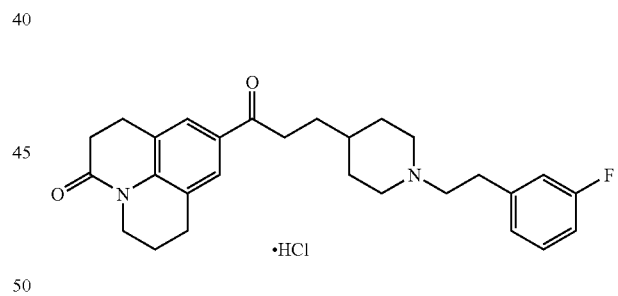

Using 9-[3-(4-piperidinyl)propanoyl]-2,3,6,7-tetrahydro-1H,5H-pyrido[3,2,1-ij]quinolin-5-one obtained in Reference Example 176 and 2-(3-fluorophenyl)ethyl methanesulfonate according to the same method as that of Example 81, the title compound was obtained as pale yellow amorphous powders.

$^1$H NMR (free base; 400 MHz, CDCl$_3$) δ 1.30-1.40 (3H, m), 1.68-1.81 (4H, m), 1.94-2.02 (4H, m), 2.55-2.59 (2H, m), 2.68 (2H, t, J=7 Hz), 2.78-2.86 (4H, m), 2.92-3.00 (6H, m), 3.89 (2H, t, J=6 Hz), 6.86-6.98 (3H, m), 7.23 (1H, q, J=4 Hz), 7.62 (2H, d, J=5 Hz).

IR (KBr) vcm$^{-1}$: 1674, 1604, 1585, 1486, 1361, 1339, 1158.

Example 284

(±)-9-{3-[1-(1-Methyl-2-phenylethyl)-4-piperidinyl]propanoyl}-2,3,6,7-tetrahydro-1H,5H-pyrido[3,2,1-ij]quinolin-5-one hydrochloride

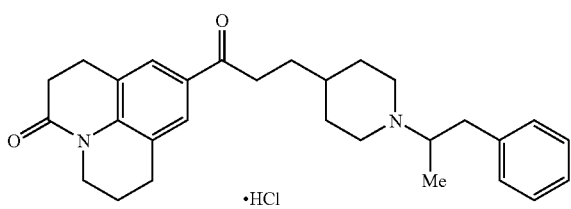

Using 9-[3-(4-piperidinyl)propanoyl]-2,3,6,7-tetrahydro-1H,5H-pyrido[3,2,1-ij]quinolin-5-one obtained in Reference Example 176 and (±)-1-methyl-2-phenylethyl methanesulfonate according to the same method as that of Example 81, the title compound was obtained as pale yellow amorphous powders.

$^1$H NMR (free base; 400 MHz, CDCl$_3$) δ 0.94 (3H, d, J=6 Hz), 1.30-1.40 (3H, m), 1.67-1.78 (4H, m), 1.94-2.00 (2H, m), 2.26-2.42 (2H, m), 2.68 (2H, t, J=7 Hz), 2.84 (2H, t, J=6 Hz),2.90-3.04 (9H, m), 3.90 (2H, t, J=6 Hz), 7.16-7.34 (5H, m), 7.62 (2H, d, J=5 Hz).

IR (KBr) vcm$^{-1}$: 1673, 1604, 1484, 1361, 1339, 1158.

Example 285

(±)-9-(3-{1-[2-(2-Methoxyphenyl)-1-methylethyl]-4-piperidinyl}propanoyl)-2,3,6,7-tetrahydro-1H,5H-pyrido[3,2,1-ij]quinolin-5-one hydrochloride

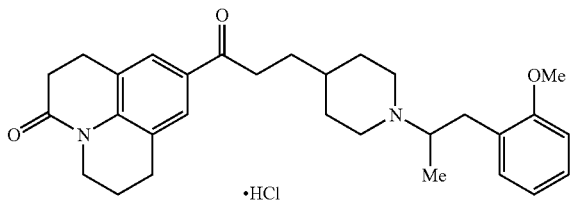

Using 9-[3-(4-piperidinyl)propanoyl]-2,3,6,7-tetrahydro-1H,5H-pyrido[3,2,1-ij]quinolin-5-one obtained in Reference Example 176 and (±)-2-(2-methoxyphenyl)-1-methylethyl methanesulfonate according to the same method as that of Example 81, the title compound was obtained as pale yellow amorphous powders.

$^1$H NMR (free base; 400 MHz, CDCl$_3$) δ 0.94 (3H, d, J=6 Hz), 1.30-1.40 (3H, m), 1.67-1.77 (4H, m), 1.94-2.00 (2H, m), 2.36-2.44 (2H, m), 2.68 (2H, t, J=7 Hz), 2.84 (2H, t, J=6 Hz),2.92-3.04 (9H, m), 3.80. (3H, s), 3.89 (2H, t, J=6 Hz), 6.83 (1H, d, J=7 Hz), 6.88 (1H, t, J=6 Hz), 7.10 (1H, d, J=7 Hz), 7.17 (1H, t, J=6 Hz), 7.62 (2H, d, J=5 Hz).

IR (KBr) vcm$^{-1}$: 1675, 1604, 1494, 1362, 1339, 1244, 1159.

Example 286

9-{3-[1-(3-Phenylpropyl)-4-piperidinyl]propanoyl}-2,3,6,7-tetrahydro-1H,5H-pyrido[3,2,1-ij]quinolin-5-one hydrochloride

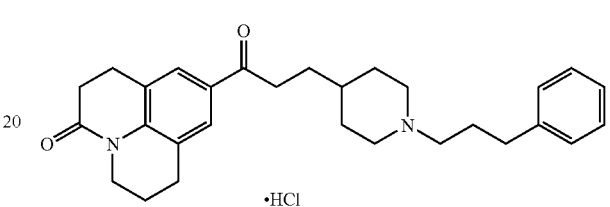

Using 9-[3-(4-piperidinyl)propanoyl]-2,3,6,7-tetrahydro-1H,5H-pyrido[3,2,1-ij]quinolin-5-one obtained in Reference Example 176 and (3-bromopropyl)benzene according to the same method as that of Example 81, the title compound was obtained as pale yellow amorphous powders.

$^1$H NMR (free base; 400 MHz, CDCl$_3$) δ 1.28-1.40. (3H, m), 1.67-1.73 (4H, m), 1.79-1.91 (4H, m), 1.93-2.04 (2H, m) 2.35 (2H, t, J=7.5 Hz), 2.60-2.70 (4H, m), 2.84 (2H, t, J=6 Hz), 2.90-2.95 (6H, m), 3.89 (2H, t, J=6 Hz), 7.15-7.29 (5H, m), 7.61 (2H, d, J=5 Hz).

IR (KBr) vcm$^{-1}$: 1675, 1604, 1361, 1339, 1166.

Example 287

(±)-9-{3-[1-(1-Methyl-2-phenoxyethyl)-4-piperidinyl]propanoyl}-2,3,6,7-tetrahydro-1H,5H-pyrido[3,2,1-ij]quinolin-5-one hydrochloride

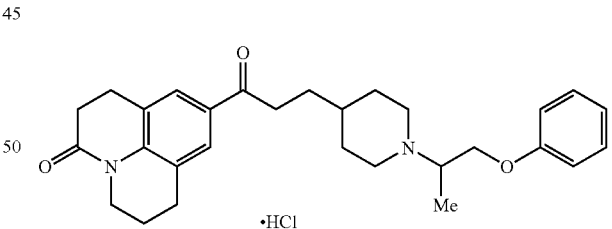

Using 9-[3-(4-piperidinyl)propanoyl]-2,3,6,7-tetrahydro-1H,5H-pyrido[3,2,1-ij]quinolin-5-one obtained in Reference Example 176 and (±)-(2-bromopropoxy)benzene according to the same method as that of Example 81, the title compound was obtained as pale yellow amorphous powders.

$^1$H NMR (free base; 400 MHz, CDCl$_3$) δ 1.19 (3H, d, J=6 Hz), 1.30-1.40. (3H, m), 1.66-1.76 (4H, m), 1.93-1.99 (2H, m), 2.28-2.40 (2H, m), 2.68 (2H, t, J=7 Hz), 2.84 (2H, t, J=6 Hz), 2.91-3.04 (7H, m), 3.89 (2H, d, J=6 Hz), 4.05-4.10 (2H, m), 6.88-6.95 (3H, m), 7.25-7.30 (2H, m), 7.61 (2H, d, J=5 Hz).

IR (KBr) vcm$^-$: 1674, 1601, 1496, 1361, 1339, 1244, 1159.

Example 288

(±)-9-(3-{1-[2-(2-Methoxyphenoxy)-1-methylethyl]-4-piperidinyl}propanoyl)-2,3,6,7-tetrahydro-1H,5H-pyrido[3,2,1-ij]quinolin-5-one hydrochloride

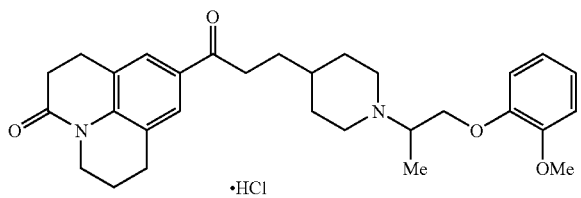

Using 9-[3-(4-piperidinyl)propanoyl]-2,3,6,7-tetrahydro-1H,5H-pyrido[3,2,1-ij]quinolin-5-one obtained in Reference Example 176 and (±)-1-((2-bromopropoxy)-2-methoxybenzene according to the same method as that of Example 81, the title compound was obtained as pale yellow amorphous powders.

$^1$H NMR (free base; 400 MHz, CDCl$_3$) δ 1.18 (3H, d, J=6 Hz), 1.30-1.40 (3H, m), 1.66-1.75 (4H, m), 1.94-2.00 (2H, m), 2.23-2.39 (2H, m), 2.68 (2H, t, J=7 Hz), 2.84 (2H, t, J=6 Hz), 2.90-2.96 (6H, m), 3.07-3.11 (1H, m), 3.85 (3H, s), 3.89 (2H, d, J=6 Hz), 4.11-4.16 (2H, m), 6.88-6.94 (4H, m), 7.61 (2H, d, J=5 Hz).

IR (KBr) νcm$^{-1}$: 1673, 1601, 1506, 1362, 1338, 1253, 1158.

Example 289

6-{5-[(2-Phenylethyl)amino]pentanoyl}-3,4-dihydro-2(1H)-quinazolinone hydrochloride

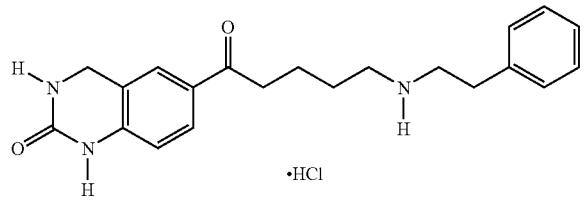

Using 6-(5-chloropentanoyl)-3,4-dihydro-2(1H)-quinazolinone obtained in Reference Example 177 and 2-phenylethylamine according to the same method as those of Reference Example 19 and Example 1, the title compound was obtained as colorless crystals having a melting point of 199 to 205° C. (dec).

$^1$H NMR (300 MHz, DMSO-d6) δ 1.68-1.66 (4H, m), 2.99-2.94 (6H, m), 3.10 (2H, m), 4.38 (2H, s), 6.86 (1H, d, J=9.0 Hz), 7.04 (1H,s), 7.28-7.25 (3H, m), 7.34-7.32 (2H, m), 7.80-7.76 (2H, m), 9.02 (2H, s), 9.47 (1H, br.s).

elementary analysis as C$_{21}$H$_{25}$N$_3$O$_2$·HCl
calculation value: C, 65.02; H, 6.76; N, 10.83.
experimental value: C, 64.42; H, 6.58; N, 10.80.
MS m/z: 352 [M+H]$^+$

Example 290

6-(5-{[2-(2-Methoxyphenyl)ethyl]amino}pentanoyl)-3,4-dihydro-2(1H)-quinazolinone hydrochloride

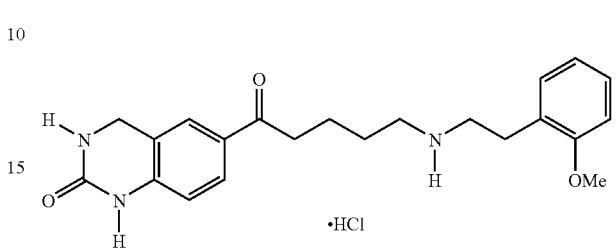

Using 6-(5-chloropentanoyl)-3,4-dihydro-2(1H)-quinazolinone obtained in Reference Example 177 and 2-(2-methoxyphenyl)ethylamine according to the same method as those of Reference Example 19 and Example 1, the title compound was obtained as colorless crystals having a melting point of 176 to 180° C. (dec).

$^1$H NMR (300 MHz, DMSO-d$_6$) δ 1.66 (4H, m), 3.03-2.95 (8H, m), 3.79 (3H, s), 4.37 (2H, s), 7.01-6.83 (4H, m), 7.27-7.16 (2H, m), 7.78-7.75 (2H, m), 8.87 (2H, br.s), 9.44 (1H, s).

elementary analysis as C$_{22}$H$_{27}$N$_3$O$_3$·HCl·H$_2$O
calculation value: C, 63.22; H, 6.75; N, 10.05.
experimental value: C, 62.98; H, 6.62; N, 10.11.
MS m/z: 382 [M+H]$^+$

Example 291

6-(5-{[2-(2-Chlorophenyl)ethyl]amino}pentanoyl)-3,4-dihydro-2(1H)-quinazolinone hydrochloride

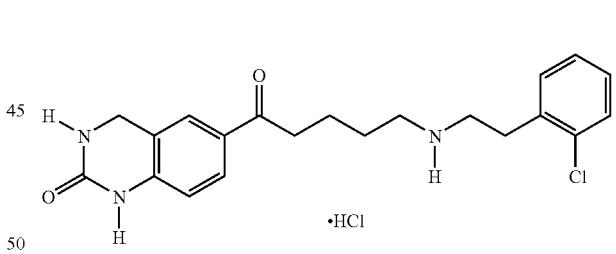

Using 6-(5-chloropentanoyl)-3,4-dihydro-2(1H)-quinazolinone obtained in Reference Example 177 and 2-(2-chlorophenyl)ethylamine according to the same methods as those of Reference Example 19 and Example 1, the title compound was obtained as colorless crystals having a melting point of 176 to 185° C. (dec).

$^1$H NMR (300 MHz, DMSO-d$_6$) δ 1.68 (4H, m), 3.11-2.96 (8H, m), 4.39 (2H, s), 6.86 (1H, d, J=8.1 Hz), 7.04 (1H, s), 7.49-7.28 (4H, m), 7.81-7.77 (2H, m), 9.17 (2H, br.s), 9.47 (1H, s).

elementary analysis as C$_{21}$H$_{24}$ClN$_3$O$_2$·HCl
calculation value: C, 59.72; H, 5.97; N, 9.95.
experimental value: C, 59.43; H, 5.69; N, 9.51.
MS m/z: 386 [M+H]$^+$

Example 292

6-{5-[Methyl(2-phenylethyl)amino]pentanoyl}-3,4-dihydro-2(1H)-quinazolinone hydrochloride

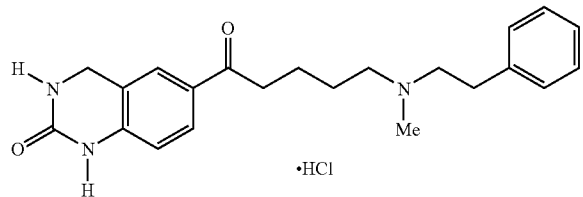

Using 6-(5-chloropentanoyl)-3,4-dihydro-2(1H)-quinazolinone obtained in Reference Example 177 and N-methyl-N-(2-phenylethyl)amine according to the same method as that of Example 9, the title compound was obtained as colorless crystals having a melting point of 164 to 166° C.

$^1$H NMR (free base; 200 MHz, CDCl$_3$) δ 1.53-1.74 (4H, m), 2.30 (3H, s), 2.42-2.47 (2H, m), 2.57-2.63 (2H, m), 2.75-2.80 (2H, m), 2.89-2.93 (2H, m), 4.59 (2H, s), 5.50 (1H, s), 6.76 (1H, d, J=8.1 Hz), 7.30-7.18 (5H, m), 7.70 (1H, s), 7.78 (1H, dd, J=8.1, 1.8 Hz), 8.34 (1H, s).

elementary analysis as C$_{22}$H$_{27}$N$_3$O$_2$.HCl
calculation value: C, 62.92; H, 7.20; N, 10.01.
experimental value: C, 62.59; H, 7.12; N, 10.13.
MS m/z: 386 [M+H]$^+$

Example 293

6-{5-[[2-(2-Methoxyphenyl)ethyl](methyl)amino]pentanoyl}-3,4-dihydro-2(1H)-quinazolinone hydrochloride

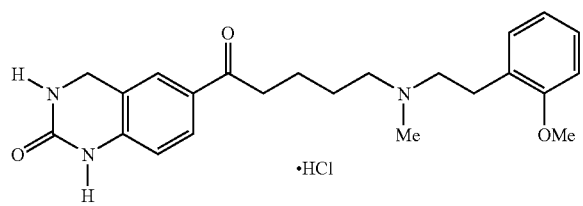

Using 6-(5-chloropentanoyl)-3,4-dihydro-2(1H)-quinazolinone obtained in Reference Example 177 and N-[2-(2-methoxyphenyl)ethyl]-N-methylamine according to the same method as that of Example 9, the title compound was obtained as colorless crystals having a melting point of 170 to 171° C. (dec).

$^1$H NMR (300 MHz, DMSO-d$_6$) δ 1.79-1.63 (4H, m), 2.79 (3H, d, J=4.8 Hz), 3.02-2.95 (4H, m), 3.24-3.07 (4H, m), 3.80 (3H, s), 4.38 (2H, m), 6.94-6.84 (2H, m), 7.04-6.99 (2H, m), 7.30-7.20 (2H, m), 7.80-7.77 (2H, m), 9.47 (H, s), 10.29 (1H, br.s).

elementary analysis as C$_{23}$H$_{29}$N$_3$O$_3$.HCl.1.5H$_2$O
calculation value: C, 60.19; H, 7.25; N, 9.16.
experimental value: C, 60.69; H, 7.17; N, 9.38.
MS m/z: 396 [M+H]$^+$

Example 294

6-{5-[[2-(2-Chlorophenyl)ethyl](methyl)amino]pentanoyl}-3,4-dihydro-2(1H)-quinazolinone hydrochloride

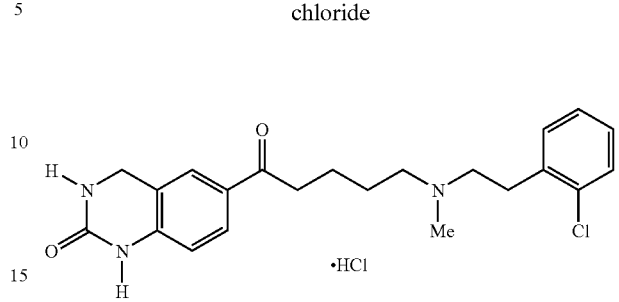

Using 6-(5-chloropentanoyl)-3,4-dihydro-2(1H)-quinazolinone obtained in Reference Example 177 and N-[2-(2-chlorophenyl)ethyl]-N-methylamine according to the same method as that of Example 9, the title compound was obtained as colorless crystals having a melting point of 192 to 195° C. (dec.).

$^1$H NMR (300 MHz, DMSO-d$_6$) δ 1.79-1.64 (4H, m), 2.82: (3H, d, J=4.8 Hz), 3.02-2.97 (2H, m), 3.26-3.10 (6H, m), 4.38 (2H, s), 6.85 (1H, d, J=8.1 Hz), 7.04 (1H, s), 7.38-7.30 (2H, m), 7.49-7.44 (2H, m), 7.80-7.76 (2H, m), 9.47 (1H, s), 10.73 (1H, br.s).

elementary analysis as C$_{22}$H$_{26}$ClN$_3$O$_2$.HCl.0.5H$_2$O
calculation value: C, 59.33; H, 6.34; N, 9.43.
experimental value: C, 59.22; H, 6.77; N, 9.58.
MS m/z: 400 [M+H]$^+$

Example 295

1,3-Dimethyl-6-{5-[methyl(2-phenylethyl)amino]pentanoyl}-3,4-dihydro-2(1H)-quinazolinone hydrochloride

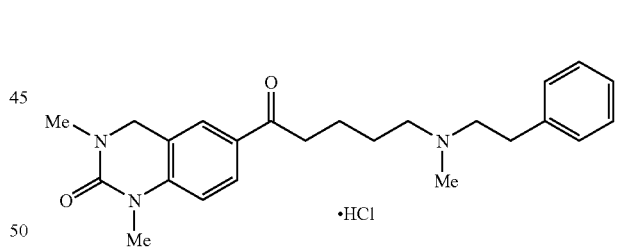

Using 6-(5-chloropentanoyl)-1,3-dimethyl-3,4-dihydro-2(1H)-quinazolinone obtained in Reference Example 178 and N-methyl-N-(2-phenylethyl)amine according to the same method as that of Example 9, the title compound was obtained as colorless crystals having a melting point of 174 to 176° C.

$^1$H NMR (300 MHz, DMSO-d$_6$) δ 1.79-1.62 (4H, m), 2.79 (3H, d, J=4.8 Hz), 2.92 (3H, s), 3.07-3.02 (4H, m), 3.24 (3H,s), 3.41-3.13 (4H, m), 4.45. (2H, s), 7.03 (1H, d, J=8.7 Hz), 7.38-7.24 (5H, m), 7.79 (1H, d, J=1.8 Hz), 7.92 (1H, dd, J=8.7, 2.1 Hz), 10.58 (1H, br.s).

elementary analysis as C$_{24}$H$_{33}$N$_3$O$_2$.HCl
calculation value: C, 67.04; H, 7.50; N, 9.77.
experimental value: C, 66.42; H, 7.67; N, 9.87.
MS m/z: 394 [M+H]$^+$

Example 296

6-{5-[[2-(2-Methoxyphenyl)ethyl](methyl)amino]pentanoyl}-1,3-dimethyl-3,4-dihydro-2(1H)-quinazolinone hydrochloride

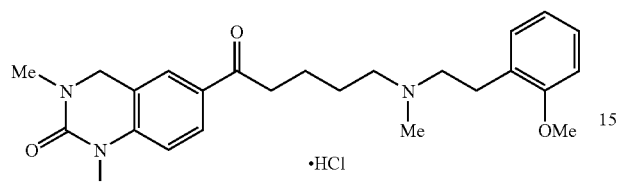

Using 6-(5-chloropentanoyl)-1,3-dimethyl-3,4-dihydro-2(1H)-quinazolinone obtained in Reference Example 178 and N-[2-(2-methoxyphenyl)ethyl]-N-methylamine according to the same method as that of Example 9, the title compound was obtained as colorless crystals having a melting point of 145 to 146° C.

$^1$H NMR (300 MHz, DMSO-$d_6$) δ 1.79-1.65 (4H, m), 2.78 (3H, s), 2.92 (3H, s), 3.18-2.96 (8H, m), 3.24 (3H, s), 3.81 (3H, s), 4.45 (2H, s), 6.94-6.89 (1H, m), 7.04-6.99 (2H, m), 7.30-7.21 (2H, m), 7.79 (1H, d, J=1.8 Hz), 7.92 (1H, dd, J=8.6, 2.0 Hz), 10.57 (1H, br.s).

elementary analysis as $C_{25}H_{33}N_3O_3 \cdot HCl$
calculation value: C, 65.27; H, 7.45;. N, 9.13.
experimental value: C, 64.68; H, 7.58; N, 9.31.
MS m/z: 424 [M+H]$^+$

Example 297

6-{5-[[2-(2-Chlorophenyl)ethyl](methyl)amino]pentanoyl}-1,3-dimethyl-3,4-dihydro-2(1H)-quinazolinone hydrochloride

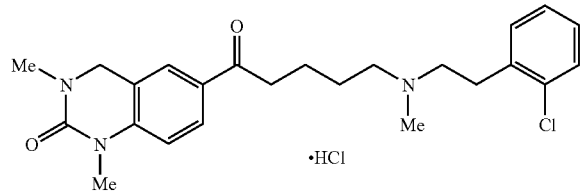

Using 6-(5-chloropentanoyl)-1,3-dimethyl-3,4-dihydro-2(1H)-quinazolinone obtained in Reference Example 178 and 2-(2-chlorophenyl)ethylamine according to the same method as that of Example 9, the title compound was obtained as colorless crystlas having a melting point of 187 to 188° C.

$^1$H NMR (300 MHz, DMSO-$d_6$) δ 1.77-1.66 (4H, m), 2.82 (3H, s), 2.92 (3H, s), 3.07-3.02 (2H, m), 3.24 (3H, s), 3.40-3.00 (6H, m), 4.44 (2H,s), 7.03 (1H, d, J=8.4 Hz), 7.37-7.30 (2H, m), 7.49-7.44 (2H, m), 7.79 (1H, s), 7.91 (1H, d, J=8.4 Hz), 10.63 (1H, br.s).

elementary analysis as $C_{24}H_{30}ClN_3O_2 \cdot HCl \cdot 2H_2O$
calculation value: C, 61.99;. H, 7.59; N, 9.04.
experimental value: C, 61.97;. H, 6.91;. N, 9.31.
MS m/z: 428 [M+H]$^+$

Example 298

8-[4-(Benzylamino)butanoyl]-1,2,5,6-tetrahydro-4H-pyrrolo[3,2,1-ij]quinolin-4-one hydrochloride

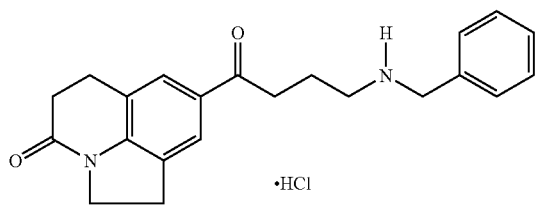

Using tert-butyl benzyl (4-oxo-4-(4-oxo-1,2,5,6-tetrahydro-4H-pyrrolo[3,2,1-ij]quinolin-8-yl)butyl)carbamate (526 mg) obtained in Reference Example 180 according to the same method as that of Example 1, the title compound (384 mg) wes obtained as colorless crystals having a melting point of 159 to 161° C.

$^1$H NMR (200 MHz, DMSO-$d_6$) δ 2.01 (2H, t, J=7.4 Hz), 2.59 (2H, t, J=7.6 Hz), 2.80-3.25 (8H, m), 3.99 (2H, t, J=8.4 Hz), 4.05-4.20 (2H, m), 7.35-7.65 (5H, m), 7.72 (2H, s), 9.40-9.60 (2H, br).

Example 299

8-(4-{[2-(2-Methoxyphenyl)ethyl]amino}butanoyl)-1,2,5,6-tetrahydro-4H-pyrrolo[3,2,1-ij]quinolin-4-one hydrochloride

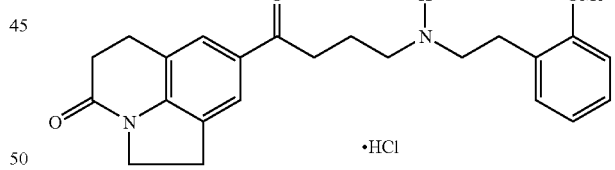

Using tert-butyl 2-(2-methoxyphenyl)ethyl[4-oxo-4-(4-oxo-1,2,5,6-tetrahydro-4H-pyrrolo[3,2,1-ij]quinolin-8-yl)butyl]carbamate (790 mg) obtained in Reference Example 181 according to the same method as that of Example 1, the title compound (452 mg) was obtained as colorless crystals having a melting point of 165 to 167° C.

$^1$H NMR (200 MHz, DMSO-$d_6$) δ 1.85-2.10 (2H, m), 2.60 (2H, t, J=7.6 Hz), 2.90-3.25 (12H, m), 3.81 (3H, s), 4.00 (2H, t, J=8.4 Hz), 6.92 (1H, dt, J=7.3, 1.2 Hz), 7.00 (1H, d, J=7.3 Hz), 7.15-7.30 (2H, m), 7.74 (2H, s), 9.00-9.20 (2H, br).

elementary analysis as $C_{24}H_{29}ClN_2O_3 \cdot 0.5H_2O$
calculation value: C, 65.82; H, 6.90; N, 6.40.
experimental value: C, 65.37; H, 6.68; N, 6.34.

Example 300

8-[5-(Benzylamino)pentanoyl]-1,2,5,6-tetrahydro-4H-pyrrolo[3,2,1-ij]quinolin-4-one hydrochloride

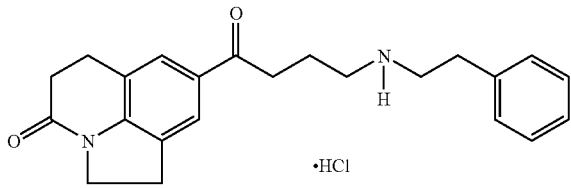

Using tert-butyl benzyl[5-oxo-5-(4-oxo-1,2,5,6-tetrahydro-4H-pyrrolo[3,2,1-ij]quinolin-8-yl)pentyl]carbamate (498 mg) obtained in Reference Example 182 according to the same method as that of Example 1, the title compound (340 mg) was obtained as colorless crystals having a melting point of 123 to 125° C.

$^1$H NMR (200 MHz, DMSO-$d_6$) δ 1.55-1.85 (4H, m), 2.59. (2H, t, J=7.6 Hz), 2.80-3.05. (6H, m), 3.17 (2H, t, J=8.4 Hz), 3.99 (2H, t, J=8.4 Hz), 4.05-4.20 (2H, m), 7.35-7.65 (5H, m), 7.73 (2H, s), 9.40-9.60 (2H, br).

Example 301

8-{5-[(2-Methoxybenzyl)amino]pentanoyl}-1,2,5,6-tetrahydro-4H-pyrrolo[3,2,1-ij]quinolin-4-one hydrochloride

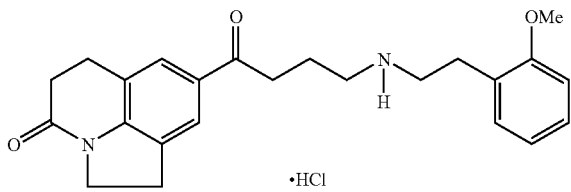

Using tert-butyl 2-methoxybenzyl[5-oxo-5-(4-oxo-1,2,5,6-tetrahydro-4H-pyrrolo[3,2,1-ij]quinolin-8-yl)pentyl]carbamate (524 mg) obtained in Reference Example 183 according to the same method as that of Example 1, the title compound (381 mg) was obtained as colorless crystals having a melting point of 90 to 92° C.

$^1$H NMR (200 MHz, DMSO-$d_6$) δ 1.55-1.80 (4H, m), 2.60 (2H, t, J=7.6 Hz), 2.80-3.05 (6H, m), 3.18 (2H, t, J=8.4 Hz), 3.75-4.10 (4H, m), 3.84 (3H, s), 6.95-7.15 (2H, m), 7.35-7.50 (2H, m), 7.73 (2H, s), 8.90-9.10 (2H, br).

Example 302

8-[6-(Benzylamino)hexanoyl]-1,2,5,6-tetrahydro-4H-pyrrolo[3,2,1-ij]quinolin-4-one hydrochloride

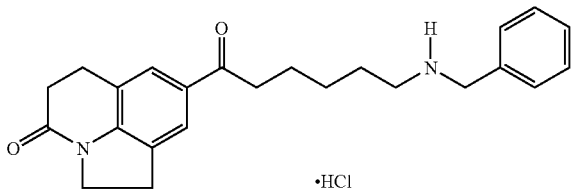

Using tert-butyl benzyl [6-oxo-6-(4-oxo-1,2,5,6-tetrahydro-4H-pyrrolo[3,2,1-ij]quinolin-8-yl)hexyl]carbamate (554 mg) obtained in Reference Example 184 according to the same method as that of Example 1, the title compound (360 mg) was obtained as colorless crystals having a melting point of 181 to 183° C.

$^1$H NMR (300 MHz, DMSO-$d_6$) δ 1.30-1.45 (2H, m), 1.55-1.80 (4H, m), 2.59 (2H, t, J=7.5 Hz), 2.80-3.00 (6H, m), 3.17 (2H, t, J=8.4 Hz), 3.98 (2H, t, J=8.4 Hz), 4.05-4.20 (2H, m), 7.35-7.65 (5H, m), 7.72 (2H, s), 9.35-9.55 (2H, br).

elementary analysis as $C_{24}H_{29}ClN_2O_2 \cdot 1.5H_2O$
calculation value: C, 65.52; H, 7.33; N, 6.37.
experimental value: C, 65.53; H, 7.25; N, 6.17.

Example 303

8-{6-[(2-Methoxybenzyl)amino]hexanoyl]-1,2,5,6-tetrahydro-4H-pyrrolo[3,2,1-ij]quinolin-4-one hydrochloride

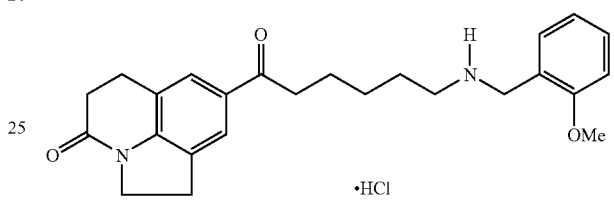

Using tert-butyl 2-methoxybenzyl[6-oxo-6-(4-oxo-1,2,5,6-tetrahydro-4H-pyrrolo[3,2,1-ij]quinolin-8-yl)hexyl]carbamate (486 mg) obtained in Reference. Example 185 according to the same method as that of Example 1, the title compound (393 mg) was obtained as pale yellow amorphous powders was obtained.

$^1$H NMR (300 MHz, DMSO-$d_6$) δ 1.30-1.45 (2H, m), 1.55-1.80 (4H, m), 2.59 (2H, t, J=7.5 Hz), 2.90-3.00 (4H, m), 3.16 (2H, t, J=8.4 Hz), 3.84 (3H, s), 3.90-4.15 (6H, m), 6.99 (1H, t, J=7.5 Hz), 7.09 (1H, d, J=8.0 Hz), 7.41 (1H, t, J=8.0 Hz), 7.51 (1H, d, J=7.5 Hz), 7.73 (2H, s), 9.00-9.20 (2H, br).

Example 304

6-{6-[(2-Phenylethyl)amino]hexanoyl}-2H-1,4-benzoxazin-3(4H)-one hydrochloride

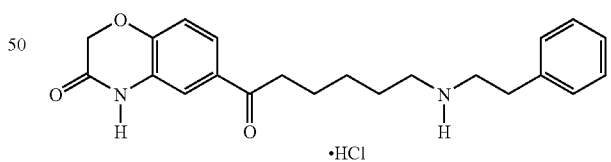

Using tert-butyl 6-oxo-6-(3-oxo-3,4-dihydro-2H-1,4-benzoxazin-6-yl)hexyl(2-phenylethyl)carbamate (842 mg) obtained in Reference Example 186 according to the same method as that of Example 1, the title compound (490 mg) was obtained as colorless crystals having a melting point of 208 to 210° C.

$^1$H NMR (300 MHz, DMSO-$d_6$) δ 1.30-1.45 (2H, m), 1.55-1.70 (4H, m), 2.85-3.00 (6H, m), 3.05-3.20 (2H, m), 4.68 (2H, s), 7.05 (1H, d, J=8.4 Hz), 7.10-7.20. (5H, m), 7.51 (1H, s), 7.62 (1H, dd, J=8.4, 2.1 Hz), 8.80-9.05 (2H, br), 10.91 (1H, s).

Example 305

6-(6-{[2-(2-Methoxyphenyl)ethyl]amino}hexanoyl)-2H-1,4-benzoxazin-3(4H)-one hydrochloride

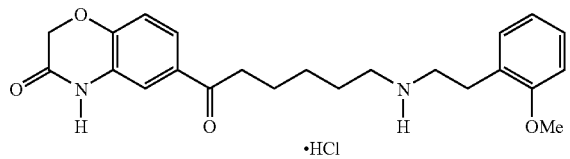

Using tert-butyl 2-(2-methoxyphenyl)ethyl[6-oxo-6-(3-oxo-3,4-dihydro-2H-1,4-benzoxazin-6-yl)hexyl]carbamate (974 mg) obtained in Reference Example 187 according to the same method as that of Example 1, the title compound (567 mg) was obtained as colorless crystals having a melting point of 151 to 153° C.

1H NMR (300 MHz, DMSO-$d_6$) δ 1.30-1.45 (2H, m), 1.55-1.75 (4H, m), 2.80-3.10 (8H, m), 3.80 (3H, s), 4.68 (2H, s), 6.91. (1H, t, J=7.5 Hz), 7.00 (1H, d, J=7.8 Hz), 7.05 (1H, d, J=8.6 Hz), 7.19 (1H, d, J=7.5 Hz), 7.26 (1H, dt, J=7.8, 1.8 Hz), 7.53 (1H, t, J=1.8 Hz), 7.62 (1H, dd, J=8.6, 1.8 Hz), 8.90-9.10 (2H, br), 10.94 (1H, s).

Example 306

6-(6-{[2-(2-Chlorophenyl)ethyl]amino}hexanoyl)-2H-1,4-benzoxazin-3(4H)-one hydrochloride

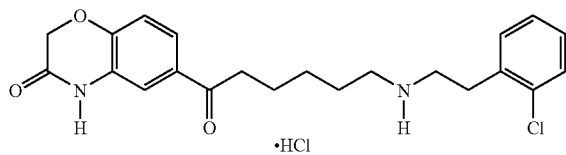

Using tert-butyl 2-(2-chlorophenyl)ethyl[6-oxo-6-(3-oxo-3,4-dihydro-2H-1,4-benzooxazin-6-yl)hexyl]carbamate (974 mg) obtained in Reference Example 188 according to the. same method as that of Example 1, the title compound (387 mg) was obtained as colorless crystals having a melting point of 183 to 185° C.

$^1$H NMR (300 MHz, DMSO-$d_6$) δ 1.30-1.45 (2H, m), 1.55-1.75 (4H, m), 2.85-3.20 (8H, m), 4.68 (2H, s), 7.05 (1H, d, J=8.7 Hz), 7.25-7.55 (5H, m), 7.62 (1H, dd, J=8.4, 1.8 Hz), 8.80-9.20 (2H, br), 10.92 (1H, s).

Example 307

8-{4-[(2-Phenylethyl)amino]butanoyl}-1,2,5,6-tetrahydro-4H-pyrrolo[3,2,1-ij]quinolin-4-one hydrochloride

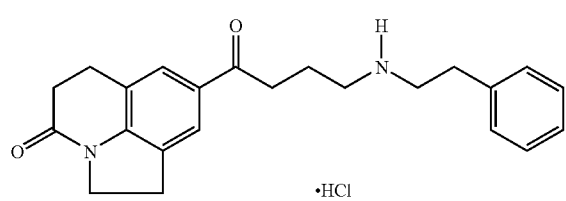

Using 8-(4-chlorobutanoyl)-1,2,5,6-tetrahydro-4H-pyrrolo[3,2,1-ij]quinolin-4-one (1.00 g) obtained in Reference Example 179 and 2-phenylethylamine. (870 mg) according to the same methods as those of Reference Example 19 and Example 1, the title compound (500 mg) was obtained as colorless crystals.

$^1$H NMR (300 MHz, DMSO-$d_6$) δ 1.90-2.05 (2H, m), 2.60 (2H, t, J=7.6 Hz), 2.90-3.25 (12H, m), 3.99 (2H, t, J=8.4 Hz), 7.20-7.40 (5H, m), 7.74 (2H, s), 9.00-9.20 (2H, br).

Example 308

8-[5-(3,4-Dihydro-2(1H)-isoquinolinyl)pentanoyl]-1,2,5,6-tetrahydro-4H-pyrrolo[3,2,1-ij]quinolin-4-one hydrochloride

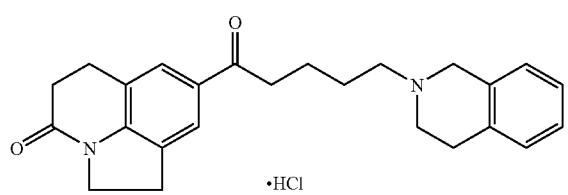

Using 8-(5-chloropentanoyl)-1,2,5,6-tetrahydro-4H-pyrrolo[3,2,1-ij]quinolin-4-one (1.00 g) obtained in Reference Example 1 and 1,2,3,4-tetrahydroisoquinoline (457 mg) according to the same method as that of Example 9, the title compound (779 mg) was obtained as colorless crystals having a melting point of 203 to 205° C.

$^1$H NMR (free base; 300 MHz, CDCl$_3$) δ 1.60-1.90 (4H, m), 2.55 (2H, t, J=7.2 Hz), 2.60-2.80 (4H, m), 2.88 (2H, t, J=5.7 Hz), 2.90-3.00 (4H, m), 3.17 (2H, t, J=8.4 Hz), 3.61 (2H, s), 4.10 (2H, t, J=8.4 Hz), 6.95-7.15 (4H, m), 7.67 (1H, s), 7.71 (1H, s).

Example 309

8-(3-{1-[2-(2-Methoxyphenyl)ethyl]-4-piperidinyl}propanoyl)-1,2,5,6-tetrahydro-4H-pyrrolo[3,2,1-ij]quinolin-4-one hydrochloride

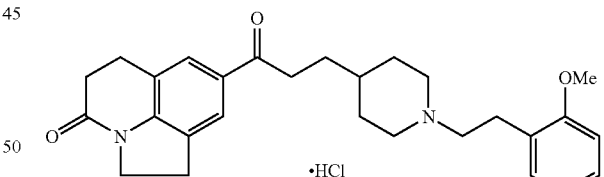

Using 8-[3-(4-piperidinyl)propanoyl]-1,2,5,6-tetrahydro-4H-pyrrolo[3,2,1-ij]quinolin-4-one (1.50 g) and 2-(2-methoxyphenyl)ethyl methanesulfonate (1.16 g) according to the same method as that of Example 81, the title compound (1.69 g) was obtained as colorless crystals having a melting point of 209 to 211° C.

$^1$H NMR (free base; 200 MHz, CDCl$_3$) δ 1.20-1.50 (3H, m), 1.60-2.10 (6H, m), 2.40-3.10 (12H, m), 3.23 (2H, t, J=8.4 Hz), 3.81 (3H, s), 4.13 (2H, t, J=8.4 Hz), 6.80-6.95 (2H, m), 7.10-7.25 (2H, m), 7.68 (1H, s), 7.72 (1H, s).

elementary analysis as $C_{28}H_{34}N_2O_3 \cdot HCl \cdot 0.5H_2O$ calculation value: C, 68.35; H, 7.37; N, 5.69.

experimental value: C, 68.85; H, 7.54; N, 5.84.

Example 310

8-(3-{1-[2-(3-Methoxyphenyl)ethyl]-4-piperidinyl}propanoyl)-1,2,5,6-tetrahydro-4H-pyrrolo[3,2,1-ij]quinolin-4-one hydrochloride

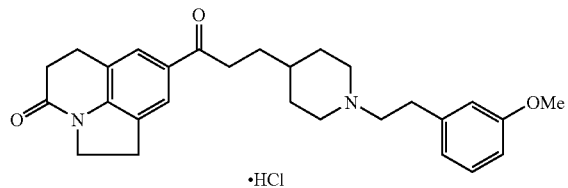

Using 8-[3-(4-piperidinyl)propanoyl]-1,2,5,6-tetrahydro-4H-pyrrolo[3,2,1-ij]quinolin-4-one (1.50 g) and 2-(3-methoxyphenyl)ethyl methanesulfonate (1.16 g) according to the same method as that of Example 81, the title compound (1.53 g) was obtained as colorless crystals having a melting point of 240 to 242° C.

$^1$H NMR (free base; 200 MHz, CDCl$_3$) δ 1.20-1.45 (3H, m), 1.55-2.10 (6H, m), 2.50-3.10 (12H, m), 3.23 (2H, t, J=8.4 Hz), 3.79 (3H, s), 4.14 (2H, t, J=8.4 Hz), 6.70-6.85 (3H, m), 7.15-7.30 (1H, m), 7.68 (1H, s), 7.72 (1H, s).

elementary analysis as C$_{28}$H$_{34}$N$_2$O$_3$.HCl.0.5H$_2$O
calculation value: C, 68.35; H, 7.37; N, 5.69.
experimental value: C, 68.92; H, 6.69; N, 5.87.

Example 311

8-(3-{1-[2-(4-Methoxyphenyl)ethyl]-4-piperidinyl}propanoyl)-1,2,5,6-tetrahydro-4H-pyrrolo[3,2,1-ij]quinolin-4-one hydrochloride

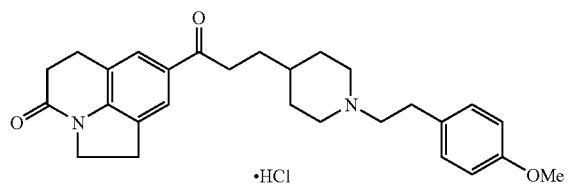

Using 8-[3-(4-piperidinyl)propanoyl]-1,2,5,6-tetrahydro-4H-pyrrolo[3,2,1-ij]quinolin-4-one and 2-(4-methoxyphenyl)ethyl methanesulfonate according to the same method as that of Example 81, the title compound was obtained as colorless crystals having a melting point of 141 to 143° C.

$^1$H NMR (free base; 200 MHz, CDCl$_3$) δ 1.30-1.60 (3H, m), 1.65-1.85 (4H, m), 2.00-2.20 (2H, m), 2.60-3.15 (12H, m), 3.23 (2H, t, J=8.4 Hz), 3.78 (3H, s), 4.14 (2H, t, J=8.4 Hz), 6.83 (2H, d, J=8.6 Hz), 7.13 (2H, d, J=8.6 Hz), 7.67 (1H, s), 7.72 (1H, s).

elementary analysis as C$_{28}$H$_{34}$N$_2$O$_3$.HCl.H$_2$O
calculation value: C, 67.12; H, 7.44; N, 5.59.
experimental value: C, 67.29; H, 7.56; N, 5.32.

Example 312

8-(3-{1-[2-(2-Ethoxyphenyl)ethyl]-4-piperidinyl}propanoyl)-1,2,5,6-tetrahydro-4H-pyrrolo[3,2,1-ij]quinolin-4-one hydrochloride

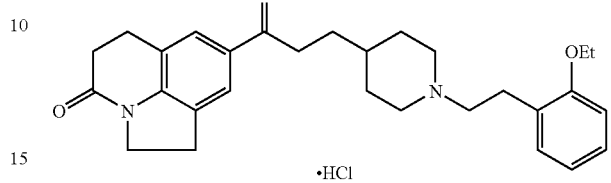

Using 8-[3-(4-piperidinyl)propanoyl]-1,2,5,6-tetrahydro-4H-pyrrolo[3,2,1-ij]quinolin-4-one and 2-(2-ethoxyphenyl)ethyl methanesulfonate according to the same method as that of Example 81, the title compound was obtained as colorless crystals having a melting point of 182 to 184° C.

$^1$H NMR (free base; 200 MHz, CDCl$_3$) δ 1.30-1.50 (3H, m), 1.41 (3H, t, J=7.0 Hz), 1.65-1.85 (4H, m), 1.95-2.10 (2H, m), 2.50-2.65 (2H, m), 2.71 (2H, t, J=7.6 Hz), 2.80-3.15 (8H, m), 3.23 (2H, t, J=8.4 Hz), 4.03 (2H, q, J=7.0 Hz), 4.14 (2H, t, J=8.4 Hz), 6.75-6.90 (2H, m), 7.10-7.20 (2H, m), 7.68 (1H, s), 7.72 (1H, s).

elementary analysis as C$_{29}$H$_{36}$N$_2$O$_3$.HCl.H$_2$O
calculation value: C, 67.62; H, 7.63; N, 5.44.
experimental value: C, 67.08; H, 7.24; N, 5.28.

Example 313

8-(3-{1-[2-(2-Hydroxyphenyl)ethyl]-4-piperidinyl}propanoyl)-1,2,5,6-tetrahydro-4H-pyrrolo[3,2,1-ij]quinolin-4-one hydrochloride

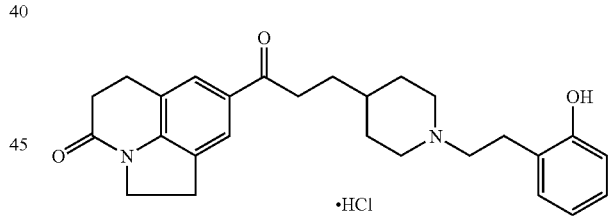

A solution of 8-(3-{1-[2-(2-methoxyphenyl)ethyl]-4-piperidinyl}propanoyl)-1,2,5,6-tetrahydro-4H-pyrrolo[3,2,1-ij]quinolin-4-one (800 mg) obtained in Example 309 in hydrobromic acid (15 ml) was stirred at 140° C. for 1 hour. A pH of the reaction solution was adjusted to 12 with an aqueous potassium carbonate solution, and the solution was extracted with ethyl acetate. The extract was washed with brine, dried over anhydrous magnesium sulfate, and the solvent was evaporated under reduced pressure to give a free base compound (622 mg) of the title compound as colorless crystals having a melting point of 143 to 145° C. The free base compound (500 mg) was treated with a hydrogen chloride-ethanol solution to give the title compound (432 mg) as colorless crystals having an melting point of 220 to 222° C.

$^1$H NMR (free base; 200 MHz, CDCl$_3$) δ 1.25-1.50 (3H, m), 1.65-1.90 (4H, m), 2.05-2.20 (2H, m), 2.60-2.70 (2H, m), 2.72 (2H, t, J=7.8 Hz), 2.75-2.85 (3H, m), 2.94 (2H, t, J=7.8 Hz), 3.03 (2H, t, J=7.8 Hz), 3.10-3.20 (2H, m), 3.26 (2H, t, J=8.5 Hz), 4.14 (2H, t, J=8.5 Hz), 6.73 (1H, dt, J=7.3, 1.2 Hz), 6.87 (1H, dd, J=5.2, 0.8 Hz), 6.98 (1H, dd, J=4.8, 0.8 Hz), 7.12 (1H, dt, J=7.9, 1.5 Hz), 7.67 (1H, s), 7.72 (1H, s).

elementary analysis as $C_{27}H_{32}N_2O_3 \cdot HCl \cdot 0.5H_2O$
calculation value: C, 67.84; H, 7.17; N, 5.86.
experimental value: C, 67.78; H, 7.51; N, 5.87.

Example 314

8-(3-{1-[2-(3-Hydroxyphenyl)ethyl]-4-piperidinyl}propanoyl)-1,2,5,6-tetrahydro-4H-pyrrolo[3,2,1-ij]quinolin-4-one hydrochloride

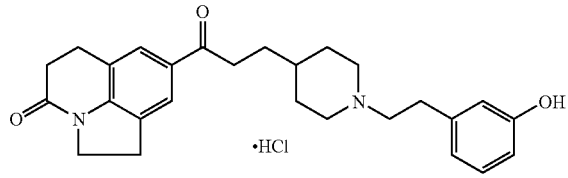

Using 8-(3-{1-[2-(3-methoxyphenyl)ethyl]-4-piperidinyl}propanoyl)-1,2,5,6-tetrahydro-4H-pyrrolo[3,2,1-ij]quinolin-4-one obtained in Example 310 according to the same method as that of Example 313, the title compound was obtained as colorless crystals having a melting point of 229 to 231° C.

$^1$H NMR (free base; 200 MHz, CDCl$_3$) δ 1.20-1.55 (3H, m), 1.60-1.85 (4H, m), 1.90-2.20 (2H, m), 2.55-3.15 (13H, m), 3.27 (2H, t, J=8.4 Hz), 4.14 (2H, t, J=8.4 Hz), 6.60-6.75 (3H, m), 7.10-7.20 (1H, m), 7.67 (1H, s), 7.72 (1H, s).

elementary analysis as $C_{27}H_{32}N_2O_3 \cdot HCl \cdot 0.5H_2O$
calculation value: C, 67.84; H, 7.17; N, 5.86.
experimental value: C, 68.07; H, 7.35; N, 5.69.

Example 315

8-(3-{1-[2-(3-Methylphenyl)ethyl]-4-piperidinyl}propanoyl)-1,2,5,6-tetrahydro-4H-pyrrolo[3,2,1-ij]quinolin-4-one hydrochloride

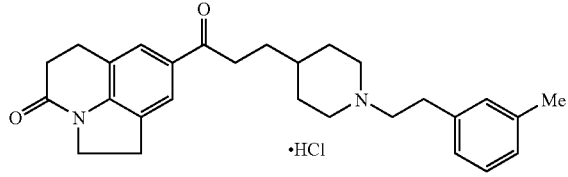

Using 8-[3-(4-piperidinyl)propanoyl]-1,2,5,6-tetrahydro-4H-pyrrolo[3,2,1-ij]quinolin-4-one (500 mg) and 2-(3-methylphenyl)ethyl methanesulfonate (360 mg) according to the same method as that of Example 81, the title compound (391 mg) was obtained as colorless crystals having a melting point of 197 to 199° C.

$^1$H NMR (free base; 200 MHz, CDCl$_3$) δ 1.25-1.50 (3H, m), 1.60-1.85 (4H, m), 1.90-2.10 (2H, m), 2.32 (3H, s), 2.45-3.10 (12H, m), 3.22 (2H, t, J=8.4 Hz), 4.13 (2H, t, J=8.4 Hz), 6.95-7.20 (4H, m), 7.68 (1H, s), 7.72 (1H, s).

elementary analysis as $C_{28}H_{34}N_2O_2 \cdot HCl \cdot 0.5H_2O$
calculation value: C, 70.64; H, 7.62; N, 5.88.
experimental value: C, 70.53; H, 7.52; N, 5.91.

Example 316

8-(3-{1-[2-(2-Chlorophenyl)ethyl]-4-piperidinyl}propanoyl)-1,2,5,6-tetrahydro-4H-pyrrolo[3,2,1-ij]quinolin-4-one hydrochloride

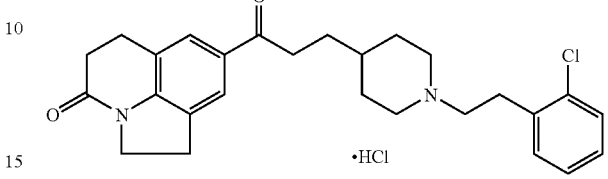

Using 8-[3-(4-piperidinyl)propanoyl]-1,2,5,6-tetrahydro-4H-pyrrolo[3,2,1-ij]quinolin-4-one. (600 mg) and 2-(2-chlorophenyl)ethyl methanesulfonate (475 mg) according to the same method as that of Example 81, the title compound (303 mg) was obtained as colorless crystals having a melting point of 207 to 210° C.

$^1$H NMR (free base; 200 MHz, CDCl$_3$) δ 1.20-1.45 (3H, m), 1.60-1.80 (4H, m), 1.95-2.10 (2H, m), 2.50-2.60 (2H, m), 2.72 (2H, t, J=7.6 Hz), 2.85-3.10 (8H, m), 3.23 (2H, t, J=8.4 Hz), 4.14 (2H, t, J=8.4 Hz), 7.10-7.40 (4H, m), 7.68 (1H, s), 7.72 (1H, s).

elementary analysis as $C_{27}H_{31}ClN_2O_2 \cdot HCl \cdot 0.5H_2O$
calculation value: C, 65.32; H, 6.70; N, 5.64.
experimental value: C, 65.77; H, 6.87; N, 5.63.

Example 317

8-(3-{1-[2-(4-Chlorophenyl)ethyl]-4-piperidinyl}propanoyl)-1,2,5,6-tetrahydro-4H-pyrrolo[3,2,1-ij]quinolin-4-one hydrochloride

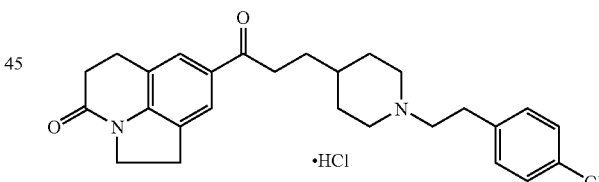

Using 8-[3-(4-piperidinyl)propanoyl]-1,2,5,6-tetrahydro-4H-pyrrolo[3,2,1-ij]quinolin-4-one and 2-(4-chlorophenyl)ethyl methanesulfonate according to the same method as that of Example. 81, the title compound was obtained as colorless crystals having a melting point of 204 to. 206° C.

$^1$H NMR (free base; 200 MHz, CDCl$_3$) δ 1.40-1.90. (7H, m), 2.10-2.30. (2H, m), 2.72 (2H, t, J=7.8 Hz), 2.85-3.30 (12H, m), 4.14 (2H, t, J=8.4 Hz), 7.10-7.30 (4H, m), 7.67 (1H, s), 7.71 (1H, s).

elementary analysis as $C_{27}H_{31}ClN_2O_2 \cdot HCl \cdot H_2O$
calculation value: C, 64.16; H, 6.78; N, 5.54.
experimental value: C, 64.15; H, 7.04; N, 5.25.

Example 318

8-(3-{1-[2-(4-Nitrophenyl)ethyl]-4-piperidinyl}propanoyl)-1,2,5,6-tetrahydro-4H-pyrrolo[3,2,1-ij]quinolin-4-one hydrochloride

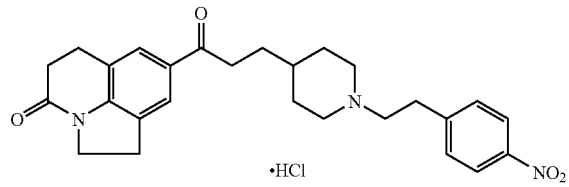

Using 8-[3-(4-piperidinyl)propanoyl]-1,2,5,6-tetrahydro-4H-pyrrolo[3,2,1-ij]quinolin-4-one (500 mg) and 1-(2-bromoethyl)-4-nitrobenzene (368 mg) according to the same method as that of Example 81, the title compound (443 mg) was obtained as colorless crystals having a melting point of 217 to 219° C.

$^1$H NMR (free base; 200 MHz, CDCl$_3$) δ 1.25-1.55 (3H, m), 1.60-1.85 (4H, m), 1.95-2.20 (2H, m), 2.60-2.75 (4H, m), 2.85-3.15 (8H, m), 3.23 (2H, t, J=8.4 Hz), 4.14 (2H, t, J=8.4 Hz), 7.37 (2H, d, J=8.6 Hz), 7.67 (1H, s), 7.72 (1H, s), 8.14 (2H, d, J=8.6 Hz).

elementary analysis as C$_{27}$H$_{31}$N$_3$O$_4$.HCl.0.5H$_2$O
calculation value: C, 63.96; H, 6.56; N, 8.29.
experimental value: C, 63.67; H, 6.77; N, 8.25.

Example 319

8-(3-{1-[2-(2,6-Dichlorophenyl)ethyl]-4-piperidinyl}propanoyl)-1,2,5,6-tetrahydro-4H-pyrrolo[3,2,1-ij]quinolin-4-one hydrochloride

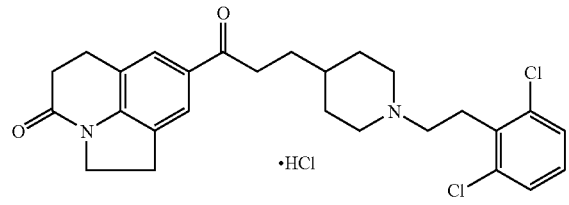

Using 8-[3-(4-piperidinyl)propanoyl]-1,2,5,6-tetrahydro-4H-pyrrolo[3,2,1-ij]quinolin-4-one (600 mg) and 2-(2,6-dichlorophenyl)ethyl methanesulfonate (545 mg) according to the same method as that of Example 81, the title compound (272 mg) was obtained as colorless crystals having a melting point of 226 to 229° C.

$^1$H NMR (free base; 200 MHz, CDCl$_3$) δ 1.25-1.50 (3H, m), 1.60-1.80 (4H, m), 2.00-2.20. (2H, m), 2.50-2.60 (2H, m), 2.68 (2H, t, J=7.6 Hz), 2.85-3.30 (10H, m), 4.14 (2H, t, J=8.4 Hz), 7.00-7.10 (1H, m), 7.20-7.30 (2H, m), 7.68. (1H, s), 7.72 (1H, s).

elementary analysis as C$_{27}$H$_{30}$Cl$_2$N$_2$O$_2$.HCl.0.5H$_2$O
calculation value: C, 61.08; H. 6.08;. N, 5.28.
experimental value: C, 60.96; H, 6.32; N, 5.04.

Example 320

8-(3-{1-[2-(1H-Indol-3-yl)ethyl]-4-piperidinyl}propanoyl)-1,2,5,6-tetrahydro-4H-pyrrolo[3,2,1-ij]quinolin-4-one hydrochloride

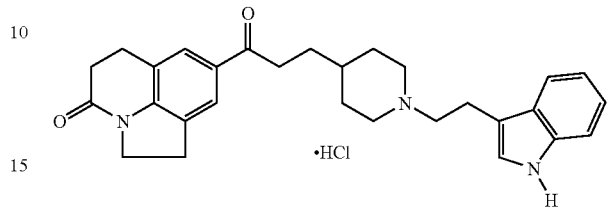

Using 8-[3-(4-piperidinyl)propanoyl]-1,2,5,6-tetrahydro-4H-pyrrolo[3,2,1-ij]quinolin-4-one (500 mg) and 3-(2-bromoethyl)-1H-indole (394 mg) according to the same method as that of Example 81, the title compound (370 mg) was obtained as colorless crystals having a melting point of 157 to 159° C.

$^1$H NMR (free base; 300 MHz, CDCl$_3$) δ 1.25-1.50 (3H, m), 1.60-1.85 (4H, m), 1.95-2.10 (2H, m), 2.60-2.80 (4H, m), 2.85-3.15 (8H, m), 3.23 (2H, t, J 8.4 Hz), 4.14 (2H, t, J=8.4 Hz), 7.00-7.25 (3H, m), 7.36 (1H, d, J=8.1 Hz), 7.62. (1H, d, J=8.1 Hz), 7.68 (1H, s), 7.73 (1H, s), 8.00-8.25 (1H, br).

elementary analysis as C$_{29}$H$_{33}$N$_3$O$_2$.HCl.H$_2$O
calculation value: C, 68.29; H, 7.11; N, 8.24.
experimental value: C, 68.77; H, 7.44; N, 7.94.

Example 321

(±)-8-{3-[1-(1-Methyl-2-phenylethyl)-4-piperidinyl]propanoyl}-1,2,5,6-tetrahydro-4H-pyrrolo[3,2,1-ij]quinolin-4-one hydrochloride

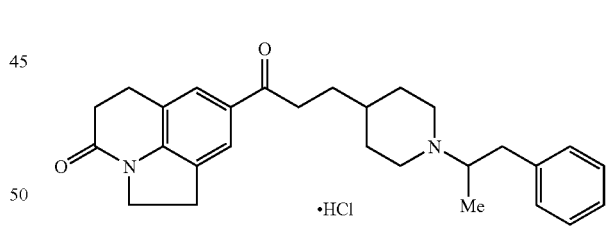

Using 8-[3-(4-piperidinyl)propanoyl]-1,2,5,6-tetrahydro-4H-pyrrolo[3,2,1-ij]quinolin-4-one (700 mg) and (±)-1-methyl-2-phenylethyl methanesulfonate (528 mg) according to the same method as that of Example 81, the title compound (257 mg) was obtained as colorless crystals having a melting point of 211 to 213° C.

$^1$H NMR (free base; 300 MHz, CDCl$_3$) δ 0.94 (3H, d, J=6.6 Hz), 1.20-1.45 (3H, m), 1.60-1.85 (4H, m), 2.10-2.45 (3H, m), 2.60-3.10 (10H, m), 3.23 (2H, t, J=8.4 Hz), 4.14 (2H, t, J=8.4 Hz), 7.10-7.40 (5H, m), 7.68 (1H, s), 7.72 (1H, s).

elementary analysis as C$_{28}$H$_{34}$N$_2$O$_2$.HCl.0.5H$_2$O
calculation value: C, 70.64; H, 7.62; N, 5.88.
experimental value: C, 70.80; H, 7.59; N, 5.88.

Example 322

(±)-8-(3-{1-[2-(2-Methoxyphenyl)-1-methylethyl]-4-piperidinyl}propanoyl)-1,2,5,6-tetrahydro-4H-pyrrolo[3,2,1-ij]quinolin-4-one hydrochloride

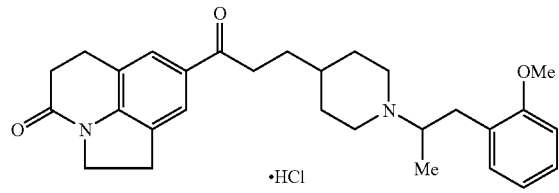

Using 8-[3-(4-piperidinyl)propanoyl]-1,2,5,6-tetrahydro-4H-pyrrolo[3,2,1-ij]quinolin-4-one (600 mg) and (±)-2-(2-methoxyphenyl)-1-methylethyl methanesulfonate (516 mg) according to the same method as that of Example 81, the title compound (204 mg) was obtained as pale yellow amorphous powders.

$^1$H NMR (free base; 300 MHz, CDCl$_3$) δ 0.93 (3H, d, J=6.6 Hz), 1.20-1.40 (3H, m), 1.60-1.80 (4H, m), 2.20-2.45 (3H, m), 2.71 (2H, t, J=7.8 Hz), 2.80-3.05 (8H, m), 3.22 (2H, t, J=8.4 Hz), 3.80 (3H, s), 4.12 (2H, t, J=8.4 Hz), 6.80-6.90 (2H, m), 7.05-7.20 (2H, m), 7.67 (1H, s), 7.71 (1H, s).

elementary analysis as C$_{29}$H$_{36}$N$_2$O$_3$·HCl·H$_2$O
calculation value: C, 67.62; H, 7.63; N, 5.44.
experimental value: C, 67.65; H, 7.52; N, 5.42.

Example 323

(±)-8-{3-[1-(1-Methyl-2-phenoxyethyl)-4-piperidinyl]propanoyl}-1,2,5,6-tetrahydro-4H-pyrrolo[3,2,1-ij]quinolin-4-one hydrochloride

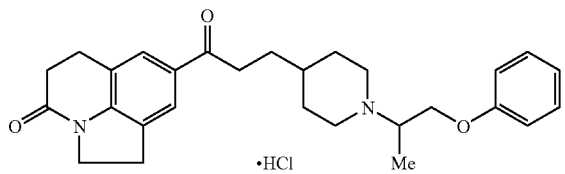

Using 8-[3-(4-piperidinyl)propanoyl]-1,2,5,6-tetrahydro-4H-pyrrolo[3,2,1-ij]quinolin-4-one (700 mg) and (±)-1-methyl-2-phenoxyethyl methanesulfonate (566 mg) according to the same method as that of Example 81, the title compound (559 mg) was obtained as pale yellow amorphous powders.

$^1$H NMR (free base; 300 MHz, CDCl$_3$) δ 1.19 (3H, d, J=6.6 Hz), 1.20-1.45 (3H, m), 1.60-1.80 (4H, m), 2.00-2.50 (3H, m), 2.71 (2H, t, J=7.8 Hz), 2.80-3.10 (6H, m), 3.22 (2H, t, J=8.4 Hz), 3.87 (1H, dd, J=9.4, 6.2 Hz), 4.00-4.20 (3H, m), 6.80-7.00 (3H, m), 7.20-7.35 (2H, m), 7.67 (1H, s), 7.71 (1H, s).

elementary analysis as C$_{28}$H$_{34}$N$_2$O$_3$·HCl·0.5H$_2$O
calculation value: C, 68.35; H, 7.37; N, 5.69.
experimental value: C, 68.37; H, 7.57; N, 5.63.

Example 324

(±)-8-(3-{1-[2-(2-Methoxyphenoxy)-1-methylethyl]-4-piperidinyl}propanoyl)-1,2,5,6-tetrahydro-4H-pyrrolo[3,2,1-ij]quinolin-4-one methanesulfonate hydrochloride

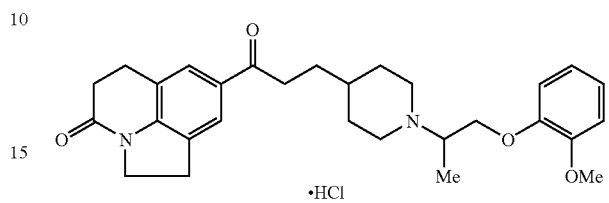

Using 8-[3-(4-piperidinyl)propanoyl]-1,2,5,6-tetrahydro-4H-pyrrolo[3,2,1-ij]quinolin-4-one (600 mg) and (±)-2-(2-methoxyphenoxy)-1-methylethyl methanesulfonate (550 mg) according to the same method as that of Example 81, the title compound (181 mg) was obtained as pale yellow amorphous powders.

$^1$H NMR (free base; 300 MHz, CDCl$_3$) δ 1.19 (3H, d, J=6.6 Hz), 1.20-1.40 (3H, m), 1.60-1.80 (4H, m), 2.25-2.40 (2H, m), 2.72 (2H, t, J=7.8 Hz), 2.85-3.15 (7H, m), 3.22 (2H, t, J=8.4 Hz), 3.80-3.90 (1H, m), 3.85 (3H, s), 4.10-4.20 (3H, m), 6.85-7.00 (4H, m), 7.67 (1H, s), 7.71 (1H, s).

elementary analysis as C$_{29}$H$_{36}$N$_2$O$_4$·HCl·0.5H$_2$O
calculation value: C, 66.72; H, 7.34; N, 5.37.
experimental value: C, 66.33; H, 7.54; N, 5.28.

Example 325

8-{3-[1-(2-Oxo-2-phenylethyl)-4-piperidinyl]propanoyl}-1,2,5,6-tetrahydro-4H-pyrrolo[3,2,1-ij]quinolin-4-one hydrochloride

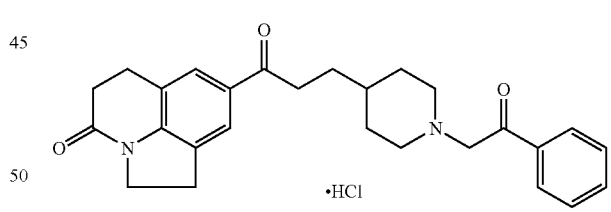

Using 8-[3-(4-piperidinyl)propanoyl]-1,2,5,6-tetrahydro-4H-pyrrolo[3,2,1-ij]quinolin-4-one (500 mg) and phenacyl chloride (248 mg) according to the same method as that of Example 81, the title compound (301 mg) was obtained as colorless crystals having a melting point of 114 to 116° C.

$^1$H NMR (free base; 200 MHz, CDCl$_3$) δ 1.35-1.60 (3H, m), 1.65-1.85 (4H, m), 2.15-2.35 (2H, m), 2.72 (2H, t, J=7.6 Hz), 2.85-3.10 (6H, m), 3.23 (2H, t, J=8.4 Hz), 3.86 (2H, s), 4.14 (2H, t, J=8.4 Hz), 7.40-7.75 (5H, m), 7.98 (1H, s), 8.02 (1H, s).

elementary analysis as C$_{27}$H$_{30}$N$_2$O$_3$·HCl
calculation value: C, 66.86; H, 6.86; N, 5.78.
experimental value: C, 66.64; H, 7.25; N, 5.36.

Example 326

(±)-8-{3-[1-(2-Hydroxy-2-phenylethyl)-4-piperidinyl]propanoyl}-1,2,5,6-tetrahydro-4H-pyrrolo[3,2,1-ij]quinolin-4-one hydrochloride

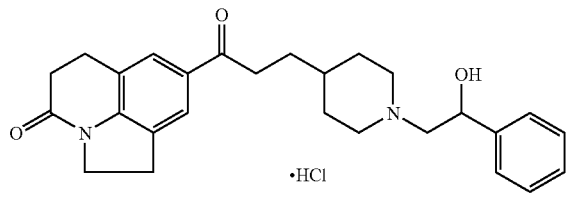

A mixture of 8-[3-(4-piperidinyl)propanoyl]-1,2,5,6-tetrahydro-4H-pyrrolo[3,2,1-ij]quinolin-4-one (500 mg) and styrene oxide (193 mg) in tetrahydrofuran (1 ml) was stirred at 100° C. for 1 hour. The reaction mixture was purified by silica gel chromatography (eluting solvent; ethyl acetate-methanol (9:1)) to give a free base compound of the title compound as colorless crystals (468 mg) having a melting point of 133 to 135° C. The free base compound (390 mg) was treated with a hydrogen chloride-ethanol solution to give the title compound (405 mg) as colorless crystals having a melting point of 235 to 237° C.

$^1$H NMR (free base; 200 MHz, CDCl$_3$) δ 1.30-1.55 (3H, m), 1.60-1.85 (4H, m), 2.00-2.20 (1H, m), 2.25-2.45 (1H, m), 2.50-2.60 (2H, m), 2.72 (2H, t, J=7.6 Hz), 2.85-3.05 (5H, m), 3.15-3.30 (3H, m), 3.40-4.40 (1H, br.), 4.14 (2H, t, J=8.4 Hz), 4.80 (1H, dd, J=8.4, 5.4 Hz), 7.20-7.40 (5H, m), 7.68 (1H, s), 7.72 (1H, s).

elementary analysis as C$_{27}$H$_{32}$N$_2$O$_3$.HCl.0.5H$_2$O
calculation value: C, 67.84; H, 7.17; N, 5.86.
experimental value: C, 68.30; H, 7.47; N, 5.72.

Example 327

1-(3-Amino-4-methoxyphenyl)-3-{1-[2-(2-ethoxyphenoxy)ethyl]-4-piperidinyl}-1-propanone dihydrochloride

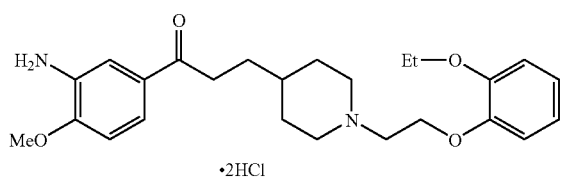

1-(2-Bromoethoxy)-2-ethoxybenzene (732 mg) was added to a suspension of 1-(3-amino-4-methoxyphenyl)-3-(4-piperidinyl)-1-propanone dihydrochloride (1.00 g) obtained in Reference Example 191 and potassium carbonate (1.00 g) in ethanol (20 ml) at room temperature. After stirring at 80° C. for 12 hours, the reaction mixture was concentrated under reduced pressure. Water (30 ml) and ethyl acetate (40 ml) were added to the residue, and the mixture was extracted with ethyl acetate. The organic layer was washed with brine, dried over anhydrous magnesium sulfate, and the solvent was evaporated under reduced pressure. The resulting residue was purified by silica gel chromatography (eluting solvent; ethyl acetate-methanol (9:1)) to give a free base compound of the title compound as colorless crystals (828 mg) having a melting point of 81 to 82° C. The free base compound (200 mg) was treated with a hydrogen chloride-ethanol solution to give the title compound (240 mg) as colorless crystals having a melting point of 123 to 125° C.

$^1$H NMR (free base; 200 MHz, CDCl$_3$) δ 1.20-1.45 (3H, m), 1.43. (3H, t, J=7.0 Hz), 1.60-1.80 (4H, m), 2.00-2.20 (2H, m), 2.50-4.50 (2H, br), 2.83. (2H, t, J=6.2 Hz), 2.91 (2H, t, J=7.2 Hz), 2.95-3.10 (2H, m), 3.91 (3H, s), 4.06 (2H, q, J=7.0 Hz), 4.16 (2H, t, J=6.2 Hz), 6.79 (1H, d, J=8.4 Hz), 6.85-6.95 (4H, m), 7.35-7.45 (2H, m).

elementary analysis as C$_{25}$H$_{34}$N$_2$O$_4$.2HCl.H$_2$O
calculation value: C, 58.02; H, 7.40; N, 5.41.
experimental value: C, 57.66; H, 7.82; N, 4.99.

Example 328

N-[5-(3-{1-[2-(2-Ethoxyphenoxy)ethyl]-4-piperidinyl}propanoyl)-2-methoxyphenyl]methanesulfonamide hydrochloride

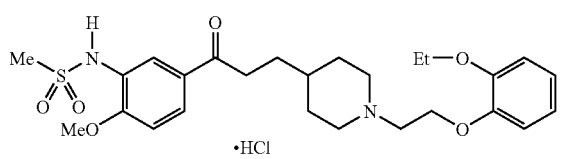

Methanesulfonyl chloride (0.108 ml) was added to a solution of 1-(3-amino-4-methoxyphenyl)-3-{1-[2-(2-ethoxyphenoxy)ethyl]-4-piperidinyl}-1-propanone dihydrochloride (300 mg) obtained in Example 327 and triethylamine (0.195 ml) in tetrahydrofuran (10 ml) at room temperature, the mixture was stirred for 12 hours, and the reaction mixture was concentrated under reduced pressure. Water (30 ml) and ethyl acetate (40 ml) were added to the residue, and the mixture was extracted with ethyl acetate. The organic layer was washed with brine, dried over anhydrous magnesium sulfate, and the solvent was evaporated under reduced pressure. The resulting residue was purified by silica gel chromatography (eluting solvent; ethyl acetate-methanol (9:1)) to give a free base compound of the title compound as a colorless oil (291 mg). The free base compound (290 mg) was treated with a hydrogen chloride-ethanol solution to give the title compound (277 mg) as colorless amorphous powders.

$^1$H NMR (free base; 200 MHz, CDCl$_3$) δ 1.20-1.45 (3H, m), 1.43 (3H, t, J=7.0 Hz), 1.60-1.80 (4H, m), 2.05-2.20 (2H, m), 2.84 (2H, t, J=6.2 Hz), 2.90-3.10 (2H, m), 2.99 (3H,s), 3.45 (3H, s), 3.95-4.20 (7H, m), 6.85-6.95 (4H, m), 6.94 (1H, d, J=5.6 Hz), 7.82 (1H, dd, J=8.4, 2.2 Hz), 8.11 (1H, d, J=2.2 Hz).

elementary analysis as C$_{26}$H$_{36}$N$_2$O$_6$S.HCl.1.5H$_2$O
calculation value: C, 54.97; H, 7.10; N, 4.93.
experimental value: C, 54.63; H, 6.93; N, 4.57.

Example 329

N-[5-(3-{1-[2-(2-Ethoxyphenoxy)ethyl]-4-piperidinyl}propanoyl)-2-methoxyphenyl]acetamide hydrochloride

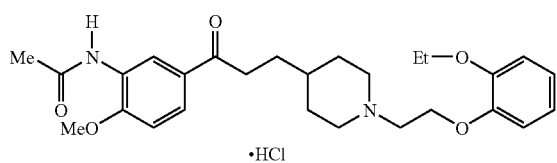

Acetic acid anhydride (0.132 ml) was added to a solution of 1-(3-amino-4-methoxyphenyl)-3-{1-[2-(2-ethoxyphenoxy)ethyl]-4-piperidinyl}-1-propanone dihydrochloride (300 mg) obtained in Example 327 and triethylamine (0.195 ml) in tetrahydrofuran (10 ml) at room temperature, the mixture was stirred for 12 hours, and the reaction mixture was concentrated under reduced pressure. Water (30 ml) and ethyl acetate (40 ml) were added to the residue, and extracted with ethyl acetate. The organic layer was washed with brine, dried over anhydrous magnesium sulfate, and the solvent was evaporated under reduced pressure. The resulting residue was purified by silica gel chromatography (eluting solvent; ethyl acetate-methanol (9:1)) to give a free base compound of the title compound as a colorless oil (276 mg). The free base compound (270 mg) was treated with a hydrogen chloride-ethanol solution to give the title compound (277 mg) as colorless crystals having a melting point of 127 to 129° C.

$^1$H NMR (free base; 200 MHz, CDCl$_3$) δ 1.20-1.45 (3H, m), 1.43 (3H, t, J=7.0 Hz), 1.60-1.80 (4H, m), 2.05-2.20 (2H, m), 2.23 (3H, s), 2.83 (2H, t, J=6.2 Hz), 2.90-3.10. (4H, m), 3.94 (3H, s), 4.07 (2H, q, J=7.0 Hz), 4.15 (2H, t, J=6.2 Hz), 6.80-7.00 (5H, m), 7.70-7.80 (2H, m), 9.01 (1H, s).

elementary analysis as $C_{27}H_{36}N_2O_5 \cdot HCl \cdot 0.5H_2O$
calculation value: C, 63.09; H, 7.45; N, 5.45.
experimental value: C, 60.19; H, 7.42; N, 5.22.

Example 330

(±)-8-{3-[1-(2,3-Dihydro-1H-inden-1-yl)-4-piperidinyl]propanoyl}-1,2,5,6-tetrahydro-4H-pyrrolo[3,2,1-ij]quinolin-4-one hydrochloride

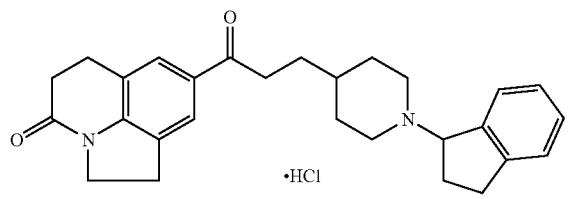

1-Chloroindane (360 mg) was added to a suspension of 8-[3-(4-piperidinyl)propanoyl]1,2,5,6-tetrahydro-4H-pyrrolo[3,2,1-ij]quinolin-4-one (700 mg), potassium carboante (700 mg) and potassium iodide (catalytic amount) in acetonitrile (10 ml) at room temperature, the mixture was stirred for 12 hours, and the reaction mixture was concentrated under reduced pressure. Water (15 ml) and ethyl acetate (20 ml) were added to the residue, and extracted with ethyl acetate. The extract was washed with brine, dried over anhydrous magnesium sulfate, and the solvent was evaporated under reduced pressure. The resulting residue was purified by silica gel chromatography (eluting solvent; ethyl acetate-methanol (9:1)) to give a free base compound of the title compound as colorless crystals (285 mg) having a melting point of 111 to 113° C. The free base compound (270 mg) was treated with a hydrogen chloride-ethanol solution to give the title compound (270 mg) as pale yellow amorphous powders.

$^1$H NMR (free base; 300 MHz, CDCl$_3$) δ 1.00-1.45. (3H, m), 1.60-1.80 (4H, m), 2.00-2.30. (4H, m), 2.60-2.95 (8H, m), 3.02 (2H, t, J=7.5 Hz), 3.22. (2H, t, J=8.4 Hz), 4.13. (2H, t, J=8.4 Hz), 4.35 (1H, t, J=7.0 Hz), 7.15-7.40 (3H, m), 7.60-7.80 (3H, m).

elementary analysis as $C_{28}H_{32}N_2O_2 \cdot HCl \cdot 2.0H_2O$
calculation value: C, 67.12; H, 7.44; N, 5.59.
experimental value: C, 67.34; H, 7.30; N, 5.45.

Example 331

(±)-8-{3-[1-(1,2,3,4-Tetrahydro-1-naphthalenyl)-4-piperidinyl]propanoyl}-1,2,5,6-tetrahydro-4H-pyrrolo[3,2,1-ij]quinolin-4-one hydrochloride

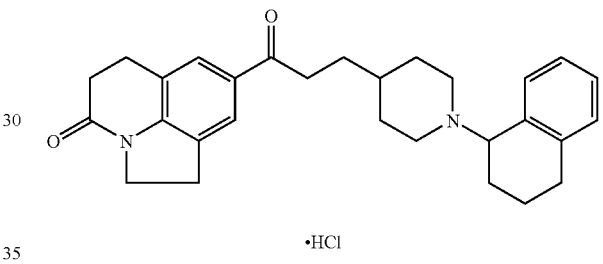

Using 8-[3-(4-piperidinyl)propanoyl]-1,2,5,6-tetrahydro-4H-pyrrolo[3,2,1-ij]quinolin-4-one (500 mg) and (±)-1-chloro-1,2,3,4-tetrahydronaphthalene (280 mg) according to the same method as that of Example 330, the title compound (43 mg) was obtained as pale yellow amorphous powders.

$^1$H NMR (free base; 200 MHz, CDCl$_3$) δ 1.10-1.45. (3H, m), 1.55-1.80 (6H, m), 1.85-2.10 (4H, m), 2.50-3.10 (10H, m), 3.23. (2H, t, J=8.4 Hz), 3.75-3.85 (1H, m), 4.14 (2H, t, J=8.4 Hz), 7.00-7.20 (3H, m), 7.65-7.75. (3H, m).

Example 332

(±)-8-{3-[1-(1,2,3,4-Tetrahydro-2-naphthalenyl)-4-piperidinyl]propanoyl}-1,2,5,6-tetrahydro-4H-pyrrolo[3,2,1-ij]quinolin-4-one hydrochloride

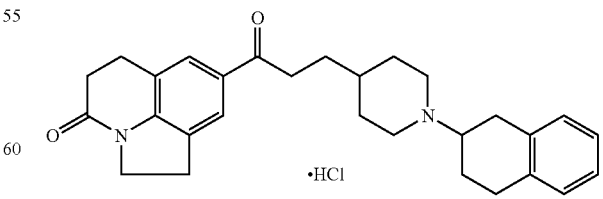

Using 8-[3-(4-piperidinyl)propanoyl]-1,2,5,6-tetrahydro-4H-pyrrolo[3,2,1-ij]quinolin-4-one (600 mg) and (±)-1,2,3,4-tetrahydro-2-naphthalenyl methanesulfonate (456 mg) according to the same method as that of Example 330, the title compound (290 mg) was obtained as colorless crystals having a melting point of 223 to 225° C.

$^1$H NMR (free base; 200 MHz, CDCl$_3$) δ 1.20-1.45 (3H, m), 1.55-1.85 (4H, m), 2.00-2.40 (3H, m), 2.60-3.10 (14H, m), 3.23 (2H, t, J=8.4 Hz), 4.14. (2H, t, J=8.4 Hz), 7.00-7.20 (4H, m), 7.68 (1H, s), 7.73 (1H, s).

elementary analysis as C$_{29}$H$_{34}$N$_2$O$_2$.HCl.H$_2$O
calculation value: C, 70.07; H, 7.50; N, 5.64.
experimental value: C, 69.77; H, 7.26; N, 5.56.

Example 333

8-{3-[1-(6,7,8,9-Tetrahydro-5H-benzo[a]cyclohepten-7-yl)-4-piperidinyl]propanoyl}-1,2,5,6-tetrahydro-4H-pyrrolo[3,2,1-ij]quinolin-4-one hydrochloride

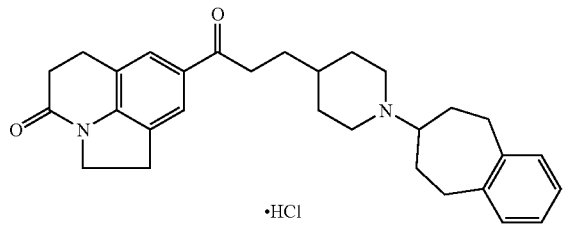

Using 8-[3-(4-piperidinyl)propanoyl]-1,2,5,6-tetrahydro-4H-pyrrolo[3,2,1-ij]quinolin-4-one (60 mg) and 6,7,8,9-tetrahydro-5H-benzo[a]cyclohepten-7-yl methanesulfonate (485 mg) according to the same method as that of Example 330, the title compound (51 mg) was obtained as pale yellow amorphous powders.

$^1$H NMR (free base; 300 MHz, CDCl$_3$) δ 1.30-1.60 (5H, m), 1.60-1.85 (4H, m), 2.15-2.50 (4H, m), 2.65-2.95 (11H, m), 3.02 (2H, t, J=7.8 Hz), 3.22 (2H, t, J=8.4 Hz), 4.13 (2H, t, J=8.4 Hz), 7.12 (4H, s), 7.67 (1H, s), 7.71 (1H, s).

Example 334

8-{3-[2,3-Dihydro-1H-inden-2-yl(ethyl)amino]propanoyl}-1,2,5,6-tetrahydro-4H-pyrrolo[3,2,1-ij]quinolin-4-one hydrochloride

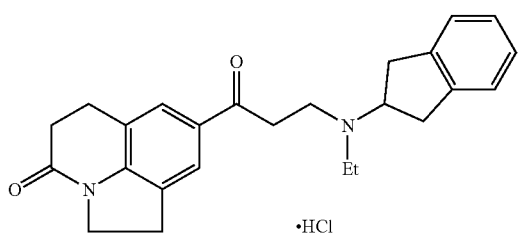

Using 8-(3-chloropropanoyl)-1,2,5,6-tetrahydro-4H-pyrrolo[3,2,1-ij]quinolin-4-one (489 mg) obtained in Reference Example 192 and N-(2,3-dihydro-1H-inden-2-yl)-N-ethylamine (330 mg) according to the same method as that of Example 9, the title compound (406 mg) was obtained as colorless crystals having a melting point of 192 to 196° C.

$^1$H NMR (free base; 200 MHz, CDCl$_3$) δ 1.10 (3H, t, J=7.2 Hz), 2.10-2.45 (1H, m), 2.60-3.30 (16H, m), 3.55-3.75 (1H, m), 4.13 (2H, t, J=8.4 Hz), 7.00-7.20 (4H, m), 7.68 (1H, s), 7.72 (1H, s).

Example 335

8-[4-(1,3,4,5-Tetrahydro-2H-2-benzazepin-2-yl)butanoyl]-1,2,5,6-tetrahydro-4H-pyrrolo[3,2,1-ij]quinolin-4-one hydrochloride

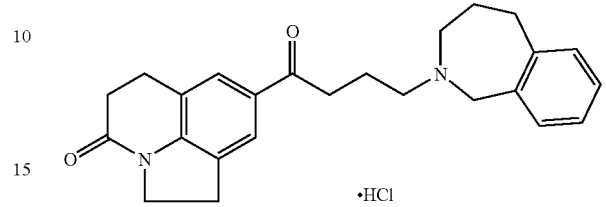

Using 8-(4-chlorobutanoyl)-1,2,5,6-tetrahydro-4H-pyrrolo[3,2,1-ij]quinolin-4-one (500 mg) obtained in Reference Example 179 and 2,3,4,5-tetrahydro-1H-2-benzazepine (290 mg) according to the same method as that of Example 9, the title compound (538 mg) was obtained as colorless crystlas having a melting point of 230 to 232° C.

$^1$H NMR (free base; 200 MHz, CDCl$_3$) δ 1.60-1.80 (2H, m), 1.90 (2H, quintet, J=7.2 Hz), 2.40 (2H, t, J=7.2 Hz), 2.70 (2H, t, J=7.6 Hz), 2.80-3.15. (8H, m), 3.20 (2H, t, J=8.4 Hz), 3.87 (2H, s), 4.12 (2H, t, J=8.4 Hz), 7.00-7.20 (4H, m), 7.66 (1H, s), 7.70 (1H, s).

elementary analysis as C$_{25}$H$_{28}$N$_2$O$_2$.HCl
calculation value: C, 70.66; H, 6.88; N, 6.59.
experimental value: C, 70.20; H, 6.80; N, 6.56.

Example 336

8-[4-(7-Methoxy-1,3,4,5-tetrahydro-2H-2-benzazepin-2-yl)butanoyl]-1,2,5,6-tetrahydro-4H-pyrrolo[3,2,1-ij]quinolin-4-one hydrochloride

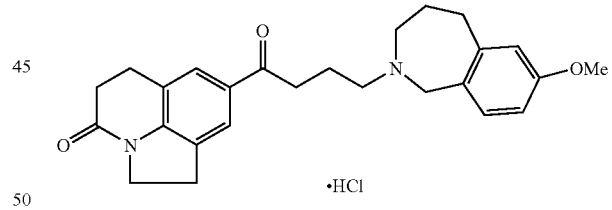

Using 8-(4-chlorobutanoyl)-1,2,5,6-tetrahydro-4H-pyrrolo[3,2,1-ij]quinolin-4-one (500 mg) obtained in Reference Example 179 and 7-methoxy-2,3,4,5-tetrahydro-1H-2-benzazepine (320 mg) according to the same method as that of Example 9, the title compound (246 mg) was obtained as colorless crystals having a melting point of 121 to 123° C.

$^1$H NMR (free base; 200 MHz, CDCl$_3$) δ 1.65-1.80 (2H, m), 1.91 (2H, quintet, J=7.0 Hz), 2.42 (2H, t, J=7.0 Hz), 2.71 (2H, t, J=7.6 Hz), 2.80-3.15 (8H, m), 3.21 (2H, t, J=8.4 Hz), 3.78 (3H, s), 3.84 (2H, s), 4.13 (2H, t, J=8.4 Hz), 6.61 (1H, dd, J 8.4, 2.6 Hz), 6.70 (1H, d, J=2.6 Hz), 7.03. (1H, d, J=8.4 Hz), 7.67 (1H, s), 7.71 (1H, s).

elementary analysis as C$_{26}$H$_{30}$N$_2$O$_3$.HCl.H$_2$O
calculation value: C, 66.02; H, 7.03; N, 5.92.
experimental value: C, 66.09; H, 7.30; N, 5.64.

Example 337

(±)-8-[5-(2,3-Dihydro-1H-inden-1-ylamino)pentanoyl]-1,2,5,6-tetrahydro-4H-pyrrolo[3,2,1-ij]quinolin-4-one hydrochloride

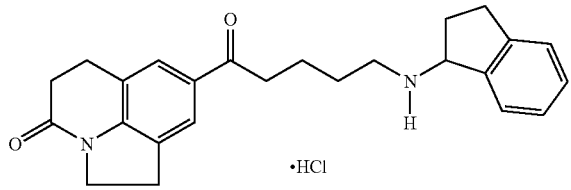

Using tert-butyl (±)-2,3-dihydro-1H-inden-1-yl[5-oxo-5-(4-oxo-1,2,5,6-tetrahydro-4H-pyrrolo[3,2,1-ij]quinolin-8-yl)pentyl]carbamate (332 mg) obtained in Reference Example 193 according to the same method as that of Example 1, the title compound (57 mg) was obtained as colorless crystals having a melting point of 98 to 100° C.

$^1$H NMR (200 MHz, DMSO-$d_6$) δ 1.50-1.75 (4H, m), 2.00-2.50 (2H, m), 2.54 (2H, t, J=7.6 Hz), 2.75-3.05 (8H, m), 3.12. (2H, t, J=8.8 Hz), 3.94 (2H, t, J=8.8 Hz), 4.60-4.75 (1H, m), 7.20-7.35. (3H, m), 7.60-7.70 (3H, m).

elementary analysis as $C_{25}H_{28}N_2O_2 \cdot HCl \cdot 1.5H_2O$ calculation value: C, 66.43; H, 7.14; N, 6.20.

experimental value: C, 66.70; H, 6.77; N, 6.09.

Example 338

8-[5-(2,3-Dihydro-1H-inden-2-ylamino)pentanoyl]-1,2,5,6-tetrahydro-4H-pyrrolo[3,2,1-ij]quinolin-4-one hydrochloride

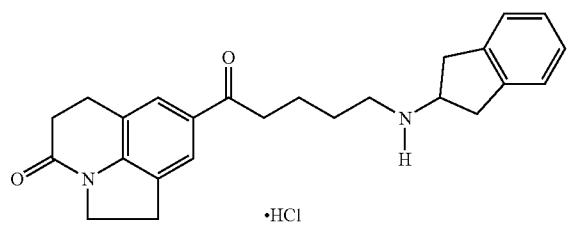

Using tert-butyl 2,3-dihydro-1H-inden-2-yl[5-oxo-5-(4-oxo-1,2,5,6-tetrahydro-4H-pyrrolo[3,2,1-ij]quinolin-8-yl) pentyl]carbamate (461 mg) obtained in Reference Example 194 according to the same method as that of Example 1, the title compound (275 mg) was obtained as colorless crystals having a melting point of 187 to 189° C.

$^1$H NMR (200 MHz, DMSO-$d_6$) δ 1.60-1.80 (4H, m), 2.59 (2H, t, J=7.6 Hz), 2.80-3.40 (12H, m), 3.80-4.05 (3H, m), 7.10-7.30 (4H, m), 7.75 (2H, s), 9.40-9.60 (2H, br).

elementary analysis as $C_{25}H_{28}N_2O_2 \cdot HCl \cdot 2H_2O$ calculation value: C, 65.13; H, 7.22; N, 6.08.

experimental value: C, 64.75; H, 7.01; N, 6.02.

Example 339

8-[5-(6,7-Dimethoxy-3,4-dihydro-2(1H)-isoquinolinyl)pentanoyl]-1,2,5,6-tetrahydro-4H-pyrrolo[3,2,1-ij]quinolin-4-one hydrochloride

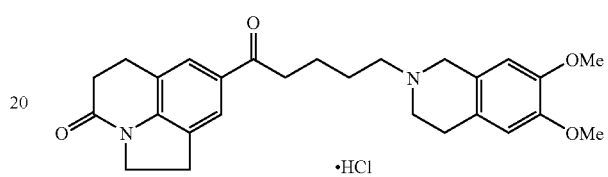

Using 8-(5-chloropentanoyl)-1,2,5,6-tetrahydro-4H-pyrrolo[3,2,1-ij]quinolin-4-one (1.00 g) obtained in Reference Example 1 and 6,7-dimethoxy-1,2,3,4-tetrahydroisoquinoline (945 mg) according to the same method as that of Reference Example 19, the title compound (430 mg) was obtained as colorless crystals having a melting point of 215 to 217° C.

$^1$H NMR (free base; 200 MHz, CDCl$_3$) δ 1.60-2.00 (6H, m), 2.56 (2H, t, J=7.0 Hz), 2.65-3.10 (8H, m), 3.20 (2H, t, J=8.4 Hz), 3.55 (2H, s), 3.84 (6H, s), 4.13 (2H, t, J=8.4 Hz), 6.52 (1H, s), 6.58 (1H, s), 7.68 (1H, s), 7.72 (1H, s).

elementary analysis as $C_{27}H_{32}N_2O_4 \cdot HCl \cdot H_2O$ calculation value: C, 64.47; H, 7.01; N, 5.57.

experimental value: C, 64.74; H, 7.25;. N, 5.30.

Example 340

8-[5-(1,2,4,5-Tetrahydro-3H-3-benzazepin-3-yl)pentanoyl]-1,2,5,6-tetrahydro-4H-pyrrolo[3,2,1-ij]quinolin-4-one hydrochloride

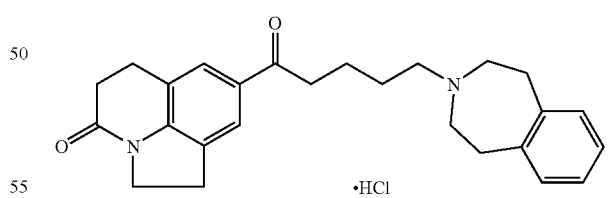

Using 8-(5-chloropentanoyl)-1,2,5,6-tetrahydro-4H-pyrrolo[3,2,1-ij]quinolin-4-one (1.00 g) obtained in Reference Example 1 and 2,3,4,5-tetrahydro-1H-3-benzazepine (605 mg) according to the same method as that of Reference Example 19, the title compound (703 mg) was obtained as colorless crystals having a melting point of 252 to 254° C.

$^1$H NMR (free base; 200 MHz, CDCl$_3$) δ 1.50-1.85 (4H, m), 2.53 (2H, t, J=7.4 Hz), 2.60-3.10 (14H, m), 3.22 (2H, t, J=8.4 Hz), 4.13 (2H, t, J=8.4 Hz), 7.00-7.20 (4H, m), 7.68 (1H, s), 7.73 (1H, s).

Example 341

8-{6-[2,3-Dihydro-1H-inden-2-yl(ethyl)amino]hex-anoyl}-1,2,5,6-tetrahydro-4H-pyrrolo[3,2,1-ij]quinolin-4-one hydrochloride

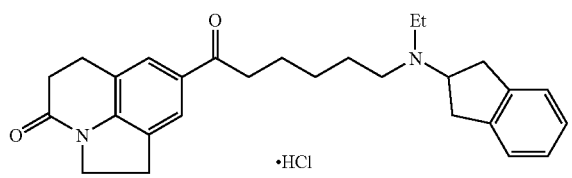

Using 8-(6-bromohexanoyl)-1,2,5,6-tetrahydro-4H-pyrrolo[3,2,1-ij]quinolin-4-one (650 mg) obtained in Reference Example 2 and N-(2,3-dihydro-1H-inden-2-yl)-N-ethylamine (330 mg) according to the same method as that of Reference Example 19, the title compound (366 mg) was obtained as colorless crystals having a melting point of 160 to 162° C.

$^1$H NMR (free base; 200 MHz, CDCl$_3$) δ 1.20 (3H, t, J=7.2 Hz), 1.30-1.85 (6H, m), 2.50-3.30 (13H, m), 3.60-3.80 (4H, m), 4.10 (2H, t, J=8.4 Hz), 7.05-7.25 (4H, m), 7.67 (1H, s), 7.71 (1H, s).

Example 342

8-[6-(6,7-Dimethoxy-3,4-dihydro-2(1H)-isoquinolinyl)hexanoyl]-1,2,5,6-tetrahydro-4H-pyrrolo[3,2,1-ij]quinolin-4-one hydrochloride

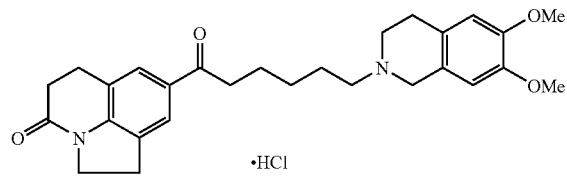

Using 8-(6-bromohexanoyl)-1,2,5,6-tetrahydro-4H-pyrrolo[3,2,1-ij]quinolin-4-one (600 mg) obtained in Reference Example. 2 and 6,7-dimethoxy-1,2,3,4-tetrahydroisoquinoline (432 mg) according to the same method as that of Reference Example 19, the title compound (540 mg) was obtained as colorless crystals having a melting point of 216 to 218° C.

$^1$H NMR (free base; 200 MHz, CDCl$_3$) δ 1.35-2.05 (8H, m), 2.51 (2H, t, J=7.6 Hz), 2.60-2.85 (4H, m), 2.93 (2H, t, J=7.6 Hz), 3.02 (2H, t, J=7.6 Hz), 3.22 (2H, t, J=8.4 Hz), 3.55 (2H, s), 3.83 (6H, s), 4.13 (2H, t, J=8.4 Hz), 6.52 (1H, s), 6.59 (1H, s), 7.68 (1H, s), 7.72 (1H, s).

elementary analysis as C$_{28}$H$_{34}$N$_2$O$_4$.HCl.2.5H$_2$O calculation value: C, 61.81; H, 7.41; N, 5.15.

experimental value: C, 62.26; H, 6.99; N, 5.14.

Example 343

8-[6-(1,2,4,5-Tetrahydro-3H-3-benzazepin-3-yl)hexanoyl]-1,2,5,6-tetrahydro-4H-pyrrolo[3,2,1-ij]quinolin-4-one hydrochloride

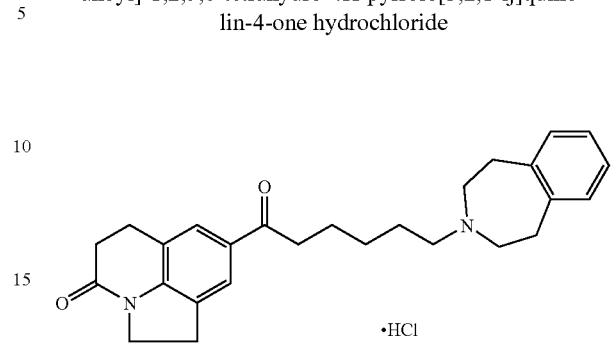

Using 8-(6-bromohexanoyl)-1,2,5,6-tetrahydro-4H-pyrrolo[3,2,1-ij]quinolin-4-one (600 mg) obtained in Reference Example 2 and 2,3,4,5-tetrahydro-1H-3-benzazepine (277 mg) according to the same method as that of Reference Example 19, the title compound (566 mg) was obtained as colorless crystals having a melting point of 222 to 225° C.

$^1$H NMR (free base; 200 MHz, CDCl$_3$) δ 1.30-1.85 (10H, m), 2.49 (2H, t, J=7.6 Hz), 2.60-2.80 (4H, m), 2.85-3.10. (6H, m), 3.21 (2H, t, J=8.4 Hz), 4.13 (2H, t, J=8.4 Hz), 7.10 (4H, s), 7.67 (1H, s), 7.72 (1H, s)

elementary analysis as C$_{27}$H$_{32}$N$_2$O$_2$.HCl.0.5H$_2$O calculation value: C, 70.19; H, 7.42; N, 6.06.

experimental value: C, 70.72; H, 7.13; N, 6.09.

Example 344

9-(3-{1-[2-(2-Methylphenyl)ethyl]piperidin-4-yl}propanoyl)-2,3,6,7-tetrahydro-1H,5H-pyrido[3,2,1-ij]quinolin-5-one hydrochloride

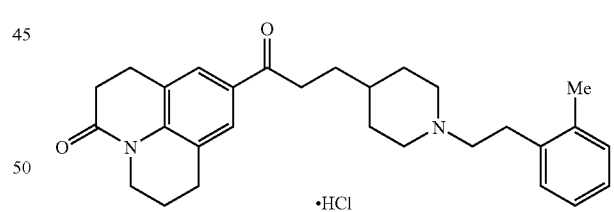

Using 9-(3-piperidin-4-ylpropanoyl)-2,3,6,7-tetrahydro-1H,5H-pyrido[3,2,1-ij]quinolin-5-one (326 mg) obtained in Reference Example 176 and 2-(2-methylphenyl)ethyl methanesulfonate (214 mg) according to the same method as that of Example 81, the title compound (172 mg) was obtained as pale yellow amorphous powders.

$^1$H NMR (free base; 400 MHz, CDCl$_3$) δ 1.30-1.40 (3H, m), 1.68-1.78 (4H, m), 1.94-2.02. (4H, m), 2.32 (3H, s), 2.49-2.53 (2H, m), 2.68 (2H, t, J=7 Hz), 2.80-2.86. (4H, m), 2.94 (4H, t, J=7 Hz), 3.04 (2H, t, J=11 Hz), 3.89(2H, t, J=6 Hz), 7.09-7.15. (4H, m), 7.62. (2H, d, J=5 Hz).

IR (neat) vcm$^{-1}$: 1674, 1604, 1489, 1361, 1339, 1168.

Example 345

9-{5-[[2-(3-Fluorophenyl)ethyl](methyl)amino]pentanoyl}-2,3,6,7-tetrahydro-1H,5H-pyrido[3,2,1-ij]quinolin-5-one hydrochloride

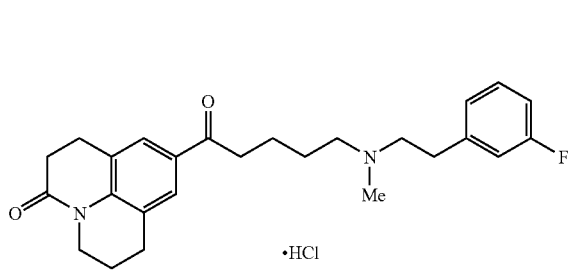

Using 9-(5-chloropentanoyl)-2,3,6,7-tetrahydro-1H,5H-pyrido[3,2,1-ij]quinolin-5-one (306 mg) obtained in Reference Example 5 and N-[2-(3-fluorophenyl)ethyl]-N-methylamine (337 mg) according to the same method as that of Example 9, the title compound (205 mg) was obtained as pale yellow amorphous powders.

$^1$H NMR (free base; 400 MHz, CDCl$_3$) δ 1.54-1.60 (2H, m), 1.70-1.77 (2H, m), 1.93-1.99 (2H, m), 2.29 (3H, s), 2.44 (2H, t, J=7.5 Hz), 2.58-2.62 (2H, m), 2.67 (2H, t, J=6 Hz), 2.74-2.79 (2H, m), 2.84 (2H, t, J=6 Hz), 2.91-2.96 (4H, m), 3.89 (2H, t, J=6 Hz), 6.85-6.91 (2H, m), 6.96 (1H, d, J=7.5 Hz), 7.19-7.25 (1H, m), 7.62 (2H, d, J=5 Hz).

IR (neat) vcm$^{-1}$: 1675, 1604, 1589, 1485, 1362, 1339, 1161.

Example 346

6-{5-[(2-Phenylethyl)amino]pentanoyl}-3,4-dihydroquinolin-2(1H)-one hydrochloride

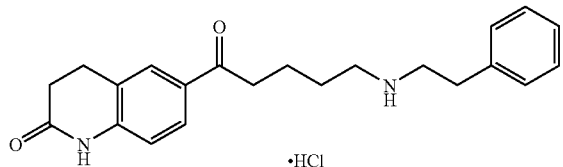

Using tert-butyl 5-oxo-5-(2-oxo-1,2,3,4-tetrahydroquinolin-6-yl)pentyl(2-phenylethyl)carbamate (520 mg) obtained in Reference Example 345 according to the same method as that of Example 1, the title compound was obtained as colorless crystals (390 mg) having a melting point of 200 to 202° C.

$^1$H NMR (400 MHz, DMSO-d$_6$) δ 1.64-1.76 (4H, m), 2.47-2.51 (2H, m), 2.93-3.02 (8H, m), 3.05-3.15 (2H, m), 6.97 (1H, d, J=8.3 Hz), 7.22-7.27 (3H, m), 7.31-7.35 (2H, m), 7.78-7.82 (2H, m), 9.25 (2H, s), 10.46 (1H, s).

IR (KBr) vcm$^{-1}$: 3305, 2937, 2775, 1684, 1604, 1508, 1367.

Example 347

6-(5-{[2-(2-Methoxyphenyl)ethyl]amino}pentanoyl)-3,4-dihydroquinolin-2(1H)-one hydrochloride

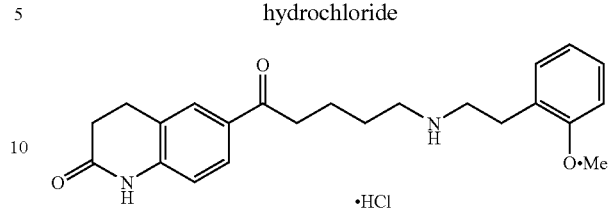

Using tert-butyl 2-(2-methoxyphenyl)ethyl[5-oxo-5-(2-oxo-1,2,3,4-tetrahydroquinolin-6-yl)pentyl]carbamate (630 mg) obtained in Reference Example 197 according to the same method as that of Example 1, the title compound was obtained as colorless crystals (449 mg) having a melting point of 176 to 177° C.

$^1$H NMR (400 MHz, DMSO-d$_6$) δ 1.63-1.72 (4H, m), 2.47-2.51 (2H, m), 2.92-3.01(10H, m), 3.79 (3H, s), 6.90 (1H, t, J=7.5 Hz), 6.98 (2H, t, J=7.3 Hz), 7.18 (1H, d, J=7.3 Hz), 7.24 (1H, t, J=7.5 Hz), 7.78-7.82 (2H, m), 9.16 (2H, s), 10.46 (1H, s).

IR (KBr) vcm$^{-1}$: 3272, 2942, 2747, 1682, 1602, 1501, 1369, 1312, 1253, 762.

Example 348

6-(5-{[2-(2-Chlorophenyl)ethyl]amino}pentanoyl)-3,4-dihydroquinolin-2(1H)-one hydrochloride

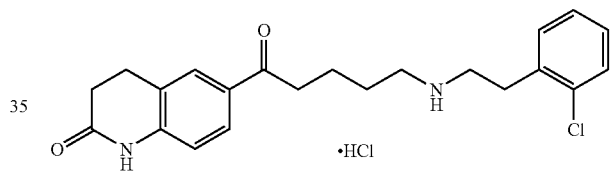

Using tert-butyl 2-(2-chlorophenyl)ethyl[5-oxo-5-(2-oxo-1,2,3,4-tetrahydroquinolin-6-yl)pentyl]carbamate (670 mg) obtained in Reference Example 198 according to the same method as that of Example 1, the title compound was obtained as colorless crystals (450 mg) having a melting point of 197 to 198° C.

$^1$H NMR (400 MHz, DMSO-d$_6$) δ 1.64-1.74 (4H, m), 2.47-2.51 (2H, m), 2.92-3.10(10H, m), 6.96 (1H, d, J=8.3 Hz), 7.28-7.35 (2H, m), 7.39-7.47 (2H, m), 7.78-7.82 (2H, m), 9.31 (2H, s), 10.45 (1H, s).

IR (KBr) vcm$^{-1}$: 3276, 2955, 2738, 1684, 1654, 1599, 1508, 1361, 1304, 1170,

Example 349

6-(5-{[2-(2-Chlorophenyl)ethyl]amino}pentanoyl)-3,4-dihydroquinolin-2(1H)-one hydrochloride

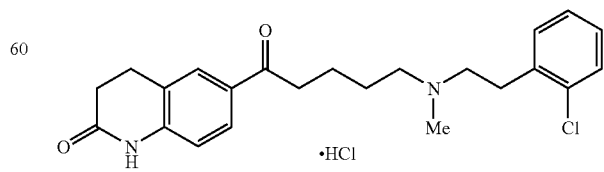

Using 6-(5-chloropentanoyl)-3,4-dihydroquinolin-2(1H)-one (133 mg) obtained in Reference Example 195 and N-[2-(2-chlorophenyl)ethyl]-N-methylamine (187 mg) according to the same method as that of Example 9, the title compound was obtained as colorless crystals (99 mg) having a melting point of 167 to 168° C.

$^1$H NMR (free base; 400 MHz, CDCl$_3$) δ 1.54-1.61 (2H, m), 1.71-1.79 (2H, m), 2.34 (3H, s), 2.47 (2H, t, J=7.3 Hz), 2.59-2.63 (2H, m), 2.68 (2H, t, J=8 Hz), 2.88-2.97 (4H, m), 3.04. (2H, t, J=7.3 Hz), 6.85 (1H, d, J=6.4 Hz), 7.10-7.19 (2H, m), 7.23 (1H, d, J=7.5 Hz), 7.32 (1H, d, J=7.5 Hz), 7.80 (1H, d, J=6.4 Hz), 7.81 (1H, s), 8.95 (1H, br).

IR (KBr) νcm$^{-1}$: 3188, 3059, 1674, 1608, 1595, 1384, 1314, 816, 751.

Example 350

6-{6-[(2-Phenylethyl)amino]hexanoyl}-3,4-dihydro-quinolin-2(1H)-one hydrochloride

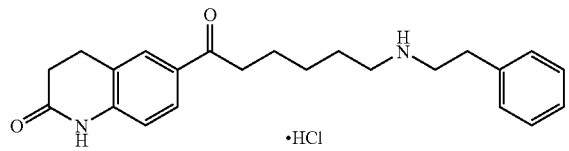

Using 6-(6-bromohexanoyl)-3,4-dihydroquinolin-2(1H)-one (486 mg) obtained in Reference Example 199 and 2-phenylethylamine (454 mg) according to the same method as that of Example 9, the title compound was obtained as colorless crystals (205 mg) having a melting point of 223 to 224° C.

$^1$H NMR (free base; 400 MHz, CDCl$_3$) δ 1.35-1.42 (2H, m), 1.46 (1H, br.s), 1.49-1.56(2H, m), 1.69-1.77(2H, m), 2.62-2.70 (4H, m), 2.80 (2H, t, J=6 Hz), 2.86-2.92 (4H, m), 3.03 (2H, t, J=7.4 Hz), 6.83 (1H, d, J=7 Hz), 7.16-7.18 (3H, m), 7.27-7.31 (2H, m), 7.79 (1H, d, J=7 Hz), 7.80 (1H, s), 8.93 (1H, br).

IR (KBr) νcm$^{-1}$: 3193, 3062, 1671, 1605, 1505, 1381, 1314.

Example 351

6-(6-{[2-(2-Methoxyphenyl)ethyl]amino}hexanoyl)-3,4-dihydroquinolin-2(1H)-one hydrochloride

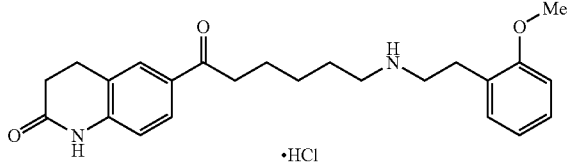

Using 6-(6-bromohexanoyl)-3,4-dihydroquinolin-2(1H)-one (486 mg) obtained in Reference Example 199 and 2-(2-methoxyphenyl)ethylamine (567 mg) according to the same method as that of Example 9, the title compound was obtained as colorless crystals (122 mg) having a melting point of 223 to 224° C.

$^1$H NMR (free base; 400 MHz, CDCl$_3$) δ 1.35-1.43 (2H, m), 1.49-1.57 (2H, m), 1.53 (1H, br), 1.69-1.77(2H, m), 2.62-2.69 (4H, m), 2.78-2.86 (4H, m), 2.90 (2H, t, J=7 Hz), 3.03 (2H, t, J=7 Hz), 3.81 (3H, s), 6.81-6.89 (3H, m), 7.13-7.20 (2H, m), 7.78 (1H, d, J=7 Hz), 7.79 (1H, s), 9.30 (1H, br).

IR (KBr) νcm$^{-1}$: 3192, 3061, 1677, 1608, 1495, 1367, 1317, 1243.

Example 352

6-(6-{([2-(2-Chlorophenyl)ethyl]amino}hexanoyl)-3,4-dihydroquinolin-2(1H)-one hydrochloride

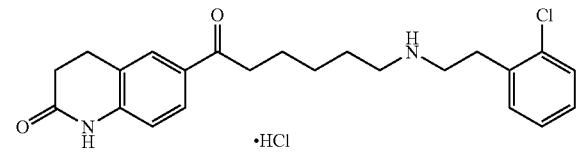

Using 6-(6-bromohexanoyl)-3,4-dihydroquinolin-2(1H)-one (486 mg) obtained in Reference Example 199 and 2-(2-chlorophenyl)ethylamine (584 mg) according to the same method as that of Example 9, the title compound was obtained as colorless crystals (196 mg) having a melting point of 213 to 214° C.

$^1$H NMR (free base; 400 MHz, CDCl$_3$) δ 1.37-1.45 (2H, m), 1.49 (1H, br), 1.51-1.58(2H, m), 1.71-1.78 (2H, m), 2.65-2.70 (4H, m), 2.86-2.96 (6H, m), 3.04 (2H, t, J=7 Hz), 6.85 (1H, d, J=7 Hz), 7.12-7.31 (3H; m), 7.34 (1H, d, J=7.4 Hz), 7.80 (1H, d, J=7 Hz), 7.81 (1H, s), 8.93 (1H, br).

IR (KBr) νcm$^{-1}$: 3191, 3059, 1672, 1608, 1506, 1380, 1316.

Example 353

6-(5-{[2-(2-Methoxyphenyl)ethyl]amino}pentanoyl)-1-methyl-3,4-dihydroquinolin-2(1H)-one hydrochloride

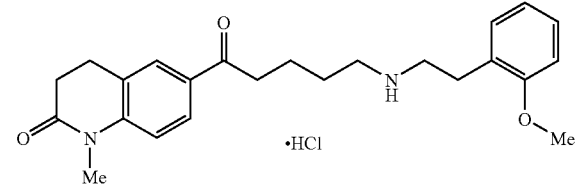

Using tert-butyl 2-(2-methoxyphenyl)ethyl[5-(1-methyl-2-oxo-1,2,3,4-tetrahydroquinolin-6-yl)-5-oxopentyl]carbamate (220 mg) obtained in Reference Example 200 according to the same method as that of Example 1, the title compound was obtained as colorless crystals (184 mg) having a melting point of 167 to 168° C.

$^1$H NMR (400 MHz, DMSO-d$_6$) δ 1.52-1.68 (4H, m), 2.49 (2H, t, J=8 Hz), 2.83-2.96(10H, m), 3.19 (3H, s), 3.71 (3H, s), 6.81 (1H, t, J=7.5 Hz), 6.90 (1H, t, J=8.3 Hz), 7.08-7.11 (2H, m), 7.16 (1H, d, J=7.5 Hz), 7.76 (1H, s), 7.80 (1H, d, J=8.3 Hz), 9.10 (2H, s).

IR (KBr) νcm$^{-1}$: 2951, 2783, 2453, 1688, 1606, 1494, 1469, 1354, 1248, 1125, 766.

Example 354

6-(5-{[2-(2-Chlorophenyl)ethyl]amino}pentanoyl)-3,4-dihydroquinolin-2(1H)-one hydrochloride

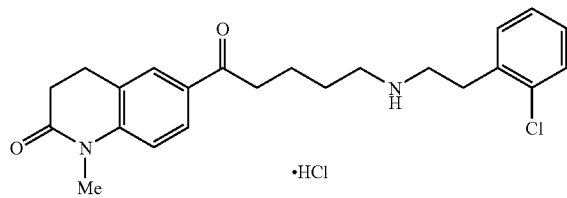

Using tert-butyl 2-(2-chlorophenyl)ethyl[5-(1-methyl-2-oxo-1,2,3,4-tetrahydro-6-quinolinyl)-5-oxopentyl]carbamate (240 mg) obtained in Reference Example 201 according to the same method as that of Example 1, the title compound was obtained as colorless crystals (193 mg) having a melting point of 102 to 103° C.

$^1$H NMR (400 MHz, DMSO-$d_6$) δ 1.52-1.68 (4H, m), 2.49 (2H, t, J=8 Hz), 2.87-3.07(10H, m), 3.19 (3H, s), 7.10 (1H, d, J=8.5 Hz), 7.19-7.26 (2H, m), 7.32 (1H, dd, J=7, 2 Hz), 7.37 (1H, dd, J=7, 2 Hz), 7.76, (1H, s), 7.81 (1H, d, J=8.5 Hz), 9.25 (2H, s).

IR (KBr) vcm$^{-1}$: 2947, 2768, 2453, 1671, 1604, 1477, 1443, 1355, 1126, 751.

Example 355

6-{5-[[2-(2-Methoxyphenyl)ethyl](methyl)amino]pentanoyl}-1-methyl-3,4-dihydroquinolin-2(1H)-one hydrochloride

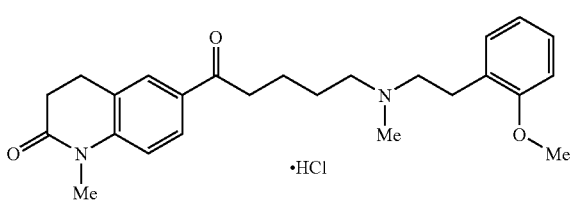

Using 6-(5-chloropentanoyl)-1-methyl-3,4-dihydroquinolin-2(1H)-one (224 mg) obtained in Reference Example 154 and N-[2-(2-methoxyphenyl)ethyl]-N-methylamine (291 mg) according to the same method as that of Example 9, the title compound was obtained as pale yellow amorphous powders (165 mg)

$^1$H NMR (free base; 400 MHz, CDCl$_3$) δ 1.55-1.62 (2H, m), 1.72-1.80(2H, m), 2.32 (3H, s) 2.46 (2H, t, J=7.3 Hz), 2.55-2.59 (2H, m), 2.68 (2H, t, J=7.5 Hz), 2.76-2.81 (2H, m), 2.93-2.98 (4H, m), 3.38, (3H, s), 3.81 (3H, s), 6.82-6.90 (2H, m), 7.01 (1H, d, J=8.5 Hz), 7.12-7.19 (2H, m), 7.79 (1H, d, J=2 Hz), 7.87 (1H, dd, J=8.5, 2 Hz).

IR (KBr) vcm$^{-1}$: 2941, 1679, 1604, 1495, 1466, 1354, 1243, 1126.

Example 356

6-{5-[[2-(2-Chlorophenyl)ethyl](methyl)amino]pentanoyl}-1-methyl-3,4-dihydroquinolin-2(1H)-one hydrochloride

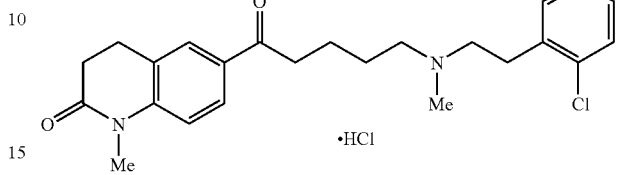

Using 6-(5-chloropentanoyl)-1-methyl-3,4-dihydroquinolin-2(1H)-one (224 mg) obtained in Reference Example 154 and N-[2-(2-chlorophenyl)ethyl]-N-methylamine (299 mg) according to the same method as that of Example 9, the title compound was obtained as colorless crystals (200 mg) having a melting point of 129 to 130° C.

$^1$H NMR (free base; 400 MHz, CDCl$_3$) δ 1.54-1.62 (2H, m), 1.72-1.79 (2H, m), 2.33 (3H, s) 2.47 (2H, t, J=7.3 Hz), 2.59-2.63 (2H, m), 2.68 (2H, t, J=7.3 Hz), 2.88-2.99 (6H, m), 3.39 (3H, s), 7.02 (1H, d, J=8.5 Hz), 7.10-7.19 (2H, m), 7.23 (1H, dd, J=7.3, 2 Hz), 7.32 (1H, dd, J=8, 2 Hz), 7.79 (1H, d, J=2 Hz), 7.87 (1H, dd, J=8.5, 2 Hz).

IR (KBr) vcm$^{-1}$: 2943, 1679, 1605, 1474, 1354, 1305, 1126.

Example 357

(±)-8-{5-[[2-(2-Chlorophenyl)ethyl](methyl)amino]hexanoyl}-1,2,5,6-tetrahydro-4H-pyrrolo[3,2,1-ij]quinolin-4-one hydrochloride

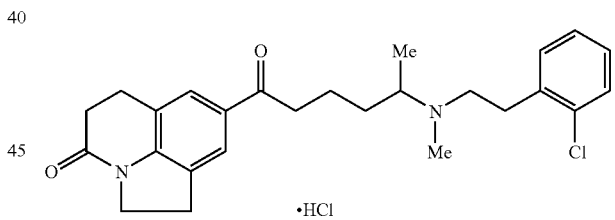

7.8 g of Polyphosphoric acid was placed in a 100 ml four-neck flask, the flask was warmed to 50 to 60° C., and 520 mg (3 mmol) of 1,2,5,6-tetrahydro-4H-pyrrolo[3,2,1-ij]quinolin-4-one and 850 mg (3.3 mmol) of (±)-5-[[2-(2-chlorophenyl)ethyl](methyl)amino]hexanoic acid obtained in Reference Example 202 were added. After stirring at an external temperature of 110° C. for 15 hours, ice-water (20 ml) was added to dissolve the reaction mixture, and 8N—NaOH (about 20 ml) was added to adjust to pH 7 to 8. The liberated oil was extracted with ethyl acetate (30 ml), washed successively with each (20 ml) of water and brine, dried over MgSO$_4$ and concentrated. The residue was purified by column (basic silica gel: 80 g, developing solvent:ethyl acetate-hexane=1:1) to give a free base compound of the title compound as a pale yellow oil (660 mg).

$^1$H NMR (free base; 400 MHz, CDCl$_3$) δ 0.95(3H, d, J=6.6 Hz), 1.30-1.37 (1H, m), 1.50-1.59 (1H, m), 1.68-1.76 (2H, m), 2.30 (3H, s), 2.50-2.58; (1H, m), 2.61-2.73 (4H, m), 2.84-2.89 (4H, m), 3.02(2H, t, J=7.6 Hz), 3.22 (2H, t, J=8.3 Hz), 4.13 (2H, t, J=7.0 Hz), 7.08-7.18 (2H, m), 7.23(1H, dd, J=7.8, 1.5 Hz), 7.30 (1H, dd, J=7.8, 1.5 Hz), 7.67 (1H, s), 7.72 (1H, s).

IR (neat) vcm$^{-1}$: 1674, 1598, 1494, 1447, 1381, 1330, 1155, 753.

The thus obtained base compound (650 mg) was dissolved in ethyl acetate (1 ml), and 4N-hydrochloric acid (ethyl acetate solution) (0.5 ml) was added at room temperature. After stirring at room temperature for 30 minutes, the reaction mixture was concentrated, ethyl acetate (2 ml) was added to the residue, and the precipitated crystals were collected by filtration to give the title compound (568 mg) as fine yellow powders having a melting point of 93 to 95° C.

Example 358

(±)-8-{5-[(2-(2-Chlorophenyl)ethyl](methyl)amino]hexanoyl}-5,6-tetrahydro-4H-pyrrolo[3,2,1-ij]quinolin-2(1H)-one hydrochloride

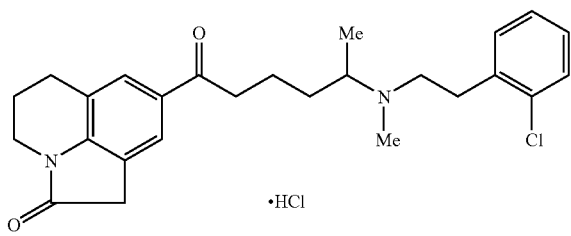

Using 520 mg (3 mmol) of 5,6-dihydro-4H-pyrrolo[3,2,1-ij]quinolin-2(1H)-one and 850 mg (3.3 mmol) of (±)-5-[[2-(2-chlorophenyl)ethyl](methyl)amino]hexanoic acid obtained in Reference Example 202 according to the same method as that of Example 357, a free base compound of the title compound was obtained as a pale yellow oil (456 mg).

$^1$H NMR (free base; 400 MHz, CDCl$_3$) δ 0.96 (3H, d, J=6.4 Hz), 1.30-1.37 (1H, m), 1.52-1.60(1H, m), 1.68-1.77 (2H, m), 2.00-2.06 (2H, m), 2.31(3H, s), 2.52-2.59 (1H, m), 2.62-2.75 (2H, m), 2.81-2.90 (6H, m), 3.54 (2H, s), 3.74 (2H, t, J=6.0 Hz), 7.10 (1H, dt, J=7.3, 1.7 Hz), 7.16 (1H, dt, J=7.3, 1.7 Hz), 7.23 (1H, dd, J=7.6, 1.7 Hz), 7.30 (1H, dd, J=7.6, 1.7 Hz), 7.73 (2H, s).

IR (neat) vcm$^{-1}$: 1718, 1673, 1604, 1496, 1343, 1154, 753.

The thus obtained free base compound (440 mg) was dissolved in ethyl acetate (1 ml), and 4N-hydrochloric acid (ethyl acetate solution) (0.5 ml) was added at room temperature. After stirring at room temperature for 30 minutes, the reaction mixture was concentrated, ethyl acetate (2 ml) was added to the residue, and the precipitated crystals were collected by filtration to give the title compound (420 mg) as fine yellow powders having a melting point of 63 to 65° C.

Example 359

(±)-1,3-Dimethyl-5-[5-[[2-(2-chlorophenyl)ethyl](methyl)amino]hexanoyl]-1,3-dihydro-2H-benzimidazol-2-one hydrochloride

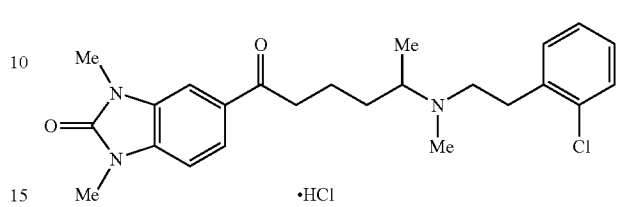

Using 484 mg (3 mmol) of 1,3-dimethyl-1,3-dihydro-2H-benzimidazol-2-one and 850 mg (3.3 mmol) of (±)-5-[[2-(2-chlorophenyl)ethyl](methyl)amino]hexanoic acid obtained in Reference Example 202 according to the same method as that of Example, a free base compound of the title compound (860 mg) was obtained as a pale yellow oil.

$^1$H NMR (free base; 400 MHz, CDCl$_3$) δ 0.96(3H, d, J=6.46 Hz), 1.32-1.39 (1H, m), 1.54-1.59 (1H,m), 1.71-1.77 (2H, m), 2.31(3H, s), 2.51-2.58 (1H, m), 2.61-2.75 (2H, m), 2.82-2.99 (4H, m), 3.45 (3H, s), 3.46 (3H, s), 6.99 (1H, d, J=8.3 Hz), 7.09 (1H, dt, J=7.3, 1.7 Hz), 7.15 (1H, dt, J=7.3, 1.7 Hz), 7.23 (1H, dd, J=7.6, 1.7 Hz), 7.30 (1H, dd, J=7.6, 1.7 Hz), 7.62 (1H, d, J=1.5 Hz), 7.78 (1H, dd, J=8.3, 1.5 Hz).

IR (KBr) vcm$^{-1}$: 1720, 1676, 1622, 1511, 1475, 1395, 1195, 750, 584

The thus obtained free base compound (850 mg) was dissolved in ethyl acetate (2 ml), and 4N-hydrochloric acid (ethyl acetate solution) (0.5 ml) was added at room temperature. After stirring at room temperature for 30 minutes, the reaction mixture was concentrated, ethyl acetate (2 ml) was added to the residue, and the precipitated crystals were collected by filtration to give the title compound (900 mg) as fine yellow amorphous powders.

Example 360

8-(5-{[2-(2-Chlorophenyl)ethyl]amino}pentanoyl)-5,6-dihydro-4H-pyrrolo[3,2,1-ij]quinolin-2(1H)-one p-toluenesulfonate 8-(5-{[2-(2-Chlorophenyl)ethyl]amino}pentanoyl)-5,6-dihydro-1H-pyrrolo[3,2,1-ij]quinolin-2(1H)-one hydrochloride (205 mg, 0.5 mmol) obtained in Example 39 was mixed with a 1 N aqueous sodium hydroxide solution (10 ml), and extracted with ethyl acetate (30ml×3). The organic layer was washed with aqueous saturated sodium chloride, dried over anhydrous sodium sulfate, and the solvent was evaporated. To the resulting residue was added ethanol (3 ml) to give a solution. Then, a solution of p-toluenesulfonic acid monohydrate (95 mg, 0.5 mmol) in ethanol (3 mmol) was added thereto, the mixture was stirred, and the ethanol (about 5.5 ml) was evaporated under reduced pressure. The residue was allowed to stand at room temperature, and the precipitated crystals were collected by filtration, and washed successively with ethanol and diethyl ether. Further drying under reduced pressure afforded the title compound as colorless crystals (258 mg) having a melting point of 172 to 173° C. (dec).

elementary analysis as $C_{24}H_{27}ClN_2O_2 \cdot C_7H_8O_3S$
calculation value:C, 63.85; H, 6.05; N. 4.80.
experimental value:C, 63.77; H, 5.99; N, 4.69.

Example 361

8-(5-{[2-(2-Chlorophenyl)ethyl]amino}pentanoyl)-5,6-dihydro-4H-pyrrolo[3,2,1-ij]quinolin-2(1H)-one sulfate Using 8-(5-{[2-(2-chlorophenyl)ethyl]amino}pentanoyl)-5,6-dihydro-4H-pyrrolo[3,2,1-ij]quinolin-2(1H)-one hydrochloride (205 mg, 0.5 mmol) obtained in Example 39 and sulfuric acid (49 mg, 0.5 mmol) according to the same method as that of Example 360, the title compound was obtained as colorless crystals (218 mg) having a melting point of 155 to 156° C. (dec).

elementary analysis as $C_{24}H_{27}ClN_2O_2 \cdot H_2SO_4$
calculation value: C, 56.63; H, 5.74; N, 5.50.
experimental value: C, 56.42; H, 5.86; N, 5.23.

Example 362

8-(5-{[2-(2-Chlorophenyl)ethyl]amino}pentanoyl)-5,6-dihydro-4H-pyrrolo[3,2,1-ij]quinolin-2(1H)-one hydrobromide Using 8-(5-{[2-(2-chlorophenyl)ethyl]amino}pentanoyl)-5,6-dihydro-4H-pyrrolo[3,2,1-ij]quinolin-2(1H)-one hydrochloride (205 mg, 0.5 mmol) obtained in Example 39 and 48% hydrobromic acid (84 mg, 0.5 mmol) according to the same method as that of Example 360, the title compound was obtained as colorless crystals (220 mg) having a melting point of 201 to 203° C. (dec).

elementary analysis as $C_{24}H_{27}ClN_2O_2 \cdot HBr$
calculation value: C, 58.61; H, 5.74; N, 5.70.
experimental value: C, 58.54; H, 5.85; N, 5.53.

Example 363

5-{[2-(2-Chlorophenyl)ethyl]amino}-1-(2,3-dihydro-2,2-dimethyl-1-benzofuran-5-yl)pentan-1-one hydrochloride

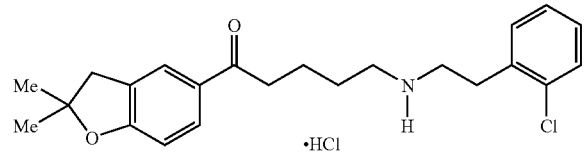

Using tert-butyl 5-(2,3-dihydro-2,2-dimethyl-1-benzofuran-5-yl)-5-oxopentyl[2-(2-chlorophenyl)ethyl]carbamate (550 mg) obtained in Reference Example 209 according to the same method as that of Example 1, the title compound was obtained as colorless crystals (350 mg) having a melting point of 132 to 133° C.

$^1$H NMR (400 MHz, DMSO-$d_6$) δ 1.42 (6H, s), 1.61-1.75 (4H, m), 2.93-3.16 (10H, m), 6.78 (1H, t, J=8.3 Hz), 7.30-7.46 (4H, m), 7.79 (1H, d, J=8.3 Hz), 7.83 (1H, s), 9.36 (2H, br).

IR (KBr) vcm$^{-1}$: 2946, 1668, 1603, 1440, 1266, 1090, 750.

Example 364

5-{[2-(2-Chlrophenyl)ethyl]amino}-1-(3,4-dihydro-2H-chromen-6-yl)-1-pentanone hydrochloride

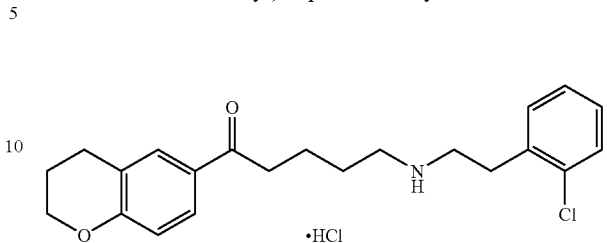

Using tert-butyl 5-(3,4-dihydro-2H-chromen-6-yl)-5-oxopentyl[2-(2-chlorophenyl)ethyl]carbamate (750 mg) obtained in Reference Example 210 according to the same method as that of Example 1, the title compound was obtained as colorless crystals (586 mg) having a melting point of 154 to 155° C.

$^1$H NMR (400 MHz, DMSO-$d_6$) δ 1.62-1.72 (4H, m), 1.91 (2H, br.s), 2.77 (2H, br.s) 2.95-2.98 (4H, m), 3.08-3.15 (4H, m), 4.18 (2H, br.s), 6.79 (1H, d, J=8.3 Hz), 7.26-7.44 (4H, m), 7.69 (1H, d, J=8.3 Hz), 7.72 (1H, s), 9.19 (2H, br.s).

IR (KBr) vcm$^{-1}$: 2958, 1673, 1605, 1499, 1476, 1257, 1138, 1019, 758.

Example 365

N-methyl-5-(5-{[2-(2-methoxyphenyl)ethyl]amino}pentanoyl)-2,3-dihydro-1-benzofuran-7-sulfonamide hydrochloride

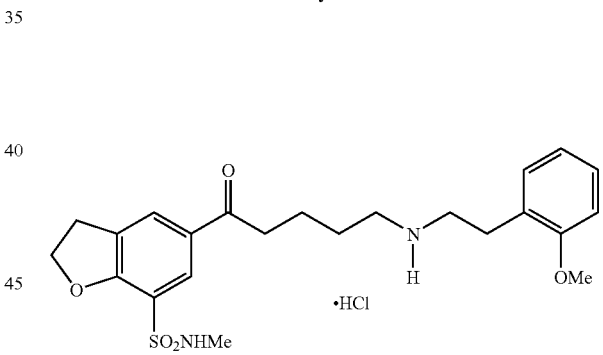

Using tert-butyl 5-{7-[(methylamino)sulfonyl]-2,3-dihydro-1-benzofuran-5-yl}-5-oxopentyl[2-(2-methoxyphenyl)ethyl]carbamate (850 mg) obtained in Reference Example 211 according to the same method as that of Example 1, the title compound was obtained as colorless crystals (673 mg) having a melting point of 167 to 168° C.

$^1$H NMR (400 MHz, DMSO-$d_6$) δ 1.62-1.76 (4H, m), 2.45 (3H, d, J=4.8 Hz), 2.94-3.05 (8H, m), 3.31 (2H, t, J=8.8 Hz), 3.79 (3H, s), 4.80 (2H, t, J=8.8 Hz), 6.89 (1H, t, J=7.6 Hz), 6.98 (1H, d, J=8.0 Hz), 7.17(1H, d, J=7.6 Hz), 7.24 (1H, t, J=8.0 Hz), 7.47(1H, br.s), 8.05 (1H, s), 8.09 (1H, s), 9.19 (2H, br).

IR (KBr) vcm$^{-1}$: 3319, 2783, 2453, 1686, 1605, 1496, 1467, 1334, 1255, 1157, 1119, 758, 586.

Example 366

N-Methyl-5-(5-{[2-(2-chlorophenyl)ethyl]amino}pentanoyl)-2,3-dihydro-1-benzofuran-7-sulfonamide hydrochloride

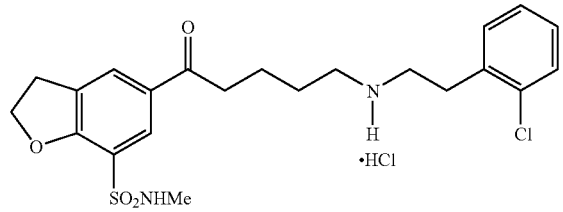

Using tert-butyl 5-{7-[(methylamino)sulfonyl]-2,3-dihydro-1-benzofuran-5-yl}-5-oxopentyl[2-(2-chlorophenyl)ethyl]carbamate (500 mg) obtained in Reference Example 212 according to the same method as that of Example 1, the title compound was obtained as colorless crystals (430 mg) having a melting point of 182 to 183° C.

$^1$H NMR (400 MHz, DMSO-d$_6$) δ 1.62-1.76 (4H, m), 2.45 (3H, d, J=4.8 Hz), 2.97-3.11 (8H, m), 3.31 (2H, t, J=8.8 Hz), 4.80 (2H, t, J=8.8 Hz), 7.28-7.34 (2H, m), 7.39-7.41 (1H, m), 7.44-7.47 (2H, m), 8.05 (1H, s), 8.09 (1H, s), 9.28 (2H, br).

IR (KBr) νcm$^{-1}$: 3155, 2808, 1677, 1613, 1480, 1431, 1326, 1228, 1150, 766, 588.

Example 367

N,N-Dimethyl-5-(5-{[2-(2-methoxyphenyl)ethyl]amino}pentanoyl)-2,3-dihydro-1-benzofuran-7-sulfonamide hydrochloride

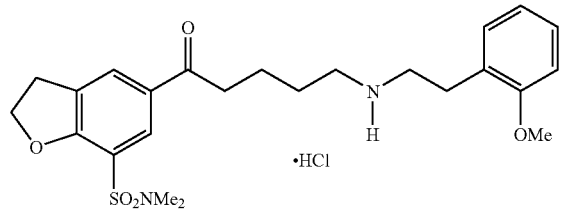

Using tert-butyl 5-{7-[(dimethylamino)sulfonyl]-2,3-dihydro-1-benzofuran-5-yl}-5-oxopentyl[2-(2-methoxyphenyl)ethyl]carbamate (860 mg) obtained in Reference Example 213 according to the same method as that of Example 1, the title compound was obtained as colorless crystals (636 mg) having a melting point of 164 to 165° C.

$^1$H NMR (400 MHz, DMSO-d$_6$) δ 1.62-1.75 (4H, m), 2.70 (6H, s), 2.93-3.06 (8H, m), 3.31 (2H, t, J=8.8 Hz), 3.79 (3H, s), 4.79 (2H, t, J=8.8 Hz), 6.89 (1H, t, J=7.6 Hz), 6.98 (1H, d, J=8.0 Hz), 7.17 (1H, d, J=7.6 Hz), 7.23 (1H, t, J=8.0 Hz), 8.00 (1H, s), 8.13(1H, s), 9.17 (2H, br).

IR (KBr) νcm$^{-1}$: 2783, 1684, 1604, 1496, 1463, 1424, 1338, 1250, 1152, 1126, 956, 766, 585.

Example 368

N-Dimethyl-5-(5-{[2-(2-chlorophenyl)ethyl]amino}pentanoyl)-2,3-dihydro-1-benzofuran-7-sulfonamide hydrochloride

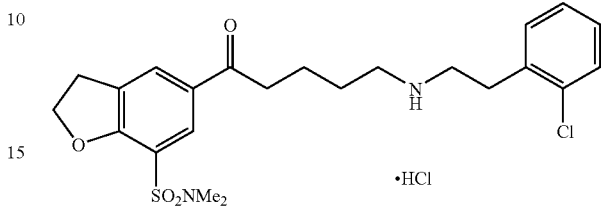

Using tert-butyl 2-(2-chlorophenyl)ethyl(5-{7-[(dimethylamino)sulfonyl]-2,3-dihydro-1-benzofuran-5-yl}-5-oxopentyl)carbamate (500 mg) obtained in Reference Example 214 according to the same method as that of Example 1, the title compound was obtained as colorless crystals (417 mg) having a melting point of 176 to 177° C.

$^1$H NMR (400 MHz, DMSO-d$_6$) δ 1.62-1.75 (4H, m), 2.70 (6H, s), 2.97-3.14 (8H, m), 3.32 (2H, t, J=8.8 Hz), 4.79 (2H, t, J=8.8 Hz), 7.29-7.33 (2H, m), 7.40 (1H, dd, J=7.0, 1.7 Hz), 7.45 (1H, dd, J=7.0, 1.7 Hz), 8.00 (1H, s), 8.13 (1H, s), 9.21 (2H, br).

IR (KBr) νcm$^{-1}$: 2776, 1684, 1601, 1461, 1424, 1334, 1265, 1151, 1121, 963, 758, 758, 584.

Example 369

6-(5-{[2-(2-Methoxyphenyl)ethyl]amino}pentanoyl)-8-chromansulfonamide hydrochloride

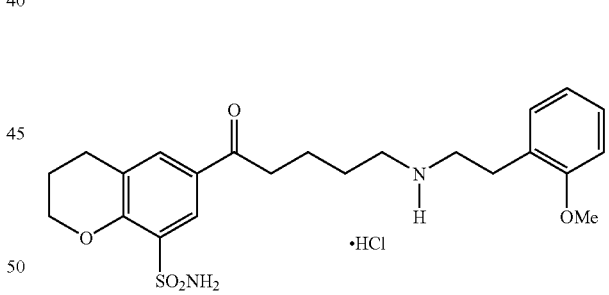

Using tert-butyl 5-[8-(aminosulfonyl)-3,4-dihydro-2H-chromen-6-yl]-5-oxopentyl[2-(2-methoxyphenyl)ethyl]carbamate (650 mg) obtained in Reference Example 215 according to the same method as that of Example 1, the title compound was obtained as colorless crystals (560 mg) having a melting point of 184 to 185° C.

$^1$H NMR (400 MHz, DMSO-d$_6$) δ 1.61-1.73 (4H, m), 1.95-1.98(2H, m), 2.86 (2H, t, J=6.2 Hz), 2.93-3.03 (8H, m), 3.78 (3H, s), 4.36 (2H, t, J=5.1 Hz), 6.89 (1H, t, J=7.3 Hz), 6.97 (1H, d, J=8.0 Hz), 7.16-7.25 (2H, m), 7.19 (2H, s), 7.96 (1H, d, J=2.0 Hz), 8.12 (1H, d, J=2.0 Hz), 9.23 (2H, br.s).

IR (KBr) νcm$^{-1}$: 3306; 3209, 2947, 1661, 1602, 1573, 1495, 1342, 1244, 1161, 1140, 766, 591.

Example 370

6-(5-{[2-(2-Chlorophenyl)ethyl]amino}pentanoyl)-8-chromansulfonamide hydrochloride

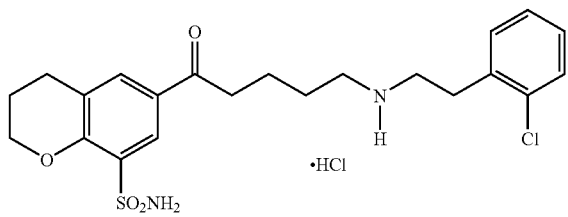

Using tert-butyl 5-[8-(aminosulfonyl)-3,4-dihydro-2H-chromen-6-yl]-5-oxopentyl[2-(2-chlorophenyl)ethyl]carbamate (650 mg) obtained in Reference Example 216 according to the same method as that of Example 1, the title compound was obtained as colorless crystals (564 mg) having a melting point of 177 to 178° C.

$^1$H NMR (400 MHz, DMSO-$d_6$) δ 1.63-1.73 (4H, m), 1.95-1.99 (2H, m), 2.86 (2H, t, J=6.2 Hz), 2.96 (2H, br.s), 3.02 (2H, t, J=7.0 Hz), 3.09-3.16 (4H, m), 4.36 (2H, t, J=5.1 Hz), 7.19(2H, s), 7.28-7.33 (2H, m), 7.40 (1H, dd, J=7, 2.2 Hz), 7.44 (1H, dd, J=7, 2.2 Hz), 7.96 (1H, d, J=2.0 Hz), 8.11 (1H, d, J=2.0 Hz), 9.36 (2H, s).

IR (KBr) vcm$^{-1}$: 3307, 3208, 1662, 1602, 1573, 1474, 1342, 1161, 1140, 1004, 907, 765, 591.

Example 371

5-{5-[[2-(2-Methoxyphenyl)ethyl](methyl)amino]pentanoyl}-N-methyl-2,3-dihydro-1-benzofuran-7-sulfonamide hydrochloride

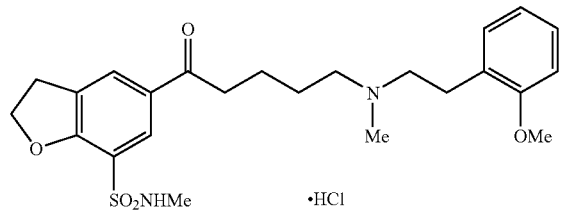

Using 5-(5-chloropentanoyl)-N-methyl-2,3-dihydro-1-benzofuran-7-sulfonamide (664 mg) obtained in Reference Example 203 and N-[2-(2-methoxyphenyl)ethyl]-N-methylamine (752 mg) according to the same method as that of Example 9, the title compound (246 mg) was obtained as pale yellow amorphous powders.

$^1$H NMR (free base; 400 MHz, CDCl$_3$) δ 1.54-1.61 (2H, m), 1.71-1.78 (2H, m), 2.32 (3H, s), 2.46 (2H, t, J=7.3 Hz), 2.56-2.60 (2H, m), 2.65 (3H, s), 2.76-2.80 (2H, m), 2.96 (2H, t, J=7.0 Hz), 3.33 (2H, t, J=8.8 Hz), 3.82 (3H, s), 4.82-4.85 (1H, br), 4.86 (2H, t, J=8.8 Hz), 6.83-6.89 (2H, m), 7.12-7.19 (2H, m), 8.04 (1H, d, J=1.6 Hz), 8.22 (1H, d, J=1.6 Hz).

IR (neat) vcm$^{-1}$: 3307, 1679, 1602, 1495, 1465, 1330, 1244, 1160, 1118, 756, 734, 587.

Example 372

5-{5-[[2-(2-Chlorophenyl)ethyl](methyl)amino]pentanoyl}-N-methyl-2,3-dihydro-1-benzofuran-7-sulfonamide hydrochloride

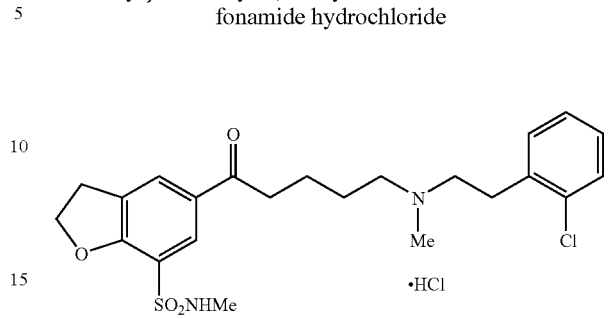

Using 5-(5-chloropentanoyl)-N-methyl-2,3-dihydro-1-benzofuran-7-sulfonamide (664 mg) obtained in Reference Example 203 and N-[2-(2-chlorophenyl)ethyl]-N-methylamine (768 mg) according to the same method as that of Example 9, the title compound (360 mg) was obtained as pale yellow amorphous powders.

$^1$H NMR (free base; 400 MHz, CDCl$_3$) δ 1.54-1.61 (2H, m), 1.71-1.78 (2H, m), 2.34 (3H, s), 2.48 (2H, t, J=7.6 Hz), 2.60-2.64 (2H, m), 2.66 (3H, d, J=4.4 Hz), 2.89-2.98 (4H, m), 3.34 (2H, t, J=8.8 Hz), 4.77 (1H, br.s), 4.87 (2H, t, J=8.8 Hz), 7.13 (1H, dt, J=7.6, 1.5 Hz), 7.18 (H, dt, J=7.6, 1.5 Hz), 7.24 (1H, dd, J=7.6, 1.5 Hz), 7.32 (1H, dd, J=7.6, 1.5 Hz), 8.06 (1H, d, J=1.5 Hz), 8.23 (1H, d, J=1.5 Hz).

IR (neat) vcm$^{-1}$: 3307, 1680, 1603, 1475, 1329, 1263, 1159, 1119, 754, 585.

Example 373

5-{5-[[2-(2-Methoxyphenyl)ethyl](methyl)amino]pentanoyl}-N,N-dimethyl-2,3-dihydro-1-benzofuran-7-sulfonamide hydrochloride

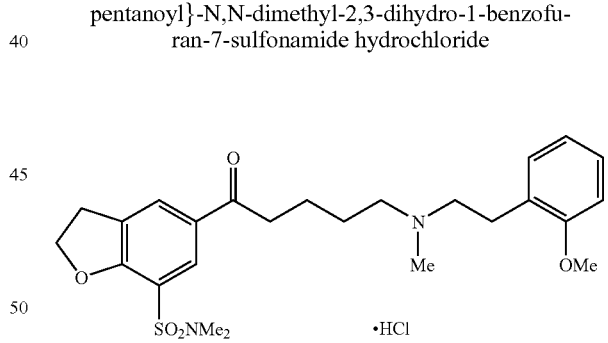

Using 5-(5-chloropentanoyl)-N,N-dimethyl-2,3-dihydro-1-benzofuran-7-sulfonamide (692 mg) obtained in Reference Example 204 and N-[2-(2-methoxyphenyl)ethyl]-N-methylamine (752 mg) according to the same method as that of Example 9, the title compound (466 mg) was obtained as pale yellow amorphous powders.

$^1$H NMR (free base; 400 MHz, CDCl$_3$) δ 1.56-1.63 (2H, m), 1.71-1.79 (2H, m), 2.34 (3H, s), 2.49 (2H, t, J=7.6 Hz), 2.58-2.62 (2H, m), 2.78-2.82 (2H, m), 2.84 (6H, s), 2.95 (2H, t, J=7.3 Hz), 3.32 (2H,t,. J=7.3 Hz), 3.82 (3H, s), 4.82 (2H, t, J=8.8 Hz), 6.83-6.89 (2H, m), 7.13-7.19 (2H, m), 8.02 (1H, d, J=1.7 Hz), 8.19, (1H, d, J=1.7 Hz).

IR (neat) vcm$^{-1}$: 3307, 1680, 1603, 1475, 1329, 1263, 1159, 1119, 754, 585.

Example 374

5-{5-[[2-(2-Chlorophenyl)ethyl](methyl)amino]pentanoyl}-N,N-dimethyl-2,3-dihydro-1-benzofuran-7-sulfonamide hydrochloride

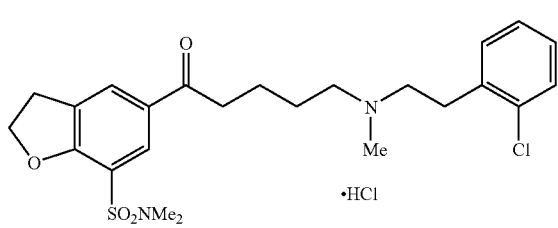

Using 5-(5-chloropentanoyl)-N,N-dimethyl-2,3-dihydro-1-benzofuran-7-sulfonamide (692 mg) obtained in Reference Example 204 and N-[2-(2-chlorophenyl)ethyl]-N-methylamine (768 mg) according to the same method as that of Example 9, the title compound (370 mg) was obtained as pale yellow amorphous powders.

$^1$H NMR (free base; 400 MHz, CDCl$_3$) δ 1.53-1.61 (2H, m), 1.70-1.78 (2H, m), 2.33 (3H, s), 2.47 (2H, t, J=7.6 Hz), 2.59-2.63 (2H, m), 2.84 (6H, s), 2.87-2.96 (4H, m), 3.32 (2H, t, J=8.8 Hz), 4.82 (2H, t, J=8.8 Hz), 7.12 (1H, dt, J=7.6, 1.5 Hz), 7.17 (1H, dt, J=7.6, 1.5 Hz), 7.24 (1H, dd, J=7.6, 1.5 Hz), 7.32 (1H, dd, J=7.6, 1.5 Hz), 8.02 (1H, d, J=1.5 Hz), 8.18 (1H, d, J=1.5 Hz).

IR (neat) vcm$^{-1}$, 1681, 1603, 1464, 1423, 1342, 1262, 1154, 1119, 958, 754, 583.

Example 375

6-{5-[[2-(2-Methoxyphenyl)ethyl](methyl)amino]pentanoyl}-8-chromansulfonamide hydrochloride

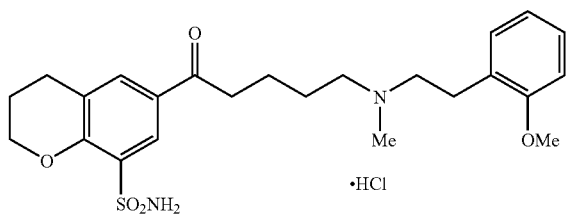

Using 6-(5-chloropentanoyl)-8-chromansulfonamide (664 mg) obtained in Reference Example 208 and N-[2-(2-methoxyphenyl)ethyl]-N-methylamine (752 mg) according to the same method as that of Example 9, the title compound was obtained as colorless crystals (447 mg) having a melting point of 121 to 122° C.

$^1$H NMR (free base; 400 MHz, CDCl$_3$) δ 1.51-1.59 (2H, m), 1.68-1.75 (2H, m), 2.09-2.15 (2H, m), 2.30 (3H, s), 2.42-2.46 (2H, m), 2.54-2.58 (2H, m), 2.74-2.78 (2H, m), 2.88-2.93 (4H, m), 3.82 (3H, s), 4.47 (2H, t, J=5.3 Hz), 5.17 (2H, br.s), 6.82-6.88 (2H, m), 7.11-7.19 (2H, m), 7.91 (H, d, J=1.7 Hz), 8.28 (1H, d, J=1.7 Hz).

IR (neat) vcm$^{-1}$: 3388, 3283, 1684, 1600, 1461, 1324, 1243, 1165, 1144, 1032, 752.

Example 376

6-{5-[[2-(2-Chlorophenyl)ethyl](methyl)amino]pentanoyl}-8-chromansulfonamide hydrochloride

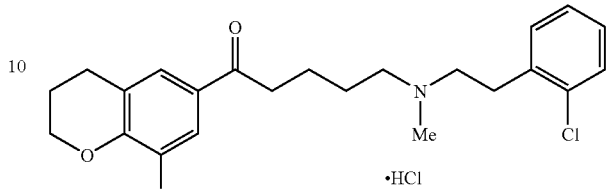

Using 6-(5-chloropentanoyl)-8-chromansulfonamide (664 mg) obtained in Reference Example 208 and N-[2-(2-chlorophenyl)ethyl]-N-methylamine (768 mg) according to the same method as that of Example 9, the title compound (360 mg) was obtained as pale yellow amorphous powders.

$^1$H NMR (free base; 400 MHz, CDCl$_3$) δ 1.51-1.59 (2H, m), 1.68-1.75 (2H, m), 2.09-2.15 (2H, m), 2.32 (3H, s), 2.46 (2H, t, J=7.3 Hz), 2.58-2.62 (2H, m), 2.87-2.93 (6H, m), 4.48 (2H, t, J=5.3 Hz), 5.31 (2H, br.s), 7.12 (1H, dt, J=7.3, 2 Hz), 7.17 (1H, dt, J=7.3, 2 Hz), 7.22 (1H, dd, J=7.3, 1.7 Hz), 7.32 (1H, dd, J=7.3, 1.7 Hz), 7.90 (1H, d, J=1.7 Hz), 8.27 (1H, d, J=1.7 Hz).

IR (neat) vcm$^{-1}$: 3384, 3276, 1684, 1599, 1477, 1324, 1161, 1144, 901, 757.

Example 377

8-(5-{[2-(2-Chlorophenyl)ethyl]amino}pentanoyl)-5,6-dihydro-4H-pyrrolo[3,2,1-ij]quinolin-2(1H)-one citrate Using 8-(5-{[2-(2-chlorophenyl)ethyl]amino}pentanoyl)-5,6-dihydro-4H-pyrrolo[3,2,1-ij]quinolin-2(1H)-one hydrochloride (205 mg, 0.5 mmol) obtained in Example 39 and citric acid (96 mg, 0.5 mmol) according to the same method as that of Example 360, the title compound was obtained as colorless crystals (278 mg) having a melting point of 100 to 102° C. (dec).

elementary analysis as C$_{24}$H$_{27}$ClN$_2$O$_2$·C$_6$H$_8$O$_7$
calculation value:C, 59.75; H, 5.85; N, 4.65.
experimental value:C, 59.34; H, 6.21; N, 4.39.

Example 378

8-(5-{[2-(2-Chlophenyl)ethyl]amide}pentanoyl)-5,6-dihydro-4H-pyrrolo[3,2,1-ij]quinolin-2(1H)-one succinate Using 8-(5-{[2-(2-chlorophenyl)ethyl]amino}pentanoyl)-5,6-dihydro-4H-pyrrolo[3,2,1-ij]quinolin-2(1H)-one hydrochloride (205 mg, 0.5 mmol) obtained in Example 39 and succinic acid (59 mg, 0.5 mmol) according to the same method as that of Example 360, the title compound was obtained as colorless crystals (217 mg) having a melting point of 138 to 140° C. (dec).

elementary analysis as C$_{24}$H$_{27}$ClN$_2$O$_2$·C$_4$H$_6$O$_4$
calculation value:C, 63.57; H, 6.29; N, 5.30.
experimental value:C, 63.37; H, 6.20; N, 5.10.

Example 379

8-(5-{[2-(2-Chlophenyl)ethyl]amide}pentanoyl)-5,6-dihydro-4H-pyrrolo[3,2,1-ij]quinolin-2(1H)-one methanesulfonate Using 8-(5-{[2-(2-chlorophenyl)ethyl]amino}pentanoyl)-5,6-dihydro-4H-pyrrolo[3,2,1-ij]quinolin-2(1H)-one hydrochloride (205 mg, 0.5 mmol) obtained in Example 39 and methanesulfonic acid (48 mg, 0.5 mmol) according to the same method as that of Example 360, the title compound was obtained as colorless crystals (213 mg) having a melting point of 186 to 188° C. (dec).

elementary analysis as $C_{24}H_{27}ClN_2O_2 \cdot CH_4O_3S$
calculation value:C, 59.22; H, 6.16; N, 5.52.
experimental value:C, 59.07; H, 6.25; N, 5.35.

Example 380

8-(5-{[2-(2-Chlophenyl)ethyl]amino}pentanoyl)-5,6-dihydro-4H-pyrrolo[3,2,1-ij]quinolin-2(1H)-one L(±)-tartarate Using 8-(5-{[2-(2-chlorophenyl)ethyl]amino}pentanoyl)-5,6-dihydro-4H-pyrrolo[3,2,1-ij]quinolin-2(1H)-one hydrochloride (205 mg, 0.5 mmol) obtained in Example 39 and L(±)-tartaric acid (75 mg, 0.5 mmol) according to the same method as that of Example 360, the title compound was obtained as colorless crystals (225 mg) having a melting point of 103 to 105° C. (dec).

Example 381

8-(5-{[2-(2-Chlorophenyl)ethyl]amino}pentanoyl)-5,6-dihydro-4H-pyrrolo[3,2,1-ij]quinolin-2(1H)-one oxalate Using 8-(5-{[2-(2-chlorophenyl)ethyl]amino}pentanoyl)-5,6-dihydro-4H-pyrrolo[3,2,1-ij]quinolin-2(1H)-one hydrochloride (205 mg, 0.5 mmol) obtained in Example 39 and oxalic acid (45 mg, 0.5 mmol) according to the same method as that of Example 360, the title compound was obtained as colorless crystals (221 mg) having a melting point of 161 to 163° C. (dec).

elementary analysis as $C_{24}H_{27}ClN_2O_2 \cdot C_2H_2O_4$
calculation value:C, 62.33; H, 5.83; N, 5.59.
experimental value:C, 62.15; H, 6.00; N, 5.44.

Example 382

5-(5-{[2-(2-Chlorophenyl)ethyl]amino}pentanoyl)-1,3-dimethyl-1,3-dihydro-2H-benzimidazol-2-one p-toluenesulfonate Using 5-(5-}[2-(2-chlorophenyl)ethyl]amino}pentanoyl)-1,3-dimethyl-1,3-dihydro-2H-benzimidazol-2-one hydrochloride (458 mg, 1.05 mmol) obtained in Example 143 and p-toluenesulfonic acid (200 mg, 1.05 mmol) according to the same method as that of Example 360, the title compound was obtained as colorless crystals (566 mg) having a melting point of 148 to 150° C.

$^1$H NMR (200 MHz, DMSO-$d_6$) δ 1.69 (4H, br), 2.28 (3H, s), 3.09 (8H, m), 3.38 (3H, s), 3.39 (3H, s), 7.10 (2H, d, J=8.0 Hz), 7.25-7.51 (7H, m), 7.73 (1H, s), 7.81 (1H, d, J=7.6 Hz), 8.52 (2H, br).

elementary analysis as $C_{22}H_{26}ClN_3O_2 \cdot C_7H_8O_3S$
calculation value:C, 60.88,; H, 5.99; N, 7.34.
experimental value:C, 60.95; H, 6.00; N, 7.47.

Example 383

5-(5-{[2-(2-Chlorophenyl)ethyl]amino}pentanoyl)-1-methyl-1,3-dihydro-2H-benzimidazol-2-one hydrochloride Using tert-butyl 2-(2-chlorophenyl)ethyl[5-(1-methyl-2-oxo-2,3-dihydro-1H-benzimidazol-5-yl)-5-oxopentyl]carbamate (500 mg) obtained in Reference Example 218 according to the same method as that of Example 1, the title compound was obtained as colorless crystals (340 mg) having a melting point of 192 to 193° C.

$^1$H NMR (400 MHz, DMSO-$d_6$) δ 1.67-1.73 (4H, m), 2.97 (2H, br.s), 3.04 (2H, t, J=6.7 Hz), 3.11 (4H, br.s), 3.31 (3H, s), 7.18 (1H, d, J=8.3 Hz), 7.27-7.34 (2H, m), 7.39 (1H, dd, J=7.0, 2.0 Hz), 7.44 (1H, dd, J=7.0, 2.0 Hz), 7.52 (1H, d, J=1.7 Hz), 7.76 (1H, dd, J=8.3, 1.7 Hz), 9.20 (2H, br.s), 11.19 (1H, s).

IR (KBr) vcm$^{-1}$: 3432, 2776, 1749, 1666, 1630, 1487, 1319, 1272, 808, 750.

Example 384

6-(5-{[2-(2-Chlorophenyl)ethyl]amino}pentanoyl)-1-methyl-1,3-dihydro-2H-benzimidazol-2-one hydrochloride Using tert-butyl 2-(2-chlorophenyl)ethyl[5-(3-methyl-2-oxo-2,3-dihydro-1H-benzimidazol-5-yl)-5-oxopentyl]carbamate (500 mg) obtained in Reference Example 218 according to the same method as that of Example 1, the title compound was obtained as colorless crystals (354 mg) having a melting-point of 127 to 129° C.

$^1$H NMR (400 MHz, DMSO-$d_6$) δ 1.68-1.74 (4H, m), 2.98(2H, br.s), 3.07 (2H, t, J=6.8 Hz), 3.11 (4H, br.s), 3.33 (3H, s), 7.06 (1H, d, J=8.3 Hz), 7.27-7.34 (2H, m), 7.39 (1H, dd, J=7.0, 2.0 Hz), 7.44 (1H, dd, J=7.0, 2.0 Hz), 7.67 (1H, d, J=1.7 Hz), 7.72 (1H, dd, J=8.3, 1.7 Hz), 9.24 (2H, br.s), 11.32 (1H, s).

IR (KBr) vcm$^{-1}$: 3356, 2733, 1703, 1677, 1623, 1474, 1370, 1252, 1181, 757, 691.

Example 385

5-(5-{[2-(2-Chloro-4-hydroxyphenyl)ethyl]amino}pentanoyl)-1-methyl-1,3-dihydro-2H-benzimidazol-2-one hydrochloride

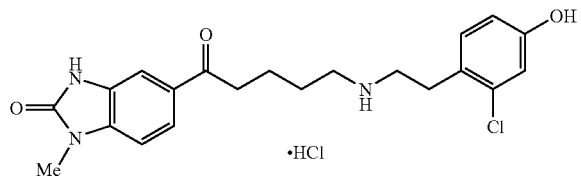

Using tert-butyl 2-(2-chloro-4-hydroxyphenyl)ethyl[5-(1-methyl-2-oxo-2,3-dihydro-1H-benzimidazol-5-yl)-5-oxopentyl]carbamate (400 mg) obtained in Reference Example 219 according to the same method as that of Example 1, the title compound was obtained as colorless crystals (330 mg) having a melting point of 202 to 204° C.

$^1$H NMR (400 MHz, DMSO-$d_6$) δ 1.66-1.68 (4H, m), 2.95-3.06 (8H, m), 3.31 (3H, s), 6.78 (1H, dd, J=8.3, 2.4 Hz), 6.85 (1H, d, J=2.4 Hz), 7.16 (1H, d, J=8.3 Hz), 7.18 (1H, d, J=8.3 Hz), 7.52 (1H, d, J=1.5 Hz), 7.76 (1H, dd, J=8.3, 1.5 Hz), 8.96 (2H, br.s), 9.92 (1H, s), 11.16 (1H, s).

IR (KBr) νcm$^{-1}$: 3206, 1703, 1665, 1622, 1502, 1438, 1310, 1083, 705.

Example 386

6-(5-{[2-(2-Chloro-4-hydroxyphenyl)ethyl]amino}pentanoyl)-1-methyl-1,3-dihydro-2H-benzimidazol-2-one hydrochloride

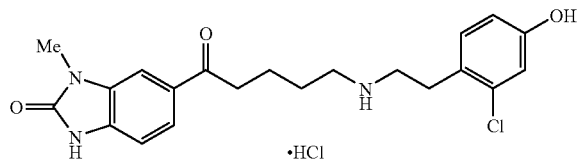

Using tert-butyl 2-(2-chloro-4-hydroxyphenyl)ethyl[5-(3-methyl-2-oxo-2,3-dihydro-1H-benzimidazol-5-yl)-5-oxopentyl]carbamate (250 mg) obtained in Reference Example 219 according to the same method as that of Example 1, the title compound was obtained as colorless crystals (202 mg) having a melting point of 201 to 203° C.

$^1$H NMR (400 MHz, DMSO-$d_6$) δ 1.67-1.68 (4H, m), 2.97-3.08 (8H, m), 3.33 (3H, s), 6.73 (1H, dd, J=8.3, 2.4 Hz), 6.85 (1H, d, J=2.4 Hz), 7.06 (1H, d, J=8.1 Hz), 7.16 (1H, d, J=8.3 Hz), 7.67 (1H, d, J=1.7 Hz), 7.72 (1H, dd, J=8.1, 1.7 Hz), 8.97 (2H, br.s), 9.92 (1H, s), 11.30 (1H, s).

IR (KBr) νcm$^{-1}$: 3120, 2946, 2797, 1695, 1673, 1612, 1502, 1469, 1180, 691.

Example 387

5-(5-{[2-(2-Chloro-4-hydroxyphenyl)ethyl]amino}pentanoyl)-1,3-dimethyl-1,3-dihydro-2H-benzimidazol-2-one hydrochloride

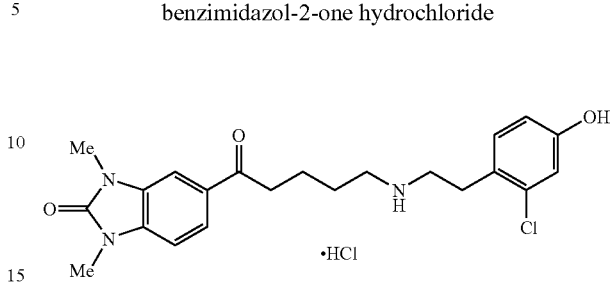

Using tert-butyl 2-(2-chloro-4-hydroxyphenyl)ethyl[5-(1,3-dimethyl-2-oxo-2,3-dihydro-1H-benzimidazol-5-yl)-5-oxopentyl]carbamate (260 mg) obtained in Reference Example 220 according to the same method as that of Example 1, the title compound was obtained as colorless crystals (212 mg) having a melting point of 195 to 197° C.

$^1$H NMR (400 MHz, DMSO-$d_6$) δ 1.67-1.70 (4H, m), 2.97-3.00 (6H, m), 3.09 (2H, t, J=6.6 Hz), 3.36 (3H, s), 3.38 (3H, s), 6.73 (1H, dd, J=8.3, 2.4 Hz), 6.85 (1H, d, J=2.4 Hz), 7.16 (1H, d, J=8.3 Hz), 7.25 (1H, d, J=8.3 Hz), 7.72 (1H, d, J=1.7 Hz), 7.80 (1H, dd, J=8.3, 1.7 Hz), 8.99 (2H, br.s), 9.92 (1H, s).

IR (KBr) νcm$^{-1}$: 3091, 2951, 2780, 1707, 1675, 1622, 1501, 1461, 1251, 1190.

Example 388

5-[[2-(2-Chlorophenyl)ethyl](methyl)amino]-1-(1-methyl-2,2-dioxide-5,6-dihydro-1H,4H-[1,2,5]thiadiazolo[4,3,2-ij]quinolin-8-yl)-1-pentanone hydrochloride

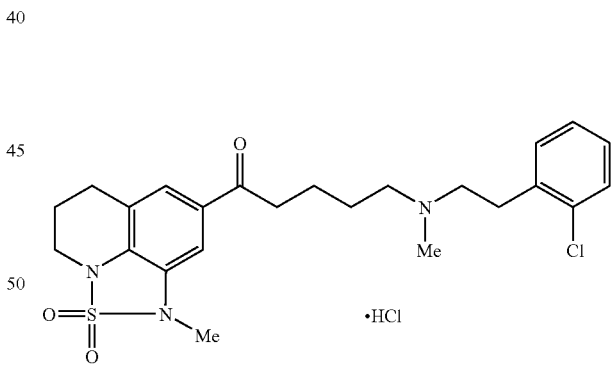

Using 5-chloro-1-(1-methyl-2,2-dioxide-5,6-dihydro-1H,4H-[1,2,5]thiadiazolo[4,3,2-ij]quinolin-8-yl)-1-pentanone obtained in Reference Example 222 and N-[2-(2-chlorophenyl)ethyl]-N-methylamine according to the same method as that of Example 9, the title compound was obtained as amorphous powders.

$^1$H NMR (free base; 200 MHz, CDCl$_3$) δ 1.53-1.78 (4H, m), 2.19 (2H, quintet, J=6.0 Hz), 2.34 (3H, s), 2.48 (2H, t, J=7.4 Hz), 2.63 (2H, m), 2.79-2.96 (6H, m), 3.31 (3H, s), 3.76 (2H, t, J=5.4 Hz), 7.11-7.34 (5H, m), 7.44 (1H, s)

Example 389

5-[[2-(2-Methoxyphenyl)ethyl](methyl)amino]-1-(1-methyl-2,2-dioxide-5,6-dihydro-1H,4H-[1,2,5]thiadiazolo[4,3,2-ij]quinolin-8-yl)-1-pentanone hydrochloride

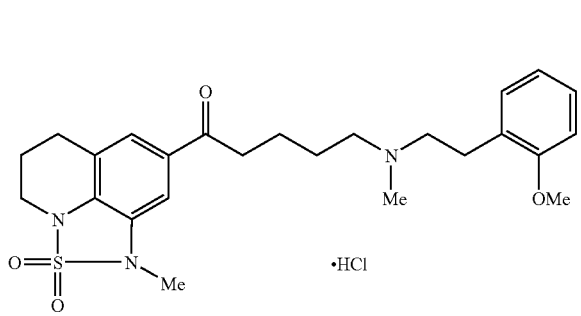

Using 5-chloro-1-(1-methyl-2,2-dioxide-5,6-dihydro-1H,4H-[1,2,5]thiadiazolo[4,3,2-ij]quinolin-8-yl)-1-pentanone obtained in Reference Example 222 and N-[2-(2-methoxyphenyl)ethyl]-N-methylamine according to the same method as that of Example 9, the title compound was obtained as amorphous powders.

$^1$H NMR (free base; 200 MHz, CDCl$_3$) δ 1.57-1.79 (4H, m), 2.19 (2H, quintet, J=6.0 Hz), 2.34 (3H, s), 2.49 (2H, t, J=7.0 Hz), 2.60 (2H, m), 2.72-2.85 (4H, m), 2.94 (2H, t, J=7.0 Hz), 3.31 (3H, s), 3.76 (2H, t, J=5.4 Hz), 3.81 (3H, s), 6.82-6.91 (2H, m), 7.12-7.28 (3H, m), 7.44 (1H, s).

Example 390

5-{[2-(2-Chlorophenyl)ethyl]amino}-1-(1-methyl-2,2-dioxide-5,6-dihydro-1H,4H-[1,2,5]thiadiazolo[4,3,2-ij]quinolin-8-yl)-1-pentanone hydrochloride

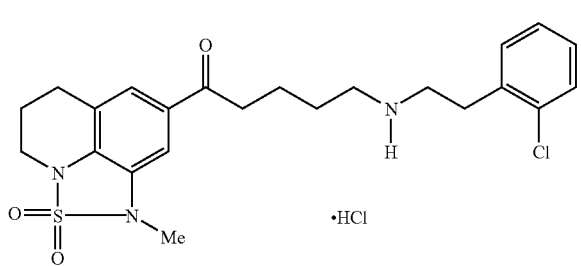

Using tert-butyl 2-(2-chlorophenyl)ethyl[5-(1-methyl-2,2-dioxide-5,6-dihydro-1H,4H-[1,2,5]thiadiazolo[4,3,2-ij]quinolin-8-yl(-5-oxopentyl)carbamate obtained in Reference Example 223 according to the same method as that of Reference Example 1, the title compound was obtained as colorless crystals having a melting point of 154 to 155° C.

$^1$H NMR (free base; 200 MHz, CDCl$_3$) δ 1.53-1.78 (4H, m), 2.19 (2H, quintet, J=6.0 Hz), 2.48 (2H, t, J=7.4 Hz), 2.63 (2H, m), 2.79-2.96 (6H, m), 3.31 (3H, s), 3.75 (2H, t, J=5.4 Hz), 4.61 (1H, br), 7.15-7.34 (5H, m), 7.44 (1H, s).

Example 391

5-{[2-(2-Chlorophenyl)ethyl]amino}-1-(2,2-dioxide-5,6-dihydro-1H,4H-[1,2,5]thiadiazolo[4,3,2-ij]quinolin-8-yl)-1-pentanone hydrochloride

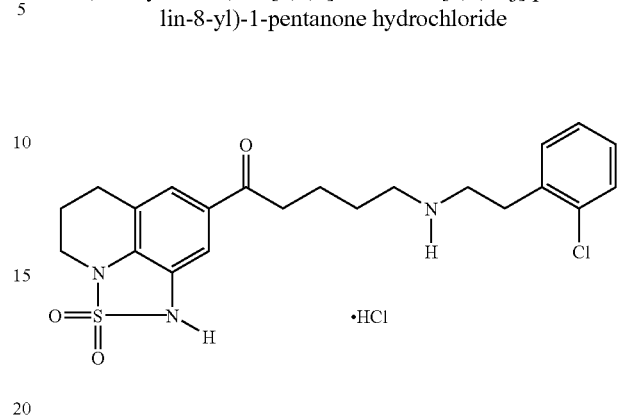

Using 5-chloro-1-(2,2-dioxide-5,6-dihydro-1H,4H-[1,2,5]thiadiazolo[4,3,2-ij]quinolin-8-yl)-1-pentanone obtained in Reference Example 224 and 2-(2-chlorophenyl)ethylamine according to the same methods as those of Reference Example 19 and Example 1, the title compound was obtained as pale yellow crystals having a melting point of 125° C. (dec).

$^1$H NMR (free base; 200 MHz, CDCl$_3$) δ 1.51-1.79 (4H, m), 2.19 (2H, quintet, J=6.0 Hz), 2.48 (2H, t, J=7.4 Hz), 2.63 (2H, m), 2.78-2.99 (6H, m), 3.75 (2H, t, J=5.4 Hz), 4.61 (1H, br), 7.15-7.34 (5H, m), 7.45 (1H, s), 11.58 (1H, s).

Example 392

5-[[2-(2-Chlorophenyl)ethyl](methyl)amino]-1-(2,2-dioxide-3,4-dihydro-1H-2,1,3-benzothiadiazin-6-yl)-1-pentanone hydrochloride

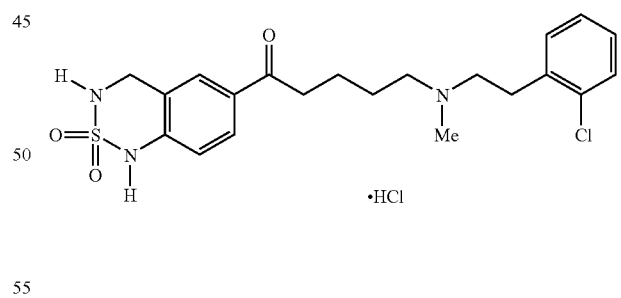

Using 5-chloro-1-(2,2-dioxide-3,4-dihydro-1H-2,1,3-benzothiadiazin-6-yl)-1-pentanone obtained in Reference Example 226 and N-[2-(2-chlorophenyl)ethyl]-N-methylamine according to the same method as that of Example 9, the title compound was obtained as amorphous powders.

$^1$H NMR (free base; 200 MHz, CDCl$_3$) δ 1.55-1.89 (4H, m), 2.53 (3H, s), 2.67-2.79 (4H, m), 2.86 (2H, m), 2.98 (2H, m), 4.54 (2H, s), 5.69 (1H, br), 6.60 (1H, d, J=8.0 Hz), 7.13-7.32 (4H, m), 7.47-7.55 (2H, m), 10.81 (1H, s).

Example 393

1-(2,2-Dioxide-3,4-dihydro-1H-2,1,3-benzothiadiazin-6-yl)-5-[[2-(2-methoxyphenyl)ethyl](methyl)amino]-1-pentanone hydrochloride

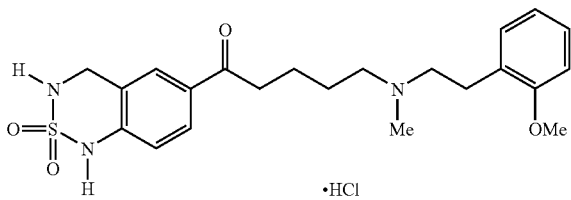

Using 5-chloro-1-(2,2-dioxide-3,4-dihydro-1H-2,1,3-benzothiadiazin-6-yl)-1-pentanone obtained in Reference Example 226 and N-[2-(2-methoxyphenyl)ethyl]-N-methylamine according to the same method as that of Example 9, the title compound was obtained as colorless amorphous powders.

$^1$H NMR (free base; 200 MHz, CDCl$_3$) δ 1.55-1.89 (4H, m), 2.60 (3H, s), 2.67-2.79 (4H, m), 2.86 (2H, m), 2.98 (2H, m), 3.76 (3H, s), 4.45 (2H, s), 5.69 (1H, br), 6.54 (1H, d, J=8.0 Hz), 6.77-6.84 (2H, m), 7.09-7.18 (2H, m), 7.47-7.55 (2H, m), 10.81 (1H, s).

Example 394

5-{[2-(2-Chlorophenyl)ethyl]amino}-1-(2,2-dioxide-3,4-dihydro-1H-2,1,3-benzothiadiazin-6-yl)-1-pentanone hydrochloride

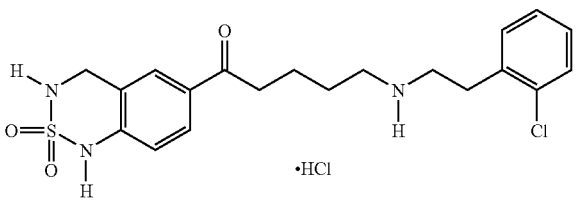

Using 5-chloro-1-(2,2-dioxide-3,4-dihydro-1H-2,1,3-benzothiadiazin-6-yl)-1-pentanone obtained in Reference Example 226 and 2-(2-chlorophenyl)ethylamine according to the same method as those of Reference Example 19 and Example 1, the title compound was obtained as colorless crystals having a melting point of 197 to 199° C.

$^1$H NMR (free base; 200 MHz, CDCl$_3$) δ 1.54-1.89 (4H, m), 2.67-2.79 (4H, m), 2.86 (2H, m), 2.98 (2H, m), 4.54, (2H, s), 4.63 (1H, br), 5.68 (1H, br), 6.61. (1H, d, J=8.0 Hz), 7.11-7.32 (4H, m), 7.43-7.49 (2H, m), 10.82 (1H, s).

Example 395

5-[[2-(2-Chlorophenyl)ethyl](methyl)amino]-1-(1,3-dimethyl-2,2-dioxide-3,4-dihydro-1H-2,1,3-benzothiadiazin-6-yl)-1-pentanone hydrochloride

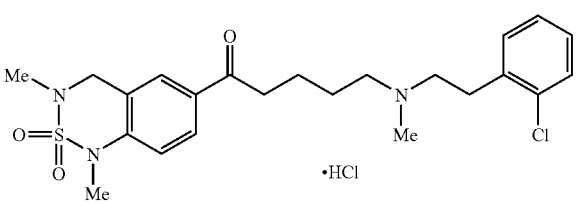

Using 5-chloro-1-(1,3-dimethyl-2,2-dioxide-3,4-dihydro-1H-2,1,3-benzothiadiazin-6-yl)-1-pentanone obtained in Reference Example 228 and N-[2-(2-chlorophenyl)ethyl]-N-methylamine according to the same method as that of Example 9, the title compound was obtained as colorless amorphous powders.

$^1$H NMR (free base; 200 MHz, CDCl$_3$) δ 1.53-1.79 (4H, m), 2.34 (3H, s), 2.48 (2H, t, J=7.0 Hz), 2.61 (2H, m), 2.77 (3H, s), 2.87-2.97 (4H, m), 3.39 (3H, s), 4.69 (2H, s), 6.92 (1H, d, J=8.8 Hz), 7.11-7.34 (4H, m), 7.74 (1H, d, J=1.8 Hz), 7.91 (1H, dd, J=8.8, 2.2 Hz).

Example 396

1-(1,3-Dimethyl-2,2-dioxide-3,4-dihydro-1H-2,1,3-benzothiadiazin-6-yl)-5-[(2-(2-methoxyphenyl)ethyl](methyl)amino]-1-pentanone hydrochloride

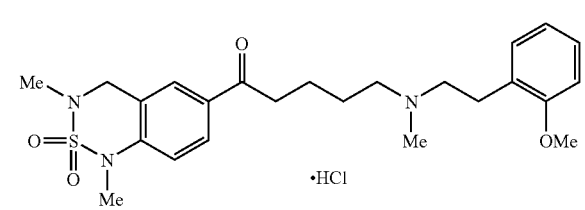

Using 5-chloro-1-(1,3-dimethyl-2,2-dioxide-3,4-dihydro-1H-2,1,3-benzothiadiazin-6-yl)-1-pentanone obtained in Reference Example 228 and N-[2-(2-methoxyphenyl)ethyl]-N-methylamine according to the same method as that of Example 9, the title compound was obtained as colorless amorphous powders.

$^1$H NMR (free base; 200 MHz, CDCl$_3$) δ 1.55-1.80 (4H, m), 2.33 (3H, s), 2.48 (2H, t, J=7.0 Hz), 2.58 (2H, m), 2.76 (3H, s), 2.80 (2H, m), 2.95 (2H, t, J=6.6 Hz), 3.39 (3H, s), 3.81 (3H, s), 4.68 (2H, s), 6.82-6.94 (3H, m), 7.12-7.21 (2H, m), 7.74 (1H, d, J=1.8 Hz), 7.92 (1H, dd, J=8.4, 1.8 Hz).

Example 397

5-{[2-(2-Chlorophenyl)ethyl]amino}-1-(1,3-dimethyl-2,2-dioxide-3,4-dihydro-1H-2,1,3-benzothiadiazin-6-yl)-1-pentanone hydrochloride

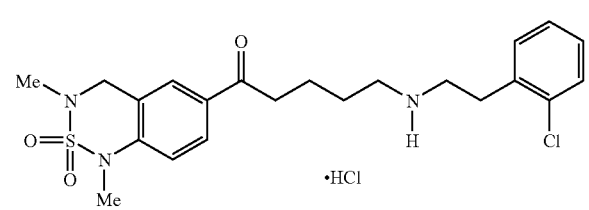

Using 5-chloro-1-(1,3-dimethyl-2,2-dioxide-3,4-dihydro-1H-2,1,3-benzothiadiazin-6-yl)-1-pentanone obtained in Reference Example 228 and 2-(2-chlorophenyl)ethylamine according to the same method as those of Reference Example 19 and Example 1, the title compound was obtained as colorless crystals having a melting point of 164 to 165° C.

$^1$H NMR (free base; 200 MHz, CDCl$_3$) δ 1.51-1.76 (4H, m), 2.48 (2H, t, J=7.0 Hz), 2.61 (2H, m), 2.77 (3H, s), 2.87-

2.97 (4H, m), 3.39 (3H, s), 3.92 (1H, br), 4.69 (2H, s), 6.92 (1H, d, J=8.8 Hz), 7.11-7.34 (4H, m), 7.74 (1H, s), 7.91 (1H, d, J=8.8 Hz).

Example 398

5-{5-[[2-(2-Chlorophenyl)ethyl](methyl)amino]pentanoyl}-2-methyl-1H-isoindole-1,3(2H)-dione hydrochloride

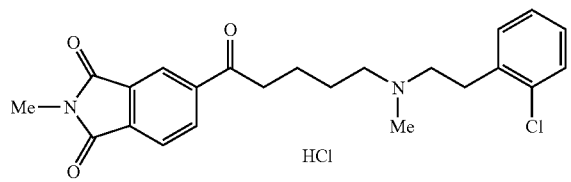

Using 5-(5-chloropentanoyl)-2-methyl-1H-isoindole-1,3(2H)-dione obtained in Reference Example 231 and N-[2-(2-chlorophenyl)ethyl]-N-methylamine according to the same method as that of Example 9, the title compound was obtained as colorless amorphous powders.

$^1$H NMR (free base; 200 MHz, CDCl$_3$) δ 1.55-1.89 (4H, m), 2.34 (3H, s), 2.49 (2H, t, J=7.0 Hz), 2.61 (2H, m), 2.86-2.97 (2H, m), 3.05 (2H, t, J=7.0 Hz), 3.22 (3H, s), 7.10-7.33 (4H, m), 7.94 (1H, d, J=7.8 Hz), 8.29 (1H, d, J=8.4 Hz), 8.37 (1H, s).

Example 399

5-{5-[[2-(2-Methoxyphenyl)ethyl](methyl)amino]pentanoyl}-2-methyl-1H-isoindole-1,3(2H)-dione hydrochloride

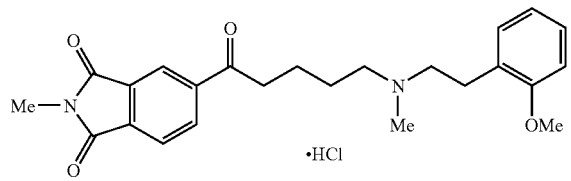

Using 5-(5-chloropentanoyl)-2-methyl-1H-isoindole-1,3(2H)-dione obtained in Reference Example 231 and N-[2-(2-methoxyphenyl)ethyl]-N-methylamine according to the same method as that of Example 9, the title compound was obtained as colorless amorphous powders.

$^1$H NMR (free base; 200 MHz, CDCl$_3$) δ 1.56-1.87 (4H, m), 2.33 (3H, s), 2.49 (2H, t, J=7.0 Hz), 2.61 (2H, m), 2.71-2.82 (2H, m), 3.05 (2H, t, J=6.8 Hz), 3.21 (3H, s), 3.82 (3H, s), 6.85 (2H, t, J=8.6 Hz), 7.13 (2H, d, J=7.4 Hz), 7.93 (1H, d, J=7.8 Hz), 8.30 (1H, d, J=8.4 Hz), 8.37 (1H, s).

Example 400

N-(5-{5-[[2-(2-Chlorophenyl)ethyl](methyl)amino]pentanoyl}-2,3-dihydro-1H-inden-2-yl)acetamide hydrochloride

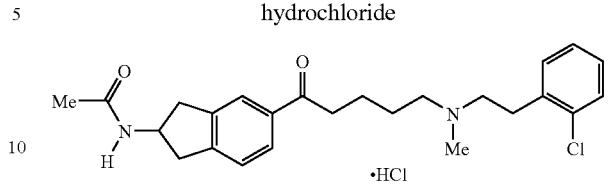

Using N-[5-(5-chloropentanoyl)-2,3-dihydro-1H-inden-2-yl]acetamide obtained in Reference Example 232 and N-[2-(2-chlorophenyl)ethyl]-N-methylamine according to the same method as that of Example 9, the title compound was obtained as colorless amorphous powders.

$^1$H NMR (free base; 200 MHz, CDCl$_3$) δ 1.53-1.78 (4H, m), 1.94 (3H, s), 2.34 (3H, s), 2.48 (2H, t, J=7.4 Hz), 2.60 (2H, m), 2.78-2.98 (6H, m), 3.31 (2H, dd, J=16.4, 6.8 Hz), 4.74 (1H, m), 5.96 (1H, d, J=7.2 Hz), 7.09-7.34 (5H, m), 7.78 (2H, m).

Example 401

N-(5-{5-[[2-(2-Methoxyphenyl)ethyl](methyl)amino]pentanoyl}-2,3-dihydro-1H-inden-2-yl)acetamide hydrochloride

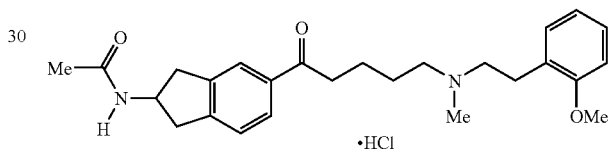

Using N-[5-(5-chloropentanoyl)-2,3-dihydro-1H-inden-2-yl]acetamide obtained in Reference Example 232 and N-[2-(2-methoxyphenyl)ethyl]-N-methylamine according to the same method as that of Example 9, the title compound was obtained as colorless amorphous powders.

$^1$H NMR (free base; 200 MHz, CDCl$_3$) δ 1.56-1.78 (4H, m), 1.94 (3H, s), 2.33 (3H, s), 2.48 (2H, t, J=7.4 Hz), 2.60 (2H, m), 2.78-2.98 (6H, m), 3.31 (2H, dd, J=16.4, 6.8 Hz), 3.81 (3H, s), 4.74 (1H, m), 6.04 (1H, d, J=7.2 Hz), 6.81-6.90 (2H, m), 7.11-7.30 (3H, m), 7.78 (2H, m).

Example 402

N-[5-(5-{[2-(2-Chlorophenyl)ethyl]amino}pentanoyl)-2,3-dihydro-1H-inden-2-yl]acetamide hydrochloride

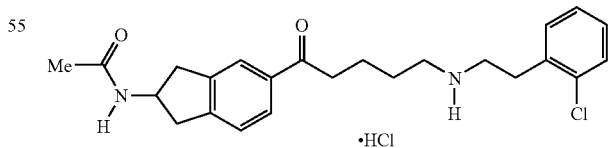

Using N-[5-(5-chloropentanoyl)-2,3-dihydro-1H-inden-2-yl]acetamide obtained in Reference Example 232 and 2-(2-chlorophenyl)ethylamine according to the same methods as those of Reference Example 19 and Example 1, the title compound was obtained as colorless crystals having a melting point of 150 to 151° C.

¹H NMR (free base; 200 MHz, CDCl₃) δ 1.53-1.78 (4H, m), 1.94 (3H, s), 2.48 (2H, t, J=7.4 Hz), 2.60 (2H, m), 2.78-2.98 (6H, m), 3.31 (2H, dd, J=16.4, 6.8 Hz), 4.53 (1H, br), 4.74 (1H, m), 5.96 (1H, d, J=7.2 Hz), 7.09-7.34 (5H, m), 7.78 (2H, m).

Example 403

5-(5-{[2-(2-Chlorophenyl)ethyl]amino}-1-hydroxypentyl)-1,3-dimethyl-1,3-dihydro-2H-benzimidazol-2-one hydrochloride

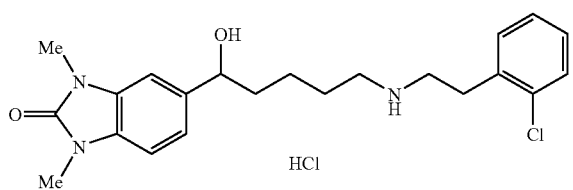

Using tert-butyl 2-(2-chlorophenyl)ethyl[5-(1,3-dimethyl-2-oxo-2,3-dihydro-1H-benzimidazol-5-yl)-5-hydroxypentyl]carbamate (1.25 g) obtained in Reference Example 235 according to the same method as that of Example 1, the title compound was obtained as colorless crystals (340 mg) having a melting point of 253 to 255° C.

¹H NMR (400 MHz, CD₃OD) δ 1.32-1.41 (1H, m), 1.46-1.57 (1H, m), 1.68-1.75 (3H, m), 1.83-1.92 (1H, m), 3.01 (2H, t, J=7.8 Hz), 3.12-3.23 (4H, m), 3.40 (3H, s), 3.41 (3H, s), 4.21-4.24 (1H, m), 4.91 (3H, s), 7.08-7.12 (3H, m), 7.27-7.31 (2H, m), 7.37-7.42 (2H, m).

IR (KBr) νcm⁻¹: 3428, 2944, 1712, 1510, 1462, 747, 584.

Example 404

8-(5-{[2-(2-Chloro-4-hydroxyphenyl)ethyl]amino}pentanoyl)-1,2,5,6-tetrahydro-4H-pyrrolo[3,2,1-ij]quinolin-4-one hydrochloride

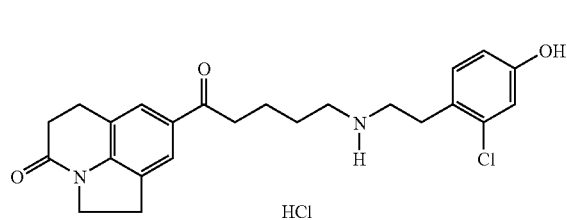

Using tert-butyl 2-(2-chlorophenyl)ethyl[5-oxo-5-(4-oxo-1,2,5,6-tetrahydro-4H-pyrrolo[3,2,1-ij]quinolin-8-yl)pentyl]carbamate (240 mg) obtained in Reference Example 236 according to the same method as that of Example 1, the title compound was obtained as colorless crystals (203 mg) having a melting point of 184 to 185° C.

Example 405

1-(1-Acetyl-2,3-dihydro-1H-indol-5-yl)-5-{[2-(2-chloro-4-hydroxyphenyl)ethyl]amino}pentan-4-one hydrochloride

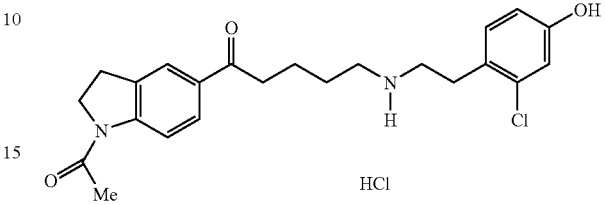

Using tert-butyl 5-(1-acetyl-2,3-dihydro-1H-indol-5-yl)-5-oxopentyl[2-(2-chloro-4-hydroxyphenyl)ethyl]carbamate (320 mg) obtained in Reference Example 237 according to the same method as that of Example 1, the title compound was obtained as colorless crystals (260 mg) having a melting point of 197 to 199° C.

¹H NMR (400 MHz, DMSO-d₆) δ 1.64-1.79 (4H, m), 2.17 (3H, s), 2.93-3.01 (8H, m), 3.16 (2H, t, J=8.3 Hz), 4.13 (2H, t, J=8.3 Hz), 6.73 (1H, dd, J=8.3, 2.4 Hz), 6.87 (1H, d, J=2.4 Hz), 7.15 (1H, d, J=8.3 Hz), 7.81 (1H, s), 7.82 (1H, d, J=8.3 Hz), 8.07 (1H, d, J=8.3 Hz), 9.18 (2H, s), 9.51 (1H, br).

IR (KBr) νcm⁻¹: 2949, 2780, 1686, 1632, 1587, 1503, 1443, 1405, 1248, 826.

Example 406

8-(5-{[2-(2-Chloro-4-hydroxyphenyl)ethyl]amino}pentanoyl)-1-methyl-5,6-dihydro-4H-imidazo[4,5,1-ij]quinolin-2(1H)-one hydrochloride

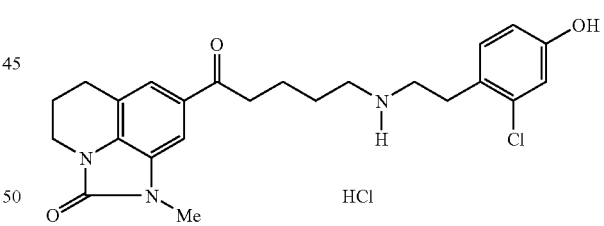

Using tert-butyl 2-(2-chloro-4-hydroxyphenyl)ethyl[5-(1-methyl-2-oxo-1,2,5,6-tetrahydro-4H-imidazo[4,5,1-ij]quinolin-8-yl)-5-oxopentyl]carbamate (114 mg) obtained in Reference Example 238 according to the same method as that of Example 1, the title compound was obtained as colorless crystals (82 mg) having a melting point of 175 to 177° C.

¹H NMR (400 MHz, DMSO-d₆) δ 1.68 (4H, br.s), 2.00-2.04. (2H, m), 2.98-3.07 (8H, m), 3.34 (2H, br.s), 3.36 (3H, s), 3.71-3.76 (2H, m), 6.73 (1H, dd, J=8.5, 2.4 Hz), 6.85 (1H, d, J=2.4 Hz), 7.16 (1H, d, J=8.5 Hz), 7.59 (2H, s), 9.00 (2H, br.), 9.93 (1H, s).

IR (KBr) νcm⁻¹: 3426, 2955, 2790, 1698, 1641, 1610, 1501, 1436, 1277, 1251.

Example 407

8-(5-{[2-(2-Chloro-4-hydroxyphenyl)ethyl]amino}pentanoyl)-5,6-dihydro-4H-imidazo[4,5,1-ij]quinolin-2(1H)-one hydrochloride

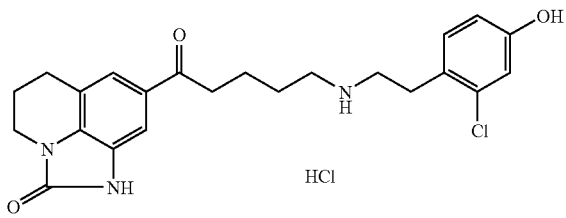

Using tert-butyl 2-(2-chloro-4-hydroxyphenyl)ethyl[5-oxo-5-(2-oxo-1,2,5,6-tetrahydro-4H-imidazo[4,5,1-ij]quinolin-8-yl)pentyl]carbamate (55 mg) obtained in Reference Example 239 according to the same method as that of Example 1, the title compound was obtained as colorless crystals (38 mg) having a melting point of 185 to 186° C.

$^1$H NMR (400 MHz, DMSO-$d_6$) δ 1.66 (4H, br.s), 2.00-2.03 (2H, m), 2.82 (2H, t, J=6.0 Hz), 2.97-3.02 (8H, m), 3.42 (1H, br.), 3.71 (2H, t, J=6.0 Hz), 6.73 (1H, dd, J=8.3, 2.2 Hz), 6.85 (1H, d, J=2.2 Hz), 7.16 (1H, d, J=8.3 Hz), 7.38 (1H, s), 7.55 (1H, s), 8.91 (2H, br.s), 9.91 (1H, s).

IR (KBr) vcm$^{-1}$: 3252, 2959, 2815, 1717, 1664, 1613, 1502, 1439, 1150, 668.

Example 408

9-(5-{[2-(2-Chloro-4-hydroxyphenyl)ethyl]amino}pentanoyl)-5,6-dihydro-4H-imidazo[4,5,1-ij]quinolin-2(1H)-one hydrochloride

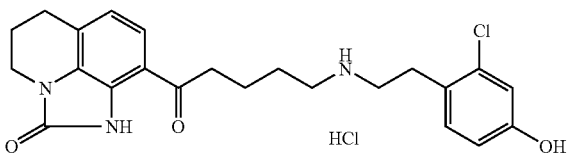

Using tert-butyl 2-(2-chloro-4-hydroxyphenyl)ethyl]-5-oxo-5-(2-oxo-1,2,5,6-tetrahydro-4H-imidazo[4,5,1-ij]quinolin-9-yl)pentyl]carbamate (64 mg) obtained in Reference Example 240 according to the same method as that of Example 1, the title compound was obtained as colorless crystals (44 mg) having a melting point of 173 to 175° C.

$^1$H NMR (400 MHz, DMSO-$d_6$) δ 1.68 (4H, br.s), 1.99-2.02 (2H, m), 2.82 (2H, t, J=6.0 Hz), 2.97-3.03 (8H, m), 3.71 (2H, t, J=6.0 Hz), 4.24 (1H, br.), 6.73 (1H, dd, J=8.3, 2.4 Hz), 6.85 (1H, d, J=2.4 Hz), 6.91 (1H, d, J=8.3 Hz), 7.16 (1H, d, J=8.0 Hz), 7.53 (1H, d, J=8.0 Hz), 8.90 (2H, br.s), 10.82 (1H, s).

IR (KBr) vcm$^{-1}$: 3152, 2958, 1689, 1610, 1502, 1488, 1442, 1229, 1041, 692.

Example 409

N-(5-{5-[[2-(2-Chlorophenyl)ethyl](methyl)amino]pentanoyl}-2,3-dihydro-1H-inden-2-yl)acetamide hydrochloride

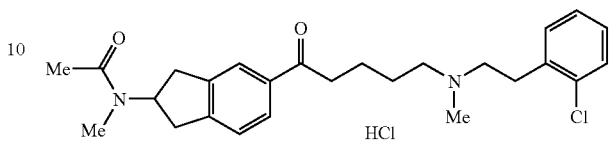

Using N-[5-(5-Chloropentanoyl)-2,3-dihydro-1H-inden-2-yl]acetamide obtained in Reference Example 241 and N-[2-(2-chlorophenyl)ethyl]-N-methylamine according to the same method as that of Example 9, the title compound was obtained as colorless amorphous powders.

$^1$H NMR (free base; 200 MHz, CDCl$_3$) δ 1.53-1.80 (4H, m), 2.15 (3H, s), 2.34 (3H, s), 2.48 (2H, t, J=7.4 Hz), 2.61 (2H, m), 2.81 (3H, s), 2.85-2.98 (6H, m), 3.18 (2H, dd, J=16.4, 6.8 Hz), 5.32 (1H, m), 7.08-7.38 (5H, m), 7.78 (2H, m).

Example 410

N-(5-{5-[[2-(2-Methoxyphenyl)ethyl](methyl)amino]pentanoyl}-2,3-dihydro-1H-inden-2-yl)acetamide hydrochloride

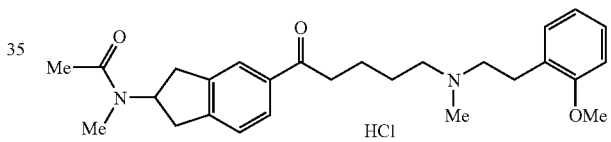

Using N-[5-(5-chloropentanoyl)-2,3-dihydro-1H-inden-2-yl]acetamide obtained in Reference Example 241 and N-[2-(2-Methoxyphenyl)ethyl]-N-methylamine according to the same method as that of Example 9, the title compound was obtained as colorless amorphous powders.

$^1$H NMR (free base; 200 MHz, CDCl$_3$) δ 1.55-1.80 (4H, m), 2.15 (3H, s), 2.34 (3H, s), 2.47 (2H, t, J=7.2 Hz), 2.58 (2H, m), 2.72-2.82 (4H, m), 2.80 (3H, s), 2.96 (2H, t, J=7.0 Hz), 3.25 (2H, dd, J=17.0, 8.8 Hz), 3.80 (3H, s), 5.25 (1H, m), 6.80-6.88 (2H, m), 7.11-7.18 (2H, m), 7.28 (1H, m), 7.79 (2H, m).

Example 411

N-[5-(5-{[2-(2-Chlorophenyl)ethyl]amino}pentanoyl)-2,3-dihydro-1H-inden-2-yl]acetamide hydrochloride

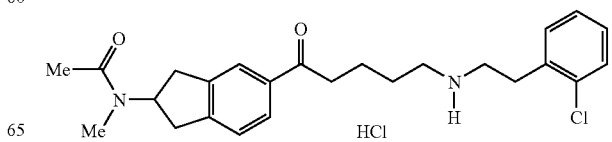

Using N-[5-(5-chloropentanoyl)-2,3-dihydro-1H-inden-2-yl]acetamide obtained in Reference Example 241 and 2-(2-chlorophenyl)ethylamine according to the same methods as those of Reference Example 19 and Example 1, the title compound was obtained as colorless crystals having a melting point of 137 to 138° C.

$^1$H NMR (free base; 200 MHz, CDCl$_3$) δ 1.53-1.79 (4H, m), 2.15 (3H, s), 2.48 (2H, t, J=7.4 Hz), 2.61 (2H, m), 2.81 (3H, 5 s), 2.85-2.98 (6H, m), 3.18 (2H, dd, J=16.4, 6.8 Hz), 4.28 (1H, br), 5.32 (1H, m), 7.09-7.37 (5H, m), 7.78 (2H, m).

Example 412

N-(5-{5-[[2-(2-Chlorophenyl)ethyl](methyl)amino]pentanoyl}-2,3-dihydro-1H-inden-2-yl)methanesulfonamide hydrochloride

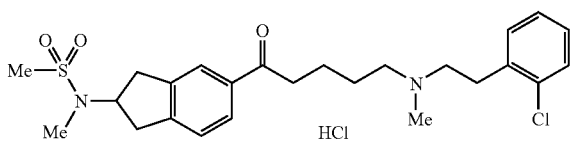

Using N-[5-(5-chloropentanoyl)-2,3-dihydro-1H-inden-2-yl]methanesulfonamide obtained in Reference Example 242 and N-[2-(2-chlorophenyl)ethyl]-N-methylamine according to the same method as that of Example 9, the title compound was obtained as colorless amorphous powders.

$^1$H, NMR (free base; 200 MHz, CDCl$_3$) δ 1.55-1.77 (4H, m), 2.34 (3H, s), 2.48 (2H, t, J=7.6 Hz), 2.61 (2H, m), 2.71 (3H, s), 2.89 (3H, s), 2.91-3.10 (6H, m), 3.35 (2H, dd, J=16.8, 8.4 Hz), 4.90 (1H, quint, J=7.0 Hz), 7.09-7.32 (5H, m), 7.78 (2H, m).

Example 413

N-(5-{5-[[2-(2-Methoxyphenyl)ethyl](methyl)amino]pentanoyl}-2,3-dihydro-1H-inden-2-yl)methansulfonamide hydrochloride

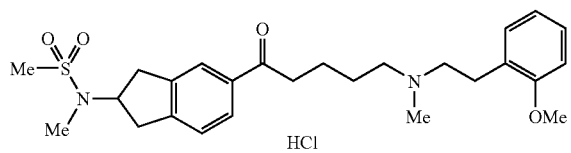

Using N-[5-(5-chloropentanoyl)-2,3-dihydro-1H-inden-2-yl]methanesulfonamide obtained in Reference Example 242 and N-[2-(2-methoxyphenyl)ethyl]-N-methylamine according to the same method as that of Example 9, the title compound was obtained as colorless amorphous powders.

$^1$H NMR (free base; 200 MHz, CDCl$_3$) δ 1.54-1.79 (4H, m), 2.33 (3H, s), 2.48 (2H, t, J=7.0 Hz), 2.58 (2H, m), 2.71 (3H, s), 2.80 (2H, m), 2.89 (3H, s), 2.96 (2H, m), 3.05 (2H, m), 3.28 (2H, dd, J=16.4, 8.0 Hz), 3.81 (3H, s), 4.91 (1H, m), 6.81-6.90 (2H, m), 7.12-7.31 (3H, m), 7.78 (2H, m).

Example 414

N-[5-(5-{[2-(2-Chlorophenyl)ethyl]amino}pentanoyl)-2,3-dihydro-1H-inden-2-yl]methanesulfonamide hydrochloride

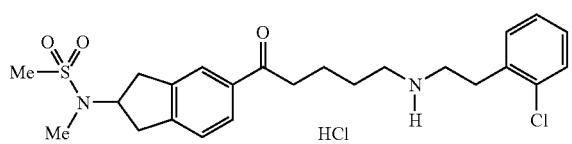

Using N-[5-(5-chloropentanoyl)-2,3-dihydro-1H-inden-2-yl]methanesulfonamide obtained in Reference Example 242 and 2-(2-chlorophenyl)ethylamine according to the same methods as those of Reference Example 19 and Example 1, the title compound was obtained as colorless amorphous powders.

$^1$H NMR (free base; 200 MHz, CDCl$_3$) δ 1.55-1.77 (4H, m), 2.47 (2H, t, J=7.4 Hz), 2.61 (2H, m), 2.71 (3H, s), 2.89 (3H, s), 2.91-3.10 (6H, m), 3.35 (2H, dd, J=16.4, 8.0 Hz), 4.08 (1H, br), 4.90 (1H, quint, J=7.0 Hz), 7.09-7.32 (5H, m), 7.78 (2H, m).

Preparation Example 1

(1) Compound of Example 20: 1 g
(2) Lactose: 197 g
(3) Corn starch: 50 g
(4) Magnesium stearate: 2 g The (1), (2) and corn starch (20 g) were kneaded, and the mixture together with a paste made of corn starch (15 g) and 25 mL of water was granulated, and corn starch (15 g) and the (4) were added thereto. The mixture was compressed with a compression tabletting machine to give 2000 tablets having a diameter of 3 mm containing 0.5 mg of the compound of Example 20 per tablet.

Preparation Example 2

(1) Compound of Example 20: 2 g
(2) Lactose: 197 g
(3) Corn starch: 50 g
(4) Magnesium stearate: 2 g According to the same method as that of Preparation Example 1, 2000 tablets having a diameter of 3 mm containing 1.0 mg of the compound of Example 20 per tablet were prepared.

Preparation Example 3

(1) Compound of Example 20: 5.0 mg
(2) Lactose: 60.0 mg
(3) Corn starch: 35.0 mg
(4) Gelatin: 3.0 mg
(5) Magnesium stearate: 2.0 mg A mixture of the (1), (2) and (3) was granulated by passing through a 1 mm mesh sieve using 0.03 ml of a 10% aqueous gelatin solution (3.0 mg in terms of gelatin), and the granule was dried at 40° C., and then passed through a sieve again. The resulting granule was mixed with the (5), and compressed. The resulting central tablet was coated with a sugar coating composed of a suspension containing sucrose, titanium dioxide, talc and gum arabic in water. The coated tablet was given luster with beewax to give a coated tablet.

Experimental Example 1 a) Measurement of Acetylcholinesterase Inhibitory Activity

Acetylcholinesterase inhibitory activity of Example compounds was measured using human erythrocyte-derived acetylcholinesterase by an acetylthiocholine method (Ellman method).

Human erythrocyte-drived acetylcholinesterase (Sigma) was dissolved in distilled water to the concentration of 0.2 IU/mL to obtain an enzyme specimen. 20 μL of a drug solution, 30 μL of 80 mM Tris-HCL (pH 7.4), 50 μL of an enzyme specimen and 50 μL of 5 mM 5,5-dithio-bis (2-nitrobenzoic acid)(Sigma) were dispensed on a 96-well microplate, and this was shaken for 10 seconds. 50 μL of 4 mM acetylthiocholine iodide (Sigma) was added, this was shaken again and, immediately after, increase in absorbance at 414 nM was measured at 30 second intervals for 10 minutes. Enzyme activity was measured by the following equation:

$$R = 5.74 \times 10^{-7} \times \Delta_A$$

(wherein R represents enzyme activity (mol), and $\Delta_A$ represents increase in absorbance at 414 nM)

Regarding each compound, the experiment was repeated at least three times to obtain 50% inhibition concentration ($IC_{50}$). According to, the similar method to the above-mentioned, acetylcholinesterase inhibitory activity of distigmine which is a known acetylcholinesterase inhibitor was measured.

b) Measurement of $\alpha_{1A}$ Receptor Binding Inhibitory Activity

The following gene manipulation method was carried out according to the method described in a textbook (Miniatis et al., Molecular Cloning, Cold Spring Harbor Laboratory, 1989) or the method described in protocol attached to a reagent.

(i) Preparation of Expression Plasmid for Human Adrenaline $\alpha_{1A}$ Receptor An adrenaline $\alpha_{1A}$ receptor gene was cloned from a human liver cDNA by a PCR method. A PCR reaction was performed with Gene Amp PCR System 9700 (Applied Biosystems) using 200 ng of a human liver cDNA library (TAKARA SHUZO Co., Ltd.) as a template and using TaKaRa Pyrobest DNA Polymerase (TAKARA SHUZO CO., Ltd) and adding each 50 pmol of a primer set 5'-CCGAATTCGGCTGGGAC-CATGGTGTTTCTC-3' [SEQ ID No.: 1] and 5'-CTGTC-GACCTTTCCTGTCCTAGACTTCCTC-3' [SEQ ID No.: 2] prepared making reference to a nucleotide sequence of an adrenaline $\alpha_{1A}$ receptor gene which was reported by Hirasawa A. et al. (Biochem. Biophys. Res. Commun., 195, 902-909(1993)) (reaction condition: 45 cycles of 15 seconds at 94° C., and 3 minutes 30 seconds at 68° C.).

The obtained PCR fragment was digested with restriction enzymes Eco RI (TAKARA SHUZO Co. Ltd.) and Sal I (TAKARA SHUZO Co. Ltd.), and agarose gel electrophoresis was performed to recover DNA fragments. The DNA fragments were mixed with an animal cell expression plasmid pMSR αneo (Administration No. A99-0013) which had been digested with Eco RI and Sal I, ligated with DNA Ligation Kit Ver.2 (TAKARA SHUZO Co. Ltd.), and a competent cell of Esherichia coli JM109 was transformed to obtain a plasmid pMSR αneoA dre$\alpha_{1A}$.

(ii) Introduction of Plasmid for Expression of Human Adrenaline $\alpha_{1A}$ Receptor into CHO—K1 Cell and Preparation of Membrane Fraction CHO—K1 cells which had been subcultured in a 150 cm² culturing flask (Corning Coaster) using Ham F12 medium (Invitrogen) containing 10% fetal bovine serum (TRACE SCIENTIFIC) was peeled with 0.5 g/L trypsin-0.2 g/L EDTA (Invitrogen), cells were washed with D-PBS(−) (Invitrogen), centrifuged (1000 rpm, 5 min.), and suspended in D-PBS(−). Then, a DNA was introduced into cells using a gene pulser (BioRad) according to the following conditions. That is, 1×10 cells and 10 μg of pMSR α neo-Adre$\alpha_{1A}$ suspended in 700 μl of D-PBS(−) were added to a cuvette (BioRad) having a 0.4 cm gap, and electroporation was performed at a voltage of 0.25 kV, and capacitance of 960 μF. Thereafter, cells were transferred to Ham F12 medium containing 10% fetal bovine serum and, after cultured for 24 hours, cells were peeled again, centrifuged, seeded on a 96-well plate (Corning) at 1000/well and cultured for 10 days using Ham F12 medium containing 10% fetal bovine serum and 500 μg/ml geneticine (Invitrogen), thereby, a geneticine-resistant strain was obtained.

A plurality of the thus obtained geneticine-resistant strains were selected, each strain was cultured in a cell culturing flask (150 cm²) to semiconfluent, and a cell membrane fraction was prepared as follows:

Semiconfluent cells were peeled with D-PBS(−) containing 0.02% EDTA, cells were recovered by centrifugation, cells were suspended in a buffer for preparing a membrane (50 mM Tris-hydrochloric acid (pH7.5), 1 mM EDTA, 10 mM magnesium chloride, 0.25 mM PMSF, 1 μg/ml pepstatin, 20 μg/ml leupeptin, 0.5% BSA), and treated with a Polytron homogenizer (model PT-3000, KINEMATICA AG) three times at 20,000 rpm for 20 seconds to grind cells. After grinding of cells, gound cells were centrifuged at 2000 rpm for 10 minutes to obtain the supernatant containing a membrane fraction. The supernatant was centrifuged with a supercentrifuge (model L8-70M, rotor 70Ti, Beckmann) at. 30,000 rpm for 1 hour to give precipitates containing a membrane fraction. The resulting membrane fraction of each clone was subjected to the following binding experiment.

A membrane fraction (100 μg/ml) diluted with a buffer for preparing a membrane and [³H]-Prazosin (2.5 nM, NEN Life Science Products) which is a ligand were added to a 96-well microplate to react at room temperature temperature for 1 hour. For measuring non-specific binding, Prazosin (Sigma) was further added to 10 μM. Then, the membrane fraction was transferred to a unifilter GF/C (Parkerd) by filtering the reaction solution using a cell harvester (Packerd), and washed with a 50 mM Tris ice-cooled buffer (pH 7.5) three times. After the filter was dried, Microsinti 0 (Packerd) was added to the filter, and radioactivity was measured with Topcount (Packerd). Using a strain exhibiting the most excellent S/B value (total binding radioactivity/non-specific binding radioactivity) in measurement of binding using the membrane fraction, a membrane fraction for the following compound assessment was prepared by the same method as that described above, and used for the following compound assessment.

(iii) Assessment of Example Compound

A membrane fraction (100 μg/ml) diluted with a buffer for preparing a membrane, the compound and [³H]-Prazosin (2.5 nM, NEN Life Science Products) were added to a 96-well microplate to react at room temperature for 1 hour. For measuring non-specific binding, Prazosin (Sigma) which is a cold ligand was added to 10 μM. Then, a membrane fraction was transferred to a unifilter GF-C (Packerd) by filtering the reaction solution with cell harvester (Packerd), and washed three times with cooled 50 mM Tris buffer (pH 7.5). After drying the filter, Microsinti 0 (Packerd) was added to the filter, and radioactivity was measured with Topcount (Packerd). The concentration ($IC_{50}$) of the compound necessary to reduce the binding amount of [³H]-Prazosin to the membrane fraction to 50% was calculated by PRISM 2.01 (Graphpad Software). $IC_{50}$ of urapidil (hydrochloride) which is a known $\alpha_1$ receptor antagonist was obtained similarly. The results measured by the aforementioned methods a) and b) are shown in the following in Table.

TABLE 1

| Compound | AchE: $IC_{50}$ (μM) | $α_{1A}$: $IC_{50}$ (μM) |
|---|---|---|
| Example 20 | 0.179 | 0.165 |
| Example 84 | 0.169 | 0.236 |
| Distigmine | 0.723 | — |
| urapidil | — | 0.357 |

From the aforementioned results, it turns out that the present Compound (I) has an excellent acetylcholinesterase inhibitory action and, at the same time, excellent $α_{1A}$ receptor binding inhibitory activity.

Experimental Example 2 a) Effect on Maximum Urine Flow Rate, Bladder Internal Pressure and Voiding Efficiency in Guinea Pigs Loaded with Phenylephrine (Pressure Flow Study)

Hartley male guinea pigs (Slc) weighing 300 to 350 g was anesthetized with urethane (1.2 g/kg, i.p.), and a median was incised to expose bladder. Two polyethylene tubes were inserted into bladder, and one of them was used for injecting a physiological saline and the other was used for measuring a bladder internal pressure. A cannulae was inserted into a left femoral vein, and phenylephrine was continuously administered intravenously at 3 μg/animal/min until the completion of experiment. A physiological saline was injected into bladder at a rate of 0.3 mL/min, and injection was stopped when urination was confirmed. The urinated urine weight was measured with an electron balance (HX-400, A & D) at real time. Analogue data of bladder internal pressure and urine weight were inputted into an AD transducer (MP-100, BIOPAC Systems), and digital signals were analyzed with exclusive analyzing software (AcqKnowledge 3.5.3, BIOPAC Systems). The sampling rate of data was 10 Hz, and data of urination amount and urine flow rate were subjected to a lowcut filter at 0.5 Hz in order to remove noises. The value of urine weight was differentiated to calculate urine flow rate (Q), and maximum urine flow rate (Qmax) at urination and bladder internal pressure (Pves (Qmax)) at maximum urine flow were calculated. The urination weight 1 g was converted into 1 mL to calculate the urination amount, and divided by bladder volume to obtain voiding efficiency (Voiding Efficiency). Example compound was dissolved in DMSO, and the solution was intravenously administered at 0.5 mL/kg. 10 minutes after administration of test compound, urinary reflection was recorded again, and change in urine flow rate (ΔQmax), and change in bladder internal pressure (ΔPves (Qmax)) and voiding efficiency were assessed. The change in urine flow rate (ΔQmax) and change in bladder internal pressure (ΔPves (Qmax)) were an amount of change (Δ value) obtained by subtracting each value before administration of test compound from each value after administration, and voiding efficiency was assessed by a relative value (% of pre-value) of after administration of test compound relative to before administration. Tamsulosin which is is a known $α_1$ receptor antagonist was measured similarly. A significance diffence was tested by a Dunnett test by comparing with each value of a vehicle (DMSO)-administered group.

b) Effect on Blood Pressure

Hartley male guinea pigs (Slc) weighing 300 to 350 g was anesthetized with urethane (1.2 g/kg), and retained, a cervical region was incised to expose a left common carotid artery. A polyethylene tube filled with physiological saline containing heparin (10 U.I./ml) was inserted into an artery, and blood pressure was measured with a pressure transducer. A cannulae for administering test compound was inserted into a vein at an end of left hind leg, and a test compound dissolved in distilled water was administered therethrough at 0.5 mL/kg. The blood pressure was recorded at 20 Hz using an analogue data inputting apparatus (MP-100, BIOPAC Systems), and analyzed by analyzing software (AcqKnowledge 3.5.3, BIOPAC Systems). Example compound and tamsulosin were studied for a dose at which effects were recognized in the aforementioned test a (Pressure Flow Study), and an average blood pressure just before administration of test compound and an average blood pressure 15 minutes after administration were measured. Data were statistically treated by Paired t-test.

The results by Pressure Flow Study for the present invention compound and tamsulosin, and effects on blood pressure were summarized in the following Table.

TABLE 2

Effects of present invention compound and tamsulosin on change in maximum urine flow rate (ΔQmax), change in bladder internal pressure (ΔPves(Qmax)) and voiding efficiency

| Compound | Dose (mg/kg, i.v.) | ΔQmax (mL/s) | ΔPves (Qmax) (cmH$_2$O) | voiding efficiency (%) | n |
|---|---|---|---|---|---|
| Vehicle | — | −0.029 ± 0.017 | 2.27 ± 1.88 | 82.3 ± 4.0 | 9 |
| tamsulosin | 0.01 | 0.036 ± 0.014* | −3.56 ± 1.09* | 118.5 ± 13.4** | 8 |
| Example 20 | 0.1 | 0.060 ± 0.016** | −1.73 ± 1.54 | 150.1 ± 20.1** | 8 |

*P ≦ 0.05,
**P ≦ 0.01

TABLE 3

Effects of present invention compound and tamsulosin on blood pressure

| | | Blood pressure (mmHg) | | |
|---|---|---|---|---|
| Compound | Dose (mg/kg, i.v.) | Before administration | After administration | n |
| tamsulosin | 0.01 | 54.5 ± 2.5 | 32.9 ± 3.0** | 6 |
| Example 20 | 0.1 | 53.5 ± 3.6 | 54.6 ± 2.8 | 6 |

**P ≦ 0.01

From the aforementioned results, it turns out that the $α_1$ receptor antagonist tamsulosin (0.01 mg/kg, i.v.) significantly reduces bladder internal pressure, and significantly increases maximum urine flow rate and voiding efficiency, but significantly reduces blood pressure by about 40% at the same dose.

On the other hand, it turns out that the present invention compound (0.1 mg/kg, i.v.) significantly increases urine flow rate and voiding efficiency and, at the same time, does not influence on blood pressure at the same dose without significantly reducing bladder internal pressure. From results of the aforementioned Experimental Examples 1 and 2, it is obvious that the present invention compound having both of an acetylcholinesterase inhibitory action and an $\alpha_1$ antagonistic action has excellent effect of preventing or treating voiding disturbance, in particular, voiding difficulty.

In addition, by the in vivo assessment method by Pressure Flow Study using guinea pigs loaded with phenylephrine shown in the aforementioned Experimental Example 1a, effects of the present invention compound and tamsulosin on maximum urine flow rate and bladder internal pressure could be properly assessed at the same time. From this, it is obvious that the present method is useful as a method for assessing a therapeutic agent for voiding disturbance accompanied with benign prostatic hyperplasia

INDUSTRIAL APPLICABILITY

Since the compound having both an acetylcholinesterase inhibitory action and an $\alpha_1$ antagonistic action used in the present invention exhibits excellent effect of improving urinary function of bladder (effect of improving urine flow rate and voiding efficiency) and, at the same time, does not influence on urinary pressure and a blood pressure, it is useful as a preventive or therapeutic agent for voiding disturbance.

In addition, the present screening method in which Pressure Flow Study is applied to an animal model loaded with an $\alpha$ agonist (phenylephrine) is useful as an excellent screening method for a compound having effect of preventing or treating voiding disturbance accompanied with benign prostatic hyperplasia or a salt thereof.

What is claimed is:

1. A compound represented by the formula:

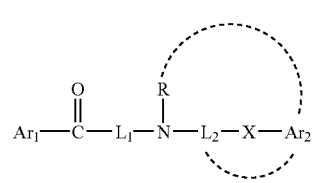

(Ia)

wherein $Ar_1$ is a group represented by the formula:

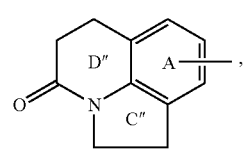

$L_1$ represents a $C_{4-6}$ alkylene group which may have a substituent, $L_2$ represents a $C_{2-4}$ alkylene group which may have a substituent, R represents a hydrogen atom or a hydrocarbon group which may have a substituent, X represents a bond, an oxygen atom or $NR^{1a}$ (wherein $R^{1a}$ represents a hydrogen atom, a hydrocarbon group which may have a substituent, an acyl group or a heterocyclic group which may have a substituent), and $Ar_2$ represents an aromatic ring group which may have a substituent, or $Ar_2$ and R, or $Ar_2$ and $L_2$ may, link together to form a ring, or a salt thereof.

2. The compound according to claim 1, wherein A ring represents a benzene ring which may have 1 or 2

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Synthetic sequence

<400> SEQUENCE: 1
ccgaattcgg ctgggaccat ggtgtttctc         30

<210> SEQ ID NO 2
<211> LENGTH: 30
<212> TYPE: DNA
<213> ORGANISM: Artificial Sequence
<220> FEATURE:
<223> OTHER INFORMATION: Synthetic sequence

<400> SEQUENCE: 2
ctgtcgacct ttcctgtcct agacttcctc         30 substituent(s) selected from the group consisting of aminosulfonyl, mono- or di-$C_{1-6}$ alkylaminosulfonyl, carbamoyl and mono- or di-$C_{1-6}$ alkyl-carbamoyl, C" ring and D" ring may have 1 or 2 substituent(s) selected from the group consisting of $C_{1-6}$ alkyl, $C_{1-6}$ alkyl-carbonylamino and $C_{1-6}$ alkyl-sulfonylamino respectively.

3. The compound according to claim 1, wherein R is a hydrogen atom or a $C_{1-4}$ alkyl group.

4. The compound according to claim 1, wherein $L_1$ is a $C_{4-5}$ alkylene group, and $L_2$ is a $C_{2-3}$ alkylene group which may have phenyl, hydroxy or oxo.

5. The compound according to claim 1, wherein $Ar_2$ is a $C_{6-10}$ aryl group or a 5- or 6-membered aromatic heterocyclic group (optionally condensed with a benzene ring) containing 1 to 4 hetero atom(s) selected from the group consisting of a nitrogen atom, an oxygen atom and a sulfur atom, each of which may have 1 to 3 substituent(s) selected from the group consisting of halogen, nitro, hydroxy, optionally halogenated $C_{1-6}$ alkyl, optionally halogenated $C_{1-6}$ alkoxy and aminosulfonyl.

6. The compound according to claim 1, wherein the ring formed by linking $Ar_2$ and R together is a ring represented by the formula:

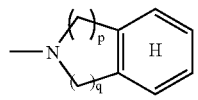

wherein p and q represent an integer of 1 to 3, respectively, and H ring represents a benzene ring which may have 1 to 3 substituent(s) selected from the group consisting of halogen, hydroxy, optionally halogenated $C_{1-6}$ alkyl and optionally halogenated $C_{1-6}$ alkoxy, and the ring formed by linking $Ar_2$ and $L_2$ together is a ring represented by the formula:

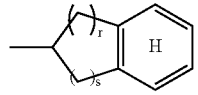

wherein r represents an integer of 0 to 2, s represents an integer of 1 to 3 and r+s is an integer of 2 to 5, and H ring represents a benzene ring which may have 1 to 3 substituents(s) selected from the group consisting of halogen, hydroxy, optionally halogenated $C_{1-6}$ alkyl and optionally halogenated $C_{1-6}$ alkoxy.

7. A process for preparing the compound according to claim 1, which comprises reacting a compound represented by the formula:

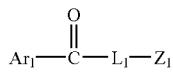

wherein $Z_1$ represents a leaving group, and the other respective symbols are as defined in claim 1, or a salt thereof with a compound represented by the formula:

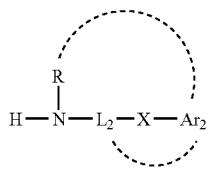

wherein respective symbols are as defined in claim 1, or a salt thereof.

8. A pharmaceutical composition comprising the compound according to claim 1, or a salt thereof.

9. 8-[5-[(2-phenylethyl)amino]pentanoyl]-1,2,5,6-tetrahydro-4H-pyrrolo[3,2,1-ij]quinolin-4-one, or a salt thereof.

* * * * *